United States Patent
Monroe et al.

(10) Patent No.: US 11,136,390 B2
(45) Date of Patent: Oct. 5, 2021

(54) ANTI-CD33 ANTIBODIES AND METHODS OF USE THEREOF

(71) Applicant: ALECTOR LLC, South San Francisco, CA (US)

(72) Inventors: Kate Monroe, Berkeley, CA (US); Helen Lam, Union City, CA (US); Francesca Avogadri-Connors, San Mateo, CA (US); Seung-Joo Lee, San Francisco, CA (US); William Monteith, San Francisco, CA (US); Herve Rhinn, San Francisco, CA (US); Arnon Rosenthal, Woodside, CA (US)

(73) Assignee: ALECTOR LLC, South San Francisco, CA (US)

( * ) Notice: Subject to any disclaimer, the term of this patent is extended or adjusted under 35 U.S.C. 154(b) by 49 days.

(21) Appl. No.: 15/735,947

(22) PCT Filed: Jun. 11, 2016

(86) PCT No.: PCT/US2016/037108
§ 371 (c)(1),
(2) Date: Dec. 12, 2017

(87) PCT Pub. No.: WO2016/201388
PCT Pub. Date: Dec. 15, 2016

(65) Prior Publication Data
US 2019/0002560 A1    Jan. 3, 2019

Related U.S. Application Data

(60) Provisional application No. 62/241,701, filed on Oct. 14, 2015, provisional application No. 62/175,152, filed on Jun. 12, 2015.

(51) Int. Cl.
| | | |
|---|---|---|
| *C07K 16/28* | (2006.01) | |
| *A61K 39/395* | (2006.01) | |
| *A61K 39/00* | (2006.01) | |
| *A61K 45/06* | (2006.01) | |
| *A61P 35/00* | (2006.01) | |
| *C12N 15/85* | (2006.01) | |

(52) U.S. Cl.
CPC ...... *C07K 16/2803* (2013.01); *A61K 39/3955* (2013.01); *A61P 35/00* (2018.01); *C12N 15/85* (2013.01); *A61K 45/06* (2013.01); *A61K 2039/505* (2013.01); *A61K 2300/00* (2013.01); *C07K 2317/21* (2013.01); *C07K 2317/24* (2013.01); *C07K 2317/31* (2013.01); *C07K 2317/34* (2013.01); *C07K 2317/55* (2013.01); *C07K 2317/70* (2013.01); *C07K 2317/73* (2013.01); *C07K 2317/76* (2013.01); *C07K 2317/92* (2013.01)

(58) Field of Classification Search
CPC ............ C07K 16/2803; C07K 16/2896; C07K 2317/31; C07K 2317/34; C07K 2317/55; C07K 2317/76; A61K 47/68; A61K 39/3955; A61K 45/06; A61K 2039/505; A61K 2300/00; A61P 35/00
See application file for complete search history.

(56) References Cited

U.S. PATENT DOCUMENTS

| | | |
|---|---|---|
| 4,469,863 A | 9/1984 | Ts'o et al. |
| 4,657,760 A | 4/1987 | Kung et al. |
| 4,676,980 A | 6/1987 | Segal et al. |
| 4,816,567 A | 3/1989 | Cabilly et al. |
| 5,206,344 A | 4/1993 | Katre et al. |
| 5,225,212 A | 7/1993 | Martin et al. |
| 5,229,275 A | 7/1993 | Goroff et al. |
| 5,530,101 A | 6/1996 | Queen et al. |
| 5,536,821 A | 7/1996 | Agrawal et al. |
| 5,541,306 A | 7/1996 | Agrawal et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,569,825 A | 10/1996 | Lonberg et al. |
| 5,571,894 A | 11/1996 | Wels et al. |
| 5,573,905 A | 11/1996 | Lerner et al. |
| 5,585,089 A | 12/1996 | Queen et al. |
| 5,587,458 A | 12/1996 | King et al. |
| 5,591,669 A | 1/1997 | Krimpenfort et al. |
| 5,614,622 A | 3/1997 | Iyer et al. |
| 5,625,126 A | 4/1997 | Lonberg et al. |
| 5,633,425 A | 5/1997 | Lonberg et al. |

(Continued)

FOREIGN PATENT DOCUMENTS

| | | |
|---|---|---|
| CN | 1078401 A | 11/1993 |
| CN | 1795009 A | 6/2006 |

(Continued)

OTHER PUBLICATIONS

Edwards et al. J. Mol. Biol. 334:103-118. (Year: 2003).*

(Continued)

*Primary Examiner* — Kimberly Ballard
(74) *Attorney, Agent, or Firm* — Morrison & Foerster LLP

(57) ABSTRACT

The present disclosure is generally directed to compositions that include antibodies, e.g., monoclonal, chimeric, humanized antibodies, antibody fragments, etc., that specifically bind one or more epitopes within a CD33 protein, e.g., human CD33 or a mammalian CD33, and use of such compositions in preventing, reducing risk, or treating an individual in need thereof.

26 Claims, 69 Drawing Sheets

Specification includes a Sequence Listing.

(56) References Cited

U.S. PATENT DOCUMENTS

| | | | |
|---|---|---|---|
| 5,637,683 A | 6/1997 | Usher et al. | |
| 5,637,684 A | 6/1997 | Cook et al. | |
| 5,641,870 A | 6/1997 | Rinderknecht et al. | |
| 5,648,237 A | 7/1997 | Carter et al. | |
| 5,661,016 A | 8/1997 | Lonberg et al. | |
| 5,693,761 A | 12/1997 | Queen et al. | |
| 5,693,762 A | 12/1997 | Queen et al. | |
| 5,700,922 A | 12/1997 | Cook | |
| 5,717,083 A | 2/1998 | Cook et al. | |
| 5,719,262 A | 2/1998 | Buchardt et al. | |
| 5,730,982 A | 3/1998 | Scheinberg | |
| 5,731,168 A | 3/1998 | Carter et al. | |
| 5,739,277 A | 4/1998 | Presta et al. | |
| 5,739,308 A | 4/1998 | Kandimalla et al. | |
| 5,739,314 A | 4/1998 | Roy et al. | |
| 5,750,373 A | 5/1998 | Garrard et al. | |
| 5,766,886 A | 6/1998 | Studnicka et al. | |
| 5,773,601 A | 6/1998 | Agrawal | |
| 5,789,199 A | 8/1998 | Joly et al. | |
| 5,821,337 A | 10/1998 | Carter et al. | |
| 5,840,523 A | 11/1998 | Simmons et al. | |
| 5,869,046 A | 2/1999 | Presta et al. | |
| 5,869,619 A | 2/1999 | Studnicka | |
| 5,886,165 A | 3/1999 | Kandimalla et al. | |
| 5,929,226 A | 7/1999 | Padmapriya et al. | |
| 5,955,599 A | 9/1999 | Iyer et al. | |
| 5,959,177 A | 9/1999 | Hein et al. | |
| 5,962,674 A | 10/1999 | Iyer et al. | |
| 5,977,296 A | 11/1999 | Nielsen et al. | |
| 6,040,498 A | 3/2000 | Stomp et al. | |
| 6,075,181 A | 6/2000 | Kucherlapati et al. | |
| 6,117,992 A | 9/2000 | Iyer | |
| 6,140,482 A | 10/2000 | Iyer et al. | |
| 6,150,584 A | 11/2000 | Kucherlapati et al. | |
| 6,248,516 B1 | 6/2001 | Winter et al. | |
| 6,350,861 B1 | 2/2002 | Co et al. | |
| 6,417,429 B1 | 7/2002 | Hein et al. | |
| 6,420,548 B1 | 7/2002 | Vézina et al. | |
| 6,455,308 B1 | 9/2002 | Freier | |
| 6,982,321 B2 | 1/2006 | Winter | |
| 7,041,870 B2 | 5/2006 | Tomizuka et al. | |
| 7,087,409 B2 | 8/2006 | Barbas, III et al. | |
| 7,125,978 B1 | 10/2006 | Vézina et al. | |
| 7,189,826 B2 | 3/2007 | Rodman | |
| 7,342,110 B2 | 3/2008 | Hoffee et al. | |
| 7,420,041 B2 * | 9/2008 | Young | C07K 16/30 530/387.1 |
| 7,527,791 B2 | 5/2009 | Adams et al. | |
| 7,557,189 B2 | 7/2009 | Hoffee et al. | |
| 8,119,787 B2 | 2/2012 | Hoffee et al. | |
| 8,124,069 B2 | 2/2012 | Bae et al. | |
| 8,337,855 B2 | 12/2012 | Hoffee et al. | |
| 8,614,299 B2 | 12/2013 | Baurin et al. | |
| 9,951,133 B2 | 4/2018 | Yu et al. | |
| 10,711,062 B2 | 7/2020 | Culp et al. | |
| 2007/0061900 A1 | 3/2007 | Murphy et al. | |
| 2007/0148167 A1 | 6/2007 | Strohl | |
| 2007/0292936 A1 | 12/2007 | Barthelemy et al. | |
| 2009/0002360 A1 | 1/2009 | Chen et al. | |
| 2009/0181855 A1 | 7/2009 | Vasquez et al. | |
| 2010/0056386 A1 | 3/2010 | Vasquez et al. | |
| 2010/0280227 A1 | 11/2010 | Ambrose et al. | |
| 2012/0082670 A1* | 4/2012 | Konopitzky | C07K 16/2851 424/139.1 |
| 2013/0309223 A1 | 11/2013 | Sutherland | |
| 2016/0038566 A1* | 2/2016 | Tanzi | C07K 16/2851 424/133.1 |
| 2019/0040131 A1 | 2/2019 | Culp | |
| 2019/0085076 A1 | 3/2019 | Rosenthal | |

FOREIGN PATENT DOCUMENTS

| | | | |
|---|---|---|---|
| CN | 102952191 A | 3/2013 | |
| CN | 103261227 A | 8/2013 | |
| EP | 0308936 B1 | 7/1994 | |
| EP | 0404097 B1 | 9/1996 | |
| EP | 546073 B1 | 9/1997 | |
| JP | 2014500003 A | 1/2014 | |
| WO | WO-1987/04462 A1 | 7/1987 | |
| WO | WO-1991/00360 A1 | 1/1991 | |
| WO | WO-1991/09058 A1 | 6/1991 | |
| WO | WO-1991/10741 A1 | 7/1991 | |
| WO | WO-1992/00373 A1 | 1/1992 | |
| WO | WO-1992200373 A1 | 11/1992 | |
| WO | WO-1993001161 A1 | 1/1993 | |
| WO | WO-1993/08829 A1 | 5/1993 | |
| WO | WO-1993/11161 A1 | 6/1993 | |
| WO | WO-1993/16185 A2 | 8/1993 | |
| WO | WO-1993/20848 A1 | 10/1993 | |
| WO | WO-1994/04690 A1 | 3/1994 | |
| WO | WO-1996/27011 A1 | 9/1996 | |
| WO | WO-1996/33735 A1 | 10/1996 | |
| WO | WO-1996/34096 A1 | 10/1996 | |
| WO | WO-1997/11971 A1 | 4/1997 | |
| WO | WO-1997/17852 A1 | 5/1997 | |
| WO | WO-1998/24893 A2 | 6/1998 | |
| WO | WO-1999/32619 A1 | 7/1999 | |
| WO | WO-1999/58572 A1 | 11/1999 | |
| WO | WO-2000/44895 A1 | 8/2000 | |
| WO | WO-2000/56746 A2 | 9/2000 | |
| WO | WO-2000/75372 A1 | 12/2000 | |
| WO | WO-2001/14398 A1 | 3/2001 | |
| WO | WO-2001/29058 A1 | 4/2001 | |
| WO | WO-2001/36646 A1 | 5/2001 | |
| WO | WO-2003/093298 A2 | 11/2003 | |
| WO | WO-2004/042072 A2 | 5/2004 | |
| WO | WO-2004/043344 A2 | 5/2004 | |
| WO | WO-2007/014743 A2 | 2/2007 | |
| WO | WO-2007/106585 A1 | 9/2007 | |
| WO | WO-2008/058021 A2 | 5/2008 | |
| WO | WO-2008/079246 A2 | 7/2008 | |
| WO | WO-2009/036379 A2 | 3/2009 | |
| WO | WO-2010/105256 A1 | 9/2010 | |
| WO | WO-2011/036183 A2 | 3/2011 | |
| WO | WO-2011/038301 A2 | 3/2011 | |
| WO | WO-2012/009568 A2 | 1/2012 | |
| WO | WO-2012/045752 A1 | 4/2012 | |
| WO | WO-2012/074097 A1 | 6/2012 | |
| WO | WO2013173496 A2 | 11/2013 | |
| WO | WO2013173496 A3 | 11/2013 | |
| WO | WO-2016087651 A1 * | 6/2016 | A61P 35/04 |
| WO | WO-2016/201389 A2 | 12/2016 | |
| WO | WO-2016/201389 A3 | 12/2016 | |

OTHER PUBLICATIONS

Lloyd et al. Protein Eng. Design & Select, 22(3): 159-168. (Year: 2009).*

Wikipedia entry for EC50, en.wikipedia.org/wiki/EC50, retrieved Sep. 16, 2019. (Year: 2019).*

Alegre, M.-L. et al. (Jun. 1, 1994). "A Non-Activating "Humanized" Anti-cd3 Monoclonal Antibody Retains Immunosuppressive Properties in Vivo," *Transplantation* 57(11):1537-1543.

Almagro, J.C. et al. (2008). "Humanization of Antibodies," *Frontiers in Bio-Science* 13:1619-1633.

Al-Shawi, R.et al. (2008). "Neurotoxic and Neurotrophic Roles of proNGF and the Receptor Sortilin in the Adult and Ageing Nervous System," *European Journal of Neuroscience* 27:2103-2114.

Angal, S. et al. (1993). "A Single Amino Acid Substitution Abolishes the Heterogeneity of Chimeric Mouse/Human (IgG4) Antibody," *Molecular Immunology* 30(1):105-108.

Armour, K.L. et al. (1999). "Recombinant Human IgG Molecules Lacking FcGamma Receptor I Binding and Monocyte Triggering Activities," *Eur. J. Immunol.* 29:2613-2624.

Armour, K.L. et al. (2003). "Differential Binding to Human Fcγriia and Fcγriib Receptors by Human IgG Wildtype and Mutant Antibodies," *Molecular Immunology* 40:585-593.

Armour, K.L. et al. (Jun. 25-28, 2000). "Mutant IgG Lacking FcγRIII Binding and ADCC Activities," *The Haematology Journal*, poster Session 1, *Presented at the 5th Annual Meeting of the European Haematology Association*, Birmingham, UK, 1(Suppl. 1):27, 2 pages.

(56) References Cited

OTHER PUBLICATIONS

Arnett, M.G. et al. (Dec. 5, 2007; e-published on Oct. 26, 2007). "proNGF, Sortilin, and p75$^{NTR}$: Potential Mediators of Injury-Induced Apoptosis in the Mouse Dorsal Root Ganglion," *Brain Res.* 1183:32-42.
Asquith, D.L. et al. (2009). "Animal Models of Rheumatoid Arthritis," *Eur. J. Immunol.* 39:2040-2044.
Attrill, H. et al. (Oct. 27, 2006; e-published on Aug. 8, 2006). "Siglec-7 Undergoes a Major Conformational Change When Complexed with the α(2,8)-Disialylganglioside GT1b," *J. Biol. Chem.* 281:32774-32783.
Baca, M. et al. (1997). "Antibody Humanization Using Monovalent Phage Display," *The Journal of Biological Chemistry* 272(16):10678-10684.
Balaian, L. et al. (Dec. 2001). "Direct Effect of Bispecific Anti-CD33 X Anti-CD64 Antibody on Proliferation and Signaling in Myeloid Cells," *Leuk Res.* 25(12):1115-1125.
Barbas III, C.F. et al. (Apr. 1994). "In Vitro Evolution of a Neutralizing Human Antibody to Human Immunodeficiency Virus Type 1 to Enhance Affinity and Broaden Strain Cross-Reactivity," *Proc Nat. Acad. Sci. USA* 91:3809-3813.
Bartholomaeus et al. (2014). "Cell Contact-Dependent Priming and Fc Interaction with CD32+ Immune Cells Contribute to the TGN1412-Triggered Cytokine Response," *The Journal of Immunology* 192: 2091-2098.
Beattie, M.S. et al. (Oct. 24, 2002). "ProNGF Induces p75-Mediated Death of Oligodendrocytes following Spinal Cord Injury," *Neuron* 36(3):375-386.
Bertram, L. et al. (Nov. 17, 2008). "Genome-wide Association Analysis Reveals Putative Alzheimer's Disease Susceptibility Loci in Addition to APOE," *Am. J. Hum. Genet.* 83(5):623-632.
Boerner, P. et al. (1991). "Production of Antigen-Specific Human Monoclonal Antibodies From In Vitro-Primed Human Splenocytes," *Journal of Immunology* 147(1):86-95.
Bolt, S. et al. (1993). "The Generation of a Humanized, Non-Mitogenic Cd3 Monoclonal Antibody Which Retains In Vitro Immunosuppressive Properties," *European Journal Immunol.* 23:403-411.
Bradshaw, E.M. et al. (Jul. 2013; e-published on May 23, 2013). "CD33 Alzheimer's Disease Locus: Altered Monocyte Function and Amyloid Biology," *Nat. Neurosci.* 16(7):848-850, fourteen pages.
Brehm, M.A. et al. (Apr. 2010). "Humanized Mouse Models to Study Human Diseases," *Curr Opin Endocrinol Diabetes Obes.* 17(2):120-125.
Brennan, M. et al. (Jul. 5, 1985). "Preparation of Bispecific Antibodies by Chemical Recombination of Monoclonal Immunoglobulin G1 Fragments," *Science* 229:81-83.
Brinkman-Van Der Linden, E.C.M. et al. (Jun. 2003). "CD33/Siglec-3 Binding Specificity, Expression Pattern, and Consequences of Gene Deletion in Mice," *Mol. Cell Biol.* 23(12):4199-4206.
Bross, P.F. et al. (Jun. 2001). "Approval Summary: Gemtuzumab Ozogamicin in Relapsed Acute Myeloid Leukemia," *Clinical Cancer Research* 7:1490-1496.
Bruggemann, M. et al. (1993). "Designer Mice: The Production of Human Antibody Repertoires in Transgenic Animals," *Year in Immunol.* 7:33-40.
Calligé, M. et al. (Jun. 2005). "CSN5/Jab1 is Involved in Ligand-Dependent Degradation of Estrogen Receptor α by the Proteasome," *Mol. Cell Biol.* 25(11):4349-4358.
Cantoni, C. et al. (Mar. 2015). "TREM2 Regulates Microglial Cell Activation in Response to Demyelination In Vivo," *Acta Neuropathol*, 129(3):429-447, thirty three pages.
Cao, X. et al. (Sep. 2011). "Macrophage Polarization in the Maculae of Age-Related Macular Degeneration: A Pilot Study," *Pathology International* 61(9):528-535, fourteen pages.
Capel, P.J.A. et al. (1994). "Heterogeneity of Human IgG Fc Receptors," *Immunomethods* 4:25-34.
Carter, P. et al. (Feb. 1992). "High Level *Escherichia coli* Expression and Production of a Bivalent Humanized Antibody Fragment," *Bio/technology* 10:163-167.
Carter, P. et al. (May 1992). "Humanization of an Anti-p185$^{HER2}$ Antibody for Human Cancer Therapy," *Proc. Natl. Acad. Sci. USA* 89:4285-4289.
Chang et al. (2002). "Retinal Degeneration Mutants in the Mouse," *Vision Research* 42:517-525.
Chothia, C. et al. (1987). "Canonical Structures for the Hypervariable Regions of Immunoglobulins," *J. Mol. Biol*, 196:901-917.
Chu, S.Y. et al. (2008, e-pub. Aug. 8, 2008). "Inhibition of B cell Receptor-Mediated Activation of Primary Human B Cells by Coengagement of CD19 and FcγRIIb with Fc-Engineered Antibodies," *Molecular Immunology* 45:3926-3933.
Clackson, T. et al. (1991). "Making Antibody Fragments Using Phage Display Libraries," *Nature* 352(15):624-628.
Cole, M.S. et al. (Aug. 27, 1999). "HuM291, A Humanized Anti-Cd3 Antibody is Immunosuppressive to T Cells While Exhibiting Reduced Mitogenicity in Vitro," *Transplantation* 68(4):563-571.
Compston, A. et al. (Oct. 25, 2008). "Multiple Sclerosis," *Lancet* 372(9648):1502-1517.
Correale, C. et al. (Feb. 2013). "Bacterial Sensor Triggering Receptor Expressed on Myeloid Cells-2 Regulates the Mucosal Inflammatory Response," *Gastroenterology* 144(2):346-356.
Crocker, P.R. et al. (Apr. 2007). "Siglecs and their Roles in the Immune System," *Nat Rev Immunol.* 7(4):255-266.
Crocker, P.R. et al. (Apr. 2012; e-published on Feb. 21, 2012). "CD33-related Siglecs as Potential Modulators of Inflammatory Responses," *Ann. NY Acad. Sci.* 1253:102-111.
Crocker, P.R. et al. (Jul. 1999). "Molecular Analysis of Sialoside Binding to Sialoadhesin by NMR and Site-Directed Mutagenesis," *Biochem J.* 341(Pt. 2):355-361.
Crocker, P . R . et al. (Jun. 1, 2001). "Siglecs, Sialic Acids and Innate Immunity," *Trends Immunol.* 22(6):337-342.
Cruts, M. et al. (2008, e-pub. Mar. 6, 2008). "Loss of Progranulin Function in Frontotemporal Lobar Degeneration," *Trends Genetics* 24(4):186-194.
Cunningham, B.C. et al. (Jun. 2, 1989). "High-Resolution Epitope Mapping of hGH-Receptor Interactions by Alanine-Scanning Mutagenesis," *Science* 244:1081-1085.
Daëron, M. (1997). "FC Receptor Biology," *Annu. Rev. Immunol.* 15:203-234.
Dall' Acqua, W.F. et al. (Aug. 18, 2006). "Properties of Human IgG1s Engineered for Enhanced Binding to the Neonatal Fc Receptor (FcRn)," *The Journal of Biological Chemistry* 281(33):23514-23524.
Daneman, R. et al. (Oct. 29, 2010). "The Mouse Blood-Brain Barrier Transcriptome: A New Resource for Understanding the Development and Function of Brain Endothelial Cells," *PLoS One* 5(10):e13741, sixteen pages.
Davis, P.M. et al. (2007). "Abatacept Binds to the Fc Receptor Cd64 But Does Not Mediate Complement-Dependent Cytotoxicity or Antibody-Dependent Cellular Cytotoxicity," *The Journal of Rheumatology* 34(11):2204-2210.
De Haas, M. et al. (1995). "Fcγ Receptors of Phagocytes," *J. Lab. Clin. Med.* 126(4):330-341.
Ducry, L. et al. (Jan. 2010; e-published on Sep. 21, 2009). "Antibody-Drug Conjugates: Linking Cytotoxic Payloads to Monoclonal Antibodies," *Bioconjugate Chemistry* 21(1):5-13.
Eksioglu, E.A. et al. (Jan. 1, 2014). "Novel Therapeutic Approach to Improve Hematopoiesis by Targeting Myeloid Derived Suppressor Cells with a Humanized Anti-CD33 Antibody," *Blood* 124(21):4597, located at < http://www.bloodjournal.org/content/124/21/4597>, last visited on Jan. 5, 2017, three pages.
El-Danaf, R.N. et al. (Feb. 11, 2015). "Characteristic Patterns of Dendritic Remodeling in Early-Stage Glaucoma: Evidence from Genetically Identified Retinal Ganglion Cell Types," *The Journal of Neuroscience* 35(6):2329-2343.
Estep, P. et al. (Mar.-Apr. 2013). "High Throughput Solution-Based Measurement of Antibody-Antigen Affinity and Epitope Binning," *mAbs.* 5(2):270-278.
Etemad, S. et al. (2012). "A Novel In Vitro Human Microglia Model: Characterization of Human Monocyte-Derived Microglia," *Journal of Neuroscience Methods* 209:79-89.

(56) References Cited

OTHER PUBLICATIONS

Fahnestock, M. et al. (2001). "The Precursor Pro-Nerve Growth Factor is the Predominant Form of Nerve Growth Factor in Brain and is Increased in Alzheimer's Disease," *Molecular and Cellular Neuroscience* 18:210-220.

Fan, Y.-J. (2008). "Differential effects of Pro-BDNF on Sensory Neurons after Sciatic Nerve Transection in Neonatal Rats," *European Journal of Neuroscience* 27:2380-2390.

Fasen, K. et al. (Feb. 2008; e-published on Dec. 19, 2007). "Ligand Binding Induces Cbl-Dependent EphB1 Receptor Degradation Through the Lysosomal Pathway," *Traffic* 9(2):251-266.

Feldhaus, M.J. et al. (2004, e-pub. May 31, 2004)."Yeast Display of Antibody Fragments: A Discovery and Characterization Platform," *Journal of Immunological Methods* 290:69-80.

Fellouse, F.A. et al. (Aug. 24, 2004). "Synthetic Antibodies from a Four-Amino-Acid Code: A Dominant Role for Tyrosine in Antigen Recognition," *PNAS* 101(34):12467-12472.

Ferlazzo, G. et al. (2000). "Engagement of CD33 Surface Molecules Prevents the Generation of Dendritic Cells From Both Monocytes and $CD34^+$ Myeloid Precursors," *Eur J Immunol.* 30:827-833.

Fishwild, D.M. et al. (Jul. 1996). "High-Avidity Human Iggκ Monoclonal Antibodies from a Novel Strain of Minilocus Transgenic Mice," *Nature Biotechnology* 14:845-851.

Gabathuler, R. (2010, e-pub. Aug. 5, 2009). "Approaches to Transport Therapeutic Drugs across the Blood-Brain Barrier to Treat Brain Diseases," *Neurobiology of Disease* 37:48-57.

Gawish, R. et al. (Apr. 2015; e.pub Dec. 4, 2014). "Triggering Receptor Expressed on Myeloid cells-2 Fine-Tunes Inflammatory Responses in Murine Gram-Negative Sepsis," *The FASEB Journal* 29(4):1247-1257.

Gerngross, T.U. (Nov. 2004, e-pub. Nov. 4, 2004). "Advances in the Production of Human Therapeutic Proteins in Yeasts and Filamentous Fungi," *Nature Biotechnology* 22(11):1409-1414.

Graham, F.L. et al. (1977). "Characteristics of a Human Cell Line Transformed by DNA from Human Adenovirus Type 5," *Journal of General Virology* 36:59-72.

Griciuc, A. et al. (May 22, 2013; e-published on Apr. 25, 2013). "Alzheimer's Disease Risk Gene CD33 Inhibits Microglial Uptake of Amyloid Beta," *Neuron* 78(4):631-643.

Griffin, J.D. et al. (1984). "A Monoclonal Antibody Reactive with Normal and Leukemic Human Myeloid Progenitor Cells," *Leukemia Research* 8(4):521-534.

Griffiths, A.D. et al. (1993). "Human Anti-Self Antibodies with High Specificity from Phage Display Libraries," *The EMBO Journal* 12(2):725-734.

Grobe, K. et al. (May 1, 2002). "Role of Protein Kinase C in the Phosphorylation of CD33 (Siglec-3) and its Effect on Lectin Activity," *Blood* 99(9):3188-3196.

Gruber, M. et al. (1994). "Efficient Tumor Cell Lysis Mediated by a Bispecific Single Chain Antibody Expressed in *Escherichia coli,*" *The Journal of Immunology* 152(11):5368-5374.

Gupta, N. et al. (2003). "Activated Microglia in Human Retinitis Pigmentosa, Late-Onset Retinal Degeneration, and Age-Related Macular Degeneration," *Experimental Eye Research* 76:463-471.

Hamann, P.R. et al. (2002, e-pub. Dec. 19, 2001). "Gemtuzumab Ozogamicin, A Potent and Selective Anti-CD33 Antibody-Calicheamicin Conjugate for Treatment of Acute Myeloid Leukemia," *Bioconjugate Chemistry* 13(1):47-58.

Hamers-Casterman, C. et al. (Jun. 3, 1993). "Naturally Occurring Antibodies Devoid of Light Chains," *Nature* 363:446-448.

Handgretinger, R. et al. (Aug. 1993). "Expression of an Early Myelopoietic Antigen (CD33) of a Subset of Human Umbilical Cord Blood-Derived Natural Killer Cells," *Immunol Lett.* 37(2-3):223-228.

Harrington, A.W. et al. (Apr. 20, 2004). "Secreted proNGF is a Pathophysiological Death-Inducing Ligand After Adult CNS Injury," *Proc. Natl. Acad. Sci USA* 101(16):6226-6230.

Harris, W.J. (Nov. 1, 1995). "Therapeutic Monoclonals—Production of Humanized Monoclonal Antibodies for In Vivo Imaging and Therapy," *Biochem. Soc. Transactions* 23(4):1035-1038.

Hawkins, R.E. et al. (1992). "Selection of Phage Antibodies by Binding Affinity: Mimicking Affinity Maturation," *Journal of Molecular Biology* 226:889-896.

Heider, K. et al. (Jan. 1, 2012). "A Novel Fc-Engineered Antibody to CD33 with Enhanced ADCC Activity for Treatment of AML," *Blood* 120(21):1363, located at <http://www.bloodjournal.org/content/120/21/1363>, last visited on Jan. 5, 2017, five pages.

Hernández-Caselles, T. et al. (Jan. 2006). "A Study of CD33 (SIGLEC-3) Antigen Expression and Function on Activated Human T and NK Cells: Two Isoforms of CD33 are Generated by Alternative Splicing," *J Leukoc Biol.* 79(1):46-58.

Hezareh, M. et al. (Dec. 2001). "Effector Function Activities of a Panel of Mutants of a Broadly Neutralizing Antibody against Human Immunodeficiency Virus Type 1," *Journal of Virology* vol. 75(24):12161-12168.

Holliger, P. et al. (Jul. 1993). ""Diabodies": Small Bivalent and Bispecific Antibody Fragments," *Proceedings of the National Academy of Sciences* 90:6444-6448.

Hollingworth, P. et al. (May 2011; e-published on Apr. 3, 2011). "Common Variants in ABCA7, MS4A6A/MS4A4E, EPHA1, CD33 and CD2AP are Associated with Alzheimer's Disease," *Nat. Genet.* 43(5):429-435.

Hongo, J.S. et al. (1995). "Development and Characterization of Murine Monoclonal Antibodies to the Latency-Associated Peptide of Transforming Growth Factor β1," *Hybridoma* 14(3):253-260.

Hoogenboom, H.R. et al. (1992). "By-Passing Immunisation. Human Antibodies from Synthetic Repertoires of Germline Hh Gene Segments Rearranged in Vitro," *Journal of Molecular Biology* 227:381-388.

Hoyer, J.D. et al. (Feb. 1, 2008). "CD33 Detection by Immunohistochemistry in Paraffin-Embedded Tissues: A New Antibody Shows Excellent Specificity and Sensitivity for Cells of Myelomonocytic Lineage," *Am. J. Clin. Pathol.* 129(2):316-323.

Humphrey, M.B. et al. (2006). "TREM2, a DAP12-Associated Receptor, Regulates Osteoclast Differentiation and Function," *J Bone Miner Res.* 21(2):237-245.

Hurle, M.R. et al. (Aug. 1994)."Protein Engineering Techniques for Antibody Humanization," *Current Opinion in Biotechnology* 5:428-433.

Hutchins, J.T. et al. (Dec. 1995). "Improved Biodistribution, Tumor Targeting, and Reduced Immunogenicity in Mice with a Gamma 4 Variant of Campath-IH," *Proc. Natl. Acad. Sci.* 92:11980-11984.

Hutton, M. et al. (Jun. 18, 1998). "Association of Missense and 5'-Splice-Site Mutations in Tau with the Inherited Dementia FTDP-17," *Nature* 393:702-705.

Ito, M. et al. (2008). "NOD/Shi-scid IL2rγ$^{null}$ (NOG) Mice More Appropriate for Humanized Mouse Models," *Curr Top Microbiol Immunol.* 324:53-76.

Ito, R. et al. (May 2012; e-published on Feb. 13, 2012). "Current Advances in Humanized Mouse Models," *Cellular & Molecular Immunology* 9(3):208-214.

Jackson, J.R. et al. (Apr. 1, 1995). "In Vitro Antibody Maturation. Improvement of a High Affinity, Neutralizing Antibody against IL-1 Beta," *The Journal of Immunology* 157(7):3310-3319.

Jakobovits, A. et al. (Mar. 18, 1993) "Germ-line Transmission and Expression of a Human-derived Yeast Artificial Chromosome," *Nature* 362:255-258.

Jakobovits, A. et al. (Mar. 1993). "Analysis of Homozygous Mutant Chimeric Mice: Deletion of The Immunoglobulin Heavy-chain Joining Region Blocks B-Cell Development and Antibody Production," *Proceedings of the National Academy of Sciences* 90:2551-2555.

Jandus, C. et al. (Aug. 15, 2011; e-published on May 31, 2011). "Targeting Siglecs—A Novel Pharmacological Strategy for Immuno- and Glycotherapy," *Biochem. Pharmacol.* 82(4):323-332.

Jansen, P. et al. (Nov. 2007, e-pub. Oct. 14, 2007). "Roles for the Pro-Neurotrophin Receptor Sortilin in Neuronal Development, Aging and Brain Injury," *Nature Neuroscience* 10(11):1449-1457.

(56) References Cited

OTHER PUBLICATIONS

Johnson, K.S. et al. (Aug. 1993). "Human antibody engineering: Current Opinion in Structural Biology," *Current Opinion in Structural Biology* 3(4):564-571.

Jones, P.T. et al. (May 29, 1986). "Replacing the Complementarity-Determining Regions in a Human Antibody with Those from a Mouse," *Nature* 321:522-525.

Jurcic, J.G. (Mar. 2012, e-pub. Nov. 23, 2011). "What Happened to Anti-CD33 Therapy for Acute Myeloid Leukemia?," *Curr Hematol Malig Rep* 7(1):65-73.

Kelm, S. et al. (1994). "Sialoadhesin, Myelin-Associated Glycoprotein and CD22 Define a New Family of Sialic Acid-Dependent Adhesion Molecules of the Immunoglobulin Superfamily," *Current Biology* 4(11):965-972.

Koga, T. et al. (Apr. 15, 2004). "Costimulatory Signals Mediated by the ITAM Motif Cooperate with RANKL for Bone Homeostasis," *Nature* 428:758-763.

Köhler, G. et al. (Aug. 7, 1975). "Continuous Cultures of Fused Cells Secreting Antibody of Predefined Specificity," *Nature* 256:495-497.

Kostelny, S.A. et al. (Mar. 1, 1992). "Formation of a Bispecific Antibody by the Use of Leucine Zippers," *The Journal of Immunology* 148(5):1547-1553.

Kozbor, D. et al. (Dec. 1984). "A Human Hybrid Myeloma for Production of Human Monoclonal Antibodies," *The Journal of Immunology* 133(6):3001-3005.

Laird, A.S. et al. (Oct. 13, 2010). "Progranulin is Neurotrophic in Vivo and Protects against a Mutant TDP-43 Induced Axonopathy," *PLOS ONE* 5(10):e13368, seven pages.

Lajaunias, F. et al. (Jan. 2005; e-published on Dec. 16, 2004). "Constitutive Repressor Activity of CD33 on Human Monocytes Requires Sialic Acid Recognition and Phosphoinositide 3-Kinase-Mediated Intracellular Signaling," *Eur J Immunol.* 35(1):243-251.

Langer, R. (Sep. 28, 1990). "New Methods of Drug Delivery," *Science* 249(4976):1527-1533.

Lavail, M.M. et al. (Jun. 30, 2011). "Retinal Degeneration Rat Model Resource Availability of P23H and S334ter Mutant Rhodopsin Transgenic Rats and RCS Inbred and RCS Congenic Strains of Rats," University of California, pp. 1-12.

Lazar, G.A. et al. (Mar. 14, 2006). "Engineered Antibody Fc variants with Enhanced Effector Function," *PNAS* 103(11):4005-4010.

Lee, C.V. et al. (2004). "Bivalent Antibody Phage Display Mimics Natural Immunoglobulin," *Journal of Immunological Methods* 284:119-132.

Lee, C.V. et al. (2004). "High-affinity Human Antibodies from Phage-displayed Synthetic Fab Libraries with a Single Framework Scaffold," *Journal of Molecular Biology* 340:1073-1093.

Li, H. et al. (Feb. 2006). "Optimization of Humanized IgGs in Glycoengineered *Pichia pastoris*," *Nature Biotechnology* 24(2):210-215.

Li, J. et al. (Mar. 7, 2006). "Human Antibodies for Immunotherapy Development Generated via a Human B Cell Hybridoma Technology," *PNAS* 103(10):3557-3562.

Lightle, S. et al. (Mar. 24, 2010; e-published on Jan. 29, 2010). "Mutations Within a Human Lgg2 Antibody Form Distinct and Homogeneous Disulfide Isomers but do not Affect Fc Gamma Receptor or C1q Binding," *Protein Science* 19:753-762.

Lipovsek, D. et al. (2004, e-pub. May 31, 2004). "In-vitro protein evolution by ribosome display and mRNA display," *Journal of Immunological Methods* 290:51-67.

Lonberg, N. et al. (1995). "Human Antibodies from Transgenic Mice," *International Reviews of Immunology.* 13:65-93.

Lonberg, N. et al. (Apr. 28, 1994). "Antigen-Specific Human Antibodies from Mice Comprising Four Distinct Genetic Modifications," *Nature* 368:856-859.

Low, D. et al. (2013). "Animal Models of Ulcerative Colitis and their Application in Drug Research," *Drug Design, Development and Therapy* 7:1341-1357.

Lütje, S. et al. (Feb. 19, 2014). "Anti-CEA Antibody Fragments Labeled with [$^{18}$F]AIF for PET Imaging of CEA-Expressing Tumors," *Bioconjugate Chemistry* 25(2):335-341.

MacAuley, M.S. et al. (Oct. 2014; e-published on Sep. 19, 2014). "Siglec Regulation of Immune Cell Function in Disease," *Nature Reviews Immunology* 14(10):653-666, twenty nine pages.

Malik, B.R. et al. (Nov. 1, 2015; e-published on Aug. 6, 2015). "VPS35 Pathogenic Mutations Confer no Dominant Toxicity but Partial Loss of Function in *Drosophila* and Genetically Interact With *Parkin*," *Human Molecular Genetics* 24(21):6106-6117.

Malik, M. et al. (Aug. 14, 2013). "CD33 Alzheimer's Risk-Altering Polymorphism, CD33 Expression, and Exon 2 Splicing," *J. Neurosci* 33(33):13320-13325.

Marks, J.D. et al. (1991). "By-passing immunization: Human antibodies from V-gene libraries displayed on phage," *Journal of Molecular Biology* 222(3): 581-597.

Marks, J.D. et al. (Jul. 1992)."By-Passing Immunization: Building High Affinity Human Antibodies by Chain Shuffling," *Bio/Technology* 10:779-782.

Martens, L.H. et al. (Nov. 2012). "Progranulin Deficiency Promotes Neuroinflammation and Neuron Loss Following Toxin-Induced Injury," *The Journal of Clinical Investigation* 122(11):3955-3959.

Mather, J.P. (1980). "Establishment and Characterization of Two Distinct Mouse Testicular Epithelial Cell Lines," *Biology of Reproduction* 23:243-252.

Mather, J.P. et al. (1982). "Culture of Testicular Cells in Hormone-Supplemented Serum-Free Medium," *Annals of the New York Academy of Sciences, Testicular Cell Culture* 383:44-68.

May, A.P. et al. (Apr. 1998). "Crystal Structure of the N-Terminal Domain of Sialoadhesin in Complex with 3' Sialyllactose at 1.85 Å Resolution," *Molecular Cell* 1(5):719-728.

McCafferty, J. et al. (Dec. 6, 1990). "Phage Antibodies: Filamentous Phage Displaying Antibody Variable Domains," *Nature* 348:552-554.

McEarchern, J.A. et al. (Feb. 1, 2007, e-pub. Oct. 12, 2006). "Engineered Anti-CD70 Antibody with Multiple Effector Functions Exhibits in Vitro and in Vivo Antitumor Activities," *Blood* 109(3):1185-1192.

McMillan, S.J. et al. (Aug. 11, 2008; e-published on Jan. 17, 2008). "CD33-related Sialic-Acid-Binding Immunoglobulin-Like Lectins in Health and Disease," *Carbohydrate Research* 343(12):2050-2056.

Milstein, C. et al. (Oct. 6, 1983). "Hybrid Hybridomas and their use in Immunohistochemistry," *Nature* 305:537-540.

Mizoguchi, A. (2012). "Animal Models of Inflammatory Bowel Disease," *Progress in Molecular Biology and Translational Science* 105:263-320, fifty eight pages.

Monsonego-Oran, E. et al. (Sep. 25, 2002; e-published on Aug. 28, 2002). "FGF Receptors Ubiquitylation: Dependence on Tyrosine Kinase Activity and Role in Downregulation," *FEBS Letters* 528(1-3):83-89.

Morimoto, K. et al. (1992). "Single-Step Purification of F(ab')2 Fragments of Mouse Monoclonal Antibodies (Immunoglobulins G1) by Hydrophobic Interaction High Performance Liquid Chromatography Using TSKgel Phenyl-5PW," *Journal of Biochemical and Biophysical Methods* 24:107-117.

Morrison, S.L. (Apr. 28, 1994). "Success in Specification," *Nature* 368:812-813.

Morrison, S.L. et al. (Nov. 1984). "Chimeric Human Antibody Molecules: Mouse Antigen-binding Domains with Human Constant Region Domains," *Proc. Nat'l Acad. Sci* 81:6851-6855.

Mortland, L. et al. (Feb. 26, 2013). "Clinical Significance of CD33 Nonsynonymous SingleNucleotide Polymorphisms in Pediatric Patients with Acute Myeloid Leukemia Treated with Gemtuzumab-Ozogamicin-Containing Chemotherapy," *Clin Cancer Res*, pp. 1-8.

Munson, P.J. et al. (1980). "Ligand: A Versatile Computerized Approach for Characterization of Ligand-binding Systems," *Analytical Biochemistry* 107:220-239.

Naito, K. et al. (2000). "Calicheamicin-Conjugated Humanized Anti-CD33 Monoclonal Antibody (gemtuzumab zogamicin, CMA-676) Shows Cytocidal effect on CD33-Positive Leukemia Cell Lines, But is Inactive on P-glycoprotein-Expressing sublines," *Leukemia* 14:1436-1443.

(56) References Cited

OTHER PUBLICATIONS

Naj, A.C. et al. (May 2011; e-published on Apr. 3, 2011). "Common Variants in MS4A4/MS4A6E, CD2uAP, CD33, and EPHA1 are Associated with Late-onset Alzheimer's Disease," *Nat Genet.* 43(5):436-441, seventeen pages.
Nakamura, K. et al. (2007)."Intracellular Sortilin Expression Pattern Regulates proNGF-Induced Naturally Occurring Cell Death during Development," *Cell Death and Differentiation* 14:1552-1554.
Neary, D. et al. (Dec. 1998). "Frontotemporal Lobar Degeneration: A Consensus on Clinical Diagnostic Criteria," *Neurology* 51:1546-1554.
Neuberger, M. (Jul. 1996). "Generating high-avidity human Mabs in mice," *Nature Biotechnology* 14:826, one page.
Neumann, M. et al. (Oct. 2007). "TDP-43 Proteinopathy in Frontotemporal Lobar Degeneration and Amyotrophic Lateral Sclerosis," *Arch Neurol.* 64(10):1388-1394.
Novack, D.V. et al. (2008). "The Osteoclast: Friend or Foe?," *Annu. Rev. Pathol. Mech. Dis.* 3:457-484.
Nykjaer, A. et al. (2005, e-pub. Jan. 26, 2005). "p75$^{NTR}$—Live or Let Die," *Current Opinion in Neurobiology* 15:49-57.
Nykjaer, A. et al. (Feb. 26, 2004). "Sortilin is Essential for proNGF Induced Neuronal Cell Death," *Nature* 427:843-848.
Oganesyan, V. et al. (2008). "Structural characterization of a Human Fc Fragment Engineered for Lack of Effector Functions," *Acta Crystallography* 64:700-704.
Ohgidani, M. et al. (May 14, 2014). "Direct induction of ramified microglia-like cells from human monocytes: Dynamic microglial dysfunction in Nasu-Hakola disease," *Scientific Reports* 4(Article No. 4957):1-7.
O'Reilly, M.K. et al. (May 2009; e-published on Apr. 7, 2009). "Siglecs as Targets for Therapy in Immune Cell Mediated Disease," *Trends Pharmacol. Sci.* 30(5):240-248, twenty three pages.
Otero, K. et al. (2012; e-published on Feb. 6, 2012). "TREM2 and β-Catenin Regulate Bone Homeostasis by Controlling the Rate of Osteoclastogenesis," *J Immunol* 188:2612-2621.
Park, M. et al. (Jan. 2015). "Triggering Receptor Expressed on Myeloid Cells 2 (TREM2) Promotes Adipogenesis and Diet-Induced Obesity," *Diabetes* 64:117-127.
Paul, S.P. et al. (Jul. 15, 2000). "Myeloid Specific Human CD33 is an Inhibitory Receptor With Differential ITIM Function in Recruiting the Phosphatases SHP-1 and SHP-2," *Blood* 96(2):483-490.
Peiper, S.C. et al. (Jul. 1988). "Molecular Cloning, Expression, and Chromosomal Localization of a Human Gene Encoding the CD33 Myeloid Differentiation Antigen," *Blood* 72(1):314-321.
Peng, Q. et al. (May 18, 2010). "TREM2- and DAP12-Dependent Activation of PI3K Requires DAP10 and is Inhibited by SHIP1," *Science Signaling* 3(122):ra38, pp. 1-15.
Pennesi, M.E. et al. (Aug. 2012). "Animal Models of Age Related Macular Degeneration," *Molecular Aspects of Medicine* 33(4):487-509, forty pages.
Pérez-Oliva, A. et al. (Jun. 1, 2011; e-published on Jan. 28, 2011). "Epitope Mapping, Expression and Post-Translational Modifications of Two Isoforms of CD33 (CD33M and CD33m) on Lymphoid and Myeloid Human Cells," *Glycobiology* 21(6):757-770.
Peters, S.J. et al. (Jul. 13, 2012). "Engineering an Improved IgG4 Molecule with Reduced Disulfide Bond Heterogeneity and Increased Fab Domain Thermal Stability," *The Journal of Biological Chemistry* 287(29):24525-24533.
Pillai, S. et al. (2012; Jan. 3, 2012). "Siglecs and Immune Regulation," *Annu. Rev. Immunol.* 30:357-392.
Plückthun, A. (Dec. 1992). "Mono- and Bivalent Antibody Fragments Produced in *Escherichia coli*: Engineering, Folding and Antigen Binding," *Immunological Reviews* 130:151-188.
Poduslo, J.F. et al. (Jun. 1994). "Macromolecular Permeability Across the Blood-Nerve and Blood-Brain Barriers," *Proc. Natl. Acad. Sci. USA* 91:5705-5709.
Pollenz, R.S. et al. (Dec. 1, 2006, e-pub. Aug. 25, 2006). "Ligand-Dependent and -Independent Degradation of the Human Aryl Hydrocarbon Receptor (hAHR) in Cell Culture Models," *Chemico-Biological Interactions* 164(1-2):49-59.

Presta, L.G. (1992). "Antibody Engineering," *Current Opinion in Structural Biology* 2:593-596.
Presta, L.G. et al. (Sep. 1, 1993). "Humanization of an Antibody Directed Against IgE," *The Journal of Immunology* 151(5):2623-2632.
Provenzano, M.J. (2008). "p75NTR and Sortilin Increase After Facial Nerve Injury," *Laryngoscope* 118:87-93.
Raj, T. et al. (May 15, 2014; e-published on Dec. 30, 2013). "CD33: Increased Inclusion of Exon 2 Implicates the Ig V-Set Domain in Alzheimer's Disease Susceptibility," *Human Molecular Genetics* 23(10):2729-2736.
Ratnavalli, E. et al. (Jun. 2002). "The Prevalence of Frontotemporal Dementia," *Neurology* 58(1 of 2):1615-1621.
Ravetch, J.V. et al. (1991). "Fc Receptors," *Annual Review Immunology* 9:457-492.
Reddy, M.P. et al. (2000). "Elimination of Fc Receptor-Dependent Effector Functions of a Modified IgG4 Monoclonal Antibody to Human CD4," *The Journal of Immunology* 164:1925-1933.
Ricart, A.D. (Oct. 15, 2011). "Antibody-Drug Conjugates of Calicheamicin Derivative: Gemtuzumab Ozogamicin and Inotuzumab Ozogamicin," *Clin Cancer Res* 17(20):6417-6427.
Riechmann, L. et al. (Mar. 24, 1988). "Reshaping Human Antibodies for Therapy," *Nature* 332:323-327.
Roberts, R.W. et al. (Nov. 1997). "RNA-Peptide Fusions for the In Vitro Selection of Peptides and Proteins," *Proc. Natl. Acad. Sci. USA* 94:12297-12302.
Rollins-Raval, M.A et al. (May 2012; e-published on Feb. 20, 2012). "The Value of Immunohistochemistry for CD14, CD123, CD33, Myeloperoxidase and CD68R in the Diagnosis of Acute and Chronic Myelomonocytic Leukaemias," *Histopathology* 60(6):933-942.
Rosok, M.J. et al. (Sep. 13, 1996). "Combinatorial Library Strategy for the Rapid Humanization of Anticarcinoma BR96 Fab," *The Journal of Biological Chemistry* 271(37):22611-22618.
Sazinsky, S.L. et al. (Dec. 23, 2008). "Aglycosylated Immunoglobulin G1 Variants Productively Engage Activating Fc Receptors," *PNAS* 105(51):20167-20172.
Schabbauer, G. et al. (Jul. 2010). "Myeloid PTEN Promotes Inflammation but Impairs Bactericidal Activities During Murine Pneumococcal Pneumonia," *The Journal of Immunology* 185(1):468-476.
Schaffitzel, C. et al. (1999). "Ribosome Display: An In Vitro Method for Selection and Evolution of Antibodies from Libraries," *Journal of Immunological Methods* 231:119-135.
Schier, R. et al. (1996). "Identification of Functional and Structural Amino-Acid Residues by Parsimonious Mutagenesis," *Gene* 169:147-155.
Schymick, J.C. et al. (2007). "Progranulin Mutations and Amyotrophic Lateral Sclerosis or Amyotrophic Lateral Sclerosis-Frontotemporal Dementia Phenotypes," *Journal of Neurology, Neurosurgery and Psychiatry* 78:754-756.
Seno, H. et al. (Jan. 6, 2009). "Efficient Colonic Mucosal Wound Repair Requires Trem2 Signaling," *PNAS* 106(1):256-261.
Shalaby, M.F. et al. (Jan. 1992). "Development of Humanized Bispecitic Antibodies Reactive with Cytotoxic Lymphocytes and Tumor Cells Overexpressing the HER2 Protooncogene," *The Journal of Experimental Medicine* 175:217-225.
Sharif, O. et al. (Jun. 12, 2014). "The Triggering Receptor Expressed on Myeloid Cells 2 Inhibits Complement Component 1 q Effector Mechanisms and Exerts Detrimental Effects during Pneumococcal Pneumonia," *PLoS Pathogen* 10(6):e1004167, sixteen pages.
Sheriff, S. et al. (Sep. 1996). "Redefining the Minimal Antigen-binding Fragment," *Nature Structural & Molecular Biology* 3(9):733-736.
Shields, R.L. et al. (Mar. 2, 2001). "High Resolution Mapping of the Binding Site on Human IgG1 for FcγRI, FcγRII, FcγRIII, and FcRn and Design of IgG1 Variants with Improved Binding to the FcγR," *The Journal of Biological Chemistry* 276(9):6591-6604.
Sidhu, S.S. et al. (Apr. 2004). "Phage-displayed Antibody Libraries of Synthetic Heavy Chain Complementarity Determining Regions," *Journal of Molecular Biology* 338(2):299-310.
Sieber, M.W. et al. (Jan. 3, 2013). "Attenuated Inflammatory Response in Triggering Receptor Expressed on Myeloid Cells 2 (TREM2) Knock-Out Mice following Stroke," *PLoS ONE* 8(1):e52982, ten pages.

(56) References Cited

OTHER PUBLICATIONS

Simmons, D. et al. (Oct. 15, 1988). "Isolation of a cDNA Encoding CD33, a Differentiation Antigen of Myeloid Progenitor Cells," *J Immunol.* 141(8):2797-2800.

Sims, M.J. et al. (Aug. 15, 1993). "A Humanized CD18 Antibody Can Block Function Without Cell Destruction," *The Journal of Immunology* 151(4):2296-2308.

Siolas, D. et al. (Sep. 2013). "Patient-Derived Tumor Xenografts: Transforming Clinical Samples into Mouse Models," *Cancer Research* 73(17):5315-5319.

Skerra, A. (1993). "Bacterial Expression of Immunoglobulin Fragments," *Current Opinion in Immunology* 5:256-262.

Sollid, L.M. et al. (Sep. 2008). "Animal Models of Inflammatory Bowel Disease at the Dawn of the New Genetics Era," *PLoS Med* 5(9):1338-1342(e198).

Strohl, W.R. (2009; e-published on Nov. 4, 2009). "Optimization of Fc-mediated Effector Functions of Monoclonal Antibodies," *Current Opinion in Biotechnology* 20:685-691.

Sun, M. et al. (May 2013). "TREM-2 Promotes Host Resistance Against *Pseudomonas aeruginosa* Infection by Suppressing Corneal Inflammation via a PI3K/Akt Signaling Pathway," *Investigative Ophthalmology & Visual Science* 54(5):3451-3462.

Suresh, M.R. et al. (1986). "Bispecific Monoclonal Antibodies from Hybrid Hybridomas," *Methods in Enzymology* 121:210-228.

Sutherland, M.K. et al. (Sep.-Oct. 2009; e-published Sep. 15, 2009). "Anti-Leukemic Activity of Lintuzumab (SGN-33) in Preclinical Models of Acute Myeloid Leukemia," *MABS* 1(5):481-490.

Takahashi, K. et al. (Apr. 10, 2007). "TREM2-Transduced Myeloid Precursors Mediate Nervous Tissue Debris Clearance and Facilitate Recovery in an Animal Model of Multiple Sclerosis," *Plos Med* 4(4):e124, pp. 0675-0689.

Takahashi, K. et al. (Feb. 21, 2005). "Clearance of apoptotic neurons without inflammation by microglial triggering receptor expressed on myeloid cells-2," *Journal of Experimental Medicine* 201(4):647-657.

Tanaka, Y. et al. (2013). "Exacerbated Inflammatory Responses Related to Activated Microglia After Traumatic Brain Injury in Progranulin-Deficient Mice," *Neuroscience* 231:49-60.

Tavaré, R. et al. (Jan. 21, 2014). "Engineered Antibody Fragments for Immuno-PET Imaging of Endogenous CD8+ T Cells in Vivo," *PNAS* 111(3):1108-1113.

Taylor, V.C. et al. (Apr. 23, 1999). "The Myeloid-specific Sialic Acid-binding Receptor, CD33, Associates with the Protein-tyrosine Phosphatases, SHP-1 and SHP-2," *Journal of Biological Chemistry* 274(17):11505-11512.

Teng, H.K. et al. (Jun. 1, 2005). "ProBDNF Induces Neuronal Apoptosis via Activation of a Receptor Complex of $p75^{NTR}$ and Sortilin," *The Journal of Neuroscience* 25(22):5455-5463.

Traunecker, A. et al. (1991). "Bispecific Single Chain Molecules (Janusins) Target Cytotoxic Lymphocytes on HIV Infected Cells," *The EMBO Journal* 10(12):3655-3659.

Tutt, A. et al. (Jul. 1, 1991). "Trispecific F(ab')3 Derivatives that Use Cooperative Signaling Via the TCR/CD3 Complex and CD2 to Activate and Redirect Resting Cytotoxic T Cells1," *The Journal of Immunology* 147(1):60-69.

Ulyanova, T. et al. (1999). "The Sialoadhesin CD33 is a Myeloid-Specific Inhibitory Receptor," *Eur J Immunol.* 29:3440-3449.

Urlaub, G. et al. (Jul. 1980). "Isolation of Chinese Hamster Cell Mutants Deficient in Dihydrofolate Reductase Activity," *Proc. Natl. Acad. Sci.* 77(7):4216-4220.

Vafa, O. et al. (2014; e-published on Jul. 17, 2013). "An Engineered Fc Variant of an IgG Eliminates All Immune Effector Functions via Structural Perturbations," *Methods* 65:114-126.

Van Dijk, M.A et al. (2001)."Human Antibodies as Next Generation Therapeutics," *Current Opinion in Chemical Biology* 5:368-374.

Varki, A. et al. (Jan. 1, 2006; e-published on Jul. 13, 2005). "Siglecs—The Major Subfamily of I-Type Lectins," *Glycobiology* 16(1):1R-27R.

Vaswani, S.K. et al. (Aug. 1998). "Humanized Antibodies as Potential Therapeutic Drugs," *Annals of Allergy, Asthma & Immunology* 81:105-119.

Verhoeyen, M. et al. (1988). "Reshaping Human Antibodies: Grafting an Antilysozyme Activity," *Science* 239:1534-1536.

Vetrano, S. et al. (2008). "Unique Role of Junctional Adhesion Molecule-A in Maintaining Mucosal Homeostasis in Inflammatory Bowel Disease," *Gastroenterology* 135(1):173-184.

Vitale, C. et al. (May 8, 2001). "Surface Expression and Function of P75/AIRM-1 or CD33 in Acute Myeloid Leukemias: Engagement of CD33 Induces Apoptosis of Leukemic Cells," *Proc Natl Acad Sci USA* 98(10):5764-5769.

Volosin, M. et al. (Jul. 19, 2006). "Interaction of Survival and Death Signaling in Basal Forebrain Neurons: Roles of Neurotrophins and Proneurotrophins," *The Journal of Neuroscience* 26(29):7756-7766.

Volosin, M. et al. (Sep. 24, 2008). "Induction of Proneurotrophins and Activation of P75ntr-Mediated Apoptosis via Neurotrophin Receptor-Interacting Factor in Hippocampal Neurons After Seizures," *The Journal of Neuroscience* 28(39):9870-9879, twenty five pages.

Von Gunten, S. et al. (Nov. 2008). "Basic and Clinical Immunology of Siglecs," *Ann. NY Acad. Sci.* 1143:61-82, twenty five pages.

Walker, D.G. et al. (Feb. 2015; e-published on Oct. 2, 2014). "Association of CD33 Polymorphism Rs3865444 With Alzheimer's Disease Pathology and CD33 Expression in Human Cerebral Cortex," *Neurobiology of Aging* 36(2):571-582, thirty two pages.

Wang, Y. et al. (Mar. 12, 2015; e-published on Feb. 26, 2015). "TREM2 Lipid Sensing Sustains the Microglial Response in an Alzheimer's Disease Model," *Cell* 160(6):1061-1071.

Waterhouse, P. et al. (1993). "Combinatorial Infection and In Vivo Recombination: A Strategy for Making Large Phage Antibody Repertoires," *Nucleic Acids Research* 21(9):2265-2266.

Wei, Y. et al. (2007). "Enhanced Protein Expressions of Sortilin and $p75^{NTR}$ in Retina of Rat Following Elevated Intraocular Pressure-Induced Retinal Ischemia," *Neuroscience Letters* 429(2-3):169-174.

White, A.L. et al. (Jan. 12, 2015). "Conformation of the Human Immunoglobulin G2 Hinge Imparts Superagonistic Properties to Immunostimulatory Anticancer Antibodies," *Cancer Cell* 27:138-148.

Wiehr, S. et al. (2014). "Pharmacokinetics and PET Imaging Properties of Two Recombinant Anti-PSMA Antibody Fragments in Comparison to their Parental Antibody," *The Prostate* 74(7):743-755.

Wilkinson, I.C. et al. (2013). "Monovalent IgG4 Molecules: Immunoglobulin Fc Mutations that Result in a Monomeric Structure," *mAbs* 5(3):406-417.

Wilson, N.S. et al. (Jan. 18, 2011). "An Fcγ Receptor-Dependent Mechanism Drives Antibody-Mediated Target-Receptor Signaling in Cancer Cells," *Cancer Cell* 19:101-113.

Xu, D. et al. (2000). "In Vitro Characterization of Five Humanized OKT3 Effector Function Variant Antibodies," *Cellular Immunology* 200(1):16-26.

Xu, J. et al. (Jul. 2000). "Diversity in the CDR3 Region of $V_H$ is Sufficient for Most Antibody Specificities," *Immunity* 13:37-45.

Xu, Y. et al. (2013). "Addressing Polyspecificity of Antibodies Selected from an in Vitro Yeast presentation system: a FACS-based, high-throughput selection and analytical tool," *Protein Engineering, Design & Selection* 26(10):663-670.

Yano, H. et al. (Nov. 25, 2009)."Proneurotrophin-3 is a Neuronal Apoptotic Ligand: Evidence for Retrograde-Directed Cell Killing," *The Journal of Neuroscience* 29(47):14790-14802.

Yelton, D.E. et al. (1995). "Affinity maturation of the BR96 anticarcinoma antibody by codon-based mutagenesis," *The Journal of Immunology* 155:1994-2004.

Yin, F. et al. (Dec. 21, 2009). "Exaggerated Inflammation, Impaired Host Defense, and Neuropathology in Progranulin-Deficient Mice," *J. Exp. Med.* 207(1):117-128.

Zapata, G. et al. (1995). "Engineering Linear F(ab')2 Fragments for Efficient Production in *Escherichia coli* and Enhanced Antiproliferative Activity," *Protein Engineering Designs and Selections* 8(10):1057-1062.

(56) References Cited

OTHER PUBLICATIONS

Zhou, Q. et al. (Mar. 1, 2014). "Humanized NOD-SCID IL2rg$^{-/-}$ Mice as a Preclinical Model for Cancer Research and its Potential Use for Individualized Cancer Therapies," *Cancer Letters* 344(1):13-19.
Zhu, Y. et al. (Sep. 15, 2014, e-pub. Jul. 31, 2014). "CSF1/CSF1 R Blockade Reprograms Tumor-Infiltrating Macrophages and Improves Response to T Cell Checkpoint Immunotherapy in Pancreatic Cancer Models," *Cancer Research* 74(18):5057-5069.
International Preliminary Report on Patentability dated Dec. 21, 2017 for International Application No. PCT/US2016/037108, filed on Jun. 11, 2016, eleven pages.
International Preliminary Report on Patentability dated Dec. 21, 2017 for International Application No. PCT/US2016/037109, filed on Jun. 11, 2016, fifteen pages.
International Search Report and Written Opinion dated Dec. 6, 2016 for International Application No. PCT/US2016/037108, filed on Jun. 11, 2016, sixteen pages.
International Search Report and Written Opinion dated Dec. 6, 2016 for PCT Application No. PCT/US2016/037109 filed on Jun. 11, 2016, twenty pages.
U.S. Appl. No. 15/735,946, filed Dec. 12, 2017 by Rosenthal et al. (not submitted herewith pursuant to the waiver of 37 C.F.R. § 1.98(a)(2)(iii) issued by the Office on Sep. 21, 2004).
U.S. Appl. No. 16/054,840, filed Aug. 3, 2018 by Culp et al. (not submitted herewith pursuant to the waiver of 37 C.F.R. § 1.98(a)(2)(iii) issued by the Office on Sep. 21, 2004).
International Search Report and Written Opinion dated Nov. 13, 2018 for PCT Application No. PCT/US2018/045056 filed on Aug. 2, 2018, sixteen pages.
Li, F. et al. "Inhibitory Fcγ Receptor Engagement Drives Adjuvant and Anti-Tumor Activities of Agonistic CD40 Antibodies," Science 333(6045):1030-1034 (Aug. 19, 2011), 13 pages.
Vasu, S. et al. (Jun. 9, 2016, e-pub. Mar. 24, 2016). "Decitabine Enhances Anti-CD33 Monoclonal Antibody BI 836858-Mediated Natural Killer ADCC Against AML Blasts," Blood 127(23):2879-2889.
Vincent, K.J. et al. (Dec. 2012, e-pub. Nov. 1, 2012). "Current Strategies in Antibody Engineering: Fc Engineering and pH-Dependent Antigen Binding, Bispecific Antibodies and Antibody Drug Conjugates," Biotechnol J. 7(12):1444-1450.
White A.L. et al. (Aug. 15, 2011, e-pub. Jul. 8, 2011). "Interaction with FcgammaRIIB is Critical for the Agonistic Activity of Anti-CD40 Monoclonal Antibody," J Immunol. 187(4):1754-1763.
International Search Report and Written Opinion dated Nov. 13, 2019 for PCT Application No. PCT/US2019/048994 filed on Aug. 30, 2019, 383 pages.
Applicant response to summons for European Patent Application No. 14773553.4 filed on Oct. 12, 2019, 10 pages.
Chan et al., (2010). "Therapeutic antibodies for autoimmunity and inflammation," Nat. Rev. Immunol., 10:301-316.
Declaration of Dr. Anna Griciuc submitted before the USPTO Patent Trial and Appeal Board for U.S. Appl. No. 15/906,681, filed Feb. 27, 2018, dated Aug. 15, 2019, 7 pages.
Estus et al., (2013). "Protective Allele of Cd33 Gwas Snp Decreases Inclusion of Exon Encoding Ligand Binding Domain; Are Cd33 Antagonists Ad Therapeutics?" 1 page. (Abstract Only).
Hudson et al. (2003). "Engineered Antibodies," Nat. Med. 9(1):129-134.
Imai et al., (2006). "Comparing antibody and small-molecule therapies for cancer," Nat. Rev. Cancer, 6:714-727.
Jiang et al., (2014). "CD33 in Alzheimer's Disease," Mol. Neurobiol., 49:529-535.
Karch et al., (2012). "Expression of Novel Alzheimer's Disease Risk Genes in Control and Alzheimer's Disease Brains," *PLOS ONE*, 7(11):1-9.
Keren-Shaul et al., (2017). "A Unique Microglia Type Associated with Restricting Development of Alzheimer's Disease," Cell, 169:1276-1290.
Lartigue, J.D. (2012). "Antibody-Drug Conjugates: Guided Missiles Deployed Against Cancerous Cells," OncologyLive, available online at <https://www.onclive.com/view/antibody-drug-conjugates-guided-missiles-deployed-against-cancerous-cells>, Obtained on Nov. 27, 2018, 4 pages.
Lonberg. (2008). "Fully Human Antibodies From Transgenic Mouse and Phage Display Platforms," Curr. Opin. Immunol. 20(4):450-459.
NCBI Blast RID-WN0V0GA1114, Seq ID No. 1 vs. murine CD33, submitted Apr. 12, 2020, 3 pages.
Vollmers et al. (2005). "Death by Stress: Natural IgM-Induced Apoptosis," Methods Find. Exp. Clin. Pharmacol. 27(3):185-191.
Vollmers et al. (2005). "The "Early Birds": Natural IgM Antibodies and Immune Surveillance," Histol. Histopathol. 20(3):927-937.
Winter et al. (1994). "Making Antibodies by Phage Display Technology," Annu. Rev. Immunol. 12:433-455.
Chinese Search Report dated Nov. 25, 2020 for Chinese Application No. 201680047246.1 filed on Jun. 11, 2016, 5 pages.
International Preliminary Report on Patentability dated Feb. 13, 2020 for International Application No. PCT/US2018/045056, filed on Aug. 2, 2018, 9 pages.
International Preliminary Report on Patentability dated Mar. 11, 2021 for International Application No. PCT/US2019/048994, filed on Aug. 30, 2019, 8 pages.
International Search Report and Written Opinion dated Apr. 15, 2021 for PCT Application No. PCT/US2020/064461 filed on Dec. 11, 2020, 14 pages.
Chen et al., (1999). "Selection and analysis of an optimized anti-VEGF antibody: crystal structure of an affinity-matured Fab in complex with antigen," J. Mol. Biol., 293:865-881.
Cheung, et al., (1990). "Epitope-specific antibody response to the surface antigen of duck hepatitis B virus in infected ducks," Virology, 176:546-552.
Kirkland et al., (1986). "Analysis of the fine specificity and cross-reactivity of monoclonal anti-lipid A antibodies," J. Immunol., 137:3614-3619.
Moldenhauer et al., (1990). "Identity of HML-1 antigen on intestinal intraepithelial T cells and of B-Iy7 antigen on hairy cell leukaemia," Scand. J. Immunol., 32:77-82.
Morel et al., (1988). "Monoclonal antibodies to bovine serum albumin: affinity and specificity determinations," Molec. Immunol., 25:7-15.

\* cited by examiner

```
HUMAN CD33        ---MPLLLLLPLLWAG-----------------ALAMDPNFWLQVQESVTVQEGLCVL
MOUSE CD33        ---MLWPLPLFLLCAG-----------------SLAQDLEFQLVAPESVTVEEGLCVH
RAT CD33          ---MLWIVLLLLLCTD-----------------SLVQDLEFQLVAPKSVTVEEALCVH
CHIMPANZEE CD33   ---MPLLLLLPLLWAG-----------------ALAMDPKIRLQVQESVTVQEGLCVL
RHESUS CD33       ----------------------------------------------------------
DOG CD33          ----MLLLLLPILWAVEWAQGKVKLGASADAGVPRSLAQDPIYWLQIQESLTVQEGLCIS
COW CD33          MLPLLLPLLLPLLWAA-----------------TLAQDPNYWLKAPWSVSVQEGLCVR
ZEBRAFISH CD33    ----MLQTLLFILAVNKMTN--------CEDS---QPGGLNDFFISVKENVTGEEGLCIR

HUMAN CD33        VPCTFFHPIPYYDKNSPVHGYWFREGAIISRDSPVATNKLDQEVQEETQGRFRLLGDPSR
MOUSE CD33        VPCSVFYPSI-KLTLGPVTGSWLRKGVSLHEDSPVATSDPRQLVQKATQGRFQLLGDPQK
RAT CD33          VPCSVSYPSI-RPTFGPVTGYWLLKGTSLHEDSPVATNDPRQLVQKATQGRFQLLGDPQK
CHIMPANZEE CD33   VPCTFFHPIPYYDKNSPVHGYWFREGPIVSGDSPVATNKPDQEVQEETQGRFRLLGDLSR
RHESUS CD33       ------------------------------------------------------------
DOG CD33          VPCYFSYPMEYWIKTYSALGYWFRNGTNVHWGAPVATNNPDRKVQEETQGQFFLLGDPQA
COW CD33          VPCSVYYPSDFRSGSTPVHGFWFREGAEVLKDAPVATNKLDREAQKETQGRFHLLGDPRD
ZEBRAFISH CD33    EQCAFRVPQN---LSEPIKKSWFKEDSENA------TAKVQF--------YHSKAESPIW

HUMAN CD33        NNCSLSIVDAR-RRDNGSYFFRMERGS-TKYSYKSPQLSVHVTDLTHRPKILIPGTLEPG
MOUSE CD33        HDCSLFIRDAQ-KNDTGMYFFRVVREPFVRYSYKKSQLSLHVTSLSRTPDIIIPGTLEAG
RAT CD33          HDCSLLIRDAQ-KNDTGVYFFRVVREPFVRYSYRANQLLLHVTPLSRTPDIIIPETLRAG
CHIMPANZEE CD33   NNCSLSIVDAR-RRDNGSYFFRMERGS-TKYSYKSPQLSVHVTDLTHRPKILIPGALDPG
RHESUS CD33       ----------------------------MPLLLLLPLLWADLTHRPQILIPGALDPD
DOG CD33          NNCSLEIRDAQ-RRDSGTYFFRVERGPYLKYSYLQNQLSVHVTALTHTPDILIPGTLESG
COW CD33          NNCSLEIRDAR-KSDRGSYFFRMEKGS-MKWSYLSELFFLNVTAFTHQPHLLSPGDLEPG
ZEBRAFISH CD33    KECSFMLNPLVLGESDGEYRLKLEWGQGN-VHIFPQTVKITVKELTQKPKINVPR-LTIG
                             . :         :::    *.:       *      *

HUMAN CD33        HSKNLTCSVSWACEQGTPPIFSWLSA--APTSLGPR-----TTHSSVLIITPRPQDHGTN
MOUSE CD33        YPSNLTCSVPWACEQGTPPTFSWMST--ALTSLSSR-----TTDSSVLTFTPQPQDHGTK
RAT CD33          HPSNLSCSVPWACEQGTPPTFSWMSD--ALTSLSSR-----TTNSSVLTLTPRPQDHGTK
CHIMPANZEE CD33   HSKNLTCSVSWACEQGTPPIFSWLSA--APTSLGPR-----TTHSSVLIITPRPQDHGTN
RHESUS CD33       HSKNLTCSVPWACEQGTPPIFSWMSA--APTSLGLR-----TTHSSVLIITPRPQDHGTN
DOG CD33          HPRNLTCSVPWACEQGIPPIFSWMSA--ALTSLGPR-----THLSSVLTLTPRPQDHGTN
COW CD33          HPGNMTCSVPWACERAMPPIFSWTSA--APSSLGPR-----TPFSSVLTLTPRPQDHGTR
ZEBRAFISH CD33    QKAEISCIFTIKCLVP-KLRFAWTGIEGKESTLGPRGVPGWNEFTSIFRFHPKPKDHNTK
                   :::*  .    *        *:* .    ::*. *      . :*:: : *:*:**  *.

HUMAN CD33        LTCQVKFAGAGVTTERTIQLNVTYVPQNPTTGIFPGDGSGK--QETRAGVVHGAIGGAGV
MOUSE CD33        LTCLVTFSGAGVTVERTIQLNVTRKSGQMR----------------ELVLVAVGEAT-
RAT CD33          LTCLVTFSGAGVTVERTIRLNVTWKSDQMR----------------QVVLVAVGEAA-
CHIMPANZEE CD33   LTCQVKFAGAGVTTERTIQLNVTYVPQNPTTGIFPGDGSGK--QETRAGVVHGAVGGAGI
RHESUS CD33       LTCQVKFPGAGVTTERTIQLNVSYASQNPRTDIFLGDGSGK--Q----GVVQGAIGGAGV
DOG CD33          LTCQVQFPAVGVMVERTIQLNVTCTTQNPTNGVCLEHSTGK--PGTRSGVTVGAIGGAGV
COW CD33          LTCQVKFPRSGVMVERTILLNVTYASRNPG-NICTGDGTGE--SGTGAGVTEGAIAGAGV
ZEBRAFISH CD33    LTCKIIVQD-RIQTEAAVTLEVRYAPEILNSSRCVMWGDELSCMCISSGVPLPLIQWPTL
                  *** :  .     :  .*  ::  *:*                              :      :
```

FIG. 2

```
HUMAN CD33        TALLALCLCLIFFIVKTHRRKAART---AVGRNDTHPTTGSASPKH-QKK---SKLHGP-
MOUSE CD33        VKLLILGLCLVFLIVMFCRRKTTKL---SVHMGCENPIKRQEAITSYNHC---LSPTASD
RAT CD33          VKLLILGLCLTLLSVVICRRKATKL---SVHMNCENPTQAHPQDSKVHSHAENSRPLRKD
CHIMPANZEE CD33   TALLALCLCLIFFIVKTHRRKAART---AVGRNDTHPTTGPASPKH-QKK---SKLHGP-
RHESUS CD33       TVLLALCLCLIFFTVKTHRRKAART---AVGRIDTHPATGPTSSKH-QKK---SKLHGA-
DOG CD33          TMLLTLCLCLIFFRVKTCRKTASRT---AVGMDNIHPVVEPAPLDY-QES---DLPDDP-
COW CD33          TMLLVLCFGLIFFVVKIYRKKVAKT---AVDMEDIYSAAEPASLDH-QQE---SKSEES-
ZEBRAFISH CD33    DDPTNYCSTYRKNTIIICNISISGIRNVKDTIECIAENVIATTSMQIQVHNQTETPKAN-
                                   :     . . :                                .

HUMAN CD33        TETSSCSGA---------APTVEMDEELH--YASLNFHGMN----P----------SKDT
MOUSE CD33        AVTPGCSIHRLISRTPRCTAILRIQDPYR--RTHLRNRAVS----T----------L---
RAT CD33          LPXEQSSIXTXI--------------PLN-------FMGAK----S----------Q---
CHIMPANZEE CD33   TETSSYSGA---------APTVEMDEELH--YASLNFHGMN----P----------SKDT
RHESUS CD33       TETSGCSGT---------TLTVEMDEELH--YASLNFHGMN----P----------SEDT
DOG CD33          ---TSSAEV---------PSTSEMEQELY--YASISFHRRT---------------EST
COW CD33          SDPTNYAGT---------TPSLELEQELH--YSSIIFRGEK----P----------QESP
ZEBRAFISH CD33    ---LGLSMS-----WIFCTLSVVLNIIFGSCTVVLCFNRRKNREKPKDVDHVYMTSLKRE
                           :                              .

HUMAN CD33        STEYSEVRTQ--------------------------------------------------
MOUSE CD33        --RFPWISWEGSLRSTQRSKCTKLCSPVKNLCPLWLPVDNSCIPLIPEWVMLLCVSLTLS
RAT CD33          --EYPEI-----------------------------------------------------
CHIMPANZEE CD33   STEYSEVRTQ--------------------------------------------------
RHESUS CD33       STEYSEVRTQ--------------------------------------------------
DOG CD33          CAEYSEIRTQ--------------------------------------------------
COW CD33          HSEYAEIRIK--------------------------------------------------
ZEBRAFISH CD33    ESVYETIKV---------------------------------------------------
                         :  :
```

| Mutation | Binding Reactivity (% WT) | | | | |
|---|---|---|---|---|---|
| | C-2E12 Fab pH9 | C-2F5 Fab | C-6A3 Fab | C-6C7 Fab | WMS3 MAb |
| D18A | 103.3 (3) | 79.5 (1) | 2.6 (5) | 96.1 (24) | 98.0 (6) |
| P19A | 95.8 (5) | 102.4 (52) | 46.9 (22) | 105.3 (3) | 116.1 (7) |
| N20A | 95.1 (14) | 111.4 (23) | 2.1 (1) | 115.0 (17) | 166.2 (88) |
| F21A | 70.1 (8) | 122.0 (37) | 1.5 (0) | 97.2 (32) | 137.1 (3) |
| F44A | 93.8 (19) | 102.1 (11) | 51.4 (3) | 112.3 (4) | 76.5 (12) |
| P46A | 78.2 (2) | 104.8 (8) | 19.9 (4) | 120.5 (17) | 152.2 (35) |
| Y49A | 23.6 (5) | 20.6 (2) | 113.3 (4) | 16.5 (24) | 1.7 (8) |
| Y50A | 45.4 (11) | 32.7 (0) | 105.7 (13) | 41.6 (29) | 75.1 (0) |
| K52A | 11.4 (4) | 8.9 (2) | 100.4 (24) | 33.6 (3) | 12.4 (6) |
| N53A | 79.5 (22) | 78.2 (44) | 136.8 (11) | 12.2 (3) | 164.5 (9) |

FIG. 6C

CD33 receptor expression

CD33 receptor expression

WT
PR/CR/Stable: 1/7, 14%

CD33 KO
PR/CR/Stable: 5/10, 50%

SEQUENCE LISTING

```
<160> NUMBER OF SEQ ID NOS: 251

<210> SEQ ID NO 1
<211> LENGTH: 364
<212> TYPE: PRT
<213> ORGANISM: Homo sapiens

<400> SEQUENCE: 1

Met Pro Leu Leu Leu Leu Leu Pro Leu Leu Trp Ala Gly Ala Leu Ala
1               5                   10                  15

Met Asp Pro Asn Phe Trp Leu Gln Val Gln Glu Ser Val Thr Val Gln
            20                  25                  30

Glu Gly Leu Cys Val Leu Val Pro Cys Thr Phe Phe His Pro Ile Pro
        35                  40                  45

Tyr Tyr Asp Lys Asn Ser Pro Val His Gly Tyr Trp Phe Arg Glu Gly
    50                  55                  60

Ala Ile Ile Ser Arg Asp Ser Pro Val Ala Thr Asn Lys Leu Asp Gln
65                  70                  75                  80

Glu Val Gln Glu Glu Thr Gln Gly Arg Phe Arg Leu Leu Gly Asp Pro
                85                  90                  95

Ser Arg Asn Asn Cys Ser Leu Ser Ile Val Asp Ala Arg Arg Arg Asp
            100                 105                 110

Asn Gly Ser Tyr Phe Phe Arg Met Glu Arg Gly Ser Thr Lys Tyr Ser
```

```
            115                 120                 125
Tyr Lys Ser Pro Gln Leu Ser Val His Val Thr Asp Leu Thr His Arg
        130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
        195                 200                 205

Asn Leu Thr Cys Gln Val Lys Phe Ala Gly Ala Gly Val Thr Thr Glu
210                 215                 220

Arg Thr Ile Gln Leu Asn Val Thr Tyr Val Pro Gln Asn Pro Thr Thr
225                 230                 235                 240

Gly Ile Phe Pro Gly Asp Gly Ser Gly Lys Gln Glu Thr Arg Ala Gly
                245                 250                 255

Val Val His Gly Ala Ile Gly Gly Ala Gly Val Thr Ala Leu Leu Ala
            260                 265                 270

Leu Cys Leu Cys Leu Ile Phe Phe Ile Val Lys Thr His Arg Arg Lys
        275                 280                 285

Ala Ala Arg Thr Ala Val Gly Arg Asn Asp Thr His Pro Thr Thr Gly
290                 295                 300

Ser Ala Ser Pro Lys His Gln Lys Lys Ser Lys Leu His Gly Pro Thr
305                 310                 315                 320

Glu Thr Ser Ser Cys Ser Gly Ala Ala Pro Thr Val Glu Met Asp Glu
                325                 330                 335

Glu Leu His Tyr Ala Ser Leu Asn Phe His Gly Met Asn Pro Ser Lys
            340                 345                 350

Asp Thr Ser Thr Glu Tyr Ser Glu Val Arg Thr Gln
        355                 360

<210> SEQ ID NO 2
<211> LENGTH: 403
<212> TYPE: PRT
<213> ORGANISM: Mus musculus

<400> SEQUENCE: 2

Met Leu Trp Pro Leu Pro Leu Phe Leu Leu Cys Ala Gly Ser Leu Ala
1               5                   10                  15

Gln Asp Leu Glu Phe Gln Leu Val Ala Pro Glu Ser Val Thr Val Glu
            20                  25                  30

Glu Gly Leu Cys Val His Val Pro Cys Ser Val Phe Tyr Pro Ser Ile
        35                  40                  45

Lys Leu Thr Leu Gly Pro Val Thr Gly Ser Trp Leu Arg Lys Gly Val
    50                  55                  60

Ser Leu His Glu Asp Ser Pro Val Ala Thr Ser Asp Pro Arg Gln Leu
65                  70                  75                  80

Val Gln Lys Ala Thr Gln Gly Arg Phe Gln Leu Leu Gly Asp Pro Gln
                85                  90                  95

Lys His Asp Cys Ser Leu Phe Ile Arg Asp Ala Gln Lys Asn Asp Thr
            100                 105                 110

Gly Met Tyr Phe Phe Arg Val Val Arg Glu Pro Phe Val Arg Tyr Ser
        115                 120                 125
```

-continued

Tyr Lys Lys Ser Gln Leu Ser Leu His Val Thr Ser Leu Ser Arg Thr
130                 135                 140

Pro Asp Ile Ile Ile Pro Gly Thr Leu Glu Ala Gly Tyr Pro Ser Asn
145                 150                 155                 160

Leu Thr Cys Ser Val Pro Trp Ala Cys Glu Gln Gly Thr Pro Pro Thr
                165                 170                 175

Phe Ser Trp Met Ser Thr Ala Leu Thr Ser Leu Ser Arg Thr Thr
                180                 185                 190

Asp Ser Ser Val Leu Thr Phe Thr Pro Gln Pro Gln Asp His Gly Thr
                195                 200                 205

Lys Leu Thr Cys Leu Val Thr Phe Ser Gly Ala Gly Val Thr Val Glu
210                 215                 220

Arg Thr Ile Gln Leu Asn Val Thr Arg Lys Ser Gly Gln Met Arg Glu
225                 230                 235                 240

Leu Val Leu Val Ala Val Gly Glu Ala Thr Val Lys Leu Leu Ile Leu
                245                 250                 255

Gly Leu Cys Leu Val Phe Leu Ile Val Met Phe Cys Arg Arg Lys Thr
                260                 265                 270

Thr Lys Leu Ser Val His Met Gly Cys Glu Asn Pro Ile Lys Arg Gln
                275                 280                 285

Glu Ala Ile Thr Ser Tyr Asn His Cys Leu Ser Pro Thr Ala Ser Asp
290                 295                 300

Ala Val Thr Pro Gly Cys Ser Ile His Arg Leu Ile Ser Arg Thr Pro
305                 310                 315                 320

Arg Cys Thr Ala Ile Leu Arg Ile Gln Asp Pro Tyr Arg Arg Thr His
                325                 330                 335

Leu Arg Asn Arg Ala Val Ser Thr Leu Arg Phe Pro Trp Ile Ser Trp
                340                 345                 350

Glu Gly Ser Leu Arg Ser Thr Gln Arg Ser Lys Cys Thr Lys Leu Cys
                355                 360                 365

Ser Pro Val Lys Asn Leu Cys Pro Leu Trp Leu Pro Val Asp Asn Ser
                370                 375                 380

Cys Ile Pro Leu Ile Pro Glu Trp Val Met Leu Leu Cys Val Ser Leu
385                 390                 395                 400

Thr Leu Ser

<210> SEQ ID NO 3
<211> LENGTH: 334
<212> TYPE: PRT
<213> ORGANISM: Rattus norvegicus
<220> FEATURE:
<221> NAME/KEY: VARIANT
<222> LOCATION: 310, 316, 318
<223> OTHER INFORMATION: Xaa = Any Amino Acid

<400> SEQUENCE: 3

Met Leu Trp Ile Val Leu Leu Leu Leu Cys Thr Asp Ser Leu Val
1               5                   10                  15

Gln Asp Leu Glu Phe Gln Leu Val Ala Pro Lys Ser Val Thr Val Glu
                20                  25                  30

Glu Ala Leu Cys Val His Val Pro Cys Ser Val Ser Tyr Pro Ser Ile
                35                  40                  45

Arg Pro Thr Phe Gly Pro Val Thr Gly Tyr Trp Leu Leu Lys Gly Thr
            50                  55                  60

Ser Leu His Glu Asp Ser Pro Val Ala Thr Asn Asp Pro Arg Gln Leu
65                  70                  75                  80

```
Val Gln Lys Ala Thr Gln Gly Arg Phe Gln Leu Leu Gly Asp Pro Gln
                85                  90                  95
Lys His Asp Cys Ser Leu Leu Ile Arg Asp Ala Gln Lys Asn Asp Thr
                100                 105                 110
Gly Val Tyr Phe Phe Arg Val Val Arg Glu Pro Phe Val Arg Tyr Ser
                115                 120                 125
Tyr Arg Ala Asn Gln Leu Leu Leu His Val Thr Pro Leu Ser Arg Thr
            130                 135                 140
Pro Asp Ile Ile Ile Pro Glu Thr Leu Arg Ala Gly His Pro Ser Asn
145                 150                 155                 160
Leu Ser Cys Ser Val Pro Trp Ala Cys Glu Gln Gly Thr Pro Pro Thr
                165                 170                 175
Phe Ser Trp Met Ser Asp Ala Leu Thr Ser Leu Ser Ser Arg Thr Thr
                180                 185                 190
Asn Ser Ser Val Leu Thr Leu Thr Pro Arg Pro Gln Asp His Gly Thr
                195                 200                 205
Lys Leu Thr Cys Leu Val Thr Phe Ser Gly Ala Gly Val Thr Val Glu
            210                 215                 220
Arg Thr Ile Arg Leu Asn Val Thr Trp Lys Ser Asp Gln Met Arg Gln
225                 230                 235                 240
Val Val Leu Val Ala Val Gly Glu Ala Ala Val Lys Leu Leu Ile Leu
                245                 250                 255
Gly Leu Cys Leu Thr Leu Leu Ser Val Val Ile Cys Arg Arg Lys Ala
                260                 265                 270
Thr Lys Leu Ser Val His Met Asn Cys Glu Asn Pro Thr Gln Ala His
            275                 280                 285
Pro Gln Asp Ser Lys Val His Ser His Ala Glu Asn Ser Arg Pro Leu
290                 295                 300
Arg Lys Asp Leu Pro Xaa Glu Gln Ser Ser Ile Xaa Thr Xaa Ile Pro
305                 310                 315                 320
Leu Asn Phe Met Gly Ala Lys Ser Gln Glu Tyr Pro Glu Ile
                325                 330

<210> SEQ ID NO 4
<211> LENGTH: 364
<212> TYPE: PRT
<213> ORGANISM: Pan troglodytes

<400> SEQUENCE: 4

Met Pro Leu Leu Leu Leu Leu Pro Leu Leu Trp Ala Gly Ala Leu Ala
1               5                   10                  15
Met Asp Pro Lys Ile Arg Leu Gln Val Gln Glu Ser Val Thr Val Gln
                20                  25                  30
Glu Gly Leu Cys Val Leu Val Pro Cys Thr Phe Phe His Pro Ile Pro
                35                  40                  45
Tyr Tyr Asp Lys Asn Ser Pro Val His Gly Tyr Trp Phe Arg Glu Gly
            50                  55                  60
Pro Ile Val Ser Gly Asp Ser Pro Val Ala Thr Asn Lys Pro Asp Gln
65                  70                  75                  80
Glu Val Gln Glu Glu Thr Gln Gly Arg Phe Arg Leu Leu Gly Asp Leu
                85                  90                  95
Ser Arg Asn Asn Cys Ser Leu Ser Ile Val Asp Ala Arg Arg Arg Asp
                100                 105                 110
Asn Gly Ser Tyr Phe Phe Arg Met Glu Arg Gly Ser Thr Lys Tyr Ser
```

```
            115                 120                 125
Tyr Lys Ser Pro Gln Leu Ser Val His Val Thr Asp Leu Thr His Arg
    130                 135                 140

Pro Lys Ile Leu Ile Pro Gly Ala Leu Asp Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
        195                 200                 205

Asn Leu Thr Cys Gln Val Lys Phe Ala Gly Ala Gly Val Thr Thr Glu
    210                 215                 220

Arg Thr Ile Gln Leu Asn Val Thr Tyr Val Pro Gln Asn Pro Thr Thr
225                 230                 235                 240

Gly Ile Phe Pro Gly Asp Gly Ser Gly Lys Gln Glu Thr Arg Ala Gly
                245                 250                 255

Val Val His Gly Ala Val Gly Gly Ala Gly Ile Thr Ala Leu Leu Ala
            260                 265                 270

Leu Cys Leu Cys Leu Ile Phe Phe Ile Val Lys Thr His Arg Arg Lys
        275                 280                 285

Ala Ala Arg Thr Ala Val Gly Arg Asn Asp Thr His Pro Thr Thr Gly
    290                 295                 300

Pro Ala Ser Pro Lys His Gln Lys Lys Ser Lys Leu His Gly Pro Thr
305                 310                 315                 320

Glu Thr Ser Ser Tyr Ser Gly Ala Ala Pro Thr Val Glu Met Asp Glu
                325                 330                 335

Glu Leu His Tyr Ala Ser Leu Asn Phe His Gly Met Asn Pro Ser Lys
            340                 345                 350

Asp Thr Ser Thr Glu Tyr Ser Glu Val Arg Thr Gln
        355                 360

<210> SEQ ID NO 5
<211> LENGTH: 232
<212> TYPE: PRT
<213> ORGANISM: Macaca mulatta

<400> SEQUENCE: 5

Met Pro Leu Leu Leu Leu Pro Leu Leu Trp Ala Asp Leu Thr His Arg
1               5                   10                  15

Pro Gln Ile Leu Ile Pro Gly Ala Leu Asp Pro Asp His Ser Lys Asn
            20                  25                  30

Leu Thr Cys Ser Val Pro Trp Ala Cys Glu Gln Gly Thr Pro Pro Ile
        35                  40                  45

Phe Ser Trp Met Ser Ala Ala Pro Thr Ser Leu Gly Leu Arg Thr Thr
    50                  55                  60

His Ser Ser Val Leu Ile Ile Thr Pro Arg Pro Gln Asp His Gly Thr
65                  70                  75                  80

Asn Leu Thr Cys Gln Val Lys Phe Pro Gly Ala Gly Val Thr Thr Glu
                85                  90                  95

Arg Thr Ile Gln Leu Asn Val Ser Tyr Ala Ser Gln Asn Pro Arg Thr
            100                 105                 110

Asp Ile Phe Leu Gly Asp Gly Ser Gly Lys Gln Gly Val Val Gln Gly
        115                 120                 125
```

```
Ala Ile Gly Gly Ala Gly Val Thr Val Leu Leu Ala Leu Cys Leu Cys
    130                 135                 140
Leu Ile Phe Phe Thr Val Lys Thr His Arg Arg Lys Ala Ala Arg Thr
145                 150                 155                 160
Ala Val Gly Arg Ile Asp Thr His Pro Ala Thr Gly Pro Thr Ser Ser
                165                 170                 175
Lys His Gln Lys Lys Ser Lys Leu His Gly Ala Thr Glu Thr Ser Gly
                180                 185                 190
Cys Ser Gly Thr Thr Leu Thr Val Glu Met Asp Glu Leu His Tyr
                195                 200                 205
Ala Ser Leu Asn Phe His Gly Met Asn Pro Ser Glu Asp Thr Ser Thr
    210                 215                 220
Glu Tyr Ser Glu Val Arg Thr Gln
225                 230
```

<210> SEQ ID NO 6
<211> LENGTH: 378
<212> TYPE: PRT
<213> ORGANISM: Canis familiaris

<400> SEQUENCE: 6

```
Met Leu Leu Leu Leu Pro Ile Leu Trp Ala Val Glu Trp Ala Gln
1               5                   10                  15
Gly Lys Val Lys Leu Gly Ala Ser Ala Asp Ala Gly Val Pro Arg Ser
                20                  25                  30
Leu Ala Gln Asp Pro Ile Tyr Trp Leu Gln Ile Gln Glu Ser Leu Thr
            35                  40                  45
Val Gln Glu Gly Leu Cys Ile Ser Val Pro Cys Tyr Phe Ser Tyr Pro
50                  55                  60
Met Glu Tyr Trp Ile Lys Thr Tyr Ser Ala Leu Gly Tyr Trp Phe Arg
65                  70                  75                  80
Asn Gly Thr Asn Val His Trp Gly Ala Pro Val Ala Thr Asn Asn Pro
                85                  90                  95
Asp Arg Lys Val Gln Glu Glu Thr Gln Gly Gln Phe Phe Leu Leu Gly
                100                 105                 110
Asp Pro Gln Ala Asn Asn Cys Ser Leu Glu Ile Arg Asp Ala Gln Arg
            115                 120                 125
Arg Asp Ser Gly Thr Tyr Phe Phe Arg Val Glu Arg Gly Pro Tyr Leu
    130                 135                 140
Lys Tyr Ser Tyr Leu Gln Asn Gln Leu Ser Val His Val Thr Ala Leu
145                 150                 155                 160
Thr His Thr Pro Asp Ile Leu Ile Pro Gly Thr Leu Glu Ser Gly His
                165                 170                 175
Pro Arg Asn Leu Thr Cys Ser Val Pro Trp Ala Cys Glu Gln Gly Ile
                180                 185                 190
Pro Pro Ile Phe Ser Trp Met Ser Ala Ala Leu Thr Ser Leu Gly Pro
            195                 200                 205
Arg Thr His Leu Ser Ser Val Leu Thr Leu Thr Pro Arg Pro Gln Asp
    210                 215                 220
His Gly Thr Asn Leu Thr Cys Gln Val Gln Phe Pro Ala Val Gly Val
225                 230                 235                 240
Met Val Glu Arg Thr Ile Gln Leu Asn Val Thr Cys Thr Thr Gln Asn
                245                 250                 255
Pro Thr Asn Gly Val Cys Leu Glu His Ser Thr Gly Lys Pro Gly Thr
                260                 265                 270
```

```
Arg Ser Gly Val Thr Val Gly Ala Ile Gly Ala Gly Val Thr Met
        275                 280                 285
Leu Leu Thr Leu Cys Leu Cys Leu Ile Phe Phe Arg Val Lys Thr Cys
    290                 295                 300
Arg Lys Thr Ala Ser Arg Thr Ala Val Gly Met Asp Asn Ile His Pro
305                 310                 315                 320
Val Val Glu Pro Ala Pro Leu Asp Tyr Gln Glu Ser Asp Leu Pro Asp
                325                 330                 335
Asp Pro Thr Ser Ser Ala Glu Val Pro Ser Thr Ser Glu Met Glu Gln
                340                 345                 350
Glu Leu Tyr Tyr Ala Ser Ile Ser Phe His Arg Arg Thr Glu Ser Thr
            355                 360                 365
Cys Ala Glu Tyr Ser Glu Ile Arg Thr Gln
            370                 375

<210> SEQ ID NO 7
<211> LENGTH: 366
<212> TYPE: PRT
<213> ORGANISM: Bos taurus

<400> SEQUENCE: 7

Met Leu Pro Leu Leu Pro Leu Leu Leu Pro Leu Leu Trp Ala Ala
1               5                   10                  15
Thr Leu Ala Gln Asp Pro Asn Tyr Trp Leu Lys Ala Pro Trp Ser Val
                20                  25                  30
Ser Val Gln Glu Gly Leu Cys Val Arg Val Pro Cys Ser Val Tyr Tyr
            35                  40                  45
Pro Ser Asp Phe Arg Ser Gly Ser Thr Pro Val His Gly Phe Trp Phe
    50                  55                  60
Arg Glu Gly Ala Glu Val Leu Lys Asp Ala Pro Val Ala Thr Asn Lys
65                  70                  75                  80
Leu Asp Arg Glu Ala Gln Lys Glu Thr Gln Gly Arg Phe His Leu Leu
                85                  90                  95
Gly Asp Pro Arg Asp Asn Asn Cys Ser Leu Glu Ile Arg Asp Ala Arg
            100                 105                 110
Lys Ser Asp Arg Gly Ser Tyr Phe Phe Arg Met Glu Lys Gly Ser Met
    115                 120                 125
Lys Trp Ser Tyr Leu Ser Glu Leu Phe Phe Leu Asn Val Thr Ala Phe
130                 135                 140
Thr His Gln Pro His Leu Leu Ser Pro Gly Asp Leu Glu Pro Gly His
145                 150                 155                 160
Pro Gly Asn Met Thr Cys Ser Val Pro Trp Ala Cys Glu Arg Ala Met
                165                 170                 175
Pro Pro Ile Phe Ser Trp Thr Ser Ala Ala Pro Ser Ser Leu Gly Pro
            180                 185                 190
Arg Thr Pro Phe Ser Ser Val Leu Thr Leu Thr Pro Arg Pro Gln Asp
    195                 200                 205
His Gly Thr Arg Leu Thr Cys Gln Val Lys Phe Pro Arg Ser Gly Val
    210                 215                 220
Met Val Glu Arg Thr Ile Leu Leu Asn Val Thr Tyr Ala Ser Arg Asn
225                 230                 235                 240
Pro Gly Asn Ile Cys Thr Gly Asp Gly Thr Gly Glu Ser Gly Thr Gly
                245                 250                 255
Ala Gly Val Thr Glu Gly Ala Ile Ala Gly Ala Gly Val Thr Met Leu
```

```
            260                 265                 270
Leu Val Leu Cys Phe Gly Leu Ile Phe Phe Val Lys Ile Tyr Arg
            275                 280                 285

Lys Lys Val Ala Lys Thr Ala Val Asp Met Glu Asp Ile Tyr Ser Ala
            290                 295                 300

Ala Glu Pro Ala Ser Leu Asp His Gln Gln Glu Ser Lys Ser Glu Glu
305                 310                 315                 320

Ser Ser Asp Pro Thr Asn Tyr Ala Gly Thr Thr Pro Ser Leu Glu Leu
                325                 330                 335

Glu Gln Glu Leu His Tyr Ser Ser Ile Ile Phe Arg Gly Glu Lys Pro
            340                 345                 350

Gln Glu Ser Pro His Ser Glu Tyr Ala Glu Ile Arg Ile Lys
            355                 360                 365

<210> SEQ ID NO 8
<211> LENGTH: 384
<212> TYPE: PRT
<213> ORGANISM: Danio rerio

<400> SEQUENCE: 8

Met Leu Gln Thr Leu Leu Phe Ile Leu Ala Val Asn Lys Met Thr Asn
1               5                   10                  15

Cys Glu Asp Ser Gln Pro Gly Gly Leu Asn Asp Phe Phe Ile Ser Val
                20                  25                  30

Lys Glu Asn Val Thr Gly Glu Gly Leu Cys Ile Arg Glu Gln Cys
            35                  40                  45

Ala Phe Arg Val Pro Gln Asn Leu Ser Glu Pro Ile Lys Lys Ser Trp
50                  55                  60

Phe Lys Glu Asp Ser Glu Asn Ala Thr Ala Lys Val Gln Phe Tyr His
65                  70                  75                  80

Ser Lys Ala Glu Ser Pro Ile Trp Lys Glu Cys Ser Phe Met Leu Asn
                85                  90                  95

Pro Leu Val Leu Gly Glu Ser Asp Gly Glu Tyr Arg Leu Lys Leu Glu
            100                 105                 110

Trp Gly Gln Gly Asn Val His Ile Phe Pro Gln Thr Val Lys Ile Thr
            115                 120                 125

Val Lys Glu Leu Thr Gln Lys Pro Lys Ile Asn Val Pro Arg Leu Thr
130                 135                 140

Ile Gly Gln Lys Ala Glu Ile Ser Cys Ile Phe Thr Ile Lys Cys Leu
145                 150                 155                 160

Val Pro Lys Leu Arg Phe Ala Trp Thr Gly Ile Glu Gly Lys Glu Ser
                165                 170                 175

Thr Leu Gly Pro Arg Gly Val Pro Gly Trp Asn Glu Phe Thr Ser Ile
            180                 185                 190

Phe Arg Phe His Pro Lys Pro Lys Asp His Asn Thr Lys Leu Thr Cys
            195                 200                 205

Lys Ile Ile Val Gln Asp Arg Ile Gln Thr Glu Ala Ala Val Thr Leu
            210                 215                 220

Glu Val Arg Tyr Ala Pro Glu Ile Leu Asn Ser Ser Arg Cys Val Met
225                 230                 235                 240

Trp Gly Asp Glu Leu Ser Cys Met Cys Ile Ser Ser Gly Val Pro Leu
                245                 250                 255

Pro Leu Ile Gln Trp Pro Thr Leu Asp Asp Pro Thr Asn Tyr Cys Ser
            260                 265                 270
```

Thr Tyr Arg Lys Asn Thr Ile Ile Ile Cys Asn Ile Ser Ile Ser Gly
            275                 280                 285

Ile Arg Asn Val Lys Asp Thr Ile Glu Cys Ile Ala Glu Asn Val Ile
        290                 295                 300

Ala Thr Thr Ser Met Gln Ile Gln Val His Asn Gln Thr Glu Thr Pro
305                 310                 315                 320

Lys Ala Asn Leu Gly Leu Ser Met Ser Trp Ile Phe Cys Thr Leu Ser
                325                 330                 335

Val Val Leu Asn Ile Ile Phe Gly Ser Cys Thr Val Val Leu Cys Phe
            340                 345                 350

Asn Arg Arg Lys Asn Arg Glu Lys Pro Lys Asp Val Asp His Val Tyr
        355                 360                 365

Met Thr Ser Leu Lys Arg Glu Glu Ser Val Tyr Glu Thr Ile Lys Val
    370                 375                 380

<210> SEQ ID NO 9
<211> LENGTH: 11
<212> TYPE: PRT
<213> ORGANISM: Artificial Sequence
<220> FEATURE:
<223> OTHER INFORMATION: Synthetic construct

<400> SEQUENCE: 9

Lys Ala Ser Gln Asp Ile Asn Lys Tyr Leu Ser
1               5                   10

<210> SEQ ID NO 10
<211> LENGTH: 15
<212> TYPE: PRT
<213> ORGANISM: Artificial Sequence
<220> FEATURE:
<223> OTHER INFORMATION: Synthetic construct

<400> SEQUENCE: 10

Arg Ala Ser Gln Ser Val Ser Thr Ser Thr Tyr Ser Tyr Met His
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Synthetic construct

<400> SEQUENCE: 11

Arg Ala Ser Lys Ser Val Ser Thr Ser Gly His Ser Tyr Met His
1               5                   10                  15

<210> SEQ ID NO 12
<211> LENGTH: 7
<212> TYPE: PRT
<213> ORGANISM: Artificial Sequence
<220> FEATURE:
<223> OTHER INFORMATION: Synthetic construct

<400> SEQUENCE: 12

Arg Ala Asn Arg Leu Val Asp
1               5

<210> SEQ ID NO 13
<211> LENGTH: 7
<212> TYPE: PRT
<213> ORGANISM: Artificial Sequence
<220> FEATURE:

```
<223> OTHER INFORMATION: Synthetic construct

<400> SEQUENCE: 13

Tyr Ala Ser Asn Leu Glu Ser
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic construct

<400> SEQUENCE: 14

Leu Ala Ser Ser Leu Glu Ser
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic construct

<400> SEQUENCE: 15

Leu Gln Tyr Asp Glu Phe Pro Leu Thr
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic construct

<400> SEQUENCE: 16

Gln Arg Ser Trp Glu Ile Pro Leu Thr
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic construct

<400> SEQUENCE: 17

Gln His Ser Arg Glu Leu Pro Leu Thr
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic construct

<400> SEQUENCE: 18

Tyr Thr Phe Thr Ser Tyr Asp Ile Asn
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic construct
```

```
<400> SEQUENCE: 19

Tyr Thr Phe Thr Asp Tyr Asn Leu His
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic construct

<400> SEQUENCE: 20

Tyr Ser Phe Thr Gly Tyr Tyr Met His
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic construct

<400> SEQUENCE: 21

Phe Thr Phe Ser Asn Tyr Cys Met Asn
1               5

<210> SEQ ID NO 22
<211> LENGTH: 14
<212> TYPE: PRT
<213> ORGANISM: Artificial Sequence
<220> FEATURE:
<223> OTHER INFORMATION: Synthetic construct

<400> SEQUENCE: 22

Ile Gly Trp Ile Phe Pro Gly Asp Gly Ser Thr Lys Tyr Asn
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Synthetic construct

<400> SEQUENCE: 23

Ile Gly Phe Ile Tyr Pro Ser Asn Gly Ile Thr Gly Tyr Asn
1               5                   10

<210> SEQ ID NO 24
<211> LENGTH: 14
<212> TYPE: PRT
<213> ORGANISM: Artificial Sequence
<220> FEATURE:
<223> OTHER INFORMATION: Synthetic construct

<400> SEQUENCE: 24

Ile Gly Glu Ile Asn Pro Ser Thr Gly Gly Thr Ser Tyr Asn
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Synthetic construct
```

```
<400> SEQUENCE: 25

Val Ala Glu Ile Arg Leu Lys Ser Asn Asn Tyr Val Thr
1               5                  10

<210> SEQ ID NO 26
<211> LENGTH: 10
<212> TYPE: PRT
<213> ORGANISM: Artificial Sequence
<220> FEATURE:
<223> OTHER INFORMATION: Synthetic construct

<400> SEQUENCE: 26

Ala Arg Gly Tyr His Tyr Ala Met Asp Ser
1               5                  10

<210> SEQ ID NO 27
<211> LENGTH: 10
<212> TYPE: PRT
<213> ORGANISM: Artificial Sequence
<220> FEATURE:
<223> OTHER INFORMATION: Synthetic construct

<400> SEQUENCE: 27

Ala Arg Ser Thr Val Asp Tyr Phe Asp Tyr
1               5                  10

<210> SEQ ID NO 28
<211> LENGTH: 13
<212> TYPE: PRT
<213> ORGANISM: Artificial Sequence
<220> FEATURE:
<223> OTHER INFORMATION: Synthetic construct

<400> SEQUENCE: 28

Thr Arg Gly His Tyr Gly Ser Tyr Leu Thr Phe Asp Tyr
1               5                  10

<210> SEQ ID NO 29
<211> LENGTH: 11
<212> TYPE: PRT
<213> ORGANISM: Artificial Sequence
<220> FEATURE:
<223> OTHER INFORMATION: Synthetic construct

<400> SEQUENCE: 29

Thr Arg Asp Gly Tyr Tyr Val Pro Phe Ala Tyr
1               5                  10

<210> SEQ ID NO 30
<211> LENGTH: 108
<212> TYPE: PRT
<213> ORGANISM: Mus musculus

<400> SEQUENCE: 30

Cys Asp Ile Lys Met Thr Gln Ser Pro Ser Met Tyr Glu Ser Leu
1               5                  10                  15

Gly Glu Arg Val Thr Ile Thr Cys Lys Ala Ser Gln Asp Ile Asn Lys
                20                  25                  30

Tyr Leu Ser Trp Leu Gln Gln Lys Pro Gly Lys Ser Pro Lys Thr Leu
            35                  40                  45

Ile Tyr Arg Ala Asn Arg Leu Val Asp Gly Val Pro Ser Arg Phe Ser
        50                  55                  60

Gly Ser Gly Ser Gly Gln Asp Tyr Ser Leu Thr Ile Ser Ser Leu Glu
65                  70                  75                  80
```

Tyr Glu Asp Met Gly Ile Tyr His Cys Leu Gln Tyr Asp Glu Phe Pro
                85                  90                  95

Leu Thr Phe Gly Ala Gly Thr Lys Leu Glu Leu Lys
            100                 105

<210> SEQ ID NO 31
<211> LENGTH: 107
<212> TYPE: PRT
<213> ORGANISM: Artificial Sequence
<220> FEATURE:
<223> OTHER INFORMATION: Synthetic construct

<400> SEQUENCE: 31

Asp Ile Gln Met Thr Gln Ser Pro Ser Thr Leu Ser Ala Ser Val Gly
1               5                   10                  15

Asp Arg Val Thr Ile Thr Cys Lys Ala Ser Gln Asp Ile Asn Lys Tyr
            20                  25                  30

Leu Ser Trp Tyr Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Leu Gln Tyr Asp Glu Phe Pro Leu
                85                  90                  95

Thr Phe Gly Gln Gly Thr Lys Val Glu Ile Lys
            100                 105

<210> SEQ ID NO 32
<211> LENGTH: 107
<212> TYPE: PRT
<213> ORGANISM: Artificial Sequence
<220> FEATURE:
<223> OTHER INFORMATION: Synthetic construct

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Lys Tyr
            20                  25                  30

Leu Ser Trp Tyr Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Tyr Asp Glu Phe Pro Leu
                85                  90                  95

Thr Phe Gly Gln Gly Thr Lys Val Glu Ile Lys
            100                 105

<210> SEQ ID NO 33
<211> LENGTH: 107
<212> TYPE: PRT
<213> ORGANISM: Artificial Sequence
<220> FEATURE:
<223> OTHER INFORMATION: Synthetic construct

<400> SEQUENCE: 33

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Lys Tyr
            20                  25                  30

Leu Ser Trp Tyr Gln Gln Lys Pro Gly Lys Ala Pro Lys Leu Leu Ile
            35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Leu
                85                  90                  95

Thr Phe Gly Gln Gly Thr Lys Val Glu Ile Lys
            100                 105
```

<210> SEQ ID NO 34
<211> LENGTH: 107
<212> TYPE: PRT
<213> ORGANISM: Artificial Sequence
<220> FEATURE:
<223> OTHER INFORMATION: Synthetic construct

<400> SEQUENCE: 34

```
Glu Ile Val Leu Thr Gln Ser Pro Ala Thr Leu Ser Leu Ser Pro Gly
1               5                   10                  15

Glu Arg Ala Thr Leu Ser Cys Lys Ala Ser Gln Asp Ile Asn Lys Tyr
            20                  25                  30

Leu Ser Trp Tyr Gln Gln Lys Pro Gly Gln Ala Pro Arg Leu Leu Ile
            35                  40                  45

Tyr Arg Ala Asn Arg Leu Val Asp Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Leu Gln Tyr Asp Glu Phe Pro Leu
                85                  90                  95

Thr Phe Gly Gln Gly Thr Lys Val Glu Ile Lys
            100                 105
```

<210> SEQ ID NO 35
<211> LENGTH: 114
<212> TYPE: PRT
<213> ORGANISM: Mus musculus

<400> SEQUENCE: 35

```
Ser Thr Gly Asp Ile Val Leu Thr Gln Ser Pro Ala Ser Leu Ala Val
1               5                   10                  15

Ser Leu Gly Gln Arg Ala Thr Met Ser Cys Arg Ala Ser Gln Ser Val
            20                  25                  30

Ser Thr Ser Thr Tyr Ser Tyr Met His Trp Tyr Gln Gln Lys Pro Gly
            35                  40                  45

Gln Pro Pro Lys Leu Leu Ile Lys Tyr Ala Ser Asn Leu Glu Ser Gly
    50                  55                  60

Val Pro Ala Arg Phe Ser Gly Ser Gly Ser Gly Thr Asp Phe Thr Leu
65                  70                  75                  80

Asn Ile His Pro Val Glu Glu Glu Asp Thr Ala Thr Tyr Tyr Cys Gln
                85                  90                  95

Arg Ser Trp Glu Ile Pro Leu Thr Phe Gly Ala Gly Thr Lys Leu Glu
```

Leu Lys

<210> SEQ ID NO 36
<211> LENGTH: 111
<212> TYPE: PRT
<213> ORGANISM: Artificial Sequence
<220> FEATURE:
<223> OTHER INFORMATION: Synthetic construct

<400> SEQUENCE: 36

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Val Ser Thr Ser
            20                  25                  30

Thr Tyr Ser Tyr Met His Trp Tyr Gln Gln Lys Pro Gly Lys Ala Pro
        35                  40                  45

Lys Leu Leu Ile Tyr Tyr Ala Ser Asn Leu Glu Ser Gly Val Pro Ser
    50                  55                  60

Arg Phe Ser Gly Ser Gly Ser Gly Thr Glu Phe Thr Leu Thr Ile Ser
65                  70                  75                  80

Ser Leu Gln Pro Asp Asp Phe Ala Thr Tyr Tyr Cys Gln Arg Ser Trp
                85                  90                  95

Glu Ile Pro Leu Thr Phe Gly Gln Gly Thr Lys Val Glu Ile Lys
            100                 105                 110

<210> SEQ ID NO 37
<211> LENGTH: 111
<212> TYPE: PRT
<213> ORGANISM: Artificial Sequence
<220> FEATURE:
<223> OTHER INFORMATION: Synthetic construct

<400> SEQUENCE: 37

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Ser Val Ser Thr Ser
            20                  25                  30

Thr Tyr Ser Tyr Met His Trp Tyr Gln Gln Lys Pro Gly Lys Ala Pro
        35                  40                  45

Lys Leu Leu Ile Tyr Tyr Ala Ser Asn Leu Glu Ser Gly Val Pro Ser
    50                  55                  60

Arg Phe Ser Gly Ser Gly Ser Gly Thr Glu Phe Thr Leu Thr Ile Ser
65                  70                  75                  80

Ser Leu Gln Pro Glu Asp Phe Ala Thr Tyr Tyr Cys Gln Arg Ser Trp
                85                  90                  95

Glu Ile Pro Leu Thr Phe Gly Gln Gly Thr Lys Val Glu Ile Lys
            100                 105                 110

<210> SEQ ID NO 38
<211> LENGTH: 111
<212> TYPE: PRT
<213> ORGANISM: Artificial Sequence
<220> FEATURE:
<223> OTHER INFORMATION: Synthetic construct

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Thr Ser
            20                  25                  30

Thr Tyr Ser Tyr Met His Trp Tyr Gln Gln Lys Pro Gly Lys Ala Pro
        35                  40                  45

Lys Leu Leu Ile Tyr Tyr Ala Ser Asn Leu Glu Ser Gly Val Pro Ser
 50                  55                  60

Arg Phe Ser Gly Ser Gly Ser Gly Thr Asp Phe Thr Phe Thr Ile Ser
 65                  70                  75                  80

Ser Leu Gln Pro Glu Asp Ile Ala Thr Tyr Tyr Cys Gln Arg Ser Trp
                85                  90                  95

Glu Ile Pro Leu Thr Phe Gly Gln Gly Thr Lys Val Glu Ile Lys
            100                 105                 110

<210> SEQ ID NO 39
<211> LENGTH: 111
<212> TYPE: PRT
<213> ORGANISM: Artificial Sequence
<220> FEATURE:
<223> OTHER INFORMATION: Synthetic construct

<400> SEQUENCE: 39

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Val Ser Thr Ser
            20                  25                  30

Thr Tyr Ser Tyr Met His Trp Tyr Gln Gln Lys Pro Gly Lys Ala Pro
        35                  40                  45

Lys Leu Leu Ile Tyr Tyr Ala Ser Asn Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Arg Ser Trp
                85                  90                  95

Glu Ile Pro Leu Thr Phe Gly Gln Gly Thr Lys Val Glu Ile Lys
            100                 105                 110

<210> SEQ ID NO 40
<211> LENGTH: 111
<212> TYPE: PRT
<213> ORGANISM: Artificial Sequence
<220> FEATURE:
<223> OTHER INFORMATION: Synthetic construct

<400> SEQUENCE: 40

Asp Ile Val Met Thr Gln Ser Pro Leu Ser Leu Pro Val Thr Pro Gly
 1               5                  10                  15

Glu Pro Ala Ser Ile Ser Cys Arg Ala Ser Gln Ser Val Ser Thr Ser
            20                  25                  30

Thr Tyr Ser Tyr Met His Trp Tyr Leu Gln Lys Pro Gly Gln Ser Pro
        35                  40                  45

Gln Leu Leu Ile Tyr Tyr Ala Ser Asn Leu Glu Ser Gly Val Pro Asp
 50                  55                  60

Arg Phe Ser Gly Ser Gly Ser Gly Thr Asp Phe Thr Leu Lys Ile Ser
 65                  70                  75                  80

Arg Val Glu Ala Glu Asp Val Gly Val Tyr Tyr Cys Gln Arg Ser Trp
                85                  90                  95

Glu Ile Pro Leu Thr Phe Gly Gln Gly Thr Lys Val Glu Ile Lys
            100                 105                 110

<210> SEQ ID NO 41
<211> LENGTH: 111
<212> TYPE: PRT
<213> ORGANISM: Artificial Sequence
<220> FEATURE:
<223> OTHER INFORMATION: Synthetic construct

<400> SEQUENCE: 41

```
Asp Val Val Met Thr Gln Ser Pro Leu Ser Leu Pro Val Thr Leu Gly
1               5                   10                  15

Gln Pro Ala Ser Ile Ser Cys Arg Ala Ser Gln Ser Val Ser Thr Ser
            20                  25                  30

Thr Tyr Ser Tyr Met His Trp Phe Gln Gln Arg Pro Gly Gln Ser Pro
        35                  40                  45

Arg Arg Leu Ile Tyr Tyr Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Arg Ser Trp
                85                  90                  95

Glu Ile Pro Leu Thr Phe Gly Gln Gly Thr Lys Val Glu Ile Lys
            100                 105                 110
```

<210> SEQ ID NO 42
<211> LENGTH: 111
<212> TYPE: PRT
<213> ORGANISM: Artificial Sequence
<220> FEATURE:
<223> OTHER INFORMATION: Synthetic construct

<400> SEQUENCE: 42

```
Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Ser Thr Ser
            20                  25                  30

Thr Tyr Ser Tyr Met His Trp Tyr Gln Gln Lys Pro Gly Gln Pro Pro
        35                  40                  45

Lys Leu Leu Ile Tyr Tyr Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Arg Ser Trp
                85                  90                  95

Glu Ile Pro Leu Thr Phe Gly Gln Gly Thr Lys Val Glu Ile Lys
            100                 105                 110
```

<210> SEQ ID NO 43
<211> LENGTH: 114
<212> TYPE: PRT
<213> ORGANISM: Mus musculus

<400> SEQUENCE: 43

```
Ser Thr Gly Asp Ile Val Leu Thr Gln Ser Pro Ala Ser Leu Ala Val
1               5                   10                  15

Ser Leu Gly Gln Arg Ala Thr Ile Ser Cys Arg Ala Ser Lys Ser Val
            20                  25                  30

Ser Thr Ser Gly His Ser Tyr Met His Trp Tyr Gln Gln Lys Pro Gly
        35                  40                  45
```

Gln Pro Pro Lys Leu Leu Ile Tyr Leu Ala Ser Ser Leu Glu Ser Gly
            50                  55                  60

Val Pro Ala Arg Phe Ser Gly Ser Gly Ser Gly Thr Asp Phe Thr Leu
 65                  70                  75                  80

Asn Ile His Pro Val Glu Glu Asp Ala Ala Thr Tyr Tyr Cys Gln
                 85                  90                  95

His Ser Arg Glu Leu Pro Leu Thr Phe Gly Ala Gly Thr Lys Leu Glu
            100                 105                 110

Leu Lys

<210> SEQ ID NO 44
<211> LENGTH: 111
<212> TYPE: PRT
<213> ORGANISM: Artificial Sequence
<220> FEATURE:
<223> OTHER INFORMATION: Synthetic construct

<400> SEQUENCE: 44

Asp Ile Gln Met Thr Gln Ser Pro Ser Thr Leu Ser Ala Ser Val Gly
 1               5                  10                  15

Asp Arg Val Thr Ile Thr Cys Arg Ala Ser Lys Ser Val Ser Thr Ser
            20                  25                  30

Gly His Ser Tyr Met His Trp Tyr Gln Gln Lys Pro Gly Lys Ala Pro
         35                  40                  45

Lys Leu Leu Ile Tyr Leu Ala Ser Ser Leu Glu Ser Gly Val Pro Ser
     50                  55                  60

Arg Phe Ser Gly Ser Gly Ser Gly Thr Glu Phe Thr Leu Thr Ile Ser
 65                  70                  75                  80

Ser Leu Gln Pro Asp Asp Phe Ala Thr Tyr Tyr Cys Gln His Ser Arg
                 85                  90                  95

Glu Leu Pro Leu Thr Phe Gly Gln Gly Thr Lys Val Glu Ile Lys
            100                 105                 110

<210> SEQ ID NO 45
<211> LENGTH: 111
<212> TYPE: PRT
<213> ORGANISM: Artificial Sequence
<220> FEATURE:
<223> OTHER INFORMATION: Synthetic construct

<400> SEQUENCE: 45

Asp Ile Gln Met Thr Gln Ser Pro Ser Ser Leu Ser Ala Ser Val Gly
 1               5                  10                  15

Asp Arg Val Thr Ile Thr Cys Arg Ala Ser Lys Ser Val Ser Thr Ser
            20                  25                  30

Gly His Ser Tyr Met His Trp Tyr Gln Gln Lys Pro Gly Lys Ala Pro
         35                  40                  45

Lys Leu Leu Ile Tyr Leu Ala Ser Ser Leu Glu Ser Gly Val Pro Ser
     50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln His Ser Arg
                 85                  90                  95

Glu Leu Pro Leu Thr Phe Gly Gln Gly Thr Lys Val Glu Ile Lys
            100                 105                 110

<210> SEQ ID NO 46

```
<211> LENGTH: 111
<212> TYPE: PRT
<213> ORGANISM: Artificial Sequence
<220> FEATURE:
<223> OTHER INFORMATION: Synthetic construct

<400> SEQUENCE: 46

Asp Ile Val Met Thr Gln Ser Pro Leu Ser Leu Pro Val Thr Pro Gly
1               5                   10                  15

Glu Pro Ala Ser Ile Ser Cys Arg Ala Ser Lys Ser Val Ser Thr Ser
            20                  25                  30

Gly His Ser Tyr Met His Trp Tyr Leu Gln Lys Pro Gly Gln Ser Pro
        35                  40                  45

Gln Leu Leu Ile Tyr Leu Ala Ser Ser Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Arg
                85                  90                  95

Glu Leu Pro Leu Thr Phe Gly Gln Gly Thr Lys Val Glu Ile Lys
            100                 105                 110

<210> SEQ ID NO 47
<211> LENGTH: 111
<212> TYPE: PRT
<213> ORGANISM: Artificial Sequence
<220> FEATURE:
<223> OTHER INFORMATION: Synthetic construct

<400> SEQUENCE: 47

Asp Val Val Met Thr Gln Ser Pro Leu Ser Leu Pro Val Thr Leu Gly
1               5                   10                  15

Gln Pro Ala Ser Ile Ser Cys Arg Ala Ser Lys Ser Val Ser Thr Ser
            20                  25                  30

Gly His Ser Tyr Met His Trp Phe Gln Gln Arg Pro Gly Gln Ser Pro
        35                  40                  45

Arg Arg Leu Ile Tyr Leu Ala Ser Ser Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Arg
                85                  90                  95

Glu Leu Pro Leu Thr Phe Gly Gln Gly Thr Lys Val Glu Ile Lys
            100                 105                 110

<210> SEQ ID NO 48
<211> LENGTH: 111
<212> TYPE: PRT
<213> ORGANISM: Artificial Sequence
<220> FEATURE:
<223> OTHER INFORMATION: Synthetic construct

<400> SEQUENCE: 48

Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Thr Ser
            20                  25                  30

Gly His Ser Tyr Met His Trp Tyr Gln Gln Lys Pro Gly Gln Pro Pro
        35                  40                  45
```

```
Lys Leu Leu Ile Tyr Leu Ala Ser Ser Leu Glu Ser Gly Val Pro Asp
         50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln His Ser Arg
                 85                  90                  95

Glu Leu Pro Leu Thr Phe Gly Gln Gly Thr Lys Val Glu Ile Lys
            100                 105                 110
```

<210> SEQ ID NO 49
<211> LENGTH: 117
<212> TYPE: PRT
<213> ORGANISM: Mus musculus

<400> SEQUENCE: 49

```
Gln Val Gln Leu Gln Gln Ser Gly Ala Glu Leu Val Lys Pro Gly Ala
 1               5                  10                  15

Ser Val Lys Leu Ser Cys Lys Ala Ser Gly Tyr Thr Phe Thr Ser Tyr
                 20                  25                  30

Asp Ile Asn Trp Val Arg Gln Arg Pro Glu Gln Gly Leu Glu Trp Ile
             35                  40                  45

Gly Trp Ile Phe Pro Gly Asp Gly Ser Thr Lys Tyr Asn Glu Lys Phe
 50                  55                  60

Lys Gly Lys Ala Thr Leu Thr Thr Asp Lys Ser Ser Asn Thr Thr Tyr
 65                  70                  75                  80

Met Gln Leu Ser Arg Leu Thr Ser Glu Asp Ser Ala Val Tyr Phe Cys
                 85                  90                  95

Ala Arg Gly Tyr His Tyr Ala Met Asp Ser Trp Gly Gln Gly Thr Ser
            100                 105                 110

Val Thr Val Ser Ser
        115
```

<210> SEQ ID NO 50
<211> LENGTH: 117
<212> TYPE: PRT
<213> ORGANISM: Artificial Sequence
<220> FEATURE:
<223> OTHER INFORMATION: Synthetic construct

<400> SEQUENCE: 50

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                 20                  25                  30

Asp Ile Asn Trp Val Arg Gln Ala Pro Gly Gln Gly Leu Glu Trp Ile
             35                  40                  45

Gly Trp Ile Phe Pro Gly Asp Gly Ser Thr Lys Tyr Asn Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Tyr His Tyr Ala Met Asp Ser Trp Gly Gln Gly Thr Leu
            100                 105                 110

Val Thr Val Ser Ser
        115
```

```
<210> SEQ ID NO 51
<211> LENGTH: 117
<212> TYPE: PRT
<213> ORGANISM: Artificial Sequence
<220> FEATURE:
<223> OTHER INFORMATION: Synthetic construct

<400> SEQUENCE: 51
```

| Gln | Val | Gln | Leu | Val | Gln | Ser | Gly | Ala | Glu | Val | Lys | Lys | Pro | Gly | Ser |
|---|---|---|---|---|---|---|---|---|---|---|---|---|---|---|---|
| 1 | | | | 5 | | | | | 10 | | | | | 15 | |

| Ser | Val | Lys | Val | Ser | Cys | Lys | Ala | Ser | Gly | Tyr | Thr | Phe | Thr | Ser | Tyr |
|---|---|---|---|---|---|---|---|---|---|---|---|---|---|---|---|
| | | | 20 | | | | | 25 | | | | | 30 | | |

| Asp | Ile | Asn | Trp | Val | Arg | Gln | Ala | Pro | Gly | Gln | Gly | Leu | Glu | Trp | Ile |
|---|---|---|---|---|---|---|---|---|---|---|---|---|---|---|---|
| | | 35 | | | | | 40 | | | | | 45 | | | |

| Gly | Trp | Ile | Phe | Pro | Gly | Asp | Gly | Ser | Thr | Lys | Tyr | Asn | Gln | Lys | Phe |
|---|---|---|---|---|---|---|---|---|---|---|---|---|---|---|---|
| 50 | | | | | 55 | | | | | 60 | | | | | |

| Gln | Gly | Arg | Val | Thr | Ile | Thr | Ala | Asp | Glu | Ser | Thr | Ser | Thr | Ala | Tyr |
|---|---|---|---|---|---|---|---|---|---|---|---|---|---|---|---|
| 65 | | | | | 70 | | | | | 75 | | | | | 80 |

| Met | Glu | Leu | Ser | Ser | Leu | Arg | Ser | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Gly | Tyr | His | Tyr | Ala | Met | Asp | Ser | Trp | Gly | Gln | Gly | Thr | Leu |
|---|---|---|---|---|---|---|---|---|---|---|---|---|---|---|---|
| | | | 100 | | | | | 105 | | | | | 110 | | |

| Val | Thr | Val | Ser | Ser |
|---|---|---|---|---|
| | | | 115 | |

```
<210> SEQ ID NO 52
<211> LENGTH: 117
<212> TYPE: PRT
<213> ORGANISM: Artificial Sequence
<220> FEATURE:
<223> OTHER INFORMATION: Synthetic construct

<400> SEQUENCE: 52
```

| Glu | Val | Gln | Leu | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Tyr | Thr | Phe | Thr | Ser | Tyr |
|---|---|---|---|---|---|---|---|---|---|---|---|---|---|---|---|
| | | | 20 | | | | | 25 | | | | | 30 | | |

| Asp | Ile | Asn | Trp | Val | Arg | Gln | Ala | Pro | Gly | Lys | Gly | Leu | Glu | Trp | Ile |
|---|---|---|---|---|---|---|---|---|---|---|---|---|---|---|---|
| | | 35 | | | | | 40 | | | | | 45 | | | |

| Gly | Trp | Ile | Phe | Pro | Gly | Asp | Gly | Ser | Thr | Lys | Tyr | Asn | Asp | Ser | Val |
|---|---|---|---|---|---|---|---|---|---|---|---|---|---|---|---|
| 50 | | | | | 55 | | | | | 60 | | | | | |

| Lys | Gly | Arg | Phe | Thr | Ile | Ser | Arg | Asp | Asn | Ser | Lys | Asn | Thr | Leu | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Gly | Tyr | His | Tyr | Ala | Met | Asp | Ser | Trp | Gly | Gln | Gly | Thr | Leu |
|---|---|---|---|---|---|---|---|---|---|---|---|---|---|---|---|
| | | | 100 | | | | | 105 | | | | | 110 | | |

| Val | Thr | Val | Ser | Ser |
|---|---|---|---|---|
| | | | 115 | |

```
<210> SEQ ID NO 53
<211> LENGTH: 117
<212> TYPE: PRT
<213> ORGANISM: Artificial Sequence
<220> FEATURE:
<223> OTHER INFORMATION: Synthetic construct

<400> SEQUENCE: 53
```

| Glu | Val | Gln | Leu | Val | Gln | Ser | Gly | Ala | Glu | Val | Lys | Lys | Pro | Gly | Glu |
|---|---|---|---|---|---|---|---|---|---|---|---|---|---|---|---|
| 1 | | | | 5 | | | | | 10 | | | | | 15 | |

```
Ser Leu Lys Ile Ser Cys Lys Gly Ser Gly Tyr Thr Phe Thr Ser Tyr
             20                  25                  30

Asp Ile Asn Trp Val Arg Gln Met Pro Gly Lys Gly Leu Glu Trp Ile
         35                  40                  45

Gly Trp Ile Phe Pro Gly Asp Gly Ser Thr Lys Tyr Asn Pro Ser Phe
     50                  55                  60

Gln Gly Gln Val Thr Ile Ser Ala Asp Lys Ser Ile Ser Thr Ala Tyr
65                   70                  75                  80

Leu Gln Trp Ser Ser Leu Lys Ala Ser Asp Thr Ala Met Tyr Tyr Cys
                 85                  90                  95

Ala Arg Gly Tyr His Tyr Ala Met Asp Ser Trp Gly Gln Gly Thr Leu
             100                 105                 110

Val Thr Val Ser Ser
            115

<210> SEQ ID NO 54
<211> LENGTH: 109
<212> TYPE: PRT
<213> ORGANISM: Mus musculus

<400> SEQUENCE: 54

Pro Glu Leu Val Lys Pro Gly Ala Ser Val Lys Ile Ser Cys Lys Ala
1               5                   10                  15

Ser Gly Tyr Thr Phe Thr Asp Tyr Asn Leu His Trp Val Lys Leu Ser
             20                  25                  30

His Gly Lys Ser Leu Glu Trp Ile Gly Phe Ile Tyr Pro Ser Asn Gly
         35                  40                  45

Ile Thr Gly Tyr Asn Gln Lys Phe Lys Asn Lys Ala Thr Leu Thr Val
     50                  55                  60

Asp Asn Ser Ser Ser Thr Ala Tyr Met Glu Leu Arg Ser Leu Thr Ser
65                  70                   75                  80

Glu Asp Ser Ala Val Tyr Tyr Cys Ala Arg Ser Thr Val Asp Tyr Phe
                 85                  90                  95

Asp Tyr Trp Gly Gln Gly Thr Thr Leu Thr Val Ser Ser
            100                 105

<210> SEQ ID NO 55
<211> LENGTH: 117
<212> TYPE: PRT
<213> ORGANISM: Artificial Sequence
<220> FEATURE:
<223> OTHER INFORMATION: Synthetic construct

<400> SEQUENCE: 55

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
             20                  25                  30

Asn Leu His Trp Val Arg Gln Ala Pro Gly Gln Gly Leu Glu Trp Ile
         35                  40                  45

Gly Phe Ile Tyr Pro Ser Asn Gly Ile Thr Gly Tyr Asn Gln Lys Phe
     50                  55                  60

Gln Gly Arg Val Thr Met Thr Arg Asp Thr Ser Thr Ser Thr Val Tyr
65                  70                  75                   80

Met Glu Leu Ser Ser Leu Arg Ser Glu Asp Thr Ala Val Tyr Tyr Cys
                 85                  90                  95
```

```
Ala Arg Ser Thr Val Asp Tyr Phe Asp Tyr Trp Gly Gln Gly Thr Leu
                100                 105                 110

Val Thr Val Ser Ser
        115

<210> SEQ ID NO 56
<211> LENGTH: 117
<212> TYPE: PRT
<213> ORGANISM: Artificial Sequence
<220> FEATURE:
<223> OTHER INFORMATION: Synthetic construct

<400> SEQUENCE: 56

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Asn Leu His Trp Val Arg Gln Ala Pro Gly Gln Gly Leu Glu Trp Ile
        35                  40                  45

Gly Phe Ile Tyr Pro Ser Asn Gly Ile Thr Gly Tyr Asn Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Val Asp Tyr Phe Asp Tyr Trp Gly Gln Gly Thr Leu
                100                 105                 110

Val Thr Val Ser Ser
        115

<210> SEQ ID NO 57
<211> LENGTH: 117
<212> TYPE: PRT
<213> ORGANISM: Artificial Sequence
<220> FEATURE:
<223> OTHER INFORMATION: Synthetic construct

<400> SEQUENCE: 57

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Thr Phe Thr Asp Tyr
            20                  25                  30

Asn Leu His Trp Val Arg Gln Ala Pro Gly Lys Gly Leu Glu Trp Ile
        35                  40                  45

Gly Phe Ile Tyr Pro Ser Asn Gly Ile Thr Gly Tyr Asn Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Thr Val Asp Tyr Phe Asp Tyr Trp Gly Gln Gly Thr Leu
                100                 105                 110

Val Thr Val Ser Ser
        115

<210> SEQ ID NO 58
<211> LENGTH: 117
<212> TYPE: PRT
<213> ORGANISM: Artificial Sequence
```

```
<220> FEATURE:
<223> OTHER INFORMATION: Synthetic construct

<400> SEQUENCE: 58

Glu Val Gln Leu Val Gln Ser Gly Ala Glu Val Lys Pro Gly Glu
1               5                   10                  15

Ser Leu Lys Ile Ser Cys Lys Gly Ser Gly Tyr Thr Phe Thr Asp Tyr
                20                  25                  30

Asn Leu His Trp Val Arg Gln Met Pro Gly Lys Gly Leu Glu Trp Ile
            35                  40                  45

Gly Phe Ile Tyr Pro Ser Asn Gly Ile Thr Gly Tyr Asn Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Thr Val Asp Tyr Phe Asp Tyr Trp Gly Gln Gly Thr Leu
            100                 105                 110

Val Thr Val Ser Ser
            115

<210> SEQ ID NO 59
<211> LENGTH: 120
<212> TYPE: PRT
<213> ORGANISM: Mus musculus

<400> SEQUENCE: 59

Glu Val Lys Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
                20                  25                  30

Tyr Met His Trp Val Lys Gln Ser Ser Glu Lys Ser Leu Glu Trp Ile
            35                  40                  45

Gly Glu Ile Asn Pro Ser Thr Gly Gly Thr Ser Tyr Asn Gln Lys Phe
        50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Thr Arg Gly His Tyr Gly Ser Tyr Leu Thr Phe Asp Tyr Trp Gly His
            100                 105                 110

Gly Thr Thr Leu Thr Val Ser Ser
        115                 120

<210> SEQ ID NO 60
<211> LENGTH: 56
<212> TYPE: PRT
<213> ORGANISM: Mus musculus

<400> SEQUENCE: 60

Ser Gly Lys Ala Thr Leu Thr Val Asp Thr Ser Ser Ser Thr Ala Tyr
1               5                   10                  15

Met Gln Leu Ser Ser Leu Thr Ser Glu Asp Ser Ala Val Tyr Phe Cys
                20                  25                  30

Thr Arg Gly His Tyr Gly Ser Tyr Leu Thr Phe Asp Tyr Trp Gly His
            35                  40                  45

Gly Thr Thr Leu Thr Val Ser Ser
```

<210> SEQ ID NO 61
<211> LENGTH: 120
<212> TYPE: PRT
<213> ORGANISM: Artificial Sequence
<220> FEATURE:
<223> OTHER INFORMATION: Synthetic construct

<400> SEQUENCE: 61

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
                20                  25                  30

Tyr Met His Trp Val Arg Gln Ala Pro Gly Gln Gly Leu Glu Trp Ile
            35                  40                  45

Gly Glu Ile Asn Pro Ser Thr Gly Thr Ser Tyr Asn Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly His Tyr Gly Ser Tyr Leu Thr Phe Asp Tyr Trp Gly Gln
                100                 105                 110

Gly Thr Leu Val Thr Val Ser Ser
            115                 120

<210> SEQ ID NO 62
<211> LENGTH: 120
<212> TYPE: PRT
<213> ORGANISM: Artificial Sequence
<220> FEATURE:
<223> OTHER INFORMATION: Synthetic construct

<400> SEQUENCE: 62

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Gly Tyr
                20                  25                  30

Tyr Met His Trp Val Arg Gln Ala Pro Gly Gln Gly Leu Glu Trp Ile
            35                  40                  45

Gly Glu Ile Asn Pro Ser Thr Gly Gly Thr Ser Tyr Asn Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly His Tyr Gly Ser Tyr Leu Thr Phe Asp Tyr Trp Gly Gln
                100                 105                 110

Gly Thr Leu Val Thr Val Ser Ser
            115                 120

<210> SEQ ID NO 63
<211> LENGTH: 120
<212> TYPE: PRT
<213> ORGANISM: Artificial Sequence
<220> FEATURE:
<223> OTHER INFORMATION: Synthetic construct

<400> SEQUENCE: 63

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Tyr Met His Trp Val Arg Gln Ala Pro Gly Lys Gly Leu Glu Trp Ile
        35                  40                  45

Gly Glu Ile Asn Pro Ser Thr Gly Gly Thr Ser Tyr Asn Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly His Tyr Gly Ser Tyr Leu Thr Phe Asp Tyr Trp Gly Gln
            100                 105                 110

Gly Thr Leu Val Thr Val Ser Ser
            115                 120

<210> SEQ ID NO 64
<211> LENGTH: 120
<212> TYPE: PRT
<213> ORGANISM: Artificial Sequence
<220> FEATURE:
<223> OTHER INFORMATION: Synthetic construct

<400> SEQUENCE: 64

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Gly Tyr
            20                  25                  30

Tyr Met His Trp Val Arg Gln Met Pro Gly Lys Gly Leu Glu Trp Ile
        35                  40                  45

Gly Glu Ile Asn Pro Ser Thr Gly Gly Thr Ser Tyr Asn Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Thr Arg Gly His Tyr Gly Ser Tyr Leu Thr Phe Asp Tyr Trp Gly Gln
            100                 105                 110

Gly Thr Leu Val Thr Val Ser Ser
            115                 120

<210> SEQ ID NO 65
<211> LENGTH: 120
<212> TYPE: PRT
<213> ORGANISM: Mus musculus

<400> SEQUENCE: 65

Glu Val Lys Leu Glu Glu Ser Gly Gly Gly Leu Val Gln Pro Gly Gly
1               5                   10                  15

Ser Met Lys Leu Ser Cys Val Gly Ser Gly Phe Thr Phe Ser Asn Tyr
            20                  25                  30

Cys Met Asn Trp Val Arg Gln Ser Pro Glu Lys Gly Leu Glu Trp Val
        35                  40                  45

Ala Glu Ile Arg Leu Lys Ser Asn Asn Tyr Val Thr Asn Tyr Val Glu
    50                  55                  60
```

Ser Val Lys Gly Arg Phe Thr Ile Ser Arg Asp Asp Ser Lys Ser Arg
 65                  70                  75                  80

Val Tyr Leu Gln Met Asn Asn Leu Arg Gly Glu Asp Thr Gly Phe Tyr
                 85                  90                  95

Tyr Cys Thr Arg Asp Gly Tyr Tyr Val Pro Phe Ala Tyr Trp Gly Gln
                100                 105                 110

Gly Thr Leu Val Thr Val Ser Ala
            115                 120

<210> SEQ ID NO 66
<211> LENGTH: 120
<212> TYPE: PRT
<213> ORGANISM: Artificial Sequence
<220> FEATURE:
<223> OTHER INFORMATION: Synthetic construct

<400> SEQUENCE: 66

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Tyr
                20                  25                  30

Cys Met Asn Trp Val Arg Gln Ala Pro Gly Lys Gly Leu Glu Trp Val
             35                  40                  45

Ala Glu Ile Arg Leu Lys Ser Asn Asn Tyr Val Thr Asn Tyr Val Ala
 50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Arg Asp Gly Tyr Tyr Val Pro Phe Ala Tyr Trp Gly Gln
                100                 105                 110

Gly Thr Leu Val Thr Val Ser Ser
            115                 120

<210> SEQ ID NO 67
<211> LENGTH: 15
<212> TYPE: PRT
<213> ORGANISM: Artificial Sequence
<220> FEATURE:
<223> OTHER INFORMATION: Synthetic construct

<400> SEQUENCE: 67

Arg Ala Ser Lys Ser Val Ser Thr Ser Gly Tyr Ser Tyr Met His
 1               5                  10                  15

<210> SEQ ID NO 68
<211> LENGTH: 15
<212> TYPE: PRT
<213> ORGANISM: Artificial Sequence
<220> FEATURE:
<223> OTHER INFORMATION: Synthetic construct

<400> SEQUENCE: 68

Arg Ala Ser Lys Arg Val Ser Thr Ser Val His Ser Tyr Met His
 1               5                  10                  15

<210> SEQ ID NO 69
<211> LENGTH: 7
<212> TYPE: PRT
<213> ORGANISM: Artificial Sequence
<220> FEATURE:
<223> OTHER INFORMATION: Synthetic construct

<400> SEQUENCE: 69

Tyr Ala Ser Asn Leu Glu Cys
1               5

<210> SEQ ID NO 70
<211> LENGTH: 7
<212> TYPE: PRT
<213> ORGANISM: Artificial Sequence
<220> FEATURE:
<223> OTHER INFORMATION: Synthetic construct

<400> SEQUENCE: 70

Leu Val Ser Asn Leu Glu Ser
1               5

<210> SEQ ID NO 71
<211> LENGTH: 7
<212> TYPE: PRT
<213> ORGANISM: Artificial Sequence
<220> FEATURE:
<223> OTHER INFORMATION: Synthetic construct

<400> SEQUENCE: 71

Leu Ala Ser Ser Leu Glu Ser
1               5

<210> SEQ ID NO 72
<211> LENGTH: 9
<212> TYPE: PRT
<213> ORGANISM: Artificial Sequence
<220> FEATURE:
<223> OTHER INFORMATION: Synthetic construct

<400> SEQUENCE: 72

Gln His Ser Trp Glu Ile Pro Leu Thr
1               5

<210> SEQ ID NO 73
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: 8
<223> OTHER INFORMATION: Xaa = Any Amino Acid

<400> SEQUENCE: 73

Asn Leu Leu Leu Ser Ala His Xaa Gly Ala Tyr Thr
1               5                   10

<210> SEQ ID NO 74
<211> LENGTH: 9
<212> TYPE: PRT
<213> ORGANISM: Artificial Sequence
<220> FEATURE:
<223> OTHER INFORMATION: Synthetic construct

<400> SEQUENCE: 74

Gln His Ser Arg Glu Val Pro Leu Thr
1               5

<210> SEQ ID NO 75
<211> LENGTH: 9
<212> TYPE: PRT

```
<213> ORGANISM: Artificial Sequence
<220> FEATURE:
<223> OTHER INFORMATION: Synthetic construct

<400> SEQUENCE: 75

Tyr Thr Phe Thr Ser Tyr Trp Met His
1               5

<210> SEQ ID NO 76
<211> LENGTH: 16
<212> TYPE: PRT
<213> ORGANISM: Artificial Sequence
<220> FEATURE:
<223> OTHER INFORMATION: Synthetic construct

<400> SEQUENCE: 76

Val Ala Glu Ile Arg Leu Lys Ser Asn Asn Tyr Val Thr Asn Tyr Val
1               5                   10                  15

<210> SEQ ID NO 77
<211> LENGTH: 14
<212> TYPE: PRT
<213> ORGANISM: Artificial Sequence
<220> FEATURE:
<223> OTHER INFORMATION: Synthetic construct

<400> SEQUENCE: 77

Ile Gly Asn Ile Tyr Pro Gly Ser Ile Ser Ser Asn Tyr Asp
1               5                   10

<210> SEQ ID NO 78
<211> LENGTH: 20
<212> TYPE: PRT
<213> ORGANISM: Artificial Sequence
<220> FEATURE:
<223> OTHER INFORMATION: Synthetic construct

<400> SEQUENCE: 78

Glx Thr Gln Ser Leu Ala Ser Leu Ala Val Ser Leu Gly Gln Arg Ala
1               5                   10                  15

Thr Met Ser Cys
            20

<210> SEQ ID NO 79
<211> LENGTH: 23
<212> TYPE: PRT
<213> ORGANISM: Artificial Sequence
<220> FEATURE:
<223> OTHER INFORMATION: Synthetic construct

<400> SEQUENCE: 79

Asp Ile Val Leu Thr Gln Ser Pro Ala Ser Leu Ala Val Ser Leu Gly
1               5                   10                  15

Gln Arg Ala Thr Ile Ser Tyr
            20

<210> SEQ ID NO 80
<211> LENGTH: 23
<212> TYPE: PRT
<213> ORGANISM: Artificial Sequence
<220> FEATURE:
<223> OTHER INFORMATION: Synthetic construct

<400> SEQUENCE: 80

Asp Phe Gln Ile Gln Gln Ser Leu Ala Ser Leu Val Val Ser Met Gly
1               5                   10                  15
```

```
Gln Arg Ala Ala Ile Ser Phe
            20

<210> SEQ ID NO 81
<211> LENGTH: 24
<212> TYPE: PRT
<213> ORGANISM: Artificial Sequence
<220> FEATURE:
<223> OTHER INFORMATION: Synthetic construct

<400> SEQUENCE: 81

Cys Asp Ile Lys Met Thr Gln Ser Pro Ser Ser Met Tyr Glu Ser Leu
1               5                   10                  15

Gly Glu Arg Val Thr Ile Thr Cys
            20

<210> SEQ ID NO 82
<211> LENGTH: 26
<212> TYPE: PRT
<213> ORGANISM: Artificial Sequence
<220> FEATURE:
<223> OTHER INFORMATION: Synthetic construct

<400> SEQUENCE: 82

Ser Thr Gly Asp Ile Val Leu Thr Gln Ser Pro Ala Ser Leu Ala Val
1               5                   10                  15

Ser Leu Gly Gln Arg Ala Thr Met Ser Cys
            20                  25

<210> SEQ ID NO 83
<211> LENGTH: 15
<212> TYPE: PRT
<213> ORGANISM: Artificial Sequence
<220> FEATURE:
<223> OTHER INFORMATION: Synthetic construct

<400> SEQUENCE: 83

Trp Tyr Gln Gln Lys Pro Gly Gln Pro Pro Lys Leu Leu Ile Lys
1               5                   10                  15

<210> SEQ ID NO 84
<211> LENGTH: 15
<212> TYPE: PRT
<213> ORGANISM: Artificial Sequence
<220> FEATURE:
<223> OTHER INFORMATION: Synthetic construct

<400> SEQUENCE: 84

Trp Asn Gln Gln Lys Pro Gly Gln Pro Pro Arg Leu Leu Ile Tyr
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: Synthetic construct

<400> SEQUENCE: 85

Trp Tyr Gln Gln Lys Pro Gly Gln Pro Pro Lys Leu Ile Ile Tyr
1               5                   10                  15

<210> SEQ ID NO 86
<211> LENGTH: 15
<212> TYPE: PRT
```

```
<213> ORGANISM: Artificial Sequence
<220> FEATURE:
<223> OTHER INFORMATION: Synthetic construct

<400> SEQUENCE: 86

Trp Leu Gln Gln Lys Pro Gly Lys Ser Pro Lys Thr Leu Ile Tyr
1               5                   10                  15

<210> SEQ ID NO 87
<211> LENGTH: 32
<212> TYPE: PRT
<213> ORGANISM: Artificial Sequence
<220> FEATURE:
<223> OTHER INFORMATION: Synthetic construct

<400> SEQUENCE: 87

Gly Val Pro Ala Arg Phe Ser Gly Ser Gly Glx Gly Thr Asp Phe Thr
1               5                   10                  15

Leu Asn Ile His Pro Val Glu Glu Glu Asp Ser Ala Thr Tyr Tyr Cys
                20                  25                  30

<210> SEQ ID NO 88
<211> LENGTH: 28
<212> TYPE: PRT
<213> ORGANISM: Artificial Sequence
<220> FEATURE:
<223> OTHER INFORMATION: Synthetic construct

<400> SEQUENCE: 88

Gly Val Pro Ala Arg Phe Ser Gly Ser Gly Glx Trp Asp Arg Leu His
1               5                   10                  15

Pro Gln His Pro Ser Cys Gly Gly Gly Cys Cys
                20                  25

<210> SEQ ID NO 89
<211> LENGTH: 32
<212> TYPE: PRT
<213> ORGANISM: Artificial Sequence
<220> FEATURE:
<223> OTHER INFORMATION: Synthetic construct

<400> SEQUENCE: 89

Gly Val Arg Ala Arg Phe Ser Gly Glx Gly Trp Gly Thr Asp Phe Thr
1               5                   10                  15

Leu Asn Ile His Pro Val Glu Glu Glu Asp Gly Ala Thr Tyr Tyr Cys
                20                  25                  30

<210> SEQ ID NO 90
<211> LENGTH: 32
<212> TYPE: PRT
<213> ORGANISM: Artificial Sequence
<220> FEATURE:
<223> OTHER INFORMATION: Synthetic construct

<400> SEQUENCE: 90

Gly Val Pro Ser Arg Phe Ser Gly Ser Gly Ser Gly Gln Asp Tyr Ser
1               5                   10                  15

Leu Thr Ile Ser Ser Leu Glu Tyr Glu Asp Met Gly Ile Tyr His Cys
                20                  25                  30

<210> SEQ ID NO 91
<211> LENGTH: 32
<212> TYPE: PRT
<213> ORGANISM: Artificial Sequence
<220> FEATURE:
```

```
<223> OTHER INFORMATION: Synthetic construct

<400> SEQUENCE: 91

Gly Val Pro Ala Arg Phe Ser Gly Ser Gly Ser Gly Thr Asp Phe Thr
1               5                   10                  15

Leu Asn Ile His Pro Val Glu Glu Asp Thr Ala Thr Tyr Tyr Cys
            20                  25                  30

<210> SEQ ID NO 92
<211> LENGTH: 10
<212> TYPE: PRT
<213> ORGANISM: Artificial Sequence
<220> FEATURE:
<223> OTHER INFORMATION: Synthetic construct

<400> SEQUENCE: 92

Phe Gly Gly Gly Thr Lys Leu Glu Met Lys
1               5                   10

<210> SEQ ID NO 93
<211> LENGTH: 10
<212> TYPE: PRT
<213> ORGANISM: Artificial Sequence
<220> FEATURE:
<223> OTHER INFORMATION: Synthetic construct

<400> SEQUENCE: 93

Phe Gly Gly Gly Thr Lys Leu Glu Ile Lys
1               5                   10

<210> SEQ ID NO 94
<211> LENGTH: 10
<212> TYPE: PRT
<213> ORGANISM: Artificial Sequence
<220> FEATURE:
<223> OTHER INFORMATION: Synthetic construct

<400> SEQUENCE: 94

Phe Gly Ala Gly Thr Lys Leu Glu Leu Lys
1               5                   10

<210> SEQ ID NO 95
<211> LENGTH: 26
<212> TYPE: PRT
<213> ORGANISM: Artificial Sequence
<220> FEATURE:
<223> OTHER INFORMATION: Synthetic construct

<400> SEQUENCE: 95

Glu Val Gln Leu Gln Gln Ser Gly Pro Glu Leu Val Lys Pro Gly Ala
1               5                   10                  15

Ser Val Lys Ile Ser Cys Lys Ala Ser Gly
            20                  25

<210> SEQ ID NO 96
<211> LENGTH: 26
<212> TYPE: PRT
<213> ORGANISM: Artificial Sequence
<220> FEATURE:
<223> OTHER INFORMATION: Synthetic construct

<400> SEQUENCE: 96

Glu Val Lys Leu Glu Glu Ser Gly Gly Gly Leu Val Gln Pro Gly Gly
1               5                   10                  15

Ser Met Lys Leu Ser Cys Val Gly Ser Gly
```

```
                    20                  25

<210> SEQ ID NO 97
<211> LENGTH: 26
<212> TYPE: PRT
<213> ORGANISM: Artificial Sequence
<220> FEATURE:
<223> OTHER INFORMATION: Synthetic construct

<400> SEQUENCE: 97

Gln Val Gln Leu Gln Gln Ser Gly Ser Glu Leu Val Arg Pro Gly Ala
1               5                   10                  15

Ser Val Lys Leu Ser Cys Lys Ala Ser Gly
            20                  25

<210> SEQ ID NO 98
<211> LENGTH: 26
<212> TYPE: PRT
<213> ORGANISM: Artificial Sequence
<220> FEATURE:
<223> OTHER INFORMATION: Synthetic construct

<400> SEQUENCE: 98

Gln Val Gln Leu Gln Gln Ser Gly Ala Glu Leu Val Lys Pro Gly Ala
1               5                   10                  15

Ser Val Lys Leu Ser Cys Lys Ala Ser Gly
            20                  25

<210> SEQ ID NO 99
<211> LENGTH: 18
<212> TYPE: PRT
<213> ORGANISM: Artificial Sequence
<220> FEATURE:
<223> OTHER INFORMATION: Synthetic construct

<400> SEQUENCE: 99

Pro Glu Leu Val Lys Pro Gly Ala Ser Val Lys Ile Ser Cys Lys Ala
1               5                   10                  15

Ser Gly

<210> SEQ ID NO 100
<211> LENGTH: 12
<212> TYPE: PRT
<213> ORGANISM: Artificial Sequence
<220> FEATURE:
<223> OTHER INFORMATION: Synthetic construct

<400> SEQUENCE: 100

Trp Val Lys Leu Ser His Gly Lys Ser Leu Glu Trp
1               5                   10

<210> SEQ ID NO 101
<211> LENGTH: 12
<212> TYPE: PRT
<213> ORGANISM: Artificial Sequence
<220> FEATURE:
<223> OTHER INFORMATION: Synthetic construct

<400> SEQUENCE: 101

Trp Val Arg Gln Ser Pro Glu Lys Gly Leu Glu Trp
1               5                   10

<210> SEQ ID NO 102
<211> LENGTH: 12
<212> TYPE: PRT
```

```
<213> ORGANISM: Artificial Sequence
<220> FEATURE:
<223> OTHER INFORMATION: Synthetic construct

<400> SEQUENCE: 102

Trp Val Lys Gln Arg Pro Gly Gln Gly Leu Glu Trp
1               5                   10

<210> SEQ ID NO 103
<211> LENGTH: 12
<212> TYPE: PRT
<213> ORGANISM: Artificial Sequence
<220> FEATURE:
<223> OTHER INFORMATION: Synthetic construct

<400> SEQUENCE: 103

Trp Val Arg Gln Arg Pro Glu Gln Gly Leu Glu Trp
1               5                   10

<210> SEQ ID NO 104
<211> LENGTH: 35
<212> TYPE: PRT
<213> ORGANISM: Artificial Sequence
<220> FEATURE:
<223> OTHER INFORMATION: Synthetic construct

<400> SEQUENCE: 104

Gln Lys Phe Lys Asn Lys Ala Thr Leu Thr Val Asp Asn Ser Ser Ser
1               5                   10                  15

Thr Ala Tyr Met Glu Leu Arg Ser Leu Thr Ser Glu Asp Ser Ala Val
                20                  25                  30

Tyr Tyr Cys
        35

<210> SEQ ID NO 105
<211> LENGTH: 35
<212> TYPE: PRT
<213> ORGANISM: Artificial Sequence
<220> FEATURE:
<223> OTHER INFORMATION: Synthetic construct

<400> SEQUENCE: 105

Glu Ser Val Lys Gly Arg Phe Thr Ile Ser Arg Asp Asp Ser Lys Ser
1               5                   10                  15

Arg Val Tyr Leu Gln Met Asn Asn Leu Arg Gly Glu Asp Thr Gly Phe
                20                  25                  30

Tyr Tyr Cys
        35

<210> SEQ ID NO 106
<211> LENGTH: 35
<212> TYPE: PRT
<213> ORGANISM: Artificial Sequence
<220> FEATURE:
<223> OTHER INFORMATION: Synthetic construct

<400> SEQUENCE: 106

Glu Lys Phe Lys Asn Lys Ala Thr Leu Thr Val Asp Thr Ser Ser Ser
1               5                   10                  15

Thr Ala Tyr Met Gln Leu Ser Ser Leu Thr Ser Glu Asp Ser Ala Val
                20                  25                  30

Tyr Phe Cys
        35
```

```
<210> SEQ ID NO 107
<211> LENGTH: 35
<212> TYPE: PRT
<213> ORGANISM: Artificial Sequence
<220> FEATURE:
<223> OTHER INFORMATION: Synthetic construct

<400> SEQUENCE: 107

Glu Lys Phe Lys Gly Lys Ala Thr Leu Thr Thr Asp Lys Ser Ser Asn
1               5                   10                  15

Thr Thr Tyr Met Gln Leu Ser Arg Leu Thr Ser Glu Asp Ser Ala Val
            20                  25                  30

Tyr Phe Cys
        35

<210> SEQ ID NO 108
<211> LENGTH: 11
<212> TYPE: PRT
<213> ORGANISM: Artificial Sequence
<220> FEATURE:
<223> OTHER INFORMATION: Synthetic construct

<400> SEQUENCE: 108

Trp Gly Gln Gly Thr Thr Leu Thr Val Ser Ser
1               5                   10

<210> SEQ ID NO 109
<211> LENGTH: 11
<212> TYPE: PRT
<213> ORGANISM: Artificial Sequence
<220> FEATURE:
<223> OTHER INFORMATION: Synthetic construct

<400> SEQUENCE: 109

Trp Gly Gln Gly Thr Leu Val Thr Val Ser Ala
1               5                   10

<210> SEQ ID NO 110
<211> LENGTH: 11
<212> TYPE: PRT
<213> ORGANISM: Artificial Sequence
<220> FEATURE:
<223> OTHER INFORMATION: Synthetic construct

<400> SEQUENCE: 110

Trp Gly His Gly Thr Thr Leu Thr Val Ser Ser
1               5                   10

<210> SEQ ID NO 111
<211> LENGTH: 11
<212> TYPE: PRT
<213> ORGANISM: Artificial Sequence
<220> FEATURE:
<223> OTHER INFORMATION: Synthetic construct

<400> SEQUENCE: 111

Trp Gly Gln Gly Thr Ser Val Thr Val Ser Ser
1               5                   10

<210> SEQ ID NO 112
<211> LENGTH: 108
<212> TYPE: PRT
<213> ORGANISM: Mus musculus

<400> SEQUENCE: 112
```

Glx Thr Gln Ser Leu Ala Ser Leu Ala Val Ser Leu Gly Gln Arg Ala
1               5                   10                  15

Thr Met Ser Cys Arg Ala Ser Gln Ser Val Ser Thr Thr Tyr Ser
            20                  25                  30

Tyr Met His Trp Tyr Gln Gln Lys Pro Gly Gln Pro Pro Lys Leu Leu
            35                  40                  45

Ile Lys Tyr Ala Ser Asn Leu Glu Cys Gly Val Pro Ala Arg Phe Ser
50                  55                  60

Gly Ser Gly Glx Gly Thr Asp Phe Thr Leu Asn Ile His Pro Val Glu
65                  70                  75                  80

Glu Glu Asp Ser Ala Thr Tyr Tyr Cys Gln His Ser Trp Glu Ile Pro
            85                  90                  95

Leu Thr Phe Gly Gly Gly Thr Lys Leu Glu Met Lys
            100                 105

<210> SEQ ID NO 113
<211> LENGTH: 111
<212> TYPE: PRT
<213> ORGANISM: Artificial Sequence
<220> FEATURE:
<223> OTHER INFORMATION: Synthetic construct

<400> SEQUENCE: 113

Asp Val Val Met Thr Gln Ser Pro Leu Ser Leu Pro Val Thr Leu Gly
1               5                   10                  15

Gln Pro Ala Ser Ile Ser Cys Arg Ala Ser Gln Ser Val Ser Thr Ser
            20                  25                  30

Thr Tyr Ser Tyr Met His Trp Phe Gln Gln Arg Pro Gly Gln Ser Pro
            35                  40                  45

Arg Arg Leu Ile Tyr Tyr Ala Ser Asn Leu Glu Cys Gly Val Pro Asp
50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Trp
            85                  90                  95

Glu Ile Pro Leu Thr Phe Gly Gln Gly Thr Lys Val Glu Ile Lys
            100                 105                 110

<210> SEQ ID NO 114
<211> LENGTH: 111
<212> TYPE: PRT
<213> ORGANISM: Artificial Sequence
<220> FEATURE:
<223> OTHER INFORMATION: Synthetic construct

<400> SEQUENCE: 114

Asp Ile Val Met Thr Gln Ser Pro Leu Ser Leu Pro Val Thr Pro Gly
1               5                   10                  15

Glu Pro Ala Ser Ile Ser Cys Arg Ala Ser Gln Ser Val Ser Thr Ser
            20                  25                  30

Thr Tyr Ser Tyr Met His Trp Tyr Leu Gln Lys Pro Gly Gln Ser Pro
            35                  40                  45

Gln Leu Leu Ile Tyr Tyr Ala Ser Asn Leu Glu Cys Gly Val Pro Asp
50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Trp
            85                  90                  95

Glu Ile Pro Leu Thr Phe Gly Gln Gly Thr Lys Val Glu Ile Lys
            100                 105                 110

<210> SEQ ID NO 115
<211> LENGTH: 111
<212> TYPE: PRT
<213> ORGANISM: Artificial Sequence
<220> FEATURE:
<223> OTHER INFORMATION: Synthetic construct

<400> SEQUENCE: 115

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Ser Thr Ser
            20                  25                  30

Thr Tyr Ser Tyr Met His Trp Tyr Gln Gln Lys Pro Gly Gln Pro Pro
        35                  40                  45

Lys Leu Leu Ile Tyr Tyr Ala Ser Asn Leu Glu Cys Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95

Glu Ile Pro Leu Thr Phe Gly Gly Thr Lys Val Glu Ile Lys
            100                 105                 110

<210> SEQ ID NO 116
<211> LENGTH: 111
<212> TYPE: PRT
<213> ORGANISM: Artificial Sequence
<220> FEATURE:
<223> OTHER INFORMATION: Synthetic construct

<400> SEQUENCE: 116

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Thr Ser
            20                  25                  30

Thr Tyr Ser Tyr Met His Trp Tyr Gln Gln Lys Pro Gly Lys Ala Pro
        35                  40                  45

Lys Leu Leu Ile Tyr Tyr Ala Ser Asn Leu Glu Cys Gly Val Pro Ser
    50                  55                  60

Arg Phe Ser Gly Ser Gly Ser Gly Thr Asp Phe Thr Phe Thr Ile Ser
65                  70                  75                  80

Ser Leu Gln Pro Glu Asp Ile Ala Thr Tyr Tyr Cys Gln His Ser Trp
                85                  90                  95

Glu Ile Pro Leu Thr Phe Gly Gln Gly Thr Lys Val Glu Ile Lys
            100                 105                 110

<210> SEQ ID NO 117
<211> LENGTH: 111
<212> TYPE: PRT
<213> ORGANISM: Artificial Sequence
<220> FEATURE:
<223> OTHER INFORMATION: Synthetic construct

<400> SEQUENCE: 117

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Val Ser Thr Ser
            20                  25                  30

Thr Tyr Ser Tyr Met His Trp Tyr Gln Gln Lys Pro Gly Lys Ala Pro
        35                  40                  45

Lys Leu Leu Ile Tyr Tyr Ala Ser Asn Leu Glu Cys Gly Val Pro Ser
    50                  55                  60

Arg Phe Ser Gly Ser Gly Ser Gly Thr Glu Phe Thr Leu Thr Ile Ser
65                  70                  75                  80

Ser Leu Gln Pro Asp Asp Phe Ala Thr Tyr Tyr Cys Gln His Ser Trp
                85                  90                  95

Glu Ile Pro Leu Thr Phe Gly Gln Gly Thr Lys Val Glu Ile Lys
                100                 105                 110

<210> SEQ ID NO 118
<211> LENGTH: 111
<212> TYPE: PRT
<213> ORGANISM: Artificial Sequence
<220> FEATURE:
<223> OTHER INFORMATION: Synthetic construct

<400> SEQUENCE: 118

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Thr Ser
            20                  25                  30

Thr Tyr Ser Tyr Met His Trp Tyr Gln Gln Lys Pro Gly Gln Ala Pro
        35                  40                  45

Arg Leu Leu Ile Tyr Tyr Ala Ser Asn Leu Glu Cys Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Trp
                85                  90                  95

Glu Ile Pro Leu Thr Phe Gly Gln Gly Thr Lys Val Glu Ile Lys
                100                 105                 110

<210> SEQ ID NO 119
<211> LENGTH: 111
<212> TYPE: PRT
<213> ORGANISM: Artificial Sequence
<220> FEATURE:
<223> OTHER INFORMATION: Synthetic construct

<400> SEQUENCE: 119

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Thr Ser
            20                  25                  30

Thr Tyr Ser Tyr Met His Trp Tyr Gln Gln Lys Pro Gly Lys Ala Pro
        35                  40                  45

Lys Leu Leu Ile Tyr Tyr Ala Ser Asn Leu Glu Cys Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Trp
                85                  90                  95

Glu Ile Pro Leu Thr Phe Gly Gln Gly Thr Lys Val Glu Ile Lys
                100                 105                 110

<210> SEQ ID NO 120
<211> LENGTH: 111
<212> TYPE: PRT
<213> ORGANISM: Artificial Sequence
<220> FEATURE:
<223> OTHER INFORMATION: Synthetic construct

<400> SEQUENCE: 120

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Ser Val Ser Thr Ser
            20                  25                  30

Thr Tyr Ser Tyr Met His Trp Tyr Gln Gln Lys Pro Gly Lys Ala Pro
        35                  40                  45

Lys Leu Leu Ile Tyr Tyr Ala Ser Asn Leu Glu Cys Gly Val Pro Ser
    50                  55                  60

Arg Phe Ser Gly Ser Gly Ser Gly Thr Glu Phe Thr Leu Thr Ile Ser
65                  70                  75                  80

Ser Leu Gln Pro Glu Asp Phe Ala Thr Tyr Tyr Cys Gln His Ser Trp
                85                  90                  95

Glu Ile Pro Leu Thr Phe Gly Gln Gly Thr Lys Val Glu Ile Lys
            100                 105                 110

<210> SEQ ID NO 121
<211> LENGTH: 111
<212> TYPE: PRT
<213> ORGANISM: Artificial Sequence
<220> FEATURE:
<223> OTHER INFORMATION: Synthetic construct

<400> SEQUENCE: 121

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Thr Ser
            20                  25                  30

Thr Tyr Ser Tyr Met His Trp Tyr Gln Gln Lys Pro Gly Gln Ala Pro
        35                  40                  45

Arg Leu Leu Ile Tyr Tyr Ala Ser Asn Leu Glu Cys Gly Ile Pro Ala
    50                  55                  60

Arg Phe Ser Gly Ser Gly Ser Gly Thr Glu Phe Thr Leu Thr Ile Ser
65                  70                  75                  80

Ser Leu Gln Ser Glu Asp Phe Ala Val Tyr Tyr Cys Gln His Ser Trp
                85                  90                  95

Glu Ile Pro Leu Thr Phe Gly Gln Gly Thr Lys Val Glu Ile Lys
            100                 105                 110

<210> SEQ ID NO 122
<211> LENGTH: 111
<212> TYPE: PRT
<213> ORGANISM: Artificial Sequence
<220> FEATURE:
<223> OTHER INFORMATION: Synthetic construct

<400> SEQUENCE: 122

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Thr Ser
            20                  25                  30

```
Thr Tyr Ser Tyr Met His Trp Tyr Gln Gln Lys Pro Gly Gln Ala Pro
            35                  40                  45

Arg Leu Leu Ile Tyr Tyr Ala Ser Asn Leu Glu Cys Gly Ile Pro Asp
 50                  55                  60

Arg Phe Ser Gly Ser Gly Ser Gly Thr Asp Phe Thr Leu Thr Ile Ser
 65                  70                  75                  80

Arg Leu Glu Pro Glu Asp Phe Ala Val Tyr Tyr Cys Gln His Ser Trp
                85                  90                  95

Glu Ile Pro Leu Thr Phe Gly Gln Gly Thr Lys Val Glu Ile Lys
               100                 105                 110

<210> SEQ ID NO 123
<211> LENGTH: 110
<212> TYPE: PRT
<213> ORGANISM: Mus musculus
<220> FEATURE:
<221> NAME/KEY: VARIANT
<222> LOCATION: 96
<223> OTHER INFORMATION: Xaa = Any Amino Acid

<400> SEQUENCE: 123

Asp Ile Val Leu Thr Gln Ser Pro Ala Ser Leu Ala Val Ser Leu Gly
 1               5                  10                  15

Gln Arg Ala Thr Ile Ser Tyr Arg Ala Ser Lys Ser Val Ser Thr Ser
                20                  25                  30

Gly Tyr Ser Tyr Met His Trp Asn Gln Gln Lys Pro Gly Gln Pro Pro
            35                  40                  45

Arg Leu Leu Ile Tyr Leu Val Ser Asn Leu Glu Ser Gly Val Pro Ala
 50                  55                  60

Arg Phe Ser Gly Ser Gly Glx Trp Asp Arg Leu His Pro Gln His Pro
 65                  70                  75                  80

Ser Cys Gly Gly Gly Gly Cys Cys Asn Leu Leu Leu Ser Ala His Xaa
                85                  90                  95

Gly Ala Tyr Thr Phe Gly Gly Gly Thr Lys Leu Glu Ile Lys
               100                 105                 110

<210> SEQ ID NO 124
<211> LENGTH: 114
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: 100
<223> OTHER INFORMATION: Xaa = Any Amino Acid

<400> SEQUENCE: 124

Asp Ile Val Met Thr Gln Ser Pro Leu Ser Leu Pro Val Thr Pro Gly
 1               5                  10                  15

Glu Pro Ala Ser Ile Ser Cys Arg Ala Ser Lys Ser Val Ser Thr Ser
                20                  25                  30

Gly Tyr Ser Tyr Met His Trp Tyr Leu Gln Lys Pro Gly Gln Ser Pro
            35                  40                  45

Gln Leu Leu Ile Tyr Leu Val Ser Asn Leu Glu Ser Gly Val Pro Asp
 50                  55                  60

Arg Phe Ser Gly Ser Gly Ser Gly Thr Asp Phe Thr Leu Lys Ile Ser
 65                  70                  75                  80

Arg Val Glu Ala Glu Asp Val Gly Val Tyr Tyr Cys Asn Leu Leu Leu
                85                  90                  95
```

Ser Ala His Xaa Gly Ala Tyr Thr Phe Gly Gln Gly Thr Lys Val Glu
            100                 105                 110

Ile Lys

<210> SEQ ID NO 125
<211> LENGTH: 114
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: 100
<223> OTHER INFORMATION: Xaa = Any Amino Acid

<400> SEQUENCE: 125

Asp Val Val Met Thr Gln Ser Pro Leu Ser Leu Pro Val Thr Leu Gly
1               5                   10                  15

Gln Pro Ala Ser Ile Ser Cys Arg Ala Ser Lys Ser Val Ser Thr Ser
            20                  25                  30

Gly Tyr Ser Tyr Met His Trp Phe Gln Gln Arg Pro Gly Gln Ser Pro
        35                  40                  45

Arg Arg Leu Ile Tyr Leu Val Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Asn Leu Leu Leu
                85                  90                  95

Ser Ala His Xaa Gly Ala Tyr Thr Phe Gly Gln Gly Thr Lys Val Glu
            100                 105                 110

Ile Lys

<210> SEQ ID NO 126
<211> LENGTH: 114
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: 100
<223> OTHER INFORMATION: Xaa = Any Amino Acid

<400> SEQUENCE: 126

Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Val Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Asn Leu Leu Leu
                85                  90                  95

Ser Ala His Xaa Gly Ala Tyr Thr Phe Gly Gln Gly Thr Lys Val Glu
            100                 105                 110

Ile Lys

<210> SEQ ID NO 127
<211> LENGTH: 114
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: 100
<223> OTHER INFORMATION: Xaa = Any Amino Acid

<400> SEQUENCE: 127

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Val Ser Thr Ser
            20                  25                  30

Gly Tyr Ser Tyr Met His Trp Tyr Gln Gln Lys Pro Gly Lys Ala Pro
        35                  40                  45

Lys Leu Leu Ile Tyr Leu Val Ser Asn Leu Glu Ser Gly Val Pro Ser
    50                  55                  60

Arg Phe Ser Gly Ser Gly Ser Gly Thr Asp Phe Thr Phe Thr Ile Ser
65                  70                  75                  80

Ser Leu Gln Pro Glu Asp Ile Ala Thr Tyr Tyr Cys Asn Leu Leu Leu
                85                  90                  95

Ser Ala His Xaa Gly Ala Tyr Thr Phe Gly Gln Gly Thr Lys Val Glu
                100                 105                 110

Ile Lys

<210> SEQ ID NO 128
<211> LENGTH: 114
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: 100
<223> OTHER INFORMATION: Xaa = Any Amino Acid

<400> SEQUENCE: 128

Asp Ile Gln Met Thr Gln Ser Pro Ser Thr Leu Ser Ala Ser Val Gly
1               5                   10                  15

Asp Arg Val Thr Ile Thr Cys Arg Ala Ser Lys Ser Val Ser Thr Ser
            20                  25                  30

Gly Tyr Ser Tyr Met His Trp Tyr Gln Gln Lys Pro Gly Lys Ala Pro
        35                  40                  45

Lys Leu Leu Ile Tyr Leu Val Ser Asn Leu Glu Ser Gly Val Pro Ser
    50                  55                  60

Arg Phe Ser Gly Ser Gly Ser Gly Thr Glu Phe Thr Leu Thr Ile Ser
65                  70                  75                  80

Ser Leu Gln Pro Asp Asp Phe Ala Thr Tyr Tyr Cys Asn Leu Leu Leu
                85                  90                  95

Ser Ala His Xaa Gly Ala Tyr Thr Phe Gly Gln Gly Thr Lys Val Glu
                100                 105                 110

Ile Lys

<210> SEQ ID NO 129
<211> LENGTH: 114
<212> TYPE: PRT

```
<213> ORGANISM: Artificial Sequence
<220> FEATURE:
<223> OTHER INFORMATION: Synthetic construct
<220> FEATURE:
<221> NAME/KEY: VARIANT
<222> LOCATION: 100
<223> OTHER INFORMATION: Xaa = Any Amino Acid

<400> SEQUENCE: 129

Asp Ile Gln Met Thr Gln Ser Pro Ser Leu Ser Ala Ser Val Gly
1               5                   10                  15

Asp Arg Val Thr Ile Thr Cys Arg Ala Ser Lys Ser Val Ser Thr Ser
            20                  25                  30

Gly Tyr Ser Tyr Met His Trp Tyr Gln Gln Lys Pro Gly Lys Ala Pro
            35                  40                  45

Lys Leu Leu Ile Tyr Leu Val Ser Asn Leu Glu Ser Gly Val Pro Ser
    50                  55                  60

Arg Phe Ser Gly Ser Gly Ser Gly Thr Asp Phe Thr Leu Thr Ile Ser
65              70                  75                  80

Ser Leu Gln Pro Glu Asp Phe Ala Thr Tyr Tyr Cys Asn Leu Leu Leu
                85                  90                  95

Ser Ala His Xaa Gly Ala Tyr Thr Phe Gly Gln Gly Thr Lys Val Glu
            100                 105                 110

Ile Lys

<210> SEQ ID NO 130
<211> LENGTH: 114
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: 100
<223> OTHER INFORMATION: Xaa = Any Amino Acid

<400> SEQUENCE: 130

Asp Ile Gln Leu Thr Gln Ser Pro Ser Phe Leu Ser Ala Ser Val Gly
1               5                   10                  15

Asp Arg Val Thr Ile Thr Cys Arg Ala Ser Lys Ser Val Ser Thr Ser
            20                  25                  30

Gly Tyr Ser Tyr Met His Trp Tyr Gln Gln Lys Pro Gly Lys Ala Pro
            35                  40                  45

Lys Leu Leu Ile Tyr Leu Val Ser Asn Leu Glu Ser Gly Val Pro Ser
    50                  55                  60

Arg Phe Ser Gly Ser Gly Ser Gly Thr Glu Phe Thr Leu Thr Ile Ser
65              70                  75                  80

Ser Leu Gln Pro Glu Asp Phe Ala Thr Tyr Tyr Cys Asn Leu Leu Leu
                85                  90                  95

Ser Ala His Xaa Gly Ala Tyr Thr Phe Gly Gln Gly Thr Lys Val Glu
            100                 105                 110

Ile Lys

<210> SEQ ID NO 131
<211> LENGTH: 114
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
```

<222> LOCATION: 100
<223> OTHER INFORMATION: Xaa = Any Amino Acid

<400> SEQUENCE: 131

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Ser Val Ser Thr Ser
                20                  25                  30

Gly Tyr Ser Tyr Met His Trp Tyr Gln Gln Lys Pro Gly Gln Ala Pro
            35                  40                  45

Arg Leu Leu Ile Tyr Leu Val Ser Asn Leu Glu Ser Gly Ile Pro Ala
        50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Asn Leu Leu
                85                  90                  95

Ser Ala His Xaa Gly Ala Tyr Thr Phe Gly Gln Gly Thr Lys Val Glu
            100                 105                 110

Ile Lys
```

<210> SEQ ID NO 132
<211> LENGTH: 114
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: 100
<223> OTHER INFORMATION: Xaa = Any Amino Acid

<400> SEQUENCE: 132

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Lys Ser Val Ser Thr Ser
                20                  25                  30

Gly Tyr Ser Tyr Met His Trp Tyr Gln Gln Lys Pro Gly Gln Ala Pro
            35                  40                  45

Arg Leu Leu Ile Tyr Leu Val Ser Asn Leu Glu Ser Gly Ile Pro Ala
        50                  55                  60

Arg Phe Ser Gly Ser Gly Ser Gly Thr Glu Phe Thr Leu Thr Ile Ser
65                  70                  75                  80

Ser Leu Gln Ser Glu Asp Phe Ala Val Tyr Tyr Cys Asn Leu Leu
                85                  90                  95

Ser Ala His Xaa Gly Ala Tyr Thr Phe Gly Gln Gly Thr Lys Val Glu
            100                 105                 110

Ile Lys
```

<210> SEQ ID NO 133
<211> LENGTH: 114
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: 100
<223> OTHER INFORMATION: Xaa = Any Amino Acid

<400> SEQUENCE: 133

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Lys Ser Val Ser Thr Ser
            20                  25                  30

Gly Tyr Ser Tyr Met His Trp Tyr Gln Gln Lys Pro Gly Gln Ala Pro
        35                  40                  45

Arg Leu Leu Ile Tyr Leu Val Ser Asn Leu Glu Ser Gly Ile Pro Asp
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Asn Leu Leu Leu
                85                  90                  95

Ser Ala His Xaa Gly Ala Tyr Thr Phe Gly Gln Gly Thr Lys Val Glu
            100                 105                 110

Ile Lys

<210> SEQ ID NO 134
<211> LENGTH: 111
<212> TYPE: PRT
<213> ORGANISM: Mus musculus

<400> SEQUENCE: 134

Asp Phe Gln Ile Gln Gln Ser Leu Ala Ser Leu Val Val Ser Met Gly
1               5                   10                  15

Gln Arg Ala Ala Ile Ser Phe Arg Ala Ser Lys Arg Val Ser Thr Ser
            20                  25                  30

Val His Ser Tyr Met His Trp Tyr Gln Gln Lys Pro Gly Gln Pro Pro
        35                  40                  45

Lys Leu Ile Ile Tyr Leu Ala Ser Ser Leu Glu Ser Gly Val Arg Ala
    50                  55                  60

Arg Phe Ser Gly Glx Gly Trp Gly Thr Asp Phe Thr Leu Asn Ile His
65                  70                  75                  80

Pro Val Glu Glu Glu Asp Gly Ala Thr Tyr Tyr Cys Gln His Ser Arg
                85                  90                  95

Glu Val Pro Leu Thr Phe Gly Gly Gly Thr Lys Leu Glu Met Lys
            100                 105                 110

<210> SEQ ID NO 135
<211> LENGTH: 111
<212> TYPE: PRT
<213> ORGANISM: Artificial Sequence
<220> FEATURE:
<223> OTHER INFORMATION: Synthetic construct

<400> SEQUENCE: 135

Asp Ile Val Met Thr Gln Ser Pro Leu Ser Leu Pro Val Thr Pro Gly
1               5                   10                  15

Glu Pro Ala Ser Ile Ser Cys Arg Ala Ser Lys Arg Val Ser Thr Ser
            20                  25                  30

Val His Ser Tyr Met His Trp Tyr Leu Gln Lys Pro Gly Gln Ser Pro
        35                  40                  45

Gln Leu Leu Ile Tyr Leu Ala Ser Ser Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Arg
                85                  90                  95
```

```
Glu Val Pro Leu Thr Phe Gly Gln Gly Thr Lys Val Glu Ile Lys
            100                 105                 110
```

<210> SEQ ID NO 136
<211> LENGTH: 111
<212> TYPE: PRT
<213> ORGANISM: Artificial Sequence
<220> FEATURE:
<223> OTHER INFORMATION: Synthetic construct

<400> SEQUENCE: 136

```
Asp Val Val Met Thr Gln Ser Pro Leu Ser Leu Pro Val Thr Leu Gly
1               5                   10                  15

Gln Pro Ala Ser Ile Ser Cys Arg Ala Ser Lys Arg Val Ser Thr Ser
            20                  25                  30

Val His Ser Tyr Met His Trp Phe Gln Gln Arg Pro Gly Gln Ser Pro
        35                  40                  45

Arg Arg Leu Ile Tyr Leu Ala Ser Ser Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Arg
                85                  90                  95

Glu Val Pro Leu Thr Phe Gly Gln Gly Thr Lys Val Glu Ile Lys
            100                 105                 110
```

<210> SEQ ID NO 137
<211> LENGTH: 111
<212> TYPE: PRT
<213> ORGANISM: Artificial Sequence
<220> FEATURE:
<223> OTHER INFORMATION: Synthetic construct

<400> SEQUENCE: 137

```
Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Arg Val Ser Thr Ser
            20                  25                  30

Val His Ser Tyr Met His Trp Tyr Gln Gln Lys Pro Gly Gln Pro Pro
        35                  40                  45

Lys Leu Leu Ile Tyr Leu Ala Ser Ser Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Arg
                85                  90                  95

Glu Val Pro Leu Thr Phe Gly Gln Gly Thr Lys Val Glu Ile Lys
            100                 105                 110
```

<210> SEQ ID NO 138
<211> LENGTH: 111
<212> TYPE: PRT
<213> ORGANISM: Artificial Sequence
<220> FEATURE:
<223> OTHER INFORMATION: Synthetic construct

<400> SEQUENCE: 138

```
Asp Ile Gln Met Thr Gln Ser Pro Ser Thr Leu Ser Ala Ser Val Gly
1               5                   10                  15
```

```
Asp Arg Val Thr Ile Thr Cys Arg Ala Ser Lys Arg Val Ser Thr Ser
             20                  25                  30

Val His Ser Tyr Met His Trp Tyr Gln Gln Lys Pro Gly Lys Ala Pro
         35                  40                  45

Lys Leu Leu Ile Tyr Leu Ala Ser Ser Leu Glu Ser Gly Val Pro Ser
     50                  55                  60

Arg Phe Ser Gly Ser Gly Ser Gly Thr Glu Phe Thr Leu Thr Ile Ser
 65                  70                  75                  80

Ser Leu Gln Pro Asp Asp Phe Ala Thr Tyr Tyr Cys Gln His Ser Arg
                 85                  90                  95

Glu Val Pro Leu Thr Phe Gly Gln Gly Thr Lys Val Glu Ile Lys
                100                 105                 110
```

<210> SEQ ID NO 139
<211> LENGTH: 111
<212> TYPE: PRT
<213> ORGANISM: Artificial Sequence
<220> FEATURE:
<223> OTHER INFORMATION: Synthetic construct

<400> SEQUENCE: 139

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Lys Arg Val Ser Thr Ser
             20                  25                  30

Val His Ser Tyr Met His Trp Tyr Gln Gln Lys Pro Gly Lys Ala Pro
         35                  40                  45

Lys Leu Leu Ile Tyr Leu Ala Ser Ser Leu Glu Ser Gly Val Pro Ser
     50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln His Ser Arg
                 85                  90                  95

Glu Val Pro Leu Thr Phe Gly Gln Gly Thr Lys Val Glu Ile Lys
                100                 105                 110
```

<210> SEQ ID NO 140
<211> LENGTH: 111
<212> TYPE: PRT
<213> ORGANISM: Artificial Sequence
<220> FEATURE:
<223> OTHER INFORMATION: Synthetic construct

<400> SEQUENCE: 140

```
Asp Ile Gln Leu Thr Gln Ser Pro Ser Phe Leu Ser Ala Ser Val Gly
 1               5                  10                  15

Asp Arg Val Thr Ile Thr Cys Arg Ala Ser Lys Arg Val Ser Thr Ser
             20                  25                  30

Val His Ser Tyr Met His Trp Tyr Gln Gln Lys Pro Gly Lys Ala Pro
         35                  40                  45

Lys Leu Leu Ile Tyr Leu Ala Ser Ser Leu Glu Ser Gly Val Pro Ser
     50                  55                  60

Arg Phe Ser Gly Ser Gly Ser Gly Thr Glu Phe Thr Leu Thr Ile Ser
 65                  70                  75                  80

Ser Leu Gln Pro Glu Asp Phe Ala Thr Tyr Tyr Cys Gln His Ser Arg
                 85                  90                  95

Glu Val Pro Leu Thr Phe Gly Gln Gly Thr Lys Val Glu Ile Lys
                100                 105                 110
```

<210> SEQ ID NO 141
<211> LENGTH: 111
<212> TYPE: PRT
<213> ORGANISM: Artificial Sequence
<220> FEATURE:
<223> OTHER INFORMATION: Synthetic construct

<400> SEQUENCE: 141

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Arg Val Ser Thr Ser
            20                  25                  30

Val His Ser Tyr Met His Trp Tyr Gln Gln Lys Pro Gly Lys Ala Pro
        35                  40                  45

Lys Leu Leu Ile Tyr Leu Ala Ser Ser Leu Glu Ser Gly Val Pro Ser
    50                  55                  60

Arg Phe Ser Gly Ser Gly Ser Gly Thr Asp Phe Thr Phe Thr Ile Ser
65                  70                  75                  80

Ser Leu Gln Pro Glu Asp Ile Ala Thr Tyr Tyr Cys Gln His Ser Arg
                85                  90                  95

Glu Val Pro Leu Thr Phe Gly Gln Gly Thr Lys Val Glu Ile Lys
            100                 105                 110
```

<210> SEQ ID NO 142
<211> LENGTH: 111
<212> TYPE: PRT
<213> ORGANISM: Artificial Sequence
<220> FEATURE:
<223> OTHER INFORMATION: Synthetic construct

<400> SEQUENCE: 142

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Arg Val Ser Thr Ser
            20                  25                  30

Val His Ser Tyr Met His Trp Tyr Gln Gln Lys Pro Gly Gln Ala Pro
        35                  40                  45

Arg Leu Leu Ile Tyr Leu Ala Ser Ser Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Glu Val Pro Leu Thr Phe Gly Gln Gly Thr Lys Val Glu Ile Lys
            100                 105                 110
```

<210> SEQ ID NO 143
<211> LENGTH: 111
<212> TYPE: PRT
<213> ORGANISM: Artificial Sequence
<220> FEATURE:
<223> OTHER INFORMATION: Synthetic construct

<400> SEQUENCE: 143

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Lys Arg Val Ser Thr Ser
            20                  25                  30
```

Val His Ser Tyr Met His Trp Tyr Gln Gln Lys Pro Gly Gln Ala Pro
            35                  40                  45

Arg Leu Leu Ile Tyr Leu Ala Ser Ser Leu Glu Ser Gly Ile Pro Asp
 50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln His Ser Arg
                85                  90                  95

Glu Val Pro Leu Thr Phe Gly Gln Gly Thr Lys Val Glu Ile Lys
                100                 105                 110

<210> SEQ ID NO 144
<211> LENGTH: 111
<212> TYPE: PRT
<213> ORGANISM: Artificial Sequence
<220> FEATURE:
<223> OTHER INFORMATION: Synthetic construct

<400> SEQUENCE: 144

Glu Ile Val Met Thr Gln Ser Pro Ala Thr Leu Ser Val Ser Pro Gly
1               5                   10                  15

Glu Arg Ala Thr Leu Ser Cys Arg Ala Ser Lys Arg Val Ser Thr Ser
            20                  25                  30

Val His Ser Tyr Met His Trp Tyr Gln Gln Lys Pro Gly Gln Ala Pro
            35                  40                  45

Arg Leu Leu Ile Tyr Leu Ala Ser Ser Leu Glu Ser Gly Ile Pro Ala
 50                  55                  60

Arg Phe Ser Gly Ser Gly Ser Gly Thr Glu Phe Thr Leu Thr Ile Ser
65                  70                  75                  80

Ser Leu Gln Ser Glu Asp Phe Ala Val Tyr Tyr Cys Gln His Ser Arg
                85                  90                  95

Glu Val Pro Leu Thr Phe Gly Gln Gly Thr Lys Val Glu Ile Lys
                100                 105                 110

<210> SEQ ID NO 145
<211> LENGTH: 107
<212> TYPE: PRT
<213> ORGANISM: Artificial Sequence
<220> FEATURE:
<223> OTHER INFORMATION: Synthetic construct

<400> SEQUENCE: 145

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asp Ile Asn Lys Tyr
            20                  25                  30

Leu Ser Trp Tyr Gln Gln Lys Pro Gly Lys Ala Pro Lys Leu Leu Ile
            35                  40                  45

Tyr Arg Ala Asn Arg Leu Val Asp Gly Val Pro Ser Arg Phe Ser Gly
 50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Leu
                85                  90                  95

Thr Phe Gly Gln Gly Thr Lys Val Glu Ile Lys
                100                 105

<210> SEQ ID NO 146

```
<211> LENGTH: 107
<212> TYPE: PRT
<213> ORGANISM: Artificial Sequence
<220> FEATURE:
<223> OTHER INFORMATION: Synthetic construct

<400> SEQUENCE: 146

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Asp Ile Asn Lys Tyr
            20                  25                  30

Leu Ser Trp Tyr Gln Gln Lys Pro Gly Gln Ala Pro Arg Leu Leu Ile
        35                  40                  45

Tyr Arg Ala Asn Arg Leu Val Asp Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Leu Gln Tyr Asp Glu Phe Pro Leu
                85                  90                  95

Thr Phe Gly Gln Gly Thr Lys Val Glu Ile Lys
            100                 105

<210> SEQ ID NO 147
<211> LENGTH: 107
<212> TYPE: PRT
<213> ORGANISM: Artificial Sequence
<220> FEATURE:
<223> OTHER INFORMATION: Synthetic construct

<400> SEQUENCE: 147

Glu Ile Val Leu Thr Gln Ser Pro Gly Thr Leu Ser Leu Ser Pro Gly
1               5                   10                  15

Glu Arg Ala Thr Leu Ser Cys Lys Ala Ser Gln Asp Ile Asn Lys Tyr
            20                  25                  30

Leu Ser Trp Tyr Gln Gln Lys Pro Gly Gln Ala Pro Arg Leu Leu Ile
        35                  40                  45

Tyr Arg Ala Asn Arg Leu Val Asp Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Leu Gln Tyr Asp Glu Phe Pro Leu
                85                  90                  95

Thr Phe Gly Gln Gly Thr Lys Val Glu Ile Lys
            100                 105

<210> SEQ ID NO 148
<211> LENGTH: 107
<212> TYPE: PRT
<213> ORGANISM: Artificial Sequence
<220> FEATURE:
<223> OTHER INFORMATION: Synthetic construct

<400> SEQUENCE: 148

Asp Ile Val Met Thr Gln Ser Pro Leu Ser Leu Pro Val Thr Pro Gly
1               5                   10                  15

Glu Pro Ala Ser Ile Ser Cys Lys Ala Ser Gln Asp Ile Asn Lys Tyr
            20                  25                  30

Leu Ser Trp Tyr Leu Gln Lys Pro Gly Gln Ser Pro Gln Leu Leu Ile
        35                  40                  45
```

-continued

Tyr Arg Ala Asn Arg Leu Val Asp Gly Val Pro Asp Arg Phe Ser Gly
    50                  55                  60

Ser Gly Ser Gly Thr Asp Phe Thr Leu Lys Ile Ser Arg Val Glu Ala
65                  70                  75                  80

Glu Asp Val Gly Val Tyr Tyr Cys Leu Gln Tyr Asp Glu Phe Pro Leu
                85                  90                  95

Thr Phe Gly Gln Gly Thr Lys Val Glu Ile Lys
            100                 105

<210> SEQ ID NO 149
<211> LENGTH: 107
<212> TYPE: PRT
<213> ORGANISM: Artificial Sequence
<220> FEATURE:
<223> OTHER INFORMATION: Synthetic construct

<400> SEQUENCE: 149

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Asp Ile Asn Lys Tyr
                20                  25                  30

Leu Ser Trp Tyr Gln Gln Lys Pro Gly Gln Pro Pro Lys Leu Leu Ile
            35                  40                  45

Tyr Arg Ala Asn Arg Leu Val Asp Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Leu Gln Tyr Asp Glu Phe Pro Leu
                85                  90                  95

Thr Phe Gly Gln Gly Thr Lys Val Glu Ile Lys
            100                 105

<210> SEQ ID NO 150
<211> LENGTH: 107
<212> TYPE: PRT
<213> ORGANISM: Artificial Sequence
<220> FEATURE:
<223> OTHER INFORMATION: Synthetic construct

<400> SEQUENCE: 150

Asp Val Val Met Thr Gln Ser Pro Leu Ser Leu Pro Val Thr Leu Gly
1               5                   10                  15

Gln Pro Ala Ser Ile Ser Cys Lys Ala Ser Gln Asp Ile Asn Lys Tyr
                20                  25                  30

Leu Ser Trp Phe Gln Gln Arg Pro Gly Gln Ser Pro Arg Arg Leu Ile
            35                  40                  45

Tyr Arg Ala Asn Arg Leu Val Asp Gly Val Pro Asp Arg Phe Ser Gly
    50                  55                  60

Ser Gly Ser Gly Thr Asp Phe Thr Leu Lys Ile Ser Arg Val Glu Ala
65                  70                  75                  80

Glu Asp Val Gly Val Tyr Tyr Cys Leu Gln Tyr Asp Glu Phe Pro Leu
                85                  90                  95

Thr Phe Gly Gln Gly Thr Lys Val Glu Ile Lys
            100                 105

<210> SEQ ID NO 151
<211> LENGTH: 111
<212> TYPE: PRT
<213> ORGANISM: Artificial Sequence

```
<220> FEATURE:
<223> OTHER INFORMATION: Synthetic construct

<400> SEQUENCE: 151

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Thr Ser
            20                  25                  30

Thr Tyr Ser Tyr Met His Trp Tyr Gln Gln Lys Pro Gly Gln Ala Pro
        35                  40                  45

Arg Leu Leu Ile Tyr Tyr Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Arg Ser Trp
                85                  90                  95

Glu Ile Pro Leu Thr Phe Gly Gln Gly Thr Lys Val Glu Ile Lys
            100                 105                 110

<210> SEQ ID NO 152
<211> LENGTH: 111
<212> TYPE: PRT
<213> ORGANISM: Artificial Sequence
<220> FEATURE:
<223> OTHER INFORMATION: Synthetic construct

<400> SEQUENCE: 152

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Thr Ser
            20                  25                  30

Thr Tyr Ser Tyr Met His Trp Tyr Gln Gln Lys Pro Gly Gln Ala Pro
        35                  40                  45

Arg Leu Leu Ile Tyr Tyr Ala Ser Asn Leu Glu Ser Gly Ile Pro Ala
    50                  55                  60

Arg Phe Ser Gly Ser Gly Ser Gly Thr Glu Phe Thr Leu Thr Ile Ser
65                  70                  75                  80

Ser Leu Gln Ser Glu Asp Phe Ala Val Tyr Tyr Cys Gln Arg Ser Trp
                85                  90                  95

Glu Ile Pro Leu Thr Phe Gly Gln Gly Thr Lys Val Glu Ile Lys
            100                 105                 110

<210> SEQ ID NO 153
<211> LENGTH: 111
<212> TYPE: PRT
<213> ORGANISM: Artificial Sequence
<220> FEATURE:
<223> OTHER INFORMATION: Synthetic construct

<400> SEQUENCE: 153

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Thr Ser
            20                  25                  30

Thr Tyr Ser Tyr Met His Trp Tyr Gln Gln Lys Pro Gly Gln Ala Pro
        35                  40                  45

Arg Leu Leu Ile Tyr Tyr Ala Ser Asn Leu Glu Ser Gly Ile Pro Asp
    50                  55                  60
```

```
Arg Phe Ser Gly Ser Gly Ser Gly Thr Asp Phe Thr Leu Thr Ile Ser
 65                  70                  75                  80

Arg Leu Glu Pro Glu Asp Phe Ala Val Tyr Tyr Cys Gln Arg Ser Trp
                 85                  90                  95

Glu Ile Pro Leu Thr Phe Gly Gln Gly Thr Lys Val Glu Ile Lys
            100                 105                 110

<210> SEQ ID NO 154
<211> LENGTH: 117
<212> TYPE: PRT
<213> ORGANISM: Mus musculus

<400> SEQUENCE: 154

Glu Val Gln Leu Gln Gln Ser Gly Pro Glu Leu Val Lys Pro Gly Ala
 1               5                  10                  15

Ser Val Lys Ile Ser Cys Lys Ala Ser Gly Tyr Thr Phe Thr Asp Tyr
             20                  25                  30

Asn Leu His Trp Val Lys Leu Ser His Gly Lys Ser Leu Glu Trp Ile
         35                  40                  45

Gly Phe Ile Tyr Pro Ser Asn Gly Ile Thr Gly Tyr Asn Gln Lys Phe
     50                  55                  60

Lys Asn Lys Ala Thr Leu Thr Val Asp Asn Ser Ser Thr Ala Tyr
 65                  70                  75                  80

Met Glu Leu Arg Ser Leu Thr Ser Glu Asp Ser Ala Val Tyr Tyr Cys
                 85                  90                  95

Ala Arg Ser Thr Val Asp Tyr Phe Asp Tyr Trp Gly Gln Gly Thr Thr
            100                 105                 110

Leu Thr Val Ser Ser
        115

<210> SEQ ID NO 155
<211> LENGTH: 117
<212> TYPE: PRT
<213> ORGANISM: Artificial Sequence
<220> FEATURE:
<223> OTHER INFORMATION: Synthetic construct

<400> SEQUENCE: 155

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Thr Phe Thr Asp Tyr
             20                  25                  30

Asn Leu His Trp Val Arg Gln Ala Pro Gly Lys Gly Leu Glu Trp Ile
         35                  40                  45

Gly Phe Ile Tyr Pro Ser Asn Gly Ile Thr Gly Tyr Asn Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Ser Thr Val Asp Tyr Phe Asp Tyr Trp Gly Gln Gly Thr Leu
            100                 105                 110

Val Thr Val Ser Ser
        115

<210> SEQ ID NO 156
<211> LENGTH: 117
<212> TYPE: PRT
```

<213> ORGANISM: Artificial Sequence
<220> FEATURE:
<223> OTHER INFORMATION: Synthetic construct

<400> SEQUENCE: 156

```
Gln Val Gln Leu Val Glu Ser Gly Gly Gly Val Val Gln Pro Gly Arg
1               5                   10                  15

Ser Leu Arg Leu Ser Cys Ala Ala Ser Gly Tyr Thr Phe Thr Asp Tyr
            20                  25                  30

Asn Leu His Trp Val Arg Gln Ala Pro Gly Lys Gly Leu Glu Trp Ile
        35                  40                  45

Gly Phe Ile Tyr Pro Ser Asn Gly Ile Thr Gly Tyr Asn Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Thr Val Asp Tyr Phe Asp Tyr Trp Gly Gln Gly Thr Leu
            100                 105                 110

Val Thr Val Ser Ser
        115
```

<210> SEQ ID NO 157
<211> LENGTH: 117
<212> TYPE: PRT
<213> ORGANISM: Artificial Sequence
<220> FEATURE:
<223> OTHER INFORMATION: Synthetic construct

<400> SEQUENCE: 157

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Thr Phe Thr Asp Tyr
            20                  25                  30

Asn Leu His Trp Ile Arg Gln Pro Pro Gly Lys Gly Leu Glu Trp Ile
        35                  40                  45

Gly Phe Ile Tyr Pro Ser Asn Gly Ile Thr Gly Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Thr Val Asp Tyr Phe Asp Tyr Trp Gly Gln Gly Thr Leu
            100                 105                 110

Val Thr Val Ser Ser
        115
```

<210> SEQ ID NO 158
<211> LENGTH: 117
<212> TYPE: PRT
<213> ORGANISM: Artificial Sequence
<220> FEATURE:
<223> OTHER INFORMATION: Synthetic construct

<400> SEQUENCE: 158

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Tyr Thr Phe Thr Asp Tyr
            20                  25                  30
```

Asn Leu His Trp Val Arg Gln Ala Pro Gly Lys Gly Leu Glu Trp Ile
            35                  40                  45

Gly Phe Ile Tyr Pro Ser Asn Gly Ile Thr Gly Tyr Asn Ala Pro Val
        50                  55                  60

Lys Gly Arg Phe Thr Ile Ser Arg Asp Asp Ser Lys Asn Thr Leu Tyr
65                  70                  75                  80

Leu Gln Met Asn Ser Leu Lys Thr Glu Asp Thr Ala Val Tyr Tyr Cys
                85                  90                  95

Ala Arg Ser Thr Val Asp Tyr Phe Asp Tyr Trp Gly Gln Gly Thr Leu
            100                 105                 110

Val Thr Val Ser Ser
        115

<210> SEQ ID NO 159
<211> LENGTH: 117
<212> TYPE: PRT
<213> ORGANISM: Artificial Sequence
<220> FEATURE:
<223> OTHER INFORMATION: Synthetic construct

<400> SEQUENCE: 159

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Thr Phe Thr Asp Tyr
            20                  25                  30

Asn Leu His Trp Ile Arg Gln Pro Pro Gly Lys Gly Leu Glu Trp Ile
            35                  40                  45

Gly Phe Ile Tyr Pro Ser Asn Gly Ile Thr Gly Tyr Asn Pro Ser Leu
        50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Thr Val Asp Tyr Phe Asp Tyr Trp Gly Gln Gly Thr Leu
            100                 105                 110

Val Thr Val Ser Ser
        115

<210> SEQ ID NO 160
<211> LENGTH: 120
<212> TYPE: PRT
<213> ORGANISM: Artificial Sequence
<220> FEATURE:
<223> OTHER INFORMATION: Synthetic construct

<400> SEQUENCE: 160

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Cys Met Asn Trp Val Arg Gln Ala Pro Gly Lys Gly Leu Glu Trp Val
            35                  40                  45

Ala Glu Ile Arg Leu Lys Ser Asn Asn Tyr Val Thr Asn Tyr Val Asp
        50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr

-continued

```
                85                   90                  95
Tyr Cys Thr Arg Asp Gly Tyr Tyr Val Pro Phe Ala Tyr Trp Gly Gln
            100                 105                 110
Gly Thr Leu Val Thr Val Ser Ser
        115                 120

<210> SEQ ID NO 161
<211> LENGTH: 120
<212> TYPE: PRT
<213> ORGANISM: Artificial Sequence
<220> FEATURE:
<223> OTHER INFORMATION: Synthetic construct

<400> SEQUENCE: 161

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Cys Met Asn Trp Val Arg Gln Ala Pro Gly Lys Gly Leu Glu Trp Val
        35                  40                  45

Ala Glu Ile Arg Leu Lys Ser Asn Asn Tyr Val Thr Asn Tyr Val Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Thr Arg Asp Gly Tyr Tyr Val Pro Phe Ala Tyr Trp Gly Gln
            100                 105                 110

Gly Thr Leu Val Thr Val Ser Ser
        115                 120

<210> SEQ ID NO 162
<211> LENGTH: 120
<212> TYPE: PRT
<213> ORGANISM: Artificial Sequence
<220> FEATURE:
<223> OTHER INFORMATION: Synthetic construct

<400> SEQUENCE: 162

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Cys Met Asn Trp Val Arg Gln Ala Pro Gly Lys Gly Leu Glu Trp Val
        35                  40                  45

Ala Glu Ile Arg Leu Lys Ser Asn Asn Tyr Val Thr Asn Tyr Val Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Thr Arg Asp Gly Tyr Tyr Val Pro Phe Ala Tyr Trp Gly Gln
            100                 105                 110

Gly Thr Leu Val Thr Val Ser Ser
        115                 120

<210> SEQ ID NO 163
<211> LENGTH: 120
```

<212> TYPE: PRT
<213> ORGANISM: Artificial Sequence
<220> FEATURE:
<223> OTHER INFORMATION: Synthetic construct

<400> SEQUENCE: 163

Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Ser Asn Tyr
            20                  25                  30

Cys Met Asn Trp Val Arg Gln Ala Pro Gly Gln Gly Leu Glu Trp Val
        35                  40                  45

Ala Glu Ile Arg Leu Lys Ser Asn Asn Tyr Val Thr Asn Tyr Val Gln
    50                  55                  60

Lys Phe Gln Gly Arg Val Thr Ile Thr Ala Asp Glu Ser Thr Ser Thr
65                  70                  75                  80

Ala Tyr Met Glu Leu Ser Ser Leu Arg Ser Glu Asp Thr Ala Val Tyr
                85                  90                  95

Tyr Cys Thr Arg Asp Gly Tyr Tyr Val Pro Phe Ala Tyr Trp Gly Gln
            100                 105                 110

Gly Thr Leu Val Thr Val Ser Ser
        115                 120

<210> SEQ ID NO 164
<211> LENGTH: 120
<212> TYPE: PRT
<213> ORGANISM: Artificial Sequence
<220> FEATURE:
<223> OTHER INFORMATION: Synthetic construct

<400> SEQUENCE: 164

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Asn Tyr
            20                  25                  30

Cys Met Asn Trp Val Arg Gln Ala Pro Gly Gln Gly Leu Glu Trp Val
        35                  40                  45

Ala Glu Ile Arg Leu Lys Ser Asn Asn Tyr Val Thr Asn Tyr Val Gln
    50                  55                  60

Lys Phe Gln Gly Arg Val Thr Met Thr Arg Asp Thr Ser Thr Ser Thr
65                  70                  75                  80

Val Tyr Met Glu Leu Ser Ser Leu Arg Ser Glu Asp Thr Ala Val Tyr
                85                  90                  95

Tyr Cys Thr Arg Asp Gly Tyr Tyr Val Pro Phe Ala Tyr Trp Gly Gln
            100                 105                 110

Gly Thr Leu Val Thr Val Ser Ser
        115                 120

<210> SEQ ID NO 165
<211> LENGTH: 120
<212> TYPE: PRT
<213> ORGANISM: Artificial Sequence
<220> FEATURE:
<223> OTHER INFORMATION: Synthetic construct

<400> SEQUENCE: 165

Glu Val Gln Leu Val Gln Ser Gly Ala Glu Val Lys Lys Pro Gly Glu
1               5                   10                  15

Ser Leu Lys Ile Ser Cys Lys Gly Ser Gly Phe Thr Phe Ser Asn Tyr

```
            20                  25                  30
Cys Met Asn Trp Val Arg Gln Met Pro Gly Lys Gly Leu Glu Trp Val
            35                  40                  45

Ala Glu Ile Arg Leu Lys Ser Asn Asn Tyr Val Thr Asn Tyr Val Pro
    50                  55                  60

Ser Phe Gln Gly Gln Val Thr Ile Ser Ala Asp Lys Ser Ile Ser Thr
 65                  70                  75                  80

Ala Tyr Leu Gln Trp Ser Ser Leu Lys Ala Ser Asp Thr Ala Met Tyr
                85                  90                  95

Tyr Cys Thr Arg Asp Gly Tyr Tyr Val Pro Phe Ala Tyr Trp Gly Gln
            100                 105                 110

Gly Thr Leu Val Thr Val Ser Ser
            115                 120

<210> SEQ ID NO 166
<211> LENGTH: 120
<212> TYPE: PRT
<213> ORGANISM: Artificial Sequence
<220> FEATURE:
<223> OTHER INFORMATION: Synthetic construct

<400> SEQUENCE: 166

Gln Val Gln Leu Gln Glu Ser Gly Pro Gly Leu Val Lys Pro Ser Glu
 1               5                  10                  15

Thr Leu Ser Leu Thr Cys Thr Val Ser Gly Phe Thr Phe Ser Asn Tyr
            20                  25                  30

Cys Met Asn Trp Ile Arg Gln Pro Pro Gly Lys Gly Leu Glu Trp Val
            35                  40                  45

Ala Glu Ile Arg Leu Lys Ser Asn Asn Tyr Val Thr Asn Tyr Val Pro
    50                  55                  60

Ser Leu Lys Ser Arg Val Thr Ile Ser Val Asp Thr Ser Lys Asn Gln
 65                  70                  75                  80

Phe Ser Leu Lys Leu Ser Ser Val Thr Ala Ala Asp Thr Ala Val Tyr
                85                  90                  95

Tyr Cys Thr Arg Asp Gly Tyr Tyr Val Pro Phe Ala Tyr Trp Gly Gln
            100                 105                 110

Gly Thr Leu Val Thr Val Ser Ser
            115                 120

<210> SEQ ID NO 167
<211> LENGTH: 120
<212> TYPE: PRT
<213> ORGANISM: Artificial Sequence
<220> FEATURE:
<223> OTHER INFORMATION: Synthetic construct

<400> SEQUENCE: 167

Gln Leu Gln Leu Gln Glu Ser Gly Pro Gly Leu Val Lys Pro Ser Glu
 1               5                  10                  15

Thr Leu Ser Leu Thr Cys Thr Val Ser Gly Phe Thr Phe Ser Asn Tyr
            20                  25                  30

Cys Met Asn Trp Ile Arg Gln Pro Pro Gly Lys Gly Leu Glu Trp Val
            35                  40                  45

Ala Glu Ile Arg Leu Lys Ser Asn Asn Tyr Val Thr Asn Tyr Val Pro
    50                  55                  60

Ser Leu Lys Ser Arg Val Thr Ile Ser Val Asp Thr Ser Lys Asn Gln
 65                  70                  75                  80
```

```
Phe Ser Leu Lys Leu Ser Ser Val Thr Ala Ala Asp Thr Ala Val Tyr
                85                  90                  95
Tyr Cys Thr Arg Asp Gly Tyr Tyr Val Pro Phe Ala Tyr Trp Gly Gln
            100                 105                 110
Gly Thr Leu Val Thr Val Ser Ser
        115                 120

<210> SEQ ID NO 168
<211> LENGTH: 120
<212> TYPE: PRT
<213> ORGANISM: Mus musculus

<400> SEQUENCE: 168

Gln Val Gln Leu Gln Gln Ser Gly Ser Glu Leu Val Arg Pro Gly Ala
1               5                   10                  15
Ser Val Lys Leu Ser Cys Lys Ala Ser Gly Tyr Thr Phe Thr Ser Tyr
            20                  25                  30
Trp Met His Trp Val Lys Gln Arg Pro Gly Gln Gly Leu Glu Trp Ile
        35                  40                  45
Gly Asn Ile Tyr Pro Gly Ser Ile Ser Ser Asn Tyr Asp Glu Lys Phe
    50                  55                  60
Lys Asn Lys Ala Thr Leu Thr Val Asp Thr Ser Ser Thr Ala Tyr
65                  70                  75                  80
Met Gln Leu Ser Ser Leu Thr Ser Glu Asp Ser Ala Val Tyr Phe Cys
                85                  90                  95
Thr Arg Gly His Tyr Gly Ser Tyr Leu Thr Phe Asp Tyr Trp Gly His
            100                 105                 110
Gly Thr Thr Leu Thr Val Ser Ser
        115                 120

<210> SEQ ID NO 169
<211> LENGTH: 120
<212> TYPE: PRT
<213> ORGANISM: Artificial Sequence
<220> FEATURE:
<223> OTHER INFORMATION: Synthetic construct

<400> SEQUENCE: 169

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Trp Met His Trp Val Arg Gln Ala Pro Gly Gln Gly Leu Glu Trp Ile
        35                  40                  45
Gly Asn Ile Tyr Pro Gly Ser Ile Ser Ser Asn Tyr Asp Gln Lys Phe
    50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Thr Arg Gly His Tyr Gly Ser Tyr Leu Thr Phe Asp Tyr Trp Gly Gln
            100                 105                 110
Gly Thr Leu Val Thr Val Ser Ser
        115                 120

<210> SEQ ID NO 170
<211> LENGTH: 120
<212> TYPE: PRT
```

```
<213> ORGANISM: Artificial Sequence
<220> FEATURE:
<223> OTHER INFORMATION: Synthetic construct

<400> SEQUENCE: 170

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Thr Ser Tyr
            20                  25                  30

Trp Met His Trp Val Arg Gln Met Pro Gly Lys Gly Leu Glu Trp Ile
        35                  40                  45

Gly Asn Ile Tyr Pro Gly Ser Ile Ser Ser Asn Tyr Asp Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Thr Arg Gly His Tyr Gly Ser Tyr Leu Thr Phe Asp Tyr Trp Gly Gln
            100                 105                 110

Gly Thr Leu Val Thr Val Ser Ser
        115                 120

<210> SEQ ID NO 171
<211> LENGTH: 120
<212> TYPE: PRT
<213> ORGANISM: Artificial Sequence
<220> FEATURE:
<223> OTHER INFORMATION: Synthetic construct

<400> SEQUENCE: 171

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Met His Trp Val Arg Gln Ala Pro Gly Lys Gly Leu Glu Trp Ile
        35                  40                  45

Gly Asn Ile Tyr Pro Gly Ser Ile Ser Ser Asn Tyr Asp Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Arg Gly His Tyr Gly Ser Tyr Leu Thr Phe Asp Tyr Trp Gly Gln
            100                 105                 110

Gly Thr Leu Val Thr Val Ser Ser
        115                 120

<210> SEQ ID NO 172
<211> LENGTH: 120
<212> TYPE: PRT
<213> ORGANISM: Artificial Sequence
<220> FEATURE:
<223> OTHER INFORMATION: Synthetic construct

<400> SEQUENCE: 172

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30
```

```
Trp Met His Trp Val Arg Gln Ala Pro Gly Gln Gly Leu Glu Trp Ile
        35                  40                  45

Gly Asn Ile Tyr Pro Gly Ser Ile Ser Ser Asn Tyr Asp Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly His Tyr Gly Ser Tyr Leu Thr Phe Asp Tyr Trp Gly Gln
                100                 105                 110

Gly Thr Leu Val Thr Val Ser Ser
            115                 120

<210> SEQ ID NO 173
<211> LENGTH: 120
<212> TYPE: PRT
<213> ORGANISM: Artificial Sequence
<220> FEATURE:
<223> OTHER INFORMATION: Synthetic construct

<400> SEQUENCE: 173

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Met His Trp Val Arg Gln Ala Pro Gly Lys Gly Leu Glu Trp Ile
        35                  40                  45

Gly Asn Ile Tyr Pro Gly Ser Ile Ser Ser Asn Tyr Asp Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly His Tyr Gly Ser Tyr Leu Thr Phe Asp Tyr Trp Gly Gln
                100                 105                 110

Gly Thr Leu Val Thr Val Ser Ser
            115                 120

<210> SEQ ID NO 174
<211> LENGTH: 120
<212> TYPE: PRT
<213> ORGANISM: Artificial Sequence
<220> FEATURE:
<223> OTHER INFORMATION: Synthetic construct

<400> SEQUENCE: 174

Gln Val Gln Leu Val Glu Ser Gly Gly Gly Val Val Gln Pro Gly Arg
1               5                   10                  15

Ser Leu Arg Leu Ser Cys Ala Ala Ser Gly Tyr Thr Phe Thr Ser Tyr
            20                  25                  30

Trp Met His Trp Val Arg Gln Ala Pro Gly Lys Gly Leu Glu Trp Ile
        35                  40                  45

Gly Asn Ile Tyr Pro Gly Ser Ile Ser Ser Asn Tyr Asp Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                    85                  90                  95
Thr Arg Gly His Tyr Gly Ser Tyr Leu Thr Phe Asp Tyr Trp Gly Gln
                100                 105                 110

Gly Thr Leu Val Thr Val Ser Ser
        115                 120

<210> SEQ ID NO 175
<211> LENGTH: 120
<212> TYPE: PRT
<213> ORGANISM: Artificial Sequence
<220> FEATURE:
<223> OTHER INFORMATION: Synthetic construct

<400> SEQUENCE: 175

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Thr Phe Thr Ser Tyr
                20                  25                  30

Trp Met His Trp Ile Arg Gln Pro Pro Gly Lys Gly Leu Glu Trp Ile
            35                  40                  45

Gly Asn Ile Tyr Pro Gly Ser Ile Ser Ser Asn Tyr Asp Pro Ser Leu
        50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Thr Arg Gly His Tyr Gly Ser Tyr Leu Thr Phe Asp Tyr Trp Gly Gln
                100                 105                 110

Gly Thr Leu Val Thr Val Ser Ser
        115                 120

<210> SEQ ID NO 176
<211> LENGTH: 120
<212> TYPE: PRT
<213> ORGANISM: Artificial Sequence
<220> FEATURE:
<223> OTHER INFORMATION: Synthetic construct

<400> SEQUENCE: 176

Glu Val Gln Leu Val Glu Ser Gly Gly Gly Leu Val Lys Pro Gly Gly
1               5                   10                  15

Ser Leu Arg Leu Ser Cys Ala Ala Ser Gly Tyr Thr Phe Thr Ser Tyr
                20                  25                  30

Trp Met His Trp Val Arg Gln Ala Pro Gly Lys Gly Leu Glu Trp Ile
            35                  40                  45

Gly Asn Ile Tyr Pro Gly Ser Ile Ser Ser Asn Tyr Asp Ala Pro Val
        50                  55                  60

Lys Gly Arg Phe Thr Ile Ser Arg Asp Asp Ser Lys Asn Thr Leu Tyr
65                  70                  75                  80

Leu Gln Met Asn Ser Leu Lys Thr Glu Asp Thr Ala Val Tyr Tyr Cys
                85                  90                  95

Thr Arg Gly His Tyr Gly Ser Tyr Leu Thr Phe Asp Tyr Trp Gly Gln
                100                 105                 110

Gly Thr Leu Val Thr Val Ser Ser
        115                 120

<210> SEQ ID NO 177
<211> LENGTH: 120
```

```
<212> TYPE: PRT
<213> ORGANISM: Artificial Sequence
<220> FEATURE:
<223> OTHER INFORMATION: Synthetic construct

<400> SEQUENCE: 177

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Thr Phe Thr Ser Tyr
            20                  25                  30

Trp Met His Trp Ile Arg Gln Pro Pro Gly Lys Gly Leu Glu Trp Ile
        35                  40                  45

Gly Asn Ile Tyr Pro Gly Ser Ile Ser Ser Asn Tyr Asp Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Thr Arg Gly His Tyr Gly Ser Tyr Leu Thr Phe Asp Tyr Trp Gly Gln
            100                 105                 110

Gly Thr Leu Val Thr Val Ser Ser
        115                 120

<210> SEQ ID NO 178
<211> LENGTH: 117
<212> TYPE: PRT
<213> ORGANISM: Artificial Sequence
<220> FEATURE:
<223> OTHER INFORMATION: Synthetic construct

<400> SEQUENCE: 178

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Asp Ile Asn Trp Val Arg Gln Ala Pro Gly Lys Gly Leu Glu Trp Ile
        35                  40                  45

Gly Trp Ile Phe Pro Gly Asp Gly Ser Thr Lys Tyr Asn Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr His Tyr Ala Met Asp Ser Trp Gly Gln Gly Thr Leu
            100                 105                 110

Val Thr Val Ser Ser
        115

<210> SEQ ID NO 179
<211> LENGTH: 117
<212> TYPE: PRT
<213> ORGANISM: Artificial Sequence
<220> FEATURE:
<223> OTHER INFORMATION: Synthetic construct

<400> SEQUENCE: 179

Gln Val Gln Leu Val Glu Ser Gly Gly Gly Val Val Gln Pro Gly Arg
1               5                   10                  15

Ser Leu Arg Leu Ser Cys Ala Ala Ser Gly Tyr Thr Phe Thr Ser Tyr
```

-continued

```
                    20                  25                  30
Asp Ile Asn Trp Val Arg Gln Ala Pro Gly Lys Gly Leu Glu Trp Ile
                35                  40                  45
Gly Trp Ile Phe Pro Gly Asp Gly Ser Thr Lys Tyr Asn Asp Ser Val
         50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Gly Tyr His Tyr Ala Met Asp Ser Trp Gly Gln Gly Thr Leu
            100                 105                 110
Val Thr Val Ser Ser
            115

<210> SEQ ID NO 180
<211> LENGTH: 117
<212> TYPE: PRT
<213> ORGANISM: Artificial Sequence
<220> FEATURE:
<223> OTHER INFORMATION: Synthetic construct

<400> SEQUENCE: 180

Gln Val Gln Leu Gln Glu Ser Gly Pro Gly Leu Val Lys Pro Ser Glu
 1               5                  10                  15
Thr Leu Ser Leu Thr Cys Thr Val Ser Gly Tyr Thr Phe Thr Ser Tyr
                20                  25                  30
Asp Ile Asn Trp Ile Arg Gln Pro Pro Gly Lys Gly Leu Glu Trp Ile
                35                  40                  45
Gly Trp Ile Phe Pro Gly Asp Gly Ser Thr Lys Tyr Asn Pro Ser Leu
         50                  55                  60
Lys Ser Arg Val Thr Ile Ser Val Asp Thr Ser Lys Asn Gln Phe Ser
 65                  70                  75                  80
Leu Lys Leu Ser Ser Val Thr Ala Ala Asp Thr Ala Val Tyr Tyr Cys
                 85                  90                  95
Ala Arg Gly Tyr His Tyr Ala Met Asp Ser Trp Gly Gln Gly Thr Leu
            100                 105                 110
Val Thr Val Ser Ser
            115

<210> SEQ ID NO 181
<211> LENGTH: 117
<212> TYPE: PRT
<213> ORGANISM: Artificial Sequence
<220> FEATURE:
<223> OTHER INFORMATION: Synthetic construct

<400> SEQUENCE: 181

Glu Val Gln Leu Val Glu Ser Gly Gly Gly Leu Val Lys Pro Gly Gly
 1               5                  10                  15
Ser Leu Arg Leu Ser Cys Ala Ala Ser Gly Tyr Thr Phe Thr Ser Tyr
                20                  25                  30
Asp Ile Asn Trp Val Arg Gln Ala Pro Gly Lys Gly Leu Glu Trp Ile
                35                  40                  45
Gly Trp Ile Phe Pro Gly Asp Gly Ser Thr Lys Tyr Asn Ala Pro Val
         50                  55                  60
Lys Gly Arg Phe Thr Ile Ser Arg Asp Asp Ser Lys Asn Thr Leu Tyr
 65                  70                  75                  80
```

-continued

Leu Gln Met Asn Ser Leu Lys Thr Glu Asp Thr Ala Val Tyr Tyr Cys
                 85                  90                  95

Ala Arg Gly Tyr His Tyr Ala Met Asp Ser Trp Gly Gln Gly Thr Leu
            100                 105                 110

Val Thr Val Ser Ser
        115

<210> SEQ ID NO 182
<211> LENGTH: 117
<212> TYPE: PRT
<213> ORGANISM: Artificial Sequence
<220> FEATURE:
<223> OTHER INFORMATION: Synthetic construct

<400> SEQUENCE: 182

Gln Leu Gln Leu Gln Glu Ser Gly Pro Gly Leu Val Lys Pro Ser Glu
1               5                   10                  15

Thr Leu Ser Leu Thr Cys Thr Val Ser Gly Tyr Thr Phe Thr Ser Tyr
            20                  25                  30

Asp Ile Asn Trp Ile Arg Gln Pro Pro Gly Lys Gly Leu Glu Trp Ile
        35                  40                  45

Gly Trp Ile Phe Pro Gly Asp Gly Ser Thr Lys Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                 85                  90                  95

Ala Arg Gly Tyr His Tyr Ala Met Asp Ser Trp Gly Gln Gly Thr Leu
            100                 105                 110

Val Thr Val Ser Ser
        115

<210> SEQ ID NO 183
<211> LENGTH: 117
<212> TYPE: PRT
<213> ORGANISM: Artificial Sequence
<220> FEATURE:
<223> OTHER INFORMATION: Synthetic construct

<400> SEQUENCE: 183

Gln Leu Gln Leu Gln Glu Ser Gly Pro Gly Leu Val Lys Pro Ser Glu
1               5                   10                  15

Thr Leu Ser Leu Thr Cys Thr Val Ser Gly Tyr Thr Phe Thr Asp Tyr
            20                  25                  30

Asn Leu His Trp Ile Arg Gln Pro Pro Gly Lys Gly Leu Glu Trp Ile
        35                  40                  45

Gly Phe Ile Tyr Pro Ser Asn Gly Ile Thr Gly Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                 85                  90                  95

Ala Arg Ser Thr Val Asp Tyr Phe Asp Tyr Trp Gly Gln Gly Thr Leu
            100                 105                 110

Val Thr Val Ser Ser
        115

<210> SEQ ID NO 184

```
<211> LENGTH: 15
<212> TYPE: PRT
<213> ORGANISM: Artificial Sequence
<220> FEATURE:
<223> OTHER INFORMATION: Synthetic construct

<400> SEQUENCE: 184

Arg Pro Ser Lys Arg Ile Ser Ala Tyr Val Phe Ser Tyr Met His
1               5                   10                  15

<210> SEQ ID NO 185
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: 7
<223> OTHER INFORMATION: Xaa = Any Amino Acid

<400> SEQUENCE: 185

Leu Ser Cys Asn Leu Glu Xaa
1               5

<210> SEQ ID NO 186
<211> LENGTH: 14
<212> TYPE: PRT
<213> ORGANISM: Artificial Sequence
<220> FEATURE:
<223> OTHER INFORMATION: Synthetic construct

<400> SEQUENCE: 186

Ile Gly Asn Ile Tyr Pro Gly Ser Gly Ser Thr Tyr Tyr Asp
1               5                   10

<210> SEQ ID NO 187
<211> LENGTH: 13
<212> TYPE: PRT
<213> ORGANISM: Artificial Sequence
<220> FEATURE:
<223> OTHER INFORMATION: Synthetic construct

<400> SEQUENCE: 187

Thr Arg Gly His Tyr Gly Asn Tyr Leu Thr Phe Asp Tyr
1               5                   10

<210> SEQ ID NO 188
<211> LENGTH: 23
<212> TYPE: PRT
<213> ORGANISM: Artificial Sequence
<220> FEATURE:
<223> OTHER INFORMATION: Synthetic construct

<400> SEQUENCE: 188

Asp Leu Glx Leu Thr Gln Ser Leu Ala Ser Leu Val Val Cys Met Gly
1               5                   10                  15

Gln Arg Ala Ala Ile Ser Phe
            20

<210> SEQ ID NO 189
<211> LENGTH: 32
<212> TYPE: PRT
<213> ORGANISM: Artificial Sequence
<220> FEATURE:
<223> OTHER INFORMATION: Synthetic construct

<400> SEQUENCE: 189
```

```
Gly Val Arg Ala Arg Leu Ser Gly Arg Arg Trp Val Thr Asp Phe Thr
1               5                   10                  15

Leu Asn Ile His Pro Ala Glu Glu Glu Asp Gly Ala Thr Tyr Tyr Cys
            20                  25                  30
```

<210> SEQ ID NO 190
<211> LENGTH: 26
<212> TYPE: PRT
<213> ORGANISM: Artificial Sequence
<220> FEATURE:
<223> OTHER INFORMATION: Synthetic construct

<400> SEQUENCE: 190

```
Gln Val Gln Leu Gln Gln Pro Gly Ser Glu Leu Val Arg Pro Gly Ala
1               5                   10                  15

Ser Val Lys Leu Ser Cys Lys Ala Ser Gly
            20                  25
```

<210> SEQ ID NO 191
<211> LENGTH: 35
<212> TYPE: PRT
<213> ORGANISM: Artificial Sequence
<220> FEATURE:
<223> OTHER INFORMATION: Synthetic construct

<400> SEQUENCE: 191

```
Glu Lys Phe Lys Ser Lys Ala Thr Leu Thr Val Asp Thr Ser Ser Gly
1               5                   10                  15

Thr Ala Tyr Met Gln Leu Ser Ser Leu Thr Ser Glu Asp Ser Ala Val
            20                  25                  30

Tyr Tyr Cys
        35
```

<210> SEQ ID NO 192
<211> LENGTH: 111
<212> TYPE: PRT
<213> ORGANISM: Mus musculus
<220> FEATURE:
<221> NAME/KEY: VARIANT
<222> LOCATION: 60
<223> OTHER INFORMATION: Xaa = Any Amino Acid

<400> SEQUENCE: 192

```
Asp Leu Glx Leu Thr Gln Ser Leu Ala Ser Leu Val Val Cys Met Gly
1               5                   10                  15

Gln Arg Ala Ala Ile Ser Phe Arg Pro Ser Lys Arg Ile Ser Ala Tyr
            20                  25                  30

Val Phe Ser Tyr Met His Trp Tyr Gln Gln Lys Pro Gly Gln Pro Pro
        35                  40                  45

Lys Leu Ile Ile Tyr Leu Ser Cys Asn Leu Glu Xaa Gly Val Arg Ala
    50                  55                  60

Arg Leu Ser Gly Arg Arg Trp Val Thr Asp Phe Thr Leu Asn Ile His
65                  70                  75                  80

Pro Ala Glu Glu Glu Asp Gly Ala Thr Tyr Tyr Cys Gln His Ser Arg
                85                  90                  95

Glu Leu Pro Leu Thr Phe Gly Gly Gly Thr Lys Leu Glu Met Lys
            100                 105                 110
```

<210> SEQ ID NO 193
<211> LENGTH: 111
<212> TYPE: PRT

<213> ORGANISM: Artificial Sequence
<220> FEATURE:
<223> OTHER INFORMATION: Synthetic construct
<220> FEATURE:
<221> NAME/KEY: VARIANT
<222> LOCATION: 60
<223> OTHER INFORMATION: Xaa = Any Amino Acid

<400> SEQUENCE: 193

Asp Ile Val Met Thr Gln Ser Pro Leu Ser Leu Pro Val Thr Pro Gly
1               5                   10                  15

Glu Pro Ala Ser Ile Ser Cys Arg Pro Ser Lys Arg Ile Ser Ala Tyr
            20                  25                  30

Val Phe Ser Tyr Met His Trp Tyr Leu Gln Lys Pro Gly Gln Ser Pro
        35                  40                  45

Gln Leu Leu Ile Tyr Leu Ser Cys Asn Leu Glu Xaa Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Arg
                85                  90                  95

Glu Leu Pro Leu Thr Phe Gly Gln Gly Thr Lys Val Glu Ile Lys
            100                 105                 110

<210> SEQ ID NO 194
<211> LENGTH: 111
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: 60
<223> OTHER INFORMATION: Xaa = Any Amino Acid

<400> SEQUENCE: 194

Asp Val Val Met Thr Gln Ser Pro Leu Ser Leu Pro Val Thr Leu Gly
1               5                   10                  15

Gln Pro Ala Ser Ile Ser Cys Arg Pro Ser Lys Arg Ile Ser Ala Tyr
            20                  25                  30

Val Phe Ser Tyr Met His Trp Phe Gln Gln Arg Pro Gly Gln Ser Pro
        35                  40                  45

Arg Arg Leu Ile Tyr Leu Ser Cys Asn Leu Glu Xaa Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Arg
                85                  90                  95

Glu Leu Pro Leu Thr Phe Gly Gln Gly Thr Lys Val Glu Ile Lys
            100                 105                 110

<210> SEQ ID NO 195
<211> LENGTH: 111
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: 60
<223> OTHER INFORMATION: Xaa = Any Amino Acid

<400> SEQUENCE: 195

```
Asp Ile Val Met Thr Gln Ser Pro Asp Ser Leu Ala Val Ser Leu Gly
1               5                   10                  15

Glu Arg Ala Thr Ile Asn Cys Arg Pro Ser Lys Arg Ile Ser Ala Tyr
            20                  25                  30

Val Phe Ser Tyr Met His Trp Tyr Gln Gln Lys Pro Gly Gln Pro Pro
        35                  40                  45

Lys Leu Leu Ile Tyr Leu Ser Cys Asn Leu Glu Xaa Gly Val Pro Asp
    50                  55                  60

Arg Phe Ser Gly Ser Gly Ser Gly Thr Asp Phe Thr Leu Thr Ile Ser
65              70                  75                  80

Ser Leu Gln Ala Glu Asp Val Ala Val Tyr Tyr Cys Gln His Ser Arg
                85                  90                  95

Glu Leu Pro Leu Thr Phe Gly Gln Gly Thr Lys Val Glu Ile Lys
            100                 105                 110
```

<210> SEQ ID NO 196
<211> LENGTH: 111
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: 60
<223> OTHER INFORMATION: Xaa = Any Amino Acid

<400> SEQUENCE: 196

```
Asp Ile Gln Met Thr Gln Ser Pro Ser Ser Leu Ser Ala Ser Val Gly
1               5                   10                  15

Asp Arg Val Thr Ile Thr Cys Arg Pro Ser Lys Arg Ile Ser Ala Tyr
            20                  25                  30

Val Phe Ser Tyr Met His Trp Tyr Gln Gln Lys Pro Gly Lys Ala Pro
        35                  40                  45

Lys Leu Leu Ile Tyr Leu Ser Cys Asn Leu Glu Xaa Gly Val Pro Ser
    50                  55                  60

Arg Phe Ser Gly Ser Gly Ser Gly Thr Asp Phe Thr Phe Thr Ile Ser
65              70                  75                  80

Ser Leu Gln Pro Glu Asp Ile Ala Thr Tyr Tyr Cys Gln His Ser Arg
                85                  90                  95

Glu Leu Pro Leu Thr Phe Gly Gln Gly Thr Lys Val Glu Ile Lys
            100                 105                 110
```

<210> SEQ ID NO 197
<211> LENGTH: 111
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: 60
<223> OTHER INFORMATION: Xaa = Any Amino Acid

<400> SEQUENCE: 197

```
Asp Ile Gln Met Thr Gln Ser Pro Ser Thr Leu Ser Ala Ser Val Gly
1               5                   10                  15

Asp Arg Val Thr Ile Thr Cys Arg Pro Ser Lys Arg Ile Ser Ala Tyr
            20                  25                  30

Val Phe Ser Tyr Met His Trp Tyr Gln Gln Lys Pro Gly Lys Ala Pro
        35                  40                  45
```

```
Lys Leu Leu Ile Tyr Leu Ser Cys Asn Leu Glu Xaa Gly Val Pro Ser
        50                  55                  60

Arg Phe Ser Gly Ser Gly Ser Gly Thr Glu Phe Thr Leu Thr Ile Ser
 65                  70                  75                  80

Ser Leu Gln Pro Asp Asp Phe Ala Thr Tyr Tyr Cys Gln His Ser Arg
                 85                  90                  95

Glu Leu Pro Leu Thr Phe Gly Gln Gly Thr Lys Val Glu Ile Lys
            100                 105                 110

<210> SEQ ID NO 198
<211> LENGTH: 111
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: 60
<223> OTHER INFORMATION: Xaa = Any Amino Acid

<400> SEQUENCE: 198

Glu Ile Val Leu Thr Gln Ser Pro Ala Thr Leu Ser Leu Ser Pro Gly
  1               5                  10                  15

Glu Arg Ala Thr Leu Ser Cys Arg Pro Ser Lys Arg Ile Ser Ala Tyr
             20                  25                  30

Val Phe Ser Tyr Met His Trp Tyr Gln Gln Lys Pro Gly Gln Ala Pro
         35                  40                  45

Arg Leu Leu Ile Tyr Leu Ser Cys Asn Leu Glu Xaa Gly Ile Pro Ala
 50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln His Ser Arg
                 85                  90                  95

Glu Leu Pro Leu Thr Phe Gly Gln Gly Thr Lys Val Glu Ile Lys
            100                 105                 110

<210> SEQ ID NO 199
<211> LENGTH: 111
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: 60
<223> OTHER INFORMATION: Xaa = Any Amino Acid

<400> SEQUENCE: 199

Asp Ile Gln Leu Thr Gln Ser Pro Ser Phe Leu Ser Ala Ser Val Gly
  1               5                  10                  15

Asp Arg Val Thr Ile Thr Cys Arg Pro Ser Lys Arg Ile Ser Ala Tyr
             20                  25                  30

Val Phe Ser Tyr Met His Trp Tyr Gln Gln Lys Pro Gly Lys Ala Pro
         35                  40                  45

Lys Leu Leu Ile Tyr Leu Ser Cys Asn Leu Glu Xaa Gly Val Pro Ser
        50                  55                  60

Arg Phe Ser Gly Ser Gly Ser Gly Thr Glu Phe Thr Leu Thr Ile Ser
 65                  70                  75                  80

Ser Leu Gln Pro Glu Asp Phe Ala Thr Tyr Tyr Cys Gln His Ser Arg
                 85                  90                  95
```

Glu Leu Pro Leu Thr Phe Gly Gln Gly Thr Lys Val Glu Ile Lys
                100                 105                 110

<210> SEQ ID NO 200
<211> LENGTH: 111
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: 60
<223> OTHER INFORMATION: Xaa = Any Amino Acid

<400> SEQUENCE: 200

Asp Ile Gln Met Thr Gln Ser Pro Ser Ser Leu Ser Ala Ser Val Gly
1               5                   10                  15

Asp Arg Val Thr Ile Thr Cys Arg Pro Ser Lys Arg Ile Ser Ala Tyr
            20                  25                  30

Val Phe Ser Tyr Met His Trp Tyr Gln Gln Lys Pro Gly Lys Ala Pro
        35                  40                  45

Lys Leu Leu Ile Tyr Leu Ser Cys Asn Leu Glu Xaa Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Leu Pro Leu Thr Phe Gly Gln Gly Thr Lys Val Glu Ile Lys
                100                 105                 110

<210> SEQ ID NO 201
<211> LENGTH: 111
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: 60
<223> OTHER INFORMATION: Xaa = Any Amino Acid

<400> SEQUENCE: 201

Glu Ile Val Met Thr Gln Ser Pro Ala Thr Leu Ser Val Ser Pro Gly
1               5                   10                  15

Glu Arg Ala Thr Leu Ser Cys Arg Pro Ser Lys Arg Ile Ser Ala Tyr
            20                  25                  30

Val Phe Ser Tyr Met His Trp Tyr Gln Gln Lys Pro Gly Gln Ala Pro
        35                  40                  45

Arg Leu Leu Ile Tyr Leu Ser Cys Asn Leu Glu Xaa Gly Ile Pro Ala
    50                  55                  60

Arg Phe Ser Gly Ser Gly Ser Gly Thr Glu Phe Thr Leu Thr Ile Ser
65                  70                  75                  80

Ser Leu Gln Ser Glu Asp Phe Ala Val Tyr Tyr Cys Gln His Ser Arg
                85                  90                  95

Glu Leu Pro Leu Thr Phe Gly Gln Gly Thr Lys Val Glu Ile Lys
                100                 105                 110

<210> SEQ ID NO 202
<211> LENGTH: 111
<212> TYPE: PRT
<213> ORGANISM: Artificial Sequence

```
<220> FEATURE:
<223> OTHER INFORMATION: Synthetic construct
<220> FEATURE:
<221> NAME/KEY: VARIANT
<222> LOCATION: 60
<223> OTHER INFORMATION: Xaa = Any Amino Acid

<400> SEQUENCE: 202

Glu Ile Val Leu Thr Gln Ser Pro Gly Thr Leu Ser Leu Ser Pro Gly
1               5                   10                  15

Glu Arg Ala Thr Leu Ser Cys Arg Pro Ser Lys Arg Ile Ser Ala Tyr
            20                  25                  30

Val Phe Ser Tyr Met His Trp Tyr Gln Gln Lys Pro Gly Gln Ala Pro
        35                  40                  45

Arg Leu Leu Ile Tyr Leu Ser Cys Asn Leu Glu Xaa Gly Ile Pro Asp
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln His Ser Arg
                85                  90                  95

Glu Leu Pro Leu Thr Phe Gly Gln Gly Thr Lys Val Glu Ile Lys
            100                 105                 110

<210> SEQ ID NO 203
<211> LENGTH: 120
<212> TYPE: PRT
<213> ORGANISM: Mus musculus

<400> SEQUENCE: 203

Gln Val Gln Leu Gln Gln Pro Gly Ser Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Asn Ile Tyr Pro Gly Ser Gly Ser Thr Tyr Tyr Asp Glu Lys Phe
    50                  55                  60

Lys Ser Lys Ala Thr Leu Thr Val Asp Thr Ser Gly Thr Ala Tyr
65                  70                  75                  80

Met Gln Leu Ser Ser Leu Thr Ser Glu Asp Ser Ala Val Tyr Tyr Cys
                85                  90                  95

Thr Arg Gly His Tyr Gly Asn Tyr Leu Thr Phe Asp Tyr Trp Gly Gln
            100                 105                 110

Gly Thr Thr Leu Thr Val Ser Ser
        115                 120

<210> SEQ ID NO 204
<211> LENGTH: 120
<212> TYPE: PRT
<213> ORGANISM: Artificial Sequence
<220> FEATURE:
<223> OTHER INFORMATION: Synthetic construct

<400> SEQUENCE: 204

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
```

-continued

```
                35                  40                  45
Gly Asn Ile Tyr Pro Gly Ser Gly Ser Thr Tyr Tyr Asp Gln Lys Phe
        50                  55                  60
Gln Gly Arg Val Thr Met Thr Arg Asp Thr Ser Thr Ser Thr Val Tyr
 65                  70                  75                  80
Met Glu Leu Ser Ser Leu Arg Ser Glu Asp Thr Ala Val Tyr Tyr Cys
                85                  90                  95
Thr Arg Gly His Tyr Gly Asn Tyr Leu Thr Phe Asp Tyr Trp Gly Gln
               100                 105                 110
Gly Thr Leu Val Thr Val Ser Ser
                115                 120

<210> SEQ ID NO 205
<211> LENGTH: 120
<212> TYPE: PRT
<213> ORGANISM: Artificial Sequence
<220> FEATURE:
<223> OTHER INFORMATION: Synthetic construct

<400> SEQUENCE: 205

Glu Val Gln Leu Val Gln Ser Gly Ala Glu Val Lys Lys Pro Gly Glu
 1               5                  10                  15
Ser Leu Lys Ile Ser Cys Lys Gly Ser Gly Tyr Thr Phe Thr Ser Tyr
                20                  25                  30
Trp Met His Trp Val Arg Gln Met Pro Gly Lys Gly Leu Glu Trp Ile
             35                  40                  45
Gly Asn Ile Tyr Pro Gly Ser Gly Ser Thr Tyr Tyr Asp Pro Ser Phe
        50                  55                  60
Gln Gly Gln Val Thr Ile Ser Ala Asp Lys Ser Ile Ser Thr Ala Tyr
 65                  70                  75                  80
Leu Gln Trp Ser Ser Leu Lys Ala Ser Asp Thr Ala Met Tyr Tyr Cys
                85                  90                  95
Thr Arg Gly His Tyr Gly Asn Tyr Leu Thr Phe Asp Tyr Trp Gly Gln
               100                 105                 110
Gly Thr Leu Val Thr Val Ser Ser
                115                 120

<210> SEQ ID NO 206
<211> LENGTH: 120
<212> TYPE: PRT
<213> ORGANISM: Artificial Sequence
<220> FEATURE:
<223> OTHER INFORMATION: Synthetic construct

<400> SEQUENCE: 206

Glu Val Gln Leu Leu Glu Ser Gly Gly Gly Leu Val Gln Pro Gly Gly
 1               5                  10                  15
Ser Leu Arg Leu Ser Cys Ala Ala Ser Gly Tyr Thr Phe Thr Ser Tyr
                20                  25                  30
Trp Met His Trp Val Arg Gln Ala Pro Gly Lys Gly Leu Glu Trp Ile
             35                  40                  45
Gly Asn Ile Tyr Pro Gly Ser Gly Ser Thr Tyr Tyr Asp Asp Ser Val
        50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                85                  90                  95
```

Thr Arg Gly His Tyr Gly Asn Tyr Leu Thr Phe Asp Tyr Trp Gly Gln
            100                 105                 110

Gly Thr Leu Val Thr Val Ser Ser
        115                 120

<210> SEQ ID NO 207
<211> LENGTH: 120
<212> TYPE: PRT
<213> ORGANISM: Artificial Sequence
<220> FEATURE:
<223> OTHER INFORMATION: Synthetic construct

<400> SEQUENCE: 207

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Met His Trp Val Arg Gln Ala Pro Gly Lys Gly Leu Glu Trp Ile
        35                  40                  45

Gly Asn Ile Tyr Pro Gly Ser Gly Ser Thr Tyr Tyr Asp Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Arg Gly His Tyr Gly Asn Tyr Leu Thr Phe Asp Tyr Trp Gly Gln
            100                 105                 110

Gly Thr Leu Val Thr Val Ser Ser
        115                 120

<210> SEQ ID NO 208
<211> LENGTH: 120
<212> TYPE: PRT
<213> ORGANISM: Artificial Sequence
<220> FEATURE:
<223> OTHER INFORMATION: Synthetic construct

<400> SEQUENCE: 208

Gln Val Gln Leu Val Glu Ser Gly Gly Gly Val Val Gln Pro Gly Arg
1               5                   10                  15

Ser Leu Arg Leu Ser Cys Ala Ala Ser Gly Tyr Thr Phe Thr Ser Tyr
            20                  25                  30

Trp Met His Trp Val Arg Gln Ala Pro Gly Lys Gly Leu Glu Trp Ile
        35                  40                  45

Gly Asn Ile Tyr Pro Gly Ser Gly Ser Thr Tyr Tyr Asp Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly His Tyr Gly Asn Tyr Leu Thr Phe Asp Tyr Trp Gly Gln
            100                 105                 110

Gly Thr Leu Val Thr Val Ser Ser
        115                 120

<210> SEQ ID NO 209
<211> LENGTH: 120
<212> TYPE: PRT
<213> ORGANISM: Artificial Sequence
<220> FEATURE:
<223> OTHER INFORMATION: Synthetic construct

<400> SEQUENCE: 209

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Met His Trp Val Arg Gln Ala Pro Gly Lys Gly Leu Glu Trp Ile
        35                  40                  45

Gly Asn Ile Tyr Pro Gly Ser Gly Ser Thr Tyr Tyr Asp Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Arg Gly His Tyr Gly Asn Tyr Leu Thr Phe Asp Tyr Trp Gly Gln
            100                 105                 110

Gly Thr Leu Val Thr Val Ser Ser
        115                 120

<210> SEQ ID NO 210
<211> LENGTH: 120
<212> TYPE: PRT
<213> ORGANISM: Artificial Sequence
<220> FEATURE:
<223> OTHER INFORMATION: Synthetic construct

<400> SEQUENCE: 210

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Asn Ile Tyr Pro Gly Ser Gly Ser Thr Tyr Tyr Asp Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly His Tyr Gly Asn Tyr Leu Thr Phe Asp Tyr Trp Gly Gln
            100                 105                 110

Gly Thr Leu Val Thr Val Ser Ser
        115                 120

<210> SEQ ID NO 211
<211> LENGTH: 120
<212> TYPE: PRT
<213> ORGANISM: Artificial Sequence
<220> FEATURE:
<223> OTHER INFORMATION: Synthetic construct

<400> SEQUENCE: 211

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Thr Phe Thr Ser Tyr
            20                  25                  30

```
Trp Met His Trp Ile Arg Gln Pro Gly Lys Gly Leu Glu Trp Ile
            35                  40                  45

Gly Asn Ile Tyr Pro Gly Ser Gly Ser Thr Tyr Tyr Asp Pro Ser Leu
 50                      55                  60

Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Thr Arg Gly His Tyr Gly Asn Tyr Leu Thr Phe Asp Tyr Trp Gly Gln
             100                 105                 110

Gly Thr Leu Val Thr Val Ser Ser
             115                 120

<210> SEQ ID NO 212
<211> LENGTH: 120
<212> TYPE: PRT
<213> ORGANISM: Artificial Sequence
<220> FEATURE:
<223> OTHER INFORMATION: Synthetic construct

<400> SEQUENCE: 212

Glu Val Gln Leu Val Glu Ser Gly Gly Gly Leu Val Lys Pro Gly Gly
 1               5                  10                  15

Ser Leu Arg Leu Ser Cys Ala Ala Ser Gly Tyr Thr Phe Thr Ser Tyr
                 20                  25                  30

Trp Met His Trp Val Arg Gln Ala Pro Gly Lys Gly Leu Glu Trp Ile
            35                  40                  45

Gly Asn Ile Tyr Pro Gly Ser Gly Ser Thr Tyr Tyr Asp Ala Pro Val
 50                      55                  60

Lys Gly Arg Phe Thr Ile Ser Arg Asp Asp Ser Lys Asn Thr Leu Tyr
 65                  70                  75                  80

Leu Gln Met Asn Ser Leu Lys Thr Glu Asp Thr Ala Val Tyr Tyr Cys
                 85                  90                  95

Thr Arg Gly His Tyr Gly Asn Tyr Leu Thr Phe Asp Tyr Trp Gly Gln
             100                 105                 110

Gly Thr Leu Val Thr Val Ser Ser
             115                 120

<210> SEQ ID NO 213
<211> LENGTH: 120
<212> TYPE: PRT
<213> ORGANISM: Artificial Sequence
<220> FEATURE:
<223> OTHER INFORMATION: Synthetic construct

<400> SEQUENCE: 213

Gln Val Gln Leu Gln Glu Ser Gly Pro Gly Leu Val Lys Pro Ser Gln
 1               5                  10                  15

Thr Leu Ser Leu Thr Cys Thr Val Ser Gly Tyr Thr Phe Thr Ser Tyr
                 20                  25                  30

Trp Met His Trp Ile Arg Gln Pro Pro Gly Lys Gly Leu Glu Trp Ile
            35                  40                  45

Gly Asn Ile Tyr Pro Gly Ser Gly Ser Thr Tyr Tyr Asp Pro Ser Leu
 50                      55                  60

Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95
```

Thr Arg Gly His Tyr Gly Asn Tyr Leu Thr Phe Asp Tyr Trp Gly Gln
            100                 105                 110

Gly Thr Leu Val Thr Val Ser Ser
        115                 120

<210> SEQ ID NO 214
<211> LENGTH: 110
<212> TYPE: PRT
<213> ORGANISM: Artificial Sequence
<220> FEATURE:
<223> OTHER INFORMATION: Synthetic construct

<400> SEQUENCE: 214

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro
            100                 105                 110

<210> SEQ ID NO 215
<211> LENGTH: 21
<212> TYPE: PRT
<213> ORGANISM: Artificial Sequence
<220> FEATURE:
<223> OTHER INFORMATION: Synthetic construct

<400> SEQUENCE: 215

Met Glu Val Gly Trp Tyr Arg Ser Pro Phe Ser Arg Val Val His Leu
1               5                   10                  15

Tyr Arg Asn Gly Lys
            20

<210> SEQ ID NO 216
<211> LENGTH: 20
<212> TYPE: DNA
<213> ORGANISM: Artificial Sequence
<220> FEATURE:
<223> OTHER INFORMATION: Synthetic construct

<400> SEQUENCE: 216
gcactcacat cgctacatca                                              20

<210> SEQ ID NO 217
<211> LENGTH: 17
<212> TYPE: DNA
<213> ORGANISM: Artificial Sequence
<220> FEATURE:
<223> OTHER INFORMATION: Synthetic construct

<400> SEQUENCE: 217
ctagagtgcc agggatg                                                 17

```
<210> SEQ ID NO 218
<211> LENGTH: 21
<212> TYPE: DNA
<213> ORGANISM: Artificial Sequence
<220> FEATURE:
<223> OTHER INFORMATION: Synthetic construct

<400> SEQUENCE: 218
ctccactcac ggcaaattca a                                              21

<210> SEQ ID NO 219
<211> LENGTH: 22
<212> TYPE: DNA
<213> ORGANISM: Artificial Sequence
<220> FEATURE:
<223> OTHER INFORMATION: Synthetic construct

<400> SEQUENCE: 219
gatgacaagc ttcccattct cg                                             22

<210> SEQ ID NO 220
<211> LENGTH: 21
<212> TYPE: DNA
<213> ORGANISM: Artificial Sequence
<220> FEATURE:
<223> OTHER INFORMATION: Synthetic construct

<400> SEQUENCE: 220
ccgtcagccg atttgctatc t                                              21

<210> SEQ ID NO 221
<211> LENGTH: 22
<212> TYPE: DNA
<213> ORGANISM: Artificial Sequence
<220> FEATURE:
<223> OTHER INFORMATION: Synthetic construct

<400> SEQUENCE: 221
acggcagaga ggaggttgac tt                                             22

<210> SEQ ID NO 222
<211> LENGTH: 22
<212> TYPE: DNA
<213> ORGANISM: Artificial Sequence
<220> FEATURE:
<223> OTHER INFORMATION: Synthetic construct

<400> SEQUENCE: 222
acaacaaaaa agcctcgtgc tg                                             22

<210> SEQ ID NO 223
<211> LENGTH: 22
<212> TYPE: DNA
<213> ORGANISM: Artificial Sequence
<220> FEATURE:
<223> OTHER INFORMATION: Synthetic construct

<400> SEQUENCE: 223
ccattgaggt ggagagcttt ca                                             22

<210> SEQ ID NO 224
<211> LENGTH: 22
<212> TYPE: DNA
<213> ORGANISM: Artificial Sequence
<220> FEATURE:
<223> OTHER INFORMATION: Synthetic construct
```

<400> SEQUENCE: 224
ggcaaaccca aggtctacgt tc        22

<210> SEQ ID NO 225
<211> LENGTH: 21
<212> TYPE: DNA
<213> ORGANISM: Artificial Sequence
<220> FEATURE:
<223> OTHER INFORMATION: Synthetic construct

<400> SEQUENCE: 225
tacctcattg gccagctgct t        21

<210> SEQ ID NO 226
<211> LENGTH: 20
<212> TYPE: DNA
<213> ORGANISM: Artificial Sequence
<220> FEATURE:
<223> OTHER INFORMATION: Synthetic construct

<400> SEQUENCE: 226
aggacctggg ttggaagtgg        20

<210> SEQ ID NO 227
<211> LENGTH: 20
<212> TYPE: DNA
<213> ORGANISM: Artificial Sequence
<220> FEATURE:
<223> OTHER INFORMATION: Synthetic construct

<400> SEQUENCE: 227
agttggcatg gtagcccttg        20

<210> SEQ ID NO 228
<211> LENGTH: 12
<212> TYPE: PRT
<213> ORGANISM: Artificial Sequence
<220> FEATURE:
<223> OTHER INFORMATION: Synthetic construct

<400> SEQUENCE: 228

Thr Leu Ser Ser Gln His Ser Thr Tyr Thr Ile Glu
1               5                   10

<210> SEQ ID NO 229
<211> LENGTH: 13
<212> TYPE: PRT
<213> ORGANISM: Artificial Sequence
<220> FEATURE:
<223> OTHER INFORMATION: Synthetic construct

<400> SEQUENCE: 229

Met Glu Leu Lys Lys Asp Gly Ser His Ser Thr Gly Asp
1               5                   10

<210> SEQ ID NO 230
<211> LENGTH: 13
<212> TYPE: PRT
<213> ORGANISM: Artificial Sequence
<220> FEATURE:
<223> OTHER INFORMATION: Synthetic construct

<400> SEQUENCE: 230

Gly Val Gly Asp Thr Ile Lys Glu Gln Phe Val Tyr Val
1               5                   10

```
<210> SEQ ID NO 231
<211> LENGTH: 13
<212> TYPE: PRT
<213> ORGANISM: Artificial Sequence
<220> FEATURE:
<223> OTHER INFORMATION: Synthetic construct

<400> SEQUENCE: 231

Lys Ala Ser Gly Tyr Thr Phe Thr Asp Tyr Asn Leu His
1               5                   10

<210> SEQ ID NO 232
<211> LENGTH: 13
<212> TYPE: PRT
<213> ORGANISM: Artificial Sequence
<220> FEATURE:
<223> OTHER INFORMATION: Synthetic construct

<400> SEQUENCE: 232

Val Gly Ser Gly Phe Thr Phe Ser Asn Tyr Cys Met Asn
1               5                   10

<210> SEQ ID NO 233
<211> LENGTH: 18
<212> TYPE: PRT
<213> ORGANISM: Artificial Sequence
<220> FEATURE:
<223> OTHER INFORMATION: Synthetic construct

<400> SEQUENCE: 233

Val Ala Glu Ile Arg Leu Lys Ser Asn Asn Tyr Val Thr Asn Tyr Val
1               5                   10                  15

Tyr Cys

<210> SEQ ID NO 234
<211> LENGTH: 23
<212> TYPE: PRT
<213> ORGANISM: Artificial Sequence
<220> FEATURE:
<223> OTHER INFORMATION: Synthetic construct

<400> SEQUENCE: 234

Asp Ile Val Leu Thr Gln Ser Pro Ala Ser Leu Ala Val Ser Leu Gly
1               5                   10                  15

Gln Arg Ala Thr Met Ser Cys
            20

<210> SEQ ID NO 235
<211> LENGTH: 22
<212> TYPE: PRT
<213> ORGANISM: Artificial Sequence
<220> FEATURE:
<223> OTHER INFORMATION: Synthetic construct

<400> SEQUENCE: 235

Gln Leu Val Leu Thr Gln Ser Ser Ser Ala Ser Phe Ser Leu Gly Ala
1               5                   10                  15

Ser Ala Lys Leu Thr Cys
            20

<210> SEQ ID NO 236
<211> LENGTH: 13
<212> TYPE: PRT
<213> ORGANISM: Artificial Sequence
<220> FEATURE:
```

<223> OTHER INFORMATION: Synthetic construct

<400> SEQUENCE: 236

Trp Tyr Gln Gln Gln Pro Leu Lys Pro Pro Lys Tyr Val
1               5                   10

<210> SEQ ID NO 237
<211> LENGTH: 32
<212> TYPE: PRT
<213> ORGANISM: Artificial Sequence
<220> FEATURE:
<223> OTHER INFORMATION: Synthetic construct

<400> SEQUENCE: 237

Gly Ile Pro Asp Arg Phe Ser Gly Ser Ser Gly Ala Asp Arg Tyr
1               5                   10                  15

Leu Ser Ile Ser Asn Ile Gln Pro Glu Asp Glu Ala Ile Tyr Ile Cys
            20                  25                  30

<210> SEQ ID NO 238
<211> LENGTH: 10
<212> TYPE: PRT
<213> ORGANISM: Artificial Sequence
<220> FEATURE:
<223> OTHER INFORMATION: Synthetic construct

<400> SEQUENCE: 238

Phe Gly Gly Gly Thr Lys Val Thr Val Leu
1               5                   10

<210> SEQ ID NO 239
<211> LENGTH: 22
<212> TYPE: PRT
<213> ORGANISM: Artificial Sequence
<220> FEATURE:
<223> OTHER INFORMATION: Synthetic construct

<400> SEQUENCE: 239

Glu Val Gln Leu Gln Gln Ser Gly Pro Glu Leu Val Lys Pro Gly Ala
1               5                   10                  15

Ser Val Lys Ile Ser Cys
            20

<210> SEQ ID NO 240
<211> LENGTH: 22
<212> TYPE: PRT
<213> ORGANISM: Artificial Sequence
<220> FEATURE:
<223> OTHER INFORMATION: Synthetic construct

<400> SEQUENCE: 240

Glu Val Lys Leu Glu Glu Ser Gly Gly Gly Leu Val Gln Pro Gly Gly
1               5                   10                  15

Ser Met Lys Leu Ser Cys
            20

<210> SEQ ID NO 241
<211> LENGTH: 111
<212> TYPE: PRT
<213> ORGANISM: Mus musculus

<400> SEQUENCE: 241

Asp Ile Val Leu Thr Gln Ser Pro Ala Ser Leu Ala Val Ser Leu Gly
1               5                   10                  15

```
Gln Arg Ala Thr Met Ser Cys Arg Ala Ser Gln Ser Val Ser Thr Ser
                 20                  25                  30

Thr Tyr Ser Tyr Met His Trp Tyr Gln Gln Lys Pro Gly Gln Pro Pro
             35                  40                  45

Lys Leu Leu Ile Lys Tyr Ala Ser Asn Leu Glu Ser Gly Val Pro Ala
         50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                 85                  90                  95

Glu Ile Pro Leu Thr Phe Gly Ala Gly Thr Lys Leu Glu Leu Lys
            100                 105                 110
```

<210> SEQ ID NO 242
<211> LENGTH: 115
<212> TYPE: PRT
<213> ORGANISM: Mus musculus

<400> SEQUENCE: 242

```
Gln Leu Val Leu Thr Gln Ser Ser Ser Ala Ser Phe Ser Leu Gly Ala
1               5                   10                  15

Ser Ala Lys Leu Thr Cys Thr Leu Ser Ser Gln His Ser Thr Tyr Thr
                 20                  25                  30

Ile Glu Trp Tyr Gln Gln Pro Leu Lys Pro Pro Lys Tyr Val Met
             35                  40                  45

Glu Leu Lys Lys Asp Gly Ser His Ser Thr Gly Asp Gly Ile Pro Asp
         50                  55                  60

Arg Phe Ser Gly Ser Ser Ser Gly Ala Asp Arg Tyr Leu Ser Ile Ser
65                  70                  75                  80

Asn Ile Gln Pro Glu Asp Glu Ala Ile Tyr Ile Cys Gly Val Gly Asp
                 85                  90                  95

Thr Ile Lys Glu Gln Phe Val Tyr Val Phe Gly Gly Gly Thr Lys Val
            100                 105                 110

Thr Val Leu
        115
```

<210> SEQ ID NO 243
<211> LENGTH: 111
<212> TYPE: PRT
<213> ORGANISM: Mus musculus

<400> SEQUENCE: 243

```
Asp Ile Val Leu Thr Gln Ser Pro Ala Ser Leu Ala Val Ser Leu Gly
1               5                   10                  15

Gln Arg Ala Thr Met Ser Cys Arg Ala Ser Gln Ser Val Ser Thr Ser
                 20                  25                  30

Thr Tyr Ser Tyr Met His Trp Tyr Gln Gln Lys Pro Gly Gln Pro Pro
             35                  40                  45

Lys Leu Leu Ile Lys Tyr Ala Ser Asn Leu Glu Ser Gly Val Pro Ala
         50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                 85                  90                  95

Glu Ile Pro Leu Thr Phe Gly Ala Gly Thr Lys Leu Glu Leu Lys
            100                 105                 110
```

<210> SEQ ID NO 244
<211> LENGTH: 117
<212> TYPE: PRT
<213> ORGANISM: Mus musculus

<400> SEQUENCE: 244

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Asn Leu His Trp Val Lys Leu Ser His Gly Lys Ser Leu Glu Trp Ile
        35                  40                  45

Gly Phe Ile Tyr Pro Ser Asn Gly Ile Thr Gly Tyr Asn Gln Lys Phe
    50                  55                  60

Lys Asn Lys Ala Thr Leu Thr Val Asp Asn Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Ser Thr Val Asp Tyr Phe Asp Tyr Trp Gly Gln Gly Thr Thr
            100                 105                 110

Leu Thr Val Ser Ser
        115

<210> SEQ ID NO 245
<211> LENGTH: 120
<212> TYPE: PRT
<213> ORGANISM: Mus musculus

<400> SEQUENCE: 245

Glu Val Lys Leu Glu Glu Ser Gly Gly Gly Leu Val Gln Pro Gly Gly
1               5                   10                  15

Ser Met Lys Leu Ser Cys Val Gly Ser Gly Phe Thr Phe Ser Asn Tyr
            20                  25                  30

Cys Met Asn Trp Val Arg Gln Ser Pro Glu Lys Gly Leu Glu Trp Val
        35                  40                  45

Ala Glu Ile Arg Leu Lys Ser Asn Asn Tyr Val Thr Asn Tyr Val Tyr
    50                  55                  60

Cys Glu Ser Val Lys Gly Arg Phe Thr Ile Ser Arg Asp Asp Ser Lys
65                  70                  75                  80

Ser Arg Val Tyr Leu Gln Met Asn Asn Leu Arg Gly Glu Asp Thr Gly
                85                  90                  95

Phe Tyr Thr Arg Asp Gly Tyr Tyr Val Pro Phe Ala Tyr Trp Gly Gln
            100                 105                 110

Gly Thr Leu Val Thr Val Ser Ala
        115                 120

<210> SEQ ID NO 246
<211> LENGTH: 117
<212> TYPE: PRT
<213> ORGANISM: Mus musculus

<400> SEQUENCE: 246

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Asn Leu His Trp Val Lys Leu Ser His Gly Lys Ser Leu Glu Trp Ile

```
                    35                  40                  45
Gly Phe Ile Tyr Pro Ser Asn Gly Ile Thr Gly Tyr Asn Gln Lys Phe
         50                  55                  60

Lys Asn Lys Ala Thr Leu Thr Val Asp Asn Ser Ser Thr Ala Tyr
 65                  70                  75                  80

Met Glu Leu Arg Ser Leu Thr Ser Glu Asp Ser Ala Val Tyr Tyr Cys
                 85                  90                  95

Ala Arg Ser Thr Val Asp Tyr Phe Asp Tyr Trp Gly Gln Gly Thr Thr
             100                 105                 110

Leu Thr Val Ser Ser
        115

<210> SEQ ID NO 247
<211> LENGTH: 19
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: 1
<223> OTHER INFORMATION: Xaa = Asp or Glu
<220> FEATURE:
<221> NAME/KEY: VARIANT
<222> LOCATION: 2, 3
<223> OTHER INFORMATION: Xaa = Any Amino Acid and up to 2 of them can be
      present or absent
<220> FEATURE:
<221> NAME/KEY: VARIANT
<222> LOCATION: 5, 6
<223> OTHER INFORMATION: Xaa = Any Amino Acid
<220> FEATURE:
<221> NAME/KEY: VARIANT
<222> LOCATION: 7
<223> OTHER INFORMATION: Xaa = Leu or Ile
<220> FEATURE:
<221> NAME/KEY: VARIANT
<222> LOCATION: 8, 9, 10, 11, 12, 13, 14, 15
<223> OTHER INFORMATION: Xaa = Any Amino Acid and up to 2 of them can be
      present or absent
<220> FEATURE:
<221> NAME/KEY: VARIANT
<222> LOCATION: 17, 18
<223> OTHER INFORMATION: Xaa = Any Amino Acid
<220> FEATURE:
<221> NAME/KEY: VARIANT
<222> LOCATION: 19
<223> OTHER INFORMATION: Xaa = Leu or Ile

<400> SEQUENCE: 247

Xaa Xaa Xaa Tyr Xaa Xaa Xaa Xaa Xaa Xaa Xaa Xaa Xaa Xaa Xaa Tyr
 1               5                  10                  15

Xaa Xaa Xaa

<210> SEQ ID NO 248
<211> LENGTH: 446
<212> TYPE: PRT
<213> ORGANISM: Artificial Sequence
<220> FEATURE:
<223> OTHER INFORMATION: Synthetic construct

<400> SEQUENCE: 248

Glu Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Ile Thr Asp Ser
             20                  25                  30

Asn Ile His Trp Val Arg Gln Ala Pro Gly Gln Ser Leu Glu Trp Ile
```

```
                35                  40                  45
Gly Tyr Ile Tyr Pro Tyr Asn Gly Gly Thr Asp Tyr Asn Gln Lys Phe
 50                  55                  60

Lys Asn Arg Ala Thr Leu Thr Val Asp Asn Pro Thr Asn Thr Ala Tyr
 65                  70                  75                  80

Met Glu Leu Ser Ser Leu Arg Ser Glu Asp Thr Ala Phe Tyr Tyr Cys
                 85                  90                  95

Val Asn Gly Asn Pro Trp Leu Ala Tyr Trp Gly Gln Gly Thr Leu Val
                100                 105                 110

Thr Val Ser Ser Ala Ser Thr Lys Gly Pro Ser Val Phe Pro Leu Ala
                115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
                275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
                435                 440                 445

<210> SEQ ID NO 249
```

```
<211> LENGTH: 163
<212> TYPE: PRT
<213> ORGANISM: Artificial Sequence
<220> FEATURE:
<223> OTHER INFORMATION: Synthetic construct

<400> SEQUENCE: 249

Asp Ile Gln Leu Thr Gln Ser Pro Ser Thr Leu Ser Ala Ser Val Gly
1               5                   10                  15

Asp Arg Val Thr Ile Thr Cys Arg Ala Ser Glu Ser Leu Asp Asn Tyr
            20                  25                  30

Gly Ile Arg Phe Leu Thr Trp Phe Gln Gln Lys Pro Gly Lys Ala Pro
        35                  40                  45

Lys Leu Leu Met Tyr Ala Ala Ser Asn Gln Gly Ser Gly Val Pro Ser
    50                  55                  60

Arg Phe Ser Gly Ser Gly Ser Gly Thr Glu Phe Thr Leu Thr Ile Ser
65                  70                  75                  80

Ser Leu Gln Pro Asp Asp Phe Ala Thr Tyr Tyr Cys Gln Gln Thr Lys
                85                  90                  95

Glu Val Pro Trp Ser Phe Gly Gln Gly Thr Lys Val Glu Val Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser

<210> SEQ ID NO 250
<211> LENGTH: 446
<212> TYPE: PRT
<213> ORGANISM: Artificial Sequence
<220> FEATURE:
<223> OTHER INFORMATION: Synthetic construct

<400> SEQUENCE: 250

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Asn Met His Trp Val Arg Gln Ala Pro Gly Gln Gly Leu Glu Trp Ile
        35                  40                  45

Gly Tyr Ile Tyr Pro Tyr Asn Gly Gly Thr Gly Tyr Asn Gln Lys Phe
    50                  55                  60

Lys Ser Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Pro Ala Met Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160
```

```
Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 251
<211> LENGTH: 163
<212> TYPE: PRT
<213> ORGANISM: Artificial Sequence
<220> FEATURE:
<223> OTHER INFORMATION: Synthetic construct

<400> SEQUENCE: 251

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Asn Tyr
            20                  25                  30

Gly Ile Ser Phe Met Asn Trp Phe Gln Gln Lys Pro Gly Lys Ala Pro
        35                  40                  45

Lys Leu Leu Ile Tyr Ala Ala Ser Asn Gln Gly Ser Gly Val Pro Ser
    50                  55                  60

Arg Phe Ser Gly Ser Gly Ser Gly Thr Asp Phe Thr Leu Thr Ile Ser
65                  70                  75                  80
```

```
Ser Leu Gln Pro Asp Asp Phe Ala Thr Tyr Tyr Cys Gln Gln Ser Lys
            85                  90                  95

Glu Val Pro Trp Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
            130                 135             140

Pro Arg Glu Ala Lys Val Gln Trp Lys Val Asp Asn Ala Leu Gln Ser
145             150                 155                 160

Gly Asn Ser
```

ANTI-CD33 ANTIBODIES AND METHODS OF USE THEREOF

CROSS-REFERENCE TO RELATED APPLICATIONS

This application is a U.S. national stage application of PCT/US2016/037108, filed internationally on Jun. 11, 2016, which claims the benefit of U.S. Provisional Application No. 62/175,152, filed Jun. 12, 2015, and U.S. Provisional Application No. 62/241,701, filed Oct. 14, 2015, each of which is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing file name: 735022000700SUBSEQLIST.TXT, date recorded: Jan. 17, 2020, size: 201 KB).

FIELD OF THE INVENTION

This present disclosure relates to anti-CD33 antibodies and therapeutic uses of such antibodies.

BACKGROUND OF THE INVENTION

Myeloid cell surface antigen CD33 precursor (CD33), also known as Siglec-3, is a type 1, immunoglobulin-like, transmembrane protein expressed on immune and hematopoietic cells, including immature and mature myeloid cells, dendritic cells, and microglial cells. (Crocker et al. (2007) Nat Rev Immunol. 7:255-266; McMillan and Crocker (2008) Carbohydr Res. 343:2050-2056; Von Gunten and Bochner (2008) Ann NY Acad Sci. 1143:61-82; Handgretinger et al. (1993) Immunol Lett. 37:223-228; and Hernández-Caselles et al. (2006) J Leukoc Biol. 79:46-58). CD33 expression is downregulated to low levels on peripheral granulocytes and resident macrophages and the protein was reported to be absent from astrocytes, oligodendrocytes, endothelial cells, and resting T cells (Griffin J D. et al., (1984) Leukemia Research Vol. S, No. 4, pp. 521-534). CD33 is a member of the Siglec family of lectins that bind sialic acid residues of glycoproteins and glycolipids. One potential binding target for Siglec proteins are gangliosides; that is, glycolipids that consist of a ceramide linked to a sialylated glycan. Most gangliosides share a common lacto-ceramide core and one or more sialic acid residues. Diversity in the Siglec ligands is generated by the addition of other neutral sugars and sialic acid in different linkages, and modification of sialic acid itself.

Fourteen Siglec proteins have been identified in humans and nine in mice that are comprised of 2-17 extracellular Ig domains including an amino-terminal V-set domain that contains the sialic acid-binding site. The sialic acid-binding region is located on the V-set Ig-like domain, which contains a two aromatic residues and one arginine motif highly conserved in all Siglecs (Crocker et al. (2007) Nat Rev Immunol. 7:255-266; McMillan and Crocker (2008) Carbohydr Res. 343:2050-2056; Von Gunten and Bochner (2008) Ann NY Acad Sci. 1143:61-82; May et al. (1998) Mol Cell. 1:719-728; Crocker et al. (1999) Biochem J. 341:355-361; and Crocker and Varki (2001) Trends Immunol. 2:337-342). The binding sites to sialylated ligands have been mapped by co-crystal structures (Attrill et al., (2006) J. Biol. Chem. 281:32774-32783; and Varki et al., Glycobiology, 16 pp. 1R-27R). Since cell membranes are rich in sialic acids, ligand binding by Siglecs can occur in cis and in trans, both affecting their functional properties. Each Siglec has a distinct preference for binding the diverse types of sialylated glycans that are found on the surface of mammalian cells (Crocker et al. (2007) Nat Rev Immunol. 7:255-266; and Crocker et al. (2007) Nat Rev Immunol. 7:255-266). Most CD33-related Siglecs, including Siglec-3, contain one or more immunoreceptor tyrosine-based inhibitory motif (ITIM) sequences in their cytoplasmic tails, which enable them as inhibitory receptors and negative regulators of immune functions through recruitment of the tyrosine phosphatases SHP1 and SHP2 (Crocker et al. (2007) Nat Rev Immunol. 7:255-266; McMillan and Crocker (2008) Carbohydr Res. 343:2050-2056; and Von Gunten and Bochner (2008) Ann NY Acad Sci. 1143:61-82). Certain Siglecs contain immunoreceptor tyrosine-based activating motif (ITAM) sequences in their cytoplasmic tails, which enable them to act as activating receptors and positive regulators of immune function through predicted recruitment of spleen tyrosine kinase (Syk) (Macauley S M. et al., (2014) *Nature Reviews Immunology* 14, 653-666). The Siglec protein family is associated with multiple human disease including, autoimmunity, susceptibility to infection, multiple types of cancer including lymphoma, leukemia and acute myeloid leukemia, systemic lupus erythematosus, rheumatoid arthritis, neurodegenerative disorders, asthma, allergy, sepsis, chronic obstructive pulmonary disease, graft-versus-host disease, eosinophilia, and osteoporosis (Macauley S M. et al., (2014) *Nature Reviews Immunology* 14, 653-666).

Siglec-3 (CD33) was cloned in 1988 (Peiper et al. (1988) *Blood.* 72:314-321; Simmons and Seed (1988) J Immunol. 141:2797-2800), and selective expression was detected on blasts, promyelocytes and myelocytes in the bone marrow, and by monocytes in the peripheral blood (Griffit J. D et al., (1984) Leukemia Research Vol. S, No. 4, pp. 521-534). Expression on subsets of mitogen or alloantigen-activated human T and natural killer (NK) cells has also been reported (Herna´ndez-Caselles T. et al., (2006) Journal of Leukocyte Biology. 79, 46-58). In addition, CD33 is expressed on 85-90% of adult and pediatric cases of acute myeloid leukemia (Griffin, J. D., et al., (1984). *Leuk Res* 8, 521-534).

CD33 contains an Ig-like C2-type (immunoglobulin-like) and an Ig-like V-type (immunoglobulin-like) extracellular domain, as well as two ITIM-like motifs in its cytoplasmic domain. Three alternatively spliced forms (isoforms) of CD33 have been identified, including a higher molecular weight variant, named CD33M and a smaller isoform CD33m that lacks the Ig-like V-type domain (the ligand-binding site), and the disulfide bond linking the V and C domains. In addition, tissue specific post-translational, modifications of CD33 have been reported (Herna´ndez-Caselles T. et al., (2006) Journal of Leukocyte Biology. 79, 46-58; and Pérez-Oliva et al., (2011) Glycobiol. 21, 757-770). CD33 undergoes ligand-induced phosphorylation of serine 307 (Ser-307) and serine 342 (Ser-342) by protein kinase C (Grobe, K et al., (2002) Blood 99, 3188-3196) and on Tyr-340, and Tyr-358 by Src family tyrosine kinases, such as LCK (Paul, S. P., et al., (2000). *Blood* 96, 483-490).

Following phosphorylation primarily on Tyr-340, but also on Tyr-358 of its ITIM domains, CD33 binds SHP-2/PTPN11 and SHP-1/PTPN6. The binding of these phosphatases to CD33 is enhanced following colligation of CD33 with CD64 (Taylor, V. C et al., (1999), J. Biol. Chem. 274, 11505-11512). Phosphatase activity is associated with decreased intracellular calcium mobilization, and decreased tyrosine phosphorylation on multiple proteins (Ulyanova, T., et al., (1999) *Eur J Immunol* 29, 3440-3449; Paul, S. P., et al., (2000). *Blood* 96, 483-490) as well as with blockade of signal transduction and immune response, in part, through dephosphorylation of signaling molecules on adjacent activating receptors, including those that contain ITAM motifs, pattern recognition receptors, Toll-like receptors and damage-associated molecular pattern (DAMP) receptors. Activation of CD33 also leads to tyrosine phosphorylation of and association with the protoconcogenes c-Cbl, Vav and Syk (Balaian, L. et al., (2001). *Leuk Res* 25, 1115-1125). c-Cbl is an E3 ubiquitin ligase and upon activation induces CBL-dependent ubiquitination and proteosomal degradation of CD33 as well as retinoic acid-inducible genes (Taylor et al. (1999) J Biol Chem. 274:11505-11512; Ulyanova et al. (1999) Eur J Immunol. 29:3440-3449; Paul et al. (2000) Blood. 96:483-490; and Lajaunias et al. (2005) Eur J Immunol. 35:243-251). Some, but not all, Siglec ligands induce receptor down regulation ((Macauley S M. et al., (2014) *Nature Reviews Immunology* 14, 653-666). A similar mechanism of ligand-induced receptor degradation has been reported for tyrosine kinase receptors (Monsonego-Oran et al., (2002) Febs letters 528, 83-89; and Fasen et al., (2008) Cell & Molecular Biology 9. 251-266), as well as steroid receptors (Callige et al., (2005) Mol. Cell. Biol. 25. 4349-4358; and Pollenz et al., (2006) Chemico-Biological Interactions. 164. 49-59).

Activation of CD33 signaling has also been shown to be associated with a decrease in production of proinflammatory cytokines IL-1βeta, IL-8, and TNF-alpha from innate immune cells. These activities of CD33 appear to be mediated through the activation of phosphoinositide 3-kinase (PI3K) (Lajaunias F. et al. (2005). Eur. J. Immunol. 2005. 35: 243-251). It has been proposed that the association between ITIM-containing Siglec receptors and activating receptors may be mediated by extracellular ligands that bind and bridge these receptors (Macauley S M. et al., (2014) *Nature Reviews Immunology* 14, 653-666).

Multiple studies indicate an inhibitory role for CD33 in regulation of innate immunity and mediating cell-cell interactions that inhibit or restrict immune responses (Crocker et al., (2012) Ann. N Y Acad. Sci. 1253, 102-111; Pillai et al., (2012) Annu. Rev. Immunol. 30, 357-392; von Gunten and Bochner (2008) Ann. N Y Acad. Sci. 1143, 61-82; Griciuc et al., (2013) Neuron 78, 1-13; Ferlazzo et al. (2000) Eur J Immunol. 30:827-833; Vitale et al. (2001) Proc Natl Acad Sci USA. 98:5764-5769; and Herna´ndez-Caselles T. et al., (2006) Journal of Leukocyte Biology. 79, 46-58). CD33 inactivation in mice does not lead to obvious developmental, histological, or behavioral abnormalities; and CD33-deficient mice breed normally, indicating that CD33 is not an essential gene and that its function may be limited to innate immunity (Brinkman-Van der Linden et al., (2003) Mol. Cell. Biol. 23, 4199-4206).

Genome-wide association studies (GWAS) performed on extended cohorts (e.g., thousands of individuals) have identified single nucleotide polymorphisms (SNPs) rs3865444$^{CC}$ (AKA rs3826656) and rs3865444$^{AA}$ in CD33 as genetic modulators of risk for late onset Alzheimer's disease. The minor homozygous allele rs3865444$^{AA}$ SNP has been associated with reduced full length CD33 protein levels and increased expression of the CD33 isoform lacking the Ig-V ligand binding domain (Raj T. et al. (2014) Human Molecular Genetics) and has been suggested to confer protection against Alzheimer's disease (AD). In contrast, the homozygous rs3865444$^{CC}$ allele has been suggested to constitute a risk allele for AD and is associated with a ~7-fold increase in cell surface expression of full length CD33 in the peripheral monocytes of young and older individuals. The heterozygous rs3865444$^{AC}$ displays a 3-4 fold increase in CD33 cell surface expression and is also considered risk for AD. CD33 is expressed at all three stages of activation in microglia and macrophages, but there is no effect of age on CD33 surface expression. The polymorphic alleles rs3865444$^{CC}$ and rs3865444$^{AC}$ are also associated with reduced ability of monocytes to phagocytose amyloid beta 42 (A-beta 42) peptide in vitro and increased neuritic amyloid pathology and fibrillar amyloid in vivo.

Increased numbers of activated human microglia that may be less functional and fail to clear amyloid beta plaques have also been reported for the risk allele, indicating that the rs3865444$^{C}$ allele may be dominant for functional traits and have a role in amyloid accumulation in the pre-symptomatic phase of Alzheimer's disease (AD). Although rs3865444$^{C}$ is associated with greater neuritic amyloid plaque burden, it is not associated with burden of neurofibrillary tangles (Bradshaw et al., (2013) *Nat. Neurosci.* 16, 848-850). This SNP is localized upstream of the 5' UTR of the CD33 gene, but may exhibit linkage disequilibrium with functional variant(s) located in the coding region (Bertram, et al. (2008). Am. J. Hum. Genet. 83, 623-632; Hollingworth, et al. (2011) Nat. Genet. 43, 429-435; and Naj, et al. (2011) Nat Genet. 43, 436-441), which may lead to alternative splicing and removal of the ligand binding domain encoded by exon 2 (Malik et al., (2013) J. Neuros, 33: 13320-13325; and Raj et al., (2014), Human Molecular Genetics, 23, 2729). CD33 mRNA and protein levels, as well as the number of CD33-positive microglia, have been shown to be increased in AD brains relative to age-matched controls. However, AD brain microglia from carriers of the rs3865444$^{AA}$ allele, were still associated with lower levels of CD33 expression and reduced levels of insoluble A-beta 42 peptide compared to AD brains from carrier of the rs3865444$^{C}$ non-protective allele.

Increased number of CD33-immunoreactive microglia has been shown to correlate with higher insoluble A-beta 42 levels and higher amyloid plaque burden in Alzheimer's disease (AD) cases. Using semiquantitative histologic measures of plaque and tangle pathology, Walker at al. have suggested no significant differences in pathology between the SNPs rs3865444$^{CC}$ (AKA rs3826656) and rs3865444$^{AA}$ alleles (Walker at al., (2015) Neurobiology of Aging 35 571-582). However, increased expression of CD33 mRNA has been associated with increasing AD pathology in temporal cortex brain samples (Walker at al., (2015) Neurobiology of Aging 36 571-582).

Gain and loss of function studies have indicated that CD33 is both required and sufficient to inhibit microglial uptake of A-beta 42. Moreover, analysis of the CD33m variant in which the sialic acid-binding V-type Immunoglobulin-like (V-Ig) domain was deleted demonstrates that sialic acid binding is required for CD33 to mediate the inhibition of A-beta 42 phagocytosis and clearance by microglia (Perez-Oliva et al., (2011) Glycobiol. 21, 757-770). Additionally, the APP/PSI transgenic mouse model of Alzheimer's disease, in which the CD33 gene is ablated, exhibits a marked reduction of insoluble A-beta 42 levels and A-beta plaque burden (Griciuc et al., (2013) Neuron 78, 1-13; and Bradshaw et al., (2013) Nat. Neurosci. 16, 848-850).

In oncology, CD33 variants that lead to decreased expression of CD33 have been shown to be associated with improved survival rate from pediatric acute myeloid leukemia (AML). The 3-year overall survival rate from remission is 84%+/−8% for those carrying the variant rs35112940$^{GG}$, which is in strong linkage disequilibrium with the rs3865444$^{AA}$ variant, associated with lower full-length expression of CD33. The remission rate for the non-protective allele is 68%+/−15%. Carriers of the protective allele also have a lower relapse risk and superior disease-free survival. Likewise, patients homozygous for the minor variant allele (TT) of rs12459419, which is associated with over 46% lower expression of the full-length CD33, are more likely to have favorable disease outcome than carriers of the variants CC and CT (52% vs. 31%) and have significantly lower diagnostic blast CD33 expression than other genotypes. This is the case even in patients undergoing treatment with anti-CD33 antibody and a toxic calicheamicin-gamma derivative (Mortland et al., (2013) Clin Cancer Res; 1-8). Carriers of the 2459419$^{TT}$ allele, as well as carriers of the rs12459419$^{CT}$ allele, which show over 25% reduction in expression of full-length CD33, also display reduced Alzheimer's disease risk (Malik M. et al. (2015) Human Molecular Genetics, 1-14). This suggests that reduced expression or functionality of CD33 may be beneficial in Alzheimer's disease and cancer. However, no data has been reported on the ability of anti-CD33 antibodies to down-regulate CD33, or block CD33 ligand/receptor interactions, in physiologically relevant, primary immune cells.

Antibodies to CD33 have been described in, for example, U.S. Pat. Nos. 7,342,110, 7,557,189, 8,119,787, 8,337,855, 8,124,069, 5,730,982, U.S. Pat. No. 7,695,71, WO2012074097, WO2004043344, WO1993020848, WO2012045752, WO2007014743, WO2003093298, WO2011036183, WO1991009058, WO2008058021, WO2011038301, Hoyer et al., (2008) Am. J. Clin. Pathol. 129, 316-323, Rollins-Raval and Roth, (2012) Histopathology 60, 933-942), Pérez-Oliva et al., (2011) Glycobiol. 21, 757-770), Ferlazzo et al. (2000) Eur J Immunol. 30:827-833, Vitale et al., (2001) Proc Natl Acad Sci USA. 98:5764-5769, Jandus et al., (2011) Biochem. Pharmacol. 82, 323-332, O'Reilly and Paulson, (2009) Trends Pharmacol. Sci. 30, 240-248, Jurcic, (2012) Curr Hematol Malig Rep 7, 65-73, and Ricart, (2011) Clin. Cancer Res. 17, 6417-6427. However, these antibodies are used primarily to either detect CD33 on cells or target toxins, such as calicheamicin-gamma derivatives, in order to kill leukemia cells that express CD33. Moreover, no data has been reported showing the ability of anti-CD33 antibodies to treat solid tumor cells that do not express CD33, by enhancing anti-tumor immune responses.

Accordingly, there is a need for therapeutic antibodies for treating one or more diseases, disorders, and conditions associated with undesired CD33 activity.

All references cited herein, including patents, patent applications and publications, are hereby incorporated by reference in their entirety.

SUMMARY OF THE INVENTION

The present disclosure is generally directed to CD33 agents, such as anti-CD33 antibodies, and methods of using such CD33 agents. The methods provided herein find use in preventing, reducing risk, or treating an individual having dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, solid and blood cancer, bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express CD33, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus* influenza. The methods provided herein also find use in inducing or promoting the survival, maturation, functionality, migration, or proliferation of one or more immune cells in an individual in need thereof. The methods provided herein find further use in decreasing the activity, functionality, or survival of regulatory T cells, tumor-imbedded immunosuppressor dendritic cells, tumor-imbedded immunosuppressor macrophages, myeloid-derived suppressor cells, tumor-associated macrophages, acute myeloid leukemia (AML) cells, chronic lymphocytic leukemia (CLL) cell, or chronic myeloid leukemia (CML) cell in an individual in need thereof.

Certain aspects of the present disclosure are based, at least in part, on the identification of anti-CD33 antibodies that are capable of decreasing cell surface levels of CD33 on human primary immune cells and CD33-expressing cell lines, and/or that are capable of inhibiting the binding of CD33 ligands on red blood cells to CD33 (see, e.g., Examples 1-5). Advantageously, the anti-CD33 antibodies decrease cellular levels of CD33 with a half-maximal effective concentration (EC$_{50}$) that ranges from 65 pM to 20 pM, decrease cellular levels of CD33 in vivo with a half-maximal effective concentration (EC$_{50}$) that ranges from 8.0 mg/kg to 2.0 mg/kg, bind to human cells, such as human dendritic cells with an EC$_{50}$ that ranges from 200 pM to 10 pM, and have a dissociation constant (K$_D$) for human CD33 that ranges from 300 pM to 10 pM.

Accordingly, certain aspects of the present disclosure relate to an isolated (e.g., monoclonal) anti-CD33 antibody, wherein the anti-CD33 antibody decreases cellular levels of CD33, or inhibits interaction between CD33 and one or more CD33 ligands, or both. In some embodiments, the anti-CD33 antibody exhibits one or more of the following properties: a. has a dissociation constant (K$_D$) for human CD33 that is lower than that of anti-CD33 antibody gemtuzumab; b. binds to human dendritic cells with an EC$_{50}$ that is lower than that of anti-CD33 antibody gemtuzumab or lintuzumab; c. decreases cellular levels of CD33 with an EC$_{50}$ that is lower than that of anti-CD33 antibody gemtuzumab or lintuzumab; d. has a dissociation constant (K$_D$) for human CD33 that ranges from 300 pM to 10 pM, wherein the K$_D$ is determined at a temperature of approximately 25° C.; e. binds to human dendritic cells with an EC$_{50}$ that ranges from 200 pM to 10 pM, wherein the EC$_{50}$ is determined at a temperature of approximately 4° C.; f. decreases cellular levels of CD33 with an EC$_{50}$ that ranges from 65 pM to 20 pM; or g. decreases cellular levels of CD33 in vivo with an EC$_{50}$ that ranges from 8.0 mg/kg to 2.0 mg/kg. In some embodiments, the dissociation constant (K$_D$) for human CD33 is less than 300 pM, wherein the K$_D$ is determined at a temperature of approximately 25° C. In some embodiment, the K$_D$ is determined using a monovalent antibody. In some embodiment, the K$_D$ is determined using a full-length antibody in a monovalent form. In some embodiments, the anti-CD33 antibody binds to human dendritic cells with an EC$_{50}$ that is less than 200 pM, wherein the EC$_{50}$ is determined at a temperature of approximately 4° C. In some embodiments, the EC$_{50}$ for decreasing cellular levels of CD33 in vivo is determined using a mouse. In some embodiments, the anti-CD33 antibody decreases cellular levels of CD33 with an EC$_{50}$ that ranges from 65 pM to 22 pM, or less than 22 pM. In some embodiments, the anti-CD33 antibody decreases cellular levels of CD33 with an EC$_{50}$ of 65 pM or less, 60 pM or less, 55 pM or less, 50 pM or less, 45 pM or less, 40 pM or less, 35 pM or less, 30 pM or less, 25 pM or less, 24 pM or less, 23 pM or less, 22 pM or less, 21 pM or less, 20 pM or less, 10 pM or less, 9 pM or less, 8 pM or less, 7 pM or less, 6 pM or less, or 5 pM or less.

Other aspects of the present disclosure relate to an isolated (e.g., monoclonal) anti-CD33 antibody, wherein the anti-CD33 antibody decreases cellular levels of CD33, inhibits interaction between CD33 and one or more CD33 ligands, or both, and wherein the anti-CD33 antibody exhibits one or more of the following properties: a. has a dissociation constant (K$_D$) for human CD33 that is lower than that of anti-CD33 antibody gemtuzumab; b. binds to human dendritic cells with an EC$_{50}$ that is lower than that of anti-CD33 antibody gemtuzumab or lintuzumab; c. decreases cellular levels of CD33 with an EC$_{50}$ that is lower than that of anti-CD33 antibody gemtuzumab or lintuzumab; d. has a dissociation constant (K$_D$) for human CD33 that ranges from 300 pM to 10 pM, wherein the K$_D$ is determined at a temperature of approximately 25° C.; e. binds to human dendritic cells with an EC$_{50}$ that ranges from 200 pM to 10 pM, wherein the EC$_{50}$ is determined at a temperature of approximately 4° C.; f. decreases cellular levels of CD33 with an EC$_{50}$ that ranges from 65 pM to 20 pM; or g. decreases cellular levels of CD33 in vivo with an EC$_{50}$ that ranges from 8.0 mg/kg to 2.0 mg/kg. In some embodiments, the dissociation constant (K$_D$) for human CD33 is less than 300 pM, wherein the K$_D$ is determined at a temperature of approximately 25° C. In some embodiment, the K$_D$ is determined using a monovalent antibody. In some embodiment, the K$_D$ is determined using a full-length antibody in a monovalent form. In some embodiments, the anti-CD33 antibody binds to human dendritic cells with an EC$_{50}$ that is less than 200 pM, wherein the EC$_{50}$ is determined at a temperature of approximately 4° C. In some embodiments, the anti-CD33 antibody decreases cellular levels of CD33 with an EC$_{50}$ that ranges from 65 pM to 22 pM, or less than 22 pM. In some embodiments, the anti-CD33 antibody decreases cellular levels of CD33 with an EC$_{50}$ of 65 pM or less, 60 pM or less, 55 pM or less, 50 pM or less, 45 pM or less, 40 pM or less, 35 pM or less, 30 pM or less, 25 pM or less, 24 pM or less, 23 pM or less, 22 pM or less, 21 pM or less, 20 pM or less, 10 pM or less, 9 pM or less, 8 pM or less, 7 pM or less, 6 pM or less, or 5 pM or less. In some embodiments, the EC$_{50}$ for decreasing cellular levels of CD33 in vivo is determined using a mouse.

In some embodiments that may be combined with any of the preceding embodiments, the anti-CD33 antibody decreases cell surface levels of CD33, decreases intracellular levels of CD33, decreases total levels of CD33, or any combination thereof. In some embodiments that may be combined with any of the preceding embodiments, the anti-CD33 antibody induces CD33 degradation, CD33 cleavage, CD33 internalization, CD33 shedding, downregulation of CD33 expression, or any combination thereof. In some embodiments that may be combined with any of the preceding embodiments, the anti-CD33 antibody decreases cellular levels of CD33 without inhibiting the interaction between CD33 and one or more CD33 ligands. In some embodiments that may be combined with any of the preceding embodiments, the anti-CD33 antibody decreases cellular levels of CD33 and inhibits the interaction between CD33 and one or more CD33 ligands. In some embodiments that may be combined with any of the preceding embodiments, the antibody decreases cellular levels of CD33 in vivo. In some embodiments that may be combined with any of the preceding embodiments, the anti-CD33 antibody decreases cellular levels of CD33 in vivo with an EC$_{50}$ that ranges from about 8.0 mg/kg to about 2.0 mg/kg, or less than 2.0 mg/kg. In some embodiments that may be combined with any of the preceding embodiments, the anti-CD33 antibody inhibits the interaction between CD33 and one or more CD33 ligands without decreasing cellular levels of CD33. In some embodiments that may be combined with any of the preceding embodiments, the anti-CD33 antibody inhibits cell surface clustering of CD33. In some embodiments that may be combined with any of the preceding embodiments, the anti-CD33 antibody inhibits one or more CD33 activities. In some embodiments that may be combined with any of the preceding embodiments, the one or more CD33 activities selected from the group consisting of: (a) CD33 binding to sialic acid-containing glycoproteins, sialic acid-containing glycolipids, or both; (b) CD33 binding to SHP1 or SHP2; (c) phosphorylation of Tyr-340, Tyr-358, or both, induced by one or more SRC family tyrosine kinases, optionally, wherein the one or more SRC family tyrosine kinases are selected from the group consisting of Syk, LCK, and FYM; (d) phosphorylation of Ser-307, Ser-342, or both, optionally wherein the phosphorylation is induced by protein kinase C; (e) modulated expression of one or more anti-inflammatory cytokines, optionally wherein the one or more anti-inflammatory cytokines are selected from a group consisting of IL-4, IL-10, IL-13, IL-35, IL-16, TGF-beta, IL-1Ra, G-CSF, and soluble receptors for TNF, IFN-beta1a, IFN-beta1b, or IL-6; (f) modulated expression of one or more anti-inflammatory cytokines in one or more cells selected from the group consisting of macrophages, dendritic cells, bone marrow-derived dendritic cells, monocytes, osteoclasts, T cells, T helper cells, cytotoxic T cells, granulocytes, neutrophils, and microglial cells; (g) modulated expression of one or more pro-inflammatory cytokines, optionally wherein the one or more pro-inflammatory cytokines are selected from the group consisting of IFN-a4, IFN-b, IL-1β, TNF-α, IL-6, IL-8, CRP, IL-20 family members, LIF, IFN-gamma, OSM, CNTF, GM-CSF, IL-11, IL-12, IL-17, IL-18, IL-23, CXCL10, IL-33, CRP, IL-33, MCP-1, and MIP-1-beta; (h) modulated expression of one or more pro-inflammatory cytokines in one or more cells selected from the group consisting of macrophages, dendritic cells, bone marrow-derived dendritic cells, monocytes, osteoclasts, T cells, T helper cells, cytotoxic T cells, granulocytes, neutrophils, and microglial cells; (i) modulated expression of one or more proteins selected from the group consisting of C1qa, C1qB, C1qC, C1s, C1R, C4, C2, C3, ITGB2, HMOX1, LAT2, CASP1, CSTA, VSIG4, MS4A4A, C3AR1, GPX1, TyroBP, ALOX5AP, ITGAM, SLC7A7, CD4, ITGAX, PYCARD, CD14, CD16, HLA-DR, and CCR2; (j) inhibition of extracellular signal-regulated kinase (ERK) phosphorylation; (k) decreasing tyrosine phosphorylation on multiple cellular proteins; (l) modulated expression of C-C chemokine receptor 7 (CCR7); (m) inhibition of microglial cell chemotaxis toward CCL19 and CCL21 expressing cells; (n) reducing T cell proliferation induced by one or more cells selected from the group consisting of dendritic cells, bone marrow-derived dendritic cells, monocytes, microglia, M1 microglia, activated M1 microglia, M2 microglia, macrophages, M1 macrophages, activated M1 macrophages, and M2 macrophages; (o) inhibition of osteoclast production, decreased rate of osteoclastogenesis, or both; (p) decreasing survival of one or more cells selected from the group consisting of dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, neutrophils, microglia, M1 microglia, activated M1 microglia, and M2 microglia; (q) decreasing proliferation of one or more cells selected from the group consisting of dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, neutrophils, microglia, M1 microglia, activated M1 microglia, and M2 microglia; (r) inhibiting migration of one or more cells selected from the group consisting of dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, neutrophils, microglia, M1 microglia, activated M1 microglia, and M2 microglia; (s) decreasing one or more functions of one or more cells selected from the group consisting of dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, neutrophils, microglia, M1 microglia, activated M1 microglia, and M2 microglia; (t) inhibiting maturation of one or more cells selected from the group consisting of dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, neutrophils, microglia, M1 microglia, activated M1 microglia, and M2 microglia; (u) inhibition of one or more types of clearance selected from the group consisting of apoptotic neuron clearance, nerve tissue debris clearance, dysfunctional synapse clearance, non-nerve tissue debris clearance, bacteria clearance, other foreign body clearance, disease-causing protein clearance, disease-causing peptide clearance, and tumor cell clearance; optionally wherein the disease-causing protein is selected from the group consisting of amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides and the tumor cell is from a cancer selected from the group consisting of bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, and thyroid cancer; (v) inhibition of phagocytosis of one or more of apoptotic neurons, nerve tissue debris, dysfunctional synapses, non-nerve tissue debris, bacteria, other foreign bodies, disease-causing proteins, disease-causing peptides, disease-causing nucleic acids, or tumor cells; optionally wherein the disease-causing nucleic acids are antisense GGCCCC (G2C4) repeat-expansion RNA, the disease-causing proteins are selected from the group consisting of amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides, and the tumor cells are from a cancer selected from the group consisting of bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, or thyroid cancer; (w) binding to CD33 ligand on tumor cells; (x) binding to CD33 ligand on cells selected from the group consisting of neutrophils, dendritic cells, bone marrow-derived dendritic cells, monocytes, microglia, and macrophages; (y) inhibition of tumor cell killing by one or more of microglia, macrophages, dendritic cells, bone marrow-derived dendritic cells, neutrophils, T cells, T helper cells, or cytotoxic T cells; (z) inhibiting anti-tumor cell proliferation activity of one or more of microglia, macrophages, dendritic cells, bone marrow-derived dendritic cells, neutrophils, T cells, T helper cells, or cytotoxic T cells; (aa) inhibiting anti-tumor cell metastasis activity of one or more of microglia, macrophages, dendritic cells, bone marrow-derived dendritic cells, neutrophils, T cells, T helper cells, or cytotoxic T cells; (bb) inhibition of one or more ITAM motif containing receptors, optionally wherein the one or more ITAM motif containing receptors are selected from the group consisting of TREM1, TREM2, FcgR, DAP10, and DAP12; (cc) inhibition of signaling by one or more pattern recognition receptors (PRRs), optionally wherein the one or more PRRs are selected from the group consisting of receptors that identify pathogen-associated molecular patterns (PAMPs), receptors that identify damage-associated molecular patterns (DAMPs), and any combination thereof; (dd) inhibition of one or more receptors comprising the motif D/Ex0-2YxxL/IX6-8YxxL/I (SEQ ID NO:247); (ee) inhibition of signaling by one or more Toll-like receptors; (ff) inhibition of the JAK-STAT signaling pathway; (gg) inhibition of nuclear factor kappa-light-chain-enhancer of activated B cells (NFκB); (hh) de-phosphorylation of an ITAM motif containing receptor; (ii) modulated expression of one or more inflammatory receptors, optionally wherein the one or more inflammatory receptors comprise CD86 and the one or more inflammatory receptors are expressed on one or more of microglia, macrophages, dendritic cells, bone marrow-derived dendritic cells, neutrophils, T cells, T helper cells, or cytotoxic T cells; (jj) increasing expression of one or more CD33-dependent genes; (kk) normalization of disrupted CD33-dependent gene expression; (11) decreasing expression of one or more ITAM-dependent genes, optionally wherein the one more ITAM-dependent genes are activated by nuclear factor of activated T cells (NFAT) transcription factors; (mm) promoting differentiation of one or more of immunosuppressor dendritic cells, immunosuppressor macrophages, myeloid derived suppressor cells, tumor-associated macrophages, immunosuppressor neutrophils, and regulatory T cells; (nn) promoting functionality of one or more of immunosuppressor dendritic cells, immunosuppressor macrophages, myeloid-derived suppressor cells, tumor-associated macrophages, immunosuppressor neutrophils, and regulatory T cells; (oo) enhancing infiltration of one or more of immunosuppressor dendritic cells, immunosuppressor macrophages, myeloid derived suppressor cells, tumor-associated macrophages, immunosuppressor neutrophils, and regulatory T cells into tumors; (pp) increasing number of tumor-promoting myeloid/granulocytic immune-suppressive cells in a tumor, in peripheral blood, or other lymphoid organ; (qq) enhancing tumor-promoting activity of myeloid-derived suppressor cells; (rr) increasing expression of tumor-promoting cytokines in a tumor or in peripheral blood, optionally wherein the tumor-promoting cytokines are TGF-beta or IL-10; (ss) increasing tumor infiltration of tumor-promoting FoxP3+ regulatory T lymphocytes; (tt) enhancing tumor-promoting activity of myeloid-derived suppressor cells (MDSC); (uu) decreasing activation of tumor-specific T lymphocytes with tumor killing potential; (vv) decreasing infiltration of tumor-specific NK cells with tumor killing potential; (ww) decreasing infiltration of tumor-specific B lymphocytes with potential to enhance immune response; (xx) decreasing infiltration of tumor-specific T lymphocytes with tumor killing potential; (yy) increasing tumor volume; (zz) increasing tumor growth rate; (aaa) increasing rate of tumor recurrence; (bbb) decreasing efficacy of one or more immune-therapies that modulate anti-tumor T cell responses, optionally wherein the one or more immune-therapies are immune-therapies that target one or more proteins selected from the group consisting of CD40, OX40, ICOS, CD28, CD137/4-1BB, CD27, GITR, PD-L1, CTLA4, PD-L2, PD-1, B7-H3, B7-H4, HVEM, BTLA, KIR, GAL9, TIM3, A2AR, LAG, DR-5, TREM1, TREM2, CSF-1 receptor, and any combination thereof, or of one or more cancer vaccines; (ccc) inhibition of PLCγ/PKC/calcium mobilization; and (ddd) inhibition of PI3K/Akt, Ras/MAPK signaling. In some embodiments that may be combined with any of the preceding embodiments, the one or more CD33 activities are selected from the group consisting of: (a) CD33 binding to sialic acid-containing glycoproteins, sialic acid-containing glycolipids, or both; (b) modulated expression of one or more anti-inflammatory cytokines, optionally wherein the one or more anti-inflammatory cytokines are selected from a group consisting of IL-4, IL-10, IL-13, IL-35, IL-16, TGF-beta, IL-1Ra, G-CSF, and soluble receptors for TNF, IFN-beta1a, IFN-beta1b, or IL-6; (c) modulated expression of one or more anti-inflammatory cytokines in one or more cells selected from the group consisting of macrophages, dendritic cells, bone marrow-derived dendritic cells, monocytes, osteoclasts, T cells, T helper cells, cytotoxic T cells, granulocytes, neutrophils, and microglial cells; (d) modulated expression of one or more pro-inflammatory cytokines, optionally wherein the one or more pro-inflammatory cytokines are selected from the group consisting of IFN-a4, IFN-b, IL-1β, TNF-α, IL-6, IL-8, CRP, IL-20 family members, LIF, IFN-gamma, OSM, CNTF, GM-CSF, IL-11, IL-12, IL-17, IL-18, IL-23, CXCL10, IL-33, CRP, IL-33, MCP-1, and MIP-1-beta; (e) modulated expression of one or more pro-inflammatory cytokines in one or more cells selected from the group consisting of macrophages, dendritic cells, bone marrow-derived dendritic cells, monocytes, osteoclasts, T cells, T helper cells, cytotoxic T cells, granulocytes, neutrophils, and microglial cells; (f) modulated expression of one or more proteins selected from the group consisting of C1qa, C1qB, C1qC, C1s, C1R, C4, C2, C3, ITGB2, HMOX1, LAT2, CASP1, CSTA, VSIG4, MS4A4A, C3AR1, GPX1, TyroBP, ALOX5AP, ITGAM, SLC7A7, CD4, ITGAX, PYCARD, CD14, CD16, HLA-DR, and CCR2; (g) reducing T cell proliferation induced by one or more cells selected from the group consisting of dendritic cells, bone marrow-derived dendritic cells, monocytes, microglia, M1 microglia, activated M1 microglia, M2 microglia, macrophages, M1 macrophages, activated M1 macrophages, and M2 macrophages; (h) decreasing proliferation of one or more cells selected from the group consisting of dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, neutrophils, microglia, M1 microglia, activated M1 microglia, and M2 microglia; (i) decreasing one or more functions of one or more cells selected from the group consisting of dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, neutrophils, microglia, M1 microglia, activated M1 microglia, and M2 microglia; (j) inhibition of phagocytosis of one or more of apoptotic neurons, nerve tissue debris, dysfunctional synapses, non-nerve tissue debris, bacteria, other foreign bodies, disease-causing proteins, disease-causing peptides, disease-causing nucleic acids, or tumor cells; optionally wherein the disease-causing nucleic acids are antisense GGCCCC (G2C4) repeat-expansion RNA, the disease-causing proteins are selected from the group consisting of amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides, and the tumor cells are from a cancer selected from the group consisting of bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, or thyroid cancer; (k) binding to CD33 ligand on tumor cells; (l) binding to CD33 ligand on cells selected from the group consisting of neutrophils, dendritic cells, bone marrow-derived dendritic cells, monocytes, microglia, and macrophages; (m) inhibition of tumor cell killing by one or more of microglia, macrophages, dendritic cells, bone marrow-derived dendritic cells, neutrophils, T cells, T helper cells, or cytotoxic T cells; (n) inhibiting anti-tumor cell proliferation activity of one or more of microglia, macrophages, dendritic cells, bone marrow-derived dendritic cells, neutrophils, T cells, T helper cells, or cytotoxic T cells; (o) promoting functionality of one or more of immunosuppressor dendritic cells, immunosuppressor macrophages, non-tumorigenic myeloid-derived suppressor cells, tumor-associated macrophages, immunosuppressor neutrophils, and regulatory T cells; (p) enhancing infiltration of one or more of immunosuppressor dendritic cells, immunosuppressor macrophages, myeloid derived suppressor cells, tumor-associated macrophages, immunosuppressor neutrophils, non-tumorigenic CD45$^+$CD14$^+$ myeloid cells, and regulatory T cells into tumors; (q) increasing number of tumor-promoting myeloid/granulocytic immune-suppressive cells in a tumor, in peripheral blood, or other lymphoid organ; (r) enhancing tumor-promoting activity of non-tumorigenic myeloid-derived suppressor cells and/or non-tumorigenic CD45$^+$CD14$^+$ myeloid cells; (s) enhancing survival of non-tumorigenic myeloid-derived suppressor cells (MDSC) and/or non-tumorigenic CD45$^+$CD14$^+$ myeloid cells; (t) decreasing activation of tumor-specific T lymphocytes with tumor killing potential; (u) decreasing activation of CD45$^+$CD3$^+$ T lymphocytes with tumor killing potential; (v) decreasing infiltration of tumor-specific NK cells with tumor killing potential; (w) decreasing infiltration of tumor-specific B lymphocytes with potential to enhance immune response; (x) decreasing infiltration of tumor-specific T lymphocytes with tumor killing potential; (y) decreasing infiltration of CD45$^+$CD3$^+$ T lymphocytes; (z) increasing tumor volume; (aa) increasing tumor growth rate; and (bb) decreasing efficacy of one or more immune-therapies that modulate anti-tumor T cell responses, optionally wherein the one or more immune-therapies are immune-therapies that target one or more proteins selected from the group consisting of CD40, OX40, ICOS, CD28, CD137/4-1BB, CD27, GITR, PD-L1, CTLA4, PD-L2, PD-1, B7-H3, B7-H4, HVEM, BTLA, KIR, GAL9, TIM3, A2AR, LAG, DR-5, TREM1, TREM2, CSF-1 receptor, and any combination thereof, or of one or more chemotherapy agent and/or cancer vaccines. In some embodiments that may be combined with any of the preceding embodiments, the anti-CD33 antibody exhibits one or more activities selected from the group consisting of consisting of: (a) increasing the number of tumor infiltrating CD3$^+$ T cells; (b) decreasing cellular levels of CD33 in non-tumorigenic CD14+ myeloid cells, optionally wherein the non-tumorigenic CD14+ myeloid cells are tumor infiltrating cells or optionally wherein the non-tumorigenic CD14+ myeloid cells are present in blood; (c) reducing the number of non-tumorigenic CD14+ myeloid cells, optionally wherein the non-tumorigenic CD14+ myeloid cells are tumor infiltrating cells or optionally wherein the non-tumorigenic CD14+ myeloid cells are present in blood; (d) reducing PD-L1 levels in one or more cells, optionally wherein the one or more cells are non-tumorigenic myeloid-derived suppressor cells (MDSC); (e) reducing PD-L2 levels in one or more cells, optionally wherein the one or more cells are non-tumorigenic myeloid-derived suppressor cells (MDSC); (f) reducing B7-H2 levels in one or more cells, optionally wherein the one or more cells are non-tumorigenic myeloid-derived suppressor cells (MDSC); (g) reducing B7-H3 levels in one or more cells, optionally wherein the one or more cells are non-tumorigenic myeloid-derived suppressor cells (MDSC); (h) reducing CD200R levels in one or more cells, optionally wherein the one or more cells are non-tumorigenic myeloid-derived suppressor cells (MDSC); (i) reducing CD163 levels in one or more cells, optionally wherein the one or more cells are non-tumorigenic myeloid-derived suppressor cells (MDSC); (j) reducing CD206 levels in one or more cells, optionally wherein the one or more cells are non-tumorigenic myeloid-derived suppressor cells (MDSC); (k) decreasing tumor growth rate of solid tumors; (l) reducing tumor volume; (m) increasing efficacy of one or more PD-1 inhibitors; (n) increasing efficacy of one or more checkpoint inhibitor therapies and/or immune-modulating therapies, optionally wherein the one or more checkpoint inhibitor therapies and/or immune-modulating therapies target one or more of CTL4, the adenosine pathway, PD-L1, PD-L2, PD-L1, PD-L2, OX40, TIM3, LAG3, or any combination thereof; (o) increasing efficacy of one or more chemotherapy agents, optionally wherein the one or more of the chemotherapy agents are gemcitabine, capecitabine, anthracyclines, doxorubicin (Adriamycin®), epirubicin (Ellence®), taxanes, paclitaxel (Taxol®), docetaxel (Taxotere®), 5-fluorouracil (5-FU), cyclophosphamide (Cytoxan®), carboplatin (Paraplatin®), and any combination thereof; (p) increasing proliferation of T cells in the presence of non-tumorigenic myeloid-derived suppressor cells (MDSC); (q) inhibiting differentiation, survival, and/or one or more functions of non-tumorigenic myeloid-derived suppressor cells (MDSC); and (r) killing CD33-expressing immunosuppressor non-tumorigenic myeloid cells and/or non-tumorigenic CD14-expressing cells in solid tumors and associated blood vessels when conjugated to a chemical or radioactive toxin. In some embodiments that may be combined with any of the preceding embodiments, the anti-CD33 antibody is not conjugated to an agent, optionally wherein the agent is drug, toxin, chemotherapeutic, or radioisotope.

In some embodiments that may be combined with any of the preceding embodiments, the anti-CD33 antibody binds a discontinuous CD33 epitope. In some embodiments that may be combined with any of the preceding embodiments, the discontinuous CD33 epitope comprises two or more peptides, three or more peptides, four or more peptides, five or more peptides, six or more peptides, seven or more peptide, eight or more peptides, nine or more peptides, or 10 or more peptides. In some embodiments that may be combined with any of the preceding embodiments, each of the peptides comprise five or more, six or more, seven or more, eight or more, nine or more, 10 or more, 11 or more, 12 or more, 13 or more 14 or more, 15 or more, 16 or more, 17 or more, 18 or more, 19 or more, or 20 or more amino acid residues of the amino acid sequence of SEQ ID NO: 1; or five or more, six or more, seven or more, eight or more, nine or more, 10 or more, 11 or more, 12 or more, 13 or more 14 or more, 15 or more, 16 or more, 17 or more, 18 or more, 19 or more, or 20 or more amino acid residues on a mammalian CD33 protein corresponding to the amino acid sequence of SEQ ID NO: 1. In some embodiments that may be combined with any of the preceding embodiments, the anti-CD33 antibody binds to a conformational epitope of CD33. In some embodiments that may be combined with any of the preceding embodiments, the anti-CD33 antibody binds to one or more amino acids within amino acid residues 19-259, 19-135, 145-228, or 229-259 of SEQ ID NO:1; or within amino acid residues on a mammalian CD33 protein corresponding to amino acid residues 19-259, 19-135, 145-228, or 229-259 of SEQ ID NO:1. In some embodiments that may be combined with any of the preceding embodiments, the anti-CD33 antibody binds to one or more amino acids within amino acid residues selected from the group consisting of: i. amino acid residues 39-51 of SEQ ID NO:1, or amino acid residues on a mammalian CD33 protein corresponding to amino acid residues 39-51 of SEQ ID NO:1; ii amino acid residues 48-54 of SEQ ID NO:1, or amino acid residues on a mammalian CD33 protein corresponding to amino acid residues 48-54 of SEQ ID NO:1; iii. amino acid residues 88-98 of SEQ ID NO:1, or amino acid residues on a mammalian CD33 protein corresponding to amino acid residues 88-98 of SEQ ID NO:1; iv amino acid residues 110-120 of SEQ ID NO:1, or amino acid residues on a mammalian CD33 protein corresponding to amino acid residues 110-120 of SEQ ID NO:1; v. amino acid residues 112-122 of SEQ ID NO:1, or amino acid residues on a mammalian CD33 protein corresponding to amino acid residues 112-122 of SEQ ID NO:1; vi amino acid residues 39-51, 88-98, and 110-120 of SEQ ID NO:1, or amino acid residues on a mammalian CD33 protein corresponding to amino acid residues 39-51, 88-98, and 110-120 of SEQ ID NO:1; vii amino acid residues 39-51, 88-98, and 112-122 of SEQ ID NO:1, or amino acid residues on a mammalian CD33 protein corresponding to amino acid residues 39-51, 88-98, and 112-122 of SEQ ID NO:1; and viii amino acid residues 39-51, 88-98, 110-120, and 112-122 of SEQ ID NO:1, or amino acid residues on a mammalian CD33 protein corresponding to amino acid residues 39-51, 88-98, 110-120, and 112-122 of SEQ ID NO:1. In some embodiments that may be combined with any of the preceding embodiments, the anti-CD33 antibody binds to one or more amino acid residues selected from the group consisting of D18, P19, N20, F21, F44, P46, Y49, Y50, K52, and N53 of SEQ ID NO: 1, or one or more amino acid residues on a mammalian CD33 protein corresponding to an amino acid residue selected from the group consisting of D18, P19, N20, F21, F44, P46, Y49, Y50, K52, and N53 of SEQ ID NO: 1. In some embodiments that may be combined with any of the preceding embodiments, the anti-CD33 antibody binds to one or more amino acid residues selected from the group consisting of Y49, Y50, and K52 of SEQ ID NO: 1, or one or more amino acid residues on a mammalian CD33 protein corresponding to an amino acid residue selected from the group consisting of Y49, Y50, and K52 of SEQ ID NO: 1. In some embodiments that may be combined with any of the preceding embodiments, the anti-CD33 antibody binds to amino acid residues Y49 and K52 of SEQ ID NO: 1, or to amino acid residues on a mammalian CD33 protein corresponding to an amino acid residues Y49 and K52 of SEQ ID NO: 1. In some embodiments that may be combined with any of the preceding embodiments, the anti-CD33 antibody binds to amino acid residues Y49, Y50, and K52 of SEQ ID NO: 1, or to amino acid residues on a mammalian CD33 protein corresponding to an amino acid residues Y49, Y50, and K52 of SEQ ID NO: 1. In some embodiments that may be combined with any of the preceding embodiments, the anti-CD33 antibody competes with one or more antibodies selected from the group consisting of 1A8, 2B4, 2E12, 2E12.1, 2F5, 2F5.1, 3A12a, 3A12b, 6A3a, 6A3b, 6C7a, 6C7b, 6C7.21A8, 2B4, 2E12, 2E12.1, 2F5, 2F5.1, 3A12a, 3A12b, 6A3a, 6A3b, 6C7a, 6C7b, 6C7.2, and any combination thereof for binding to CD33. In some embodiments that may be combined with any of the preceding embodiments, the anti-CD33 antibody binds essentially the same CD33 epitope as an antibody selected from the group consisting of: 1A8, 2B4, 2E12, 2E12.1, 2F5, 2F5.1, 3A12a, 3A12b, 6A3a, 6A3b, 6C7a, 6C7b, and 6C7.21A8, 2B4, 2E12, 2E12.1, 2F5, 2F5.1, 3A12a, 3A12b, 6A3a, 6A3b, 6C7a, 6C7b, and 6C7.2. In some embodiments that may be combined with any of the preceding embodiments, the cellular levels of CD33 are measured on primary cells selected from the group consisting of dendritic cells, bone marrow-derived dendritic cells, monocytes, microglia, T cells, and macrophages, or on cell lines, and wherein the cellular levels of CD33 are measured utilizing an in vitro cell assay. In some embodiments that may be combined with any of the preceding embodiments, the one or more CD33 ligands are selected from the group consisting of CD33 ligands expressed on red blood cells, CD33 ligands expressed on bacterial cells, CD33 ligands expressed on apoptotic cells, CD33 ligands expressed on tumor cells, CD33 ligands expressed on viruses, CD33 ligands expressed on dendritic cells, CD33 ligands expressed on nerve cells, CD33 ligands expressed on glial cells, CD33 ligands expressed on microglial cells, CD33 ligands expressed on astrocytes, CD33 ligands on beta amyloid plaques, CD33 ligands on Tau tangles, CD33 ligands on disease-causing proteins, CD33 ligands on disease-causing peptides, CD33 ligands expressed on macrophages, CD33 ligands expressed on natural killer cells, CD33 ligands expressed on T cells, CD33 ligands expressed on T helper cells, CD33 ligands expressed on cytotoxic T cells, CD33 ligands expressed on B cells, CD33 ligands expressed on tumor-imbedded immunosuppressor dendritic cells, CD33 ligands expressed on tumor-imbedded immunosuppressor macrophages, CD33 ligands expressed on non-tumorigenic myeloid-derived suppressor cells, CD33 ligands expressed on regulatory T cells, secreted mucins, sialic acid, sialic acid-containing glycolipids, sialic acid-containing glycoproteins, alpha-2,6-linked sialic acid-containing glycolipids, alpha-2,6-linked sialic acid-containing glycoproteins, alpha-2,3-linked sialic acid-containing glycolipids, alpha-2,3-linked sialic acid-containing glycoproteins, alpha-1-acid glycoprotein (AGP), CD24 protein, and gangliosides.

In some embodiments that may be combined with any of the preceding embodiments, the anti-CD33 antibody comprises a light chain variable domain and a heavy chain variable domain, wherein the light chain variable domain, the heavy chain variable domain, or both comprise at least one, two, three, four, five, or six HVRs selected from HVR-L1, HVR-L2, HVR-L3, HVR-H1, HVR-H2, and HVR-H3 of an antibody selected from the group consisting of: 1A8, 2B4, 2E12, 2E12.1, 2F5, 2F5.1, 3A12a, 3A12b, 6A3a, 6A3b, 6C7a, 6C7b, and 6C7.21A8, 2B4, 2E12, 2E12.1, 2F5, 2F5.1, 3A12a, 3A12b, 6A3a, 6A3b, 6C7a, 6C7b, and 6C7.2. In some embodiments that may be combined with any of the preceding embodiments: (a) the HVR-L1 comprises the amino acid sequence of SEQ ID NO:9, the HVR-L2 comprises the amino acid sequence of SEQ ID NO:12, the HVR-L3 comprises the amino acid sequence of SEQ ID NO:15, the HVR-H1 comprises the amino acid sequence of SEQ ID NO:18, the HVR-H2 comprises the amino acid sequence of SEQ ID NO:22, and the HVR-H3 comprises the amino acid sequence of SEQ ID NO:26; (b) the HVR-L1 comprises the amino acid sequence of SEQ ID NO:10, the HVR-L2 comprises the amino acid sequence of SEQ ID NO:13, the HVR-L3 comprises the amino acid sequence of SEQ ID NO:16, the HVR-H1 comprises the amino acid sequence of SEQ ID NO:19, the HVR-H2 comprises the amino acid sequence of SEQ ID NO:23, and the HVR-H3 comprises the amino acid sequence of SEQ ID NO:27; (c) the HVR-L1 comprises the amino acid sequence of SEQ ID NO:10, the HVR-L2 comprises the amino acid sequence of SEQ ID NO:69, the HVR-L3 comprises the amino acid sequence of SEQ ID NO:72, the HVR-H1 comprises the amino acid sequence of SEQ ID NO:19, the HVR-H2 comprises the amino acid sequence of SEQ ID NO:23, and the HVR-H3 comprises the amino acid sequence of SEQ ID NO:27; (d) the HVR-L1 comprises the amino acid sequence of SEQ ID NO:11, the HVR-L2 comprises the amino acid sequence of SEQ ID NO:14, the HVR-L3 comprises the amino acid sequence of SEQ ID NO:17, the HVR-H1 comprises the amino acid sequence of SEQ ID NO:20, the HVR-H2 comprises the amino acid sequence of SEQ ID NO:24, and the HVR-H3 comprises the amino acid sequence of SEQ ID NO:28; (e) the HVR-L1 comprises the amino acid sequence of SEQ ID NO:68, the HVR-L2 comprises the amino acid sequence of SEQ ID NO:71, the HVR-L3 comprises the amino acid sequence of SEQ ID NO:74, the HVR-H1 comprises the amino acid sequence of SEQ ID NO:75, the HVR-H2 comprises the amino acid sequence of SEQ ID NO:77, and the HVR-H3 comprises the amino acid sequence of SEQ ID NO:28; (f) the HVR-L1 comprises the amino acid sequence of SEQ ID NO:67, the HVR-L2 comprises the amino acid sequence of SEQ ID NO:70, the HVR-L3 comprises the amino acid sequence of SEQ ID NO:73, the HVR-H1 comprises the amino acid sequence of SEQ ID NO:21, the HVR-H2 comprises the amino acid sequence of SEQ ID NO:25, and the HVR-H3 comprises the amino acid sequence of SEQ ID NO:29; (g) the HVR-L1 comprises the amino acid sequence of SEQ ID NO:67, the HVR-L2 comprises the amino acid sequence of SEQ ID NO:70, the HVR-L3 comprises the amino acid sequence of SEQ ID NO:73, the HVR-H1 comprises the amino acid sequence of SEQ ID NO:21, the HVR-H2 comprises the amino acid sequence of SEQ ID NO:76, and the HVR-H3 comprises the amino acid sequence of SEQ ID NO:29; (h) the HVR-H1 comprises the amino acid sequence of SEQ ID NO:21, the HVR-H2 comprises the amino acid sequence of SEQ ID NO:25, and the HVR-H3 comprises the amino acid sequence of SEQ ID NO:29; (i) the HVR-H1 comprises the amino acid sequence of SEQ ID NO:21, the HVR-H2 comprises the amino acid sequence of SEQ ID NO:76, and the HVR-H3 comprises the amino acid sequence of SEQ ID NO:29; (j) the HVR-L1 comprises the amino acid sequence of SEQ ID NO:184, the HVR-L2 comprises the amino acid sequence of SEQ ID NO:185, the HVR-L3 comprises the amino acid sequence of SEQ ID NO:17, the HVR-H1 comprises the amino acid sequence of SEQ ID NO:75, the HVR-H2 comprises the amino acid sequence of SEQ ID NO:186, and the HVR-H3 comprises the amino acid sequence of SEQ ID NO:187; (k) the HVR-L1 comprises the amino acid sequence of SEQ ID NO:10, the HVR-L2 comprises the amino acid sequence of SEQ ID NO:13, the HVR-L3 comprises the amino acid sequence of SEQ ID NO:72, the HVR-H1 comprises the amino acid sequence of SEQ ID NO:231, the HVR-H2 comprises the amino acid sequence of SEQ ID NO:23, and the HVR-H3 comprises the amino acid sequence of SEQ ID NO:27; or (l) the HVR-L1 comprises the amino acid sequence of SEQ ID NO:228, the HVR-L2 comprises the amino acid sequence of SEQ ID NO:229, the HVR-L3 comprises the amino acid sequence of SEQ ID NO:230, the HVR-H1 comprises the amino acid sequence of SEQ ID NO:232, the HVR-H2 comprises the amino acid sequence of SEQ ID NO:233, and the HVR-H3 comprises the amino acid sequence of SEQ ID NO:29. In some embodiments that may be combined with any of the preceding embodiments, the anti-CD33 antibody comprises a light chain variable domain and a heavy chain variable domain, wherein the light chain variable domain comprises: (a) an HVR-L1 comprising an amino acid sequence selected from the group consisting of SEQ ID NOs: 9-11, 67, 68, 184, and 228, or an amino acid sequence with at least about 90% homology to an amino acid sequence selected from the group consisting of SEQ ID NOs: 9-11, 67, 68, 184, and 228; (b) an HVR-L2 comprising an amino acid sequence selected from the group consisting of SEQ ID NOs: 12-14, 69-71, 185, and 229, or an amino acid sequence with at least about 90% homology to an amino acid sequence selected from the group consisting of SEQ ID NOs: 12-14, 69-71, 185, and 229; and (c) an HVR-L3 comprising an amino acid sequence selected from the group consisting of SEQ ID NOs: 15-17, 72-74, and 230, or an amino acid sequence with at least about 90% homology to an amino acid sequence selected from the group consisting of SEQ ID NOs: 15-17, 72-74, and 230; and wherein the heavy chain variable domain comprises: (a) an HVR-H1 comprising an amino acid sequence selected from the group consisting of SEQ ID NOs: 18-21, 75, 231, and 232, or an amino acid sequence with at least about 90% homology to an amino acid sequence selected from the group consisting of SEQ ID NOs: 18-21, 75, 231, and 232; (b) an HVR-H2 comprising an amino acid sequence selected from the group consisting of SEQ ID NOs: 22-25, 76, 77, 186, and 233, or an amino acid sequence with at least about 90% homology to an amino acid sequence selected from the group consisting of SEQ ID NOs: 22-25, 76, 77, 186, and 233; and (c) an HVR-H3 comprising an amino acid sequence selected from the group consisting of SEQ ID NOs: 26-29, and 187, or an amino acid sequence with at least about 90% homology to an amino acid sequence selected from the group consisting of SEQ ID NOs: 26-29, and 187. In some embodiments that may be combined with any of the preceding embodiments, the anti-CD33 antibody comprises a light chain variable domain and a heavy chain variable domain, wherein the light chain variable domain comprises HVR-L1, HVR-L2, HVR-L3, the heavy chain variable domain comprises HVR-H1, HVR-H2, and HVR-H3, and wherein the HVR-H3 is the HVR-H3 of an antibody selected from the group consisting of: 1A8, 2B4, 2E12, 2E12.1, 2F5, 2F5.1, 3A12a, 3A12b, 6A3a, 6A3b, 6C7a, 6C7b, and 6C7.21A8, 2B4, 2E12, 2E12.1, 2F5, 2F5.1, 3A12a, 3A12b, 6A3a, 6A3b, 6C7a, 6C7b, and 6C7.2. In some embodiments that may be combined with any of the preceding embodiments, the anti-CD33 antibody comprises a light chain variable domain and a heavy chain variable domain, wherein the light chain variable domain comprises HVR-L1, HVR-L2, HVR-L3, the heavy chain variable domain comprises HVR-H1, HVR-H2, and HVR-H3, and wherein the HVR-H3 comprises an amino acid sequence selected from the group consisting of SEQ ID NOs: 26-29, and 187, or an amino acid sequence with at least about 90% homology to an amino acid sequence selected from the group consisting of SEQ ID NOs: 26-29, and 187. In some embodiments that may be combined with any of the preceding embodiments, the anti-CD33 antibody comprises a light chain variable domain comprising an amino acid sequence selected from the group consisting of SEQ ID NOs: 30-48, 112-153, 192-202, and 241-243; and/or a heavy chain variable domain comprising an amino acid sequence selected from the group consisting of SEQ ID NOs: 49-66, 154-183, 203-213, and 244-246. In some embodiments that may be combined with any of the preceding embodiments, the anti-CD33 antibody comprises a light chain variable domain of an antibody selected from the group consisting of: 1A8, 2B4, 2E12, 2E12.1, 2F5, 2F5.1, 3A12a, 3A12b, 6A3a, 6A3b, 6C7a, 6C7b, and 6C7.21A8, 2B4, 2E12, 2E12.1, 2F5, 2F5.1, 3A12a, 3A12b, 6A3a, 6A3b, 6C7a, 6C7b, and 6C7.2; and/or a heavy chain variable domain of an antibody selected from the group consisting of: 1A8, 2B4, 2E12, 2E12.1, 2F5, 2F5.1, 3A12a, 3A12b, 6A3a, 6A3b, 6C7a, 6C7b, and 6C7.21A8, 2B4, 2E12, 2E12.1, 2F5, 2F5.1, 3A12a, 3A12b, 6A3a, 6A3b, 6C7a, 6C7b, and 6C7.2.

Other aspects of the present disclosure relate to an isolated (e.g., monoclonal) anti-CD33 antibody, wherein the anti-CD33 antibody binds to one or more amino acids within amino acid residues 19-259, 19-135, 145-228, or 229-259 of SEQ ID NO:1; or within amino acid residues on a mammalian CD33 protein corresponding to amino acid residues 19-259, 19-135, 145-228, or 229-259 of SEQ ID NO:1. In some embodiments, the anti-CD33 antibody binds to one or more amino acids within amino acid residues selected from the group consisting of: i. amino acid residues 39-51 of SEQ ID NO:1, or amino acid residues on a mammalian CD33 protein corresponding to amino acid residues 39-51 of SEQ ID NO:1; ii. amino acid residues 48-54 of SEQ ID NO:1, or amino acid residues on a mammalian CD33 protein corresponding to amino acid residues 48-54 of SEQ ID NO:1; iii. amino acid residues 88-98 of SEQ ID NO:1, or amino acid residues on a mammalian CD33 protein corresponding to amino acid residues 88-98 of SEQ ID NO:1; iv amino acid residues 110-120 of SEQ ID NO:1, or amino acid residues on a mammalian CD33 protein corresponding to amino acid residues 110-120 of SEQ ID NO:1; v. amino acid residues 112-122 of SEQ ID NO:1, or amino acid residues on a mammalian CD33 protein corresponding to amino acid residues 112-122 of SEQ ID NO:1; vi amino acid residues 39-51, 88-98, and 110-120 of SEQ ID NO:1, or amino acid residues on a mammalian CD33 protein corresponding to amino acid residues 39-51, 88-98, and 110-120 of SEQ ID NO:1; vii amino acid residues 39-51, 88-98, and 112-122 of SEQ ID NO:1, or amino acid residues on a mammalian CD33 protein corresponding to amino acid residues 39-51, 88-98, and 112-122 of SEQ ID NO:1; and viii amino acid residues 39-51, 88-98, 110-120, and 112-122 of SEQ ID NO:1, or amino acid residues on a mammalian CD33 protein corresponding to amino acid residues 39-51, 88-98, 110-120, and 112-122 of SEQ ID NO:1.

Other aspects of the present disclosure relate to an isolated (e.g., monoclonal) anti-CD33 antibody, wherein the anti-CD33 antibody binds to one or more amino acids within amino acid residues 19-228 of SEQ ID NO:1; or within amino acid residues on a mammalian CD33 protein corresponding to amino acid residues 19-228 of SEQ ID NO:1. In some embodiments, the anti-CD33 antibody binds to one or more amino acids within amino acid residues selected from the group consisting of: i. amino acid residues 39-51 of SEQ ID NO:1, or amino acid residues on a mammalian CD33 protein corresponding to amino acid residues 39-51 of SEQ ID NO:1; ii amino acid residues 48-54 of SEQ ID NO:1, or amino acid residues on a mammalian CD33 protein corresponding to amino acid residues 48-54 of SEQ ID NO:1; iii amino acid residues 88-98 of SEQ ID NO:1, or amino acid residues on a mammalian CD33 protein corresponding to amino acid residues 88-98 of SEQ ID NO:1; iv amino acid residues 110-120 of SEQ ID NO:1, or amino acid residues on a mammalian CD33 protein corresponding to amino acid residues 110-120 of SEQ ID NO:1; v amino acid residues 112-122 of SEQ ID NO:1, or amino acid residues on a mammalian CD33 protein corresponding to amino acid residues 112-122 of SEQ ID NO:1; vi amino acid residues 39-51, 88-98, and 110-120 of SEQ ID NO:1, or amino acid residues on a mammalian CD33 protein corresponding to amino acid residues 39-51, 88-98, and 110-120 of SEQ ID NO:1; vii amino acid residues 39-51, 88-98, and 112-122 of SEQ ID NO:1, or amino acid residues on a mammalian CD33 protein corresponding to amino acid residues 39-51, 88-98, and 112-122 of SEQ ID NO:1; and viii. amino acid residues 39-51, 88-98, 110-120, and 112-122 of SEQ ID NO:1, or amino acid residues on a mammalian CD33 protein corresponding to amino acid residues 39-51, 88-98, 110-120, and 112-122 of SEQ ID NO:1.

Other aspects of the present disclosure relate to an isolated (e.g., monoclonal) anti-CD33 antibody, wherein the anti-CD33 antibody binds to one or more amino acid residues selected from the group consisting of D18, P19, N20, F21, F44, P46, Y49, Y50, K52, and N53 of SEQ ID NO: 1, or one or more amino acid residues on a mammalian CD33 protein corresponding to an amino acid residue selected from the group consisting of D18, P19, N20, F21, F44, P46, Y49, Y50, K52, and N53 of SEQ ID NO: 1. In some embodiments that may be combined with any of the preceding embodiments, the anti-CD33 antibody binds to one or more amino acid residues selected from the group consisting of Y49, Y50, and K52 of SEQ ID NO: 1, or one or more amino acid residues on a mammalian CD33 protein corresponding to an amino acid residue selected from the group consisting of Y49, Y50, and K52 of SEQ ID NO: 1. In some embodiments that may be combined with any of the preceding embodiments, the anti-CD33 antibody binds to amino acid residues Y49 and K52 of SEQ ID NO: 1, or to amino acid residues on a mammalian CD33 protein corresponding to an amino acid residues Y49 and K52 of SEQ ID NO: 1. In some embodiments that may be combined with any of the preceding embodiments, the anti-CD33 antibody binds to amino acid residues Y49, Y50, and K52 of SEQ ID NO: 1, or to amino acid residues on a mammalian CD33 protein corresponding to an amino acid residues Y49, Y50, and K52 of SEQ ID NO: 1.

Other aspects of the present disclosure relate to an isolated (e.g., monoclonal) anti-CD33 antibody, wherein the anti-CD33 antibody comprises a light chain variable domain and a heavy chain variable domain, wherein the heavy chain variable domain, the light chain variable domain, or both comprises at least one, two, three, four, five, or six HVRs selected from HVR-L1, HVR-L2, HVR-L3, HVR-H1, HVR-H2, and HVR-H3 of an antibody selected from the group consisting of: 1A8, 2B4, 2E12, 2E12.1, 2F5, 2F5.1, 3A12a, 3A12b, 6A3a, 6A3b, 6C7a, 6C7b, 6C7.21A8, 2B4, 2E12, 2E12.1, 2F5, 2F5.1, 3A12a, 3A12b, 6A3a, 6A3b, 6C7a, 6C7b, 6C7.2, and any combination thereof. In some embodiments: (a) the HVR-L1 comprises the amino acid sequence of SEQ ID NO:9, the HVR-L2 comprises the amino acid sequence of SEQ ID NO:12, the HVR-L3 comprises the amino acid sequence of SEQ ID NO:15, the HVR-H1 comprises the amino acid sequence of SEQ ID NO:18, the HVR-H2 comprises the amino acid sequence of SEQ ID NO:22, and the HVR-H3 comprises the amino acid sequence of SEQ ID NO:26; (b) the HVR-L1 comprises the amino acid sequence of SEQ ID NO:10, the HVR-L2 comprises the amino acid sequence of SEQ ID NO:13, the HVR-L3 comprises the amino acid sequence of SEQ ID NO:16, the HVR-H1 comprises the amino acid sequence of SEQ ID NO:19, the HVR-H2 comprises the amino acid sequence of SEQ ID NO:23, and the HVR-H3 comprises the amino acid sequence of SEQ ID NO:27; (c) the HVR-L1 comprises the amino acid sequence of SEQ ID NO:10, the HVR-L2 comprises the amino acid sequence of SEQ ID NO:69, the HVR-L3 comprises the amino acid sequence of SEQ ID NO:72, the HVR-H1 comprises the amino acid sequence of SEQ ID NO:19, the HVR-H2 comprises the amino acid sequence of SEQ ID NO:23, and the HVR-H3 comprises the amino acid sequence of SEQ ID NO:27; (d) the HVR-L1 comprises the amino acid sequence of SEQ ID NO:11, the HVR-L2 comprises the amino acid sequence of SEQ ID NO:14, the HVR-L3 comprises the amino acid sequence of SEQ ID NO:17, the HVR-H1 comprises the amino acid sequence of SEQ ID NO:20, the HVR-H2 comprises the amino acid sequence of SEQ ID NO:24, and the HVR-H3 comprises the amino acid sequence of SEQ ID NO:28; (e) the HVR-L1 comprises the amino acid sequence of SEQ ID NO:68, the HVR-L2 comprises the amino acid sequence of SEQ ID NO:71, the HVR-L3 comprises the amino acid sequence of SEQ ID NO:74, the HVR-H1 comprises the amino acid sequence of SEQ ID NO:75, the HVR-H2 comprises the amino acid sequence of SEQ ID NO:77, and the HVR-H3 comprises the amino acid sequence of SEQ ID NO:28; (f) the HVR-L1 comprises the amino acid sequence of SEQ ID NO:67, the HVR-L2 comprises the amino acid sequence of SEQ ID NO:70, the HVR-L3 comprises the amino acid sequence of SEQ ID NO:73, the HVR-H1 comprises the amino acid sequence of SEQ ID NO:21, the HVR-H2 comprises the amino acid sequence of SEQ ID NO:25, and the HVR-H3 comprises the amino acid sequence of SEQ ID NO:29; (g) the HVR-L1 comprises the amino acid sequence of SEQ ID NO:67, the HVR-L2 comprises the amino acid sequence of SEQ ID NO:70, the HVR-L3 comprises the amino acid sequence of SEQ ID NO:73, the HVR-H1 comprises the amino acid sequence of SEQ ID NO:21, the HVR-H2 comprises the amino acid sequence of SEQ ID NO:76, and the HVR-H3 comprises the amino acid sequence of SEQ ID NO:29; (h) the HVR-H1 comprises the amino acid sequence of SEQ ID NO:21, the HVR-H2 comprises the amino acid sequence of SEQ ID NO:25, and the HVR-H3 comprises the amino acid sequence of SEQ ID NO:29; (i) the HVR-H1 comprises the amino acid sequence of SEQ ID NO:21, the HVR-H2 comprises the amino acid sequence of SEQ ID NO:76, and the HVR-H3 comprises the amino acid sequence of SEQ ID NO:29; (j) the HVR-L1 comprises the amino acid sequence of SEQ ID NO:184, the HVR-L2 comprises the amino acid sequence of SEQ ID NO:185, the HVR-L3 comprises the amino acid sequence of SEQ ID NO:17, the HVR-H1 comprises the amino acid sequence of SEQ ID NO:75, the HVR-H2 comprises the amino acid sequence of SEQ ID NO:186, and the HVR-H3 comprises the amino acid sequence of SEQ ID NO:187; (k) the HVR-L1 comprises the amino acid sequence of SEQ ID NO:10, the HVR-L2 comprises the amino acid sequence of SEQ ID NO:13, the HVR-L3 comprises the amino acid sequence of SEQ ID NO:72, the HVR-H1 comprises the amino acid sequence of SEQ ID NO:231, the HVR-H2 comprises the amino acid sequence of SEQ ID NO:23, and the HVR-H3 comprises the amino acid sequence of SEQ ID NO:27; or (l) the HVR-L1 comprises the amino acid sequence of SEQ ID NO:228, the HVR-L2 comprises the amino acid sequence of SEQ ID NO:229, the HVR-L3 comprises the amino acid sequence of SEQ ID NO:230, the HVR-H1 comprises the amino acid sequence of SEQ ID NO:232, the HVR-H2 comprises the amino acid sequence of SEQ ID NO:233, and the HVR-H3 comprises the amino acid sequence of SEQ ID NO:29. In some embodiments that may be combined with any of the preceding embodiments, the light chain variable domain comprises: (a) an HVR-L1 comprising an amino acid sequence selected from the group consisting of SEQ ID NOs: 9-11, 67, 68, 184, and 228, or an amino acid sequence with at least about 90% homology to an amino acid sequence selected from the group consisting of SEQ ID NOs: 9-11, 67, 68, 184, and 228; (b) an HVR-L2 comprising an amino acid sequence selected from the group consisting of SEQ ID NOs: 12-14, 69-71, 185, and 229, or an amino acid sequence with at least about 90% homology to an amino acid sequence selected from the group consisting of SEQ ID NOs: 12-14, 69-71, 185, and 229; and (c) an HVR-L3 comprising an amino acid sequence selected from the group consisting of SEQ ID NOs: 15-17, 72-74, and 230, or an amino acid sequence with at least about 90% homology to an amino acid sequence selected from the group consisting of SEQ ID NOs: 15-17, 72-74, and 230; and wherein the heavy chain variable domain comprises: (a) an HVR-H1 comprising an amino acid sequence selected from the group consisting of SEQ ID NOs: 18-21, 75, 231, and 232, or an amino acid sequence with at least about 90% homology to an amino acid sequence selected from the group consisting of SEQ ID NOs: 18-21, 75, 231, and 232; (b) an HVR-H2 comprising an amino acid sequence selected from the group consisting of SEQ ID NOs: 22-25, 76, 77, 186, and 233, or an amino acid sequence with at least about 90% homology to an amino acid sequence selected from the group consisting of SEQ ID NOs: 22-25, 76, 77, 186, and 233; and (c) an HVR-H3 comprising an amino acid sequence selected from the group consisting of SEQ ID NOs: 26-29, and 187, or an amino acid sequence with at least about 90% homology to an amino acid sequence selected from the group consisting of SEQ ID NOs: 226-29, and 187.

Other aspects of the present disclosure relate to an isolated (e.g., monoclonal) anti-CD33 antibody, wherein the anti-CD33 antibody comprises a light chain variable domain comprising an amino acid sequence selected from the group consisting of SEQ ID NOs: 30-48, 112-153, 192-202, and 241-243; and/or a heavy chain variable domain comprising an amino acid sequence selected from the group consisting of SEQ ID NOs: 49-66, 154-183, 203-213, and 244-246. Other aspects of the present disclosure relate to an isolated (e.g., monoclonal) anti-CD33 antibody, wherein the anti-CD33 antibody comprises a light chain variable domain of an antibody selected from the group consisting of: 1A8, 2B4, 2E12, 2E12.1, 2F5, 2F5.1, 3A12a, 3A12b, 6A3a, 6A3b, 6C7a, 6C7b, and 6C7.2; and/or a heavy chain variable domain of an antibody selected from the group consisting of: 1A8, 2B4, 2E12, 2E12.1, 2F5, 2F5.1, 3A12a, 3A12b, 6A3a, 6A3b, 6C7a, 6C7b, and 6C7.21A8, 2B4, 2E12, 2E12.1, 2F5, 2F5.1, 3A12a, 3A12b, 6A3a, 6A3b, 6C7a, 6C7b, and 6C7.2 Other aspects of the present disclosure relate to an isolated (e.g., monoclonal) anti-CD33 antibody, wherein the anti-CD33 antibody competes with one or more antibodies selected from the group consisting of 1A8, 2B4, 2E12, 2E12.1, 2F5, 2F5.1, 3A12a, 3A12b, 6A3a, 6A3b, 6C7a, 6C7b, 6C7.21A8, 2B4, 2E12, 2E12.1, 2F5, 2F5.1, 3A12a, 3A12b, 6A3a, 6A3b, 6C7a, 6C7b, 6C7.2 and any combination thereof for binding to CD33. Other aspects of the present disclosure relate to an isolated (e.g., monoclonal) anti-CD33 antibody which binds essentially the same CD33 epitope as an antibody selected from the group consisting of: 1A8, 2B4, 2E12, 2E12.1, 2F5, 2F5.1, 3A12a, 3A12b, 6A3a, 6A3b, 6C7a, 6C7b, and 6C7.21A8, 2B4, 2E12, 2E12.1, 2F5, 2F5.1, 3A12a, 3A12b, 6A3a, 6A3b, 6C7a, 6C7b, and 6C7.2.

Other aspects of the present disclosure relate to an isolated (e.g., monoclonal) anti-CD33 antibody, wherein the anti-CD33 antibody comprises a light chain variable domain and a heavy chain variable domain, wherein the light chain variable domain comprises: (a) an HVR-L1 comprising an amino acid sequence selected from the group consisting of SEQ ID NOs: 9-11, 67, 68, 184, and 228, or an amino acid sequence with at least about 90% homology to an amino acid sequence selected from the group consisting of SEQ ID NOs: 9-11, 67, 68, 184, and 228; (b) an HVR-L2 comprising an amino acid sequence selected from the group consisting of SEQ ID NOs: 12-14, 69-71, 185, and 229, or an amino acid sequence with at least about 90% homology to an amino acid sequence selected from the group consisting of SEQ ID NOs: 12-14, 69-71, 185, and 229; and (c) an HVR-L3 comprising an amino acid sequence selected from the group consisting of SEQ ID NOs: 15-17, 72-74, and 230, or an amino acid sequence with at least about 90% homology to an amino acid sequence selected from the group consisting of SEQ ID NOs: 15-17, 72-74, and 230; or wherein the heavy chain variable domain comprises: (a) an HVR-H1 comprising an amino acid sequence selected from the group consisting of SEQ ID NOs: 18-21, 75, 231, and 232, or an amino acid sequence with at least about 90% homology to an amino acid sequence selected from the group consisting of SEQ ID NOs: 18-21, 75, 231, and 232; (b) an HVR-H2 comprising an amino acid sequence selected from the group consisting of SEQ ID NOs: 22-25, 76, 77, 186, and 233, or an amino acid sequence with at least about 90% homology to an amino acid sequence selected from the group consisting of SEQ ID NOs: 22-25, 76, 77, 186, and 233; and (c) an HVR-H3 comprising an amino acid sequence selected from the group consisting of SEQ ID NOs: 26-29, and 187, or an amino acid sequence with at least about 90% homology to an amino acid sequence selected from the group consisting of SEQ ID NOs: 26-29, and 187. Other aspects of the present disclosure relate to an isolated (e.g., monoclonal) anti-CD33 antibody, wherein the anti-CD33 antibody comprises a light chain variable domain and a heavy chain variable domain, wherein the light chain variable domain comprises HVR-L1, HVR-L2, HVR-L3, the heavy chain variable domain comprises HVR-H1, HVR-H2, and HVR-H3, and wherein the HVR-H3 is the HVR-H3 of an antibody selected from the group consisting of: 1A8, 2B4, 2E12, 2E12.1, 2F5, 2F5.1, 3A12a, 3A12b, 6A3a, 6A3b, 6C7a, 6C7b, and 6C7.2 1A8, 2B4, 2E12, 2E12.1, 2F5, 2F5.1, 3A12a, 3A12b, 6A3a, 6A3b, 6C7a, 6C7b, and 6C7.2. Other aspects of the present disclosure relate to an isolated (e.g., monoclonal) anti-CD33 antibody, wherein anti-CD33 antibody comprises a light chain variable domain and a heavy chain variable domain, wherein the light chain variable domain comprises HVR-L1, HVR-L2, HVR-L3, the heavy chain variable domain comprises HVR-H1, HVR-H2, and HVR-H3, and wherein the HVR-H3 comprises an amino acid sequence selected from the group consisting of SEQ ID NOs: 26-29, and 187, or an amino acid sequence with at least about 90% homology to an amino acid sequence selected from the group consisting of SEQ ID NOs: 26-29, and 187.

In some embodiments that may be combined with any of the preceding embodiments, the antibody is of the IgG class the IgM class, or the IgA class. In some embodiments that may be combined with any of the preceding embodiments, the anti-CD33 antibody has an IgG1, IgG2, IgG3, or IgG4 isotype. In some embodiments that may be combined with any of the preceding embodiments, the antibody binds an inhibitory Fc receptor. In some embodiments that may be combined with any of the preceding embodiments, the inhibitory Fc receptor is inhibitory Fc-gamma receptor IIB (FcγIIB). In some embodiments that may be combined with any of the preceding embodiments: (a) the anti-CD33 antibody has a human IgG1 isotype and comprises one or more amino acid substitutions in the Fc region at a residue position selected from the group consisting of: N297A, D265A, D270A, L234A, L235A, G237A, P238D, L328E, E233D, G237D, H268D, P271G, A330R, C226S, C229S, E233P, L234V, L234F, L235E, P331S, S267E, L328F, A330L, M252Y, S254T, T256E, N297Q, P238S, P238A, A327Q, A327G, P329A, K322A, T394D, and any combination thereof, wherein the numbering of the residues is according to EU numbering, or comprises an amino acid deletion in the Fc region at a position corresponding to glycine 236; (b) the anti-CD33 antibody has a human IgG1 isotype and comprises an IgG2 isotype heavy chain constant domain 1 (CH1) and hinge region, optionally wherein the IgG2 isotype CH1 and hinge region comprises the amino acid sequence of ASTKGPSVFP LAPCSRSTSE STAAL-GCLVK DYFPEPVTVS WNSGALTSGVHTFPAVLQSS GLYSLSSVVT VPSSNFGTQT YTCNVDHKPS NTKVDKTVERKCCVECPPCP (SEQ ID NO:214), and optionally wherein the antibody Fc region comprises a S267E amino acid substitution, a L328F amino acid substitution, or both, and/or a N297A or N297Q amino acid substitution, wherein the numbering of the residues is according to EU numbering; (c) the anti-CD33 antibody has a human IgG2 isotype and comprises one or more amino acid substitutions in the Fc region at a residue position selected from the group consisting of: P238S, V234A, G237A, H268A, H268Q, V309L, A330S, P331S, C214S, C232S, C233S, S267E, L328F, M252Y, S254T, T256E, H268E, N297A, N297Q, A330L, and any combination thereof, wherein the numbering of the residues is according to EU numbering; (d) the anti-CD33 antibody has a human IgG4 isotype and comprises one or more amino acid substitutions in the Fc region at a residue position selected from the group consisting of: L235A, G237A, S228P, L236E, S267E, E318A, L328F, M252Y, S254T, T256E, E233P, F234V, L234A/F234A, S228P, S241P, L248E, T394D, N297A, N297Q, L235E, and any combination thereof, wherein the numbering of the residues is according to EU numbering; or (e) the anti-CD33 antibody has a hybrid IgG2/4 isotype, and optionally wherein the antibody comprises an amino acid sequence comprising amino acids 118 to 260 of human IgG2 and amino acids 261 to 447 of human IgG4, wherein the numbering of the residues is according to EU numbering. In some embodiments that may be combined with any of the preceding embodiments: (a) the anti-CD33 antibody has a human IgG1 isotype and comprises one or more amino acid substitutions in the Fc region at a residue position selected from the group consisting of: N297A, N297Q, D270A, D265A, L234A, L235A, C226S, C229S, P238S, E233P, L234V, P238A, A327Q, A327G, P329A, K322A, L234F, L235E, P331S, T394D, A330L, M252Y, S254T, T256E, and any combination thereof, wherein the numbering of the residues is according to EU numbering; (b) the anti-CD33 antibody has a human IgG2 isotype and comprises one or more amino acid substitutions in the Fc region at a residue position selected from the group consisting of: P238S, V234A, G237A, H268A, H268Q, H268E, V309L, N297A, N297Q, A330S, P331S, C232S, C233S, M252Y, S254T, T256E, and any combination thereof, wherein the numbering of the residues is according to EU numbering; or (c) the anti-CD33 antibody has a human IgG4 isotype and comprises one or more amino acid substitutions in the Fc region at a residue position selected from the group consisting of: E233P, F234V, L234A/F234A, L235A, G237A, E318A, S228P, L236E, S241P, L248E, T394D, M252Y, S254T, T256E, N297A, N297Q, and any combination thereof, wherein the numbering of the residues is according to EU numbering. In some embodiments that may be combined with any of the preceding embodiments: (a) the Fc region further comprises one or more additional amino acid substitutions at a position selected from the group consisting of A330L, L234F; L235E, P331S, and any combination thereof, wherein the numbering of the residues is according to EU numbering; (b) the Fc region further comprises one or more additional amino acid substitutions at a position selected from the group consisting of M252Y, S254T, T256E, and any combination thereof, wherein the numbering of the residues is according to EU numbering; or (c) the Fc region further comprises a S228P amino acid substitution according to EU numbering. In some embodiments that may be combined with any of the preceding embodiments, the CD33 protein is a mammalian protein or a human protein. In some embodiments that may be combined with any of the preceding embodiments, the CD33 protein is a wild-type protein. In some embodiments that may be combined with any of the preceding embodiments, the CD33 protein is a naturally occurring variant. In some embodiments that may be combined with any of the preceding embodiments, the CD33 protein is expressed on one or more cells selected from the group consisting of human dendritic cells, human macrophages, human monocytes, human osteoclasts, human neutrophils, human T cells, human T helper cell, human cytotoxic T cells, human granulocytes, and human microglia. In some embodiments that may be combined with any of the preceding embodiments, the anti-CD33 antibody binds specifically to a mammalian CD33 protein, human CD33 protein, or both. In some embodiments that may be combined with any of the preceding embodiments, the anti-CD33 antibody binds specifically to human CD33, mouse CD33, or both. In some embodiments that may be combined with any of the preceding embodiments, the anti-CD33 antibody binds CD33 in a pH dependent manner. In some embodiments that may be combined with any of the preceding embodiments, the anti-CD33 antibody binds CD33 at a pH that ranges from 5.5 to 8.0. In some embodiments that may be combined with any of the preceding embodiments, the anti-CD33 antibody dissociates from CD33 at a pH of less than 5.0. In some embodiments that may be combined with any of the preceding embodiments, the anti-CD33 antibody is an antibody fragment that binds to an epitope comprising amino acid residues on human CD33 or a mammalian CD33 protein. In some embodiments that may be combined with any of the preceding embodiments, the anti-CD33 antibody is an antibody fragment that binds to one or more human proteins selected from the group consisting of human CD33, a naturally occurring variant of human CD33, and a disease variant of human CD33. In some embodiments that may be combined with any of the preceding embodiments, the antibody fragment is cross-linked to a second antibody fragment that binds to one or more human proteins selected from the group consisting of human CD33, a naturally occurring variant of human CD33, and a disease variant of human CD33. In some embodiments that may be combined with any of the preceding embodiments, the fragment is an Fab, Fab', Fab'-SH, F(ab')2, Fv, or scFv fragment. In some embodiments that may be combined with any of the preceding embodiments, the anti-CD33 antibody is a murine antibody. In some embodiments that may be combined with any of the preceding embodiments, the anti-CD33 antibody is a humanized antibody, a bispecific antibody, a monoclonal antibody, a multivalent antibody, a conjugated antibody, or a chimeric antibody. In some embodiments that may be combined with any of the preceding embodiments, the anti-CD33 antibody is a bispecific antibody recognizing a first antigen and a second antigen. In some embodiments that may be combined with any of the preceding embodiments, the first antigen is CD33 and the second antigen is: (a) an antigen facilitating transport across the blood-brain-barrier; (b) an antigen facilitating transport across the blood-brain-barrier selected from the group consisting of transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, an angiopep peptide, and ANG1005; (c) a disease-causing agent selected from the group consisting of disease-causing peptides or proteins and disease-causing nucleic acids, wherein the disease-causing peptides or proteins are selected from the group consisting of amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides, and the disease-causing nucleic acids are antisense GGCCCC (G2C4) repeat-expansion RNA; (d) ligands and/or proteins expressed on immune cells, wherein the ligands and/or proteins selected from the group consisting of CD40, OX40, ICOS, CD28, CD137/4-1BB, CD27, GITR, PD-L1, CTLA4, PD-L2, PD-1, B7-H3, B7-H4, HVEM, BTLA, KIR, GAL9, TIM3, A2AR, LAG, and phosphatidylserine; and (e) a protein, lipid, polysaccharide, or glycolipid expressed on one or more tumor cells. In some embodiments that may be combined with any of the preceding embodiments, the anti-CD33 antibody is a conjugated antibody. In some embodiments that may be combined with any of the preceding embodiments, the anti-CD33 antibody is conjugated to a detectable marker, a toxin, or a therapeutic agent. In some embodiments that may be combined with any of the preceding embodiments, the anti-CD33 antibody is conjugated to a toxin selected from the group consisting of ricin, ricin A-chain, doxorubicin, daunorubicin, a maytansinoid, taxol, ethidium bromide, mitomycin, etoposide, tenoposide, vincristine, vinblastine, colchicine, dihydroxy anthracin dione, actinomycin, diphtheria toxin, *Pseudomonas* exotoxin (PE) A, PE40, abrin, abrin A chain, modeccin A chain, alpha-sarcin, gelonin, mitogellin, retstrictocin, phenomycin, enomycin, curicin, crotin, calicheamicin, *Saponaria officinalis* inhibitor, glucocorticoid, auristatin, auromycin, yttrium, bismuth, combrestatin, duocarmycins, dolastatin, cc1065, and a cisplatin. In some embodiments that may be combined with any of the preceding embodiments, the anti-CD33 antibody is used in combination with one or more antibodies that specifically bind a disease-causing agent selected from the group consisting of disease-causing peptides, disease-causing proteins, amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides, and any combination thereof; or with one or more antibodies that bind an immunomodulatory protein selected from the group consisting of: CD40, OX40, ICOS, CD28, CD137/4-1BB, CD27, GITR, PD-L1, CTLA4, PD-L2, PD-1, B7-H3, B7-H4, HVEM, BTLA, KIR, GAL9, TIM3, A2AR, LAG, TREM1, TREM2, Siglec-5, Siglec-7, Siglec-9, Siglec-11, phosphatidylserine, disease-causing nucleic acids, antisense GGCCCC (G2C4) repeat-expansion RNA, and any combination thereof. In some embodiments that may be combined with any of the preceding embodiments, the anti-CD33 antibody has a dissociation constant ($K_D$) for human CD33 and mouse CD33 that ranges from about 100 nM to about 100 pM, or less than 100 pM, and wherein the $K_D$ is determined at a temperature of 25° C. In some embodiments that may be combined with any of the preceding embodiments, the anti-CD33 antibody has a dissociation constant ($K_D$) for human CD33 that ranges from about 10 nM to about 500 pM, or less than 500 pM, and wherein the $K_D$ is determined at a temperature of 25° C. In some embodiments that may be combined with any of the preceding embodiments, the anti-CD33 antibody has a dissociation constant ($K_D$) for human CD33 that ranges from about 100 nM to about 100 pM, or less than 100 pM, and wherein the $K_D$ is determined at a temperature of 25° C. In some embodiments that may be combined with any of the preceding embodiments, the anti-CD33 antibody has a dissociation constant ($K_D$) for mouse CD33 that ranges from about 100 nM to about 100 pM, or less than 100 pM, and wherein the $K_D$ is determined at a temperature of 25° C. In some embodiments that may be combined with any of the previous embodiments, the $K_D$ is determined using a monovalent antibody. In some embodiments that may be combined with any of the previous embodiments, the $K_D$ is determined using a full-length antibody in a monovalent form. In some embodiments that may be combined with any of the preceding embodiments, the anti-CD33 antibody is not conjugated to an agent, optionally wherein the agent is drug, toxin, chemotherapeutic, or radioisotope.

Other aspects of the present disclosure relate to an isolated nucleic acid comprising a nucleic acid sequence encoding the anti-CD33 antibody of any of the preceding embodiments. Other aspects of the present disclosure relate to a vector comprising the nucleic acid any of the preceding embodiments. Other aspects of the present disclosure relate to a host cell comprising the vector of any of the preceding embodiments. Other aspects of the present disclosure relate to a method of producing an anti-CD33 antibody, comprising culturing the host cell of any of the preceding embodiments so that the anti-CD33 antibody is produced. In some embodiments, the method further comprises recovering the anti-CD33 antibody produced by the host cell. Other aspects of the present disclosure relate to an isolated anti-CD33 antibody produced by the method of any of the preceding embodiments. Other aspects of the present disclosure relate to a pharmaceutical composition comprising the anti-CD33 antibody of any of the preceding embodiments, and a pharmaceutically acceptable carrier.

Other aspects of the present disclosure relate to a method of preventing, reducing risk, or treating a disease, disorder, or injury selected from the group consisting of dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, cancer, bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express CD33, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus* influenza, comprising administering to an individual in need thereof a therapeutically effective amount of an agent that decreases cellular levels of CD33, inhibits interaction between CD33 and one or more CD33 ligands, or both. Other aspects of the present disclosure relate to an agent that decreases cellular levels of CD33, inhibits interaction between CD33 and one or more CD33 ligands, or both for use in preventing, reducing risk, or treating a disease, disorder, or injury selected from the group consisting of dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, cancer, bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express CD33, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus* influenza. Other aspects of the present disclosure relate to use of an agent that decreases cellular levels of CD33, inhibits interaction between CD33 and one or more CD33 ligands, or both in the manufacture of a medicament for preventing, reducing risk, or treating a disease, disorder, or injury selected from the group consisting of dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, cancer, bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express CD33, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus* influenza. In some embodiments, the agent is selected from the group consisting of an antibody, a soluble CD33 receptor, a CD33-Fc fusion protein, a CD33 immunoadhesin, a soluble Siglec receptor that binds one or more CD33 ligands, a Siglec-Fc fusion protein, a Siglec immunoadhesin, an antisense molecule, an siRNA, a small molecule inhibitor, a protein, and a peptide. In some embodiments, the agent is an isolated anti-CD33 antibody. In some embodiments, the anti-CD33 antibody is the anti-CD33 antibody of any of the preceding embodiments. In some embodiments that may be combined with any of the preceding embodiments, the disease, disorder, or injury is cancer. In some embodiments that may be combined with any of the preceding embodiments, the agent inhibits one or more CD33 activities selected from the group consisting of: (a) promoting proliferation, maturation, migration, differentiation, and/or functionality of one or more of immunosuppressor dendritic cells, immunosuppressor macrophages, immunosuppressor neutrophils, non-tumorigenic myeloid derived suppressor cells, tumor-associated macrophages, non-tumorigenic $CD14^+$ myeloid cells, and regulatory T cells; (b) enhancing infiltration of one or more of immunosuppressor dendritic cells, immunosuppressor macrophages, immunosuppressor neutrophils, non-tumorigenic myeloid derived suppressor cells, tumor-associated macrophages, and regulatory T cells into tumors; (c) increasing number of tumor-promoting myeloid/granulocytic immune-suppressive cells and/or non-tumorigenic $CD14^+$ myeloid cells in a tumor, in peripheral blood, or other lymphoid organ; (d) enhancing tumor-promoting activity of non-tumorigenic myeloid-derived suppressor cells and/or non-tumorigenic $CD14^+$ myeloid cells; (e) increasing expression of tumor-promoting cytokines in a tumor or in peripheral blood, optionally wherein the tumor-promoting cytokines are TGF-beta or IL-10; (f) increasing tumor infiltration of tumor-promoting FoxP3+ regulatory T lymphocytes; (g) decreasing activation of tumor-specific T lymphocytes with tumor killing potential; (h) decreasing infiltration of tumor-specific T lymphocytes with tumor killing potential; (i) decreasing infiltration of tumor-specific NK cells with tumor killing potential; (j) decreasing tumor killing potential of NK cells; (k) decreasing infiltration of tumor-specific B lymphocytes with potential to enhance immune response; (l) increasing tumor volume; (m) increasing tumor growth rate; (n) increasing metastasis; (o) increasing rate of tumor recurrence; (p) increasing expression of one or more PD-1 ligands; (q) decreasing efficacy of one or more immune-therapies that modulate anti-tumor T cell responses, optionally wherein the one or more immune-therapies are immune-therapies that target one or more proteins selected from the group consisting of CD40, OX40, ICOS, CD28, CD137/4-1BB, CD27, GITR, PD-L1, CTLA4, PD-L2, PD-1, B7-H3, B7-H4, HVEM, BTLA, KIR, GAL9, TIM3, A2AR, LAG, DR-5, TREM1, TREM2, CSF-1 receptor, and any combination thereof, or of one or more cancer vaccines; (r) inhibition of PLCγ/PKC/calcium mobilization; (s) inhibition of PI3K/Akt, Ras/MAPK signaling; and (t) decreasing efficacy of one or more chemotherapy agents, optionally wherein the one or more of the chemotherapy agents are gemcitabine, capecitabine, anthracyclines, doxorubicin (Adriamycin®), epirubicin (Ellence®), taxanes, paclitaxel (Taxol®), docetaxel (Taxotere®), 5-fluorouracil (5-FU), cyclophosphamide (Cytoxan®), carboplatin (Paraplatin®), and any combination thereof. In some embodiments that may be combined with any of the preceding embodiments, the agent exhibits one or more activities selected from the group consisting of consisting of: (a) increasing the number of tumor infiltrating $CD3^+$ T cells; (b) decreasing cellular levels of CD33 in non-tumorigenic $CD14^+$ myeloid cells, optionally wherein the non-tumorigenic $CD14^+$ myeloid cells are tumor infiltrating cells or optionally wherein the non-tumorigenic $CD14^+$ myeloid cells are present in blood; (c) reducing the number of non-tumorigenic $CD14^+$ myeloid cells, optionally wherein the non-tumorigenic CD14+ myeloid cells are tumor infiltrating cells or optionally wherein the non-tumorigenic CD14+ myeloid cells are present in blood; (d) reducing PD-L1 levels in one or more cells, optionally wherein the one or more cells are non-tumorigenic myeloid-derived suppressor cells (MDSC); (e) reducing PD-L2 levels in one or more cells, optionally wherein the one or more cells are non-tumorigenic myeloid-derived suppressor cells (MDSC); (f) reducing B7-H2 levels in one or more cells, optionally wherein the one or more cells are non-tumorigenic myeloid-derived suppressor cells (MDSC); (g) reducing B7-H3 levels in one or more cells, optionally wherein the one or more cells are non-tumorigenic myeloid-derived suppressor cells (MDSC); (h) reducing CD200R levels in one or more cells, optionally wherein the one or more cells are non-tumorigenic myeloid-derived suppressor cells (MDSC); (i) reducing CD163 levels in one or more cells, optionally wherein the one or more cells are non-tumorigenic myeloid-derived suppressor cells (MDSC); (j) reducing CD206 levels in one or more cells, optionally wherein the one or more cells are non-tumorigenic myeloid-derived suppressor cells (MDSC); (k) decreasing tumor growth rate of solid tumors; (l) reducing tumor volume; (m) increasing efficacy of one or more PD-1 inhibitors; (n) increasing efficacy of one or more checkpoint inhibitor therapies and/or immune-modulating therapies, optionally wherein the one or more checkpoint inhibitor therapies and/or immune-modulating therapies target one or more of CTL4, the adenosine pathway, PD-L1, PD-L2, OX40, TIM3, LAG3, or any combination thereof; (o) increasing efficacy of one or more chemotherapy agents, optionally wherein the one or more of the chemotherapy agents are gemcitabine, capecitabine, anthracyclines, doxorubicin (Adriamycin®), epirubicin (Ellence®), taxanes, paclitaxel (Taxol®), docetaxel (Taxotere®), 5-fluorouracil (5-FU), cyclophosphamide (Cytoxan®), carboplatin (Paraplatin®), and any combination thereof; (p) increasing proliferation of T cells in the presence of non-tumorigenic myeloid-derived suppressor cells (MDSC); and (q) inhibiting differentiation, survival, and/or one or more functions of non-tumorigenic myeloid-derived suppressor cells (MDSC); and (r) killing CD33-expressing immunosuppressor myeloid cells and/or CD14-expressing cells in solid tumors and associated blood vessels when conjugated to a chemical or radioactive toxin.

Other aspects of the present disclosure relate to a method of preventing, reducing risk, or treating a disease, disorder, or injury selected from the group consisting of d dementia, frontotemporal dementia, Alzheimer's disease, vascular dementia, mixed dementia, taupathy disease, infections, and cancer, comprising administering to an individual in need thereof a therapeutically effective amount of an agent that decreases cellular levels of CD33, inhibits interaction between CD33 and one or more CD33 ligands, or both. Other aspects of the present disclosure relate to an agent that decreases cellular levels of CD33, inhibits interaction between CD33 and one or more CD33 ligands, or both for use in preventing, reducing risk, or treating a disease, disorder, or injury selected from the group consisting of dementia, frontotemporal dementia, Alzheimer's disease, vascular dementia, mixed dementia, taupathy disease, infections, and cancer. Other aspects of the present disclosure relate to use of an agent that decreases cellular levels of CD33, inhibits interaction between CD33 and one or more CD33 ligands, or both in the manufacture of a medicament for preventing, reducing risk, or treating a disease, disorder, or injury selected from the group consisting of dementia, frontotemporal dementia, Alzheimer's disease, vascular dementia, mixed dementia, taupathy disease, infections, and cancer. In some embodiments, the agent is selected from the group consisting of an antibody, a soluble CD33 receptor, a CD33-Fc fusion protein, a CD33 immunoadhesin, a soluble Siglec receptor that binds one or more CD33 ligands, a Siglec-Fc fusion protein, a Siglec immunoadhesin, an antisense molecule, an siRNA, a small molecule inhibitor, a protein, and a peptide. In some embodiments, the agent is an isolated anti-CD33 antibody. In some embodiments, the anti-CD33 antibody is the anti-CD33 antibody of any of the preceding embodiments. In some embodiments that may be combined with any of the preceding embodiments, the disease, disorder, or injury is cancer. In some embodiments that may be combined with any of the preceding embodiments, the cancer expresses CD33. In some embodiments that may be combined with any of the preceding embodiments, the cancer is selected from the group consisting of bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), and multiple myeloma. In some embodiments that may be combined with any of the preceding embodiments, the agent inhibits one or more CD33 activities selected from the group consisting of: (a) promoting proliferation, maturation, migration, differentiation, and/or functionality of one or more of immunosuppressor dendritic cells, immunosuppressor macrophages, immunosuppressor neutrophils, non-tumorigenic myeloid derived suppressor cells, tumor-associated macrophages, non-tumorigenic CD14+ myeloid cells, and regulatory T cells; (b) enhancing infiltration of one or more of immunosuppressor dendritic cells, immunosuppressor macrophages, immunosuppressor neutrophils, non-tumorigenic myeloid derived suppressor cells, tumor-associated macrophages, and regulatory T cells into tumors; (c) increasing number of tumor-promoting myeloid/granulocytic immune-suppressive cells and/or non-tumorigenic CD14+ myeloid cells in a tumor, in peripheral blood, or other lymphoid organ; (d) enhancing tumor-promoting activity of non-tumorigenic myeloid-derived suppressor cells and/or non-tumorigenic CD14+ myeloid cells; (e) increasing expression of tumor-promoting cytokines in a tumor or in peripheral blood, optionally wherein the tumor-promoting cytokines are TGF-beta or IL-10; (f) increasing tumor infiltration of tumor-promoting FoxP3+ regulatory T lymphocytes; (g) decreasing activation of tumor-specific T lymphocytes with tumor killing potential; (h) decreasing infiltration of tumor-specific T lymphocytes with tumor killing potential; (i) decreasing infiltration of tumor-specific NK cells with tumor killing potential; (j) decreasing tumor killing potential of NK cells; (k) decreasing infiltration of tumor-specific B lymphocytes with potential to enhance immune response; (l) increasing tumor volume; (m) increasing tumor growth rate; (n) increasing metastasis; (o) increasing rate of tumor recurrence; (p) increasing expression of one or more PD-1 ligands; (q) decreasing efficacy of one or more immune-therapies that modulate anti-tumor T cell responses, optionally wherein the one or more immune-therapies are immune-therapies that target one or more proteins selected from the group consisting of CD40, OX40, ICOS, CD28, CD137/4-1BB, CD27, GITR, PD-L1, CTLA4, PD-L2, PD-1, B7-H3, B7-H4, HVEM, BTLA, KIR, GAL9, TIM3, A2AR, LAG, DR-5, TREM1, TREM2, CSF-1 receptor, and any combination thereof, or of one or more cancer vaccines; (r) inhibition of PLCγ/PKC/calcium mobilization; (s) inhibition of PI3K/Akt, Ras/MAPK signaling; and (t) decreasing efficacy of one or more chemotherapy agents, optionally wherein the one or more of the chemotherapy agents are gemcitabine, capecitabine, anthracyclines, doxorubicin (Adriamycin®), epirubicin (Ellence®), taxanes, paclitaxel (Taxol®), docetaxel (Taxotere®), 5-fluorouracil (5-FU), cyclophosphamide (Cytoxan®), carboplatin (Paraplatin®), and any combination thereof. In some embodiments that may be combined with any of the preceding embodiments, the agent exhibits one or more activities selected from the group consisting of consisting of: (a) increasing the number of tumor infiltrating CD3$^+$ T cells; (b) decreasing cellular levels of CD33 in non-tumorigenic CD14$^+$ myeloid cells, optionally wherein the non-tumorigenic CD14$^+$ myeloid cells are tumor infiltrating cells or optionally wherein the non-tumorigenic CD14$^+$ myeloid cells are present in blood; (c) reducing the number of non-tumorigenic CD14$^+$ myeloid cells, optionally wherein the non-tumorigenic CD14$^+$ myeloid cells are tumor infiltrating cells or optionally wherein the non-tumorigenic CD14$^+$ myeloid cells are present in blood; (d) reducing PD-L1 levels in one or more cells, optionally wherein the one or more cells are non-tumorigenic myeloid-derived suppressor cells (MDSC); (e) reducing PD-L2 levels in one or more cells, optionally wherein the one or more cells are non-tumorigenic myeloid-derived suppressor cells (MDSC); (f) reducing B7-H2 levels in one or more cells, optionally wherein the one or more cells are non-tumorigenic myeloid-derived suppressor cells (MDSC); (g) reducing B7-H3 levels in one or more cells, optionally wherein the one or more cells are non-tumorigenic myeloid-derived suppressor cells (MDSC); (h) reducing CD200R levels in one or more cells, optionally wherein the one or more cells are non-tumorigenic myeloid-derived suppressor cells (MDSC); (i) reducing CD163 levels in one or more cells, optionally wherein the one or more cells are non-tumorigenic myeloid-derived suppressor cells (MDSC); (j) reducing CD206 levels in one or more cells, optionally wherein the one or more cells are non-tumorigenic myeloid-derived suppressor cells (MDSC); (k) decreasing tumor growth rate of solid tumors; (l) reducing tumor volume; (m) increasing efficacy of one or more PD-1 inhibitors; (n) increasing efficacy of one or more checkpoint inhibitor therapies and/or immune-modulating therapies, optionally wherein the one or more checkpoint inhibitor therapies and/or immune-modulating therapies target one or more of CTL4, the adenosine pathway, PD-L1, PD-L2, OX40, TIM3, LAG3, or any combination thereof; (o) increasing efficacy of one or more chemotherapy agents, optionally wherein the one or more of the chemotherapy agents are gemcitabine, capecitabine, anthracyclines, doxorubicin (Adriamycin®), epirubicin (Ellence®), taxanes, paclitaxel (Taxol®), docetaxel (Taxotere®), 5-fluorouracil (5-FU), cyclophosphamide (Cytoxan®), carboplatin (Paraplatin®), and any combination thereof; (p) increasing proliferation of T cells in the presence of non-tumorigenic myeloid-derived suppressor cells (MDSC); and (q) inhibiting differentiation, survival, and/or one or more functions of non-tumorigenic myeloid-derived suppressor cells (MDSC); and (r) killing CD33-expressing immunosuppressor myeloid cells and/or CD14-expressing cells in solid tumors and associated blood vessels when conjugated to a chemical or radioactive toxin. In some embodiments that may be combined with any of the preceding embodiments, the disease, disorder, or injury is an infection. In some embodiments that may be combined with any of the preceding embodiments, the infection is selected from the group consisting of CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus* influenza.

Other aspects of the present disclosure relate to a method of preventing, reducing risk, or treating cancer, comprising administering to an individual in need thereof a therapeutically effective amount of an agent that decreases cellular levels of CD33, inhibits interaction between CD33 and one or more CD33 ligands, or both. Other aspects of the present disclosure relate to an agent that decreases cellular levels of CD33, inhibits interaction between CD33 and one or more CD33 ligands, or both for use in preventing, reducing risk, or treating cancer in an individual in need thereof. Other aspects of the present disclosure relate to use of an agent that decreases cellular levels of CD33, inhibits interaction between CD33 and one or more CD33 ligands, or both in the manufacture of a medicament for preventing, reducing risk, or treating cancer in an individual in need thereof. In some embodiments, the agent is selected from the group consisting of an antibody, a soluble CD33 receptor, a CD33-Fc fusion protein, a CD33 immunoadhesin, a soluble Siglec receptor that binds one or more CD33 ligands, a Siglec-Fc fusion protein, a Siglec immunoadhesin, an antisense molecule, an siRNA, a small molecule inhibitor, a protein, and a peptide. In some embodiments, the agent is an isolated anti-CD33 antibody. In some embodiments, the anti-CD33 antibody is the anti-CD33 antibody of any of the preceding embodiments. In some embodiments, the cancer is selected from the group consisting of bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), and multiple myeloma. In some embodiments, the cancer is a CD33-expressing cancer. In some embodiments, the cancer comprises tumors that express CD33. In some embodiments that may be combined with any of the preceding embodiments, the agent inhibits one or more CD33 activities selected from the group consisting of: (a) promoting proliferation, maturation, migration, differentiation, and/or functionality of one or more of immunosuppressor dendritic cells, immunosuppressor macrophages, immunosuppressor neutrophils, non-tumorigenic myeloid derived suppressor cells, tumor-associated macrophages, non-tumorigenic CD14$^+$ myeloid cells, and regulatory T cells; (b) enhancing infiltration of one or more of immunosuppressor dendritic cells, immunosuppressor macrophages, immunosuppressor neutrophils, non-tumorigenic myeloid derived suppressor cells, tumor-associated macrophages, and regulatory T cells into tumors; (c) increasing number of tumor-promoting myeloid/granulocytic immune-suppressive cells and/or non-tumorigenic CD14$^+$ myeloid cells in a tumor, in peripheral blood, or other lymphoid organ; (d) enhancing tumor-promoting activity of non-tumorigenic myeloid-derived suppressor cells and/or non-tumorigenic CD14$^+$ myeloid cells; (e) increasing expression of tumor-promoting cytokines in a tumor or in peripheral blood, optionally wherein the tumor-promoting cytokines are TGF-beta or IL-10; (f) increasing tumor infiltration of tumor-promoting FoxP3+ regulatory T lymphocytes; (g) decreasing activation of tumor-specific T lymphocytes with tumor killing potential; (h) decreasing infiltration of tumor-specific T lymphocytes with tumor killing potential; (i) decreasing infiltration of tumor-specific NK cells with tumor killing potential; (j) decreasing tumor killing potential of NK cells; (k) decreasing infiltration of tumor-specific B lymphocytes with potential to enhance immune response; (l) increasing tumor volume; (m) increasing tumor growth rate; (n) increasing metastasis; (o) increasing rate of tumor recurrence; (p) increasing expression of one or more PD-1 ligands; (q) decreasing efficacy of one or more immune-therapies that modulate anti-tumor T cell responses, optionally wherein the one or more immune-therapies are immune-therapies that target one or more proteins selected from the group consisting of CD40, OX40, ICOS, CD28, CD137/4-1BB, CD27, GITR, PD-L1, CTLA4, PD-L2, PD-1, B7-H3, B7-H4, HVEM, BTLA, KIR, GAL9, TIM3, A2AR, LAG, DR-5, TREM1, TREM2, CSF-1 receptor, and any combination thereof, or of one or more cancer vaccines; (r) inhibition of PLCγ/PKC/calcium mobilization; (s) inhibition of PI3K/Akt, Ras/MAPK signaling; and (t) decreasing efficacy of one or more chemotherapy agents, optionally wherein the one or more of the chemotherapy agents are gemcitabine, capecitabine, anthracyclines, doxorubicin (Adriamycin®), epirubicin (Ellence®), taxanes, paclitaxel (Taxol®), docetaxel (Taxotere®), 5-fluorouracil (5-FU), cyclophosphamide (Cytoxan®), carboplatin (Paraplatin®), and any combination thereof. In some embodiments that may be combined with any of the preceding embodiments, the agent exhibits one or more activities selected from the group consisting of consisting of: (a) increasing the number of tumor infiltrating $CD3^+$ T cells; (b) decreasing cellular levels of CD33 in non-tumorigenic $CD14^+$ myeloid cells, optionally wherein the non-tumorigenic $CD14^+$ myeloid cells are tumor infiltrating cells or optionally wherein the non-tumorigenic $CD14^+$ myeloid cells are present in blood; (c) reducing the number of non-tumorigenic $CD14^+$ myeloid cells, optionally wherein the non-tumorigenic $CD14^+$ myeloid cells are tumor infiltrating cells or optionally wherein the non-tumorigenic $CD14^+$ myeloid cells are present in blood; (d) reducing PD-L1 levels in one or more cells, optionally wherein the one or more cells are non-tumorigenic myeloid-derived suppressor cells (MDSC); (e) reducing PD-L2 levels in one or more cells, optionally wherein the one or more cells are non-tumorigenic myeloid-derived suppressor cells (MDSC); (f) reducing B7-H2 levels in one or more cells, optionally wherein the one or more cells are non-tumorigenic myeloid-derived suppressor cells (MDSC); (g) reducing B7-H3 levels in one or more cells, optionally wherein the one or more cells are non-tumorigenic myeloid-derived suppressor cells (MDSC); (h) reducing CD200R levels in one or more cells, optionally wherein the one or more cells are non-tumorigenic myeloid-derived suppressor cells (MDSC); (i) reducing CD163 levels in one or more cells, optionally wherein the one or more cells are non-tumorigenic myeloid-derived suppressor cells (MDSC); (j) reducing CD206 levels in one or more cells, optionally wherein the one or more cells are non-tumorigenic myeloid-derived suppressor cells (MDSC); (k) decreasing tumor growth rate of solid tumors; (l) reducing tumor volume; (m) increasing efficacy of one or more PD-1 inhibitors; (n) increasing efficacy of one or more checkpoint inhibitor therapies and/or immune-modulating therapies, optionally wherein the one or more checkpoint inhibitor therapies and/or immune-modulating therapies target one or more of CTL4, the adenosine pathway, PD-L1, PD-L2, OX40, TIM3, LAG3, or any combination thereof; (o) increasing efficacy of one or more chemotherapy agents, optionally wherein the one or more of the chemotherapy agents are gemcitabine, capecitabine, anthracyclines, doxorubicin (Adriamycin®), epirubicin (Ellence®), taxanes, paclitaxel (Taxol®), docetaxel (Taxotere®), 5-fluorouracil (5-FU), cyclophosphamide (Cytoxan®), carboplatin (Paraplatin®), and any combination thereof; (p) increasing proliferation of T cells in the presence of non-tumorigenic myeloid-derived suppressor cells (MDSC); and (q) inhibiting differentiation, survival, and/or one or more functions of non-tumorigenic myeloid-derived suppressor cells (MDSC); and (r) killing CD33-expressing immunosuppressor myeloid cells and/or CD14-expressing cells in solid tumors and associated blood vessels when conjugated to a chemical or radioactive toxin.

Other aspects of the present disclosure relate to a method of inducing or promoting the survival, maturation, functionality, migration, or proliferation of one or more immune cells in an individual in need thereof, comprising administering to the individual a therapeutically effective amount of an agent that decreases cellular levels of CD33, inhibits interaction between CD33 and one or more CD33 ligands, or both. Other aspects of the present disclosure relate to an agent that decreases cellular levels of CD33, inhibits interaction between CD33 and one or more CD33 ligands, or both for use in inducing or promoting the survival, maturation, functionality, migration, or proliferation of one or more immune cells in an individual in need thereof. Other aspects of the present disclosure relate to use of an agent that decreases cellular levels of CD33, inhibits interaction between CD33 and one or more CD33 ligands, or both in the manufacture of a medicament for inducing or promoting the survival, maturation, functionality, migration, or proliferation of one or more immune cells in an individual in need thereof. In some embodiments, the agent is selected from the group consisting of an antibody, a soluble CD33 receptor, a CD33-Fc fusion protein, a CD33 immunoadhesin, a soluble Siglec receptor that binds one or more CD33 ligands, a Siglec-Fc fusion protein, a Siglec immunoadhesin, an antisense molecule, an siRNA, a small molecule inhibitor, a protein, and a peptide. In some embodiments, the agent is an isolated anti-CD33 antibody. In some embodiments, the anti-CD33 antibody is the anti-CD33 antibody of any of the preceding embodiments. In some embodiments, the one or more immune cells are selected from the group consisting of dendritic cells, macrophages, microglia, neutrophils, T cells, T helper cells, cytotoxic T cells, and any combination thereof.

Other aspects of the present disclosure relate to a method of decreasing the activity, functionality, or survival of regulatory T cells, tumor-imbedded immunosuppressor dendritic cells, tumor-imbedded immunosuppressor macrophages, non-tumorigenic myeloid-derived suppressor cells, tumor-associated macrophages, acute myeloid leukemia (AML) cells, chronic lymphocytic leukemia (CLL) cell, or chronic myeloid leukemia (CML) cells in an individual in need thereof, comprising administering to the individual a therapeutically effective amount of an agent that binds or interacts with CD33. Other aspects of the present disclosure relate to an agent that binds or interacts with CD33 for use in decreasing the activity, functionality, or survival of regulatory T cells, tumor-imbedded immunosuppressor dendritic cells, tumor-imbedded immunosuppressor macrophages, non-tumorigenic myeloid-derived suppressor cells, tumor-associated macrophages, acute myeloid leukemia (AML) cells, chronic lymphocytic leukemia (CLL) cell, or chronic myeloid leukemia (CML) cells in an individual in need thereof. Other aspects of the present disclosure relate to use of an agent that binds or interacts with CD33 in the manufacture of a medicament for decreasing the activity, functionality, or survival of regulatory T cells, tumor-imbedded immunosuppressor dendritic cells, tumor-imbedded immunosuppressor macrophages, non-tumorigenic myeloid-derived suppressor cells, tumor-associated macrophages, acute myeloid leukemia (AML) cells, chronic lymphocytic leukemia (CLL) cell, or chronic myeloid leukemia (CML) cells in an individual in need thereof. In some embodiments, the agent is selected from the group consisting of an antibody, an antagonist antibody, an inert antibody, an agonist antibody, a CD33 ligand, a CD33 ligand agonist fragment, a CD33 immunoadhesin, a CD33 ligand mimetic, a soluble CD33 receptor, a CD33-Fc fusion protein, a soluble Siglec receptor that binds one or more CD33 ligands, a Siglec-Fc fusion protein that binds one or more CD33 ligands, and a small molecule compound. In some embodiments, the agent is an isolated anti-CD33 antibody or anti-CD33 antibody conjugate. In some embodiments, the anti-CD33 antibody conjugate comprises an anti-CD33 antibody conjugated to a detectable marker, a toxin, or a therapeutic agent. In some embodiments, the anti-CD33 antibody conjugate comprises an anti-CD33 antibody conjugated to a toxin selected from the group consisting of ricin, ricin A-chain, doxorubicin, daunorubicin, a maytansinoid, taxol, ethidium bromide, mitomycin, etoposide, tenoposide, vincristine, vinblastine, colchicine, dihydroxy anthracin dione, actinomycin, diphtheria toxin, *Pseudomonas* exotoxin (PE) A, PE40, abrin, abrin A chain, modeccin A chain, alpha-sarcin, gelonin, mitogellin, retstrictocin, phenomycin, enomycin, curicin, crotin, calicheamicin, *Saponaria officinalis* inhibitor, glucocorticoid, auristatin, auromycin, yttrium, bismuth, combrestatin, duocarmycins, dolastatin, cc1065, and a cisplatin. In some embodiments that may be combined with any of the preceding embodiments, the anti-CD33 antibody is an anti-CD33 antibody of any of the preceding embodiments that does not significantly decrease cell surface levels of CD33 and/or does not inhibit interaction between CD33 and one or more CD33 ligands.

Other aspects of the present disclosure relate to a method of decreasing cellular levels of CD33, inhibiting interaction between CD33 and one or more CD33 ligands, or both on one or more cells in an individual in need thereof, comprising administering to the individual a therapeutically effective amount of an isolated anti-CD33 antibody. Other aspects of the present disclosure relate to an isolated anti-CD33 antibody for use in decreasing cellular levels of CD33, inhibiting interaction between CD33 and one or more CD33 ligands, or both on one or more cells in an individual in need thereof. Other aspects of the present disclosure relate to use of an isolated anti-CD33 antibody in the manufacture of a medicament for decreasing cellular levels of CD33, inhibiting interaction between CD33 and one or more CD33 ligands, or both on one or more cells in an individual in need thereof. In some embodiments, the one or more cells are selected from dendritic cells, bone marrow-derived dendritic cells, monocytes, microglia, T cells, and macrophages; and/or cell lines. In some embodiments, the anti-CD33 antibody decreases cellular levels of CD33 in vivo. In some embodiments that may be combined with any of the preceding embodiments, the anti-CD33 antibody decreases cellular levels of CD33 with an $EC_{50}$ that ranges from 65 pM to 20 pM. In some embodiments that may be combined with any of the preceding embodiments, the anti-CD33 antibody decreases cellular levels of CD33 with an $EC_{50}$ of 65 pM or less, 60 pM or less, 55 pM or less, 50 pM or less, 45 pM or less, 40 pM or less, 35 pM or less, 30 pM or less, 25 pM or less, 24 pM or less, 23 pM or less, 22 pM or less, 21 pM or less, 20 pM or less, 10 pM or less, 9 pM or less, 8 pM or less, 7 pM or less, 6 pM or less, or 5 pM or less. In some embodiments that may be combined with any of the preceding embodiments, the anti-CD33 antibody decreases cellular levels of CD33 with an $EC_{50}$ that ranges from 65 pM to 22 pM, or less than 22 pM. In some embodiments that may be combined with any of the preceding embodiments, the anti-CD33 antibody decreases cellular levels of CD33 in vivo with an $EC_{50}$ that ranges from about 8.0 mg/kg to about 2.0 mg/kg. In some embodiments that may be combined with any of the preceding embodiments, the anti-CD33 antibody has a dissociation constant ($K_D$) for human CD33 that ranges from 300 pM to 10 pM, wherein the $K_D$ is determined at a temperature of approximately 25° C. In some embodiments that may be combined with any of the preceding embodiments, the anti-CD33 antibody has a dissociation constant ($K_D$) for human CD33 that is less than 300 pM, wherein the $K_D$ is determined at a temperature of approximately 25° C. In some embodiments that may be combined with any of the previous embodiments, the $K_D$ is determined using a monovalent antibody. In some embodiments that may be combined with any of the previous embodiments, the $K_D$ is determined using a full-length antibody in a monovalent form. In some embodiments that may be combined with any of the preceding embodiments, the anti-CD33 antibody binds to human dendritic cells with an $EC_{50}$ that ranges from 200 pM to 10 pM, wherein the $EC_{50}$ is determined at a temperature of approximately 4° C. In some embodiments that may be combined with any of the preceding embodiments, the anti-CD33 antibody binds to human dendritic cells with an $EC_{50}$ that is less than 200 pM, wherein the $EC_{50}$ is determined at a temperature of approximately 4° C. In some embodiments, the anti-CD33 antibody is selected from the group consisting of an antagonist anti-CD33 antibody, an inert anti-CD33 antibody, and an agonist anti-CD33 antibody. In some embodiments, the anti-CD33 antibody is the anti-CD33 antibody of any of the preceding embodiments.

In some embodiments that may be combined with any of the preceding embodiments, the individual comprises a variant of CD33. In some embodiments that may be combined with any of the preceding embodiments, the variant comprises one or more polymorphisms selected from the group consisting of: (a) SNP rs3865444$^{AC}$; (b) SNP rs3865444$^{CC}$; (c) SNP rs35112940$^{GG,\ AA,\ AG}$; (d) SNP rs12459419$^{CC,\ CT\ or\ TT}$; and any combinations thereof. In some embodiments that may be combined with any of the preceding embodiments, the method further comprising administering to the individual at least one antibody that specifically binds to an inhibitory checkpoint molecule, and/or one or more standard or investigational anti-cancer therapies. In some embodiments that may be combined with any of the preceding embodiments, the at least one antibody that specifically binds to an inhibitory checkpoint molecule is administered in combination with the anti-CD33 antibody. In some embodiments that may be combined with any of the preceding embodiments, the at least one antibody that specifically binds to an inhibitory checkpoint molecule is selected from the group consisting of an anti-PD-L1 antibody, an anti-CTLA4 antibody, an anti-PD-L2 antibody, an anti-PD-1 antibody, an anti-B7-H3 antibody, an anti-B7-H4 antibody, and anti-HVEM antibody, an anti-B- and T-lymphocyte attenuator (BTLA) antibody, an anti-Killer inhibitory receptor (KIR) antibody, an anti-GAL9 antibody, an anti-TIM3 antibody, an anti-AZAR antibody, an anti-LAG-3 antibody, an anti-phosphatidylserine antibody, an anti-CD27 antibody, an anti-TNFa antibody, an anti-Siglec-5 antibody, an anti-Siglec-7 antibody, an anti-Siglec-9 antibody, an anti-Siglec-11 antibody, an antagonistic anti-TREM1 antibody, an antagonistic anti-TREM2 antibody, and any combination thereof. In some embodiments that may be combined with any of the preceding embodiments, the one or more standard or investigational anti-cancer therapies are selected from the group consisting of radiotherapy, cytotoxic chemotherapy, targeted therapy, imatinib therapy, trastuzumab therapy, etanercept therapy, adoptive cell transfer (ACT) therapy, chimeric antigen receptor T cell transfer (CAR-T) therapy, vaccine therapy, and cytokine therapy. In some embodiments that may be combined with any of the preceding embodiments, the method further comprising administering to the individual at least one antibody that specifically binds to an inhibitory cytokine. In some embodiments that may be combined with any of the preceding embodiments, the at least one antibody that specifically binds to an inhibitory cytokine is administered in combination with the anti-CD33 antibody. In some embodiments that may be combined with any of the preceding embodiments, the at least one antibody that specifically binds to an inhibitory cytokine is selected from the group consisting of an anti-CCL2 antibody, an anti-CSF-1 antibody, an anti-IL-2 antibody, and any combination thereof. In some embodiments that may be combined with any of the preceding embodiments, the method further comprising administering to the individual at least one agonistic antibody that specifically binds to a stimulatory checkpoint protein. In some embodiments that may be combined with any of the preceding embodiments, the at least one agonistic antibody that specifically binds to a stimulatory checkpoint protein is administered in combination with the anti-CD33 antibody. In some embodiments that may be combined with any of the preceding embodiments, the at least one agonistic antibody that specifically binds to a stimulatory checkpoint protein is selected from the group consisting of an agonist anti-CD40 antibody, an agonist anti-OX40 antibody, an agonist anti-ICOS antibody, an agonist anti-CD28 antibody, an agonistic anti-TREM1 antibody, an agonistic anti-TREM2 antibody, an agonist anti-CD137/4-1BB antibody, an agonist anti-CD27 antibody, an agonist anti-glucocorticoid-induced TNFR-related protein GITR antibody, and any combination thereof. In some embodiments that may be combined with any of the preceding embodiments, the method further comprising administering to the individual at least one stimulatory cytokine. In some embodiments that may be combined with any of the preceding embodiments, the at least one stimulatory cytokine is administered in combination with the anti-CD33 antibody. In some embodiments that may be combined with any of the preceding embodiments, the at least one stimulatory cytokine is selected from the group consisting of IFN-a4, IFN-b, IL-1β, TNF-α, IL-6, IL-8, CRP, IL-20 family members, LIF, IFN-gamma, OSM, CNTF, GM-CSF, IL-11, IL-12, IL-17, IL-18, IL-23, CXCL10, IL-33, CRP, IL-33, MCP-1, MIP-1-beta, and any combination thereof.

Other aspects of the present disclosure relate to a method of selecting a subject in need thereof for treatment with an agent that binds or interacts with CD33, the method comprising: a. obtaining a sample from the subject; b. detecting the CD33 alleles present in the subject; and c. selecting the subject for treatment with the agent that binds or interacts with CD33 is the subject has one or more CD33 alleles, wherein the one or more CD33 alleles are selected from the group consisting of rs3865444$^{AC}$, and rs3865444$^{CC}$. Other aspects of the present disclosure relate to a method of assessing responsiveness of a subject in need thereof to an agent that binds or interacts with CD33, the method comprising: a. measuring the expression levels of CD45$^+$ and CD14$^+$ on non-tumorigenic myeloid cells in a blood sample obtained from the subject prior to administering to the subject an anti-CD33 antibody; b. administering to the subject a therapeutically effective amount of the agent; and c. measuring the expression levels of CD45$^+$ and CD14$^+$ on non-tumorigenic myeloid cells in a blood sample obtained from the subject after administration of the anti-CD33 antibody, wherein a reduction in the levels of CD45$^+$ CD14$^+$ on non-tumorigenic myeloid cells after administration of the anti-CD33 antibody indicates the subject is responsive to the agent. In some embodiments, the method of assessing responsiveness further comprises administering one or more additional therapeutically effective amounts of the agent. In some embodiments that may be combined with any of the preceding embodiments, the agent is selected from the group consisting of an antibody, a soluble CD33 receptor, a CD33-Fc fusion protein, a CD33 immunoadhesin, a soluble Siglec receptor, a Siglec-Fc fusion protein, a Siglec immunoadhesin, an antisense molecule, an siRNA, a small molecule inhibitor, a protein, and a peptide. In some embodiments that may be combined with any of the preceding embodiments, the agent is an isolated anti-CD33 antibody or anti-CD33 antibody conjugate. In some embodiments that may be combined with any of the preceding embodiments, the anti-CD33 antibody is the anti-CD33 antibody of any of the preceding embodiments.

BRIEF DESCRIPTION OF THE DRAWINGS

FIG. 2 depicts an amino acid sequence alignment between human CD33 (SEQ ID NO:1) and mouse CD33 (SEQ ID NO:2), rat CD33 (SEQ ID NO:3), chimpanzee CD33 (SEQ ID NO:4), rhesus CD33 (SEQ ID NO:5), dog CD33 (SEQ ID NO:6), cow CD33 (SEQ ID NO:7), and zebrafish CD33 (SEQ ID NO:8). An asterisk ("*") indicates positions which have a single, fully conserved residue; A colon (":") indicates conservation between groups of strongly similar properties—scoring >0.5 in the Gonnet PAM 250 matrix; and a period (".") indicates conservation between groups of weakly similar properties—scoring=<0.5 in the Gonnet PAM 250 matrix.

FIG. 3 shows glycan-binding specificities of human Siglec proteins, such as CD33. This figure shows a summary of the most commonly reported specificities for the most commonly studied sialylated glycans. Relative binding within studies of each Siglec is indicated as ++, strong binding; +, detectable binding; and −, very weak or undetectable binding. Not shown is the recently reported strong-binding preference of hSiglec-8 and mSiglec-F for 6'-sulfated-sialyl-Lewis x (sLex) and of hSiglec-9 for 6-sulfated-sLex. With a few exceptions (CD22 and MAG), results of binding specificity studies of human Siglecs by different investigators using different assays have varied significantly. In addition to assay formats and glycan linker issues, the density and arrangement of the ligands studied could be responsible for this variation (Varki et al., (2006) Glycobiol. 16:1R-27R).

FIG. 6A shows linear epitope binding sites of anti-CD33 antibodies utilizing anti-CD33 antibodies of the present disclosure. The CD33 backbone is rendered in a transparent grey representation. Linear binding regions identified for antibodies are listed in the figure. FIG. 6B depicts a cartoon rendering of binding sites of a discontinuous epitope for antibody 1A8. The discontinuous binding regions $^{39}$VPCTFFHPIPYYD$^{51}$, $^{88}$GRFRLLGDPSR$^{98}$, and $^{110}$RRDNGSYFFRM$^{120}$ are listed in the figure and correspond to amino acid residues 39-51, 88-98, and 110-120 of SEQ ID NO:1. FIG. 6C depicts binding reactivity in percentage to wild-type CD33 (% WT) of antibodies of the present disclosure to CD33 mutants.

FIG. 9A and FIG. 9B depict results showing an increase in CD33 expression on human primary dendritic cells after treatment with tumor supernatant. FIG. 9C and FIG. 9D depict results showing an increase in CD33 expression on human dendritic cells during LPS-induced inflammation. FIG. 9E and FIG. 9F depict results showing an increase in sialic acid expression on human myeloid cells during LPS-induced inflammation.

FIG. 11A depicts Bioparticle control, mIgG1 isotype control antibody, and anti-CD33 antibody 2E12. FIG. 11B depicts anti-CD33 antibody 2F5, anti-CD33 antibody 6A3, and anti-CD33 antibody 6C7.

FIG. 12A depicts immunohistochemistry staining of CD33-Fc in AD and non-AD brains. A control IgG1-Fc does not bind to these cells. FIG. 12B depicts results of one way ANOVA statistical analysis of CD33-Fc and control receptor staining from 5 AD and 5 non-AD brain samples, indicating that inhibitory CD33 ligand contributes to AD pathology.

FIG. 13A depicts immunohistochemistry staining of a CD33 antibody compared to an isotype control in AD and non-AD brain sections. FIG. 13B depicts results of one way ANOVA statistical analysis of CD33 antibody and isotype control staining from 5 AD and 5 non-AD brain samples.

FIG. 14A depicts results showing that the expression of an inhibitory CD33 ligand is increased by approximately 20-fold in melanoma cells, lung tumor cells, and colon cancer cells. FIG. 14B depicts results showing CD33 expression in human immune cells from peripheral blood and spleen, and cell infiltrates from patient-derived melanoma from an immunodeficient mouse model lacking mature mouse T cells, B cells, and NK cells that was transplanted with human CD45+ immune cells and with patient-derived melanoma. FIG. 14C depicts results showing CD33 expression in CD3+ T cells, CD11b+ immune cells, and Gr1+ CD11b+ immune cells from spleen and cell infiltrated from a breast cancer tumor EMT-6 from a mouse tumor model. FIG. 14D depicts results showing CD33 expression in CD45− T cells, Gr1+ cells and Gr1− CD11b-immune cells from spleen and cell infiltrates from a breast cancer tumor EMT-6 from a mouse tumor model. The results indicate that CD33 and a CD33 immune inhibitory ligand play a role in immune response to multiple types of solid tumors.

FIG. 15A depicts control mice having normal CD33 expression (WT mice). FIG. 15B depicts mice in which CD33 was genetically inactivated (CD33 KO mice). FIG. 15C depicts a summary of the results of FIGS. 15A and 15B, showing median tumor volume. FIG. 15D depicts a Kaplan-Meier survival plot demonstrating that CD33 KO mice having colon carcinoma survive better than corresponding WT mice having colon carcinoma. FIG. 15E depicts FACS analysis of mouse CD33 expression. Specific cellular population analysis was performed on spleens and tumors, as well as a naïve spleen, from a WT mouse and a CD33 KO mouse. The results indicate that blockade of CD33 function (either genetically or pharmacologically) leads to a beneficial outcome in cancer. FIG. 15AA depicts in vivo reduction in cell surface levels of CD33 in peripheral blood human (h) CD45$^+$CD14$^+$ myeloid cells from mice containing the Alzheimer's disease rs3865444 C/C allele and that were treated with anti-CD33 antibody 2F5 or isotype control (Ctl) antibody. *: $p<0.001$ for 2F5 vs Isotype Ctl, correcting for donor and day of animal sacrifice, +: mean; boxplot midline: median; upper and lower boundaries of the boxes correspond to the first and third quartiles (25th and 75th percentiles). FIG. 15BB depicts in vivo reduction in cell surface levels of CD33 in peripheral blood human (h) CD45$^+$CD14$^+$ myeloid cells from mice containing the Alzheimer's disease rs3865444 A/A allele and that were treated with anti-CD33 antibody 2F5 or isotype control (Ctl) antibody. "n.s.": not statistically significant; +: mean; boxplot midline: median; upper and lower boundaries of the boxes correspond to the first and third quartiles (25th and 75th percentiles). FIG. 15CC depicts in vivo reduction in cell surface levels of CD33 in tumor infiltrating human (h) CD45$^+$CD14$^+$ myeloid cells from mice treated with anti-CD33 antibody 2F5 or isotype control (Ctl) antibody. *: p<0.001 for 2F5 vs Isotype Ctl, correcting for donor and day of animal sacrifice; +: mean; boxplot midline: median; upper and lower boundaries of the boxes correspond to the first and third quartiles (25th and 75th percentiles). FIG. 15DD depicts in vivo reduction in cell surface levels of CD33 in tumor infiltrating human (h) CD45$^+$CD14$^+$ myeloid cells from mice containing any of the Alzheimer's disease CD33 alleles rs3865444 A/A allele, A/C allele and C/C allele and that were treated with anti-CD33 antibody 2F5 or isotype control (Ctl) antibody. *: p<0.001 for 2F5 vs Isotype Ctl, correcting for donor and day of animal sacrifice; +: mean; boxplot midline: median; upper and lower boundaries of the boxes correspond to the first and third quartiles (25th and 75th percentiles). FIG. 15EE depicts in vivo reduction in cell surface levels of CD33 in tumor infiltrating human (h) CD45$^+$ CD14$^+$ myeloid cells from mice containing the Alzheimer's disease rs3865444 C/C allele and that were treated with anti-CD33 antibody 2F5 or isotype control (Ctl) antibody. *: p<0.001 for 2F5 vs Isotype Ctl, correcting for donor and day of animal sacrifice; +: mean; boxplot midline: median; upper and lower boundaries of the boxes correspond to the first and third quartiles (25th and 75th percentiles). FIG. 15FF depicts in vivo reduction in cell surface levels of CD33 in tumor infiltrating human (h) CD45$^+$ CD14$^+$ myeloid cells from mice containing the Alzheimer's disease rs3865444 A/A allele and that were treated with anti-CD33 antibody 2F5 or isotype control (Ctl) antibody. "n.s.": not statistically significant; +: mean; boxplot midline: median; upper and lower boundaries of the boxes correspond to the first and third quartiles (25th and 75th percentiles). FIG. 15GG depicts in vivo reduction in tumor infiltrating human (h) CD45$^+$CD14$^+$ myeloid cells from mice treated with anti-CD33 antibody 2F5 or isotype control (Ctl) antibody. *: p<0.01; *: p<0.001 for 2F5 vs Isotype Ctl, correcting for donor and day of animal sacrifice +: mean; boxplot midline: median; upper and lower boundaries of the boxes correspond to the first and third quartiles (25th and 75th percentiles). FIG. 15HH depicts in vivo reduction in tumor infiltrating human (h) CD45$^+$CD14$^+$ myeloid cells from mice containing any of the Alzheimer's disease CD33 alleles rs3865444 A/A allele, A/C allele and C/C allele and that were treated with anti-CD33 antibody 2F5 or isotype control (Ctl) antibody. *: p<0.001 for 2F5 vs Isotype Ctl, correcting for donor and day of animal sacrifice; +: mean; boxplot midline: median; upper and lower boundaries of the boxes correspond to the first and third quartiles (25th and 75th percentiles). FIG. 15II depicts in vivo reduction in tumor infiltrating human (h) CD45$^+$CD14$^+$ myeloid cells from mice containing the Alzheimer's disease rs3865444 C/C allele and that were treated with anti-CD33 antibody 2F5 or isotype control (Ctl) antibody. : p<0.01 for 2F5 vs Isotype Ctl, correcting for donor and day of animal sacrifice; +: mean; boxplot midline: median; upper and lower boundaries of the boxes correspond to the first and third quartiles (25th and 75th percentiles). FIG. 15JJ depicts in vivo reduction in tumor infiltrating human (h) CD45$^+$ CD14$^+$ myeloid cells from mice containing the Alzheimer's disease rs3865444 A/A allele and that were treated with anti-CD33 antibody 2F5 or isotype control (Ctl) antibody. *: p<0.05; correcting for donor and day of animal sacrifice; +: mean; boxplot midline: median; upper and lower boundaries of the boxes correspond to the first and third quartiles (25th and 75th percentiles). FIG. 15KK depicts in vivo increase in tumor infiltrating human (h) CD45$^+$ CD3$^+$ T cells from mice treated with anti-CD33 antibody 2F5 or isotype control (Ctl) antibody. (*): p<0.10, : p<0.01 for 2F5 vs Isotype Ctl, correcting for donor and day of animal sacrifice; +: mean; boxplot midline: median; upper and lower boundaries of the boxes correspond to the first and third quartiles (25th and 75th percentiles). FIG. 15LL** depicts in vivo increase in tumor infiltrating human (h) CD45$^+$ CD3$^+$ T cells from mice containing any of the Alzheimer's disease CD33 alleles rs3865444 A/A allele, A/C allele and C/C allele and that were treated with anti-CD33 antibody 2F5 or isotype control (Ctl) antibody. (*): p<0.10 for 2F5 vs Isotype Ctl, correcting for donor and day of animal sacrifice; +: mean; boxplot midline: median; upper and lower boundaries of the boxes correspond to the first and third quartiles (25th and 75th percentiles). p=0.0042 for rs3865444 A/A allele and p=0.59 for rs3865444 C/C allele. FIG. 15MM depicts in vivo increase in tumor infiltrating human (h) CD45$^+$ CD3$^+$ T cells from mice containing the Alzheimer's disease rs3865444 C/C allele and that were treated with anti-CD33 antibody 2F5 or isotype control (Ctl) antibody. "n.s.": not statistically significant; +: mean; boxplot midline: median; upper and lower boundaries of the boxes correspond to the first and third quartiles (25th and 75th percentiles). FIG. 15NN depicts in vivo increase in tumor infiltrating human (h) CD45$^+$ CD3$^+$ T cells from mice containing the Alzheimer's disease rs3865444 A/A allele and that were treated with anti-CD33 antibody 2F5 or isotype control (Ctl) antibody. : p<0.001 for 2F5 vs Isotype Ctl, correcting for donor and day of animal sacrifice; +: mean; boxplot midline: median; upper and lower boundaries of the boxes correspond to the first and third quartiles (25th and 75th percentiles). FIG. 15OO** depicts in vivo reduction in peripheral blood human (h) CD45$^+$ CD14$^+$ myeloid cells from mice treated with anti-CD33 antibody 2F5 or isotype control (Ctl) antibody. *: p<0.05 for 2F5 vs Isotype Ctl, correcting for donor and day of animal sacrifice; +: mean; boxplot midline: median; upper and lower boundaries of the boxes correspond to the first and third quartiles (25th and 75th percentiles). FIG. 15PP depicts in vivo reduction in peripheral blood human (h) CD45$^+$ CD14$^+$ myeloid cells from mice containing any of the Alzheimer's disease CD33 alleles rs3865444 A/A allele, A/C allele and C/C allele and that were treated with anti-CD33 antibody 2F5 or isotype control (Ctl) antibody. *: p<0.05 for 2F5 vs Isotype Ctl, correcting for donor and day of animal sacrifice; +: mean; boxplot midline: median; upper and lower boundaries of the boxes correspond to the first and third quartiles (25th and 75th percentiles). FIG. 15QQ depicts in vivo reduction in peripheral blood human (h) CD45$^+$ CD14$^+$ myeloid cells from mice containing the Alzheimer's disease rs3865444 C/C allele and that were treated with anti-CD33 antibody 2F5 or isotype control (Ctl) antibody. *: p<0.05 for 2F5 vs Isotype Ctl, correcting for donor and day of animal sacrifice; +: mean; boxplot midline: median; upper and lower boundaries of the boxes correspond to the first and third quartiles (25th and 75th percentiles). FIG. 15RR depicts in vivo reduction in peripheral blood human (h) CD45$^+$ CD14$^+$ myeloid cells from mice containing the Alzheimer's disease rs3865444 A/A allele and that were treated with anti-CD33 antibody 2F5 or isotype control (Ctl) antibody. "n.s.": not statistically significant; +: mean; boxplot midline: median; upper and lower boundaries of the boxes correspond to the first and third quartiles (25th and 75th percentiles).

FIG. 16A-16C depict results showing a reduction in cell surface levels of CD33 on human primary microglia treated with anti-CD33 antibodies. FIG. 16A depicts no antibody control (No mAb) and isotype control antibody (Isotype). FIG. 16B depicts anti-CD33 antibodies 1A8 (1A8.2), 2E12, and 2F5. FIG. 16C depicts anti-CD33 antibodies 6A3 and 6C7 (6C7.2). FIG. 16D depicts results showing a dose dependent reduction in cell surface levels of CD33 on human primary monocytes treated with anti-CD33 antibodies 2E12, 6A3, and 6C7. FIG. 16E depicts results showing a dose dependent reduction in cell surface levels of CD33 on human primary dendritic cells treated with anti-CD33 antibodies 2E12, 6A3, and 6C7. FIG. 16F-16H depict results showing a reduction in cell surface levels of CD33 on human primary dendritic cells treated with deglycosyatled anti-CD33 antibodies 1A8 (1A8.2), 2E12, 6A3, and 6C7 (6C7.2). FIG. 16F depicts reduction in cell surface levels of CD33 on human primary dendritic cells obtained from patient donor 258. FIG. 16G depicts reduction in cell surface levels of CD33 on human primary dendritic cells obtained from patient donor 259. FIG. 16H depicts the percent change (% Delta) in cell surface reduction (downregulation) between cells from donors 258 and 259 treated with the anti-CD33 antibodies. FIG. 16I and FIG. 16J depict FACS analysis of CD33 expression and Siglec-9 expression in human monocytes isolated from NOD-scid IL2Rgnull-3/GM/SF, NSG-SGM3, triple transgenic NSG-SGM3 (NSGS) mice expressing human IL3, GM-CSF and SCF (NSGS) mice that were treated with anti-CD33 antibody 2F5 or isotype control antibody (mIgG1). FIG. 16I depicts a 12-point titration curve showing the half-maximal concentration ($EC_{50}$) of CD33 antibodies 2F5, 6C7, gemtuzumab, and lintuzumab for reducing cell surface expression of CD33. FIG. 16J depicts a 12-point titration curve showing the half-maximal concentration ($EC_{50}$) of CD33 antibodies 2F5, 6C7, and gemtuzumab for reducing cell surface expression of CD11c.

DETAILED DESCRIPTION OF THE INVENTION

General Techniques

Figure 1:
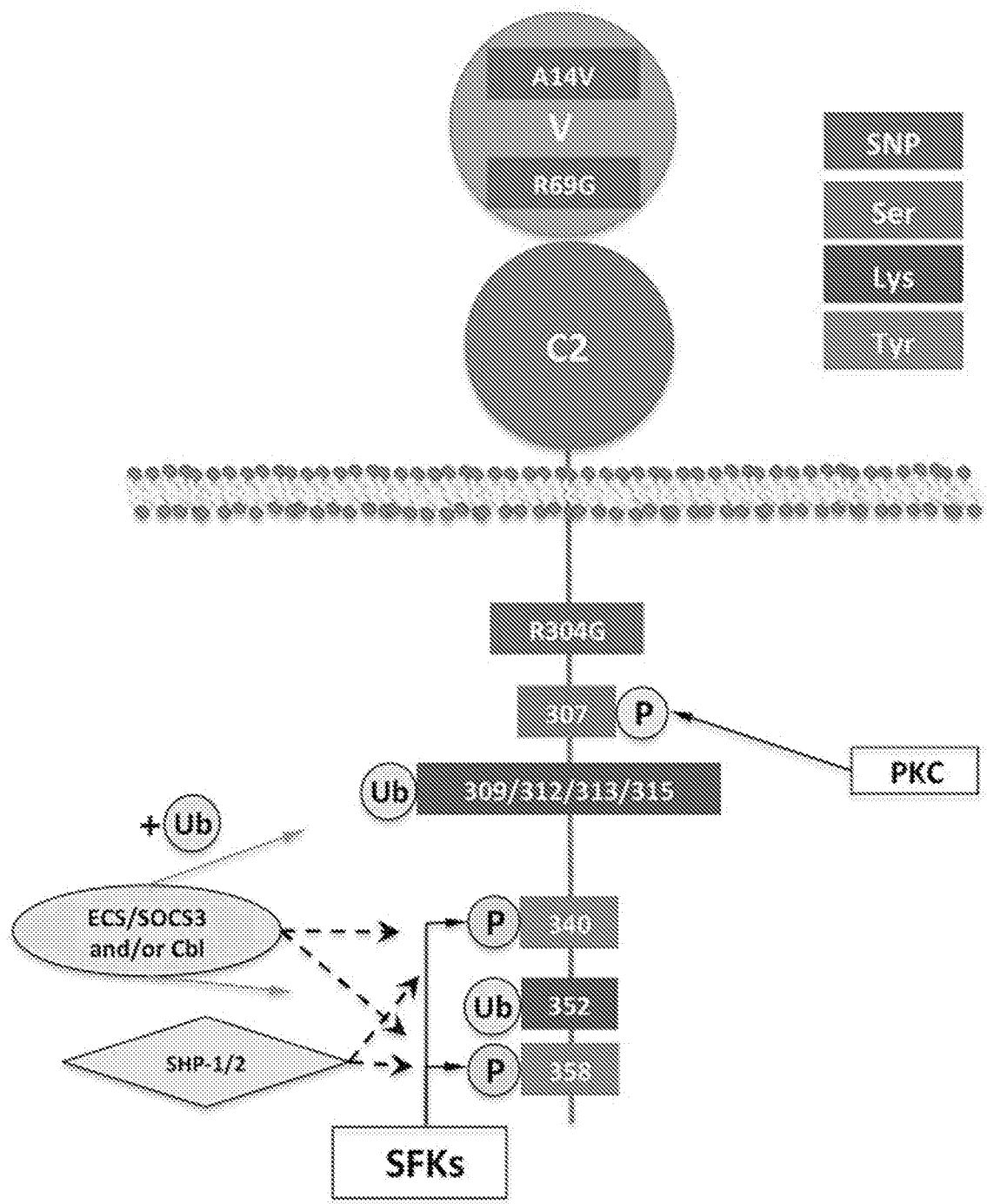
FIG. 1 shows the structure of CD33, and a scheme depicting the domain structure of CD33 as well as individual amino acids that have been implicated in phosphorylation or ubiquitination events or that have been identified as residues of relatively frequent non-synonymous single nucleotide polymorphisms (SNPs). Abbreviations: CBL: casitas B-lineage lymphoma E3 ubiquitin ligase; C2: C2-set Ig-like domain; ECS: Elongin B/C-Cullin-5 SPRY domain ubiquitin ligase; P: phospho-; PKC: protein kinase C; SFKs: Src-family kinases; SHP-1/2: Src homology region 2 domain-containing phosphatase-1 and -2; SOCS3: suppressor of cytokine signaling 3; Ub: ubiquitin; V: V-set Ig-like domain. (Cowan et al., (2013) Frontiers in Bioscience 18:1311-1334).

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988) *Antibodies, A Laboratory Manual*, and *Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short*

*Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty, ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 1993).

Definitions

As used herein, the term "preventing" includes providing prophylaxis with respect to occurrence or recurrence of a particular disease, disorder, or condition in an individual. An individual may be predisposed to, susceptible to a particular disease, disorder, or condition, or at risk of developing such a disease, disorder, or condition, but has not yet been diagnosed with the disease, disorder, or condition.

As used herein, an individual "at risk" of developing a particular disease, disorder, or condition may or may not have detectable disease or symptoms of disease, and may or may not have displayed detectable disease or symptoms of disease prior to the treatment methods described herein. "At risk" denotes that an individual has one or more risk factors, which are measurable parameters that correlate with development of a particular disease, disorder, or condition, as known in the art. An individual having one or more of these risk factors has a higher probability of developing a particular disease, disorder, or condition than an individual without one or more of these risk factors.

As used herein, the term "treatment" refers to clinical intervention designed to alter the natural course of the individual being treated during the course of clinical pathology. Desirable effects of treatment include decreasing the rate of progression, ameliorating or palliating the pathological state, and remission or improved prognosis of a particular disease, disorder, or condition. An individual is successfully "treated", for example, if one or more symptoms associated with a particular disease, disorder, or condition are mitigated or eliminated.

An "effective amount" refers to at least an amount effective, at dosages and for periods of time necessary, to achieve the desired therapeutic or prophylactic result. An effective amount can be provided in one or more administrations. An effective amount herein may vary according to factors such as the disease state, age, sex, and weight of the individual, and the ability of the treatment to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. An effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

A "therapeutically effective amount" is at least the minimum concentration required to effect a measurable improvement of a particular disease, disorder, or condition. A therapeutically effective amount herein may vary according to factors such as the disease state, age, sex, and weight of the patient, and the ability of the CD33 protein antagonist to elicit a desired response in the individual. A therapeutically effective amount is also one in which any toxic or detrimental effects of the CD33 protein antagonist are outweighed by the therapeutically beneficial effects.

As used herein, administration "in conjunction" with another compound or composition includes simultaneous administration and/or administration at different times. Administration in conjunction also encompasses administration as a co-formulation or administration as separate compositions, including at different dosing frequencies or intervals, and using the same route of administration or different routes of administration.

An "individual" for purposes of treatment, prevention, or reduction of risk refers to any animal classified as a mammal, including humans, domestic and farm animals, and zoo, sport, or pet animals, such as dogs, horses, rabbits, cattle, pigs, hamsters, gerbils, mice, ferrets, rats, cats, and the like. Preferably, the individual is human.

The term "immunoglobulin" (Ig) is used interchangeably with "antibody" herein. The term "antibody" herein is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity.

The basic 4-chain antibody unit is a heterotetrameric glycoprotein composed of two identical light (L) chains and two identical heavy (H) chains. The pairing of a $V_H$ and $V_L$ together forms a single antigen-binding site. For the structure and properties of the different classes of antibodies, see, e.g., *Basic and Clinical Immunology*, 8th Ed., Daniel P. Stites, Abba I. Ten and Tristram G. Parslow (eds.), Appleton & Lange, Norwalk, Conn., 1994, page 71 and Chapter 6.

The L chain from any vertebrate species can be assigned to one of two clearly distinct types, called kappa ("κ") and lambda ("λ"), based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated alpha ("α"), delta ("β"), epsilon ("ε"), gamma ("γ") and mu ("μ"), respectively. The γ and α classes are further divided into subclasses (isotypes) on the basis of relatively minor differences in the CH sequence and function, e.g., humans express the following subclasses: IgG1, IgG2, IgG3, IgG4, IgA1, and IgA2. The subunit structures and three dimensional configurations of different classes of immunoglobulins are well known and described generally in, for example, Abbas et al., Cellular and Molecular Immunology, $4^{th}$ ed. (W.B. Saunders Co., 2000).

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

An "isolated" antibody, such as an anti-CD33 antibody of the present disclosure, is one that has been identified, separated and/or recovered from a component of its production environment (e.g., naturally or recombinantly). Preferably, the isolated polypeptide is free of association with all other contaminant components from its production environment. Contaminant components from its production environment, such as those resulting from recombinant transfected cells, are materials that would typically interfere with research, diagnostic or therapeutic uses for the antibody, and may include enzymes, hormones, and other proteinaceous or non-proteinaceous solutes. In preferred embodiments, the polypeptide will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant T cells since at least one component of the antibody's natural environment will not be present. Ordinarily, however, an isolated polypeptide or antibody will be prepared by at least one purification step.

The "variable region" or "variable domain" of an antibody, such as an anti-CD33 antibody of the present disclosure, refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites.

The term "variable" refers to the fact that certain segments of the variable domains differ extensively in sequence among antibodies, such as anti-CD33 antibodies of the present disclosure. The V domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen binding site of antibodies (see Kabat et al., *Sequences of Immunological Interest*, Fifth Edition, National Institute of Health, Bethesda, Md. (1991)). The constant domains are not involved directly in the binding of antibody to an antigen, but exhibit various effector functions, such as participation of the antibody in antibody-dependent-cellular toxicity.

The term "monoclonal antibody" as used herein refers to an antibody, such as an anti-CD33 antibody of the present disclosure, obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against one or more antigenic sites. In some embodiments, a monoclonal antibody of the present disclosure can be a bispecific antibody. In contrast to polyclonal antibody preparations which typically include different antibodies directed against different determinants (epitopes), each monoclonal antibody is directed against a single determinant on the one or more antigenic sites. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by a variety of techniques, including, for example, phage-display technologies (see, e.g., Clackson et al., *Nature*, 352:624-628 (1991); Marks et al., *J. Mol. Biol.* 222:581-597 (1992); Sidhu et al., *J. Mol. Biol.* 338(2): 299-310 (2004); Lee et al., *J. Mol. Biol.* 340(5):1073-1093 (2004); Fellouse, *Proc. Nat'l Acad. Sci. USA* 101(34):12467-472 (2004); and Lee et al., *J. Immunol. Methods* 284(1-2):119-132 (2004), the hybridoma method (e.g., Kohler and Milstein, *Nature*, 256:495-97 (1975); Hongo et al., *Hybridoma*, 14 (3):253-260 (1995), Harlow et al., *Antibodies: A Laboratory Manual*, (Cold Spring Harbor Laboratory Press, 2d ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Nat'l Acad. Sci. USA* 90:2551 (1993); Jakobovits et al., *Nature* 362:255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10:779-783 (1992); Lonberg et al., *Nature* 368:856-859 (1994); Morrison, *Nature* 368:812-813 (1994); Fishwild et al., *Nature Biotechnol.* 14:845-851 (1996); Neuberger, *Nature Biotechnol.* 14:826 (1996); and Lonberg and Huszar, *Intern. Rev. Immunol.* 13:65-93 (1995).

The terms "full-length antibody," "intact antibody" or "whole antibody" are used interchangeably to refer to an antibody, such as an anti-CD33 antibody of the present disclosure, in its substantially intact form, as opposed to an antibody fragment. Specifically whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, preferably the antigen binding and/or the variable region of the intact antibody. Examples of antibody fragments include Fab, Fab', F(ab')$_2$ and Fv fragments; diabodies; linear antibodies (see U.S. Pat. No. 5,641,870, Example 2; Zapata et al., *Protein Eng.* 8(10):1057-1062 (1995)); single-chain antibody molecules and multispecific antibodies formed from antibody fragments.

Papain digestion of antibodies, such as anti-CD33 antibodies of the present disclosure, produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the $V_H$ and $V_L$ domains which enables the sFv to form the desired structure for antigen binding. For a review of the sFv, see Pluckthun in *The Pharmacology of Monoclonal Antibodies*, vol. 113, Rosenburg and Moore eds., Springer-Verlag, New York, pp. 269-315 (1994).

"Functional fragments" of antibodies, such as anti-CD33 antibodies of the present disclosure, comprise a portion of an intact antibody, generally including the antigen binding or variable region of the intact antibody or the F region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al., *Proc. Nat'l Acad. Sci. USA* 90:6444-48 (1993).

As used herein, a "chimeric antibody" refers to an antibody (immunoglobulin), such as an anti-CD33 antibody of the present disclosure, in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Nat'l Acad. Sci. USA*, 81:6851-55 (1984)). Chimeric antibodies of interest herein include PRIMATIZED® antibodies wherein the antigen-binding region of the antibody is derived from an antibody produced by, e.g., immunizing macaque monkeys with an antigen of interest. As used herein, "humanized antibody" is used a subset of "chimeric antibodies."

"Humanized" forms of non-human (e.g., murine) antibodies, such as anti-CD33 antibodies of the present disclosure, are chimeric antibodies that contain minimal sequence derived from non-human immunoglobulin. In one embodiment, a humanized antibody is a human immunoglobulin (recipient antibody) in which residues from an HVR of the recipient are replaced by residues from an HVR of a non-human species (donor antibody) such as mouse, rat, rabbit or non-human primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, and the like. The number of these amino acid substitutions in the FR is typically no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, for example, Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is one that possesses an amino-acid sequence corresponding to that of an antibody, such as an anti-CD33 antibody of the present disclosure, produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.,* 227: 381 (1991); Marks et al., *J. Mol. Biol.,* 222:581 (1991). Also available for the preparation of human monoclonal antibodies are methods described in Cole et al., *Monoclonal Antibodies and Cancer Therapy,* Alan R. Liss, p. 77 (1985); Boerner et al., *J. Immunol.,* 147(1):86-95 (1991). See also van Dijk and van de Winkel, *Curr. Opin. Pharmacol.* 5:368-74 (2001). Human antibodies can be prepared by administering the antigen to a transgenic animal that has been modified to produce such antibodies in response to antigenic challenge, but whose endogenous loci have been disabled, e g, immunized xenomice (see, e.g., U.S. Pat. Nos. 6,075,181 and 6,150,584 regarding XENOMOUSE™ technology). See also, for example, Li et al., *Proc. Nat'l Acad. Sci. USA,* 103:3557-3562 (2006) regarding human antibodies generated via a human B-cell hybridoma technology.

The term "hypervariable region," "HVR," or "HV," when used herein refers to the regions of an antibody-variable domain, such as that of an anti-CD33 antibody of the present disclosure, that are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu in *Methods in Molecular Biology* 248:1-25 (Lo, ed., Human Press, Totowa, N.J., 2003)). Indeed, naturally occurring camelid antibodies consisting of a heavy chain only are functional and stable in the absence of light chain. See, e.g., Hamers-Casterman et al., *Nature* 363:446-448 (1993) and Sheriff et al., *Nature Struct. Biol.* 3:733-736 (1996).

A number of HVR delineations are in use and are encompassed herein. The HVRs that are EU or Kabat complementarity-determining regions (CDRs) are based on sequence variability and are the most commonly used (Kabat et al., supra). Chothia refers instead to the location of the structural loops (Chothia and Lesk *J. Mol. Biol.* 196:901-917 (1987)). The AbM HVRs represent a compromise between the EU or Kabat CDRs and Chothia structural loops, and are used by Oxford Molecular's AbM antibody-modeling software. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat numbering) |
| H1 | H31-H35 | H26-H35 | H26-H32 | H30-H35 (Chothia numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2), and 89-97 or 89-96 (L3) in the VL, and 26-35 (H1), 50-65 or 49-65 (a preferred embodiment) (H2), and 93-102, 94-102, or 95-102 (H3) in the VH. The variable-domain residues are numbered according to EU or Kabat et al., supra, for each of these extended-HVR definitions.

"Framework" or "FR" residues are those variable-domain residues other than the HVR residues as herein defined.

The phrase "variable-domain residue-numbering as in EU or Kabat" or "amino-acid-position numbering as in EU or Kabat," and variations thereof, refers to the numbering system used for heavy-chain variable domains or light-chain variable domains of the compilation of antibodies in EU or Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g., residues 82a, 82b, and 82c, etc. according to Kabat) after heavy-chain FR residue 82. The EU or Kabat numbering of residues may be determined for a given antibody by alignment at regions of homology of the sequence of the antibody with a "standard" Kabat numbered sequence.

The EU or Kabat numbering system is generally used when referring to a residue in the variable domain (approximately residues 1-107 of the light chain and residues 1-113 of the heavy chain) (e.g., Kabat et al., Sequences of Immunological Interest. 5th Ed. Public Health Service, National Institutes of Health, Bethesda, Md. (1991)). The "EU or Kabat numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU or Kabat numbering system (e.g., see United States Patent Publication No. 2010-280227).

An "acceptor human framework" as used herein is a framework comprising the amino acid sequence of a VL or VH framework derived from a human immunoglobulin framework or a human consensus framework. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less. Where pre-existing amino acid changes are present in a VH, preferable those changes occur at only three, two, or one of positions 71H, 73H and 78H; for instance, the amino acid residues at those positions may by 71A, 73T and/or 78A. In one embodiment, the VL acceptor human framework is identical in sequence to the VL human immunoglobulin framework sequence or human consensus framework sequence.

A "human consensus framework" is a framework that represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest,* 5th Ed. Public Health Service, National Institutes of Health, Bethesda, Md. (1991).

Examples include for the VL, the subgroup may be subgroup kappa I, kappa II, kappa III or kappa IV as in Kabat et al., supra. Additionally, for the VH, the subgroup may be subgroup I, subgroup II, or subgroup III as in Kabat et al., supra.

An "amino-acid modification" at a specified position, e.g., of an anti-CD33 antibody of the present disclosure, refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. The preferred amino acid modification herein is a substitution.

An "affinity-matured" antibody, such as an anti-CD33 antibody of the present disclosure, is one with one or more alterations in one or more HVRs thereof that result in an improvement in the affinity of the antibody for antigen, compared to a parent antibody that does not possess those alteration(s). In one embodiment, an affinity-matured antibody has nanomolar or even picomolar affinities for the target antigen. Affinity-matured antibodies are produced by procedures known in the art. For example, Marks et al., *Bio/Technology* 10:779-783 (1992) describes affinity maturation by VH- and VL-domain shuffling. Random mutagenesis of HVR and/or framework residues is described by, for example: Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

As use herein, the term "specifically recognizes" or "specifically binds" refers to measurable and reproducible interactions such as attraction or binding between a target and an antibody, such as an anti-CD33 antibody of the present disclosure, that is determinative of the presence of the target in the presence of a heterogeneous population of molecules including biological molecules. For example, an antibody, such as an anti-CD33 antibody of the present disclosure, that specifically or preferentially binds to a target or an epitope is an antibody that binds this target or epitope with greater affinity, avidity, more readily, and/or with greater duration than it binds to other targets or other epitopes of the target. It is also understood by reading this definition that, for example, an antibody (or a moiety) that specifically or preferentially binds to a first target may or may not specifically or preferentially bind to a second target. As such, "specific binding" or "preferential binding" does not necessarily require (although it can include) exclusive binding. An antibody that specifically binds to a target may have an association constant of at least about $10^3$ $M^{-1}$ or $10^4$ $M^{-1}$, sometimes about $10^5$ $M^{-1}$ or $10^6$ $M^{-1}$, in other instances about $10^6$ $M^{-1}$ or $10^7$ $M^{-1}$, about $10^8$ $M^{-1}$ to $10^9$ $M^{-1}$, or about $10^{10}$ $M^{-1}$ to $10^{11}$ $M^{-1}$ or higher. A variety of immunoassay formats can be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity.

As used herein, an "interaction" between a CD33 protein and a second protein encompasses, without limitation, protein-protein interaction, a physical interaction, a chemical interaction, binding, covalent binding, and ionic binding. As used herein, an antibody "inhibits interaction" between two proteins when the antibody disrupts, reduces, or completely eliminates an interaction between the two proteins. An antibody of the present disclosure, or fragment thereof, "inhibits interaction" between two proteins when the antibody or fragment thereof binds to one of the two proteins.

An "agonist" antibody or an "activating" antibody is an antibody, such as an agonist anti-CD33 antibody of the present disclosure, that induces (e.g., increases) one or more activities or functions of the antigen after the antibody binds the antigen.

A "blocking" antibody, an "antagonist" antibody, or an "inhibitory" antibody is an antibody, such as an anti-CD33 antibody of the present disclosure, that inhibits or reduces (e.g., decreases) antigen binding to one or more ligand after the antibody binds the antigen, and/or that inhibits or reduces (e.g., decreases) one or more activities or functions of the antigen after the antibody binds the antigen. In some embodiments, blocking antibodies, antagonist antibodies, or inhibitory antibodies substantially or completely inhibit antigen binding to one or more ligand and/or one or more activities or functions of the antigen.

Antibody "effector functions" refer to those biological activities attributable to the Fc region (a native sequence Fc region or amino acid sequence variant Fc region) of an antibody, and vary with the antibody isotype.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU or Kabat numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the present disclosure include human IgG1, IgG2, IgG3 and IgG4.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif ("ITAM") in its cytoplasmic domain. Inhibiting receptor FcγRIIB contains an immunoreceptor tyrosine-based inhibition motif ("ITIM") in its cytoplasmic domain (see, e.g., M. Daëron, *Annu. Rev. Immunol.* 15:203-234 (1997)). FcRs are reviewed in Ravetch and Kinet, *Annu. Rev. Immunol.* 9:457-92 (1991); Capel et al., *Immunomethods* 4:25-34 (1994); and de Haas et al., *J. Lab. Clin. Med.* 126: 330-41 (1995). Other FcRs, including those to be identified in the future, are encompassed by the term "FcR" herein. FcRs can also increase the serum half-life of antibodies.

Binding to FcRn in vivo and serum half-life of human FcRn high-affinity binding polypeptides can be assayed, e.g., in transgenic mice or transfected human cell lines expressing human FcRn, or in primates to which the polypeptides having a variant Fc region are administered. WO 2004/42072 (Presta) describes antibody variants with improved or diminished binding to FcRs. See also, e.g., Shields et al., *J. Biol. Chem.* 9(2):6591-6604 (2001).

As used herein, "percent (%) amino acid sequence identity" and "homology" with respect to a peptide, polypeptide or antibody sequence refers to the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms known in the art needed to achieve maximal alignment over the full length of the sequences being compared.

An "isolated" nucleic acid molecule encoding an antibody, such as an anti-CD33 antibody of the present disclosure, is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acid encoding the polypeptides and antibodies herein existing naturally in cells.

The term "vector," as used herein, is intended to refer to a nucleic acid molecule capable of transporting another nucleic acid to which it has been linked. One type of vector is a "plasmid," which refers to a circular double stranded DNA into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors," or simply, "expression vectors." In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may comprise modification(s) made after synthesis, such as conjugation to a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs, and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR2 ("amidate"), P(O)R, P(O)OR', CO, or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of the present disclosure.

"Carriers" as used herein include pharmaceutically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

As used herein, the term "apoptosis" refers to gene-directed process of intracellular cell destruction. Apoptosis is distinct from necrosis; it includes cytoskeletal disruption, cytoplasmic shrinkage and condensation, expression of phosphatidylserine on the outer surface of the cell membrane and blebbing, resulting in the formation of cell membrane bound vesicles or apoptotic bodies. The process is also referred to as "programmed cell death." During apoptosis, characteristic phenomena such as curved cell surfaces, condensation of nuclear chromatin, fragmentation of chromosomal DNA, and loss of mitochondrial function are observed. Various known technologies may be used to detect apoptosis, such as staining cells with Annexin V, propidium iodide, DNA fragmentation assay and YO-PRO-1 (Invitrogen). In some embodiments, staining with Annexin V and propidium iodide may be used, and the combined percentages of the Annexin V+/PI+, Annexin V+/PI− and Annexin V−/PI+ populations are considered as dead cells.

As used herein, the term "agent that decreases cellular levels of CD33, inhibits interaction between CD33 and one or more CD33 ligands, or both" refers to a molecule that reduces (including significantly), decreases, blocks, inhibits, or interferes with a CD33 (mammalian, such as a human CD33) biological activity in vitro, in situ, and/or in vivo. The term "agent" implies no specific mechanism of biological action whatsoever, and expressly includes and encompasses all possible pharmacological, physiological, and biochemical interactions with a CD33 whether direct or indirect, and whether interacting with a CD33, one or more of its ligands, or through another mechanism, and its consequences which can be achieved by a variety of different, and chemically divergent, compositions. Exemplary agents include, without limitation, an anti-CD33 antibody that specifically binds to a CD33, a soluble CD33 receptor protein, a soluble CD33-Fc fusion protein (e.g., CD33 immunoadhesin), a soluble Siglec receptor that binds to a CD33 ligand, a Siglec-Fc fusion protein (e.g., Siglec immunoadhesin) that binds to a CD33 ligand, an anti-sense molecule directed to a nucleic acid encoding a CD33, a short interfering RNA ("siRNA") molecule directed to a nucleic acid encoding a CD33, a CD33 inhibitory compound, an RNA or DNA aptamer that binds to a CD33, and a CD33 structural analog. In some embodiments, a CD33 inhibitor (e.g., an antibody) binds (physically interacts with) an agent that decreases cellular levels of CD33, inhibits interaction between CD33 and one or more CD33 ligands, or both, binds to a CD33 ligand, and/or inhibits (reduces) CD33 synthesis or production. In other embodiments, an agent of the present disclosure inhibitor binds a CD33 and prevents its binding to one or more of its ligands. In still other embodiments, an agent of the present disclosure reduces or eliminates expression (i.e., transcription or translation) of a CD33. Examples of types of agent that decreases cellular levels of CD33, inhibits interaction between CD33 and one or more CD33 ligands, or both are provided herein.

As used herein, the term "agent that binds or interacts with CD33" refers to a molecule that either directly or indirectly interacts with a CD33 protein. The term "agent" implies no specific mechanism of biological action whatsoever, and expressly includes and encompasses all possible pharmacological, physiological, and biochemical interactions with a CD33 whether direct or indirect, and whether interacting with a CD33 or through another mechanism, and its consequences which can be achieved by a variety of different, and chemically divergent, compositions. Exemplary agents include, without limitation, an anti-CD33 antibody that specifically binds to a CD33.

As used herein, the term "RNA interference" or "RNAi" refers generally to a process in which a double-stranded RNA molecule or a short hairpin RNA molecule reducing or inhibiting the expression of a nucleic acid sequence with which the double-stranded or short hairpin RNA molecule shares substantial or total homology. The term "short interfering RNA" or "siRNA" or "RNAi agent" refers to an RNA sequence that elicits RNA interference. See Kreutzer et al., WO 00/44895; Zernicka-Goetz et al., WO 01/36646; Fire, WO 99/32619; Mello and Fire, WO 01/29058. As used herein, siRNA molecules include RNA molecules encompassing chemically modified nucleotides and non-nucleotides. The term "ddRNAi agent" refers to a DNA-directed RNAi agent that is transcribed from an exogenous vector. The terms "short hairpin RNA" or "shRNA" refer to an RNA structure having a duplex region and a loop region. In certain embodiments, ddRNAi agents are expressed initially as shRNAs.

As used herein, the term "aptamer" refers to a heterologous oligonucleotide capable of binding tightly and specifically to a desired molecular target, such as, for example, common metabolic cofactors (e.g., Coenzyme A, S-adenosyl methionine, and the like), proteins (e.g., complement protein C5, antibodies, and the like), or conserved structural elements in nucleic acid molecules (e.g., structures important for binding of transcription factors and the like). Aptamers typically comprise DNA or RNA nucleotide sequences ranging from about 10 to about 100 nucleotides in length, from about 10 to about 75 nucleotides in length, from about 10 to about 50 nucleotides in length, from about 10 to about 35 nucleotides in length, and from about 10 to about 25 nucleotides in length. Synthetic DNA or RNA oligonucleotides can be made using standard solid phase phosphoramidite methods and equipment, such as by using a 3900 High Throughput DNA Synthesizer™, available from Applied Biosystems (Foster City, Calif.). Aptamers frequently incorporate derivatives or analogs of the commonly occurring nucleotides found in DNA and RNA (e.g., A, G, C, and T/U), including backbone or linkage modifications (e.g., peptide nucleic acid (PNA) or phosphothioate linkages) to increase resistance to nucleases, binding avidity, or to otherwise alter their pharmacokinetic properties. Exemplary modifications are set forth in U.S. Pat. Nos. 6,455,308; 4,469,863; 5,536,821; 5,541,306; 5,637,683; 5,637,684; 5,700,922; 5,717,083; 5,719,262; 5,739,308; 5,773,601; 5,886,165; 5,929,226; 5,977,296; 6,140,482; and in WIPO publications WO 00/56746 and WO 01/14398. Methods for synthesizing oligonucleotides comprising such analogs or derivatives are disclosed, for example, in the patent publications cited above, and in U.S. Pat. Nos. 6,455,308; 5,614,622; 5,739,314; 5,955,599; 5,962,674; 6,117,992; and in WO 00/75372.

The term "about" as used herein refers to the usual error range for the respective value readily known to the skilled person in this technical field. Reference to "about" a value or parameter herein includes (and describes) embodiments that are directed to that value or parameter per se.

As used herein and in the appended claims, the singular forms "a," "an," and "the" include plural reference unless the context clearly indicates otherwise. For example, reference to an "antibody" is a reference to from one to many antibodies, such as molar amounts, and includes equivalents thereof known to those skilled in the art, and so forth.

It is understood that aspect and embodiments of the present disclosure described herein include "comprising," "consisting," and "consisting essentially of" aspects and embodiments.

Overview

The present disclosure relates to agents that decrease cellular levels of CD33 and/or inhibit interaction between CD33 and one or more CD33 ligands (e.g., anti-CD33 antibodies), methods of making and using such agents (e.g., anti-CD33 antibodies); pharmaceutical compositions containing such agents (e.g., anti-CD33 antibodies); nucleic acids encoding such agents (e.g., anti-CD33 antibodies); and host cells containing nucleic acids encoding such agents (e.g., anti-CD33 antibodies).

In some embodiments, the anti-CD33 antibodies of the present disclosure have one or more antagonistic activities that are due, at least in part, to the ability of the antibodies inhibit the interaction between CD33 and one or more natural glycan ligands. In some embodiments, the anti-CD33 antibodies of the present disclosure may have one or more antagonistic activities that are due, at least in part, to the ability of the antibodies to reduce cellular expression (e.g., cell surface expression) of CD33 by inducing degradation, down regulation, cleavage, receptor desensitization, and/or lysosomal targeting of CD33. In some embodiments, the anti-CD33 antibodies exhibits one or more of the following properties: a. have a dissociation constant ($K_D$) for human CD33 that is lower than that of anti-CD33 antibody gemtuzumab; b. bind to human cells, such as human dendritic cells with a half-maximal effective concentration ($EC_{50}$) that is lower than that of anti-CD33 antibody gemtuzumab or lintuzumab; c. decrease cellular levels of CD33 with a half-maximal effective concentration ($EC_{50}$) that is lower than that of anti-CD33 antibody gemtuzumab or lintuzumab; d. have a dissociation constant ($K_D$) for human CD33 that may range from 300 pM to 10 pM, for example when the $K_D$ is determined at a temperature of approximately 25° C.; e. bind to human cells, such as human dendritic cells with a half-maximal effective concentration ($EC_{50}$) that may range from 200 pM to 10 pM, for example when the $EC_{50}$ is determined at a temperature of approximately 4° C.; f. decrease cellular levels of CD33 with a half-maximal effective concentration ($EC_{50}$) that may range from 65 pM to 20 pM, or g. decrease cellular levels of CD33 in vivo with a half-maximal effective concentration ($EC_{50}$) that may range from 8.0 mg/kg to 2.0 mg/kg. As disclosed herein half-maximal effective concentration ($EC_{50}$) refers to the concentration at which an anti-CD33 antibody of the present disclosure reduces cellular levels of CD33 on a cell or in a cell, or the concentration at which the antibody achieves half-maximal binding to CD33 on a cell.

Advantageously, anti-CD33 antibodies of the present disclosure have an improved $EC_{50}$ for binding CD33 as compared to commercial anti-CD33 antibodies, such as gemtuzumab and lintuzumab (e.g., approximately 3-fold better), and reduce cell surface expression more potently (e.g., lower $EC_{50}$) than commercial anti-CD33 antibodies, such as gemtuzumab and lintuzumab (e.g., approximately 5-fold better) (Examples 1 and 3). The amino acid sequence of the heavy chain variable region of commercially available anti-CD33 antibody gemtuzumab is set forth in SEQ ID NO:248, and the amino acid sequence of the light chain variable region of anti-CD33 antibody gemtuzumab is set forth in SEQ ID NO:249. The amino acid sequence of the heavy chain variable region of commercially available anti-CD33 antibody lintuzumab is set forth in SEQ ID NO:250, and the amino acid sequence of the light chain variable region of anti-CD33 antibody lintuzumab is set forth in SEQ ID NO:251.

In some embodiments, an antibody-induced CD33 activity can be determined or tested in vitro by any of the techniques disclosed herein (see, e.g., Examples 1-5), including, without limitation, testing plate-binding of full-length anti-CD33 antibodies to increase the density of antibodies exposed to CD33, cross-linking anti-CD33 antibodies with a secondary antibody, cross-linking anti-CD33 antibodies with cells that express one or more Fcg receptors (e.g., FcgRIIB), using CD33 antibodies in solution, and using Fab fragments of CD33 antibodies.

Certain aspects of the present disclosure are based, at least in part, on the identification of agents, such as anti-CD33 antibodies, that exhibit the ability to compete with one or more CD33 ligands for binding to CD33 and/or the ability to decrease cell surface levels of CD33 on cells, resulting in the reduction, neutralization, prevention, or curbing of one or more CD33 activities, including, without limitation, counteracting one or more phosphorylation of Tyr-340 and Tyr-358 by a Src family tyrosine kinase, such as LCK and FYN; recruitment of and binding to the tyrosine-specific protein phosphatases SHP1 and SHP2; recruitment of and binding to PLC-gamma1, which acts as a guanine nucleotide exchange factor for Dynamini-1; recruitment of and binding to SH2-domain containing protein (e.g., Crkl); recruitment of and binding to the spleen tyrosine kinase Syk; recruitment of and binding to SH3-SH2-SH3 growth factor receptor-bound protein 2 (Grb2); recruitment of and binding to multiple SH2-containing proteins; phosphorylation of Ser-307 and Ser-342 by protein kinase C; modulated expression of one or more anti-inflammatory cytokines, such as IL-4, IL-10, IL-13, IL-35, IL-16, TGF-beta, IL-1Ra, G-CSF, and soluble receptors for TNF, IFN-beta1a, IFN-beta1b, or IL-6 in macrophages, dendritic cells, bone marrow-derived dendritic cells, monocytes, osteoclasts, T cells, T helper cells, cytotoxic T cells, granulocytes, neutrophils, and/or microglial cells; decreasing intracellular calcium mobilization; modulated expression of one or more pro-inflammatory cytokines, such as IFN-a4, IFN-b, IL-1β, TNF-α, IL-6, IL-8, CRP, IL-20 family members, LIF, IFN-gamma, OSM, CNTF, GM-CSF, IL-11, IL-12, IL-17, IL-18, IL-23, CXCL10, IL-33, CRP, IL-33, MCP-1, and MIP-1-beta in macrophages, dendritic cells, bone marrow-derived dendritic cells, monocytes, osteoclasts, T cells, T helper cells, cytotoxic T cells, granulocytes, neutrophils, and/or microglial cells; modulated expression of one or more proteins selected from C1qa, C1qB, C1qC, C1s, C1R, C4, C2, C3, ITGB2, HMOX1, LAT2, CASP1, CSTA, VSIG4, MS4A4A, C3AR1, GPX1, TyroBP, ALOX5AP, ITGAM, SLC7A7, CD4, ITGAX, PYCARD, CD14, CD16, HLA-DR, and CCR2; inhibition of extracellular signal-regulated kinase (ERK) phosphorylation; decreasing tyrosine phosphorylation on multiple cellular proteins; modulated expression of C-C chemokine receptor 7 (CCR7); inhibition of microglial cell chemotaxis toward CCL19 and CCL21 expressing cells; activation of phosphoinositide 3-kinase; reducing cell growth of monocytes, macrophages, T cells, dendritic cells and/or microglia; reducing T cell proliferation induced by dendritic cells, bone marrow-derived dendritic cells, monocytes, microglia, M1 microglia, activated M1 microglia, M2 microglia, macrophages, M1 macrophages, activated M1 macrophages, and/or M2 macrophages; inhibition of osteoclast production, decreased rate of osteoclastogenesis, or both; decreasing survival of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; decreasing proliferation of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; inhibiting migration of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; decreasing one or more functions of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; inhibiting maturation of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; increasing cell death and apoptosis of monocytes, macrophages, T cells, dendritic cells, neutrophils, and/or microglia; reducing phagocytic activity of monocytes, macrophages, T cells, dendritic cells, neutrophils, and/or microglia; reducing proliferation of monocytes, macrophages, T cells, dendritic cells, neutrophils, and/or microglia; reducing the overall functionality of monocytes, macrophages, T cells, dendritic cells, neutrophils, and/or microglia, phosphorylation of an ITAM containing receptor; phosphorylation of a signaling molecules that mediates ITAM signaling; reducing the activation of pattern recognition receptors; reducing the activation of Toll-like receptors; reducing the activation of damage-associated of clearance of cellular and protein debris; interaction between CD33 and one or more of its ligands; interaction between CD33 and a co-receptor such as CD64; reducing one or more types of clearance selected from apoptotic neuron clearance, nerve tissue debris clearance, dysfunctional synapse clearance, non-nerve tissue debris clearance, bacteria or other foreign body clearance, disease-causing protein clearance, and tumor cell clearance; inhibition of phagocytosis of one or more of apoptotic neurons, nerve tissue debris, dysfunctional synapses, non-nerve tissue debris, bacteria, other foreign bodies, disease-causing proteins, disease-causing peptides, disease-causing nucleic acid, disease-causing lipids, or tumor cells; inhibition of clearance of a disease-causing nucleic acid, such as the disease-causing nucleic acid is antisense GGCCCC (G2C4) repeat-expansion RNA; activation of clearance of, a disease-causing protein selected from amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides; inhibition of beneficial immune response to different types of cancer selected from bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, acute myeloid leukemia, pancreatic cancer, prostate cancer, ovarian cancer, fibrosarcoma, and thyroid cancer; inhibition of beneficial immune response to different types of neurological disorders selected from dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, essential tremor, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, Sarcoidosis, diseases of aging, seizures, spinal cord injury, -traumatic brain injury, age related macular degeneration, glaucoma, retinitis pigmentosa, retinal degeneration, and multiple sclerosis; inhibition of beneficial immune response-to different types of inflammatory and infectious disorders selected from lupus, acute and chronic colitis, wound healing, Crohn's disease, inflammatory bowel disease, ulcerative colitis, obesity, malaria, respiratory tract infection, sepsis, eye infection, systemic infection, lupus, arthritis, low bone density, osteoporosis, osteogenesis, osteopetrotic disease, and Paget's disease of bone; binding to CD33 ligand on tumor cells; binding to CD33 ligand on dendritic cells, bone marrow-derived dendritic cells, monocytes, microglia, T cells, neutrophils, and/or macrophages; inhibition of tumor cell killing by one or more of microglia, macrophages, dendritic cells, bone marrow-derived dendritic cells, neutrophils, T cells, T helper cells, or cytotoxic T cells; inhibition of anti-tumor cell proliferation activity of one or more of microglia, macrophages, dendritic cells, bone marrow-derived dendritic cells, neutrophils, T cells, T helper cells, or cytotoxic T cells; inhibition of anti-tumor cell metastasis activity of one or more of microglia, macrophages, dendritic cells, bone marrow-derived dendritic cells, neutrophils, T cells, T helper cells, or cytotoxic T cells; promotion of immunosuppressor dendritic cells, immunosuppressor macrophages, myeloid-derived suppressor cells, tumor-associated macrophages, or regulatory T cells; inhibition of one or more ITAM motif containing receptors, such as TREM1, TREM2, FcgR, DAP10, and DAP12; inhibition of one or more receptors containing the motif D/Ex0-2YxxL/IX6-8YxxL/I (SEQ ID NO:247); inhibition of signaling by one or more pattern recognition receptors (PRRs), such as receptors that identify pathogen-associated molecular patterns (PAMPs), and receptors that identify damage-associated molecular patterns (DAMPs); inhibition of signaling by one or more Toll-like receptors; inhibition of the JAK-STAT signaling pathway; inhibition of nuclear factor kappa-light-chain-enhancer of activated B cells (NFκB); modulated expression of one or more inflammatory receptors, such as CD86, expressed on one or more of microglia, macrophages, dendritic cells, bone marrow-derived dendritic cells, neutrophils, T cells, T helper cells, or cytotoxic T cells; increasing expression of one or more CD33-dependent genes; normalization of disrupted CD33-dependent gene expression; and decreasing expression of one or more ITAM-dependent genes, such as NFAT transcription factors; promoting differentiation of one or more of immunosuppressor dendritic cells, immunosuppressor macrophages, myeloid derived suppressor cells, tumor-associated macrophages, immunosuppressor neutrophils, and regulatory T cells; promoting functionality of one or more of immunosuppressor dendritic cells, immunosuppressor macrophages, myeloid-derived suppressor cells, tumor-associated macrophages, immunosuppressor neutrophils, and regulatory T cells; enhancing infiltration of one or more of immunosuppressor dendritic cells, immunosuppressor macrophages, myeloid derived suppressor cells, tumor-associated macrophages, immunosuppressor neutrophils, and regulatory T cells into tumors; increasing number of tumor-promoting myeloid/granulocytic immune-suppressive cells in a tumor, in peripheral blood, or other lymphoid organ; enhancing tumor-promoting activity of myeloid-derived suppressor cells; increasing expression of tumor-promoting cytokines, such as TGF-beta or IL-10, in a tumor or in peripheral blood; increasing tumor infiltration of tumor-promoting FoxP3+ regulatory T lymphocytes; enhancing tumor-promoting activity of myeloid-derived suppressor cells (MDSC); decreasing activation of tumor-specific T lymphocytes with tumor killing potential; decreasing activation of CD45+ CD3+ T lymphocytes with tumor killing potential; decreasing infiltration of tumor-specific NK cells with tumor killing potential; decreasing infiltration of tumor-specific B lymphocytes with potential to enhance immune response; decreasing infiltration of tumor-specific T lymphocytes with tumor killing potential; decreasing infiltration of CD45+ CD3+ T lymphocytes; increasing tumor volume; increasing tumor growth rate; increasing rate of tumor recurrence; decreasing efficacy of one or more immune-therapies that modulate anti-tumor T cell responses, optionally wherein the one or more immune-therapies are immune-therapies that target one or more proteins selected from CD40, OX40, ICOS, CD28, CD137/4-1BB, CD27, GITR, PD-L1, CTLA4, PD-L2, PD-1, B7-H3, B7-H4, HVEM, BTLA, KIR, GAL9, TIM3, A2AR, LAG, DR-5, TREM1, TREM2, CSF-1 receptor, and any combination thereof, or of one or chemotherapy agents and/or more cancer vaccines; inhibition of PLCγ/PKC/calcium mobilization; and inhibition of PI3K/Akt, Ras/MAPK signaling.

In some embodiments, treatment of cancer with agents, such as CD33 blocking antibodies: (i) directly or indirectly decrease the survival, proliferation, maturation, differentiation, and/or functionality of tumor-promoting myeloid/granulocytic immune-suppressive cells that accumulate in the tumor, in peripheral blood, and in lymphoid organs of cancer patients; (ii) decrease the number of tumor-promoting myeloid/granulocytic immune-suppressive cells in the tumor, in the peripheral blood, and in other lymphoid organs of a cancer patient; (iii) block tumor-promoting activity of myeloid-derived suppressor cells (MDSC); (iv) decrease expression of tumor-promoting cytokines, such as TGF-beta and IL-10, in the tumor and in the peripheral blood of a cancer patient; (v) decrease tumor-promoting FoxP3+ regulatory T lymphocyte infiltration in the tumor; (vi) increase tumor cell killing by one or more of microglia, macrophages, dendritic cells, bone marrow-derived dendritic cells, neutrophils, T cells, T helper cells, or cytotoxic T cells; (vii) increase anti-tumor cell proliferation activity of one or more of microglia, macrophages, dendritic cells, bone marrow-derived dendritic cells, neutrophils, T cells, T helper cells, or cytotoxic T cells; (viii) increase anti-tumor cell metastasis activity of one or more of microglia, macrophages, dendritic cells, bone marrow-derived dendritic cells, neutrophils, T cells, T helper cells, or cytotoxic T cells; (ix) increase one or more ITAM motif containing receptors, such as TREM1, TREM2, FcgR, DAP10, and DAP12; (x) increase signaling by one or more pattern recognition receptors (PRRs), such as receptors that identify pathogen-associated molecular patterns (PAMPs), receptors that identify damage-associated molecular patterns (DAMPs), and any combination thereof; (xi) increase one or more receptors comprising the motif D/Ex0-2YxxL/IX6-8YxxL/I (SEQ ID NO:247); (xii) increase signaling by one or more Toll-like receptors; (xiii) increase the JAK-STAT signaling pathway; (xiv) increase nuclear factor kappa-light-chain-enhancer of activated B cells (NFκB); (xv) phosphorylate an ITAM motif containing receptor; (xvi) increasing expression of one or more ITAM-dependent genes, such as activated by nuclear factor of activated T cells (NFAT) transcription factors; (xvii) inhibiting differentiation and/or functionality of one or more of immunosuppressor dendritic cells, immunosuppressor macrophages, myeloid derived suppressor cells, tumor-associated macrophages, immunosuppressor neutrophils, and regulatory T cells; (xviii) reducing or inhibiting infiltration of one or more of immunosuppressor dendritic cells, immunosuppressor macrophages, myeloid derived suppressor cells, tumor-associated macrophages, immunosuppressor neutrophils, and regulatory T cells into tumors; (xix) decreasing number of tumor-promoting myeloid/granulocytic immune-suppressive cells in a tumor, in peripheral blood, or other lymphoid organ; (xx) reducing or inhibiting tumor-promoting activity of myeloid-derived suppressor cells; (xxi) decreasing expression of tumor-promoting cytokines, such as TGF-beta or IL-10, in a tumor or in peripheral blood; (xxii) increase activation of tumor-specific T lymphocytes with tumor killing potential; (xxiii) increase infiltration of tumor-specific NK cells with tumor killing potential, (xxiv) increase tumor killing potential of NK cells; (xxv) increase infiltration of tumor-specific B lymphocytes with potential to enhance immune response; (xxvi) reduce or inhibit tumor volume; (xxvii) reduce or inhibit tumor growth rate; (xxviii) reduce or inhibit metastasis; (xxix) reduce or inhibit rate of tumor recurrence; (xxx) increase efficacy of one or more immune-therapies that modulate anti-tumor T cell responses, such as immune-therapies that target one or more proteins selected from the group consisting of CD40, OX40, ICOS, CD28, CD137/4-1BB, CD27, GITR, PD-L1, CTLA4, PD-L2, PD-1, B7-H3, B7-H4, HVEM, BTLA, KIR, GAL9, TIM3, A2AR, LAG, DR-5, TREM1, TREM2, CSF1 receptor, and any combination thereof, or of one or more cancer vaccines; (xxxi) activate PLCγ/PKC/calcium mobilization; and (xxxii) activate PI3K/Akt, Ras/MAPK signaling. In some embodiments, myeloid cells of the present disclosure include, without limitation, $CD45^+CD14^+$ myeloid cells, $CD14^+$ myeloid cells, and myeloid-derived suppressor cells (MDSC). In some embodiments, myeloid cells of the present disclosure are non-tumorigenic myeloid cells.

Immunosuppressor cells are sometimes also referred to as myeloid-derived suppressor cells (MDSC). In humans, MDSCs can be defined by one of the following combination of markers: (1) $CD14^+$ HLA-$DR^{low/-}$, (2) $CD14^+$ $IL4R\alpha^+$, (3) $CD14^+$ HLA-$DR^-$ $IL4R\alpha^+$, (4) $CD34^+$ $CD14^+$ $CD11b^+$ $CD33^+$, (5) $CD11b^+$ $CD14^+$ $CD33^+$, (6) $CD33^+$ HLA-$DR^-$, (7) $Lin^-$ HLA-$DR^-$, (8) $Lin^-$ HLA-$DR^-$ $CD33^+$, (9) $Lin^-$ HLA-$DR^-$ $CD33^+$ $CD11b^+$, (10) $Lin^-$ $CD33^+$ $CD11b^+$ $CD15^+$, (11) $Lin^-$ HLA-$DR^-$ $CD33^+$ $CD11b^+$ $CD14^-$ $CD15^+$, (12) $CD11b^+$ $CD14^-$ $CD33^+$, (13) $CD11b^+$ $CD14^-$ HLA-$DR^-$ $CD33^+$ $CD15^+$, (14) $CD33^+$ HLA-$DR^-$ $CD15^+$, (15) $CD15^+$ $IL4R\alpha^+$, (16) $CD11b^+$ $CD15^+$ $CD66b^+$, (17) $CD15^+$ $FSC^{low}$ $SSC^{high}$, (18) $CD15^{high}$ $CD33^+$, (19) $CD11b^+$ $CD14^-$ $CD15^+$, (20) $CD66b^+$ $SSC^{high}$, and (21) $CD11b^+$ $CD15^+$ (see also Solito S et al. Annals of the NY Academy of Sciences, 2014). In mice, MDSCs can be defined by the expression of the surface markers $CD45^+$, $CD11b^+$, $Gr1^+$, and/or $Il4R\alpha^+$. Additional exemplary immunosuppressive monocytic lineages are $CD45^+$, $CD11b^+$, $Gr1^{low}$; and $CD45^+$, $CD11c^+$.

The present disclosure further relates to agents that bind or interact with CD33, such as anti-CD33 antibodies. In certain embodiments, the anti-CD33 antibodies do not significantly decrease cell surface levels of CD33, and/or do not inhibit interaction between CD33 and one or more CD33 ligands.

CD33 Proteins

In one aspect, the present disclosure provides agents, such as isolated (e.g., monoclonal) antibodies, that interact with or otherwise bind to a regions, such as an epitope, within a CD33 protein of the present disclosure. In some embodiments, agents of the present disclosure, such as anti-CD33 antibodies of the present disclosure, bind to a CD33 protein and modulate one or more CD33 activities after binding to the CD33 protein, for example, an activity associated with CD33 expression in a cell. CD33 proteins of the present disclosure include, without limitation, a mammalian CD33 protein, human CD33 protein, mouse CD33 protein, and rat CD33 protein.

CD33 is variously referred to as a CD33 molecule, Siglec3, Siglec-3, CD33 antigen (Gp67), P67, Gp67, sialic acid-binding-Ig-like lectin 3, myeloid cell surface antigen CD33, or FLJ00391.

CD33 is an immunoglobulin-like receptor primarily expressed on myeloid lineage cells, including without limitation, macrophages, dendritic cells, osteoclasts, monocytes, and microglia. In some embodiments, CD33 forms a receptor-signaling complex with CD64. In some embodiments, CD33 signaling results in the downstream inhibition of PI3K or other intracellular signals. On myeloid cells, Toll-like receptor (TLR) signals are important for the inhibition of CD33 activities, e.g., in the context of an infection response. TLRs also play a key role in the pathological inflammatory response, e.g., TLRs expressed in macrophages and dendritic cells.

Various CD33 homologs are known, including without limitation, human CD33, mouse CD33, rat CD33, chimpanzee CD33, rhesus CD33, dog CD33, cow CD33, zebrafish CD33, platypus CD33, and lizard CD33. The amino acid sequence of human CD33 is set forth below as SEQ ID NO:1:

```
          10         20         30         40         50         60
  MPLLLLLPLL WAGALAMDPN FWLQVQESVT VQEGLCVLVP CTFFHPIPYY DKNSPVHGYW 70         80         90        100        110        120
  FREGAIISRD SPVATNKLDQ EVQEETQGRF RLLGDPSRNN CSLSIVDARR RDNGSYFFRM 130        140        150        160        170        180
  ERGSTKYSYK SPQLSVHVTD LTHRPKILIP GTLEPGHSKN LTCSVSWACE QGTPPIFSWL 190        200        210        220        230        240
  SAAPTSLGPR TTHSSVLIIT PRPQDHGTNL TCQVKFAGAG VTTERTIQLN VTYVPQNPTT 250        260        270        280        290        300
  GIFPGDGSGK QETRAGVVHG AIGGAGVTAL LALCLCLIFF IVKTHRRKAA RTAVGRNDTH 310        320        330        340        350        360
  PTTGSASPKH QKKSKLHGPT ETSSCSGAAP TVEMDEELHY ASLNFHGMNP SKDTSTEYSE

VRTQ
```

In some embodiments, the CD33 is a preprotein that includes a signal sequence. In some embodiments, the CD33 is a mature protein. In some embodiments, the mature CD33 protein does not include a signal sequence. In some embodiments, the mature CD33 protein is expressed on a cell. In some embodiments, the mature CD33 protein is expressed on a cell, such as the surface of a cell, including, without limitation, human dendritic cells, human macrophages, human monocytes, human osteoclasts, human neutrophils, human T cells, human T helper cell, human cytotoxic T cells, human granulocytes, and human microglia. Agents of the present disclosure, such as anti-CD33 antibodies of the present disclosure, may bind any of the CD33 proteins of the present disclosure expressed on any cell disclosed herein.

CD33 proteins of the present disclosure, such as human CD33, contain several domains, including without limitation, a signal sequence located at amino acid residues 1-17 of SEQ ID NO:1, an extracellular immunoglobulin-like variable-type (IgV) domain located at amino acid residues 19-135 of SEQ ID NO:1, an Ig-like C2-type domain located at amino acid residues 145-228 of SEQ ID NO:1, a transmembrane domain located at amino acid residues 260-282 of SEQ ID NO:1, an ITIM motif 1 located at amino acid residues 338-343 of SEQ ID NO:1, and an ITIM motif 2 located at amino acid residues 356-361 of SEQ ID NO:1. As one of skill in the art will appreciate, the beginning and ending residues of the domains of the present disclosure may vary depending upon the computer modeling program used or the method used for determining the domain.

Certain aspects of the present disclosure provide anti-CD33 antibodies that bind to a human CD33, or a homolog thereof, including without limitation a mammalian CD33 protein and Cd33 orthologs from other species. Exemplary CD33 homologs and orthologs are listed in Table A.

TABLE A

| CD33 homologs and orthologs | |
|---|---|
| Organism | CD33 Accession Number |
| Mouse (*Mus musculus*) | NCBI Accession No. NP_001104528.1 |
| Rat (*Rattus norvegicus*) | NCBI Accession No. XP_008757645.1 |
| Chimpanzee (*Pan troglodytes*) | NCBI Accession No. XP_512850.3 |
| Rhesus macaque (*Macaca mulatta*) | NCBI Accession No. XP_001114616.2 |
| Dog (*Canis familiaris*) | NCBI Accession No. XP_005616306.1 |
| Cow (*Bos taurus*) | NCBI Accession No. XP_005219197.1 |
| Zebrafish (*Danio rerio*) | NCBI Accession No. XP_002664698.3 |
| Platypus (*Ornithorhynchus anatinus*) | Ensembl Accession No. Contig28422(4-11599) |
| Lizard (*Anolis carolinensis*) | Ensembl Accession Nos. GL343281.1 (1713612-1717084) and GL343281.1 (1573835-1580218) |

Accordingly, as used herein a "CD33" protein of the present disclosure includes, without limitation, a mammalian CD33 protein, human CD33 protein, primate CD33 protein, mouse CD33 protein, and rat CD33 protein. Additionally, anti-CD33 antibodies of the present disclosure may bind an epitope within one or more of a mammalian CD33 protein, human CD33 protein, primate CD33, mouse CD33 protein, and rat CD33 protein. In some embodiments, anti-CD33 antibodies of the present disclosure may bind specifically to a mammalian CD33 protein, human CD33 protein, or both. In certain embodiments, anti-CD33 antibodies of the present disclosure may bind specifically to human CD33, mouse CD33, or both.

In some embodiments, agents of the present disclosure that decrease cellular levels of CD33 and/or inhibit interaction between CD33 and one or more CD33 ligands, or that bind or interact with CD33, such as anti-CD33 antibodies of the present disclosure, may bind CD33 in a pH dependent manner. In some embodiments, agents of the present disclosure, such as anti-CD33 antibodies, can bind to CD33 at a neutral pH and be internalized without dissociating from the CD33 protein. Alternatively, at an acidic pH agents of the present disclosure, such as anti-CD33 antibodies, may dissociate from CD33 once they are internalized and are then degraded by endosome/lysosome pathway. In certain embodiments, an anti-CD33 antibody binds CD33 at a pH that ranges from 5.5 to 8.0, from 5.5 to 7.5, from 5.5 to 7.0, from 5.5 to 6.5, from 5.5 to 6.0, from 6.0 to 8.0, from 6.5 to 8.0, from 7.0 to 8.0, from 7.5 to 8.0, from 6.0 to 7.5, from 6.0 to 7.0, from 6.5 to 7.5. In certain embodiments, an anti-CD33 antibody dissociates from CD33 at a pH of less than 6.0, less than 5.5, less than 5.0, less than 4.5, less than 4.0, less than 3.5, less than 3.0, less than 2.5, or less than 2.0.

In some embodiments, agents of the present disclosure that decrease cellular levels of CD33 and/or inhibit interaction between CD33 and one or more CD33 ligands, or that bind or interact with CD33, such as anti-CD33 antibodies of the present disclosure, bind to a wild-type CD33 protein of the present disclosure, naturally occurring variants thereof, and/or disease variants thereof.

In some embodiments, agents of the present disclosure that decrease cellular levels of CD33 and/or inhibit interaction between CD33 and one or more CD33 ligands, or that bind or interact with CD33, such as anti-CD33 antibodies of the present disclosure, bind a variant of human CD33, wherein the variant contains a single nucleotide polymorphism (SNP) rs3865444$^C$ with a (C) nucleotide. In some embodiments, agents of the present disclosure that decrease cellular levels of CD33 and/or inhibit interaction between CD33 and one or more CD33 ligands, or that bind or interact with CD33, such as anti-CD33 antibodies of the present disclosure, a variant of human CD33, wherein the variant contains a SNP rs3865444 with an (A) nucleotide. In some embodiments, anti-CD33 antibodies of the present disclosure bind a variant of human CD33, wherein the variant contains a SNP rs3865444$^{AC}$ or rs3865444$^{CC}$.

In some embodiments, agents of the present disclosure that decrease cellular levels of CD33 and/or inhibit interaction between CD33 and one or more CD33 ligands, or that bind or interact with CD33, such as anti-CD33 antibodies of the present disclosure, bind a variant of human CD33, wherein the variant contains a SNP rs35112940 with GG nucleotides, AA nucleotides, or AG nucleotides. In some embodiments, agents of the present disclosure that decrease cellular levels of CD33 and/or inhibit interaction between CD33 and one or more CD33 ligands, or that bind or interact with CD33, such as anti-CD33 antibodies of the present disclosure, bind a variant of human CD33, wherein the variant contains a SNP rs12459419 with CC, CT or TT genotypes. In certain embodiments, the subject has a homozygous or heterozygous for the coding SNPs, rs1803 with GG nucleotides, CG nucleotides, or CC nucleotides.

In some embodiments, agents of the present disclosure that decrease cellular levels of CD33 and/or inhibit interaction between CD33 and one or more CD33 ligands, or that bind or interact with CD33, such as anti-CD33 antibodies of the present disclosure, bind to a CD33 protein expressed on the surface of a cell including, without limitation, human dendritic cells, human macrophages, human monocytes, human osteoclasts, human neutrophils, human T cells, human T helper cell, human cytotoxic T cells, human granulocytes, and human microglia. In some embodiments, agents of the present disclosure that decrease cellular levels of CD33 and/or inhibit interaction between CD33 and one or more CD33 ligands, or that bind or interact with CD33, such as anti-CD33 antibodies of the present disclosure, bind to a CD33 protein expressed on the surface of a cell and modulate (e.g., induce or inhibit) at least one CD33 activity of the present disclosure after binding to the surface expressed CD33 protein. In some embodiments of the present disclosure, the anti-CD33 antibody binds specifically to a CD33 protein. In some embodiments of the present disclosure, the anti-CD33 antibody further binds to at least one additional Siglec protein. In some embodiments, the anti-CD33 antibody modulates one or more activities of the at least one additional Siglec protein or of a cell expressing the at least one additional Siglec protein.

CD33 Ligands

CD33 proteins of the present disclosure can interact with (e.g., bind to) one or more CD33 ligands.

Figure 3:
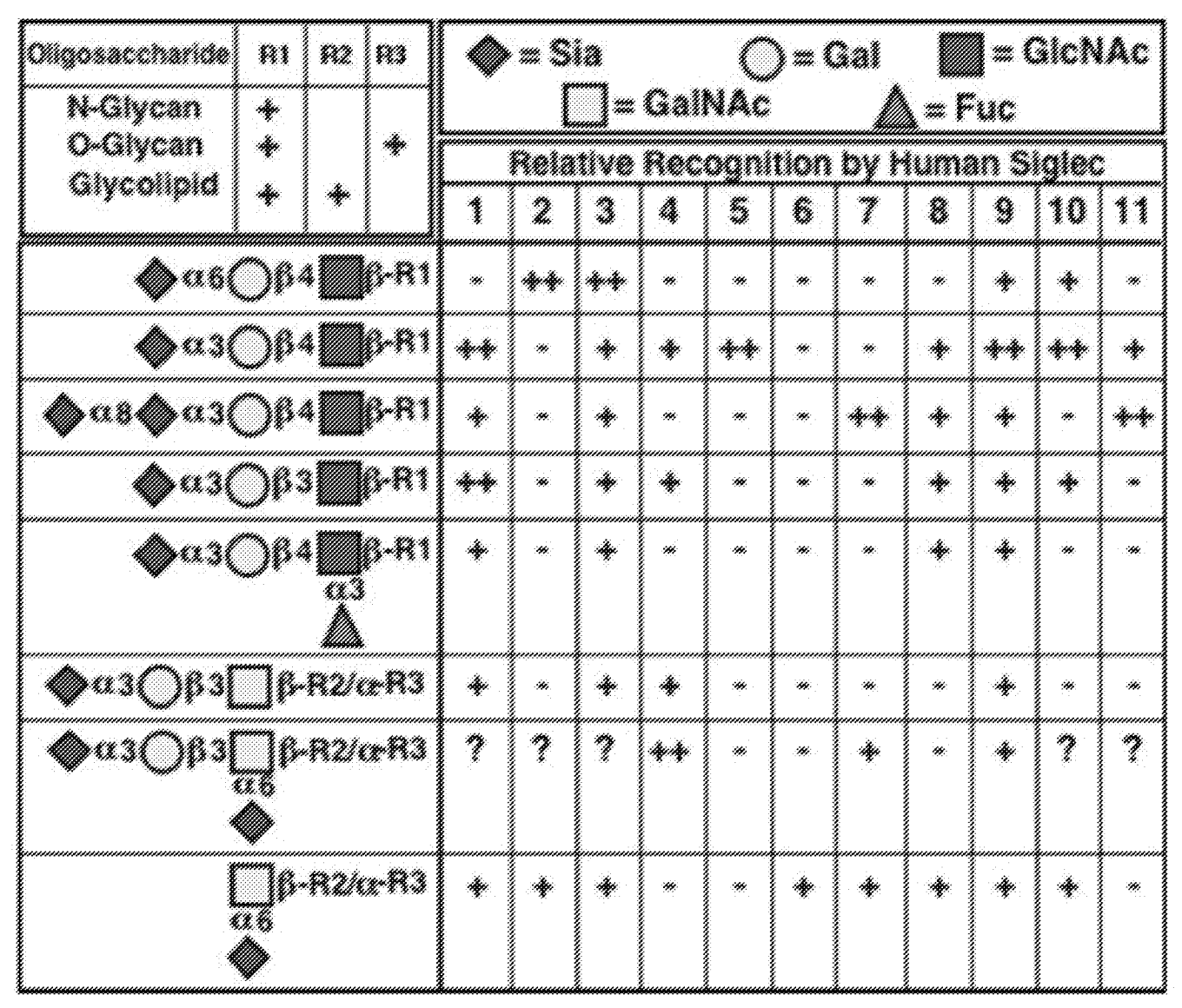

Further examples of suitable CD33 ligands are depicted in FIG. 3.

Figure 4:
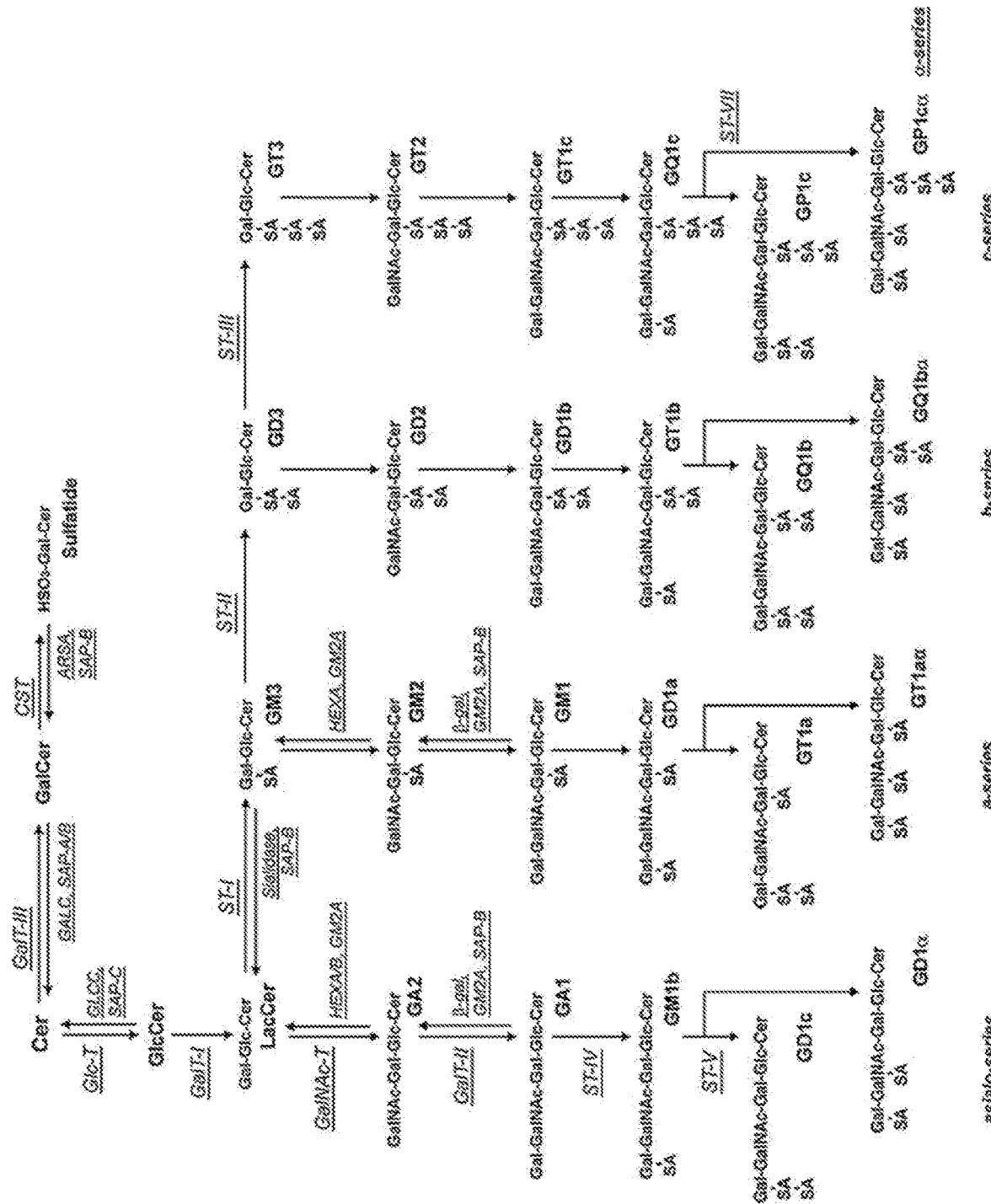
FIG. 4 shows the structure and metabolism of gangliosides in mammalian brain. The nomenclature of gangliosides in the figure follows the system of Svennerholm (1964) J. Lipid Res. 5:145-155 (Ariga T et al. (2008) J. Lipid Res. 49:1157-1175).

Further examples of suitable ganglioside ligands are depicted in FIG. 4 and listed in Table B. Generally, a ganglioside is a molecule composed of a glycosphingolipid with one or more sialic acids (e.g., n-acetyl-neuraminic acid, NANA) linked on the sugar chain.

TABLE B

Structures of exemplary ganglioside CD33 ligands

GM2-1 = aNeu5Ac(2-3)bDGalp(1-?)bDGalNAc(1-?)bDGalNAc(1-?)bDGlcp(1-1)Cer
GM3 = aNeu5Ac(2-3)bDGalp(1-4)bDGlcp(1-1)Cer
GM2, GM2a(?) = bDGalpNAc(1-4)[aNeu5Ac(2-3)]bDGalp(1-4)bDGlcp(1-1)Cer
GM2b(?) = aNeu5Ac(2-8)aNeu5Ac(2-3)bDGalp(1-4)bDGlcp(1-1)Cer
GM1, GM1a = bDGalp(1-3)bDGalNAc[aNeu5Ac(2-3)]bDGalp(1-4)bDGlcp(1-1)Cer
asialo-GM1, GA1 = bDGalp(1-3)bDGalpNAc(1-4)bDGalp(1-4)bDGlcp(1-1)Cer
asialo-GM2, GA2 = bDGalpNAc(1-4)bDGalp(1-4)bDGlcp(1-1)Cer
GM1b = aNeu5Ac(2-3)bDGalp(1-3)bDGalNAc(1-4)bDGalp(1-4)bDGlcp(1-1)Cer
GD3 = aNeu5Ac(2-8)aNeu5Ac(2-3)bDGalp(1-4)bDGlcp(1-1)Cer
GD2 = bDGalpNAc(1-4)[aNeu5Ac(2-8)aNeu5Ac(2-3)]bDGalp(1-4)bDGlcp(1-1)Cer
GD1a = aNeu5Ac(2-3)bDGalp(1-3)bDGalNAc(1-4)[aNeu5Ac(2-3)]bDGalp(1-4)bDGlcp(1-1)Cer
GD1alpha = aNeu5Ac(2-3)bDGalp(1-3)bDGalNAc(1-4)[aNeu5Ac(2-6)]bDGalp(1-4)bDGlcp(1-1)Cer
GD1b = bDGalp(1-3)bDGalNAc(1-4)[aNeu5Ac(2-8)aNeu5Ac(2-3)]bDGalp(1-4)bDGlcp(1-1)Cer
GT1a = aNeu5Ac(2-8)aNeu5Ac(2-3)bDGalp(1-3)bDGalNAc(1-4)[aNeu5Ac(2-3)]bDGalp(1-4)bDGlcp(1-1)Cer
GT1, GT1b = aNeu5Ac(2-3)bDGalp(1-3)bDGalNAc(1-4)[aNeu5Ac(2-8)aNeu5Ac(2-3)]bDGalp(1-4)bDGlcp(1-1)Cer
OAc-GT1b = aNeu5Ac(2-3)bDGalp(1-3)bDGalNAc(1-4)aXNeu5Ac9Ac(2-8)aNeu5Ac(2-3)]bDGalp(1-4)bDGlcp(1-1)Cer
GT1c = bDGalp(1-3)bDGalNAc(1-4)[aNeu5Ac(2-8)aNeu5Ac(2-8)aNeu5Ac(2-3)]bDGalp(1-4)bDGlcp(1-1)Cer
GT3 = aNeu5Ac(2-8)aNeu5Ac(2-8)aNeu5Ac(2-3)bDGal(1-4)bDGlc(1-1)CerGQ1b = aNeu5Ac(2-8)aNeu5Ac(2-3)bDGalp(1-3)bDGalNAc(1-4)[aNeu5Ac(2-8)aNeu5Ac(2-3)]bDGalp(1-4)bDGlcp(1-1)Cer
GGal = aNeu5Ac(2-3)bDGalp(1-1)Cer
where:
aNeu5Ac = 5-acetyl-alpha-neuraminic acid
aNeu5Ac9Ac = 5,9-diacetyl-alpha-neuraminic acid
bDGalp = beta-D-galactopyranose
bDGalpNAc = N-acetyl-beta-D-galactopyranose
bDGlcp = beta-D-glucopyranose
Cer = ceramide (general N-acylated sphingoid)

Exemplary CD33 ligands include, without limitation, sialic acid, sialic acid-containing glycolipids, sialic acid-containing glycoproteins, alpha-2,6-linked sialic acid-containing glycolipids, alpha-2,6-linked sialic acid-containing glycoproteins, alpha-2,3-linked sialic acid-containing glycolipids, alpha-2,3-linked sialic acid-containing glycoproteins, alpha-1-acid glycoprotein (AGP), CD24 protein, gangliosides (e.g., glycolipids containing a ceramide linked to a sialylated glycan), secreted mucins, CD33 ligands expressed on red blood cells, CD33 ligands expressed on bacterial cells, CD33 ligands expressed on apoptotic cells, CD33 ligands expressed on tumor cells, CD33 ligands expressed on viruses, CD33 ligands expressed on dendritic cells, CD33 ligands expressed on nerve cells, CD33 ligands expressed on glial cells, CD33 ligands expressed on microglia, CD33 ligands expressed on astrocytes, CD33 ligands on beta amyloid plaques, CD33 ligands on Tau tangles, CD33 ligands on disease-causing proteins, CD33 ligands on disease-causing peptides, CD33 ligands expressed on macrophages, CD33 ligands expressed on natural killer cells, CD33 ligands expressed on T cells, CD33 ligands expressed on T helper cells, CD33 ligands expressed on cytotoxic T cells, CD33 ligands expressed on B cells, CD33 ligands expressed on tumor-imbedded immunosuppressor dendritic cells, CD33 ligands expressed on tumor-imbedded immunosuppressor macrophages, CD33 ligands expressed on myeloid-derived suppressor cells, and CD33 ligands expressed on regulatory T cells. In some embodiments, CD33 ligands of the present disclosure are gangliosides. Gangliosides generally share a common lacto-ceramide core and one or more sialic acid residues.

CD33 Agents

Certain aspects of the present disclosure relate to agents (e.g., CD33 agents) that decrease cellular levels of CD33 and/or inhibit interaction between CD33 and one or more CD33 ligands. Other aspects of the present disclosure relate to agents (e.g., CD33 agents) that bind or interact with CD33. In some embodiments, agents of the present disclosure block, inhibit, reduce, or interfere with one or more activities of a CD33 protein in vitro, in situ, and/or in vivo. In some embodiments, agents of the present disclosure do not block, inhibit, reduce, or interfere with one or more activities of a CD33 protein in vitro, in situ, and/or in vivo. In some embodiments, agents of the present disclosure, increase, activate or induce one or more activities of a CD33 protein in vitro, in situ, and/or in vivo.

In certain embodiments, agents of the present disclosure are agents (e.g., CD33 agents) that decrease cellular levels of CD33 and/or inhibit interaction between CD33 and one or more CD33 ligands. An agent of the present disclosure that decreases cellular levels of CD33 and/or inhibits interaction between CD33 and one or more CD33 ligands is a molecule having one or more of the following characteristics: (1) inhibits or reduces one or more CD33 activities; (2) the ability to inhibit or reduce binding of a CD33 to one or more of its ligands; (3) the ability to reduce CD33 expression (such as at the mRNA level and/or at protein level) in CD33-expressing cells; (4) the ability to interact, bind, or recognize a CD33 protein; (5) the ability to specifically interact with or bind to a CD33 protein; and (6) the ability to treat, ameliorate, or prevent any aspect of a disease or disorder described or contemplated herein.

Exemplary agents that inhibit the production of CD33 include, without limitation, compounds that specifically inhibit CD33 synthesis and/or release, antisense molecules directed to a CD33, or a short interfering RNA (siRNA) molecule directed to a nucleic acid encoding a CD33. Additional exemplary agents that inhibit one or more CD33 activities include, without limitation, anti-CD33 antibodies that specifically bind to a CD33 protein, compounds that specifically inhibit one or more CD33 activities such as small molecule inhibitors and/or peptide inhibitors, compounds that specifically inhibit CD33 binding to one or more ligands, a CD33 structural analog, or an RNA or DNA aptamer that binds a CD33. In some embodiments, an agent that decreases cellular levels of CD33 and/or inhibits interaction between CD33 and one or more CD33 ligands is an allosteric inhibitor. In some embodiments, an agent that decreases cellular levels of CD33 and/or inhibits interaction between CD33 and one or more CD33 ligands is an orthosteric inhibitor.

In certain embodiments, an agent that decreases cellular levels of CD33 and/or inhibits interaction between CD33 and one or more CD33 ligands is a small molecule inhibitor, including, without limitation, small peptides or peptide-like molecules, soluble peptides, and synthetic non-peptidyl organic or inorganic compounds. A small molecule inhibitor may have a molecular weight of any of about 100 to about 20,000 daltons (Da), about 500 to about 15,000 Da, about 1000 to about 10,000 Da. Methods for making and testing the inhibitory effect a small molecule has on one or more CD33 activities are well known in the art and such methods can be used to assess the effect of the small molecule inhibitor on CD33 activity. For example, any of the methods and assays disclosed herein may be used to screen for small molecule inhibitors that decrease cellular levels of CD33 and/or inhibit interaction between CD33 and one or more CD33 ligands.

In certain embodiments, an agent that decreases cellular levels of CD33 and/or inhibits interaction between CD33 and one or more CD33 ligands is an anti-CD33 antibody that binds or physically interacts with a CD33. The antibody may have nanomolar or even picomolar affinities for the target antigen (e.g., CD33). In certain embodiments, the $K_D$ of the antibody is about 0.05 to about 100 nM. In certain embodiments, the dissociation constant ($K_D$) of the antibody is about 0.5 to about 10 nM. For example, $K_D$ of the antibody is any of about 100 nM, about 50 nM, about 10 nM, about 9 nM, about 8 nM, about 7 nM, about 6 nM, about 5 nM, about 4 nM, about 3 nM, about 2 nM, about 1 nM, about 500 pM, about 400 pM, about 300 pM, about 200 pM, about 175 pM, about 170 pM, about 169 pM, about 168 pM, about 167 pM, about 166 pM, about 166.2 pM, about 165 pM, about 164 pM, about 163 pM, about 162 pM, about 161 pM, about 160 pM, about 150 pM, about 145 pM, about 140 pM, about 139 pM, about 138 pM, about 138.2 pM, about 137 pM, about 136 pM, about 135 pM, about 134 pM, about 133 pM, about 132 pM, about 131 pM, about 130 pM, about 120 pM, about 110 pM, about 100 pM, or about 50 pM to any of about 2 pM, about 5 pM, about 10 pM, about 15 pM, about 20 pM, or about 40 pM. In some embodiments, the dissociation constant ($K_D$) for CD33 is determined at a temperature of approximately 25° C. In some embodiments, the $K_D$ is determined using a monovalent antibody (e.g., a Fab) or a full-length antibody in a monovalent form. Methods for the preparation and selection of antibodies that interact and/or bind with specificity to a CD33 are described herein (e.g., see Example 1).

In certain embodiments, an agent that decreases cellular levels of CD33 and/or inhibits interaction between CD33 and one or more CD33 ligands comprises at least one antisense molecule capable of blocking or decreasing the expression of a functional CD33 by targeting nucleic acids encoding a CD33. Nucleic acid sequences of CD33 are known in the art. For example, a human CD33 can have a nucleic acid sequence as shown in NCBI Accession number NM_001082618.1 and a mouse CD33 can have a nucleic acid sequence as shown in NCBI Accession number NM_001111058.1. Methods are known for the preparation of antisense oligonucleotide molecules and such methods can be used to prepare antisense oligonucleotides that will specifically bind one or more of a CD33 mRNA without cross-reacting with other polynucleotides. Exemplary sites of targeting include, but are not limited to, the initiation codon, the 5' regulatory regions, the coding sequence, including any conserved consensus regions, and the 3' untranslated region. In certain embodiments, the antisense oligonucleotides are about 10 to about 100 nucleotides in length, about 15 to about 50 nucleotides in length, about 18 to about 25 nucleotides in length, or more. In certain embodiments, the oligonucleotides further comprise chemical modifications to increase nuclease resistance and the like, such as, for example, phosphorothioate linkages and 2'-O-sugar modifications known to those of ordinary skill in the art.

In certain embodiments, an agent that decreases cellular levels of CD33 and/or inhibits interaction between CD33 and one or more CD33 ligands comprises at least one siRNA molecule capable of blocking or decreasing the expression of a functional CD33 by targeting nucleic acids encoding a CD33. Methods for preparation of siRNA molecules are well known in the art and such methods can be used to prepare siRNA molecules that will specifically target a CD33 mRNA without cross-reacting with other polynucleotides. siRNA molecules may be generated by methods such as by typical solid phase oligonucleotide synthesis, and often will incorporate chemical modifications to increase half-life and/or efficacy of the siRNA agent, and/or to allow for a more robust delivery formulation. Alternatively, siRNA molecules are delivered using a vector encoding an expression cassette for intracellular transcription of siRNA.

In certain embodiments, an agent that decreases cellular levels of CD33 and/or inhibits interaction between CD33 and one or more CD33 ligands is an RNA or DNA aptamer that binds or physically interacts with a CD33, and blocks interactions between a CD33 and one or more of its ligands. In certain embodiments, the aptamer comprises at least one RNA or DNA aptamer that binds to a mature form of CD33.

In certain embodiments, an agent that decreases cellular levels of CD33 and/or inhibits interaction between CD33 and one or more CD33 ligands comprises at least one CD33 structural analog. The term CD33 structural analog refers to compounds that have a similar three dimensional structure as part of that of a CD33 and which bind to one or more CD3 ligands under physiological conditions in vitro or in vivo, wherein the binding at least partially inhibits a CD33 biological activity. Suitable CD33 structural analogs can be designed and synthesized through molecular modeling of CD33 binding to a ligand, such as a CD33 ligand of the present disclosure. The CD33 structural analogs can be monomers, dimers, or higher order multimers in any desired combination of the same or different structures to obtain improved affinities and biological effects. In some embodiments, the agent binds to or interacts with an amino acid sequence of a CD33.

In certain embodiments, an agent that decreases cellular levels of CD33 and/or inhibits interaction between CD33 and one or more CD33 ligands comprises a soluble CD33 receptor protein, a soluble CD33-Fc fusion protein (e.g., CD33 immunoadhesin), a soluble Siglec receptor that binds to a CD33 ligand, a Siglec-Fc fusion protein (e.g., Siglec immunoadhesin) that binds to a CD33 ligand. In certain embodiments, such agents bind one or more CD33 ligands and thereby prevent the interaction between a given CD33 ligand and a functional CD33 receptor.

In certain embodiments, agents of the present disclosure are agents (e.g., CD33 agents) that bind or interact with CD33. Exemplary agents that bind or interact with CD33 include, without limitation, inert anti-CD33 antibodies, agonist anti-CD33 antibodies, CD33 ligands, CD33 ligand agonist fragments, CD33 immunoadhesins, CD33 soluble receptors, Siglec-Fc fusion proteins (e.g., Siglec immunoadhesins), soluble Siglec receptors, CD33 ligand mimetics, and small molecule compounds. A small molecule compound may have a molecular weight of any of about 100 to about 20,000 daltons (Da), about 500 to about 15,000 Da, about 1000 to about 10,000 Da. Methods for making and testing the effect an agent has on one or more CD33 activities are well known in the art and such methods can be used to assess the effect of the small molecule inhibitor on CD33 activity. For example, any of the methods and assays disclosed herein may be used to screen for small molecule inhibitors that bind or interact with CD33.

Assays

Agents that decrease cellular levels of CD33 and/or inhibit interaction between CD33 and one or more CD33 ligands may be identified and/or characterized using methods well known in the art, such as, for example, radiolabeled inhibitor assays, optical assays, protein binding assays, biochemical screening assays, immunoassays, mass shift measurement assays, fluorescence assays, and/or fluorogenic peptide cleavage assays.

Binding Assays and Other Assays

In certain embodiments, agents that decrease cellular levels of CD33 and/or inhibit interaction between CD33 and one or more CD33 ligands can be identified by techniques well known in the art for detecting the presence of a CD33 agent candidate's interaction and/or binding affinity to a CD33.

In certain embodiments, agents that interact with a CD33 can be identified using a radiolabeled inhibitor assay. For example, a known amount of a radiolabeled agent candidate may be incubated with a known amount of immobilized CD33 and a buffer. Subsequently, the immobilized CD33 may be washed with a buffer and the immobilized CD33 may be measured for the remaining presence of the radiolabeled CD33 agent candidate using techniques known in the art, such as, for example, a gamma counter. A measurement indicating the presence of a radiolabeled substance may indicate the radiolabeled agent candidate is capable of interacting with and/or binding to CD33.

In certain embodiments, an agent that interacts with a CD33 may be identified using an optical technique. An exemplary optical technique to detect a CD33 agent may include, e.g., attaching CD33 to a colorimetric resonant grafting surface, thereby shifting the wavelength of reflected light due to changes in the optical path the light must take, and subsequently measuring additional changes in the wavelength of reflected light when a candidate agent is allowed to interact with CD33. For example, no change in the measured wavelength of reflected light when an agent is incubated with CD33 may indicate that the agent candidate is unable to interact with CD33. Changes in the measured wavelength of reflected light when an agent candidate is incubated with CD33 may indicate that the agent candidate is capable of binding and/or interacting with CD33.

In certain embodiments, an agent that interacts with a CD33 may be identified using a protein binding assay. An exemplary protein binding assay to detect a CD33 agent may include, e.g., co-immunoprecipitation of a CD33 in the presence of the agent candidate. For example, a CD33 may be incubated with the agent candidate in buffer, and subsequently an immobilized molecule specific to capture a CD33, such as, for example, an anti-CD33 antibody, may be used to capture CD33 in the presence of the agent candidate and bind the CD33, potentially with an interacting agent candidate, during wash procedures known in the art. Subsequently, CD33, potentially with an interacting agent candidate, can be released and the presence of an agent candidate may be detected, based on the agent candidate characteristics, by techniques, such as, for example, mass spectrometry and/or Western blot.

In certain embodiments, an agent that interacts with a CD33 may be identified using a biochemical and/or an immunoassay assay well known in the art. An exemplary technique may include, e.g., an assay to quantitatively measure changes in CD33 concentration and/or protein half-life using techniques, such as, for example, Western blot, immunostaining, and co-immunoprecipitation. For example, an agent candidate may be incubated with a sample containing a CD33, such as a cell expressing CD33, and subsequently CD33 protein quantity and/or cellular levels may be measured at points during a time course study. Changes in protein quantity, cellular levels, and/or protein half-life in comparison to a control treatment may indicate that the CD33 agent candidate may be capable of altering CD33 half-life and/or activity.

In certain embodiments, a mass shift measurement assay may be used to identify an agent that interacts with a CD33. An exemplary mass shift measurement assay may include, e.g., detecting the presence of a strongly and/or covalently bound CD33 agent by measuring a change in CD33 mass when the agent candidate is interacting with CD33 by using instruments, such as, but not limited to, a mass spectrometer. For example, a mass shift assay may be performed on a whole protein and/or a peptide-based analysis, depending on the nature of the agent candidate interaction. Detection of a mass shift correlating with the addition of said agent candidate to CD33 may indicate that the agent candidate may be capable of interacting with or otherwise inhibiting a CD33. Additionally, an exemplary mass shift measurement assay may include, e.g., detecting the addition of mass to CD33 correlating with the respective agent candidate mass when the agent candidate is interacting with CD33 using techniques, such as, for example, surface plasmon resonance. For example, the change in the refractive index of light may be measured and correlated with a change in mass of CD33 attached to a sensor surface.

In certain embodiments, a chemical cross-linking assay may be used to identify a CD33 agent that interacts with a CD33. For example, an agent candidate may be incubated with a CD33, in vivo or in vitro, with a molecule cross-linker capable of covalently linking an agent candidate interacting with CD33 to said CD33 molecule. Subsequently, techniques, such as, but not limited to, mass spectrometry and/or Western blot, may be used to identify an agent candidate that may be capable of interacting with or otherwise inhibiting CD33. For example, detection of CD33 covalently cross-linked with the agent candidate may indicate that the agent candidate may be capable of interacting with or otherwise inhibiting CD33.

In certain embodiments, agents that interact with a CD33 may be identified using a fluorescence assay. For example, a known amount of a fluorescent agent candidate may be incubated with a known amount of immobilized CD33 and a buffer. Subsequently, the immobilized CD33 may be washed with a buffer and the immobilized CD33 may be measured for the remaining presence of a fluorescent CD33 agent candidate using techniques known in the art, such as, but not limited to, fluorescence detection. A measurement indicating the presence of a fluorescent substance may indicate the fluorescent agent candidate is capable of interacting with and/or binding to CD33.

Activity Assays

Assays known in the art and described herein (e.g., Examples 1-10) can be used for identifying and testing biological activities of CD33 agents of the present disclosure. In some embodiments, assays for testing the ability of CD33 agents for modulating one or more CD33 activities are provided.

Anti-CD33 Antibodies

Certain aspects of the present disclosure relate to anti-CD33 antibodies that decrease cellular levels of CD33 and/or inhibit interaction (e.g., binding) between CD33 and one or more CD33 ligands. In some embodiments, the anti-CD33 antibody decreases cellular levels of CD33 without inhibiting the interaction (e.g., binding) between CD33 and one or more CD33 ligands. In some embodiments, the anti-CD33 antibody inhibits the interaction (e.g., binding) between CD33 and one or more CD33 ligands without decreasing cellular levels of CD33. In some embodiments, the anti-CD33 antibody decreases cellular levels of CD33 and inhibits the interaction (e.g., binding) between CD33 and one or more CD33 ligands. In some embodiments, the anti-CD33 antibodies have a dissociation constant ($K_D$) for human CD33 that is lower than that of commercial anti-CD33 antibodies (e.g., gemtuzumab). In some embodiments, the anti-CD33 antibodies bind to human cells, such as dendritic cells with a half-maximal effective concentration ($EC_{50}$) that is lower than that of commercial anti-CD33 antibodies (e.g., gemtuzumab or lintuzumab). In some embodiments, the anti-CD33 antibodies decrease cellular levels of CD33 with a half-maximal effective concentration ($EC_{50}$) that is lower than that of commercial anti-CD33 antibodies (e.g., gemtuzumab or lintuzumab). In some embodiments, the anti-CD33 antibodies have a dissociation constant ($K_D$) for human CD33 that may range from 300 pM to 10 pM, for example when the $K_D$ is determined at a temperature of approximately 25° C. In some embodiments the $K_D$ is determined using a monovalent antibody, or a full-length antibody in monovalent form. In some embodiments, the dissociation constant ($K_D$) for human CD33 is less than 300 pM, for example when the $K_D$ is determined at a temperature of approximately 25° C. In some embodiments, the anti-CD33 antibodies bind to human cells, such as dendritic cells with a half-maximal effective concentration ($EC_{50}$) that may range from 200 pM to 10 pM, for example when the $EC_{50}$ is determined at a temperature of approximately 4° C. In some embodiments, the anti-CD33 antibodies decrease cellular levels of CD33 with an $EC_{50}$ that may range from 65 pM to 20 pM. In some embodiments, the anti-CD33 antibodies decrease cellular levels of CD33 in vivo with an $EC_{50}$ that may range from 8.0 mg/kg to 2.0 mg/kg. In some embodiments, the $EC_{50}$ for decreasing cellular levels of CD33 in vivo is determined using a suitable rodent, such as a rat or mouse. In some embodiments, the $EC_{50}$ for decreasing cellular levels of CD33 in vivo is determined using a mouse model, such as that described in Example 3.

In some embodiments, anti-CD33 antibodies of the present disclosure have a dissociation constant ($K_D$) for human CD33 that is at least 10%, at least 15%, at least 20%, at least 20%, at least 20%, at least 20%, at least 20%, at least 25%, at least 30%, at least 35%, at least 40%, at least 45%, at least 50%, at least 55%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 85%, at least 90%, at least 95%, or a higher percentage lower than the $K_D$ for human CD33 of commercial anti-CD33 antibodies (e.g., gemtuzumab). Any suitable methods described herein (e.g., see Example 1) may be used to determine the dissociation constant ($K_D$). In some embodiments, the $K_D$ is determined at a temperature of approximately 25° C. In some embodiments, the $K_D$ is determined using a monovalent antibodies or full-length antibodies in monovalent form (e.g., with BiaCore assays as described in Example 1).

In some embodiments, the anti-CD33 antibodies bind to human cells, such as primary dendritic cells with a half-maximal effective concentration ($EC_{50}$) that is at least 10%, at least 15%, at least 20%, at least 20%, at least 20%, at least 20%, at least 20%, at least 25%, at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 95%, or a higher percentage lower than that of commercial anti-CD33 antibodies (e.g., gemtuzumab or lintuzumab). Any suitable methods described herein (e.g., see Example 1) may be used to calculate the $EC_{50}$. In some embodiments, the $EC_{50}$ is determined at a temperature of approximately 4° C.

In some embodiments, the anti-CD33 antibodies decrease cellular levels of CD33 with a half-maximal effective concentration ($EC_{50}$) that is that is at least 10%, at least 15%, at least 20%, at least 20%, at least 20%, at least 20%, at least 20%, at least 25%, at least 30%, at least 35%, at least 40%, at least 45%, at least 50%, at least 55%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 95%, or a higher percentage lower than that of commercial anti-CD33 antibodies (e.g., gemtuzumab or lintuzumab). Any suitable methods described herein (e.g., see Examples 4 and 45) may be used to calculate the $EC_{50}$.

In some embodiments, anti-CD33 antibodies of the present disclosure bind to human cells, such as primary dendritic cells, with a half-maximal effective concentration ($EC_{50}$) that may be less than 500 pM, less than 400 pM, less than 300 pM, less than 200 pM, less than 175 pM, less than 170 pM, less than 169 pM, less than 168 pM, less than 167 pM, less than 166 pM, less than 166.2 pM, less than 165 pM, less than 164 pM, less than 163 pM, less than 162 pM, less than 161 pM, less than 160 pM, less than 150 pM, less than 145 pM, less than 140 pM, less than 139 pM, less than 138 pM, less than 138.2 pM, less than 137 pM, less than 136 pM, less than 135 pM, less than 134 pM, less than 133 pM, less than 132 pM, less than 131 pM, less than 130 pM, less than 120 pM, less than 110 pM, less than 100 pM, less than 90 pM, less than 80 pM, less than 70 pM, less than 60 pM, less than 50 pM, less than 40 pM, less than 30 pM, less than 20 pM, or less than 10 pM. In some embodiments, anti-CD33 antibodies of the present disclosure bind to human cells, such as primary dendritic cells, with an $EC_{50}$ that ranges from about 300 pM, to about 10 pM, or less than 10 pM. Any suitable methods described herein (e.g., see Example 1) may be used to calculate the $EC_{50}$. In some embodiments, the $EC_{50}$ is determined at a temperature of approximately 4° C.

In some embodiments, anti-CD33 antibodies of the present disclosure decrease cellular levels of CD33 with a half-maximal effective concentration ($EC_{50}$) that may be less than 70 pM, less than 69 pM, less than 68 pM, less than 67 pM, less than 66 pM, less than 65 pM, less than 64 pM, less than 63 pM, less than 62 pM, less than 61 pM, less than 60 pM, less than 55 pM, less than 50 pM, less than 45 pM, less than 40 pM, less than 39 pM, less than 38 pM, less than 37 pM, less than 36 pM, less than 35 pM, less than 34.8 pM, less than 34 pM, less than 33 pM, less than 32 pM, less than 31 pM, less than 30 pM, less than 25 pM, less than 24 pM, less than 23 pM, less than 22 pM, less than 21 pM, less than 21.5 pM, less than 20 pM, less than 19 pM, less than 18 pM, less than 17 pM, less than 16 pM, less than 15 pM, less than 14 pM, less than 13 pM, less than 12 pM, less than 11 pM, or less than 10 pM. In some embodiments, anti-CD33 antibodies of the present disclosure decrease cellular levels of CD33 with a half-maximal effective concentration ($EC_{50}$) that ranges from about 65 pM to about 20 pM, or less than 20 pM. Any suitable method (e.g., those described in Examples 1 and 3) may be used to measure the with a half-maximal effective concentration ($EC_{50}$) for reducing cellular levels of CD33 in a cell, as compared to a corresponding cell that is not administered the CD33 antibody.

Cellular levels of CD33 may refer to, without limitation, cell surface levels of CD33, intracellular levels of CD33, and total levels of CD33. In some embodiments, a decrease in cellular levels of CD33 comprises decrease in cell surface levels of CD33. As used herein, an anti-CD33 antibody decreases cell surface levels of CD33 if it induces a decrease of 21% or more in cell surface levels of CD33 as measured by any in vitro cell-based assays or suitable in vivo model described herein or known in the art, for example, utilizing flow cytometry, such as fluorescence-activated cell sorting (FACS), to measure cell surface levels of CD33. In some embodiments, a decrease in cellular levels of CD33 comprises a decrease in intracellular levels of CD33. As used herein, an anti-CD33 antibody decreases intracellular levels of CD33 if it induces a decrease of 21% or more in intracellular levels of CD33 as measured by any in vitro cell-based assays or suitable in vivo model described herein or known in the art, for example immunostaining, Western blot analysis, co-immunoprecipitation, and cell cytometry. In some embodiments, a decrease in cellular levels of CD33 comprises a decrease in total levels of CD33. As used herein, an anti-CD33 antibody decreases total levels of CD33 if it induces a decrease of 21% or more in total levels of CD33 as measured by any in vitro cell-based assays or suitable in vivo model described herein or known in the art, for example immunostaining, Western blot analysis, co-immunoprecipitation, and cell cytometry. In some embodiments, the anti-CD33 antibodies induce CD33 degradation, CD33 cleavage, CD33 internalization, CD33 shedding, and/or downregulation of CD33 expression. In some embodiments, cellular levels of CD33 are measured on primary cells (e.g., dendritic cells, bone marrow-derived dendritic cells, monocytes, microglia, and macrophages) or on cell lines utilizing an in vitro cell assay.

In some embodiments, anti-CD33 antibodies of the present disclosure decrease cellular levels of CD33 by at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more as compared to cellular levels of CD33 in the absence of the anti-CD33 antibody.

In some embodiments, an anti-CD33 antibody of the present disclosure decrease cellular levels of CD33 in vivo with an $EC_{50}$ of less than 40 mg/kg, less than 35 mg/kg, less than 30 mg/kg, less than 25 mg/kg, less than 20 mg/kg, less than 15 mg/kg, less than 10 mg/kg, less than 9.0 mg/kg, less than 8.0 mg/kg, less than 7.0 mg/kg, less than 6.0 mg/kg, less than 5.0 mg/kg, less than 4.0 mg/kg, less than 3.0 mg/kg, less than 2.0 mg/kg, less than 1.9 mg/kg, less than 1.8 mg/kg, less than 1.6 mg/kg, less than 1.5 mg/kg, less than 1.4 mg/kg, less than 1.3 mg/kg, less than 1.2 mg/kg, less than 1.1 mg/kg, or less than 1.0 mg/kg. In some embodiments, anti-CD33 antibodies of the present disclosure decrease cellular levels of CD33 in vivo with an $EC_{50}$ that ranges from about 8.0 mg/kg to about 2.0 mg/kg, or less than 2.0 mg/kg. Any suitable methods (e.g., those described in Examples 1 and 3) may be used to measure the $EC_{50}$ for reducing cellular levels of CD33 in a subject (i.e., in vivo), as compared to a corresponding subject that is not administered the CD33 antibody. In some embodiments, the $EC_{50}$ for decreasing cellular levels of CD33 in vivo is determined using a suitable rodent, such as a rat or mouse. In some embodiments, the $EC_{50}$ for decreasing cellular levels of CD33 in vivo is determined using a mouse model, such as that described in Example 3.

Any in vitro cell-based assays or suitable in vivo model described herein or known in the art may be used to measure inhibition of interaction (e.g., binding) between CD33 and one or more CD33 ligands. In some embodiments, anti-CD33 antibodies of the present disclosure inhibit interaction (e.g., binding) between CD33 and one or more CD33 ligands by at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more at saturating antibody concentrations (e.g., 67 nM) utilizing any in vitro assay or cell-based culture assay described herein or known in the art.

In some embodiments, anti-CD33 antibodies of the present disclosure inhibit cell surface clustering of CD33. In some embodiments, anti-CD33 antibodies of the present disclosure inhibit one or more activities of a CD33 protein, including, without limitation, counteracting one or more of phosphorylation of Tyr-340 and Tyr-358 by a Src family tyrosine kinase, such as LCK and FYN; recruitment of and binding to the tyrosine-specific protein phosphatases SHP1 and SHP2; recruitment of and binding to PLC-gamma1, which acts as a guanine nucleotide exchange factor for Dynamini-1; recruitment of and binding to SH2-domain containing protein (e.g., Crkl); recruitment of and binding to the spleen tyrosine kinase Syk; recruitment of and binding to SH3-SH2-SH3 growth factor receptor-bound protein 2 (Grb2); recruitment of and binding to multiple SH2-containing proteins; phosphorylation of Ser-307 and Ser-342 by protein kinase C; modulated expression of one or more anti-inflammatory cytokines, IL-4, IL-10, IL-13, IL-35, IL-16, TGF-beta, IL-1Ra, G-CSF, and soluble receptors for TNF, IFN-beta1a, IFN-beta1b, or IL-6 in monocytes, macrophages, T cells, dendritic cells neutrophils, and/or microglia; decreasing intracellular calcium mobilization; modulated expression of one or more pro-inflammatory cytokines IFN-a4, IFN-b, IL-1β, TNF-α, IL-6, IL-8, CRP, IL-20 family members, LIF, IFN-gamma, OSM, CNTF, GM-CSF, IL-11, IL-12, IL-17, IL-18, IL-23, CXCL10, IL-33, CRP, IL-33, MCP-1, and MIP-1-beta in monocytes, macrophages, T cells, dendritic cells, neutrophils, and/or microglia; modulated expression of one or more proteins selected from C1qa, C1qB, C1qC, C1s, C1R, C4, C2, C3, ITGB2, HMOX1, LAT2, CASP1, CSTA, VSIG4, MS4A4A, C3AR1, GPX1, TyroBP, ALOX5AP, ITGAM, SLC7A7, CD4, ITGAX, PYCARD, CD14, CD16, HLA-DR, and CCR2; inhibition of extracellular signal-regulated kinase (ERK) phosphorylation; decreasing tyrosine phosphorylation on multiple cellular proteins; modulated expression of C-C chemokine receptor 7 (CCR7); inhibition of microglial cell chemotaxis toward CCL19 and CCL21 expressing cells; activation of phosphoinositide 3-kinase; reducing cell growth of monocytes, macrophages, T cells, dendritic cells and/or microglia; reducing T cell proliferation induced by dendritic cells, bone marrow-derived dendritic cells, monocytes, microglia, M1 microglia, activated M1 microglia, M2 microglia, macrophages, M1 macrophages, activated M1 macrophages, and/or M2 macrophages; inhibition of osteoclast production, decreased rate of osteoclastogenesis, or both; decreasing survival of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; decreasing proliferation of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; inhibiting migration of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; decreasing one or more functions of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; inhibiting maturation of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; increasing cell death and apoptosis of monocytes, macrophages, T cells, dendritic cells, neutrophils, and/or microglia; reducing phagocytic activity of monocytes, macrophages, T cells, dendritic cells, neutrophils, and/or microglia; reducing proliferation of monocytes, macrophages, T cells, dendritic cells, neutrophils, and/or microglia; reducing the overall functionality of monocytes, macrophages, T cells, dendritic cells, neutrophils, and/or microglia, phosphorylation of an ITAM containing receptor; phosphorylation of a signaling molecules that mediates ITAM signaling; reducing the activation of pattern recognition receptors; reducing the activation of Toll-like receptors; reducing the activation of damage-associated of clearance of cellular and protein debris; interaction between CD33 and one or more of its ligands; interaction between CD33 and a co-receptor such as CD64; reducing one or more types of clearance selected from apoptotic neuron clearance, nerve tissue debris clearance, dysfunctional synapse clearance, non-nerve tissue debris clearance, bacteria or other foreign body clearance, disease-causing protein clearance, and tumor cell clearance; inhibition of phagocytosis of one or more of apoptotic neurons, nerve tissue debris, non-nerve tissue debris, bacteria, other foreign bodies, disease-causing proteins, disease-causing peptides, disease-causing nucleic acid, disease-causing lipids, or tumor cells; inhibition of clearance of a disease-causing nucleic acid, such as the disease-causing nucleic acid is antisense GGCCCC (G2C4) repeat-expansion RNA; activation of clearance of, a disease-causing protein selected from amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides; inhibition of beneficial immune response to different types of cancer selected from bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, acute myeloid leukemia, pancreatic cancer, prostate cancer, ovarian cancer, fibrosarcoma, and thyroid cancer; inhibition of beneficial immune response to different types of neurological disorders selected from dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, essential tremor, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, Sarcoidosis, diseases of aging, seizures, spinal cord injury, -traumatic brain injury, age related macular degeneration, glaucoma, retinitis pigmentosa, retinal degeneration, and multiple sclerosis; inhibition of beneficial immune response-to different types of inflammatory and infectious disorders selected from lupus, acute and chronic colitis, wound healing, Crohn's disease, inflammatory bowel disease, ulcerative colitis, obesity, malaria, respiratory tract infection, sepsis, eye infection, systemic infection, lupus, arthritis, low bone density, osteoporosis, osteogenesis, osteopetrotic disease, and Paget's disease of bone; binding to CD33 ligand on tumor cells; binding to CD33 ligand on dendritic cells, bone marrow-derived dendritic cells, monocytes, microglia, T cells, neutrophils, and/or macrophages; inhibition of tumor cell killing by one or more of microglia, macrophages, dendritic cells, bone marrow-derived dendritic cells, neutrophils, T cells, T helper cells, or cytotoxic T cells; inhibition of anti-tumor cell proliferation activity of one or more of microglia, macrophages, dendritic cells, bone marrow-derived dendritic cells, neutrophils, T cells, T helper cells, or cytotoxic T cells; inhibition of anti-tumor cell metastasis activity of one or more of microglia, macrophages, dendritic cells, bone marrow-derived dendritic cells, neutrophils, T cells, T helper cells, or cytotoxic T cells; promotion of immunosuppressor dendritic cells, immunosuppressor macrophages, myeloid-derived suppressor cells, tumor-associated macrophages, or regulatory T cells; inhibition of one or more ITAM motif containing receptors, such as TREM1, TREM2, FcgR, DAP10, and DAP12; inhibition of one or more receptors containing the motif D/Ex0-2YxxL/IX6-8YxxL/I (SEQ ID NO:247); inhibition of signaling by one or more pattern recognition receptors (PRRs), such as receptors that identify pathogen-associated molecular patterns (PAMPs), and receptors that identify damage-associated molecular patterns (DAMPs); inhibition of signaling by one or more Toll-like receptors; inhibition of the JAK-STAT signaling pathway; inhibition of nuclear factor kappa-light-chain-enhancer of activated B cells (NFκB); inhibition of PLCγ/PKC/calcium mobilization; inhibition of PI3K/Akt, Ras/MAPK signaling; reduced expression of one or more inflammatory receptors, such as CD86, expressed on one or more of microglia, macrophages, dendritic cells, bone marrow-derived dendritic cells, neutrophils, T cells, T helper cells, or cytotoxic T cells; increasing expression of one or more CD33-dependent genes; normalization of disrupted CD33-dependent gene expression; and decreasing expression of one or more ITAM-dependent genes, such as NFAT transcription factors.

In some embodiments, anti-CD33 antibodies of the present disclosure exhibit one or more activities of a CD33 protein, including, without limitation, increasing the number of tumor infiltrating CD3$^+$ T cells; decreasing cellular levels of CD33 in CD14$^+$ myeloid cells, such as tumor infiltrating CD14$^+$ myeloid cells and CD14$^+$ myeloid cells present in blood; reducing the number of CD14$^+$ myeloid cells, such as tumor infiltrating CD14$^+$ myeloid cells and CD14$^+$ myeloid cells present in blood; reducing PD-L1 levels in one or more cells, such as myeloid-derived suppressor cells (MDSC); reducing PD-L2 levels in one or more cells, such as myeloid-derived suppressor cells (MDSC); reducing B7-H2 levels in one or more cells, such as myeloid-derived suppressor cells (MDSC); reducing B7-H3 levels in one or more cells, such as myeloid-derived suppressor cells (MDSC); reducing CD200R levels in one or more cells, such as myeloid-derived suppressor cells (MDSC); reducing CD163 levels in one or more cells, such as myeloid-derived suppressor cells (MDSC); reducing CD206 levels in one or more cells, such as myeloid-derived suppressor cells (MDSC); decreasing tumor growth rate of solid tumors; reducing tumor volume; increasing efficacy of one or more PD-1 inhibitors; increasing efficacy of one or more checkpoint inhibitor therapies and/or immune-modulating therapies, such as checkpoint inhibitor therapies and/or immune-modulating therapies that target one or more of CTL4, the adenosine pathway, PD-L1, PD-L2, OX40, TIM3, LAG3, or any combination thereof; increasing efficacy of one or more chemotherapy agents, optionally wherein the one or more of the chemotherapy agents are gemcitabine, capecitabine, anthracyclines, doxorubicin (Adriamycin®), epirubicin (Ellence®), taxanes, paclitaxel (Taxol®), docetaxel (Taxotere®), 5-fluorouracil (5-FU), cyclophosphamide (Cytoxan®), carboplatin (Paraplatin®), and any combination thereof; increasing proliferation of T cells in the presence of myeloid-derived suppressor cells (MDSC); inhibiting differentiation, survival, and/or one or more functions of myeloid-derived suppressor cells (MDSC); and killing CD33-expressing immunosuppressor non-tumorigenic myeloid cells and/or non-tumorigenic CD14-expressing cells in solid tumors and associated blood vessels when conjugated to a chemical or radioactive toxin.

In some embodiments, the anti-CD33 antibodies inhibit interaction (e.g., binding) between a CD33 protein of the present disclosure and one or more CD33 ligands including, without limitation, CD33 ligands expressed on red blood cells, CD33 ligands expressed on bacterial cells, CD33 ligands expressed on apoptotic cells, CD33 ligands expressed on tumor cells, CD33 ligands expressed on viruses, CD33 ligands expressed on dendritic cells, CD33 ligands expressed on nerve cells, CD33 ligands expressed on glial cells, CD33 ligands expressed on microglia, CD33 ligands expressed on astrocytes, CD33 ligands on beta amyloid plaques, CD33 ligands on Tau tangles, CD33 ligands on disease-causing proteins, CD33 ligands on disease-causing peptides, CD33 ligands expressed on macrophages, CD33 ligands expressed on natural killer cells, CD33 ligands expressed on T cells, CD33 ligands expressed on T helper cells, CD33 ligands expressed on cytotoxic T cells, CD33 ligands expressed on B cells, CD33 ligands expressed on tumor-imbedded immunosuppressor dendritic cells, CD33 ligands expressed on tumor-imbedded immunosuppressor macrophages, CD33 ligands expressed on myeloid-derived suppressor cells, CD33 ligands expressed on regulatory T cells, secreted mucins, sialic acid, sialic acid-containing glycolipids, sialic acid-containing glycoproteins, alpha-2,6-linked sialic acid-containing glycolipids, alpha-2,6-linked sialic acid-containing glycoproteins, alpha-2,3-linked sialic acid-containing glycolipids, alpha-2,3-linked sialic acid-containing glycoproteins, alpha-1-acid glycoprotein (AGP), CD24 protein, and gangliosides.

In some embodiments, anti-CD33 antibodies of the present disclosure bind to a CD33 protein of the present disclosure expressed on the surface of cell and the naked antibodies inhibit interaction (e.g., binding) between the CD33 protein and one or more CD33 ligands. In some embodiments, anti-CD33 antibodies of the present disclosure that bind to a CD33 protein of the present inhibit interaction (e.g., binding) between the CD33 protein and one or more CD33 ligands by reducing the effective levels of CD33 that is available to interact with these proteins either on the cell surface or inside the cell. In some embodiments, anti-CD33 antibodies of the present disclosure that bind to a CD33 protein of the present inhibit interaction (e.g., binding) between the CD33 protein and one or more CD33 ligands by inducing degradation of CD33.

Other aspects of the present disclosure relate to anti-CD33 antibodies that do not significantly decrease cell surface levels of CD33 and/or do not inhibit interaction between CD33 and one or more CD33 ligands.

As used herein, an anti-CD33 antibody does not significantly decrease cell surface levels of CD33 if it decreases ligand binding to CD33 by less than 20% as compared to cellular levels of CD33 in the absence of the anti-CD33 antibody utilizing any in vitro cell-based assays or suitable in vivo model described herein or known in the art. In some embodiments, anti-CD33 antibodies of the present disclosure decrease cell surface levels of CD33 by less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1% as compared to cellular levels of CD33 in the absence of the anti-CD33 antibody.

As used herein, an anti-CD33 antibody does not inhibit the interaction (e.g., binding) between CD33 and one or more CD33 ligands if it decreases ligand binding to CD33 by less than 20% at saturating antibody concentrations (e.g., 67 nM) utilizing any in vitro assay or cell-based culture assay described herein or known in the art. In some embodiments, anti-CD33 antibodies of the present disclosure inhibit interaction (e.g., binding) between CD33 and one or more CD33 ligands by less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1% at saturating antibody concentrations (e.g., 67 nM) utilizing any in vitro assay or cell-based culture assay described herein or known in the art.

As used herein, levels of CD33 may refer to expression levels of the gene encoding CD33; to expression levels of one or more transcripts encoding CD33; to expression levels of CD33 protein; and/or to the amount of CD33 protein present within cells and/or on the cell surface. Any methods known in the art for measuring levels of gene expression, transcription, translation, and/or protein abundance or localization may be used to determine the levels of CD33.

Additionally, anti-CD33 antibodies of the present disclosure can be used to prevent, reduce risk of, or treat dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express CD33, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and/or *Haemophilus* influenza. In some embodiments, anti-CD33 antibodies of the present disclosure can be used for inducing or promoting the survival, maturation, functionality, migration, or proliferation of one or more immune cells in an individual in need thereof; or for decreasing the activity, functionality, or survival of regulatory T cells, tumor-imbedded immunosuppressor dendritic cells, tumor-imbedded immunosuppressor macrophages, myeloid-derived suppressor cells, tumor-associated macrophages, acute myeloid leukemia (AML) cells, chronic lymphocytic leukemia (CLL) cell, and/or chronic myeloid leukemia (CML) cell in an individual in need thereof. In some embodiments, anti-CD33 antibodies of the present disclosure are monoclonal antibodies.

In some embodiments, an isolated anti-CD33 antibody of the present disclosure decreases cellular levels of CD33 (e.g., cell surface levels, intracellular levels, and/or total levels). In some embodiments, an isolated anti-CD33 antibody of the present disclosure induces downregulation of CD33. In some embodiments, an isolated anti-CD33 antibody of the present disclosure induces cleavage of CD33. In some embodiments, an isolated anti-CD33 antibody of the present disclosure induces internalization of CD33. In some embodiments, an isolated anti-CD33 antibody of the present disclosure induces shedding of CD33. In some embodiments, an isolated anti-CD33 antibody of the present disclosure induces degradation of CD33. In some embodiments, an isolated anti-CD33 antibody of the present disclosure induces desensitization of CD33. In some embodiments, an isolated anti-CD33 antibody of the present disclosure acts as a ligand mimetic to transiently activate CD33. In some embodiments, an isolated anti-CD33 antibody of the present disclosure acts as a ligand mimetic and transiently activates CD33 before inducing a decrease in cellular levels of CD33 and/or inhibition of interaction (e.g., binding) between CD33 and one or more CD33 ligands. In some embodiments, an isolated anti-CD33 antibody of the present disclosure acts as a ligand mimetic and transiently activates CD33 before inducing degradation of CD33. In some embodiments, an isolated anti-CD33 antibody of the present disclosure acts as a ligand mimetic and transiently activates CD33 before inducing cleavage of CD33. In some embodiments, an isolated anti-CD33 antibody of the present disclosure acts as a ligand mimetic and transiently activates CD33 before inducing internalization of CD33. In some embodiments, an isolated anti-CD33 antibody of the present disclosure acts as a ligand mimetic and transiently activates CD33 before inducing shedding of CD33. In some embodiments, an isolated anti-CD33 antibody of the present disclosure acts as a ligand mimetic and transiently activates CD33 before inducing downregulation of CD33 expression. In some embodiments, an isolated anti-CD33 antibody of the present disclosure acts as a ligand mimetic and transiently activates CD33 before inducing desensitization of CD33.

In some embodiments, an isolated anti-CD33 antibody of the present disclosure is a murine antibody. In some embodiments, an isolated anti-CD33 antibody of the present disclosure is a human antibody, a humanized antibody, a bispecific antibody, a monoclonal antibody, a multivalent antibody, or a chimeric antibody. Exemplary descriptions of such antibodies are found throughout the present disclosure.

In some embodiments, anti-CD33 antibodies of the present disclosure bind to a human CD33, or a homolog thereof, including without limitation, a mammalian CD33 protein, mouse CD33 protein (NCBI Accession No. NP_001104528.1), rat CD33 protein (NCBI Accession No. XP_008757645.1), chimpanzee CD33 protein (NCBI Accession No. XP_512850.3), rhesus macaque CD33 protein (NCBI Accession No. XP_001114616.2), dog CD33 protein (NCBI Accession No. XP_005616306.1), or cow CD33 protein (NCBI Accession No. XP_005219197.1). In some embodiments, anti-CD33 antibodies of the present disclosure specifically bind to human CD33. In some embodiments, anti-CD33 antibodies of the present disclosure specifically bind to mouse CD33. In some embodiments, anti-CD33 antibodies of the present disclosure specifically bind to both human CD33 and mouse CD33.

In some embodiments, anti-CD33 antibodies of the present disclosure are agonist antibodies or antagonist antibodies that bind to a CD33 protein of the present disclosure expressed on the surface of a cell and modulate (e.g., induce or inhibit) one or more CD33 activities of the present disclosure after binding to the surface-expressed CD33 protein. In some embodiments, anti-CD33 antibodies of the present disclosure are inert antibodies.

Anti-CD33 Antibody-Binding Regions

Certain aspects of the preset disclosure provide anti-CD33 antibodies that bind to one or more amino acids within amino acid residues 19-259, 19-135, 145-228, or 229-259 of human CD33 (SEQ ID NO:1), or within amino acid residues on a CD33 homolog or ortholog corresponding to amino acid residues 19-259, 19-135, 145-228, or 229-259 of SEQ ID NO:1. In some embodiments, the anti-CD33 antibody binds to one or more amino acids within amino acid residues 39-51 of human CD33 (SEQ ID NO:1), or within amino acid residues on a CD33 homolog or ortholog corresponding to amino acid residues 39-51 of SEQ ID NO:1. In some embodiments, the anti-CD33 antibody binds to one or more amino acids within amino acid residues 48-54 of human CD33 (SEQ ID NO:1), or within amino acid residues on a CD33 homolog or ortholog corresponding to amino acid residues 48-54 of SEQ ID NO:1. In some embodiments, the anti-CD33 antibody binds to one or more amino acids within amino acid residues 88-98 of human CD33 (SEQ ID NO:1), or within amino acid residues on a CD33 homolog or ortholog corresponding to amino acid residues 88-98 of SEQ ID NO:1. In some embodiments, the anti-CD33 antibody binds to one or more amino acids within amino acid residues 110-120 of human CD33 (SEQ ID NO:1), or within amino acid residues on a CD33 homolog or ortholog corresponding to amino acid residues 110-120 of SEQ ID NO:1. In some embodiments, the anti-CD33 antibody binds to one or more amino acids within amino acid residues 112-122 of human CD33 (SEQ ID NO:1), or within amino acid residues on a CD33 homolog or ortholog corresponding to amino acid residues 112-122 of SEQ ID NO:1. In some embodiments, the anti-CD33 antibody binds to one or more amino acids within amino acid residues 39-51, 88-98, and 110-120 of human CD33 (SEQ ID NO:1), or within amino acid residues on a CD33 homolog or ortholog corresponding to amino acid residues 39-51, 88-98, and 110-120 of SEQ ID NO:1. In some embodiments, the anti-CD33 antibody binds to one or more amino acids within amino acid residues 39-51, 88-98, and 112-122 of human CD33 (SEQ ID NO:1), or within amino acid residues on a CD33 homolog or ortholog corresponding to amino acid residues 39-51, 88-98, and 112-122 of SEQ ID NO:1. In some embodiments, the anti-CD33 antibody binds to one or more amino acids within amino acid residues 39-51, 88-98, 110-120, and 112-122 of human CD33 (SEQ ID NO:1), or within amino acid residues on a CD33 homolog or ortholog corresponding to amino acid residues 39-51, 88-98, 110-120, and 112-122 of SEQ ID NO:1. In some embodiments, the anti-CD33 antibody binds to one or more amino acids within amino acid residues 137-147 of human CD33 (SEQ ID NO:1), or within amino acid residues on a CD33 homolog or ortholog corresponding to amino acid residues 137-147 of SEQ ID NO:1. In some embodiments, the anti-CD33 antibody binds to one or more amino acid residues selected from D18, P19, N20, F21, F44, P46, Y49, Y50, K52, and N53 of SEQ ID NO: 1, or one or more amino acid residues on a mammalian CD33 protein corresponding to an amino acid residue selected from D18, P19, N20, F21, F44, P46, Y49, Y50, K52, and N53 of SEQ ID NO: 1.

Other aspects of the preset disclosure provide anti-CD33 antibodies that decrease cellular levels of CD33 and/or inhibit interaction (e.g., binding) between CD33, and that bind one or more CD33 ligands bind to one or more amino acids within amino acid residues 19-228 of human CD33 (SEQ ID NO:1), or within amino acid residues on a CD33 homolog or ortholog corresponding to amino acid residues 19-228 of SEQ ID NO:1. In some embodiments, the anti-CD33 antibody binds to one or more amino acids within amino acid residues 39-51 of human CD33 (SEQ ID NO:1), or within amino acid residues on a CD33 homolog or ortholog corresponding to amino acid residues 39-51 of SEQ ID NO:1. In some embodiments, the anti-CD33 antibody binds to one or more amino acids within amino acid residues 48-54 of human CD33 (SEQ ID NO:1), or within amino acid residues on a CD33 homolog or ortholog corresponding to amino acid residues 48-54 of SEQ ID NO:1. In some embodiments, the anti-CD33 antibody binds to one or more amino acids within amino acid residues 88-98 of human CD33 (SEQ ID NO:1), or within amino acid residues on a CD33 homolog or ortholog corresponding to amino acid residues 88-98 of SEQ ID NO:1. In some embodiments, the anti-CD33 antibody binds to one or more amino acids within amino acid residues 110-120 of human CD33 (SEQ ID NO:1), or within amino acid residues on a CD33 homolog or ortholog corresponding to amino acid residues 110-120 of SEQ ID NO:1. In some embodiments, the anti-CD33 antibody binds to one or more amino acids within amino acid residues 112-122 of human CD33 (SEQ ID NO:1), or within amino acid residues on a CD33 homolog or ortholog corresponding to amino acid residues 112-122 of SEQ ID NO:1. In some embodiments, the anti-CD33 antibody binds to one or more amino acids within amino acid residues 39-51, 88-98, and 110-120 of human CD33 (SEQ ID NO:1), or within amino acid residues on a CD33 homolog or ortholog corresponding to amino acid residues 39-51, 88-98, and 110-120 of SEQ ID NO:1. In some embodiments, the anti-CD33 antibody binds to one or more amino acids within amino acid residues 39-51, 88-98, and 112-122 of human CD33 (SEQ ID NO:1), or within amino acid residues on a CD33 homolog or ortholog corresponding to amino acid residues 39-51, 88-98, and 112-122 of SEQ ID NO:1. In some embodiments, the anti-CD33 antibody binds to one or more amino acids within amino acid residues 39-51, 88-98, 110-120, and 112-122 of human CD33 (SEQ ID NO:1), or within amino acid residues on a CD33 homolog or ortholog corresponding to amino acid residues 39-51, 88-98, 110-120, and 112-122 of SEQ ID NO:1. In some embodiments, the anti-CD33 antibody binds to one or more amino acids within amino acid residues 137-147 of human CD33 (SEQ ID NO:1), or within amino acid residues on a CD33 homolog or ortholog corresponding to amino acid residues 137-147 of SEQ ID NO:1. In some embodiments, the anti-CD33 antibody binds to one or more amino acid residues selected from D18, P19, N20, F21, F44, P46, Y49, Y50, K52, and N53 of SEQ ID NO: 1, or one or more amino acid residues on a mammalian CD33 protein corresponding to an amino acid residue selected from D18, P19, N20, F21, F44, P46, Y49, Y50, K52, and N53 of SEQ ID NO: 1. In some embodiments, the anti-CD33 antibody binds to one or more amino acid residues selected from Y49, Y50, and K52 of SEQ ID NO: 1, or one or more amino acid residues on a mammalian CD33 protein corresponding to an amino acid residue selected from Y49, Y50, and K52 of SEQ ID NO: 1. In some embodiments, the anti-CD33 antibody binds to amino acid residues Y49 and K52 of SEQ ID NO: 1, or to amino acid residues on a mammalian CD33 protein corresponding to an amino acid residues Y49 and K52 of SEQ ID NO: 1. In some embodiments, the anti-CD33 antibody binds to amino acid residues Y49, Y50, and K52 of SEQ ID NO: 1, or to amino acid residues on a mammalian CD33 protein corresponding to an amino acid residues Y49, Y50, and K52 of SEQ ID NO: 1.

Other aspects of the preset disclosure provide anti-CD33 antibodies that do not significantly decrease cell surface levels of CD33 and/or do not inhibit interaction (e.g., binding) between CD33 and one or more CD33 ligands, and that bind to one or more amino acids within amino acid residues 19-259 of human CD33 (SEQ ID NO:1), or within amino acid residues on a CD33 homolog or ortholog corresponding to amino acid residues 19-259 of SEQ ID NO:1. In some embodiments, the anti-CD33 antibody binds to one or more amino acids within amino acid residues 39-51 of human CD33 (SEQ ID NO:1), or within amino acid residues on a CD33 homolog or ortholog corresponding to amino acid residues 39-51 of SEQ ID NO:1. In some embodiments, the anti-CD33 antibody binds to one or more amino acids within amino acid residues 48-54 of human CD33 (SEQ ID NO:1), or within amino acid residues on a CD33 homolog or ortholog corresponding to amino acid residues 48-54 of SEQ ID NO:1. In some embodiments, the anti-CD33 antibody binds to one or more amino acids within amino acid residues 88-98 of human CD33 (SEQ ID NO:1), or within amino acid residues on a CD33 homolog or ortholog corresponding to amino acid residues 88-98 of SEQ ID NO:1. In some embodiments, the anti-CD33 antibody binds to one or more amino acids within amino acid residues 110-120 of human CD33 (SEQ ID NO:1), or within amino acid residues on a CD33 homolog or ortholog corresponding to amino acid residues 110-120 of SEQ ID NO:1. In some embodiments, the anti-CD33 antibody binds to one or more amino acids within amino acid residues 112-122 of human CD33 (SEQ ID NO:1), or within amino acid residues on a CD33 homolog or ortholog corresponding to amino acid residues 112-122 of SEQ ID NO:1. In some embodiments, the anti-CD33 antibody binds to one or more amino acids within amino acid residues 39-51, 88-98, and 110-120 of human CD33 (SEQ ID NO:1), or within amino acid residues on a CD33 homolog or ortholog corresponding to amino acid residues 39-51, 88-98, and 110-120 of SEQ ID NO:1. In some embodiments, the anti-CD33 antibody binds to one or more amino acids within amino acid residues 39-51, 88-98, and 112-122 of human CD33 (SEQ ID NO:1), or within amino acid residues on a CD33 homolog or ortholog corresponding to amino acid residues 39-51, 88-98, and 112-122 of SEQ ID NO:1. In some embodiments, the anti-CD33 antibody binds to one or more amino acids within amino acid residues 39-51, 88-98, 110-120, and 112-122 of human CD33 (SEQ ID NO:1), or within amino acid residues on a CD33 homolog or ortholog corresponding to amino acid residues 39-51, 88-98, 110-120, and 112-122 of SEQ ID NO:1. In some embodiments, the anti-CD33 antibody binds to one or more amino acids within amino acid residues 137-147 of human CD33 (SEQ ID NO:1), or within amino acid residues on a CD33 homolog or ortholog corresponding to amino acid residues 137-147 of SEQ ID NO:1. In some embodiments, the anti-CD33 antibody binds to one or more amino acid residues selected from D18, P19, N20, F21, F44, P46, Y49, Y50, K52, and N53 of SEQ ID NO: 1, or one or more amino acid residues on a mammalian CD33 protein corresponding to an amino acid residue selected from D18, P19, N20, F21, F44, P46, Y49, Y50, K52, and N53 of SEQ ID NO: 1.

In some embodiments, anti-CD33 antibodies of the present disclosure may bind a conformational epitope. In some embodiments, anti-CD33 antibodies of the present disclosure may bind a discontinuous CD33 epitope. In some embodiments, the discontinuous CD33 epitope comprises two or more peptides, three or more peptides, four or more peptides, five or more peptides, six or more peptides, seven or more peptide, eight or more peptides, nine or more peptides, or 10 or more peptides. In some embodiments, anti-CD33 antibodies of the present disclosure may bind a CD33 epitope comprising one or more peptides. As disclosed herein, CD33 epitopes may comprise one or more peptides comprising five or more, six or more, seven or more, eight or more, nine or more, 10 or more, 11 or more, 12 or more, 13 or more 14 or more, 15 or more, 16 or more, 17 or more, 18 or more, 19 or more, or 20 or more amino acid residues of the amino acid sequence of SEQ ID NO:1, or five or more, six or more, seven or more, eight or more, nine or more, 10 or more, 11 or more, 12 or more, 13 or more 14 or more, 15 or more, 16 or more, 17 or more, 18 or more, 19 or more, or 20 or more amino acid residues on a mammalian CD33 protein corresponding to the amino acid sequence of SEQ ID NO:1.

In some embodiments, anti-CD33 antibodies of the present disclosure competitively inhibit binding of at least one antibody selected from any of the antibodies listed in Tables 1, 2, 3A, 3B, 6A, and 6B. In some embodiments, anti-CD33 antibodies of the present disclosure competitively inhibit binding of at least one antibody selected from 1A8, 2B4, 2E12, 2E12.1, 2F5, 2F5.1, 3A12a, 3A12b, 6A3a, 6A3b, 6C7a, 6C7b, and 6C7.2. In some embodiments, an anti-CD33 antibody of the present disclosure competes with one or more antibodies selected from 1A8, 2B4, 2E12, 2E12.1, 2F5, 2F5.1, 3A12a, 3A12b, 6A3a, 6A3b, 6C7a, 6C7b, and 6C7.2, and any combination thereof, for binding to CD33 when the anti-CD33 antibody reduces the binding of one or more antibodies selected from 1A8, 2B4, 2E12, 2E12.1, 2F5, 2F5.1, 3A12a, 3A12b, 6A3a, 6A3b, 6C7a, 6C7b, and 6C7.2, and any combination thereof to CD33 by an amount the ranges from about 50% to 100%, as compared to binding to CD33 in the absence of the anti-CD33 antibody. In some embodiments, an anti-CD33 antibody of the present disclosure competes with one or more antibodies selected from 1A8, 2B4, 2E12, 2E12.1, 2F5, 2F5.1, 3A12a, 3A12b, 6A3a, 6A3b, 6C7a, 6C7b, and 6C7.2, and any combination thereof for binding to CD33 when the anti-CD33 antibody reduces the binding of one or more antibodies selected from 1A8, 2B4, 2E12, 2E12.1, 2F5, 2F5.1, 3A12a, 3A12b, 6A3a, 6A3b, 6C7a, 6C7b, and 6C7.2, and any combination thereof to CD33 by at least 50%, at least 55%, by at least 60%, at least 65%, at least 70%, at least 75%, at least 80%, at least 85%, at least 90%, at least 95%, or 100%, as compared to binding to CD33 in the absence of the anti-CD33 antibody. In some embodiments, an anti-CD33 antibody of the present disclosure that reduces the binding of one or more antibodies selected from 1A8, 2B4, 2E12, 2E12.1, 2F5, 2F5.1, 3A12a, 3A12b, 6A3a, 6A3b, 6C7a, 6C7b, and 6C7.2, and any combination thereof to CD33 by 100% indicates that the anti-CD33 antibody essential completely blocks the binding of one or more antibodies selected from 1A8, 2B4, 2E12, 2E12.1, 2F5, 2F5.1, 3A12a, 3A12b, 6A3a, 6A3b, 6C7a, 6C7b, and 6C7.2, and any combination thereof to CD33. In some embodiments, the anti-CD33 antibody and the one or more antibodies selected from 1A8, 2B4, 2E12, 2E12.1, 2F5, 2F5.1, 3A12a, 3A12b, 6A3a, 6A3b, 6C7a, 6C7b, and 6C7.2, and any combination thereof are present in an amount that corresponds to a 10:1 ratio, 9:1 ratio, 8:1 ratio, 7:1 ratio, 6:1 ratio, 5:1 ratio, 4:1 ratio, 3:1 ratio, 2:1 ratio, 1:1 ratio, 0.75:1 ratio, 0.5:1 ratio, 0.25:1 ratio, 0.1:1 ratio, 0.075:1 ratio, 0.050:1 ratio, 0.025:1 ratio, 0.01:1 ratio, 0.0075: ratio, 0.0050:1 ratio, 0.0025:1 ratio, 0.001: ratio, 0.00075:1 ratio, 0.00050:1 ratio, 0.00025:1 ratio, 0.0001: ratio, 1:10 ratio, 1:9 ratio, 1:8 ratio, 1:7 ratio, 1:6 ratio, 1:5 ratio, 1:4 ratio, 1:3 ratio, 1:2 ratio, 1:0.75 ratio, 1:0.5 ratio, 1:0.25 ratio, 1:0.1 ratio, 1:0.075 ratio, 1:0.050 ratio, 1:0.025 ratio, 1:0.01 ratio, 1:0.0075 ratio, 1:0.0050 ratio, 1:0.0025 ratio, 1:0.001 ratio, 1:0.00075 ratio, 1:0.00050 ratio, 1:0.00025 ratio, or 1:0.0001 ratio of anti-CD33 antibody to one or more antibodies selected from 1A8, 2B4, 2E12, 2E12.1, 2F5, 2F5.1, 3A12a, 3A12b, 6A3a, 6A3b, 6C7a, 6C7b, and 6C7.2, and any combination thereof. In some embodiments, the anti-CD33 antibody is present in excess by an amount that ranges from about 1.5-fold to 100-fold, or greater than 100-fold compared to the amount of the one or more antibodies selected from 1A8, 2B4, 2E12, 2E12.1, 2F5, 2F5.1, 3A12a, 3A12b, 6A3a, 6A3b, 6C7a, 6C7b, and 6C7.2, and any combination thereof. In some embodiments, the anti-CD33 antibody is present in an amount that is about a 2-fold, 3-fold, 4-fold, 5-fold, 6-fold, 7-fold, 8-fold, 9-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, or 100-fold excess compared to the amount of the one or more antibodies selected from 1A8, 2B4, 2E12, 2E12.1, 2F5, 2F5.1, 3A12a, 3A12b, 6A3a, 6A3b, 6C7a, 6C7b, and 6C7.2, and any combination thereof.

In some embodiments, anti-CD33 antibodies of the present disclosure bind to an epitope of human CD33 that is the same as or overlaps with the CD33 epitope bound by at least one antibody selected from any of the antibodies listed in Tables 1, 2, 3A, 3B, 6A, and 6B. In some embodiments, anti-CD33 antibodies of the present disclosure bind to an epitope of human CD33 that is the same as or overlaps with the CD33 epitope bound by at least one antibody selected from 1A8, 2B4, 2E12, 2E12.1, 2F5, 2F5.1, 3A12a, 3A12b, 6A3a, 6A3b, 6C7a, 6C7b, and 6C7.2.

In some embodiments, anti-CD33 antibodies of the present disclosure bind essentially the same CD33 epitope bound by at least one antibody selected from any of the antibodies listed in Tables 1, 2, 3A, 3B, 6A, and 6B. In some embodiments, anti-CD33 antibodies of the present disclosure bind essentially the same CD33 epitope bound by at least one antibody selected from 1A8, 2B4, 2E12, 2E12.1, 2F5, 2F5.1, 3A12a, 3A12b, 6A3a, 6A3b, 6C7a, 6C7b, and 6C7.2. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In some embodiments, anti-CD33 antibodies of the present disclosure compete with one or more antibodies selected from 1A8, 2B4, 2E12, 2E12.1, 2F5, 2F5.1, 3A12a, 3A12b, 6A3a, 6A3b, 6C7a, 6C7b, 6C7.2, and any combination thereof for binding to CD33.

Any suitable competition assay or CD33 binding assay known in the art, such as BIAcore analysis, ELISA assays, or flow cytometry, may be utilized to determine whether an anti-CD33 antibody competes with one or more antibodies selected from 1A8, 2B4, 2E12, 2E12.1, 2F5, 2F5.1, 3A12a, 3A12b, 6A3a, 6A3b, 6C7a, 6C7b, 6C7.2, and any combination thereof for binding to CD33. In an exemplary competition assay, immobilized CD33 or cells expressing CD33 on the cell surface are incubated in a solution comprising a first labeled antibody that binds to CD33 (e.g., human or non-human primate) and a second unlabeled antibody that is being tested for its ability to compete with the first antibody for binding to CD33. The second antibody may be present in a hybridoma supernatant. As a control, immobilized CD33 or cells expressing CD33 is incubated in a solution comprising the first labeled antibody but not the second unlabeled antibody. After incubation under conditions permissive for binding of the first antibody to CD33, excess unbound antibody is removed, and the amount of label associated with immobilized CD33 or cells expressing CD33 is measured. If the amount of label associated with immobilized CD33 or cells expressing CD33 is substantially reduced in the test sample relative to the control sample, then that indicates that the second antibody is competing with the first antibody for binding to CD33. See, Harlow and Lane (1988) *Antibodies: A Laboratory Manual* ch. 14 (Cold Spring Harbor Laboratory, Cold Spring Harbor, N.Y.). In some embodiments, the competition assay that is utilized is one or more of the competition assays described in Examples 2 and 4.

Anti-CD33 Antibody Light Chain and Heavy Chain Variable Regions

In some embodiments, anti-CD33 antibodies of the present disclosure comprise (a) a light chain variable region comprising at least one, two, or three HVRs selected from HVR-L1, HVR-L2, and HVR-L3 of any one of the antibodies listed in Tables 1, 2, 3A, 3B, 6A, and 6B, or selected from 1A8, 2B4, 2E12, 2E12.1, 2F5, 2F5.1, 3A12a, 3A12b, 6A3a, 6A3b, 6C7a, 6C7b, 6C7.2, and any combination thereof; and/or (b) a heavy chain variable region comprising at least one, two, or three HVRs selected from HVR-H1, HVR-H2, and HVR-H3 of any one of the antibodies listed in Tables 1, 2, 3A, 3B, 6A, and 6B, or selected from 1A8, 2B4, 2E12, 2E12.1, 2F5, 2F5.1, 3A12a, 3A12b, 6A3a, 6A3b, 6C7a, 6C7b, 6C7.2, and any combination thereof. In some embodiments, the HVR-L1, HVR-L2, HVR-L3, HVR-H1, HVR-H2, and HVR-H3 comprise EU or Kabat CDR, Chothia CDR, or Contact CDR sequences as shown in Tables 1, 2, 3A, 3B, 6A, and 6B, or from an antibody selected from 1A8, 2B4, 2E12, 2E12.1, 2F5, 2F5.1, 3A12a, 3A12b, 6A3a, 6A3b, 6C7a, 6C7b, 6C7.2, and any combination thereof.

In some embodiments, anti-CD33 antibodies of the present disclosure comprise at least one, two, three, four, five, or six HVRs selected from (i) HVR-L1 comprising the amino acid sequence of any of the HVR-L1 sequences listed in Tables 1, 2, 3A, 3B, 6A, and 6B, or from an antibody selected from 1A8, 2B4, 2E12, 2E12.1, 2F5, 2F5.1, 3A12a, 3A12b, 6A3a, 6A3b, 6C7a, 6C7b, and 6C7.2; (ii) HVR-L2 comprising the amino acid sequence of any of the HVR-L2 sequences listed in Tables 1, 2, 3A, 3B, 6A, and 6B, or from an antibody selected from 1A8, 2B4, 2E12, 2E12.1, 2F5, 2F5.1, 3A12a, 3A12b, 6A3a, 6A3b, 6C7a, 6C7b, and 6C7.2; (iii) HVR-L3 comprising the amino acid sequence of any of the HVR-L3 sequences listed in Tables 1, 2, 3A, 3B, 6A, and 6B, or from an antibody selected from 1A8, 2B4, 2E12, 2E12.1, 2F5, 2F5.1, 3A12a, 3A12b, 6A3a, 6A3b, 6C7a, 6C7b, and 6C7.2; (iv) HVR-H1 comprising the amino acid sequence of any of the HVR-H1 sequences listed in Tables 1, 2, 3A, 3B, 6A, and 6B, or from an antibody selected from 1A8, 2B4, 2E12, 2E12.1, 2F5, 2F5.1, 3A12a, 3A12b, 6A3a, 6A3b, 6C7a, 6C7b, and 6C7.2; (v) HVR-H2 comprising the amino acid sequence of any of the HVR-H2 sequences listed in Tables 1, 2, 3A, 3B, 6A, and 6B, or from an antibody selected from 1A8, 2B4, 2E12, 2E12.1, 2F5, 2F5.1, 3A12a, 3A12b, 6A3a, 6A3b, 6C7a, 6C7b, and 6C7.2; and (vi) HVR-H3 comprising the amino acid sequence of any of the HVR-H3 sequences listed in Tables 1, 2, 3A, 3B, 6A, and 6B, or from an antibody selected from 1A8, 2B4, 2E12, 2E12.1, 2F5, 2F5.1, 3A12a, 3A12b, 6A3a, 6A3b, 6C7a, 6C7b, and 6C7.2.

In some embodiments, anti-CD33 antibodies of the present disclosure comprise a light chain variable domain and a heavy chain variable domain, wherein the light chain variable domain comprises one or more of: (a) an HVR-L1 comprising an amino acid sequence selected from the group consisting of SEQ ID NOs: 9-11, 67, 68, 184, and 228, or an amino acid sequence with at least about 90% homology to an amino acid sequence selected from the group consisting of SEQ ID NOs: 9-11, 67, 68, 184, and 228; (b) an HVR-L2 comprising an amino acid sequence selected from the group consisting of SEQ ID NOs: 2-14, 69-71, 185, and 229, or an amino acid sequence with at least about 90% homology to an amino acid sequence selected from the group consisting of SEQ ID NOs: 2-14, 69-71, 185, and 229; and (c) an HVR-L3 comprising an amino acid sequence selected from the group consisting of SEQ ID NOs: 15-17, 72-74, and 230, or an amino acid sequence with at least about 90% homology to an amino acid sequence selected from the group consisting of SEQ ID NOs: 15-17, 72-74, and 230; and/or wherein the heavy chain variable domain comprises one or more of: (a) an HVR-H1 comprising an amino acid sequence selected from the group consisting of SEQ ID NOs: 18-21, 75, 231, and 232, or an amino acid sequence with at least about 90% homology to an amino acid sequence selected from the group consisting of SEQ ID NOs: 18-21, 75, 231, and 232; (b) an HVR-H2 comprising an amino acid sequence selected from the group consisting of SEQ ID NOs: 22-25, 76, 77, 186, and 233, or an amino acid sequence with at least about 90% homology to an amino acid sequence selected from the group consisting of SEQ ID NOs: 22-25, 76, 77, 186, and 233; and (c) an HVR-H3 comprising an amino acid sequence selected from the group consisting of SEQ ID NOs: 26-29, and 187, or an amino acid sequence with at least about 90% homology to an amino acid sequence selected from the group consisting of SEQ ID NOs: 26-29, and 187.

In some embodiments, anti-CD33 antibodies of the present disclosure antibodies of the present disclosure comprise a light chain variable domain and a heavy chain variable domain, wherein: (a) the HVR-L1 comprises the amino acid sequence of SEQ ID NO:9, the HVR-L2 comprises the amino acid sequence of SEQ ID NO:12, the HVR-L3 comprises the amino acid sequence of SEQ ID NO:15, the HVR-H1 comprises the amino acid sequence of SEQ ID NO:18, the HVR-H2 comprises the amino acid sequence of SEQ ID NO:22, and the HVR-H3 comprises the amino acid sequence of SEQ ID NO:26; (b) the HVR-L1 comprises the amino acid sequence of SEQ ID NO:10, the HVR-L2 comprises the amino acid sequence of SEQ ID NO:13, the HVR-L3 comprises the amino acid sequence of SEQ ID NO:16, the HVR-H1 comprises the amino acid sequence of SEQ ID NO:19, the HVR-H2 comprises the amino acid sequence of SEQ ID NO:23, and the HVR-H3 comprises the amino acid sequence of SEQ ID NO:27; (c) the HVR-L1 comprises the amino acid sequence of SEQ ID NO:10, the HVR-L2 comprises the amino acid sequence of SEQ ID NO:69, the HVR-L3 comprises the amino acid sequence of SEQ ID NO:72, the HVR-H1 comprises the amino acid sequence of SEQ ID NO:19, the HVR-H2 comprises the amino acid sequence of SEQ ID NO:23, and the HVR-H3 comprises the amino acid sequence of SEQ ID NO:27; (d) the HVR-L1 comprises the amino acid sequence of SEQ ID NO:11, the HVR-L2 comprises the amino acid sequence of SEQ ID NO:14, the HVR-L3 comprises the amino acid sequence of SEQ ID NO:17, the HVR-H1 comprises the amino acid sequence of SEQ ID NO:20, the HVR-H2 comprises the amino acid sequence of SEQ ID NO:24, and the HVR-H3 comprises the amino acid sequence of SEQ ID NO:28; (e) the HVR-L1 comprises the amino acid sequence of SEQ ID NO:68, the HVR-L2 comprises the amino acid sequence of SEQ ID NO:71, the HVR-L3 comprises the amino acid sequence of SEQ ID NO:74, the HVR-H1 comprises the amino acid sequence of SEQ ID NO:75, the HVR-H2 comprises the amino acid sequence of SEQ ID NO:77, and the HVR-H3 comprises the amino acid sequence of SEQ ID NO:28; (f) the HVR-L1 comprises the amino acid sequence of SEQ ID NO:67, the HVR-L2 comprises the amino acid sequence of SEQ ID NO:70, the HVR-L3 comprises the amino acid sequence of SEQ ID NO:73, the HVR-H1 comprises the amino acid sequence of SEQ ID NO:21, the HVR-H2 comprises the amino acid sequence of SEQ ID NO:25, and the HVR-H3 comprises the amino acid sequence of SEQ ID NO:29; (g) the HVR-L1 comprises the amino acid sequence of SEQ ID NO:67, the HVR-L2 comprises the amino acid sequence of SEQ ID NO:70, the HVR-L3 comprises the amino acid sequence of SEQ ID NO:73, the HVR-H1 comprises the amino acid sequence of SEQ ID NO:21, the HVR-H2 comprises the amino acid sequence of SEQ ID NO:76, and the HVR-H3 comprises the amino acid sequence of SEQ ID NO:29; (h) the HVR-H1 comprises the amino acid sequence of SEQ ID NO:21, the HVR-H2 comprises the amino acid sequence of SEQ ID NO:25, and the HVR-H3 comprises the amino acid sequence of SEQ ID NO:29; (i) the HVR-H1 comprises the amino acid sequence of SEQ ID NO:21, the HVR-H2 comprises the amino acid sequence of SEQ ID NO:76, and the HVR-H3 comprises the amino acid sequence of SEQ ID NO:29; (j) the HVR-L1 comprises the amino acid sequence of SEQ ID NO:184, the HVR-L2 comprises the amino acid sequence of SEQ ID NO:185, the HVR-L3 comprises the amino acid sequence of SEQ ID NO:17, the HVR-H1 comprises the amino acid sequence of SEQ ID NO:75, the HVR-H2 comprises the amino acid sequence of SEQ ID NO:186, and the HVR-H3 comprises the amino acid sequence of SEQ ID NO:187; (k) the HVR-L1 comprises the amino acid sequence of SEQ ID NO:10, the HVR-L2 comprises the amino acid sequence of SEQ ID NO:13, the HVR-L3 comprises the amino acid sequence of SEQ ID NO:72, the HVR-H1 comprises the amino acid sequence of SEQ ID NO:231, the HVR-H2 comprises the amino acid sequence of SEQ ID NO:23, and the HVR-H3 comprises the amino acid sequence of SEQ ID NO:27; or (l) the HVR-L1 comprises the amino acid sequence of SEQ ID NO:228, the HVR-L2 comprises the amino acid sequence of SEQ ID NO:229, the HVR-L3 comprises the amino acid sequence of SEQ ID NO:230, the HVR-H1 comprises the amino acid sequence of SEQ ID NO:232, the HVR-H2 comprises the amino acid sequence of SEQ ID NO:233, and the HVR-H3 comprises the amino acid sequence of SEQ ID NO:29.

In some embodiments, anti-CD33 antibodies of the present disclosure comprise a light chain variable region of any one of the antibodies listed in Tables 1, 2, 3A, 3B, 6A, and 6B, or selected from 1A8, 2B4, 2E12, 2E12.1, 2F5, 2F5.1, 3A12a, 3A12b, 6A3a, 6A3b, 6C7a, 6C7b, and 6C7.2; and/or a heavy chain variable region of any one of the antibodies listed in Tables 1, 2, 3A, 3B, 6A, and 6B, or selected from 1A8, 2B4, 2E12, 2E12.1, 2F5, 2F5.1, 3A12a, 3A12b, 6A3a, 6A3b, 6C7a, 6C7b, and 6C7.2. In some embodiments, anti-CD33 antibodies of the present disclosure comprise a light chain variable region comprising an amino acid sequence selected from any of SEQ ID NOs: 30-48, 112-153, 192-202, and 241-243; and/or a heavy chain variable domain comprising an amino acid sequence selected from the group consisting of SEQ ID NOs: 49-66, 154-183, 203-213, and 244-246.

Any of the antibodies of the present disclosure may be produced by a cell line. In some embodiments, the cell line may be a mammalian cell line. In certain embodiments, the cell line may be a hybridoma cell line. In other embodiments, the cell line may be a yeast cell line. Any cell line known in the art suitable for antibody production may be used to produce an antibody of the present disclosure. Exemplary cell lines for antibody production are described throughout the present disclosure.

In some embodiments, the anti-CD33 antibody is an anti-CD33 monoclonal antibody selected from 1A8, 2B4, 2E12, 2E12.1, 2F5, 2F5.1, 3A12a, 3A12b, 6A3a, 6A3b, 6C7a, 6C7b, and 6C7.2. In certain embodiments, the anti-CD33 antibody is an antagonist antibody. In certain embodiments, the anti-CD33 antibody is an agonist antibody or an inert antibody.

Anti-CD33 Antibody Binding Affinity

The dissociation constants ($K_D$) of anti-CD33 antibodies for human CD33, mouse CD33, or both, may be less than 100 nM, less than 90 nM, less than 80 nM, less than 70 nM, less than 60 nM, less than 50 nM, less than 40 nM, less than 30 nM, less than 20 nM, less than 10 nM, less than 9 nM, less than 8 nM, less than 7 nM, less than 6 nM, less than 5 nM, less than 4 nM, less than 3 nM, less than 2 nM, less than 1 nM, less than 0.9 nM, less than 0.8 nM, less than 0.7 nM, less than 0.6 nM, less than 0.5 nM, 1 less than 0.4 nM, less than 0.3 nM, less than 0.2 nM, less than 0.19 nM, less than 0.18 nM, less than 0.17 nM, less than 0.16 nM, less than 0.15 nM, less than 0.14 nM, less than 0.13 nM, less than 0.12 nM, less than 0.11 nM, less than 0.1 nM, less than 0.05 nM, less than 0.01 nM, or less than 0.005 nM. In some embodiments, the antibody has a dissociation constant ($K_D$) for human CD33, mouse CD33, or both, that ranges from about 100 nM to about 100 pM, or less than 100 pM (i.e., 0.1 nM). In some embodiments, the antibody has a dissociation constant ($K_D$) for human CD33, mouse CD33, or both, that ranges from about 10 nM to about 500 pM, or less than 500 pM (i.e., 0.5 nM).

The dissociation constants ($K_D$) of anti-CD33 antibodies for human CD33 and mouse CD33 may be less than 100 nM, less than 90 nM, less than 80 nM, less than 70 nM, less than 60 nM, less than 50 nM, less than 40 nM, less than 30 nM, less than 20 nM, less than 10 nM, less than 9 nM, less than 8 nM, less than 7 nM, less than 6 nM, less than 5 nM, less than 4 nM, less than 3 nM, less than 2 nM, less than 1 nM, less than 0.9 nM, less than 0.8 nM, less than 0.7 nM, less than 0.6 nM, less than 0.5 nM, 1 less than 0.4 nM, less than 0.3 nM, less than 0.2 nM, less than 0.1 nM, less than 0.05 nM, less than 0.01 nM, or less than 0.005 nM. In some embodiments, dissociation constants of anti-CD33 antibodies for human CD33 proteins range from about 100 nM to about 100 pM, or less than 100 pM (i.e., 0.1 nM). In some embodiments, dissociation constants of anti-CD33 antibodies for human CD33 proteins range from about 10 nM to about 500 pM, or less than 500 pM (i.e., 0.5 nM). In some embodiments, dissociation constants of anti-CD33 antibodies for mouse CD33 proteins range from about 100 nM to about 100 pM, or less than 100 pM (i.e., 0.1 nM). In some embodiments, the dissociation constant ($K_D$) for CD33 is determined at a temperature of approximately 25° C. In some embodiments, the $K_D$ is determined using a monovalent antibody (e.g., a Fab) or a full-length antibody in a monovalent form.

The dissociation constants ($K_D$) of anti-CD33 antibodies for human CD33 and/or mouse CD33 may be less than 500 pM, less than 450 pM, less than 400 pM, less than 350 pM, less than 300 pM, less than 250 pM, less than 200 pM, less than 175 pM, less than 150 pM, less than 145 pM, less than 140 pM, less than 135 pM, less than 130 pM, less than 125 pM, less than 120 pM, less than 115 pM, less than 110 pM, less than 100 pM, less than 90 pM, less than 80 pM, less than 70 pM, less than 60 pM, less than 50 pM, less than 40 pM, less than 30 pM, less than 20 pM, or less than 10 pM. In some embodiments, dissociation constants of anti-CD33 antibodies for human CD33 proteins range from about 300 pM to about 10 pM, or less than 10 pM. In some embodiments, dissociation constants of anti-CD33 antibodies for human CD33 proteins is about 300 pM or less. Dissociation constants may be determined through any analytical technique, including any biochemical or biophysical technique such as ELISA, surface plasmon resonance (SPR), bio-layer interferometry (see, e.g., Octet System by ForteBio), isothermal titration calorimetry (ITC), differential scanning calorimetry (DSC), circular dichroism (CD), stopped-flow analysis, and colorimetric or fluorescent protein melting analyses. In some embodiments, the dissociation constant ($K_D$) for CD33 is determined at a temperature of approximately 25° C. In some embodiments, the $K_D$ is determined using a monovalent antibody (e.g., a Fab) or a full-length antibody. In some embodiments, the $K_D$ is determined using a full-length antibody in a monovalent form. Utilizing, for example, a surface plasmon resonance assay as described herein (see, e.g., Example 1).

Additional anti-CD33 antibodies, e.g., antibodies that specifically bind to a CD33 protein of the present disclosure, may be identified, screened, and/or characterized for their physical/chemical properties and/or biological activities by various assays known in the art.

Anti-CD33 Antibodies Capable of Binding Fc Gamma Receptors

In some embodiments, anti-CD33 antibodies of the present disclosure retain the ability to bind Fc gamma receptors. In some embodiments, such antibodies when they have the correct epitope specificity that is compatible with receptor activation may have features that enable them to cluster and transiently stimulate, for example, the CD33 receptor. In some embodiments, such antibodies may subsequently act as longer-term inhibitors of CD33 expression and/or one or more activities of a CD33 protein by inducing CD33 degradation, CD33 desensitization, CD33 cleavage, CD33 internalization, CD33 shedding, downregulation of CD33 expression, and/or lysosomal degradation of CD33.

In vivo, anti-CD33 antibodies of the present disclosure may cluster receptors and transiently activate CD33 by any one or more of multiple potential mechanisms. Some isotypes of human antibodies such as IgG2 have, due to their unique structure, an intrinsic ability to cluster receptors, or retain receptors in a clustered configuration, thereby transiently activating receptors such as CD33 without binding to an Fc receptor (e.g., White et al., (2015) Cancer Cell 27, 138-148).

In some embodiments, other antibodies may cluster receptors (e.g., CD33) by binding to Fcg receptors on adjacent cells. In some embodiments, binding of the constant IgG Fc region of the antibody to Fcg receptors may lead to aggregation of the antibodies, and the antibodies in turn may aggregate the receptors to which they bind through their variable region (Chu et al (2008) Mol Immunol, 45:3926-3933; and Wilson et al., (2011) Cancer Cell 19, 101-113). In some embodiments, binding to the inhibitory Fcg receptor FcgR (FcgRIIB) that does not elicit cytokine secretion, oxidative burst, increased phagocytosis, and enhanced antibody-dependent, cell-mediated cytotoxicity (ADCC) is a preferred way to cluster antibodies in vivo, since binding to FcgRIIB is not associated with adverse immune response effects.

There are other mechanisms by which anti-CD33 antibodies of the present disclosure can cluster receptors. For example, antibody fragments (e.g., Fab fragments) that are cross-linked together may be used to cluster receptors (e.g., CD33) in a manner similar to antibodies with Fc regions that bind Fcg receptors, as described above. In some embodiments, cross-linked antibody fragments (e.g., Fab fragments) may transiently function as agonist antibodies if they induce receptor clustering on the cell surface and bind an appropriate epitope on the target (e.g., CD33).

Therefore, in some embodiments, antibodies of the present disclosure that bind a CD33 protein may include agonist antibodies that due to their epitope specificity bind CD33 and transiently activate one or more CD33 activities before they, for example, decrease cellular levels of CD33, inhibit one or more CD33 activities, and/or inhibit interaction (e.g., binding) between CD33 and one or more CD33 ligands. In some embodiments, such antibodies may bind to the ligand-binding site on CD33 and transiently mimic the action of a natural ligand, or stimulate the target antigen to transduce signal by binding to one or more domains that are not the ligand-binding sites. In some embodiments, such antibodies would not interfere with ligand binding. In some embodiments, regardless of whether antibodies bind or do not bind to the ligand-binding site on CD33, the antibodies may subsequently act as longer term inhibitors of CD33 expression and/or one or more activities of a CD33 protein by inducing CD33 degradation, CD33 desensitization, CD33 cleavage, CD33 internalization, CD33 shedding, downregulation of CD33 expression, and/or lysosomal degradation of CD33.

In some embodiments, an anti-CD33 antibody of the present disclosure is a transient agonist antibody that transiently induces one or more activities of a CD33 protein. In some embodiments, the antibody transiently induces the one or more activities after binding to a CD33 protein that is expressed in a cell. In some embodiments, the CD33 protein is expressed on a cell surface. In some embodiments, the one or more activities of a CD33 protein that are transiently induced by transient agonist anti-CD33 antibodies of the present disclosure may include, without limitation, phosphorylation of Tyr-340 and Tyr-358 by a Src family tyrosine kinase, such as LCK and FYN; recruitment of and binding to the tyrosine-specific protein phosphatases SHP1 and SHP2; recruitment of and binding to PLC-gamma1, which acts as a guanine nucleotide exchange factor for Dynamini-1; recruitment of and binding to SH2-domain containing protein (e.g., Crkl); recruitment of and binding to the spleen tyrosine kinase Syk; recruitment of and binding to SH3-SH2-SH3 growth factor receptor-bound protein 2 (Grb2); recruitment of and binding to multiple SH2-containing proteins; phosphorylation of Ser-307 and Ser-342 by protein kinase C; modulated expression of one or more anti-inflammatory cytokines, IL-4, IL-10, IL-13, IL-35, IL-16, TGF-beta, IL-1Ra, G-CSF, and soluble receptors for TNF, IFN-beta1a, IFN-beta1b, or IL-6 in monocytes, macrophages, T cells, dendritic cells neutrophils, and/or microglia; decreasing intracellular calcium mobilization; modulated expression of one or more pro-inflammatory cytokines IFN-a4, IFN-b, IL-1β, TNF-α, IL-6, IL-8, CRP, IL-20 family members, LIF, IFN-gamma, OSM, CNTF, GM-CSF, IL-11, IL-12, IL-17, IL-18, IL-23, CXCL10, IL-33, CRP, IL-33, MCP-1, and MIP-1-beta in monocytes, macrophages, T cells, dendritic cells, neutrophils, and/or microglia; modulated expression of one or more proteins selected from C1qa, C1qB, C1qC, C1s, C1R, C4, C2, C3, ITGB2, HMOX1, LAT2, CASP1, CSTA, VSIG4, MS4A4A, C3AR1, GPX1, TyroBP, ALOX5AP, ITGAM, SLC7A7, CD4, ITGAX, PYCARD, CD14, CD16, HLA-DR, and CCR2; inhibition of extracellular signal-regulated kinase (ERK) phosphorylation; decreasing tyrosine phosphorylation on multiple cellular proteins; modulated expression of C-C chemokine receptor 7 (CCR7); inhibition of microglial cell chemotaxis toward CCL19 and CCL21 expressing cells; activation of phosphoinositide 3-kinase; reducing cell growth of monocytes, macrophages, T cells, dendritic cells and/or microglia; reducing T cell proliferation induced by dendritic cells, bone marrow-derived dendritic cells, monocytes, microglia, M1 microglia, activated M1 microglia, M2 microglia, macrophages, M1 macrophages, activated M1 macrophages, and/or M2 macrophages; inhibition of osteoclast production, decreased rate of osteoclastogenesis, or both; decreasing survival of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; decreasing proliferation of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; inhibiting migration of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; decreasing one or more functions of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; inhibiting maturation of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; increasing cell death and apoptosis of monocytes, macrophages, T cells, dendritic cells, neutrophils, and/or microglia; reducing phagocytic activity of monocytes, macrophages, T cells, dendritic cells, neutrophils, and/or microglia; reducing proliferation of monocytes, macrophages, T cells, dendritic cells, neutrophils, and/or microglia; reducing the overall functionality of monocytes, macrophages, T cells, dendritic cells, neutrophils, and/or microglia, phosphorylation of an ITAM containing receptor; phosphorylation of a signaling molecules that mediates ITAM signaling; reducing the activation of pattern recognition receptors; reducing the activation of Toll-like receptors; reducing the activation of damage-associated of clearance of cellular and protein debris; interaction between CD33 and one or more of its ligands; interaction between CD33 and a co-receptor such as CD64; reducing one or more types of clearance selected from apoptotic neuron clearance, dysfunctional synapse clearance, nerve tissue debris clearance, non-nerve tissue debris clearance, bacteria or other foreign body clearance, disease-causing protein clearance, and tumor cell clearance; inhibition of phagocytosis of one or more of apoptotic neurons, nerve tissue debris, non-nerve tissue debris, bacteria, other foreign bodies, disease-causing proteins, disease-causing peptides, disease-causing nucleic acid, disease-causing lipids, or tumor cells; inhibition of clearance of a disease-causing nucleic acid, such as the disease-causing nucleic acid is antisense GGCCCC (G2C4) repeat-expansion RNA; activation of clearance of, a disease-causing protein selected from amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides; inhibition of beneficial immune response to different types of cancer selected from bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, acute myeloid leukemia, pancreatic cancer, prostate cancer, ovarian cancer, fibrosarcoma, and thyroid cancer; inhibition of beneficial immune response to different types of neurological disorders selected from dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, essential tremor, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, Sarcoidosis, diseases of aging, seizures, spinal cord injury, -traumatic brain injury, age related macular degeneration, glaucoma, retinitis pigmentosa, retinal degeneration, and multiple sclerosis; inhibition of beneficial immune response-to different types of inflammatory and infectious disorders selected from lupus, acute and chronic colitis, wound healing, Crohn's disease, inflammatory bowel disease, ulcerative colitis, obesity, malaria, respiratory tract infection, sepsis, eye infection, systemic infection, lupus, arthritis, low bone density, osteoporosis, osteogenesis, osteopetrotic disease, and Paget's disease of bone; inhibition of phagocytosis of one or more of apoptotic neurons, nerve tissue debris, dysfunctional synapses, non-nerve tissue debris, bacteria, other foreign bodies, disease-causing proteins, disease-causing peptides, disease-causing nucleic acids, or tumor cells, where the disease-causing nucleic acids may be an antisense GGCCCC (G2C4) repeat-expansion RNA, the disease-causing proteins may include amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides, and the tumor cells may be from a cancer selected from bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, or thyroid cancer; binding to CD33 ligand on tumor cells; binding to CD33 ligand on dendritic cells, bone marrow-derived dendritic cells, monocytes, microglia, T cells, neutrophils, and/or macrophages; inhibition of tumor cell killing by one or more of microglia, macrophages, dendritic cells, bone marrow-derived dendritic cells, neutrophils, T cells, T helper cells, or cytotoxic T cells; inhibition of anti-tumor cell proliferation activity of one or more of microglia, macrophages, dendritic cells, bone marrow-derived dendritic cells, neutrophils, T cells, T helper cells, or cytotoxic T cells; inhibition of anti-tumor cell metastasis activity of one or more of microglia, macrophages, dendritic cells, bone marrow-derived dendritic cells, neutrophils, T cells, T helper cells, or cytotoxic T cells; promotion of immunosuppressor dendritic cells, immunosuppressor macrophages, myeloid-derived suppressor cells, tumor-associated macrophages, or regulatory T cells; inhibition of one or more ITAM motif containing receptors, such as TREM1, TREM2, FcgR, DAP10, and DAP12; inhibition of one or more receptors containing the motif D/Ex0-2YxxL/IX6-8YxxL/I (SEQ ID NO:247); inhibition of signaling by one or more pattern recognition receptors (PRRs), such as receptors that identify pathogen-associated molecular patterns (PAMPs), and receptors that identify damage-associated molecular patterns (DAMPs); inhibition of signaling by one or more Toll-like receptors; inhibition of the JAK-STAT signaling pathway; inhibition of nuclear factor kappa-light-chain-enhancer of activated B cells (NFκB); inhibition of PLCγ/PKC/calcium mobilization; inhibition of PI3K/Akt, Ras/MAPK signaling; modulated expression of one or more inflammatory receptors, such as CD86, expressed on one or more of microglia, macrophages, dendritic cells, bone marrow-derived dendritic cells, neutrophils, T cells, T helper cells, or cytotoxic T cells; increasing expression of one or more CD33-dependent genes; normalization of disrupted CD33-dependent gene expression; and decreasing expression of one or more ITAM-dependent genes, such as NFAT transcription factors. Anti-CD33 antibodies of the present disclosure may be tested for their ability to transiently induce one or more activities of a CD33 protein utilizing any suitable technique or assay known in the art and disclosed herein. Regardless of the activities that such antibodies transiently induce, such antibodies may subsequently act as longer-term inhibitors of CD33 expression and/or one or more activities of a CD33 protein by inducing CD33 degradation, CD33 desensitization, CD33 cleavage, CD33 internalization, CD33 shedding, downregulation of CD33 expression, and/or lysosomal degradation of CD33. In some embodiments, the CD33 antibody transiently induces one or more activities of a CD33 protein independently of binding to an Fc receptor.

Exemplary antibody Fc isotypes and modifications are provided in Table C below. In some embodiments, an anti-CD33 antibody of the present disclosure that is capable of binding an Fc gamma receptor has an Fc isotype listed in Table C below.

TABLE C

Exemplary anti-CD33 antibody Fc isotypes that are capable of binding Fc gamma receptor

| Fc Isotype | Mutation (EU numbering scheme) |
|---|---|
| IgG1 | N297A |
| IgG1 | D265A and N297A |
| IgG1 | E234A and E235A |
| | E234A and G237A |
| | E234A and E235A and G237A |
| IgG1 | D270A, and/or P238D, and/or E328E, and/or E233D, and/or G237D and/or H268D, and/or P271G, and/or A330R |
| IgG2 | V234A and G237A |
| IgG4 | E235A and G237A and E318A |
| IgG4 | S228P and E236E |
| IgG2/4 hybrid | IgG2 aa 118 to 260 and IgG4 aa 261 to 447 H268Q and V309L; and A330S and P331S |
| IgG1 | C226S and C229S and E233P and L234V and L235A |
| IgG1 | L234F and L235E and P331S |
| IgG2 | C232S or C233S |
| IgG2 | A330S and P331S |
| IgG1 | S267E, and L328F |
| | S267E alone |
| IgG2 | S267E and L328F |
| IgG4 | S267E and L328F |
| IgG2 | WT HC with Kappa (light chain) LC |
| | HC C127S with Kappa LC |
| | Kappa LC C214S |
| | Kappa LC C214S and HC C233S |
| | Kappa LC C214S and HC C232S |

TABLE C-continued

Exemplary anti-CD33 antibody Fc isotypes that are capable of binding Fc gamma receptor

| Fc Isotype | Mutation (EU numbering scheme) |
|---|---|
| | Any of the above listed mutations together with P330S and P331S mutations |
| | F(ab')2 fragment of WT IgG1 and any of the above listed mutations |
| IgG1 | Substitute the Constant Heavy 1 (CH1) and hinge region of IgG1 With CH1 and hinge region of IGg2 ASTKGPSVFP LAPCSRSTSE STAALGCLVK DYFPEPVTVS WNSGALTSGV HTFPAVLQSS GLYSLSSVVT VPSSNFGTQT YTCNVDHKPS NTKVDKTVER KCCVECPPCP (SEQ ID NO: 214) With a Kappa LC |
| IgG1 | Any of the above listed mutations together with A330L and/or L234F and/or L235E and/or P331S |
| IgG1, IgG2, or IgG4 | Any of the above listed mutations together with M252Y and/or S254T and/or T256E |
| Mouse IgG1 | For mouse disease models |
| IgG4 | WT |

In addition to the isotypes described in Table C, and without wishing to be bound to theory, it is thought that antibodies with human IgG1 or IgG3 isotypes and mutants thereof (e.g. Strohl (2009) Current Opinion in Biotechnology 2009, 20:685-691) that bind the Fcg Receptors I, IIA, IIC, IIIA, IIIB in human and/or Fcg Receptors I, III and IV in mouse, may also act as transient agonist antibodies.

In some embodiments, the Fc gamma receptor-binding antibody is of the IgG class, the IgM class, or the IgA class. In some embodiments, the Fc gamma receptor-binding antibody has an IgG1, IgG2, IgG3, or IgG4 isotype.

In certain embodiments, the Fc gamma receptor-binding antibody has an IgG2 isotype. In some embodiments, the Fc gamma receptor-binding antibody contains a human IgG2 constant region. In some embodiments, the human IgG2 constant region includes an Fc region. In some embodiments, the Fc gamma receptor-binding antibody binds an inhibitory Fc receptor. In certain embodiments, the inhibitory Fc receptor is inhibitory Fc-gamma receptor IIB (FcγIIB). In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from V234A (Alegre et al., (1994) *Transplantation* 57:1537-1543. 31; Xu et al., (2000) *Cell Immunol*, 200:16-26), G237A (Cole et al. (1999) *Transplantation*, 68:563-571), H268Q, V309L, A330S, P331S (US 2007/0148167; Armour et al. (1999) *Eur J Immunol* 29: 2613-2624; Armour et al. (2000) *The Haematology Journal* 1(Suppl.1):27; Armour et al. (2000) *The Haematology Journal* 1(Suppl.1):27), C232S, and/or C233S (White et al. (2015) Cancer Cell 27, 138-148), S267E, L328F (Chu et al., (2008) *Mol Immunol*, 45:3926-3933), M252Y, S254T, and/or T256E, where the amino acid position is according to the EU or Kabat numbering convention.

In some embodiments, the Fc gamma receptor-binding antibody has an IgG2 isotype with a heavy chain constant domain that contains a C127S amino acid substitution, where the amino acid position is according to the EU or Kabat numbering convention (White et al., (2015) Cancer Cell 27, 138-148; Lightle et al., (2010) *PROTEIN SCIENCE* 19:753-762; and WO2008079246).

In some embodiments, the Fc gamma receptor-binding antibody has an IgG2 isotype with a Kappa light chain constant domain that contains a C214S amino acid substitution, where the amino acid position is according to the EU or Kabat numbering convention (White et al., (2015) Cancer Cell 27, 138-148; Lightle et al., (2010) PROTEIN SCIENCE 19:753-762; and WO2008079246).

In certain embodiments, the Fc gamma receptor-binding antibody has an IgG1 isotype. In some embodiments, the Fc gamma receptor-binding antibody contains a mouse IgG1 constant region. In some embodiments, the Fc gamma receptor-binding antibody contains a human IgG1 constant region. In some embodiments, the human IgG1 constant region includes an Fc region. In some embodiments, the Fc gamma receptor-binding antibody binds an inhibitory Fc receptor. In certain embodiments, the inhibitory Fc receptor is inhibitory Fc-gamma receptor IIB (FcγIIB). In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from N297A (Bolt S et al. (1993) Eur J Immunol 23:403-411), D265A (Shields et al. (2001) R. J. Biol. Chem. 276, 6591-6604), D270A, L234A, L235A (Hutchins et al. (1995) Proc Natl Acad Sci USA, 92:11980-11984; Alegre et al., (1994) Transplantation 57:1537-1543. 31; Xu et al., (2000) Cell Immunol, 200:16-26), G237A (Alegre et al. (1994) Transplantation 57:1537-1543. 31; Xu et al. (2000) Cell Immunol, 200:16-26), P238D, L328E, E233D, G237D, H268D, P271G, A330R, C226S, C229S, E233P, L234V, L234F, L235E (McEarchern et al., (2007) Blood, 109:1185-1192), P331S (Sazinsky et al., (2008) Proc Natl Acad Sci USA 2008, 105:20167-20172), S267E, L328F, A330L, M252Y, S254T, T256E, N297Q, P238S, P238A, A327Q, A327G, P329A, K322A, and/or T394D, where the amino acid position is according to the EU or Kabat numbering convention.

In some embodiments, the antibody includes an IgG2 isotype heavy chain constant domain 1 (CH1) and hinge region (White et al., (2015) Cancer Cell 27, 138-148). In certain embodiments, the IgG2 isotype CH1 and hinge region contain the amino acid sequence of ASTKGPSVF-PLAPCSRSTSESTAALGCLVKDYFPEPVTVSW-NSGALTSGVHTFPAVLQSSGLY SLSSVVTVPSSNFG-TQTYTCNVDHKPSNTKVDKTVERKCCVECPPCP (SEQ ID NO:214). In some embodiments, the antibody Fc region contains a S267E amino acid substitution, a L328F amino acid substitution, or both, and/or a N297A or N297Q amino acid substitution, where the amino acid position is according to the EU or Kabat numbering convention.

In certain embodiments, the Fc gamma receptor-binding antibody has an IgG4 isotype. In some embodiments, the Fc gamma receptor-binding antibody contains a human IgG4 constant region. In some embodiments, the human IgG4 constant region includes an Fc region. In some embodiments, the Fc gamma receptor-binding antibody binds an inhibitory Fc receptor. In certain embodiments, the inhibitory Fc receptor is inhibitory Fc-gamma receptor IIB (FcγIIB). In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from L235A, G237A, S228P, L236E (Reddy et al., (2000) J Immunol, 164:1925-1933), S267E, E318A, L328F, M252Y, S254T, and/or T256E, where the amino acid position is according to the EU or Kabat numbering convention.

In certain embodiments, the Fc gamma receptor-binding antibody has a hybrid IgG2/4 isotype. In some embodiments, the Fc gamma receptor-binding antibody includes an amino acid sequence containing amino acids 118 to 260 according to EU or, Kabat numbering of human IgG2 and amino acids 261-447 according to EU or, Kabat numbering of human IgG4 (WO 1997/11971; WO 2007/106585).

In certain embodiments, the antibody contains a mouse IgG4 constant region (Bartholomaeus, et al. (2014). J. Immunol. 192, 2091-2098).

In some embodiments, the Fc region further contains one or more additional amino acid substitutions selected from the group consisting of A330L, L234F; L235E, or P331S according to EU or, Kabat numbering; and any combination thereof.

Inert Antibodies

Another class of anti-CD33 antibodies of the present disclosure includes inert antibodies. As used herein, "inert" antibodies refer to antibodies that specifically bind their target antigen (e.g., CD33) but do not modulate (e.g., decrease/inhibit or activate/induce) antigen function. For example, in the case of CD33, inert antibodies do not modulate cellular levels of CD33, do not modulate interaction (e.g., binding) between CD33 and one or more CD33 ligands, or do not modulate one or more activities of a CD33 protein. In some embodiments, antibodies that do not have the ability to cluster CD33 on the cell surface may be inert antibodies even if they have an epitope specificity that is compatible with receptor activation.

In some embodiments, antibodies that bind a CD33 protein may include antibodies that bind CD33 but, due to their epitope specificity, or characteristics, do not decrease cellular levels of CD33 and/or inhibit interaction (e.g., binding) between CD33 and one or more CD33 ligands. In some embodiments, such antibodies can be used as cargo to, for example, transport toxins (e.g., chemotherapeutics) into tumor cells. Such antibodies may be superior to current commercially available anti-CD33 antibodies that reduce cellular levels of CD33, such as gemtuzumab zogamicin, which is conjugated to a cytotoxic agent from the class of calicheamicins and is used to target and kill acute myelogenous leukemia tumors (Naito et al., (2000), Leukemia, 14, 1436-1443; Ricart (2011) Clin Cancer Res 17; 6417-6436; Hamann et al., (2002) Journal: Bioconjugate Chemistry, 13, 47-58; Beitz et al., (2001) Clin Cancer Res 7; 1490-6; and Malik M. et al. (2015) Human Molecular Genetics, 1-14). In some embodiments, inert anti-CD33 antibodies of the present disclosure may be superior to commercial antibodies, such as gemtuzumab zogamicin, because antibodies that do not decrease cellular levels of CD33 will leave CD33 intact on the surface of tumor cells for targeting by additional toxin-conjugated antibodies. In contrast, antibodies that decrease cellular levels of CD33 will remove CD33 from the cell surface and will lead to protection of the tumor cells from further targeting by toxin-conjugated antibodies. Therefore, in some embodiments, antibodies of the present disclosure are inert antibodies that bind CD33 but are incapable of decreasing cellular levels of CD33, inhibiting interaction (e.g., binding) between CD33 and one or more CD33 ligands, or inducing one or more activities of a CD33 protein.

Antibodies that either decrease or do not decrease cellular levels of CD33 on cells can be combined with an inert Fc region that displays reduced binding to one or more Fcg Receptor. Examples of such Fc regions and modifications are provided in Table D below. In some embodiments, the antibody with an inert Fc region has an Fc isotype listed in Table D below.

Antagonist Anti-CD33 Antibodies

A third class of anti-CD33 antibodies of the present disclosure includes antagonist antibodies. In some embodiments, antibodies that bind a CD33 protein may include antagonist antibodies that reduce cellular levels of CD33, inhibit interaction (e.g., binding) between CD33 and/or one or more CD33 ligands, and inhibit one or more activities of a CD33 protein. Such antibodies inhibit one or more activities of a CD33 protein either by preventing interaction (e.g., binding) between CD33 and one or more CD33 ligands or by preventing signal transduction from the extracellular domain of CD33 into the cell cytoplasm in the presence of one or more CD33 ligands. Antagonist antibodies also can inhibit one or more activities of a CD33 protein by decreasing cell surface levels of CD33 by inducing CD33 degradation, CD33 desensitization, CD33 cleavage, CD33 internalization, CD33 shedding, downregulation of CD33 expression, and/or lysosomal degradation of CD33. In some embodiments, such antagonist anti-CD33 antibodies may not transiently activate CD33.

In some embodiments, antagonist anti-CD33 antibodies of the present disclosure may have the epitope specificity of a transient agonist anti-CD33 antibody of the present disclosure, but have an Fc domain that is not capable of binding Fcg receptors and thus is unable to, for example, transiently clustering and activating CD33.

In some embodiments, antagonist anti-CD33 antibodies of the present disclosure have, without limitation, one or more of the following activities: the ability to decrease binding of a CD33 protein to one or more CD33 ligands, such as sialic acid-containing glycolipid s or sialic acid-containing glycoproteins, the ability to decrease the binding of a suppressor of cytokine signaling (SOCS) protein (e.g., SOCS3 protein) to a CD33 protein, the ability to increase the proteasomal degradation of a CD33 protein, the ability to reduce functional expression of CD33 on the surface of circulating dendritic cells, macrophages, monocytes, T cells, and/or microglia, the ability to decrease phosphorylation of Tyr-340 and Tyr-358 by a Src family tyrosine kinase such as LCK and FYN, the ability to decrease recruitment of and binding to the tyrosine-specific protein phosphatases SHP1 and SHP2, the ability to decrease recruitment of and binding to PLC-g1, which acts as a guanine nucleotide, exchange factor for Dynamin-1, the ability to decrease recruitment of and binding to Crkl, the ability to decrease recruitment of and binding to the Spleen tyrosine kinase Syk, the ability to decrease recruitment of and binding to SH3-SH2-SH3 growth factor receptor-bound protein 2 (Grb2), the ability to decrease recruitment of and binding to multiple SH2 containing proteins, the ability to increase intracellular calcium mobilization, the ability to modulate production of pro-inflammatory cytokines IL-1β, IL-8, and TNF-α, the ability to decrease activation of phosphoinositide 3-kinase, the ability to increase the growth of monocytes, macrophages, dendritic cells, T cells, and/or microglia, the ability to increase the survival of monocytes, macrophages, dendritic cells, T cells, and/or microglia, the ability to increase tyrosine phosphorylation on multiple cellular proteins, the ability to increase phagocytic activity of monocytes, macrophages, dendritic cells and/or microglia, the ability to increase cell proliferation of monocytes, macrophages, dendritic cells, T cells, and/or microglia, the ability to increase phosphorylation of signaling molecules that mediates ITAM signaling, the ability to increase the function of pattern recognition receptors, the ability to increase the function of Toll-like receptors, the ability to increases the function of damage-associated molecular pattern (DAMP) receptors, the ability to modulate expression of C-C chemokine receptor 7 (CCR7), and the ability to increase of clearance of cellular and protein debris.

In some embodiments, antagonist anti-CD33 antibodies of the present disclosure have an Fc region that displays reduced binding to one or more Fcg Receptor. Examples of such Fc regions and modifications are provided in Table D below. In some embodiments, the antibody has an Fc isotype listed in Table D below.

Antibody Fc Isotypes with Reduced Binding to Fc Gamma Receptors

In some embodiments, anti-CD33 antibodies with reduced binding to Fc gamma receptors have an Fc isotype listed in Table D below.

TABLE D

Exemplary anti-CD33 antibody Fc isotypes with reduced binding to Fc gamma receptor

| Fc Isotype | Mutation (EU numbering scheme) |
|---|---|
| IgG1 | N297A or N297Q and/or D270A |
| IgG1 | D265A and N297A |
| IgG1 | L234A and L235A |
| IgG2 | V234A and G237A |
| IgG4 | F235A and G237A and E318A |
| | E233P and/or F234V |
| | N297A or N297Q |
| IgG4 | S228P and L236E |
| | S241P |
| | S241P and L248E |
| | S228P and F234A and L235A |
| IgG2 | H268Q and V309L and A330S and P331S |
| IgG1 | C220S and C226S and C229S and P238S |
| IgG1 | C226S and C229S and E233P and L234V, and L235A |
| IgG1 | E233P and L234V and L235A and G236-deleted |
| | P238A |
| | D265A |
| | N297A |
| | A327Q or A327G |
| | P329A |
| IgG1 | K322A and L234A and L235A |
| IgG1 | L234F and L235E and P331S |
| IgG1 or IgG4 | T394D |
| IgG2 | C232S or C233S |
| | N297A or N297Q |
| IgG2 | V234A and G237A and P238S and H268A and V309L and A330S and P331S |
| IgG1, IgG2, or IgG4 | delta a, b, c, ab, ac, g modifications |
| IgG1 | Any of the above listed mutations together with A330L or L234F and/or L235E and/or P331S |
| IgG1, IgG2, or IgG4 | Any of the above listed mutations together with M252Y and/or S254T and/or T256E |

In certain embodiments, the anti-CD33 antibody has an IgG1 isotype. In some embodiments, the antibody contains a mouse IgG1 constant region. In some embodiments, the antibody contains a human IgG1 constant region. In some embodiments, the human IgG1 constant region includes an Fc region. In some embodiments, the Fc region contains one or more modifications. For example, in some embodiments, the Fc region contains one or more amino acid substitutions (e.g., relative to a wild-type Fc region of the same isotype).

In some embodiments, the one or more amino acid substitutions are selected from N297A, N297Q (Bolt S et al. (1993) *Eur J Immunol* 23:403-411), D265A, D270A, L234A, L235A (McEarchern et al., (2007) *Blood,* 109:1185-1192), C226S, C229S (McEarchern et al., (2007) *Blood,*

109:1185-1192), P238S (Davis et al., (2007) *J Rheumatol,* 34:2204-2210), E233P, L234V (McEarchern et al., (2007) *Blood,* 109:1185-1192), P238A, A327Q, A327G, P329A (Shields R L. et al., (2001) *J Biol Chem.* 276(9):6591-604), K322A, L234F, L235E (Hezareh, et al., (2001) *J Virol* 75, 12161-12168; Oganesyan et al., (2008). *Acta Crystallographica* 64, 700-704), P331S (Oganesyan et al., (2008) *Acta Crystallographica* 64, 700-704), T394D (Wilkinson et al. (2013) MAbs 5(3): 406-417), A330L, M252Y, S254T, and/or T256E, where the amino acid position is according to the EU or Kabat numbering convention. In certain embodiments, the Fc region further includes an amino acid deletion at a position corresponding to glycine 236 according to the EU or Kabat numbering convention.

In some embodiments, the anti-CD33 antibody has an IgG1 isotype with a heavy chain constant region that contains a C220S amino acid substitution according to the EU or Kabat numbering convention. In some embodiments, the Fc region further contains one or more additional amino acid substitutions selected from A330L, L234F; L235E, and/or P331S according to EU or Kabat numbering convention. In certain embodiments, the anti-CD33 antibody has an IgG2 isotype. In some embodiments, the anti-CD33 antibody contains a human IgG2 constant region. In some embodiments, the human IgG2 constant region includes an Fc region. In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from P238S, V234A, G237A, H268A, H268Q, H268E, V309L, N297A, N297Q, V309L, A330S, P331S, C232S, C233S, M252Y, S254T, and/or T256E, where the amino acid position is according to the EU or Kabat numbering convention (Vafa O. et al., (2014) Methods 65:114-126).

In certain embodiments, the anti-CD33 antibody has an IgG4 isotype. In some embodiments, the anti-CD33 antibody contains a human IgG4 constant region. In some embodiments, the human IgG4 constant region includes an Fc region. In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from E233P, F234V, L235A, G237A, E318A (Hutchins et al. (1995) *Proc Natl Acad Sci USA,* 92:11980-11984), S228P, L234A/F234A, L236E, S241P, L248E (Reddy et al., (2000) *J Immunol,* 164:1925-1933; Angal et al., (1993) *Mol Immunol.* 30(1):105-8; U.S. Pat. No. 8,614,299 B2; Vafa O. et al., (2014) *Methods* 65:114-126), T394D, M252Y, S254T, T256E, N297A, and/or N297Q, where the amino acid position is according to the EU or Kabat numbering convention.

In some embodiments, the Fc region further contains one or more additional amino acid substitutions selected from a M252Y, S254T, and/or T256E, where the amino acid position is according to the EU or Kabat numbering convention.

Further IgG Mutations

In some embodiments, one or more of the IgG1 variants described herein may be combined with an A330L mutation (Lazar et al., (2006) Proc Natl Acad Sci USA, 103:4005-4010), or one or more of L234F, L235E, and/or P331S mutations (Sazinsky et al., (2008) Proc Natl Acad Sci USA, 105:20167-20172), where the amino acid position is according to the EU or Kabat numbering convention, to eliminate complement activation. In some embodiments, the IgG variants described herein may be combined with one or more mutations to enhance the anti-CD33 antibody half-life in human serum (e.g. M252Y, S254T, T256E mutations according to the EU or Kabat numbering convention) (Dall'Acqua et al., (2006) J Biol Chem, 281:23514-23524; and Strohl e al., (2009) Current Opinion in Biotechnology, 20:685-691).

In some embodiments, an IgG4 variant of the present disclosure may be combined with an S228P mutation according to the EU or Kabat numbering convention (Angal et al., (1993) Mol Immunol, 30:105-108) and/or with one or more mutations described in Peters et al., (2012) J Biol Chem. 13; 287(29):24525-33) to enhance antibody stabilization.

Bispecific Antibodies

Certain aspects of the present disclosure relate to bispecific antibodies that bind to one or more domains on a CD33 protein of the present disclosure and a second antigen. Methods of generating bispecific antibodies are well known in the art and described herein. In some embodiments, bispecific antibodies of the present disclosure bind to one or more amino acid residues of a CD33 protein of the present disclosure, such as one or more amino acid residues of human CD33 (SEQ ID NO:1), or amino acid residues on a CD33 protein corresponding to amino acid residues of SEQ ID NO:1. In some embodiments, bispecific antibodies of the present disclosure recognize a first antigen and a second antigen. In some embodiments, the first antigen is a CD33 protein or a naturally occurring variant thereof. In some embodiments, the second antigen is also a CD33 protein, or a naturally occurring variant thereof. In some embodiments, the second antigen is an antigen facilitating transport across the blood-brain-barrier (see, e.g., Gabathuler R., *Neurobiol. Dis.* 37 (2010) 48-57). Such second antigens include, without limitation, transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, Angiopep peptides such as ANG1005 (see, e.g., Gabathuler, 2010), and other cell surface proteins that are enriched on blood-brain barrier endothelial cells (see, e.g., Daneman et al., PLoS One. 2010 Oct. 29; 5(10):e13741). In some embodiments, the second antigen is a disease-causing protein including, without limitation, amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides. In some embodiments, the second antigen is one or more ligands and/or proteins expressed on immune cells, including without limitation, CD40, OX40, ICOS, CD28, CD137/4-1BB, CD27, GITR, PD-L1, CTLA4, PD-L2, PD-1, B7-H3, B7-H4, HVEM, BTLA, KIR, GAL9, TIM3, A2AR, LAG, DR-5, CD3, and phosphatidylserine. In some embodiments, the second antigen is a protein, lipid, polysaccharide, or glycolipid expressed on one or more tumor cells.

Antibody Fragments

Certain aspects of the present disclosure relate to antibody fragments that bind to one or more of a CD33 protein of the present disclosure, a naturally occurring variant of a CD33 protein, and a disease variant of a CD33 protein. In some embodiments, the antibody fragment is an Fab, Fab', Fab'-SH, F(ab')2, Fv or scFv fragment.

In some embodiments, the antibody fragment is used in combination with a second CD33 antibody and/or with one or more antibodies that specifically bind a disease-causing protein selected from: amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides, and any combination thereof; or with one or more antibodies that bind an immunomodulatory protein selected from the group consisting of: CD40, OX40, ICOS, CD28, CD137/4-1BB, CD27, GITR, PD-L1, CTLA4, PD-L2, PD-1, B7-H3, B7-H4, HVEM, BTLA, KIR, GAL9, TIM3, A2AR, LAG, DR5, TREM1, TREM2, CSF-1 receptor, Siglec-5, Siglec-7, Siglec-9, Siglec-11, phosphatidylserine, and any combination thereof.

In some embodiments, antibody fragments of the present disclosure may be functional fragments that bind the same epitope as any of the anti-CD33 antibodies of the present disclosure. In some embodiments, the antibody fragments are miniaturized versions of the anti-CD33 antibodies or antibody fragments of the present disclosure that have the same epitope of the corresponding full-length antibody, but have much smaller molecule weight. Such miniaturized anti-CD33 antibody fragments may have better brain penetration ability and a shorter half-life, which is advantageous for imaging and diagnostic utilities (see e.g., Lütje S et al., Bioconjug Chem. 2014 Feb. 19; 25(2):335-41; Tavaré R et al., Proc Natl Acad Sci USA. 2014 Jan. 21; 111(3):1108-13; and Wiehr S et al., Prostate. 2014 May; 74(7):743-55). Accordingly, in some embodiments, anti-CD33 antibody fragments of the present disclosure have better brain penetration as compared to their corresponding full-length antibodies and/or have a shorter half-life as compared to their corresponding full-length antibodies.

Antibody Frameworks

Any of the antibodies described herein further include a framework. In some embodiments, the framework is a human immunoglobulin framework. For example, in some embodiments, an antibody (e.g., an anti-CD33 antibody) comprises HVRs as in any of the above embodiments and further comprises an acceptor human framework, e.g., a human immunoglobulin framework or a human consensus framework. Human immunoglobulin frameworks may be part of the human antibody, or a non-human antibody may be humanized by replacing one or more endogenous frameworks with human framework region(s). Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J. Biol. Chem. 271:22611-22618 (1996)).

In some embodiments, an antibody comprises a light chain variable region comprising an HVR-L1, an HVR-L2, and an HVR-L3 of the present disclosure and one, two, three or four of the light chain framework regions of the light chain variable regions depicted in Table 3A. In some embodiments, an antibody comprises a heavy chain variable region comprising an HVR-H1, an HVR-H2, and an HVR-H3 of the present disclosure and one, two, three or four of the heavy chain framework regions of the heavy chain variable regions depicted in Table 3B. In some embodiments, an antibody comprises a light chain variable region comprising an HVR-L1, an HVR-L2, and an HVR-L3 of the present disclosure and one, two, three or four of the light chain framework regions of the light chain variable regions depicted in Table 3A, and further comprises a heavy chain variable region comprising an HVR-H1, an HVR-H2, and an HVR-H3 of the present disclosure and one, two, three or four of the heavy chain framework regions of the heavy chain variable regions depicted in Table 3B.

Antibody Preparation

Anti-CD33 antibodies of the present disclosure can encompass polyclonal antibodies, monoclonal antibodies, humanized and chimeric antibodies, human antibodies, antibody fragments (e.g., Fab, Fab'-SH, Fv, scFv, and F(ab')$_2$), bispecific and polyspecific antibodies, multivalent antibodies, heteroconjugate antibodies, conjugated antibodies, library derived antibodies, antibodies having modified effector functions, fusion proteins containing an antibody portion, and any other modified configuration of the immunoglobulin molecule that includes an antigen recognition site, such as an epitope having amino acid residues of a CD33 protein of the present disclosure, including glycosylation variants of antibodies, amino acid sequence variants of antibodies, and covalently modified antibodies. The anti-CD33 antibodies may be human, murine, rat, or of any other origin (including chimeric or humanized antibodies).

(1) Polyclonal Antibodies

Polyclonal antibodies, such as polyclonal anti-CD33 antibodies, are generally raised in animals by multiple subcutaneous (sc) or intraperitoneal (ip) injections of the relevant antigen and an adjuvant. It may be useful to conjugate the relevant antigen (e.g., a purified or recombinant CD33 protein of the present disclosure) to a protein that is immunogenic in the species to be immunized, e.g., keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, SOCl$_2$, or $R^1N=C=NR$, where R and $R^1$ are independently lower alkyl groups. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The animals are immunized against the desired antigen, immunogenic conjugates, or derivatives by combining, e.g., 100 μg (for rabbits) or 5 μg (for mice) of the protein or conjugate with 3 volumes of Freund's complete adjuvant and injecting the solution intradermally at multiple sites. One month later, the animals are boosted with ⅕ to ¹⁄₁₀ the original amount of peptide or conjugate in Freund's complete adjuvant by subcutaneous injection at multiple sites. Seven to fourteen days later, the animals are bled and the serum is assayed for antibody titer Animals are boosted until the titer plateaus. Conjugates also can be made in recombinant cell culture as protein fusions. Also, aggregating agents such as alum are suitable to enhance the immune response.

(2) Monoclonal Antibodies

Monoclonal antibodies, such as monoclonal anti-CD33 antibodies, are obtained from a population of substantially homogeneous antibodies, i.e., the individual antibodies comprising the population are identical except for possible naturally occurring mutations and/or post-translational modifications (e.g., isomerizations, amidations) that may be present in minor amounts. Thus, the modifier "monoclonal" indicates the character of the antibody as not being a mixture of discrete antibodies.

For example, the monoclonal anti-CD33 antibodies may be made using the hybridoma method first described by Kohler et al., Nature, 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization (e.g., a purified or recombinant CD33 protein of the present disclosure). Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The immunizing agent will typically include the antigenic protein (e.g., a purified or recombinant CD33 protein of the present disclosure) or a fusion variant thereof. Generally peripheral blood lymphocytes ("PBLs") are used if cells of human origin are desired, while spleen or lymph node cells are used if non-human mammalian sources are desired. The lymphoctyes are then fused with an immortalized cell line using a suitable fusing agent, such as polyethylene glycol, to form a hybridoma cell. Goding, *Monoclonal Antibodies: Principles and Practice*, Academic Press (1986), pp. 59-103.

Immortalized cell lines are usually transformed mammalian cells, particularly myeloma cells of rodent, bovine or human origin. Usually, rat or mouse myeloma cell lines are employed. The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which are substances that prevent the growth of HGPRT-deficient cells.

Preferred immortalized myeloma cells are those that fuse efficiently, support stable high-level production of antibody by the selected antibody-producing cells, and are sensitive to a medium such as HAT medium. Among these, preferred are murine myeloma lines, such as those derived from MOPC-21 and MPC-11 mouse tumors (available from the Salk Institute Cell Distribution Center, San Diego, Calif. USA), as well as SP-2 cells and derivatives thereof (e.g., X63-Ag8-653) (available from the American Type Culture Collection, Manassas, Va. USA). Human myeloma and mouse-human heteromyeloma cell lines have also been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen (e.g., a CD33 protein of the present disclosure). Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The culture medium in which the hybridoma cells are cultured can be assayed for the presence of monoclonal antibodies directed against the desired antigen (e.g., a CD33 protein of the present disclosure). Preferably, the binding affinity and specificity of the monoclonal antibody can be determined by immunoprecipitation or by an in vitro binding assay, such as radioimmunoassay (RIA) or enzyme-linked assay (ELISA). Such techniques and assays are known in the art. For example, binding affinity may be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as tumors in a mammal.

The monoclonal antibodies secreted by the subclones are suitably separated from the culture medium, ascites fluid, or serum by conventional immunoglobulin purification procedures such as, for example, protein A-Sepharose chromatography, hydroxylapatite chromatography, gel electrophoresis, dialysis, affinity chromatography, and other methods as described above.

Anti-CD33 monoclonal antibodies may also be made by recombinant DNA methods, such as those disclosed in U.S. Pat. No. 4,816,567, and as described above. DNA encoding the monoclonal antibodies is readily isolated and sequenced using conventional procedures (e.g., by using oligonucleotide probes that specifically bind to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, in order to synthesize monoclonal antibodies in such recombinant host cells. Review articles on recombinant expression in bacteria of DNA encoding the antibody include Skerra et al., *Curr. Opin. Immunol.*, 5:256-262 (1993) and Plückthun, *Immunol. Rev.* 130:151-188 (1992).

In certain embodiments, anti-CD33 antibodies can be isolated from antibody phage libraries generated using the techniques described in McCafferty et al., *Nature*, 348:552-

554 (1990). Clackson et al., *Nature*, 352:624-628 (1991) and Marks et al., *J. Mol. Biol.*, 222:581-597 (1991) described the isolation of murine and human antibodies, respectively, from phage libraries. Subsequent publications describe the production of high affinity (nanomolar ("nM") range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nucl. Acids Res.*, 21:2265-2266 (1993)). Thus, these techniques are viable alternatives to traditional monoclonal antibody hybridoma techniques for isolation of monoclonal antibodies of desired specificity (e.g., those that bind a CD33 protein of the present disclosure).

The DNA encoding antibodies or fragments thereof may also be modified, for example, by substituting the coding sequence for human heavy- and light-chain constant domains in place of the homologous murine sequences (U.S. Pat. No. 4,816,567; Morrison, et al., *Proc. Natl Acad. Sci. USA*, 81:6851 (1984)), or by covalently joining to the immunoglobulin coding sequence all or part of the coding sequence for a non-immunoglobulin polypeptide. Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

The monoclonal antibodies described herein (e.g., anti-CD33 antibodies of the present disclosure or fragments thereof) may by monovalent, the preparation of which is well known in the art. For example, one method involves recombinant expression of immunoglobulin light chain and a modified heavy chain. The heavy chain is truncated generally at any point in the Fc region so as to prevent heavy chain crosslinking. Alternatively, the relevant cysteine residues may be substituted with another amino acid residue or are deleted so as to prevent crosslinking. In vitro methods are also suitable for preparing monovalent antibodies. Digestion of antibodies to produce fragments thereof, particularly Fab fragments, can be accomplished using routine techniques known in the art.

Chimeric or hybrid anti-CD33 antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

(3) Humanized Antibodies

Anti-CD33 antibodies of the present disclosure or antibody fragments thereof may further include humanized or human antibodies. Humanized forms of non-human (e g, murine) antibodies are chimeric immunoglobulins, immunoglobulin chains or fragments thereof (such as Fab, Fab'-SH, Fv, scFv, F(ab')$_2$ or other antigen-binding subsequences of antibodies) which contain minimal sequence derived from non-human immunoglobulin. Humanized antibodies include human immunoglobulins (recipient antibody) in which residues from a complementarity determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally will also comprise at least a portion of an immunoglobulin constant region (Fc), typically that of a human immunoglobulin. Jones et al., *Nature* 321: 522-525 (1986); Riechmann et al., *Nature* 332: 323-329 (1988) and Presta, *Curr. Opin. Struct. Biol.* 2: 593-596 (1992).

Methods for humanizing non-human anti-CD33 antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers, Jones et al., *Nature* 321:522-525 (1986); Riechmann et al., *Nature* 332: 323-327 (1988); Verhoeyen et al., *Science* 239:1534-1536 (1988), or through substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody. Sims et al., *J. Immunol.*, 151:2296 (1993); Chothia et al., *J. Mol. Biol.*, 196:901 (1987). Another method uses a particular framework derived from the consensus sequence of all human antibodies of a particular subgroup of light or heavy chains. The same framework may be used for several different humanized antibodies. Carter et al., *Proc. Nat'l Acad. Sci. USA* 89:4285 (1992); Presta et al., *J. Immunol.* 151:2623 (1993).

Furthermore, it is important that antibodies be humanized with retention of high affinity for the antigen and other favorable biological properties. To achieve this goal, according to a preferred method, humanized antibodies are prepared by a process of analyzing the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen or antigens (e.g., CD33 proteins of the present disclosure), is achieved. In general, the CDR residues are directly and most substantially involved in influencing antigen binding.

Various forms of the humanized anti-CD33 antibody are contemplated. For example, the humanized anti-CD33 antibody may be an antibody fragment, such as an Fab, which is optionally conjugated with one or more cytotoxic agent(s) in order to generate an immunoconjugate. Alternatively, the humanized anti-CD33 antibody may be an intact antibody, such as an intact IgG1 antibody.

(4) Human Antibodies

Alternatively, human anti-CD33 antibodies can be generated. For example, it is now possible to produce transgenic animals (e.g., mice) that are capable, upon immunization, of producing a full repertoire of human antibodies in the absence of endogenous immunoglobulin production. The homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Nat'l Acad. Sci. USA*, 90:2551 (1993); Jakobovits et al., *Nature*, 362:255-258 (1993); Bruggermann et al., *Year in Immunol.*, 7:33 (1993); U.S. Pat. No. 5,591,669 and WO 97/17852.

Alternatively, phage display technology can be used to produce human anti-CD33 antibodies and antibody fragments in vitro, from immunoglobulin variable (V) domain gene repertoires from unimmunized donors. McCafferty et al., *Nature* 348:552-553 (1990); Hoogenboom and Winter, *J. Mol. Biol.* 227: 381 (1991). According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S. and Chiswell, David J., *Curr. Opin Struct. Biol.* 3:564-571 (1993). Several sources of V-gene segments can be used for phage display. Clackson et al., Nature 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991), or Griffith et al., EMBO J. 12:725-734 (1993). See also U.S. Pat. Nos. 5,565,332 and 5,573,905. Additionally, yeast display technology can be used to produce human anti-CD33 antibodies and antibody fragments in vitro (e.g., WO 2009/036379; WO 2010/105256; WO 2012/009568; US 2009/0181855; US 2010/0056386; and Feldhaus and Siegel (2004) J. Immunological Methods 290:69-80). In other embodiments, ribosome display technology can be used to produce human anti-CD33 antibodies and antibody fragments in vitro (e.g., Roberts and Szostak (1997) Proc Natl Acad Sci 94:12297-12302; Schaffitzel et al. (1999) J Immunological Methods 231:119-135; Lipovsek and Plückthun (2004) J. Immunological Methods 290:51-67).

The techniques of Cole et al., and Boerner et al., are also available for the preparation of human anti-CD33 monoclonal antibodies (Cole et al., Monoclonal Antibodies and Cancer Therapy, Alan R. Liss, p. 77 (1985) and Boerner et al., *J. Immunol.* 147(1): 86-95 (1991). Similarly, human anti-CD33 antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly and antibody repertoire. This approach is described, for example, in U.S. Pat. Nos. 5,545,807; 5,545,806, 5,569,825, 5,625,126, 5,633,425, 5,661,016 and in the following scientific publications: Marks et al., *Bio/Technology* 10: 779-783 (1992); Lonberg et al., *Nature* 368: 856-859 (1994); Morrison, *Nature* 368: 812-13 (1994), Fishwild et al., *Nature Biotechnology* 14: 845-51 (1996), Neuberger, *Nature Biotechnology* 14: 826 (1996) and Lonberg and Huszar, *Intern. Rev. Immunol.* 13: 65-93 (1995).

Finally, human anti-CD33 antibodies may also be generated in vitro by activated B-cells (see U.S. Pat. Nos. 5,567,610 and 5,229,275).

(5) Antibody Fragments

In certain embodiments there are advantages to using anti-CD33 antibody fragments, rather than whole anti-CD33 antibodies. Smaller fragment sizes allow for rapid clearance and better brain penetration.

Various techniques have been developed for the production of antibody fragments. Traditionally, these fragments were derived via proteolytic digestion of intact antibodies (see, e.g., Morimoto et al., *J. Biochem. Biophys. Method.* 24:107-117 (1992); and Brennan et al., *Science* 229:81 (1985)). However, these fragments can now be produced directly by recombinant host cells, for example, using nucleic acids encoding anti-CD33 antibodies of the present disclosure. Fab, Fv and scFv antibody fragments can all be expressed in and secreted from *E. coli*, thus allowing the straightforward production of large amounts of these fragments. A anti-CD33 antibody fragments can also be isolated from the antibody phage libraries as discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host cell culture. Production of Fab and F(ab')$_2$ antibody fragments with increased in vivo half-lives are described in U.S. Pat. No. 5,869,046. In other embodiments, the antibody of choice is a single chain Fv fragment (scFv). See WO 93/16185; U.S. Pat. Nos. 5,571,894 and 5,587,458. The anti-CD33 antibody fragment may also be a "linear antibody," e.g., as described in U.S. Pat. No. 5,641,870. Such linear antibody fragments may be monospecific or bispecific.

(6) Bispecific and Polyspecific Antibodies

Bispecific antibodies (BsAbs) are antibodies that have binding specificities for at least two different epitopes, including those on the same or another protein (e.g., one or more CD33 proteins of the present disclosure). Alternatively, one part of a BsAb can be armed to bind to the target CD33 antigen, and another can be combined with an arm that binds to a second protein. Such antibodies can be derived from full length antibodies or antibody fragments (e.g., F(ab')$_2$ bispecific antibodies).

Methods for making bispecific antibodies are known in the art. Traditional production of full length bispecific antibodies is based on the coexpression of two immunoglobulin heavy-chain/light chain pairs, where the two chains have different specificities. Millstein et al., *Nature,* 305:537-539 (1983). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829 and in Traunecker et al., *EMBO J.,* 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, $C_H2$, and $C_H3$ regions. It is preferred to have the first heavy-chain constant region ($C_H1$) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only half of the bispecific molecules provides for an easy way of separation. This approach is disclosed in WO 94/04690. For further details of generating bispecific antibodies, see, for example, Suresh et al., *Methods in Enzymology* 121: 210 (1986).

According to another approach described in WO 96/27011 or U.S. Pat. No. 5,731,168, the interface between a pair of antibody molecules can be engineered to maximize the percentage of heterodimers which are recovered from recombinant cell culture. The preferred interface comprises at least a part of the $C_H3$ region of an antibody constant domain. In this method, one or more small amino acid side chains from the interface of the first antibody molecule are replaced with larger side chains (e.g., tyrosine or tryptophan). Compensatory "cavities" of identical or similar size to the large side chains(s) are created on the interface of the second antibody molecule by replacing large amino acid side chains with smaller ones (e.g., alanine or threonine). This provides a mechanism for increasing the yield of the heterodimer over other unwanted end-products such as homodimers.

Techniques for generating bispecific antibodies from antibody fragments have been described in the literature. For example, bispecific antibodies can be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shalaby et al., *J. Exp. Med.* 175: 217-225 (1992) describes the production of fully humanized bispecific antibody F(ab')$_2$ molecules. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bivalent antibody fragments directly from recombinant cell culture have also been described. For example, bivalent heterodimers have been produced using leucine zippers. Kostelny et al., *J. Immunol.,* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. The "diabody" technology described by Hollinger et al., *Proc. Nat'l Acad. Sci. USA,* 90: 6444-6448 (1993) has provided an alternative mechanism for making bispecific/bivalent antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific/bivalent antibody fragments by the use of single-chain Fv (sFv) dimers has also been reported. See Gruber et al., *J. Immunol.,* 152:5368 (1994).

Antibodies with more than two valencies are also contemplated. For example, trispecific antibodies can be prepared. Tutt et al., *J. Immunol.* 147:60 (1991).

Exemplary bispecific antibodies may bind to two different epitopes on a given molecule (e.g., a CD33 protein of the present disclosure). Alternatively, an arm targeting a CD33 signaling component may be combined with an arm which binds to a triggering molecule on a leukocyte such as a T cell receptor molecule (e.g., CD2, CD3, CD28 or B7), or Fc receptors for IgG (FcγR), such as FcγRI (CD64), FcγRII (CD32) and FcγRIII (CD16) so as to focus cellular defense mechanisms to the cell expressing the particular protein. Bispecific antibodies may also be used to localize cytotoxic agents to cells which express a particular protein. Such antibodies possess a protein-binding arm and an arm which binds a cytotoxic agent or a radionuclide chelator, such as EOTUBE, DPTA, DOTA or TETA. Another bispecific antibody of interest binds the protein of interest and further binds tissue factor (TF).

(7) Multivalent Antibodies

A multivalent antibody may be internalized (and/or catabolized) faster than a bivalent antibody by a cell expressing an antigen to which the antibodies bind. The anti-CD33 antibodies of the present disclosure or antibody fragments thereof can be multivalent antibodies (which are other than of the IgM class) with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises an Fc region or a hinge region. In this scenario, the antibody will comprise an Fc region and three or more antigen binding sites amino-terminal to the Fc region. The preferred multivalent antibody herein contains three to about eight, but preferably four, antigen binding sites. The multivalent antibody contains at least one polypeptide chain (and preferably two polypeptide chains), wherein the polypeptide chain or chains comprise two or more variable domains. For instance, the polypeptide chain or chains may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. Similarly, the polypeptide chain or chains may comprise $V_H$-$C_H$1-flexible linker-$V_H$-$C_H$1-Fc region chain; or $V_H$-$C_H$1-$V_H$-$C_H$1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain. The multivalent antibodies may recognize the CD33 antigen as well as, without limitation, additional antigens A beta peptide, antigen or an alpha synuclain protein antigen or, Tau protein antigen or, TDP-43 protein antigen or, prion protein antigen or, huntingtin protein antigen, or RAN, translation Products antigen, including the DiPeptide Repeats, (DPRs peptides) composed of glycine-alanine (GA), glycine-proline (GP), glycine-arginine (GR), proline-alanine (PA), or proline-arginine (PR), insulin receptor, insulin like growth factor receptor, transferrin receptor, or any other antigen that facilitates antibody transfer across the blood brain barrier.

(8) Heteroconjugate Antibodies

Heteroconjugate antibodies are also within the scope of the present disclosure. Heteroconjugate antibodies are composed of two covalently joined antibodies (e.g., anti-CD33 antibodies of the present disclosure or antibody fragments thereof). For example, one of the antibodies in the heteroconjugate can be coupled to avidin, the other to biotin. Such antibodies have, for example, been proposed to target immune system cells to unwanted cells, U.S. Pat. No. 4,676,980, and have been used to treat HIV infection. International Publication Nos. WO 91/00360, WO 92/200373 and EP 0308936. It is contemplated that the antibodies may be prepared in vitro using known methods in synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980. Heteroconjugate antibodies may be made using any convenient cross-linking methods. Suitable cross-linking agents are well known in the art, and are disclosed in U.S. Pat. No. 4,676,980, along with a number of cross-linking techniques.

(9) Effector Function Engineering

It may also be desirable to modify an anti-CD33 antibody of the present disclosure to modify effector function and/or to increase serum half-life of the antibody. For example, the Fc receptor binding site on the constant region may be modified or mutated to remove or reduce binding affinity to certain Fc receptors, such as FcγRI, FcγRII, and/or FcγRIII. In some embodiments, the effector function is impaired by removing N-glycosylation of the Fc region (e.g., in the CH 2 domain of IgG) of the antibody. In some embodiments, the effector function is impaired by modifying regions such as 233-236, 297, and/or 327-331 of human IgG as described in PCT WO 99/58572 and Armour et al., *Molecular Immunology* 40: 585-593 (2003); Reddy et al., *J. Immunology* 164:1925-1933 (2000).

To increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

(10) Other Amino Acid Sequence Modifications

Amino acid sequence modifications of anti-CD33 antibodies of the present disclosure, or antibody fragments thereof, are also contemplated. For example, it may be desirable to improve the binding affinity and/or other biological properties of the antibodies or antibody fragments Amino acid sequence variants of the antibodies or antibody fragments are prepared by introducing appropriate nucleotide changes into the nucleic acid encoding the antibodies or antibody fragments, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics (i.e., the ability to bind or physically interact with a CD33 protein of the present disclosure). The amino acid changes also may alter post-translational processes of the antibody, such as changing the number or position of glycosylation sites.

A useful method for identification of certain residues or regions of the anti-CD33 antibody that are preferred locations for mutagenesis is called "alanine scanning mutagenesis" as described by Cunningham and Wells in *Science*, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with the target antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, alanine scanning or random mutagenesis is conducted at the target codon or region and the expressed antibody variants are screened for the desired activity.

Amino acid sequence insertions include amino- ("N") and/or carboxy- ("C") terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in the Table E below under the heading of "preferred substitutions". If such substitutions result in a change in biological activity, then more substantial changes, denominated "exemplary substitutions" in Table E, or as further described below in reference to amino acid classes, may be introduced and the products screened.

TABLE E

Amino acid substitutions

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | Ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions entail exchanging a member of one of these classes for another class.

Any cysteine residue not involved in maintaining the proper conformation of the antibody also may be substituted, generally with serine, to improve the oxidative stability of the molecule and prevent aberrant crosslinking Conversely, cysteine bond(s) may be added to the antibody to improve its stability (particularly where the antibody is an antibody fragment, such as an Fv fragment).

A particularly preferred type of substitutional variant involves substituting one or more hypervariable region residues of a parent antibody (e.g. a humanized or human anti-CD33 antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and the antigen (e.g., a CD33 protein of the present disclosure). Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-IgE antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibodies (e.g., anti-CD33 antibodies of the present disclosure) or antibody fragments.

(11) Antibody Conjugates

Anti-CD33 antibodies of the present disclosure, or antibody fragments thereof, can be conjugated to a detectable marker, a toxin, or a therapeutic agent. Any suitable method known in the art for conjugating molecules, such as a detectable marker, a toxin, or a therapeutic agent to antibodies may be used.

For example, drug conjugation involves coupling of a biological active cytotoxic (anticancer) payload or drug to an antibody that specifically targets a certain tumor marker (e.g. a protein that, ideally, is only to be found in or on tumor cells). Antibodies track these proteins down in the body and attach themselves to the surface of cancer cells. The biochemical reaction between the antibody and the target protein (antigen) triggers a signal in the tumor cell, which then absorbs or internalizes the antibody together with the cytotoxin. After the ADC is internalized, the cytotoxic drug is released and kills the cancer. Due to this targeting, ideally the drug has lower side effects and gives a wider therapeutic window than other chemotherapeutic agents. Technics to conjugate antibodies are disclosed are known in the art (see, e.g., Jane de Lartigue, OncLive Jul. 5, 2012; ADC Review on antibody-drug conjugates; and Ducry et al., (2010). *Bioconjugate Chemistry* 21 (1): 5-13).

In some embodiments, an anti-CD33 antibody of the present disclosure may be conjugated to a toxin selected from ricin, ricin A-chain, doxorubicin, daunorubicin, a maytansinoid, taxol, ethidium bromide, mitomycin, etoposide, tenoposide, vincristine, vinblastine, colchicine, dihydroxy anthracin dione, actinomycin, diphtheria toxin, *Pseudomonas* exotoxin (PE) A, PE40, abrin, abrin A chain, modeccin A chain, alpha-sarcin, gelonin, mitogellin, retstrictocin, phenomycin, enomycin, curicin, crotin, calicheamicin, *Saponaria officinalis* inhibitor, glucocorticoid, auristatin, auromycin, yttrium, bismuth, combrestatin, duocarmycins, dolastatin, cc1065, and a cisplatin.

(12) Other Antibody Modifications

Anti-CD33 antibodies of the present disclosure, or antibody fragments thereof, can be further modified to contain additional non-proteinaceous moieties that are known in the art and readily available. Preferably, the moieties suitable for derivatization of the antibody are water-soluble polymers. Non-limiting examples of water-soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, polypropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc. Such techniques and other suitable formulations are disclosed in *Remington: The Science and Practice of Pharmacy,* 20th Ed., Alfonso Gennaro, Ed., Philadelphia College of Pharmacy and Science (2000).

Binding Assays and Other Assays

Anti-CD33 antibodies of the present disclosure may be tested for antigen binding activity, e.g., by known methods such as ELISA, surface plasmon resonance (SPR), Western blot, etc.

In some embodiments, competition assays may be used to identify an antibody that competes with any of the antibodies listed in Tables 1, 2, 3A, 3B, 6A, and 6B, or selected from 1A8, 2B4, 2E12, 2E12.1, 2F5, 2F5.1, 3A12a, 3A12b, 6A3a, 6A3b, 6C7a, 6C7b, and 6C7.2. In certain embodiments, such a competing antibody binds to the same epitope (e.g., a linear or a conformational epitope) that is bound by any of the antibodies listed in Tables 1, 2, 3A, 3B, 6A, and 6B, or selected from 1A8, 2B4, 2E12, 2E12.1, 2F5, 2F5.1, 3A12a, 3A12b, 6A3a, 6A3b, 6C7a, 6C7b, and 6C7.2. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized CD33 or cells expressing CD33 on a cell surface are incubated in a solution comprising a first labeled antibody that binds to CD33 (e.g., human or non-human primate) and a second unlabeled antibody that is being tested for its ability to compete with the first antibody for binding to CD33. The second antibody may be present in a hybridoma supernatant. As a control, immobilized CD33 or cells expressing CD33 is incubated in a solution comprising the first labeled antibody but not the second unlabeled antibody. After incubation under conditions permissive for binding of the first antibody to CD33, excess unbound antibody is removed, and the amount of label associated with immobilized CD33 or cells expressing CD33 is measured. If the amount of label associated with immobilized CD33 or cells expressing CD33 is substantially reduced in the test sample relative to the control sample, then that indicates that the second antibody is competing with the first antibody for binding to CD33. See, Harlow and Lane (1988) *Antibodies: A Laboratory Manual* ch. 14 (Cold Spring Harbor Laboratory, Cold Spring Harbor, N.Y.).

Nucleic Acids, Vectors, and Host Cells

Anti-CD33 antibodies of the present disclosure may be produced using recombinant methods and compositions, e.g., as described in U.S. Pat. No. 4,816,567. In some embodiments, isolated nucleic acids having a nucleotide sequence encoding any of the anti-CD33 antibodies of the present disclosure are provided. Such nucleic acids may encode an amino acid sequence containing the VL and/or an amino acid sequence containing the VH of the anti-CD33 antibody (e.g., the light and/or heavy chains of the antibody). In some embodiments, one or more vectors (e.g., expression vectors) containing such nucleic acids are provided. In some embodiments, a host cell containing such nucleic acid is also provided. In some embodiments, the host cell contains (e.g., has been transduced with): (1) a vector containing a nucleic acid that encodes an amino acid sequence containing the VL of the antibody and an amino acid sequence containing the VH of the antibody, or (2) a first vector containing a nucleic acid that encodes an amino acid sequence containing the VL of the antibody and a second vector containing a nucleic acid that encodes an amino acid sequence containing the VH of the antibody. In some embodiments, the host cell is eukaryotic, e.g., a Chinese Hamster Ovary (CHO) cell or lymphoid cell (e.g., Y0, NS0, Sp20 cell).

Methods of making an anti-CD33 antibody of the present disclosure are provided. In some embodiments, the method includes culturing a host cell of the present disclosure containing a nucleic acid encoding the anti-CD33 antibody, under conditions suitable for expression of the antibody. In some embodiments, the antibody is subsequently recovered from the host cell (or host cell culture medium).

For recombinant production of an anti-CD33 antibody of the present disclosure, a nucleic acid encoding the anti-CD33 antibody is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable vectors containing a nucleic acid sequence encoding any of the anti-CD33 antibodies of the present disclosure, or fragments thereof polypeptides (including antibodies) described herein include, without limitation, cloning vectors and expression vectors. Suitable cloning vectors can be constructed according to standard techniques, or may be selected from a large number of cloning vectors available in the art. While the cloning vector selected may vary according to the host cell intended to be used, useful cloning vectors generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mpl8, mpl9, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors generally are replicable polynucleotide constructs that contain a nucleic acid of the present disclosure. The expression vector may replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the nucleic acids of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell. In some embodiments, the vector contains a nucleic acid containing one or more amino acid sequences encoding an anti-CD33 antibody of the present disclosure.

Suitable host cells for cloning or expression of antibody-encoding vectors include prokaryotic or eukaryotic cells. For example, anti-CD33 antibodies of the present disclosure may be produced in bacteria, in particular when glycosylation and Fc effector function are not needed. For expression of antibody fragments and polypeptides in bacteria (e.g., U.S. Pat. Nos. 5,648,237, 5,789,199, and 5,840,523; and Charlton, *Methods in Molecular Biology*, Vol. 248 (B. K. C. Lo, ed., Humana Press, Totowa, N.J., 2003), pp. 245-254, describing expression of antibody fragments in *E. coli*). After expression, the antibody may be isolated from the bacterial cell paste in a soluble fraction and can be further purified.

In addition to prokaryotes, eukaryotic microorganisms, such as filamentous fungi or yeast, are also suitable cloning or expression hosts for antibody-encoding vectors, including fungi and yeast strains whose glycosylation pathways have been "humanized," resulting in the production of an antibody with a partially or fully human glycosylation pattern (e.g., Gerngross, *Nat. Biotech.* 22:1409-1414 (2004); and Li et al., *Nat. Biotech.* 24:210-215 (2006)).

Suitable host cells for the expression of glycosylated antibody can also be derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts (e.g., U.S. Pat. Nos. 5,959,177, 6,040,498, 6,420,548, 7,125,978, and 6,417,429, describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR-CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

CD33 Activities

PI3K Activation

In some embodiments, CD33 agents of the present disclosure, such as anti-CD33 antibodies of the present disclosure, may induce PI3K activation after binding to a CD33 protein expressed in a cell.

PI3Ks are a family of related intracellular signal transducer kinases capable of phosphorylating the 3-position hydroxyl group of the inositol ring of phosphatidylinositol (PtdIns). The PI3K family is divided into three different classes (Class I, Class II, and Class III) based on primary structure, regulation, and in vitro lipid substrate specificity.

Activated PI3K produces various 3-phosphorylated phosphoinositides, including without limitation, PtdIns3P, PtdIns(3,4)P2, PtdIns(3,5)P2, and PtdIns(3,4,5)P3. These 3-phosphorylated phosphoinositides function in a mechanism by which signaling proteins are recruited to various cellular membranes. These signaling proteins contain phosphoinositide-binding domains, including without limitation, PX domains, pleckstrin homology domains (PH domains), and FYVE domains. Any method known in the art for determining PI3K activation may be used.

In some embodiments, CD33 agents of the present disclosure, such as anti-CD33 antibodies of the present disclosure, are beneficial for preventing, lowering the risk of, or treating conditions and/or diseases associated with decreased levels of PI3K activity, including, without limitation, dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express CD33, thyroid cancer, infections, CNS herpes, parasitic infections, Trypanosome infection, Cruzi infection, Pseudomonas aeruginosa infection, Leishmania donovani infection, group B Streptococcus infection, Campylobacter jejuni infection, Neisseria meningiditis infection, type I HIV, and Haemophilus influenza.

Modulated Expression of Cytokines

In some embodiments, CD33 agents of the present disclosure, such as anti-CD33 antibodies of the present disclosure, may modulate (e.g., increase or decrease) pro-inflammatory mediators in the brain after binding to a CD33 protein expressed on a cell surface. In certain embodiments, CD33 agents of the present disclosure, such as anti-CD33 antibodies of the present disclosure, modulate the expression of cytokines (e.g., proinflammatory mediators) and/or modulate the expression of anti-inflammatory mediators after binding to a CD33 protein expressed in a cell.

Inflammation is part of a complex biological response of vascular tissues to harmful stimuli, such as pathogens, damaged cells, and irritants. The classical signs of acute inflammation are pain, heat, redness, and swelling. Inflammation is an immune response that protects an organism by limiting the site of injury or clearing an infection by recruiting and activating cells of the immune system. The inflammatory response is tightly regulated and restricted in its duration and severity to avoid causing damage to the organism. Inflammation can be classified as either acute or chronic. Acute inflammation is driven by the innate immune response, which initially recognizes harmful stimuli and recruits leukocytes from the blood into the injured tissues. A cascade of biochemical events, including cytokine and chemokine release, propagates the inflammatory response, involving the local vascular system, the immune system, and various cells within the injured tissue. Chronic inflammation is prolonged and persistent which leads to a progressive shift in the type of immune cells participating in the inflammatory response. Chronic inflammation is characterized by progressive destruction and fibrosis of the tissue as a result of the inflammatory process.

As used herein, anti-inflammatory mediators are proteins involved either directly or indirectly (e.g., by way of an anti-inflammatory signaling pathway) in a mechanism that reduces, inhibits, or inactivates an inflammatory response. Any method known in the art for identifying and characterizing anti-inflammatory mediators may be used. Examples of anti-inflammatory mediators include, without limitation, cytokines, such as IL-4, IL-10, IL-13, IL-35, IL-16, IFN-alpha, TGF-beta, IL-1ra, G-CSF, and soluble receptors for TNF-alpha or IL-6. Examples of pro-inflammatory mediators include, without limitation, cytokines, such as IFN-a4, IFN-b, IL-1β, TNF-α, IL-6, IL-8, CRP, IL-20 family members, LIF, IFN-gamma, OSM, CNTF, GM-CSF, IL-11, IL-12, IL-17, IL-18, IL-23, CXCL10, IL-33, CRP, IL-33, MCP-1, and MIP-1-beta.

In some embodiments, the CD33 agents of the present disclosure, such as anti-CD33 antibodies of the present disclosure, may modulate (e.g., increase or decrease) expression of cytokines, such as IL-1β, IL-8, and TNF-α. In certain embodiments, modulated expression of the cytokines occurs in macrophages, dendritic cells, monocytes, osteoclasts, Langerhans cells of skin, Kupffer cells, T cells, natural killer cells, and/or microglial cells. Modulated expression may include, without limitation, an increase in gene expression, an increase in transcriptional expression, or an increase in protein expression. Any method known in the art for determining gene, transcript (e.g., mRNA), and/or protein expression may be used. For example, Northern blot analysis may be used to determine cytokine gene expression levels, RT-PCR may be used to determine the level of cytokine transcription, and Western blot analysis may be used to determine cytokine protein levels.

As used herein, a cytokine may have modulated expression if its expression in one or more cells of a subject treated with an CD33 agents of the present disclosure, such as anti-CD33 antibodies of the present disclosure, is modulated as compared to the expression of the same cytokine expressed in one or more cells of a corresponding subject that is not treated with the CD33 agent. In some embodiments, CD33 agents of the present disclosure, such as anti-CD33 antibodies of the present disclosure, may modulate cytokine expression in one or more cells of a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to cytokine expression in one or more cells of a corresponding subject that is not treated with the CD33 agent. In other embodiments, CD33 agents of the present disclosure, such as anti-CD33 antibodies of the present disclosure, modulate cytokine expression in one or more cells of a subject by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to cytokine expression in one or more cells of a corresponding subject that is not treated with the CD33 agent.

In some embodiments, CD33 agents of the present disclosure, such as anti-CD33 antibodies of the present disclosure, are useful for preventing, lowering the risk of, or treating conditions and/or diseases associated with abnormal levels of one or more pro-inflammatory mediators, including without limitation, dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express CD33, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus* influenza.

Modulated Expression of Pro-Inflammatory Mediators

In some embodiments, CD33 agents of the present disclosure, such as anti-CD33 antibodies of the present disclosure, may modulate (e.g., increase or decrease) the expression of pro-inflammatory mediators after binding to a CD33 protein expressed in a cell.

As used herein, pro-inflammatory mediators are proteins involved either directly or indirectly (e.g., by way of pro-inflammatory signaling pathways) in a mechanism that induces, activates, promotes, or otherwise increases an inflammatory response. Any method known in the art for identifying and characterizing pro-inflammatory mediators may be used.

Examples of pro-inflammatory mediators include, without limitation, cytokines, such as type I and II interferons, IL-1β, TNF-α, IL-6, IL-8, IL-20 family members, IL-33, LIF, OSM, CNTF, GM-CSF, IL-11, IL-12, IL-17, IL-18, and CRP.

In some embodiments, the anti-CD33 antibodies of the present disclosure may modulate functional expression and/or secretion of pro-inflammatory mediators, such as type I and II interferons, IFN-a4, IFN-b, IL-1β, TNF-α, IL-6, IL-8, CRP, IL-20 family members, LIF, IFN-gamma, OSM, CNTF, GM-CSF, IL-11, IL-12, IL-17, IL-18, IL-23, CXCL10, IL-33, CRP, IL-33, MCP-1, and MIP-1-beta. In certain embodiments, modulated expression of the pro-inflammatory mediators occurs in macrophages, dendritic cells, monocytes, osteoclasts, Langerhans cells of skin, Kupffer cells, T cells, and/or microglial cells. Modulated expression may include, without limitation, a modulated gene expression, modulated transcriptional expression, or modulated protein expression. Any method known in the art for determining gene, transcript (e.g., mRNA), and/or protein expression may be used. For example, Northern blot analysis may be used to determine pro-inflammatory mediator gene expression levels, RT-PCR may be used to determine the level of pro-inflammatory mediator transcription, and Western blot analysis may be used to determine pro-inflammatory mediator protein levels.

In certain embodiments, pro-inflammatory mediators include inflammatory cytokines. Accordingly, in certain embodiments, the CD33 agents of the present disclosure, such as anti-CD33 antibodies of the present disclosure, may modulate secretion of one or more inflammatory cytokines. Examples of inflammatory cytokines whose secretion may be modulated by the anti-CD33 antibodies of the present disclosure include, without limitation, such as type I and II interferons, IFN-a4, IFN-b, IL-1β, TNF-α, IL-6, IL-8, CRP, IL-20 family members, LIF, IFN-gamma, OSM, CNTF, GM-CSF, IL-11, IL-12, IL-17, IL-18, IL-23, CXCL10, IL-33, CRP, IL-33, MCP-1, and MIP-1-beta.

In certain embodiments, pro-inflammatory mediators include inflammatory receptors. Accordingly, in certain embodiments, the CD33 agents of the present disclosure, such as anti-CD33 antibodies of the present disclosure, may modulate expression of one or more inflammatory receptors. Examples of inflammatory receptors whose expression may be modulated by the CD33 agents of the present disclosure, such as anti-CD33 antibodies of the present disclosure, include, without limitation, CD86, CD80, and CD83.

As used herein, a pro-inflammatory mediator may have modulated expression if its expression in one or more cells of a subject treated with a CD33 agent, such as an agonist anti-CD33 antibody of the present disclosure is modulated (e.g., increased or decreased) as compared to the expression of the same pro-inflammatory mediator expressed in one or more cells of a corresponding subject that is not treated with the agonist anti-CD33 antibody. In some embodiments, the anti-CD33 antibody of the present disclosure may modulate pro-inflammatory mediator expression in one or more cells of a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to pro-inflammatory mediator expression in one or more cells of a corresponding subject that is not treated with the anti-CD33 antibody. In other embodiments, the anti-CD33 antibody may modulate pro-inflammatory mediator expression in one or more cells of a subject by at least at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to pro-inflammatory mediator expression in one or more cells of a corresponding subject that is not treated with the anti-CD33 antibody.

In some embodiments, CD33 agents of the present disclosure, such as anti-CD33 antibodies of the present disclosure, may be useful for preventing, lowering the risk of, or treating conditions and/or diseases associated with abnormal levels of one or more pro-inflammatory mediators, including without limitation, dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express CD33, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus* influenza.

ERK Phosphorylation

In some embodiments, CD33 agents of the present disclosure, such as anti-CD33 antibodies of the present disclosure, may induce extracellular signal-regulated kinase (ERK) phosphorylation after binding to a CD33 protein expressed in a cell.

Extracellular-signal-regulated kinases (ERKs) are widely expressed protein kinase intracellular signaling kinases that are involved in, for example, the regulation of meiosis, mitosis, and postmitotic functions in differentiated cells. Various stimuli, such as growth factors, cytokines, virus infection, ligands for heterotrimeric G protein-coupled receptors, transforming agents, and carcinogens, activate ERK pathways. Phosphorylation of ERKs leads to the activation of their kinase activity.

In some embodiments, CD33 agents of the present disclosure, such as anti-CD33 antibodies of the present disclosure, are beneficial for preventing, lowering the risk of, or treating conditions and/or diseases associated with decreased levels of ERK phosphorylation, including without limitation, dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express CD33, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus* influenza.

Syk Phosphorylation

In some embodiments, CD33 agents of the present disclosure, such as anti-CD33 antibodies of the present disclosure, may induce spleen tyrosine kinase (Syk) phosphorylation after binding to a CD33 protein expressed in a cell.

Spleen tyrosine kinase (Syk) is an intracellular signaling molecule that functions downstream of CD33 by phosphorylating several substrates, thereby facilitating the formation of a signaling complex leading to cellular activation and inflammatory processes.

In some embodiments, CD33 agents of the present disclosure, such as anti-CD33 antibodies of the present disclosure, are beneficial for preventing, lowering the risk of, or treating conditions and/or diseases associated with decreased levels of Syk phosphorylation, including without limitation, dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express CD33, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus* influenza.

CD33 Phosphorylation

In some embodiments, CD33 agents of the present disclosure, such as anti-CD33 antibodies of the present disclosure, may transiently induce CD33 phosphorylation of Tyr-340 and Tyr-358 by a by Src family tyrosine kinase such as Src, Syk, Fyn, Fgr, Lck, Hck, Blk, Lyn, and Frk after binding to a CD33 protein expressed in a cell.

In some embodiments, CD33 agents of the present disclosure, such as anti-CD33 antibodies of the present disclosure, are beneficial for preventing, lowering the risk of, or treating conditions and/or diseases associated with decreased levels of CD33 phosphorylation, including without limitation, dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express CD33, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus* influenza.

Phosphorylation of ITAM Motif Containing Receptors

In some embodiments, CD33 agents of the present disclosure, such as anti-CD33 antibodies of the present disclosure, may induce phosphorylate ITAM motif-containing receptors, such as TREM1, TREM2, FcgR, DAP10, and DAP12, after binding to a CD33 protein expressed in a cell.

In some embodiments, CD33 agents of the present disclosure, such as anti-CD33 antibodies of the present disclosure, are beneficial for preventing, lowering the risk of, or treating conditions and/or diseases associated with decreased levels of phosphorylation of ITAM motif-containing receptors, including without limitation, dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express CD33, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus* influenza.

Modulated Expression of C-C Chemokine Receptor 7

In some embodiments, CD33 agents of the present disclosure, such as anti-CD33 antibodies of the present disclosure, may modulate expression of C-C chemokine receptor 7 (CCR7) after binding to a CD33 protein expressed in a cell. Modulated (e.g., increased or decreased) expression may include, without limitation, modulation in gene expression, modulation in transcriptional expression, or modulation in protein expression. Any method known in the art for determining gene, transcript (e.g., mRNA), and/or protein expression may be used. For example, Northern blot analysis may be used to determine anti-inflammatory mediator gene expression levels, RT-PCR may be used to determine the level of anti-inflammatory mediator transcription, and Western blot analysis may be used to determine anti-inflammatory mediator protein levels.

C-C chemokine receptor 7 (CCR7) is a member of the G protein-coupled receptor family CCR7 is expressed in various lymphoid tissues and can activate B cells and T cells. In some embodiments, CCR7 may modulate the migration of memory T cells to secondary lymphoid organs, such as lymph nodes. In other embodiments, CCR7 may stimulate dendritic cell maturation. CCR7 is a receptor protein that can bind the chemokine (C-C motif) ligands CCL19/ELC and CCL21.

As used herein, CCR7 may have modulated expression if its expression in one or more cells of a subject treated with an CD33 agents of the present disclosure, such as anti-CD33 antibodies of the present disclosure, is modulated (e.g., increased or decreased) as compared to the expression of CCR7 expressed in one or more cells of a corresponding subject that is not treated with the CD33 agent. In some embodiments, an CD33 agent of the present disclosure, such as an anti-CD33 antibody of the present disclosure, may modulate CCR7 expression in one or more cells of a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to CCR7 expression in one or more cells of a corresponding subject that is not treated with the Cd33 agent. In other embodiments, an CD33 agent of the present disclosure, such as an anti-CD33 antibody of the present disclosure, modulates CCR7 expression in one or more cells of a subject by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to CCR7 expression in one or more cells of a corresponding subject that is not treated with the CD33 agent.

In some embodiments, modulated expression of CCR7 occurs in macrophages, dendritic cells, and/or microglial cells. Modulated expression of CCR7 may induce microglial cell chemotaxis toward cells expressing the chemokines CCL19 and CCL21. Accordingly, in certain embodiments, anti-CD33 antibodies of the present disclosure may induce microglial cell chemotaxis toward CCL19 and CCL21 expressing cells.

In some embodiments, CD33 agents of the present disclosure, such as anti-CD33 antibodies of the present disclosure, are useful for preventing, lowering the risk of, or treating conditions and/or diseases associated with abnormal levels of CCR7, including without limitation, dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express CD33, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus* influenza.

Modulated Expression of Immune-Related Proteins

In some embodiments, CD33 agents of the present disclosure, such as anti-CD33 antibodies of the present disclosure, may modulate expression of PD-L1, PD-L2, B7-H2, B7-H3, CD200R, CD163 and/or CD206 after binding to a CD33 protein expressed in a cell. Modulated (e.g., increased or decreased) expression may include, without limitation, modulation in gene expression, modulation in transcriptional expression, or modulation in protein expression. Any method known in the art for determining gene, transcript (e.g., mRNA), and/or protein expression may be used. For example, Northern blot analysis may be used to determine anti-inflammatory mediator gene expression levels, RT-PCR may be used to determine the level of anti-inflammatory mediator transcription, and Western blot analysis may be used to determine anti-inflammatory mediator protein levels.

As used herein, PD-L1, PD-L2, B7-H2, B7-H3, CD200R, CD163 and/or CD206 may have modulated expression if its expression in one or more cells of a subject treated with an CD33 agents of the present disclosure, such as anti-CD33 antibodies of the present disclosure, is modulated (e.g., increased or decreased) as compared to the expression of PD-L1, PD-L2, B7-H2, B7-H3, CD200R, CD163 and/or CD206 expressed in one or more cells of a corresponding subject that is not treated with the CD33 agent. In some embodiments, an CD33 agent of the present disclosure, such as an anti-CD33 antibody of the present disclosure, may modulate PD-L1, PD-L2, B7-H2, B7-H3, CD200R, CD163 and/or CD206 expression in one or more cells of a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to PD-L1, PD-L2, B7-H3, CD200R, CD163 and/or CD206 expression in one or more cells of a corresponding subject that is not treated with the Cd33 agent. In other embodiments, an CD33 agent of the present disclosure, such as an anti-CD33 antibody of the present disclosure, modulates PD-L1, PD-L2, B7-H2, B7-H3, CD200R, CD163 and/or CD206 expression in one or more cells of a subject by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to PD-L1, PD-L2, B7-H2, B7-H3, CD200R, CD163 and/or CD206 expression in one or more cells of a corresponding subject that is not treated with the CD33 agent.

In some embodiments, CD33 agents of the present disclosure, such as anti-CD33 antibodies of the present disclosure, are useful for preventing, lowering the risk of, or treating conditions and/or diseases associated with abnormal levels of PD-L1, PD-L2, B7-H2, B7-H3, CD200R, CD163 and/or CD206, including without limitation, dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express CD33, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus* influenza.

Enhancement or Normalization of the Ability of Bone Marrow-Derived Dendritic Cells to Induce Antigen-Specific T Cell Proliferation In some embodiments, CD33 agents of the present disclosure, such as anti-CD33 antibodies of the present disclosure, may enhance and/or normalize the ability of bone marrow-derived dendritic cells to induce antigen-specific T cell proliferation after binding to a CD33 protein expressed in a cell.

In some embodiments, CD33 agents of the present disclosure, such as antagonist anti-CD33 antibodies of the present disclosure, may enhance and/or normalize the ability of bone marrow-derived dendritic cells to induce antigen-specific T cell proliferation in one or more bone marrow-derived dendritic cells of a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to the ability of bone marrow-derived dendritic cells to induce antigen-specific T cell proliferation in one or more bone marrow-derived dendritic cells of a corresponding subject that is not treated with the agent. In other embodiments, the CD33 agent, such as an antagonist anti-CD33 antibody, may enhance and/or normalize the ability of bone marrow-derived dendritic cells to induce antigen-specific T cell proliferation in one or more bone marrow-derived dendritic cells of a subject by at least at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to the ability of bone marrow-derived dendritic cells to induce antigen-specific T cell proliferation in one or more bone marrow-derived dendritic cells of a corresponding subject that is not treated with the CD33 agent.

In some embodiments, CD33 agents of the present disclosure, such as anti-CD33 antibodies of the present disclosure, are beneficial for preventing, lowering the risk of, or treating conditions and/or diseases associated with decreased or dysregulated ability of bone marrow-derived dendritic cells to induce antigen-specific T cell proliferation, including without limitation, dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express CD33, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus* influenza.

Osteoclast Production

In some embodiments, CD33 agents of the present disclosure, such as anti-CD33 antibodies of the present disclosure, may induce osteoclast production and/or increase the rate of osteoclastogenesis after binding to a CD33 protein expressed in a cell.

As used herein, an osteoclast is a type of bone cell that can remove bone tissue by removing its mineralized matrix and breaking up the organic bone (e.g., bone resorption). Osteoclasts can be formed by the fusion of cells of the myeloid lineage. In some embodiments, osteoclasts may be characterized by high expression of tartrate resistant acid phosphatase (TRAP) and cathepsin K.

As used herein, the rate of osteoclastogenesis may be increased if the rate of osteoclastogenesis in a subject treated with a CD33 agent of the present disclosure, such as antagonist anti-CD33 antibody, is greater than the rate of osteoclastogenesis in a corresponding subject that is not treated with the CD33 agent. In some embodiments, a CD33 agent, such as an antagonist anti-CD33 antibody of the present disclosure, may increase the rate of osteoclastogenesis in a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to rate of osteoclastogenesis in a corresponding subject that is not treated with the CD33 agent. In other embodiments, a CD33 agent, such as an antagonist anti-CD33 antibody of the present disclosure, may increase the rate of osteoclastogenesis in a subject by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to rate of osteoclastogenesis in a corresponding subject that is not treated with the CD33 agent.

As used herein, the rate of osteoclastogenesis may be decreased if the rate of osteoclastogenesis in a subject treated with a CD33 agent, such as an agonist anti-CD33 antibody of the present disclosure, is smaller than the rate of osteoclastogenesis in a corresponding subject that is not treated with the CD33 agent. In some embodiments, a CD33 agent, such as an agonist anti-CD33 antibody of the present disclosure, may decrease the rate of osteoclastogenesis in a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to rate of osteoclastogenesis in a corresponding subject that is not treated with the CD33 agent. In other embodiments, a CD33 agent, such as an agonist anti-CD33 antibody of the present disclosure, may decrease the rate of osteoclastogenesis in a subject by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to rate of osteoclastogenesis in a corresponding subject that is not treated with the CD33 agent.

In some embodiments, CD33 agents of the present disclosure, such as anti-CD33 antibodies of the present disclosure, are beneficial for preventing, lowering the risk of, or treating conditions and/or diseases associated with abnormal bone formation and maintenance including osteoporosis, which is associated with pathological decrease in bone density and osteoporotic diseases which are associated with pathological increase in bone density.

Proliferation and Survival of CD33-Expressing Cells

In some embodiments, CD33 agents of the present disclosure, such as anti-CD33 antibodies of the present disclosure, may increase the proliferation, survival, and/or function of dendritic cells, macrophages, monocytes, neutrophils, osteoclasts, Langerhans cells of skin, Kupffer cells, T cells, T helper cells, cytotoxic T cells, and microglial cells after binding to CD33 protein expressed on a cell.

Microglial cells are a type of glial cell that are the resident macrophages of the brain and spinal cord, and thus act as the first and main form of active immune defense in the central nervous system (CNS). Microglial cells constitute 20% of the total glial cell population within the brain. Microglial cells are constantly scavenging the CNS for plaques, damaged neurons and infectious agents. The brain and spinal cord are considered "immune privileged" organs in that they are separated from the rest of the body by a series of endothelial cells known as the blood-brain barrier, which prevents most pathogens from reaching the vulnerable nervous tissue. In the case where infectious agents are directly introduced to the brain or cross the blood-brain barrier, microglial cells must react quickly to limit inflammation and destroy the infectious agents before they damage the sensitive neural tissue. Due to the unavailability of antibodies from the rest of the body (few antibodies are small enough to cross the blood brain barrier), microglia must be able to recognize foreign bodies, swallow them, and act as antigen-presenting cells activating T cells. Since this process must be done quickly to prevent potentially fatal damage, microglial cells are extremely sensitive to even small pathological changes in the CNS. They achieve this sensitivity in part by having unique potassium channels that respond to even small changes in extracellular potassium.

As used herein, macrophages of the present disclosure include, without limitation, M1 macrophages, activated M1 macrophages, and M2 macrophages. As used herein, microglial cells of the present disclosure include, without limitation, M1 microglial cells, activated M1 microglial cells, and M2 microglial cells.

In some embodiments, anti-CD33 antibodies of the present disclosure may increase the expression of CD80, CD83 and/or CD86 on dendritic cells, monocytes, and/or macrophages.

As used herein, the rate of proliferation, survival, and/or function of macrophages, dendritic cells, monocytes, T cells, neutrophils, and/or microglia may include increased expression if the rate of proliferation, survival, and/or function of dendritic cells, macrophages, monocytes, neutrophils, osteoclasts, Langerhans cells of skin, Kupffer cells, and/or microglia in a subject treated with a CD33 agent, such as an anti-CD33 antibody of the present disclosure, is greater than the rate of proliferation, survival, and/or function of dendritic cells, macrophages, monocytes, osteoclasts, Langerhans cells of skin, Kupffer cells, T cells, neutrophils, and/or microglia in a corresponding subject that is not treated with the CD33 agent. In some embodiments, a CD33 agent, such as an anti-CD33 antibody of the present disclosure, may increase the rate of proliferation, survival, and/or function of dendritic cells, macrophages, monocytes, osteoclasts, Langerhans cells of skin, Kupffer cells, T cells, and/or microglia in a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to the rate of proliferation, survival, and/or function of dendritic cells, macrophages, monocytes, osteoclasts, Langerhans cells of skin, Kupffer cells, T cells, and/or microglia in a corresponding subject that is not treated with the CD33 agent. In other embodiments, a CD33 agent, such as an anti-CD33 antibody of the present disclosure, may increase the rate of proliferation, survival, and/or function of dendritic cells, macrophages, monocytes, osteoclasts, Langerhans cells of skin, Kupffer cells, T cells, and/or microglia in a subject by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to the rate of proliferation, survival, and/or function of dendritic cells, macrophages, monocytes, osteoclasts, Langerhans cells of skin, Kupffer cells, T cells, and/or microglia in a corresponding subject that is not treated with the CD33 agent.

In some embodiments, CD33 agents of the present disclosure, such as anti-CD33 antibodies of the present disclosure, are beneficial for preventing, lowering the risk of, or treating conditions and/or diseases associated with a reduction in proliferation, survival, increased apoptosis and/or function of dendritic cells, neutrophils, macrophages, monocytes, osteoclasts, Langerhans cells of skin, Kupffer cells, T cells, and/or microglia including without limitation, dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express CD33, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus* influenza.

Clearance and Phagocytosis

In some embodiments, CD33 agents of the present disclosure, such as anti-CD33 antibodies of the present disclosure, may induce clearance and/or phagocytosis after binding to a CD33 protein expressed in a cell of one or more of apoptotic neurons, nerve tissue debris of the nervous system, dysfunctional synapses, non-nerve tissue debris of the nervous system, bacteria, other foreign bodies, disease-causing proteins, disease-causing peptides, disease-causing nucleic acid, or tumor cells. In certain embodiments, disease-causing proteins include, without limitation, amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides. In certain embodiments, disease-causing nucleic acids include, without limitation, antisense GGCCCC (G2C4) repeat-expansion RNA.

In some embodiments, the CD33 agents of the present disclosure, such as anti-CD33 antibodies of the present disclosure, may induce of one or more types of clearance, including without limitation, apoptotic neuron clearance, nerve tissue debris clearance, non-nerve tissue debris clearance, bacteria or other foreign body clearance, disease-causing protein clearance, disease-causing peptide clearance, disease-causing nucleic acid clearance, and tumor cell clearance.

In some embodiments, the CD33 agents of the present disclosure, such as anti-CD33 antibodies of the present disclosure, may induce phagocytosis of one or more of apoptotic neurons, nerve tissue debris, non-nerve tissue debris, bacteria, other foreign bodies, disease-causing proteins, disease-causing peptides, disease-causing nucleic acid, and/or tumor cells.

In some embodiments, the CD33 agents of the present disclosure, such as anti-CD33 antibodies of the present disclosure, may increase phagocytosis by neutrophils, macrophages, dendritic cells, monocytes, and/or microglia under conditions of reduced levels of macrophage colony-stimulating factor (M-CSF).

In some embodiments, CD33 agents of the present disclosure, such as anti-CD33 antibodies of the present disclosure, are beneficial for preventing, lowering the risk of, or treating conditions and/or diseases associated with apoptotic neurons, nerve tissue debris of the nervous system, dysfunctional synapses, non-nerve tissue debris of the nervous system, bacteria, other foreign bodies, disease-causing proteins, including without limitation, dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express CD33, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus* influenza.

CD33-Dependent Gene Expression

In some embodiments, CD33 agents of the present disclosure, such as antagonist anti-CD33 antibodies of the present disclosure, may decrease the activity and/or expression of CD33-dependent genes, and by that increase gene expression associated with signaling cascade that activate the immune system such as gene expression associated with ITAM containing receptors, pattern recognition receptors, of Toll-like receptors, of damage-associated molecular pattern (DAMP) receptors such as one or more transcription factors of the nuclear factor of activated T cells (NFAT) family of transcription factors.

In some embodiments, CD33 agents of the present disclosure, such as antagonist anti-CD33 antibodies of the present disclosure, are beneficial for preventing, lowering the risk of, or treating conditions and/or diseases associated with high levels of CD33-dependent genes, including without limitation, dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express CD33, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus* influenza.

CD33-Dependent Activation of Immune Cells

In some embodiments, CD33 agents of the present disclosure, such as antagonist anti-CD33 antibodies of the present disclosure, may increase the activity of cytotoxic T cells helper T cells or both. In some embodiments, CD33 agents of the present disclosure, such as antagonist anti-CD33 antibodies of the present disclosure, are beneficial for preventing, lowering the risk of, or treating conditions and/or diseases associated with decreased activity of cytotoxic T cells helper T cells or both, including without limitation, tumors, including solid tumors such as bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, and thyroid cancer.

In some embodiments, CD33 agents of the present disclosure, such as antagonist anti-CD33 antibodies of the present disclosure, may induce an increase in proliferation, survival, activity, and/or number of T cells, cytotoxic T cells, CD3$^+$ T cells, helper T cells, dendritic cells, macrophages, monocytes, neutrophils, osteoclasts, Langerhans cells of skin, Kupffer cells, and/or microglial cells. In some embodiments, CD33 agents of the present disclosure, such as antagonist anti-CD33 antibodies of the present disclosure, induce an increase in proliferation, survival, activity, and/or number of T cells, cytotoxic T cells, CD3$^+$ T cells, helper T cells, dendritic cells, macrophages, monocytes, neutrophils, osteoclasts, Langerhans cells of skin, Kupffer cells, and/or microglial cells in the presence of myeloid-derived suppressor cells (MDSC).

As used herein, the rate of proliferation, survival, activity, and/or number of T cells, cytotoxic T cells, CD3$^+$ T cells, helper T cells, dendritic cells, macrophages, monocytes, neutrophils, osteoclasts, Langerhans cells of skin, Kupffer cells, and/or microglial cells may include an increased rate if the rate of proliferation, survival, activity, and/or number of T cells, cytotoxic T cells, CD3$^+$ T cells, helper T cells, dendritic cells, macrophages, monocytes, neutrophils, osteoclasts, Langerhans cells of skin, Kupffer cells, and/or microglial cells in a subject treated with a CD33 agent, such as an anti-CD33 antibody of the present disclosure, is greater than the rate of proliferation, survival, activity, and/or number of T cells, cytotoxic T cells, CD3$^+$ T cells, helper T cells, dendritic cells, macrophages, monocytes, neutrophils, osteoclasts, Langerhans cells of skin, Kupffer cells, and/or microglial cells in a corresponding subject that is not treated with the CD33 agent. In some embodiments, a CD33 agent, such as an anti-CD33 antibody of the present disclosure, may increase proliferation, survival, activity, and/or number of T cells, cytotoxic T cells, CD3$^+$ T cells, helper T cells, dendritic cells, macrophages, monocytes, neutrophils, osteoclasts, Langerhans cells of skin, Kupffer cells, and/or microglial cells in a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to the level of proliferation, survival, activity, and/or number of T cells, cytotoxic T cells, CD3$^+$ T cells, helper T cells, dendritic cells, macrophages, monocytes, neutrophils, osteoclasts, Langerhans cells of skin, Kupffer cells, and/or microglial cells in a corresponding subject that is not treated with the CD33 agent. In other embodiments, a CD33 agent, such as an anti-CD33 antibody of the present disclosure, may increase proliferation, survival, activity, and/or number of T cells, cytotoxic T cells, CD3$^+$ T cells, helper T cells, dendritic cells, macrophages, monocytes, neutrophils, osteoclasts, Langerhans cells of skin, Kupffer cells, and/or microglial cells in a subject by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to the level of proliferation, survival, activity, and/or number of T cells, cytotoxic T cells, CD3$^+$ T cells, helper T cells, dendritic cells, macrophages, monocytes, neutrophils, osteoclasts, Langerhans cells of skin, Kupffer cells, and/or microglial cells in a corresponding subject that is not treated with the CD33 agent.

CD33-Dependent Activation of Neutrophils

In some embodiments, CD33 agents of the present disclosure, such as agonist anti-CD33 antibodies of the present disclosure, may increase the activity of, neutrophils, or both. In some embodiments, CD33 agents of the present disclosure, such as agonist anti-CD33 antibodies of the present disclosure, are beneficial for preventing, lowering the risk of, or treating conditions and/or diseases associated with decreased activity of the activity of natural killer cells, neutrophils or both, including without limitation, tumors, including solid tumors such as bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, and thyroid cancer.

CD33-dependent inhibition of tumor-associated immune cells

In some embodiments, CD33 agents of the present disclosure, such as agonist anti-CD33 antibodies of the present disclosure, may decrease the activity, decrease the proliferation, decrease the survival, decrease the functionality, decrease infiltration to tumors or lymphoid organs (e.g., the spleen and lymph nodes), the number of CD14$^+$ myeloid cells, decrease tumor growth rate, reduce tumor volume, reduce or inhibit differentiation, survival, and/or one or more functions of myeloid-derived suppressor cells (MDSC), and/or promote apoptosis of T-regulatory cells or inhibitory tumor-imbedded immunosuppressor dendritic cells or, tumor-associated macrophages or, myeloid-derived suppressor cells. In some embodiments, CD33 agents of the present disclosure, such as agonist anti-CD33 antibodies of the present disclosure, are beneficial for preventing, lowering the risk of, or treating conditions and/or diseases associated with the activity of one or more type of immune suppressor cells, including without limitation, tumors, including solid tumors that do not express CD33 such as bladder cancer, brain cancer, breast cancer, colon cancer, rectal cancer, endometrial cancer, kidney cancer, renal cell cancer, renal pelvis cancer, lung cancer, melanoma, non-Hodgkin's lymphoma, pancreatic cancer, prostate cancer, ovarian cancer, fibrosarcoma, thyroid cancer, and blood tumors that express CD33, such as leukemia cells.

In some embodiments, CD33 agents of the present disclosure, such as antagonist anti-CD33 antibodies of the present disclosure, may decrease the number of CD14$^+$ myeloid cells, decrease tumor growth rate, reduce tumor volume, or reduce or inhibit differentiation, survival, and/or one or more functions of myeloid-derived suppressor cells (MDSC).

In some embodiments, a CD33 agent, such as an anti-CD33 antibody of the present disclosure, may decrease the number of CD14$^+$ myeloid cells, decrease tumor growth rate, reduce tumor volume, or reduce or inhibit differentiation, survival, and/or one or more functions of myeloid-derived suppressor cells (MDSC) in a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to the number of CD14$^+$ myeloid cells, tumor growth rate, tumor volume, or level of differentiation, survival, and/or one or more functions of myeloid-derived suppressor cells (MDSC) in a corresponding subject that is not treated with the CD33 agent. In other embodiments, a CD33 agent, such as an anti-CD33 antibody of the present disclosure, may decrease the number of CD14$^+$ myeloid cells, decrease tumor growth rate, reduce tumor volume, or reduce or inhibit differentiation, survival, and/or one or more functions of myeloid-derived suppressor cells (MDSC) in a subject by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to the number of CD14$^+$ myeloid cells, tumor growth rate, tumor volume, or level of differentiation, survival, and/or one or more functions of myeloid-derived suppressor cells (MDSC) in a corresponding subject that is not treated with the CD33 agent.

Increased Efficacy of Checkpoint Inhibitor Therapies

In some embodiments, CD33 agents of the present disclosure, such as antagonist anti-CD33 antibodies of the present disclosure, may increase the efficacy of one or more checkpoint inhibitor therapies and/or immune-modulating therapies, such as PD-1 inhibitors or therapies that target one or more of CTL4, the adenosine pathway, PD-L1, PD-L2, OX40, TIM3, and/or LAG3.

In some embodiments, a CD33 agent, such as an anti-CD33 antibody of the present disclosure, may increase the efficacy of one or more checkpoint inhibitor therapies and/or immune-modulating therapies, such as PD-1 inhibitors or therapies that target one or more of CTL4, the adenosine pathway, PD-L1, PD-L2, OX40, TIM3, and/or LAG3 in a subject receiving such one or more therapies by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to the level of effectiveness of one or more checkpoint inhibitor therapies and/or immune-modulating therapies, such as PD-1 inhibitors or therapies that target one or more of CTL4, the adenosine pathway, PD-L1, PD-L2, OX40, TIM3, and/or LAG3 in a corresponding subject receiving such one or more therapies that is not treated with the CD33 agent. In other embodiments, a CD33 agent, such as an anti-CD33 antibody of the present disclosure, may increase the efficacy of one or more checkpoint inhibitor therapies and/or immune-modulating therapies, such as PD-1 inhibitors or therapies that target one or more of CTL4, the adenosine pathway, PD-L1, PD-L2, OX40, TIM3, and/or LAG3 in a subject receiving such one or more therapies by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to the level of effectiveness of one or more checkpoint inhibitor therapies and/or immune-modulating therapies, such as PD-1 inhibitors or therapies that target one or more of CTL4, the adenosine pathway, PD-L1, PD-L2, OX40, TIM3, and/or LAG3 in a corresponding subject receiving such one or more therapies that is not treated with the CD33 agent.

Increased Efficacy of Chemotherapeutic Agents

In some embodiments, CD33 agents of the present disclosure, such as antagonist anti-CD33 antibodies of the present disclosure, may increase the efficacy of one or more chemotherapy agents, such as gemcitabine, capecitabine, anthracyclines, doxorubicin (Adriamycin®), epirubicin (Ellence®), taxanes, paclitaxel (Taxol®), docetaxel (Taxotere®), 5-fluorouracil (5-FU), cyclophosphamide (Cytoxan®), and/orcarboplatin (Paraplatin®).

In some embodiments, a CD33 agent, such as an anti-CD33 antibody of the present disclosure, may increase the efficacy of one or more chemotherapy agents in a subject receiving such one or more therapies by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to the level of effectiveness of one or more chemotherapy agents in a corresponding subject receiving such one or more therapies that is not treated with the CD33 agent. In other embodiments, a CD33 agent, such as an anti-CD33 antibody of the present disclosure, may increase the efficacy of one or more chemotherapy agents in a subject receiving such one or more therapies by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to the level of effectiveness of one or more chemotherapy agents in a corresponding subject receiving such one or more therapies that is not treated with the CD33 agent.

Pharmaceutical Compositions

CD33 agents of the present disclosure, such as anti-CD33 antibodies of the present disclosure, can be incorporated into a variety of formulations for therapeutic administration by combining the agents, such as anti-CD33 antibodies, with appropriate pharmaceutically acceptable carriers or diluents, and may be formulated into preparations in solid, semi-solid, liquid or gaseous forms. Examples of such formulations include, without limitation, tablets, capsules, powders, granules, ointments, solutions, suppositories, injections, inhalants, gels, microspheres, and aerosols. Pharmaceutical compositions can include, depending on the formulation desired, pharmaceutically-acceptable, non-toxic carriers of diluents, which are vehicles commonly used to formulate pharmaceutical compositions for animal or human administration. The diluent is selected so as not to affect the biological activity of the combination. Examples of such diluents include, without limitation, distilled water, buffered water, physiological saline, PBS, Ringer's solution, dextrose solution, and Hank's solution. A pharmaceutical composition or formulation of the present disclosure can further include other carriers, adjuvants, or non-toxic, nontherapeutic, non-immunogenic stabilizers, excipients and the like. The compositions can also include additional substances to approximate physiological conditions, such as pH adjusting and buffering agents, toxicity adjusting agents, wetting agents and detergents.

A pharmaceutical composition of the present disclosure can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, and enhance solubility or uptake). Examples of such modifications or complexing agents include, without limitation, sulfate, gluconate, citrate and phosphate. The polypeptides of a composition can also be complexed with molecules that enhance their in vivo attributes. Such molecules include, without limitation, carbohydrates, polyamines, amino acids, other peptides, ions (e.g., sodium, potassium, calcium, magnesium, manganese), and lipids.

Further examples of formulations that are suitable for various types of administration can be found in Remington's *Pharmaceutical Sciences*, Mace Publishing Company, Philadelphia, Pa., 17th ed. (1985). For a brief review of methods for drug delivery, see, Langer, *Science* 249:1527-1533 (1990).

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

Formulations may be optimized for retention and stabilization in the brain or central nervous system. When the agent is administered into the cranial compartment, it is desirable for the agent to be retained in the compartment, and not to diffuse or otherwise cross the blood brain barrier. Stabilization techniques include cross-linking, multimerizing, or linking to groups such as polyethylene glycol, polyacrylamide, neutral protein carriers, etc. in order to achieve an increase in molecular weight.

Other strategies for increasing retention include the entrapment of an agent of the present disclosure, such as an anti-CD33 antibody of the present disclosure, in a biodegradable or bioerodible implant. The rate of release of the therapeutically active agent is controlled by the rate of transport through the polymeric matrix, and the biodegradation of the implant. The transport of drug through the polymer barrier will also be affected by compound solubility, polymer hydrophilicity, extent of polymer cross-linking, expansion of the polymer upon water absorption so as to make the polymer barrier more permeable to the drug, geometry of the implant, and the like. The implants are of dimensions commensurate with the size and shape of the region selected as the site of implantation. Implants may be particles, sheets, patches, plaques, fibers, microcapsules and the like and may be of any size or shape compatible with the selected site of insertion.

The implants may be monolithic, i.e. having the active agent homogenously distributed through the polymeric matrix, or encapsulated, where a reservoir of active agent is encapsulated by the polymeric matrix. The selection of the polymeric composition to be employed will vary with the site of administration, the desired period of treatment, patient tolerance, the nature of the disease to be treated and the like. Characteristics of the polymers will include biodegradability at the site of implantation, compatibility with the agent of interest, ease of encapsulation, a half-life in the physiological environment.

Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked. Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. By employing the L-lactate or D-lactate, a slowly biodegrading polymer is achieved, while degradation is substantially enhanced with the racemate. Copolymers of glycolic and lactic acid are of particular interest, where the rate of biodegradation is controlled by the ratio of glycolic to lactic acid. The most rapidly degraded copolymer has roughly equal amounts of glycolic and lactic acid, where either homopolymer is more resistant to degradation. The ratio of glycolic acid to lactic acid will also affect the brittleness of in the implant, where a more flexible implant is desirable for larger geometries. Among the polysaccharides of interest are calcium alginate, and functionalized celluloses, particularly carboxymethylcellulose esters characterized by being water insoluble, a molecular weight of about 5 kD to 500 kD, etc. Biodegradable hydrogels may also be employed in the implants of the present disclosure. Hydrogels are typically a copolymer material, characterized by the ability to imbibe a liquid. Exemplary biodegradable hydrogels which may be employed are described in Heller in: Hydrogels in Medicine and Pharmacy, N. A. Peppes ed., Vol. III, CRC Press, Boca Raton, Fla., 1987, pp 137-149.

Pharmaceutical Dosages

Pharmaceutical compositions of the present disclosure containing a CD33 agent of the present disclosure, such as an anti-CD33 antibody of the present disclosure, may be administered to an individual in need of treatment with the CD33 agent, preferably a human, in accord with known methods, such as intravenous administration as a bolus or by continuous infusion over a period of time, by intramuscular, intraperitoneal, intracerobrospinal, intracranial, intraspinal, subcutaneous, intra-articular, intrasynovial, intrathecal, oral, topical, or inhalation routes.

Dosages and desired drug concentration of pharmaceutical compositions of the present disclosure may vary depending on the particular use envisioned. The determination of the appropriate dosage or route of administration is well within the skill of an ordinary artisan Animal experiments provide reliable guidance for the determination of effective doses for human therapy. Interspecies scaling of effective doses can be performed following the principles described in Mordenti, J. and Chappell, W. "The Use of Interspecies Scaling in Toxicokinetics," In Toxicokinetics and New Drug Development, Yacobi et al., Eds, Pergamon Press, New York 1989, pp. 42-46.

For in vivo administration of any of the CD33 agents of the present disclosure, such as any of the anti-CD33 antibodies of the present disclosure, normal dosage amounts may vary from about 10 ng/kg up to about 100 mg/kg of an individual's body weight or more per day, preferably about 1 mg/kg/day to 10 mg/kg/day, depending upon the route of administration. For repeated administrations over several days or longer, depending on the severity of the disease, disorder, or condition to be treated, the treatment is sustained until a desired suppression of symptoms is achieved.

An exemplary dosing regimen may include administering an initial dose of a CD33 agent of the present disclosure, such as an anti-CD33 antibody, of about 2 mg/kg, followed by a weekly maintenance dose of about 1 mg/kg every other week. Other dosage regimens may be useful, depending on the pattern of pharmacokinetic decay that the physician wishes to achieve. For example, dosing an individual from one to twenty-one times a week is contemplated herein. In certain embodiments, dosing ranging from about 3 μg/kg to about 2 mg/kg (such as about 3 μg/kg, about 10 μg/kg, about 30 μg/kg, about 100 μg/kg, about 300 μg/kg, about 1 mg/kg, and about 2/mg/kg) may be used. In certain embodiments, dosing frequency is three times per day, twice per day, once per day, once every other day, once weekly, once every two weeks, once every four weeks, once every five weeks, once every six weeks, once every seven weeks, once every eight weeks, once every nine weeks, once every ten weeks, or once monthly, once every two months, once every three months, or longer. Progress of the therapy is easily monitored by conventional techniques and assays. The dosing regimen, including the CD33 agent, such as the anti-CD33 antibody administered, can vary over time independently of the dose used.

Dosages for a particular CD33 agent, such as a particular anti-CD33 antibody, may be determined empirically in individuals who have been given one or more administrations of the CD33 agent, such as the anti-CD33 antibody. Individuals are given incremental doses of a CD33 agent, such as an anti-CD33 antibody. To assess efficacy of a CD33 agent, such as an anti-CD33 antibody, a clinical symptom of any of the diseases, disorders, or conditions of the present disclosure (e.g., frontotemporal dementia, Alzheimer's disease, vascular dementia, seizures, retinal dystrophy, a traumatic brain injury, a spinal cord injury, long-term depression, atherosclerotic vascular diseases, and undesirable symptoms of normal aging) can be monitored.

Administration of a CD33 agent, such as an anti-CD33 antibody of the present disclosure, can be continuous or intermittent, depending, for example, on the recipient's physiological condition, whether the purpose of the administration is therapeutic or prophylactic, and other factors known to skilled practitioners. The administration of a CD33 agent, such as an anti-CD33 antibody, may be essentially continuous over a preselected period of time or may be in a series of spaced doses.

Guidance regarding particular dosages and methods of delivery is provided in the literature; see, for example, U.S. Pat. No. 4,657,760; 5,206,344; or 5,225,212. It is within the scope of the present disclosure that different formulations will be effective for different treatments and different disorders, and that administration intended to treat a specific organ or tissue may necessitate delivery in a manner different from that to another organ or tissue. Moreover, dosages may be administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

Therapeutic Uses

Further aspects of the present disclosure provide methods of modulating (e.g., activating or inhibiting) one or more CD33 activities, including with limitation, modulating (e.g., activating or inhibiting) a CD33 protein of the present disclosure, recruitment of and binding to the tyrosine-specific protein phosphatases SHP1 and SHP2, modulating (e.g., activating or inhibiting) recruitment of and binding to PLC-gamma1 which acts as a guanine nucleotide exchange factor for Dynamini-1, modulating (e.g., activating or inhibiting) recruitment of and binding to SH2 domain containing protein, Crkl, modulating (e.g., activating or inhibiting) recruitment of and binding to SH3-SH2-SH3 growth factor receptor-bound protein 2 (Grb2), modulating (e.g., activating or inhibiting) recruitment of and binding to multiple SH2 containing proteins, modulating (e.g., activating or inhibiting) phosphorylation of Ser-307 and Ser-342 by protein kinase C, modulating (e.g., activating or inhibiting) association with and activation of, the protoconcogenes c-Cbl, Vav and Syk, modulating (e.g., activating or inhibiting) Cbl-dependent ubiquitination and proteosomal degradation of CD33 itself as well as of retinoic acid-inducible genes, modulating (e.g., activating or inhibiting) intracellular calcium mobilization, modulating (e.g., activating or inhibiting) production of proinflammatory cytokines IL-1β, IL-8, and TNF-α, activation of phosphoinositide 3-kinase, modulating (e.g., activating or inhibiting) cell growth of monocytes, macrophages, T cells, neutrophils, natural killer cells, dendritic cells, tumor-embedded immunosuppressor dendritic cells, tumor-associated macrophages, myeloid-derived suppressor cells, and/or regulatory T cells, and/or microglia, modulating (e.g., activating or inhibiting) cell death and apoptosis of monocytes, macrophages, T cells, Natural Killer cells, neutrophils, dendritic cells, of tumor-embedded immunosuppressor dendritic cells, immunosuppressor macrophages, myeloid-derived suppressor cells, tumor-associated macrophages, and/or regulatory T cells, and/or microglia, modulating (e.g., activating or inhibiting) tyrosine phosphorylation on multiple cellular proteins, modulating (e.g., activating or inhibiting) phagocytic activity of monocytes, macrophages, dendritic cells and/or microglia, modulating (e.g., activating or inhibiting) proliferation of monocytes, macrophages, T cells, Natural Killer cells, dendritic cells and/or microglia, modulating (e.g., activating or inhibiting) the overall functionality of monocytes, macrophages, T cells, natural killer cells, neutrophils, dendritic cells, tumor embedded immunosuppressor dendritic cells, immunosuppressor macrophages, myeloid derived suppressor cells, tumor associated macrophages, regulatory T cells, and/or microglia, modulating (e.g., activating or inhibiting) phosphorylation of an ITAM containing receptor, modulating (e.g., activating or inhibiting) phosphorylation of a signaling molecules that mediates ITAM signaling, modulating (e.g., activating or inhibiting) the activity of pattern recognition receptors, modulating (e.g., activating or inhibiting) the activity of Toll-like receptors, or modulating (e.g., activating or inhibiting) the activity of damage-associated molecular pattern (DAMP) receptors in an individual in need thereof, by administering to the individual a therapeutically effective amount of a CD33 agent of the present disclosure, such as an anti-CD33 antibody of the present disclosure, to modulate (e.g., activate or inhibit) one or more of the CD33 activities in the individual.

As disclosed herein, CD33 agents of the present disclosure that decrease cellular levels of CD33 and/or inhibit interaction between CD33 and one or more CD33 ligands, such as anti-CD33 antibodies of the present disclosure, may be used for preventing, reducing risk, or treating dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express CD33, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and/or *Haemophilus* influenza. In some embodiments, the agents are selected from antibodies, soluble CD33 receptors, CD33-Fc fusion proteins, CD33 immunoadhesins, soluble Siglec receptors that binds one or more CD33 ligands, Siglec-Fc fusion proteins, Siglec immunoadhesins, antisense molecules, siRNAs, small molecule inhibitors, proteins, and peptides. In some embodiments, the CD33 agents are agonist antibodies. In some embodiments, the CD33 agents are inert antibodies. In some embodiments, the CD33 agents are antagonist antibodies.

In some embodiments, the present disclosure provides methods of preventing, reducing risk, or treating dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, cancer, bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express CD33, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and/or *Haemophilus* influenza, by administering to an individual in need thereof a therapeutically effective amount of an agent of the present disclosure that decreases cellular levels of CD33, inhibits interaction between CD33 and one or more CD33 ligands, or both. In some embodiments, the agent is selected from an antibody, a soluble CD33 receptor, a CD33-Fc fusion protein, a CD33 immunoadhesin, a soluble Siglec receptor that binds one or more CD33 ligands, a Siglec-Fc fusion protein, a Siglec immunoadhesin, an antisense molecule, an siRNA, a small molecule inhibitor, a protein, and a peptide. In some embodiments, the agent is an anti-CD33 antibody of the present disclosure.

In some embodiments, the present disclosure provides methods of preventing, reducing risk, or treating cancer, by administering to an individual in need thereof, a therapeutically effective amount of an agent of the present disclosure that decreases cellular levels of CD33, inhibits interaction between CD33 and one or more CD33 ligands, or both. In some embodiments, the agent is selected from the group consisting of an antibody, a soluble CD33 receptor, a CD33-Fc fusion protein, a CD33 immunoadhesin, a soluble Siglec receptor that binds one or more CD33 ligands, a Siglec-Fc fusion protein, a Siglec immunoadhesin, an antisense molecule, an siRNA, a small molecule inhibitor, a protein, and a peptide. In certain embodiments, the agent is an anti-CD33 antibody of the present disclosure. In some embodiments, the agent inhibits one or more CD33 activities selected from: (a) promoting proliferation, maturation, migration, differentiation, and/or functionality of one or more of immunosuppressor dendritic cells, immunosuppressor macrophages, immunosuppressor neutrophils, non-tumorigenic myeloid derived suppressor cells, tumor-associated macrophages, non-tumorigenic CD14$^+$ myeloid cells, and regulatory T cells; (b) enhancing infiltration of one or more of immunosuppressor dendritic cells, immunosuppressor macrophages, immunosuppressor neutrophils, non-tumorigenic myeloid derived suppressor cells, tumor-associated macrophages, and regulatory T cells into tumors; (c) increasing number of tumor-promoting myeloid/granulocytic immune-suppressive cells and/or non-tumorigenic CD14$^+$ myeloid cells in a tumor, in peripheral blood, or other lymphoid organ; (d) enhancing tumor-promoting activity of non-tumorigenic myeloid-derived suppressor cells and/or non-tumorigenic CD14$^+$ myeloid cells; (e) increasing expression of tumor-promoting cytokines in a tumor or in peripheral blood, optionally wherein the tumor-promoting cytokines are TGF-beta or IL-10; (f) increasing tumor infiltration of tumor-promoting FoxP3+ regulatory T lymphocytes; (g) decreasing activation of tumor-specific T lymphocytes with tumor killing potential; (h) decreasing infiltration of tumor-specific T lymphocytes with tumor killing potential; (i) decreasing infiltration of tumor-specific NK cells with tumor killing potential; (j) decreasing tumor killing potential of NK cells; (k) decreasing infiltration of tumor-specific B lymphocytes with potential to enhance immune response; (l) increasing tumor volume; (m) increasing tumor growth rate; (n) increasing metastasis; (o) increasing rate of tumor recurrence; (p) increasing expression of one or more PD-1 ligands; (q) decreasing efficacy of one or more immune-therapies that modulate anti-tumor T cell responses, optionally wherein the one or more immune-therapies are immune-therapies that target one or more proteins selected from the group consisting of CD40, OX40, ICOS, CD28, CD137/4-1BB, CD27, GITR, PD-L1, CTLA4, PD-L2, PD-1, B7-H3, B7-H4, HVEM, BTLA, KIR, GAL9, TIM3, A2AR, LAG, DR-5, TREM1, TREM2, CSF-1 receptor, and any combination thereof, or of one or more cancer vaccines; (r) inhibition of PLCγ/PKC/calcium mobilization; (s) inhibition of PI3K/Akt, Ras/MAPK signaling; and (t) decreasing efficacy of one or more chemotherapy agents, optionally wherein the one or more of the chemotherapy agents are gemcitabine, capecitabine, anthracyclines, doxorubicin (Adriamycin®), epirubicin (Ellence®), taxanes, paclitaxel (Taxol®), docetaxel (Taxotere®), 5-fluorouracil (5-FU), cyclophosphamide (Cytoxan®), carboplatin (Paraplatin®), and any combination thereof. In some embodiments, the agent exhibits one or more activities selected from: (a) increasing the number of tumor infiltrating CD3$^+$ T cells; (b) decreasing cellular levels of CD33 in non-tumorigenic CD14$^+$ myeloid cells, optionally wherein the non-tumorigenic CD14$^+$ myeloid cells are tumor infiltrating cells or optionally wherein the non-tumorigenic CD14$^+$ myeloid cells are present in blood; (c) reducing the number of non-tumorigenic CD14$^+$ myeloid cells, optionally wherein the non-tumorigenic CD14$^+$ myeloid cells are tumor infiltrating cells or optionally wherein the non-tumorigenic CD14$^+$ myeloid cells are present in blood; (d) reducing PD-L1 levels in one or more cells, optionally wherein the one or more cells are non-tumorigenic myeloid-derived suppressor cells (MDSC); (e) reducing PD-L2 levels in one or more cells, optionally wherein the one or more cells are non-tumorigenic myeloid-derived suppressor cells (MDSC); (f) reducing B7-H2 levels in one or more cells, optionally wherein the one or more cells are non-tumorigenic myeloid-derived suppressor cells (MDSC); (g) reducing B7-H3 levels in one or more cells, optionally wherein the one or more cells are non-tumorigenic myeloid-derived suppressor cells (MDSC); (h) reducing CD200R levels in one or more cells, optionally wherein the one or more cells are non-tumorigenic myeloid-derived suppressor cells (MDSC); (i) reducing CD163 levels in one or more cells, optionally wherein the one or more cells are non-tumorigenic myeloid-derived suppressor cells (MDSC); (j) reducing CD206 levels in one or more cells, optionally wherein the one or more cells are non-tumorigenic myeloid-derived suppressor cells (MDSC); (k) decreasing tumor growth rate of solid tumors; (l) reducing tumor volume; (m) increasing efficacy of one or more PD-1 inhibitors; (n) increasing efficacy of one or more checkpoint inhibitor therapies and/or immune-modulating therapies, optionally wherein the one or more checkpoint inhibitor therapies and/or immune-modulating therapies target one or more of CTL4, the adenosine pathway, PD-L1, PD-L2, OX40, TIM3, LAG3, or any combination thereof; (o) increasing efficacy of one or more chemotherapy agents, optionally wherein the one or more of the chemotherapy agents are gemcitabine, capecitabine, anthracyclines, doxorubicin (Adriamycin®), epirubicin (Ellence®), taxanes, paclitaxel (Taxol®), docetaxel (Taxotere®), 5-fluorouracil (5-FU), cyclophosphamide (Cytoxan®), carboplatin (Paraplatin®), and any combination thereof; (p) increasing proliferation of T cells in the presence of non-tumorigenic myeloid-derived suppressor cells (MDSC); and (q) inhibiting differentiation, survival, and/or one or more functions of non-tumorigenic myeloid-derived suppressor cells (MDSC); and (r) killing CD33-expressing immunosuppressor myeloid cells and/or CD14-expressing cells in solid tumors and associated blood vessels when conjugated to a chemical or radioactive toxin.

As disclosed herein, agents of the present disclosure, such as anti-CD33 antibodies of the present disclosure, may also be used for inducing and/or promoting the survival maturation, functionality, migration, or proliferation of one or more immune cells (e.g., innate immune cells or adaptive immune cells). In some embodiments, the present disclosure provides methods of inducing or promoting the survival, maturation, functionality, migration, or proliferation of one or more immune cells in an individual in need thereof, by administering to the individual a therapeutically effective amount of an agent of the present disclosure that decreases cellular levels of CD33, inhibits interaction between CD33 and one or more CD33 ligands, or both. In some embodiments, the agent is selected from the group consisting of an antibody, a soluble CD33 receptor, a CD33-Fc fusion protein, a CD33 immunoadhesin, a soluble Siglec receptor that binds one or more CD33 ligands, a Siglec-Fc fusion protein, a Siglec immunoadhesin, an antisense molecule, an siRNA, a small molecule inhibitor, a protein, and a peptide. In some embodiments, the agent is an isolated anti-CD33 antibody of the present disclosure. In some embodiments, the one or more immune cells are selected from dendritic cells, macrophages, microglia, neutrophils, T cells, T helper cells, cytotoxic T cells, and any combination thereof.

In some embodiments, the agent is an agonist anti-CD33 antibody. In some embodiments, the agent is a transient agonist anti-CD33 antibody of the present disclosure that initially acts as an agonist and then acts as a long-term antagonist antibody. In some embodiments, the agent is an inert anti-CD33 antibody. In some embodiments, the agent is an antagonist anti-CD33 antibody. In some embodiments, the anti-CD33 antibody reduces cellular (e.g., cell surface, intracellular, or total) levels of CD33. In some embodiments, the anti-CD33 antibody induces degradation of CD33. In some embodiments, the anti-CD33 antibody induces cleavage of CD33. In some embodiments, the anti-CD33 antibody induces internalization of CD33. In some embodiments, the anti-CD33 antibody induces shedding of CD33. In some embodiments, the anti-CD33 antibody induces downregulation of CD33 expression. In some embodiments, the anti-CD33 antibody inhibits interaction (e.g., binding) between CD33 and one or more CD33 ligands. In some embodiments, the anti-CD33 antibody transiently activates and then induces degradation of CD33. In some embodiments, the anti-CD33 antibody transiently activates and then induces cleavage of CD33. In some embodiments, the anti-CD33 antibody transiently activates and then induces internalization of CD33. In some embodiments, the anti-CD33 antibody transiently activates and then induces shedding of CD33. In some embodiments, the anti-CD33 antibody transiently activates and then induces downregulation of CD33 expression. In some embodiments, the anti-CD33 antibody transiently activates and then induces decreased expression of CD33. In certain embodiments, the individual has a CD33 variant allele having single nucleotide polymorphisms (SNPs) rs3865444 CC or AC. In certain embodiments, the individual has a CD33 variant allele having single nucleotide polymorphisms (SNPs) 2459419 CC or CT.

As disclosed herein, agents of the present disclosure that bind or interact with CD33, such as anti-CD33 antibodies of the present disclosure, may further be used for decreasing the activity, functionality, or survival of regulatory T cells, tumor-imbedded immunosuppressor dendritic cells, tumor-imbedded immunosuppressor macrophages, myeloid-derived suppressor cells, tumor-associated macrophages, acute myeloid leukemia (AML) cells, chronic lymphocytic leukemia (CLL) cell, and/or chronic myeloid leukemia (CML) cells. In some embodiments, the present disclosure provides methods of decreasing the activity, functionality, or survival of regulatory T cells, tumor-imbedded immunosuppressor dendritic cells, tumor-imbedded immunosuppressor macrophages, myeloid-derived suppressor cells, tumor-associated macrophages, acute myeloid leukemia (AML) cells, chronic lymphocytic leukemia (CLL) cell, or chronic myeloid leukemia (CML) cells in an individual in need thereof, by administering to the individual a therapeutically effective amount of an agent that binds or interacts with CD33. In some embodiments, the agent is selected from an antibody, an antagonist antibody, an inert antibody, an agonist antibody, a CD33 ligand, a CD33 ligand agonist fragment, a CD33 immunoadhesin, a CD33 ligand mimetic, a soluble CD33 receptor, a CD33-Fc fusion protein, a soluble Siglec receptor that binds one or more CD33 ligands, a Siglec-Fc fusion protein that binds one or more CD33 ligands, and a small molecule compound. In some embodiments, the agent is an isolated anti-CD33 antibody or anti-CD33 antibody conjugate of the present disclosure. In some embodiments, the anti-CD33 antibody conjugate comprises an anti-CD33 antibody conjugated to a detectable marker, a toxin, or a therapeutic agent.

As disclosed herein, anti-CD33 antibodies of the present disclosure may be used for decreasing cellular levels of CD33, inhibiting interaction between CD33 and one or more CD33 ligands, or both on one or more cells in vitro or in vivo. In some embodiments, the present disclosure provides methods of decreasing cellular levels of CD33, inhibiting interaction between CD33 and one or more CD33 ligands, or both on one or more cells in an individual in need thereof, by administering to the individual a therapeutically effective amount of an isolated anti-CD33 antibody of the present disclosure. In some embodiments, the anti-CD33 antibody decreases cellular levels of CD33 in vivo.

As disclosed herein, anti-CD33 antibodies of the present disclosure may be used for decreasing cellular levels of CD33 on one or more cells, including without limitation, dendritic cells, bone marrow-derived dendritic cells, monocytes, microglia, T cells, and macrophages, and/or cell lines. In some embodiments, the present disclosure provides methods of decreasing cellular levels of CD33 on one or more cells in an individual in need thereof, by administering to the individual a therapeutically effective amount of an anti-CD33 antibody of the present disclosure. In some embodiments, the one or more cells are selected from dendritic cells, bone marrow-derived dendritic cells, monocytes, microglia, T cells, and macrophages, and any combination thereof. In some embodiments, the anti-CD33 antibody decreases cellular levels of CD33 in vivo. Cellular levels of CD33 may refer to, without limitation, cell surface levels of CD33, intracellular levels of CD33, and total levels of CD33. In some embodiments, a decrease in cellular levels of CD33 comprises decrease in cell surface levels of CD33. As used herein, cell surface levels of CD33 may be measured by any in vitro cell-based assays or suitable in vivo model described herein or known in the art. In some embodiments, a decrease in cellular levels of CD33 comprises a decrease in intracellular levels of CD33. As used herein, intracellular levels of CD33 may be measured by any in vitro cell-based assays or suitable in vivo model described herein or known in the art. In some embodiments, a decrease in cellular levels of CD33 comprises a decrease in total levels of CD33. As used herein, total levels of CD33 may be measured by any in vitro cell-based assays or suitable in vivo model described herein or known in the art. In some embodiments, the anti-CD33 antibodies induce CD33 degradation, CD33 cleavage, CD33 internalization, CD33 shedding, and/or downregulation of CD33 expression. In some embodiments, cellular levels of CD33 are measured on primary cells (e.g., dendritic cells, bone marrow-derived dendritic cells, monocytes, microglia, T cells, and macrophages) or on cell lines utilizing an in vitro cell assay.

Other aspects of the present disclosure relate to a method of selecting a subject in need thereof for treatment with an agent that binds or interacts with CD33, the method comprising: a. obtaining a sample (e.g., blood sample) from the subject; b. detecting the CD33 alleles present in the subject; and c. selecting the subject for treatment with the agent that binds or interacts with CD33 is the subject has one or more CD33 alleles, wherein the one or more CD33 alleles are selected from the group consisting of rs3865444$^{AC}$, and rs3865444$^{CC}$. Other aspects of the present disclosure relate to a method of assessing responsiveness of a subject in need thereof to an agent that binds or interacts with CD33, the method comprising: a. measuring the expression levels of CD45$^+$ and CD14$^+$ on non-tumorigenic myeloid cells in a blood sample obtained from the subject prior to administering to the subject an anti-CD33 antibody; b. administering to the subject a therapeutically effective amount of the agent; and c. measuring the expression levels of CD45$^+$ and CD14$^+$ on non-tumorigenic myeloid cells in a blood sample obtained from the subject after administration of the anti-CD33 antibody, wherein a reduction in the levels of CD45$^+$ CD14$^+$ on non-tumorigenic myeloid cells after administration of the anti-CD33 antibody indicates the subject is responsive to the agent. Any suitable methods for obtaining a sample, such as a blood sample, may be used. Further, it will be appreciated that any known method of detecting CD33 variants and/or alleles, such as SNP analysis, may be used. In some embodiments, the method of assessing responsiveness further comprises administering one or more additional therapeutically effective amounts of the agent. In some embodiments, the agent is selected from the group consisting of an antibody, a soluble CD33 receptor, a CD33-Fc fusion protein, a CD33 immunoadhesin, a soluble Siglec receptor, a Siglec-Fc fusion protein, a Siglec immunoadhesin, an antisense molecule, an siRNA, a small molecule inhibitor, a protein, and a peptide. In some embodiments, the agent is an isolated anti-CD33 antibody or anti-CD33 antibody conjugate. In some embodiments, the anti-CD33 antibody is the anti-CD33 antibody of the present disclosure. In some embodiments, the subject is human.

In some embodiments the individual has a variant of CD33. In some embodiments, the variant includes, without limitation, one or more polymorphisms selected from: (a) SNP rs3865444$^{AC}$; (b) SNP rs3865444$^{CC}$; (c) SNP rs35112940$^{GG,\ AA,\ AG}$; and (d) SNP rs12459419$^{CC,\ CT\ or\ TT}$; and any combinations thereof.

In some embodiments, the methods of the present disclosure may further involve the coadministration of CD33 agents, such as anti-CD33 antibodies or bispecific anti-CD33 antibodies, with antibodies that bind to pattern recognition receptors, antibodies that bind to Toll-like receptors, antibodies that bind to damage-associated molecular pattern (DAMP) receptors, and/or antibodies that bind to cytokine or antibodies to interleukins).

In some embodiments, the methods of the present disclosure may further include administering to the individual at least one antibody that specifically binds to an inhibitory checkpoint molecule, and/or one or more standard or investigational anti-cancer therapies. In some embodiments, the at least one antibody that specifically binds to an inhibitory checkpoint molecule is administered in combination with the anti-CD33 antibody. In some embodiments, the at least one antibody that specifically binds to an inhibitory checkpoint molecule is selected from an anti-PD-L1 antibody, an anti-CTLA4 antibody, an anti-PD-L2 antibody, an anti-PD-1 antibody, an anti-B7-H3 antibody, an anti-B7-H4 antibody, and anti-HVEM antibody, an anti-B- and T-lymphocyte attenuator (BTLA) antibody, an anti-Killer inhibitory receptor (KIR) antibody, an anti-GAL9 antibody, an anti-TIM3 antibody, an anti-AZAR antibody, an anti-LAG-3 antibody, an anti-phosphatidylserine antibody, an anti-CD27 antibody, an anti-TNFa antibody, an anti-Siglec-5 antibody, an anti-Siglec-7 antibody, an anti-Siglec-9 antibody, an anti-Siglec-11 antibody, an antagonistic anti-TREM1 antibody, an antagonistic anti-TREM2 antibody, and any combination thereof. In some embodiments, the one or more standard or investigational anti-cancer therapies are selected from radiotherapy, cytotoxic chemotherapy, targeted therapy, imatinib therapy, trastuzumab therapy, etanercept therapy, adoptive cell transfer (ACT) therapy, chimeric antigen receptor T cell transfer (CAR-T) therapy, vaccine therapy, and cytokine therapy.

In some embodiments, the methods of the present disclosure may further include administering to the individual at least one antibody that specifically binds to an inhibitory cytokine. In some embodiments, the at least one antibody that specifically binds to an inhibitory cytokine is administered in combination with the CD33 agent, such as an anti-CD33 antibody. In some embodiments, the at least one antibody that specifically binds to an inhibitory cytokine is selected from an anti-CCL2 antibody, an anti-CSF-1 antibody, an anti-IL-2 antibody, and any combination thereof.

In some embodiments, the methods of the present disclosure may further include administering to the individual at least one agonistic antibody that specifically binds to a stimulatory checkpoint protein. In some embodiments, the at least one agonistic antibody that specifically binds to a stimulatory checkpoint protein is administered in combination with the CD33 agent, such as an anti-CD33 antibody. In some embodiments, the at least one agonistic antibody that specifically binds to a stimulatory checkpoint protein is selected from an agonist anti-CD40 antibody, an agonist anti-OX40 antibody, an agonist anti-ICOS antibody, an agonist anti-CD28 antibody, an agonistic anti-TREM1 antibody, an agonistic anti-TREM2 antibody, an agonist anti-CD137/4-1BB antibody, an agonist anti-CD27 antibody, an agonist anti-glucocorticoid-induced TNFR-related protein GITR antibody, and any combination thereof.

In some embodiments, the methods of the present disclosure may further include administering to the individual at least one stimulatory cytokine. In some embodiments, the at least one stimulatory cytokine is administered in combination with the CD33 agent, such as an anti-CD33 antibody. In some embodiments, the at least one stimulatory cytokine is selected from IFN-a4, IFN-b, IL-1β, TNF-α, IL-6, IL-8, CRP, IL-20 family members, LIF, IFN-gamma, OSM, CNTF, GM-CSF, IL-11, IL-12, IL-17, IL-18, IL-23, CXCL10, IL-33, CRP, IL-33, MCP-1, MIP-1-beta, and any combination thereof.

In some embodiments. a subject or individual is a mammal. Mammals include, without limitation, domesticated animals (e.g., cows, sheep, cats, dogs, and horses), primates (e.g., humans and non-human primates such as monkeys), rabbits, and rodents (e.g., mice and rats). In some embodiments, the subject or individual is a human.

Dementia

Dementia is a non-specific syndrome (i.e., a set of signs and symptoms) that presents as a serious loss of global cognitive ability in a previously unimpaired person, beyond what might be expected from normal ageing. Dementia may be static as the result of a unique global brain injury. Alternatively, dementia may be progressive, resulting in long-term decline due to damage or disease in the body. While dementia is much more common in the geriatric population, it can also occur before the age of 65. Cognitive areas affected by dementia include, without limitation, memory, attention span, language, and problem solving. Generally, symptoms must be present for at least six months to before an individual is diagnosed with dementia.

Exemplary forms of dementia include, without limitation, frontotemporal dementia, Alzheimer's disease, vascular dementia, semantic dementia, and dementia with Lewy bodies.

In some embodiments, administering a CD33 agent of the present disclosure, such as an anti-CD33 antibody of the present disclosure, can prevent, reduce the risk, and/or treat dementia. In some embodiments, administering a CD33 agent, such as an anti-CD33 antibody, may modulate one or more CD33 activities in an individual having dementia.

Frontotemporal Dementia

Frontotemporal dementia (FTD) is a condition resulting from the progressive deterioration of the frontal lobe of the brain. Over time, the degeneration may advance to the temporal lobe. Second only to Alzheimer's disease (AD) in prevalence, FTD accounts for 20% of pre-senile dementia cases. The clinical features of FTD include memory deficits, behavioral abnormalities, personality changes, and language impairments (Cruts, M. & Van Broeckhoven, C., Trends Genet. 24:186-194 (2008); Neary, D., et al., Neurology 51:1546-1554 (1998); Ratnavalli, E., Brayne, C., Dawson, K. & Hodges, J. R., Neurology 58:1615-1621 (2002)).

A substantial portion of FTD cases are inherited in an autosomal dominant fashion, but even in one family, symptoms can span a spectrum from FTD with behavioral disturbances, to Primary Progressive Aphasia, to Cortico-Basal Ganglionic Degeneration. FTD, like most neurodegenerative diseases, can be characterized by the pathological presence of specific protein aggregates in the diseased brain. Historically, the first descriptions of FTD recognized the presence of intraneuronal accumulations of hyperphosphorylated Tau protein in neurofibrillary tangles or Pick bodies. A causal role for the microtubule associated protein Tau was supported by the identification of mutations in the gene encoding the Tau protein in several families (Hutton, M., et al., Nature 393:702-705 (1998). However, the majority of FTD brains show no accumulation of hyperphosphorylated Tau but do exhibit immunoreactivity to ubiquitin (Ub) and TAR DNA binding protein (TDP43) (Neumann, M., et al., Arch. Neurol. 64:1388-1394 (2007)). A majority of those FTD cases with Ub inclusions (FTD-U) were shown to carry mutations in the Progranulin gene.

In some embodiments, administering a CD33 agent of the present disclosure, such as an anti-CD33 antibody of the present disclosure, can prevent, reduce the risk, and/or treat FTD. In some embodiments, administering a CD33 agent, such as an anti-CD33 antibody, may modulate one or more CD33 activities in an individual having FTD.

Alzheimer's Disease

Alzheimer's disease (AD), is the most common form of dementia. There is no cure for the disease, which worsens as it progresses, and eventually leads to death. Most often, AD is diagnosed in people over 65 years of age. However, the less-prevalent early-onset Alzheimer's can occur much earlier.

Common symptoms of Alzheimer's disease include, behavioral symptoms, such as difficulty in remembering recent events; cognitive symptoms, confusion, irritability and aggression, mood swings, trouble with language, and long-term memory loss. As the disease progresses bodily functions are lost, ultimately leading to death. Alzheimer's disease develops for an unknown and variable amount of time before becoming fully apparent, and it can progress undiagnosed for years.

In some embodiments, administering a CD33 agent of the present disclosure, such as an anti-CD33 antibody of the present disclosure, can prevent, reduce the risk, and/or treat Alzheimer's disease. In some embodiments, administering a CD33 agent, such as an anti-CD33 antibody, may modulate one or more CD33 activities in an individual having Alzheimer's disease.

Parkinson's Disease

Parkinson's disease, which may be referred to as idiopathic or primary parkinsonism, hypokinetic rigid syndrome (HRS), or paralysis agitans, is a neurodegenerative brain disorder that affects motor system control. The progressive death of dopamine-producing cells in the brain leads to the major symptoms of Parkinson's. Most often, Parkinson's disease is diagnosed in people over 50 years of age. Parkinson's disease is idiopathic (having no known cause) in most people. However, genetic factors also play a role in the disease.

Symptoms of Parkinson's disease include, without limitation, tremors of the hands, arms, legs, jaw, and face, muscle rigidity in the limbs and trunk, slowness of movement (bradykinesia), postural instability, difficulty walking, neuropsychiatric problems, changes in speech or behavior, depression, anxiety, pain, psychosis, dementia, hallucinations, and sleep problems.

In some embodiments, administering a CD33 agent of the present disclosure, such as an anti-CD33 antibody of the present disclosure, can prevent, reduce the risk, and/or treat Parkinson's disease. In some embodiments, administering a CD33 agent, such as an anti-CD33 antibody, may modulate one or more CD33 activities in an individual having Parkinson's disease.

Amyotrophic Lateral Sclerosis (ALS)

As used herein, amyotrophic lateral sclerosis (ALS) or, motor neuron disease or, Lou Gehrig's disease are used interchangeably and refer to a debilitating disease with varied etiology characterized by rapidly progressive weakness, muscle atrophy and fasciculations, muscle spasticity, difficulty speaking (dysarthria), difficulty swallowing (dysphagia), and difficulty breathing (dyspnea).

It has been shown that Progranulin plays a role in ALS (Schymick, J C et al., (2007) J Neurol Neurosurg Psychiatry.; 78:754-6) and protects again the damage caused by ALS causing proteins such as TDP-43 (Laird, A S et al., (2010). PLoS ONE 5: e13368). It was also demonstrated that pro-NGF induces p75 mediated death of oligodendrocytes and corticospinal neurons following spinal cord injury (Beatty et al., Neuron (2002), 36, pp. 375-386; Giehl et al, Proc. Natl. Acad. Sci USA (2004), 101, pp 6226-30).

In some embodiments, administering a CD33 agent of the present disclosure, such as an anti-CD33 antibody of the present disclosure, can prevent, reduce the risk, and/or treat ALS. In some embodiments, administering a CD33 agent, such as an anti-CD33 antibody, may modulate one or more CD33 activities in an individual having amyotrophic lateral sclerosis.

Huntington's Disease

Huntington's disease (HD) is an inherited neurodegenerative disease caused by an autosomal dominant mutation in the Huntingtin gene (HTT). Expansion of a cytokine-adenine-guanine (CAG) triplet repeat within the Huntingtin gene results in production of a mutant form of the Huntingtin protein (Htt) encoded by the gene. This mutant Huntingtin protein (mHtt) is toxic and contributes to neuronal death. Symptoms of Huntington's disease most commonly appear between the ages of 35 and 44, although they can appear at any age.

Symptoms of Huntington's disease, include, without limitation, motor control problems, jerky, random movements (chorea), abnormal eye movements, impaired balance, seizures, difficulty chewing, difficulty swallowing, cognitive problems, altered speech, memory deficits, thinking difficulties, insomnia, fatigue, dementia, changes in personality, depression, anxiety, and compulsive behavior.

In some embodiments, administering a CD33 agent of the present disclosure, such as an anti-CD33 antibody of the present disclosure, can prevent, reduce the risk, and/or treat Huntington's disease (HD). In some embodiments, administering a CD33 agent, such as an anti-CD33 antibody, may modulate one or more CD33 activities in an individual having Huntington's disease.

Taupathy Disease

Taupathy diseases, or Tauopathies, are a class of neurodegenerative disease caused by aggregation of the microtubule-associated protein tau within the brain. Alzheimer's disease (AD) is the most well-known taupathy disease, and involves an accumulation of tau protein within neurons in the form of insoluble neurofibrillary tangles (NFTs). Other taupathy diseases and disorders include progressive supranuclear palsy, dementia pugilistica (chromic traumatic encephalopathy), frontotemporal dementia and parkinsonism linked to chromosome 17, Lytico-Bodig disease (Parkinson-dementia complex of Guam), Tangle-predominant dementia, Ganglioglioma and gangliocytoma, Meningioangiomatosis, Subacute sclerosing panencephalitis, lead encephalopathy, tuberous sclerosis, Hallervorden-Spatz disease, lipofuscinosis, Pick's disease, corticobasal degeneration, Argyrophilic grain disease (AGD), Huntington's disease, and frontotemporal lobar degeneration.

In some embodiments, administering a CD33 agent of the present disclosure, such as an anti-CD33 antibody of the present disclosure, can prevent, reduce the risk, and/or treat taupathy disease. In some embodiments, administering a CD33 agent, such as an anti-CD33 antibody, may modulate one or more CD33 activities in an individual having a taupathy disease.

Multiple Sclerosis

Multiple sclerosis (MS) can also be referred to as disseminated sclerosis or encephalomyelitis disseminata. MS is an inflammatory disease in which the fatty myelin sheaths around the axons of the brain and spinal cord are damaged, leading to demyelination and scarring as well as a broad spectrum of signs and symptoms. MS affects the ability of nerve cells in the brain and spinal cord to communicate with each other effectively. Nerve cells communicate by sending electrical signals called action potentials down long fibers called axons, which are contained within an insulating substance called myelin. In MS, the body's own immune system attacks and damages the myelin. When myelin is lost, the axons can no longer effectively conduct signals. MS onset usually occurs in young adults, and is more common in women.

Symptoms of MS include, without limitation, changes in sensation, such as loss of sensitivity or tingling; pricking or numbness, such as hypoesthesia and paresthesia; muscle weakness; clonus; muscle spasms; difficulty in moving; difficulties with coordination and balance, such as ataxia; problems in speech, such as dysarthria, or in swallowing, such as dysphagia; visual problems, such as nystagmus, optic neuritis including phosphenes, and diplopia; fatigue; acute or chronic pain; and bladder and bowel difficulties; cognitive impairment of varying degrees; emotional symptoms of depression or unstable mood; Uhthoff's phenomenon, which is an exacerbation of extant symptoms due to an exposure to higher than usual ambient temperatures; and Lhermitte's sign, which is an electrical sensation that runs down the back when bending the neck.

In some embodiments, administering a CD33 agent of the present disclosure, such as an anti-CD33 antibody of the present disclosure, can prevent, reduce the risk, and/or treat multiple sclerosis. In some embodiments, administering a CD33 agent, such as an anti-CD33 antibody, may modulate one or more CD33 activities in an individual having multiple sclerosis.

Cancer

Further aspects of the present disclosure provide methods for preventing, reducing risk, or treating cancer, by administering to an individual in need thereof a therapeutically effective amount of a CD33 agent of the present disclosure, such as an isolated anti-CD33 antibody of the present disclosure. Any of the isolated antibodies of the present disclosure may be used in these methods. In some embodiments, the isolated antibody is an agonist antibody of the present disclosure. In other embodiments, the isolated antibody is an antagonist antibody of the present disclosure. In other embodiments, the isolated antibody is an inert antibody of the present disclosure. In other embodiments, the isolated antibody is an antibody conjugate of the present disclosure.

As disclosed herein, the tumor microenvironment is known to contain a heterogeneous immune infiltrate, which includes T lymphocytes, macrophages and cells of myeloid/granulocytic lineage. The presence and activity of T-regulatory cells, tumor-imbedded immunosuppressor myeloid cells, and/or M2-macrophages in tumors is associated with poor prognosis. In contrast, the presence and activity of cytotoxic T cells is beneficial for cancer therapy. Therapies that directly or indirectly enhance the activity of cytotoxic T cells and reduce the number and activity of the various immunosuppressor cells, are expected to provide significant therapeutic benefit. A seminal preclinical study has shown synergies between drugs that target immunosuppressor cells (e.g., CSF1/CSF1R blocking antibodies) and immune checkpoint blocking antibodies that activate cytotoxic T cells, indicating that manipulating both cell types shows efficacy in tumor models where individual therapies are poorly effective (Zhu Y; Cancer Res. 2014 Sep. 15; 74(18): 5057-69). Therefore, in some embodiments, blocking CD33, which is expressed on myeloid cells, subset of T cells, and tumor-associated immune cells, may stimulate beneficial anti-tumor immune response, resulting in a therapeutic anti-tumor immune response.

In some embodiments, the methods for preventing, reducing risk, or treating an individual having cancer further include administering to the individual at least one antibody that specifically binds to an inhibitory checkpoint molecule. Examples of antibodies that specifically bind to an inhibitory checkpoint molecule include, without limitation, an anti-PD-L1 antibody, an anti-CTLA4 antibody, an anti-PD-L2 antibody, an anti-PD-1 antibody, an anti-B7-H3 antibody, an anti-B7-H4 antibody, and anti-HVEM antibody, an anti-BTLA antibody, an anti-GAL9 antibody, an anti-TIM3 antibody, an anti-AZAR antibody, an anti-LAG-3 antibody, an anti-phosphatidylserine antibody, and any combination thereof. In some embodiments, the at least one antibody that specifically binds to an inhibitory checkpoint molecule is administered in combination with a CD33 agent of the present disclosure, such as an antagonist anti-CD33 antibody of the present disclosure.

In some embodiments, a cancer to be prevented or treated by the methods of the present disclosure includes, without limitation, squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer and gastrointestinal stromal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, superficial spreading melanoma, lentigo maligna melanoma, acral lentiginous melanomas, nodular melanomas, multiple myeloma and B cell lymphoma; chronic lymphocytic leukemia (CLL); acute lymphoblastic leukemia (ALL); hairy cell leukemia; chronic myeloblastic leukemia; and post-transplant lymphoproliferative disorder (PTLD), as well as abnormal vascular proliferation associated with phakomatoses, edema (such as that associated with brain tumors), Meigs' syndrome, brain, as well as head and neck cancer, and associated metastases. In some embodiments, the cancer is colorectal cancer. In some embodiments, the cancer is selected from non-small cell lung cancer, glioblastoma, neuroblastoma, renal cell carcinoma, bladder cancer, ovarian cancer, melanoma, breast carcinoma, gastric cancer, and hepatocellular carcinoma. In some embodiments, the cancer is triple-negative breast carcinoma. In some embodiments, the cancer may be an early stage cancer or a late stage cancer. In some embodiments, the cancer may be a primary tumor. In some embodiments, the cancer may be a metastatic tumor at a second site derived from any of the above types of cancer.

In some embodiments, CD33 agents of the present disclosure, such as anti-CD33 antibodies of the present disclosure, may be used for preventing, reducing risk, or treating cancer, including, without limitation, bladder cancer breast cancer, colon and rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, and thyroid cancer.

In some embodiments, the present disclosure provides methods of preventing, reducing risk, or treating an individual having cancer, by administering to the individual a therapeutically effective amount of a CD33 agent of the present disclosure, such as an anti-CD33 antibody of the present disclosure.

In some embodiments, the method further includes administering to the individual at least one antibody that specifically binds to an inhibitory immune checkpoint molecule, and/or another standard or investigational anti-cancer therapy. In some embodiments, the at least one antibody that specifically binds to an inhibitory checkpoint molecule is administered in combination with the CD33 agent, such as an anti-CD33 antibody of the present disclosure. In some embodiments, the at least one antibody that specifically binds to an inhibitory checkpoint molecule is selected from an anti-PD-L1 antibody, an anti-CTLA4 antibody, an anti-PD-L2 antibody, an anti-PD-1 antibody, an anti-B7-H3 antibody, an anti-B7-H4 antibody, and anti-HVEM antibody, an anti-B- and T-lymphocyte attenuator (BTLA) antibody, an anti-Killer inhibitory receptor (KIR) antibody, an anti-GAL9 antibody, an anti-TIM3 antibody, an anti-AZAR antibody, an anti-LAG-3 antibody, an anti-phosphatidylserine antibody, an anti-CD27 antibody, and any combination thereof. In some embodiments, the standard or investigational anti-cancer therapy is one or more therapies selected from radiotherapy, cytotoxic chemotherapy, targeted therapy, imatinib (Gleevec®), trastuzumab (Herceptin®), adoptive cell transfer (ACT), chimeric antigen receptor T cell transfer (CAR-T), vaccine therapy, and cytokine therapy.

In some embodiments, the method further includes administering to the individual at least one antibody that specifically binds to an inhibitory cytokine. In some embodiments, the at least one antibody that specifically binds to an inhibitory cytokine is administered in combination with the CD33 agent, such as an anti-CD33 antibody of the present disclosure. In some embodiments, the at least one antibody that specifically binds to an inhibitory cytokine is selected from an anti-CCL2 antibody, an anti-CSF-1 antibody, an anti-IL-2 antibody, and any combination thereof.

In some embodiments, the method further includes administering to the individual at least one agonistic antibody that specifically binds to a stimulatory immune checkpoint protein. In some embodiments, the at least one agonistic antibody that specifically binds to a stimulatory checkpoint protein is administered in combination with the CD33 agent, such as an anti-CD33 antibody of the present disclosure. In some embodiments, the at least one agonistic antibody that specifically binds to a stimulatory checkpoint protein is selected from an agonist anti-CD40 antibody, an agonist anti-OX40 antibody, an agonist anti-ICOS antibody, an agonist anti-CD28 antibody, an agonist anti-CD137/4-1BB antibody, an agonist anti-CD27 antibody, an agonist anti-glucocorticoid-induced TNFR-related protein GITR antibody, and any combination thereof.

In some embodiments, the method further includes administering to the individual at least one stimulatory cytokine. In some embodiments, the at least one stimulatory cytokine is administered in combination with the CD33 agent, such as an anti-CD33 antibody of the present disclosure. In some embodiments, the at least one stimulatory cytokine is selected from TNF-α, IL-6, IL-8, CRP, IL-20 family member, LIF, OSM, CNTF, IL-11, IL-12, IL-17, IL-8, CRP, IFN-α, IFN-β, IL-2, IL-18, GM-CSF, G-CSF, and any combination thereof.

Kits/Articles of Manufacture

The present disclosure also provides kits and/or articles of manufacture containing a CD33 agent of the present disclosure (e.g., an anti-CD33 antibody described herein), or a functional fragment thereof. Kits and/or articles of manufacture of the present disclosure may include one or more containers comprising a purified antibody of the present disclosure. In some embodiments, the kits and/or articles of manufacture further include instructions for use in accordance with the methods of this disclosure. In some embodiments, these instructions comprise a description of administration of the CD33 agent of the present disclosure (e.g., an anti-CD33 antibody described herein) to prevent, reduce risk, or treat an individual having a disease, disorder, or injury selected from dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express CD33, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus* influenza, according to any methods of this disclosure.

In some embodiments, the instructions comprise a description of how to detect a CD33 protein, for example in an individual, in a tissue sample, or in a cell. The kit and/or article of manufacture may further comprise a description of selecting an individual suitable for treatment based on identifying whether that individual has the disease and the stage of the disease.

In some embodiments, the kits and/or articles of manufacture may further include another antibody of the present disclosure (e.g., at least one antibody that specifically binds to an inhibitory checkpoint molecule, at least one antibody that specifically binds to an inhibitory cytokine, and/or at least one agonistic antibody that specifically binds to a stimulatory checkpoint protein) and/or at least one stimulatory cytokine. In some embodiments, the kits and/or articles of manufacture may further include instructions for using the antibody and/or stimulatory cytokine in combination with a CD33 agent of the present disclosure (e.g., an anti-CD33 antibody described herein), instructions for using a CD33 agent of the present disclosure (e.g., an anti-CD33 antibody described herein) in combination with an antibody and/or stimulatory cytokine, or instructions for using a CD33 agent of the present disclosure (e.g., an anti-CD33 antibody described herein) and an antibody and/or stimulatory cytokine, according to any methods of this disclosure.

The instructions generally include information as to dosage, dosing schedule, and route of administration for the intended treatment. The containers may be unit doses, bulk packages (e.g., multi-dose packages) or sub-unit doses. Instructions supplied in the kits and/or articles of manufacture of the present disclosure are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, e.g., a disease of the present disclosure. Instructions may be provided for practicing any of the methods described herein.

The kits and/or articles of manufacture of this disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit and/or article of manufacture may have a sterile access port (for example the container may be an intravenous solution bag or a vial having a stopper pierceable by a hypodermic injection needle). The container may also have a sterile access port (e.g., the container may be an intravenous solution bag or a vial having a stopper pierceable by a hypodermic injection needle). At least one active agent in the composition is a CD33 agent of the present disclosure (e.g., an anti-CD33 antibody described herein). The container may further comprise a second pharmaceutically active agent.

Kits and/or articles of manufacture may optionally provide additional components such as buffers and interpretive information. Normally, the kit comprises a container and a label or package insert(s) on or associated with the container.

Diagnostic Uses

The CD33 agents of the present disclosure, such as the isolated antibodies of the present disclosure (e.g., an anti-CD33 antibody described herein) also have diagnostic utility. This disclosure therefore provides for methods of using the antibodies of this disclosure, or functional fragments thereof, for diagnostic purposes, such as the detection of a CD33 protein in an individual or in tissue samples derived from an individual.

In some embodiments, the individual is a human. In some embodiments, the individual is a human patient suffering from, or at risk for developing a disease, disorder, or injury of the present disclosure. In some embodiments, the diagnostic methods involve detecting a CD33 protein in a biological sample, such as a biopsy specimen, a tissue, or a cell. A CD33 agent of the present disclosure (e.g., an anti-CD33 antibody described herein) is contacted with the biological sample and antigen-bound antibody is detected. For example, a biopsy specimen may be stained with an anti-CD33 antibody described herein in order to detect and/or quantify disease-associated cells. The detection method may involve quantification of the antigen-bound antibody. Antibody detection in biological samples may occur with any method known in the art, including immunofluorescence microscopy, immunocytochemistry, immunohistochemistry, ELISA, FACS analysis, immunoprecipitation, or micro-positron emission tomography. In certain embodiments, the antibody is radiolabeled, for example with $^{18}F$ and subsequently detected utilizing micro-positron emission tomography analysis. Antibody-binding may also be quantified in a patient by non-invasive techniques such as positron emission tomography (PET), X-ray computed tomography, single-photon emission computed tomography (SPECT), computed tomography (CT), and computed axial tomography (CAT).

In other embodiments, an isolated antibody of the present disclosure (e.g., an anti-CD33 antibody described herein) may be used to detect and/or quantify, for example, microglia in a brain specimen taken from a preclinical disease model (e.g., a non-human disease model). As such, an isolated antibody of the present disclosure (e.g., an anti-CD33 antibody described herein) may be useful in evaluating therapeutic response after treatment in a model for a nervous system disease or injury such as frontotemporal dementia, Alzheimer's disease, vascular dementia, seizures, retinal dystrophy, atherosclerotic vascular diseases, Nasu-Hakola disease, or multiple sclerosis, as compared to a control.

The present disclosure will be more fully understood by reference to the following Examples. They should not, however, be construed as limiting the scope of the present disclosure. All citations throughout the disclosure are hereby expressly incorporated by reference.

EXAMPLES

Example 1: Production, Identification, and Characterization of Anti-CD33 Antibodies Introduction The amino acid sequence of human CD33 is set forth below in SEQ ID NO:1. Human CD33 contains a signal sequence located at amino acid residues 1-17 of SEQ ID NO:1, an extracellular immunoglobulin-like variable-type (IgV) domain located at amino acid residues 19-135 of SEQ ID NO:1, an Ig-like C2-type domain located at amino acid residues 145-228 of SEQ ID NO:1, a transmembrane domain located at amino acid residues 260-282 of SEQ ID NO:1, an ITIM motif 1 located at amino acid residues 338-343 of SEQ ID NO:1, and an ITIM motif 2 located at amino acid residues 356-361 of SEQ ID NO:1. The structure of CD33 is depicted in FIG. 1. Alignment of a portion of CD33 with CD33 homologs is shown in FIG. 2.

CD33 amino acid sequence (SEQ ID NO:1):

```
        10         20         30         40         50         60
MPLLLLLPLL WAGALAMDPN FWLQVQESVT VQEGLCVLVP CTFFHPIPYY DKNSPVHGYW 70         80         90        100        110        120
FREGAIISRD SPVATNKLDQ EVQEETQGRF RLLGDPSRNN CSLSIVDARR RDNGSYFFRM 130        140        150        160        170        180
ERGSTKYSYK SPQLSVHVTD LTHRPKILIP GTLEPGHSKN LTCSVSWACE QGTPPIFSWL 190        200        210        220        230        240
SAAPTSLGPR TTHSSVLIIT PRPQDHGTNL TCQVKFAGAG VTTERTIQLN VTYVPQNPTT 250        260        270        280        290        300
GIFPGDGSGK QETRAGVVHG AIGGAGVTAL LALCLCLIFF IVKTHRRKAA RTAVGRNDTH 310        320        330        340        350        360
PTTGSASPKH QKKSKLHGPT ETSSCSGAAP TVEMDEELHY ASLNFHGMNP SKDTSTEYSE

VRTQ
```

The purpose of the following Example was to produce CD33-binding antibodies (e.g., antagonistic antibodies, CD33 specific antibodies) that enhance the beneficial effects of dendritic cells, monocytes, macrophages, T cells, neutrophils, NK cells and/or microglia. Antibodies that bind the extracellular domain of CD33, particularly the IgV domain (amino acid residues 19-135 of SEQ ID NO:1) are generated using mouse hybridoma technology, phage display technology, and yeast display technology. Antibodies are identified and then screened for their ability to compete with CD33 ligands on binding to CD33, to induce CD33 downregulation, to induce CD33 desensitization, to induce CD33 degradation, to induce CD33 targeting to the lysosome, to induce CD33 cleavage, to modulate CD33 signaling and/or one or more functions in cells and in animals in vivo, as described in the following Examples. Exemplary ligands bound by CD33 are depicted in FIG. 3 and FIG. 4.

For example, anti-CD33 antibodies are selected that target the IgV domain (amino acid residues 19-135 of CD33. The IgV domain binds to sialic acid targets, and this binding can be blocked with the antibody. Thus, amino acid residues 19-135 correspond to a CD33 peptide target for antibodies that will block binding of CD33 to one or more endogenous targets (e.g., ligands).

Another approach for identifying a useful site within human CD33 protein is by selecting antibodies targeting sites that are not present on CD33m as compared to CD33M, which are generally found within the IgV domain. CD33m is not able to inhibit clearance of the amyloid beta peptide. Another approach for identifying useful antibodies is to select for antibodies that decrease the level of CD33 on the cell surface of monocytes, macrophages, dendritic cells, neutrophils, microglia and/or T cells.

As described herein, 7 anti-CD33 antibodies were identified and characterized.

Results

Anti-CD33 Antibody Production

Immunization Procedure

Rapid prime method: Four 50-day old female BALB/c mice were immunized with using the following procedure. A series of subcutaneous aqueous injections containing human CD33 antigen but no adjuvant were given over a period of 19 days. Mice were housed in a ventilated rack system from Lab Products. All four mice were euthanized on Day 19 and lymphocytes were harvested for hybridoma cell line generation.

Standard method: Four 50-day old female BALB/c or NZB/W mice were immunized using the following procedure. Mice were housed in a ventilated rack system from Lab Products. Mice were injected intraperitoneally every 3 weeks with a human CD33 antigen mixed in CpG-ODN adjuvant at 25 µg protein antigen per mouse (total volume 125 µL per mouse). Test bleeds were done by saphenous vein lancing seven days after the second boost. The test bleed (immune sera) was tested by indirect ELISA assay to determine the best two responding mice for the fusion. The mice may require a 3rd and 4th boost and another test bleed 7 days after boost to assess titer before fusion. When the antibody titer is high enough the best two responding mice are given a final intravenous boost via lateral tail vein. Four days after the IV boost the mice were euthanized for fusion. The spleens were harvested and lymphocytes isolated from the spleen were used in the fusion process to produce hybridomas.

Hybridoma Development

Lymphocytes were isolated and fused with murine SP2/0 myeloma cells in the presence of poly-ethylene glycol (PEG 1500) as per standard Roche Protocol. Fused cells were cultured using a single-step cloning method (HAT selection). This method uses a semi-solid methylcellulose-based HAT selective medium to combine the hybridoma selection and cloning into one step. Single cell-derived hybridomas grow to form monoclonal colonies on the semi-solid media. Ten days after the fusion event, 948 of the resulting hybridoma clones were transferred to 96-well tissue culture plates and grown in HT containing medium until mid-log growth was reached (5 days).

Hybridoma Screening

Tissue culture supernatants from the 948 hybridomas were tested by indirect ELISA on screening antigen (Primary Screening) and probed for both IgG and IgM antibodies using a Goat anti-IgG/IgM(H&L)-HRP secondary and developed with TMB substrate. Clones>0.2 OD in this assay were taken to the next round of testing. Positive cultures were retested on screening antigen to confirm secretion and on an irrelevant antigen (Human Transferrin) to eliminate non-specific or "sticky" mAbs and rule out false positives. All clones of interest were isotyped by antibody trapping ELISA to determine if they are IgG or IgM isotype.

Hybridoma Cell Culture

The hybridoma cell lines of interest were maintained in culture in 24-well culture plates for 32 days post transfer to 96-well plates. This is referred to as the stability period and tests whether clones remain stable and secreting. During this stability period time temporary frozen cell line back up is made of all the clones of interest for −80° C. storage (viable 6 months). Hybridomas were periodically tested during this time period for secretion and specificity.

Subcloning

The top hybridoma cell lines (clones) were subcloned to ensure monoclonality. Subcloning was performed by plating parental clones out again using the single-step cloning system. Between 24 and 90 subclones were transferred to 96-well culture plates. Subclones were screened by indirect ELISA and antibody trapping ELISA. The top subclones for each parent were taken for expansion in culture. Any parental clones that were <50% clonal had a second round of subcloning performed.

The antibodies were then screened for CD33 binding. Antibodies that were positive for binding to human CD33 were tested for ability to block ligand binding and ability to reduce surface levels of CD33 in multiple cell types.

Antibody Heavy Chain and Light Chain Variable Domain Sequences

Using standard techniques, the amino acid sequences encoding the light chain variable and the heavy chain variable domains of the generated antibodies were determined. The EU or Kabat light chain CDR sequences of the antibodies are set forth in Table 1. The EU or Kabat heavy chain CDR sequences of the antibodies are set forth in Table 2. The EU or Kabat light chain framework (FR) sequences of the antibodies are set forth in Table 3A. The EU or Kabat heavy chain framework (FR) sequences of the antibodies are set forth in Table 3B.

TABLE 1

EU or Kabat light chain HVR sequences of anti-CD33 antibodies

| Ab | HVR L1 | HVR L2 | HVR L3 |
|---|---|---|---|
| 2F5 | RASQSVSTSTYSYMH (SEQ ID NO: 10) | YASNLEC (SEQ ID NO: 69) | QHSWEIPLT (SEQ ID NO: 72) |
| 2F5.1 | RASQSVSTSTYSYMH (SEQ ID NO: 10) | YASNLES (SEQ ID NO: 13) | QHSWEIPLT (SEQ ID NO: 72) |
| 3A12 | RASKSVSTSGYSYMH (SEQ ID NO: 67) | LVSNLES (SEQ ID NO: 70) | NLLLSAHXGAYT (SEQ ID NO: 73) |
| 6A3a | RASKSVSTSGHSYMH (SEQ ID NO: 11) | LASSLES (SEQ ID NO: 14) | QHSRELPLT (SEQ ID NO: 17) |
| 6A3b | RASKRVSTSVHSYMH (SEQ ID NO: 68) | LASSLES (SEQ ID NO: 71) | QHSREVPLT (SEQ ID NO: 74) |
| 6C7.2 | TLSSQHSTYTIE (SEQ ID NO: 228) | MELKKDGSHSTGD (SEQ ID NO: 229) | GVGDTIKEQFVYV (SEQ ID NO: 230) |
| 1A8 | KASQDINKYLS (SEQ ID NO: 9) | RANRLVD (SEQ ID NO: 12) | LQYDEFPLT (SEQ ID NO: 15) |
| 2E12 | RASQSVSTSTYSYMH (SEQ ID NO: 10) | YASNLES (SEQ ID NO: 13) | QRSWEIPLT (SEQ ID NO: 16) |
| 2E12.1 | RASQSVSTSTYSYMH (SEQ ID NO: 10) | YASNLES (SEQ ID NO: 13) | QHSWEIPLT (SEQ ID NO: 72) |
| 2B4 | RPSKRISAYVFSYMH (SEQ ID NO: 184) | LSCNLEX (SEQ ID NO: 185) | QHSRELPLT (SEQ ID NO: 17) |

TABLE 2

EU or Kabat heavy chain HVR sequences of anti-CD33 antibodies

| Ab | HVR H1 | HVR H2 | HVR H3 |
|---|---|---|---|
| 2F5 | YTFTDYNLH (SEQ ID NO: 19) | IGFIYPSNGITGYN (SEQ ID NO: 23) | ARSTVDYFDY (SEQ ID NO: 27) |
| 2F5.1 | KASGYTFTDYNLH (SEQ ID NO: 231) | IGFIYPSNGITGYN (SEQ ID NO: 23) | ARSTVDYFDY (SEQ ID NO: 27) |
| 3A12a | FTFSNYCMN (SEQ ID: 21) | VAEIRLKSNNYVT (SEQ ID NO: 25) | TRDGYYVPFAY (SEQ ID NO: 29) |

TABLE 2-continued

EU or Kabat heavy chain HVR sequences of anti-CD33 antibodies

| Ab | HVR H1 | HVR H2 | HVR H3 |
| --- | --- | --- | --- |
| 3A12b | FTFSNYCMN (SEQ ID: 21) | VAEIRLKSNNYVTNYV (SEQ ID NO: 76) | TRDGYYVPFAY (SEQ ID NO: 29) |
| 6A3a | YSFTGYYMH (SEQ ID NO: 20) | IGEINPSTGGTSYN (SEQ ID NO: 24) | TRGHYGSYLTFDY (SEQ ID NO: 28) |
| 6A3b | YTFTSYWMH (SEQ ID NO: 75) | IGNIYPGSISSNYD (SEQ ID NO: 77) | TRGHYGSYLTFDY (SEQ ID NO: 28) |
| 6C7a | FTFSNYCMN (SEQ ID: 21) | VAEIRLKSNNYVT (SEQ ID NO: 25) | TRDGYYVPFAY (SEQ ID NO: 29) |
| 6C7b | FTFSNYCMN (SEQ ID: 21) | VAEIRLKSNNYVTNYV (SEQ ID NO: 76) | TRDGYYVPFAY (SEQ ID NO: 29) |
| 6C7.2 | VGSGFTFSNYCMN (SEQ ID NO: 232) | VAEIRLKSNNYVTNYV YC (SEQ ID NO: 233) | TRDGYYVPFAY (SEQ ID NO: 29) |
| 1A8 | YTFTSYDIN (SEQ ID NO: 18) | IGWIFPGDGSTKYN (SEQ ID NO: 22) | ARGYHYAMDS (SEQ ID NO: 26) |
| 2E12 | YTFTDYNLH (SEQ ID NO: 19) | IGFIYPSNGITGYN (SEQ ID NO: 23) | ARSTVDYFDY (SEQ ID NO: 27) |
| 2E12.1 | KASGYTFTDYNLH (SEQ ID NO: 231) | IGFIYPSNGITGYN (SEQ ID NO: 23) | ARSTVDYFDY (SEQ ID NO: 27) |
| 2B4 | YTFTSYWMH (SEQ ID NO: 75) | IGNIYPGSGSTYYD (SEQ ID NO: 186) | TRGHYGNYLTFDY (SEQ ID NO: 187) |

TABLE 3A

EU or Kabat light chain Framework sequences of mouse anti-CD33 antibodies

| Ab | VL FR1 | VL FR2 | VL FR3 | VL FR4 |
| --- | --- | --- | --- | --- |
| 2F5 | ZTQSLASLAVSLG QRATMSC (SEQ ID NO: 78) | WYQQKPGQPPKLLIK (SEQ ID NO: 83) | GVPARFSGSGZGTDFT LNIHPVEEEDSATYYC (SEQ ID NO: 87) | FGGGTKLEMK (SEQ ID NO: 92) |
| 2F5.1 | DIVLTQSPASLAV SLGQRATMSC (SEQ ID NO: 234) | WYQQKPGQPPKLLIK (SEQ ID NO: 83) | GVPARFSGSGSGTDFT LNIHPVEEEDTATYYC (SEQ ID NO: 91) | FGAGTKLELK (SEQ ID NO: 94) |
| 3A12 | DIVLTQSPASLAV SLGQRATISY (SEQ ID NO: 79) | WNQQKPGQPPRLLIY (SEQ ID NO: 84) | GVPARFSGSGZWDRL HPQHPSCGGGGCC (SEQ ID NO: 88) | FGGGTKLEIK (SEQ ID NO: 93) |
| 6A3 | DFQIQQSLASLVV SMGQRAAISF (SEQ ID NO: 80) | WYQQKPGQPPKLIIY (SEQ ID NO: 85) | GVRARFSGZGWGTDF TLNIHPVEEEDGATYY C (SEQ ID NO: 89) | FGGGTKLEMK (SEQ ID NO: 92) |
| 6C7.2 | QLVLTQSSSASFS LGASAKLTC (SEQ ID NO: 235) | WYQQQPLKPPKYV (SEQ ID NO: 236) | GIPDRFSGSSSGADRYL SISNIQPEDEAIYIC (SEQ ID NO: 237) | FGGGTKVTVL (SEQ ID NO: 238) |
| 1A8 | CDIKMTQSPSSMY ESLGERVTITC (SEQ ID NO: 81) | WLQQKPGKSPKTLIY (SEQ ID NO: 86) | GVPSRFSGSGSGQDYS LTISSLEYEDMGIYHC (SEQ ID NO: 90) | FGAGTKLELK (SEQ ID NO: 94) |
| 2E12 | STGDIVLTQSPASL AVSLGQRATMSC (SEQ ID NO: 82) | WYQQKPGQPPKLLIK (SEQ ID NO: 83) | GVPARFSGSGSGTDFT LNIHPVEEEDTATYYC (SEQ ID NO: 91) | FGAGTKLELK (SEQ ID NO: 94) |
| 2E12.1 | DIVLTQSPASLAVS LGQRATMSC (SEQ ID NO: 234) | WYQQKPGQPPKLLIK (SEQ ID NO: 83) | GVPARFSGSGSGTDFT LNIHPVEEEDTATYYC (SEQ ID NO: 91) | FGAGTKLELK (SEQ ID NO: 94) |
| 2B4 | DLZLTQSLASLVV CMGQRAAISF (SEQ ID NO: 188) | WYQQKPGQPPKLIIY (SEQ ID NO: 85) | GVRARLSGRRWVTDF TLNIHPAEEEDGATYY C (SEQ ID NO: 189) | FGGGTKLEMK (SEQ ID NO: 92) |

TABLE 3B

EU or Kabat heavy chain Framework sequences of mouse anti-CD33 antibodies

| Ab | VH FR1 | VH FR2 | VH FR3 | VH FR4 |
|---|---|---|---|---|
| 2F5 | EVQLQQSGPELV KPGASVKISCKAS G (SEQ ID NO: 95) | WVKLSHGKSLEW (SEQ ID NO: 100) | QKFKNKATLTVDNSSSTA YMELRSLTSEDSAVYYC (SEQ ID NO: 104) | WGQGTTLTVSS (SEQ ID NO: 108) |
| 2F5.1 | EVQLQQSGPELV KPGASVKISC (SEQ ID NO: 239) | WVKLSHGKSLEW (SEQ ID NO: 100) | QKFKNKATLTVDNSSSTA YMELRSLTSEDSAVYYC (SEQ ID NO: 104) | WGQGTTLTVSS (SEQ ID NO: 108) |
| 3A12 | EVKLEESGGGLV QPGGSMKLSCVG SG (SEQ ID NO: 96) | WVRQSPEKGLEW (SEQ ID NO: 101) | ESVKGRFTISRDDSKSRV YLQMNNLRGEDTGFYYC (SEQ ID NO: 105) | WGQGTLVTVSA (SEQ ID NO: 109) |
| 6A3 | QVQLQQSGSELV RPGASVKLSCKA SG (SEQ ID NO: 97) | WVKQRPGQGLEW (SEQ ID NO: 102) | EKFKNKATLTVDTSSSTA YMQLSSLTSEDSAVYFC (SEQ ID NO: 106) | WGHGTTLTVSS (SEQ ID NO: 110) |
| 6C7 | EVKLEESGGGLV QPGGSMKLSCVG SG (SEQ ID NO: 96) | WVRQSPEKGLEW (SEQ ID NO: 101) | ESVKGRFTISRDDSKSRV YLQMNNLRGEDTGFYYC (SEQ ID NO: 105) | WGQGTLVTVSA (SEQ ID NO: 109) |
| 6C7.2 | EVKLEESGGGLV QPGGSMKLSC (SEQ ID NO: 240) | WVRQSPEKGLEW (SEQ ID NO: 101) | ESVKGRFTISRDDSKSRV YLQMNNLRGEDTGFY (SEQ ID NO: 105) | WGQGTLVTVSA (SEQ ID NO: 109) |
| 1A8 | QVQLQQSGAELV KPGASVKLSCKA SG (SEQ ID NO: 98) | WVRQRPEQGLEW (SEQ ID NO: 103) | EKFKGKATLTTDKSSNTT YMQLSRLTSEDSAVYFC (SEQ ID NO: 107) | WGQGTSVTVSS (SEQ ID NO: 111) |
| 2E12 | PELVKPGASVKIS CKASG (SEQ ID NO: 99) | WVKLSHGKSLEW (SEQ ID NO: 100) | QKFKNKATLTVDNSSSTA YMELRSLTSEDSAVYYC (SEQ ID NO: 104) | WGQGTTLTVSS (SEQ ID NO: 108) |
| 2E12.1 | EVQLQQSGPELV KPGASVKISC (SEQ ID NO: 239) | WVKLSHGKSLEW (SEQ ID NO: 100) | QKFKNKATLTVDNSSSTA YMELRSLTSEDSAVYYC (SEQ ID NO: 104) | WGQGTTLTVSS (SEQ ID NO: 108) |
| 2B4 | QVQLQQPGSELV RPGASVKLSCKA SG (SEQ ID NO: 190) | WVKQRPGQGLEW (SEQ ID NO: 102) | EKFKSKATLTVDTSSGTA YMQLSSLTSEDSAVYYC (SEQ ID NO: 191) | WGQGTTLTVSS (SEQ ID NO: 108) |

Characterization of CD33 Antibody Binding

Initial characterization of CD33 antibodies involved determining their ability to bind CD33 expressed on a CHO cell line, on human primary monocytes, human primary dendritic cells, and human primary macrophages. Cells were harvested, plated at $10^6$/ml in a 96-well plate, and incubated in 100 μl PBS containing 2% FBS, 2 mM EDTA and 10 μg/ml antibody and Fc blocking reagent for 1 hour in ice. Cells were washed twice and incubated in 100 ul PBS containing 2% FBS, 2 mM EDTA and 5 μg/ml PE-conjugated secondary antibody for 30 minutes on ice. Cells were washed twice in cold PBS and analyze by flow cytometry on a BD FACS Canto. Data analysis and calculation of mean fluorescence intensity (MFI) values was performed with FlowJo (TreeStar) software version 10.0.7.

Figure 5A:
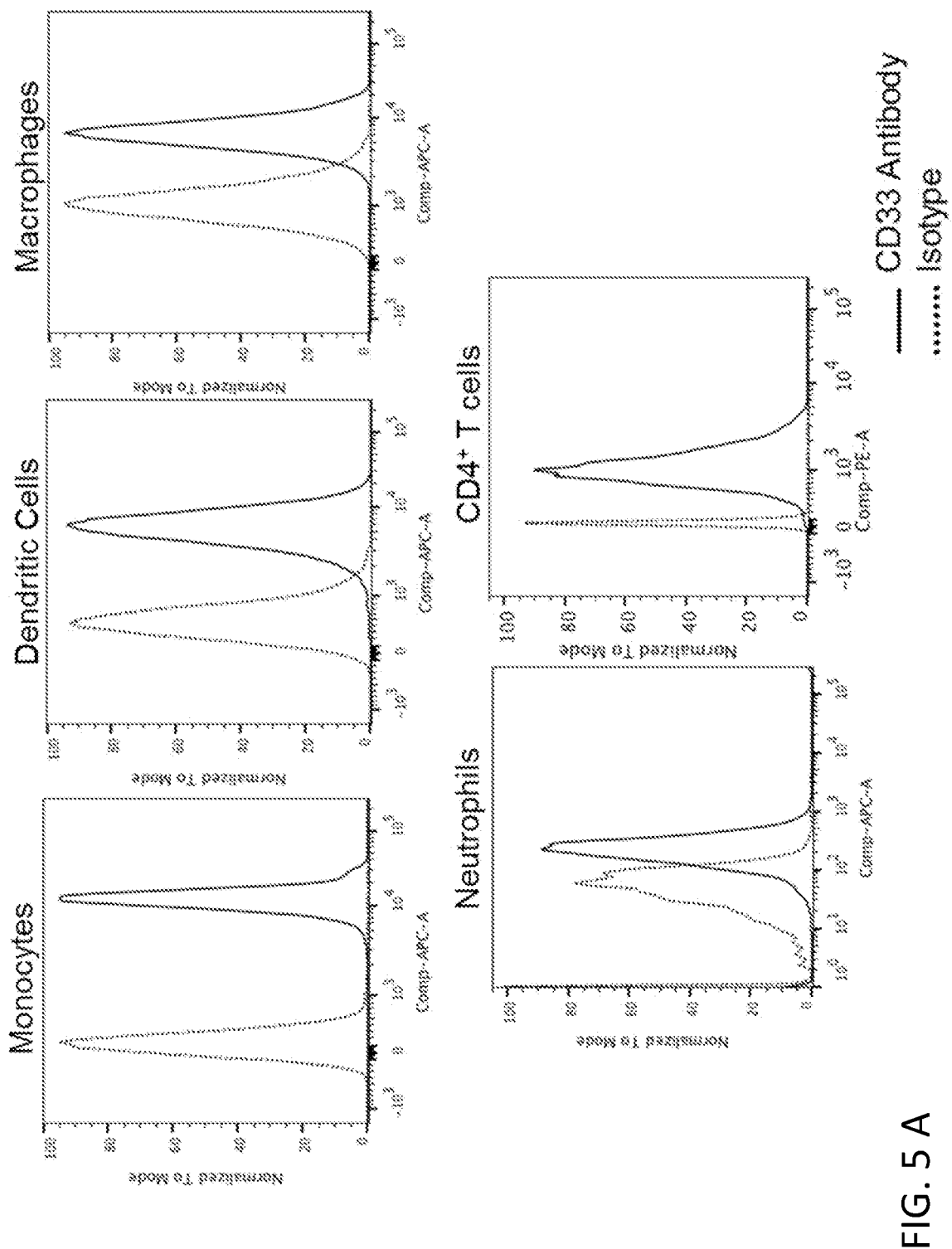
FIG. 5A depicts results of FACS analysis demonstrating CD33 expression in human primary immune cells.
Figure 5D:
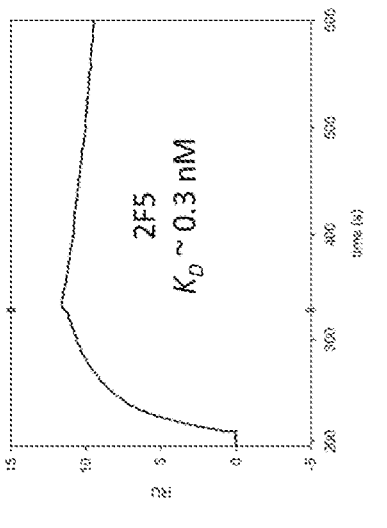
FIG. 5D depicts a Biacore sensorgram showing binding affinity of CD33 antibody 2F5 to purified CD33-his tagged protein.
Figure 5C:
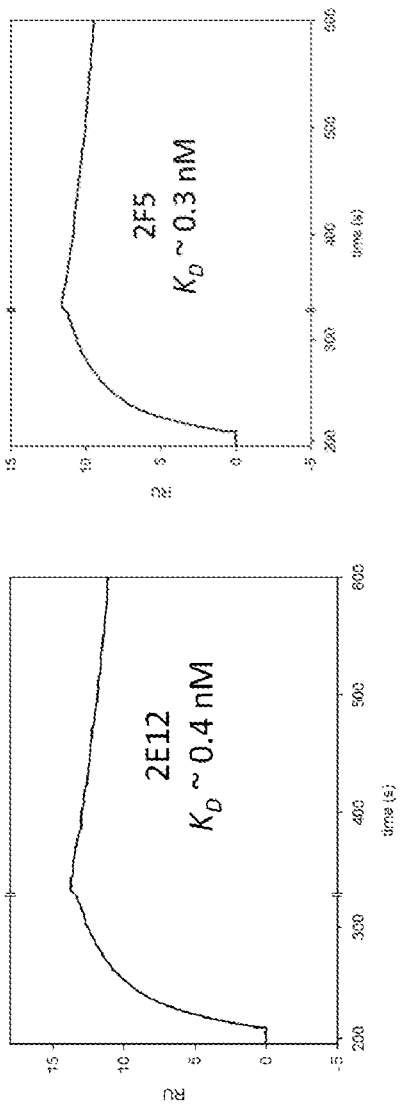
FIG. 5C depicts a Biacore sensorgram showing binding affinity of CD33 antibody 2E12 to purified CD33-his tagged protein.
Figure 5B:
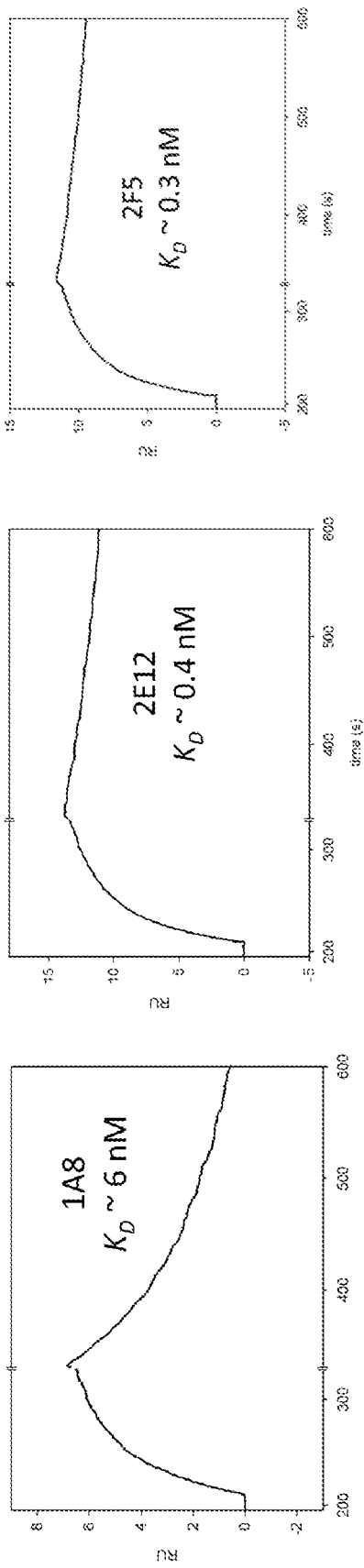
FIG. 5B depicts a Biacore sensorgram showing binding affinity of CD33 antibody 1A8 to purified CD33-his tagged protein.
Figure 5G:
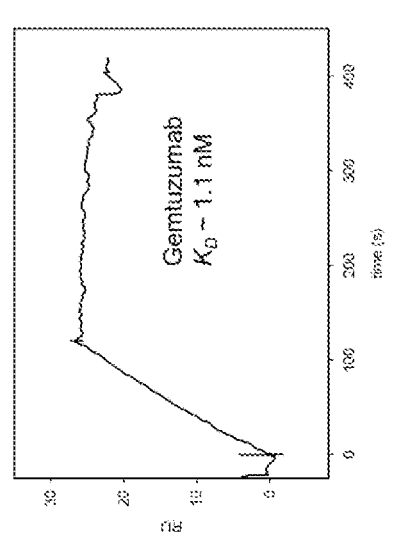
FIG. 5G depicts a Biacore sensorgram showing binding affinity of CD33 antibody gemtuzumab to purified CD33-his tagged protein.
Figure 5F:
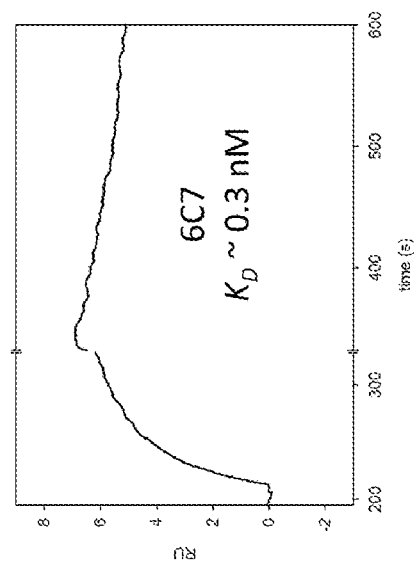
FIG. 5F depicts a Biacore sensorgram showing binding affinity of CD33 antibody 6C7 to purified CD33-his tagged protein.
Figure 5E:
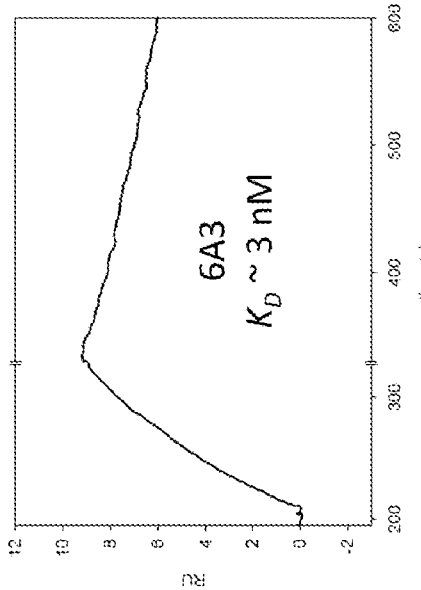
FIG. 5E depicts a Biacore sensorgram showing binding affinity of CD33 antibody 6A3 to purified CD33-his tagged protein.

FACS staining analysis indicates that CD33 is expressed on primary myeloid and lymphoid cells, including human primary monocytes, macrophages, dendritic cells, CD4+ T cells, and neutrophils (FIG. 5A).

Table 4 demonstrates antibody binding to a CHO cell line expressing recombinant human CD33 (CHO hCD33). Percent positive binding and mean fluorescent intensity (MFI) values for cell types bound by CD33 antibodies are listed in Table 4. Binding is compared to a parental CHO cell line. In Table 4, "Isotype" refers to an isotype mIgG1 control antibody.

TABLE 4

CD33 antibody binding to CHO cells

| | % Positive | | MFI | |
|---|---|---|---|---|
| Antibody | CHO Parental | CHO hCD33 | CHO Parental | CHO hCD33 |
| 1A8 | 0.15 | 84.4 | 359 | 8830 |
| 2B4 | 0.032 | 86.8 | 289 | 3730 |
| 2E12 | 0.064 | 87.7 | 388 | 10386 |
| 2F5 | 0.065 | 87 | 384 | 9517 |
| 3A12 | 0.081 | 86.8 | 350 | 8304 |
| 6A3 | 0.038 | 86.9 | 375 | 20343 |
| 6C7 | 0.054 | 86.2 | 334 | 8067 |
| Isotype | 0.076 | 0.47 | 396 | 227 |

Percent positive binding and mean fluorescent intensity (MFI) values for cell types bound by CD33 antibodies are listed in Table 5. Binding is compared to an isotype control. The antibodies bind to human primary monocytes, human primary dendritic cells and human primary macrophages. In Table 5, "Isotype" refers to an isotype mIgG1 control antibody; and "DCs" refers to dendritic cells.

TABLE 5A

CD33 antibody binding to human primary cells

| Antibody | % Positive | | | MFI | | |
|---|---|---|---|---|---|---|
| | Monocytes | DCs | Macrophages | Monocytes | DCs | Macrophages |
| 1A8 | 94.00 | 99.00 | 96.00 | 1188 | 4580 | 2373 |
| 2B4 | 59.80 | 67.80 | 86.80 | 495 | 1683 | 1987 |
| 2E12 | 96.70 | 99.30 | 97.30 | 1569 | 4750 | 2423 |
| 2F5 | 97.50 | 99.00 | 96.70 | 1196 | 4304 | 2509 |
| 3A12 | 90.60 | 98.50 | 92.80 | 1024 | 3426 | 1891 |
| 6A3 | 93.10 | 98.40 | 92.10 | 849 | 3806 | 1745 |
| 6C7 | 90.00 | 97.50 | 92.20 | 1053 | 3363 | 2085 |
| Isotype | 2.38 | 1.97 | 4.16 | 109 | 861 | 1220 |

The apparent affinity constants of the CD33 antibodies were then determined. SPR data was collected at a rate of 10 Hz at 25° C. on a BiaCore T200 instrument. Data analysis was performed using BiaCore T200 Evaluation Software, version 2.0. HBS-EP+ (100 mM HEPES, 1.5 M NaCl, 30 mM EDTA, 0.5% v/v Surfactant P20, pH 7.4) was used as running buffer and for preparing reagents. Each of anti-CD33 antibodies 1A8, 2E12, 2F5, 6A3, 6C7, and gemtuzumab (20 nM) was captured (60 s contact time, 30 µL/min flow rate, 0 s stabilization time) on a CM5 sensor chip (GE Healthcare) immobilized with anti-mouse IgG. Twenty nM histidine-tagged human CD33 (Sino Biological) was then flowed over the captured anti-CD33 surface (120 s contact time, 30 µL/min flow rate, 300 s dissociation time). Duplicate single-concentration trials were performed and bracketed by a blank (0 nM antigen) sample. The chip surface was regenerated in between cycles using 10 mM glycine-HCl, pH 1.7 (60 s contact time, 30 µL/min flow rate, 60 s stabilization time). The resulting SPR signal was obtained as the difference in response from measurements performed on a blank flow cell. Single-concentration kinetic analysis (Canziani, et al. Analytical Biochemistry 325 (2004), 301-307) was performed using a 1:1 interaction model to extract association and dissociation rate constants ($k_a$ and $k_d$, respectively) for each antibody. Apparent affinity constants ($K_D$) were calculated from the ratio $k_d/k_a$. The single-concentration analysis was validated with a multiple-concentration approach (five concentrations of antigen used, plus one blank) in a previous set of experiments. The results are depicted in FIG. 5B-5G and Table 5B.

TABLE 5B

CD33 antibody binding to human CD33

| Antibody | Apparent $K_D$ for human CD33 |
|---|---|
| 1A8 | 6 nM |
| 2E12 | 0.4 nM |
| 2F5 | 0.3 nM |
| 6A3 | 3 nM |
| 6C7 | 0.3 nM |
| gemtuzumab | 1.1 nM |

Figure 5H:
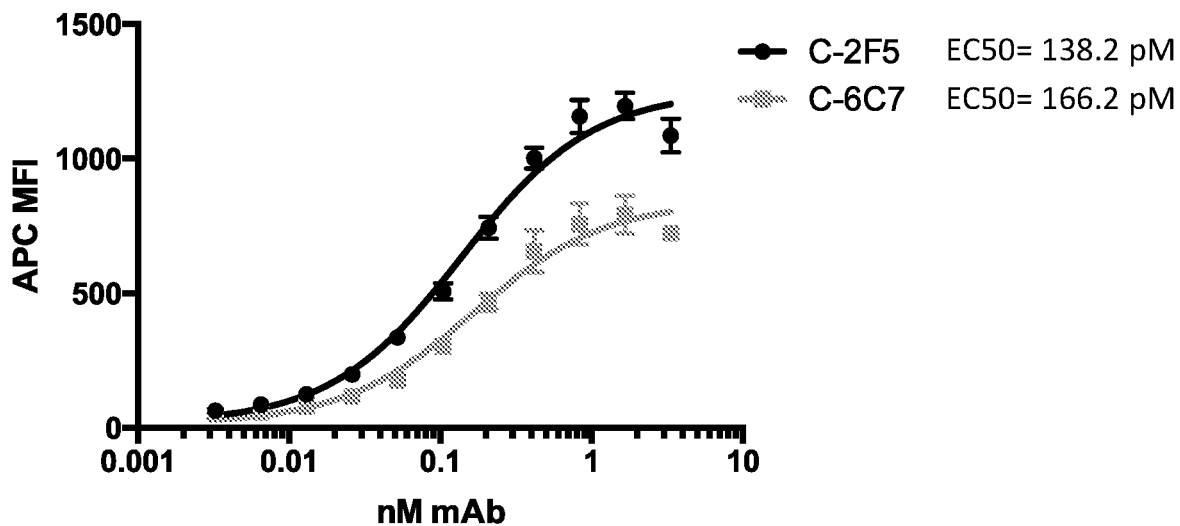
FIG. 5H depicts binding curves of CD33 antibodies 2F5 and 6C7 binding to CD33 on human primary dendritic cells.
Figure 5I:
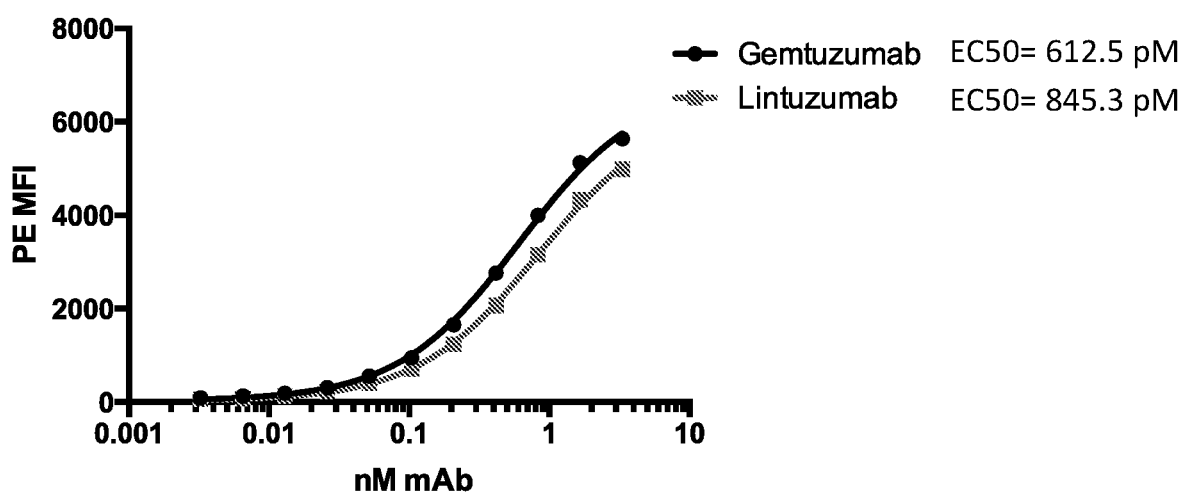
FIG. 5I depicts binding curves of CD33 antibodies gemtuzumab and lintuzumab binding to CD33 on human primary dendritic cells.

Half-maximal effective concentration ($EC_{50}$) of CD33 antibodies 2F5, 6C7, gemtuzumab, and lintuzumab for binding to human primary dendritic cells was also determined by binding curves using antibody concentrations that ranged from approximately 0.003 nM to approximately 3 nM. As shown in FIG. 5H, the CD33 antibodies bound to human primary dendritic cells with an $EC_{50}$ of less than 200 pM. In particular, antibody 2F5 bound with an $EC_{50}$ of 138.2 pM and antibody 6C7 bound with an $EC_{50}$ of 166.2 pM (FIG. 5H). In contrast, commercial antibodies gemtuzumab and lintuzumab bound to human primary dendritic cells with an $EC_{50}$ of 612.5 pM and 845.3 pM, respectively (FIG. 5I). The results in FIGS. 5H and 5I demonstrate that antibodies 2F5 and 6C7 have improved binding to human cells (e.g., primary dendritic cells) with a lower $EC_{50}$ than do commercial antibodies gemtuzumab and lintuzumab. The results further indicate that antibodies 2F5 and 6C7 have improved target engagement in human primary myeloid cells as compared to commercial anti-CD33 antibodies.

Antibody Humanization

Antibody humanization is used to transform antibodies generated in a different species to best resemble a human antibody through sequence and structural relationships in order to prevent immunogenicity in human administration. Antibodies from different species share characteristic sequence and structural features that allow the grafting of the specificity-determining regions (SDRs) of the non-human antibody onto a human antibody framework. This results in retention of the specificity of the non-human antibody. The humanization process involves identification of the non-human antibody sequence and features, including the framework regions and SDRs. The following criteria are used to humanize an antibody: 1) percent similarity in framework regions between non-human and known human antibodies, 2) length similarity in SDRs between non-human and known human antibodies, 3) genes used to generate the framework regions of the human antibody, and 4) previous use of human antibody frameworks in humanizations and as therapeutics. Similarity in framework regions and SDR lengths are important because differences can generate structural differences in the antibody that can alter the specificity of the antibody. Specific genes used to generate the framework of human antibodies are known to be beneficial or detrimental to the stability or specificity of the antibody and are selectively used or avoided, accordingly. Lastly, previously successful humanization frameworks, including those used in human therapeutics, which are well tolerated with good half-lives, are likely candidates for future successful humanizations.

As shown in Tables 6A and 6B, four humanized light chain and heavy variable region sequences were identified for antibody 1A8; seven light chain variable region sequences and four heavy chain variable region sequences were identified for antibody 2E12; five light chain variable region sequences and four heavy chain variable region sequences were identified for antibody 6A3; one heavy chain variable region sequence was identified for antibody 6C7; and one heavy chain variable region sequence was identified for antibody 3A12. In Tables 6A and 6B, bolded letters indicate CDR sequences.

TABLE 6A

Humanized light chain variable regions

| Antibody variant | Humanized sequences |
|---|---|
| Antibody 2F5 | 2F5 |
| 2F5V2-30 | DVVMTQSPLSLPVTLGQPASISCRASQSVSTSTYSYMHWFQQRPGQSPRRLIYYAS NLECGVPDRFSGSGSGTDFTLKISRVEAEDVGVYYCQHSWEIPLTFGQGTKVEIK (SEQ ID NO: 113) |
| 2F5V2-28 | DIVMTQSPLSLPVTPGEPASISCRASQSVSTSTYSYMHWYLQKPGQSPQLLIYYASN LECGVPDRFSGSGSGTDFTLKISRVEAEDVGVYYCQHSWEIPLTFGQGTKVEIK (SEQ ID NO: 114) |
| 2F5V4-1 | DIVMTQSPDSLAVSLGERATINCRASQSVSTSTYSYMHWYQQKPGQPPKLLIYYAS NLECGVPDRFSGSGSGTDFTLTISSLQAEDVAVYYCQHSWEIPLTFGQGTKVEIK (SEQ ID NO: 115) |
| 2F5V1-33 | DIQMTQSPSSLSASVGDRVTITCRASQSVSTSTYSYMHWYQQKPGKAPKLLIYYAS NLECGVPSRFSGSGSGTDFTFTISSLQPEDIATYYCQHSWEIPLTFGQGTKVEIK (SEQ ID NO: 116) |
| 2F5V1-5 | DIQMTQSPSTLSASVGDRVTITCRASQSVSTSTYSYMHWYQQKPGKAPKLLIYYAS NLECGVPSRFSGSGSGTEFTLTISSLQPDDFATYYCQHSWEIPLTFGQGTKVEIK (SEQ ID NO: 117) |
| 2F5V3-11 | EIVLTQSPATLSLSPGERATLSCRASQSVSTSTYSYMHWYQQKPGQAPRLLIYYASN LECGIPARFSGSGSGTDFTLTISSLEPEDFAVYYCQHSWEIPLTFGQGTKVEIK (SEQ ID NO: 118) |
| 2F5V1-39 | DIQMTQSPSSLSASVGDRVTITCRASQSVSTSTYSYMHWYQQKPGKAPKLLIYYAS NLECGVPSRFSGSGSGTDFTLTISSLQPEDFATYYCQHSWEIPLTFGQGTKVEIK (SEQ ID NO: 119) |
| 2F5V1-9 | DIQLTQSPSFLSASVGDRVTITCRASQSVSTSTYSYMHWYQQKPGKAPKLLIYYAS NLECGVPSRFSGSGSGTEFTLTISSLQPEDFATYYCQHSWEIPLTFGQGTKVEIK (SEQ ID NO: 120) |
| 2F5V3-15 | EIVMTQSPATLSVSPGERATLSCRASQSVSTSTYSYMHWYQQKPGQAPRLLIYYAS NLECGIPARFSGSGSGTEFTLTISSLQSEDFAVYYCQHSWEIPLTFGQGTKVEIK (SEQ ID NO: 121) |
| 2F5V3-20 | EIVLTQSPGTLSLSPGERATLSCRASQSVSTSTYSYMHWYQQKPGQAPRLLIYYASN LECGIPDRFSGSGSGTDFTLTISRLEPEDFAVYYCQHSWEIPLTFGQGTKVEIK (SEQ ID NO: 122) |
| Antibody 3A12 | 3A12 |
| 3A12V2-28 | DIVMTQSPLSLPVTPGEPASISCRASKSVSTSGYSYMHWYLQKPGQSPQLLIYLVSN LESGVPDRFSGSGSGTDFTLKISRVEAEDVGVYYCNLLLSAHXGAYTFGQGTKVEI K (SEQ ID NO: 124) |
| 3A12V2-30 | DVVMTQSPLSLPVTLGQPASISCRASKSVSTSGYSYMHWFQQRPGQSPRRLIYLVS NLESGVPDRFSGSGSGTDFTLKISRVEAEDVGVYYCNLLLSAHXGAYTFGQGTKV EIK (SEQ ID NO: 125) |
| 3A12V4-1 | DIVMTQSPDSLAVSLGERATINCRASKSVSTSGYSYMHWYQQKPGQPPKWYLVS NLESGVPDRFSGSGSGTDFTLTISSLQAEDVAVYYCNLLLSAHXGAYTFGQGTKVE IK (SEQ ID NO: 126) |
| 3A12V1-33 | DIQMTQSPSSLSASVGDRVTITCRASKSVSTSGYSYMHWYQQKPGKAPKLLIYLVS NLESGVPSRFSGSGSGTDFTFTISSLQPEDIATYYCNLLLSAHXGAYTFGQGTKVEI K (SEQ ID NO: 127) |
| 3A12V1-5 | DIQMTQSPSTLSASVGDRVTITCRASKSVSTSGYSYMHWYQQKPGKAPKLLIYLVS NLESGVPSRFSGSGSGTEFTLTISSLQPDDFATYYCNLLLSAHXGAYTFGQGTKVEI K (SEQ ID NO: 128) |
| 3A12V1-39 | DIQMTQSPSSLSASVGDRVTITCRASKSVSTSGYSYMHWYQQKPGKAPKLLIYLVS NLESGVPSRFSGSGSGTDFTLTISSLQPEDFATYYCNLLLSAHXGAYTFGQGTKVEI K (SEQ ID NO: 129) |
| 3A12V1-9 | DIQLTQSPSFLSASVGDRVTITCRASKSVSTSGYSYMHWYQQKPGKAPKLLIYLVS NLESGVPSRFSGSGSGTEFTLTISSLQPEDFATYYCNLLLSAHXGAYTFGQGTKVEI K (SEQ ID NO: 130) |
| 3A12V3-11 | EIVLTQSPATLSLSPGERATLSCRASKSVSTSGYSYMHWYQQKPGQAPRLLIYLVS NLESGIPARFSGSGSGTDFTLTISSLEPEDFAVYYCNLLLSAHXGAYTFGQGTKVEI K (SEQ ID NO: 131) |

TABLE 6A-continued

Humanized light chain variable regions

| Antibody variant | Humanized sequences |
|---|---|
| 3A12V3-15 | EIVMTQSPATLSVSPGERATLSCRASKSVSTSGYSYMHWYQQKPGQAPRLLIYLVS NLESGIPARFSGSGSGTEFTLTISSLQSEDFAVYYCNLLLSAHXGAYTFGQGTKVEI K (SEQ ID NO: 132) |
| 3A12V3-20 | EIVLTQSPGTLSLSPGERATLSCRASKSVSTSGYSYMHWYQQKPGQAPRLLIYLVS NLESGIPDRFSGSGSGTDFTLTISRLEPEDFAVYYCNLLLSAHXGAYTFGQGTKVEI K (SEQ ID NO: 133) |

| Antibody 6A3a | 6A3a |
|---|---|
| 6A3aV1-5 | DIQMTQSPSTLSASVGDRVTITCRASKSVSTSGHSYMHWYQQKPGKAPKLLIYLAS SLESGVPSRFSGSGSGTEFTLTISSLQPDDFATYYCQHSRELPLTFGQGTKVEIK (SEQ ID NO: 44) |
| 6A3aV1-39 | DIQMTQSPSSLSASVGDRVTITCRASKSVSTSGHSYMHWYQQKPGKAPKLLIYLAS SLESGVPSRFSGSGSGTDFTLTISSLQPEDFATYYCQHSRELPLTFGQGTKVEIK (SEQ ID NO: 45) |
| 6A3aV2-28 | DIVMTQSPLSLPVTPGEPASISCRASKSVSTSGHSYMHWYLQKPGQSPQLLIYLASSL ESGVPDRFSGSGSGTDFTLKISRVEAEDVGVYYCQHSRELPLTFGQGTKVEIK (SEQ ID NO: 46) |
| 6A3aV2-30 | DVVMTQSPLSLPVTLGQPASISCRASKSVSTSGHSYMHWFQQRPGQSPRRLIYLAS SLESGVPDRFSGSGSGTDFTLKISRVEAEDVGVYYCQHSRELPLTFGQGTKVEIK (SEQ ID NO: 47) |
| 6A3aV4-1 | DIVMTQSPDSLAVSLGERATINCRASKSVSTSGHSYMHWYQQKPGQPPKLLIYLAS SLESGVPDRFSGSGSGTDFTLTISSLQAEDVAVYYCQHSRELPLTFGQGTKVEIK (SEQ ID NO: 48) |

| Antibody 6A3b | 6A3 |
|---|---|
| 6A3bV2-28 | DIVMTQSPLSLPVTPGEPASISCRASKRVSTSVHSYMHWYLQKPGQSPQLLIYLASS LESGVPDRFSGSGSGTDFTLKISRVEAEDVGVYYCQHSREVPLTFGQGTKVEIK (SEQ ID NO: 135) |
| 6A3bV2-30 | DVVMTQSPLSLPVTLGQPASISCRASKRVSTSVHSYMHWFQQRPGQSPRRLIYLAS SLESGVPDRFSGSGSGTDFTLKISRVEAEDVGVYYCQHSREVPLTFGQGTKVEIK (SEQ ID NO: 136) |
| 6A3bV4-1 | DIVMTQSPDSLAVSLGERATINCRASKRVSTSVHSYMHWYQQKPGQPPKLLIYLAS SLESGVPDRFSGSGSGTDFTLTISSLQAEDVAVYYCQHSREVPLTFGQGTKVEIK (SEQ ID NO: 137) |
| 6A3bV1-5 | DIQMTQSPSTLSASVGDRVTITCRASKRVSTSVHSYMHWYQQKPGKAPKLLIYLAS SLESGVPSRFSGSGSGTEFTLTISSLQPDDFATYYCQHSREVPLTFGQGTKVEIK (SEQ ID NO: 138) |
| 6A3bV1-39 | DIQMTQSPSSLSASVGDRVTITCRASKRVSTSVHSYMHWYQQKPGKAPKLLIYLAS SLESGVPSRFSGSGSGTDFTLTISSLQPEDFATYYCQHSREVPLTFGQGTKVEIK (SEQ ID NO: 139) |
| 6A3bV1-9 | DIQLTQSPSFLSASVGDRVTITCRASKRVSTSVHSYMHWYQQKPGKAPKLLIYLAS SLESGVPSRFSGSGSGTEFTLTISSLQPEDFATYYCQHSREVPLTFGQGTKVEIK (SEQ ID NO: 140) |
| 6A3bV1-33 | DIQMTQSPSSESASVGDRVTITCRASKRVSTSVHSYMHWYQQKPGKAPKELIYLAS SLESGVPSRFSGSGSGTDFTFTISSLQPEDIATYYCQHSREVPLTFGQGTKVEIK (SEQ ID NO: 141) |
| 6A3bV3-11 | EIVETQSPATESESPGERATESCRASKRVSTSVHSYMHWYQQKPGQAPRELIYLAS SLESGIPARFSGSGSGTDFTLTISSLEPEDFAVYYCQHSREVPLTFGQGTKVEIK (SEQ ID NO: 142) |
| 6A3bV3-20 | EIVETQSPGTESESPGERATESCRASKRVSTSVHSYMHWYQQKPGQAPRELIYLAS SLESGIPDRFSGSGSGTDFTLTISRLEPEDFAVYYCQHSREVPLTFGQGTKVEIK (SEQ ID NO: 143) |
| 6A3bV3-15 | EIVMTQSPATLSVSPGERATESCRASKRVSTSVHSYMHWYQQKPGQAPRELIYLAS SLESGIPARFSGSGSGTEFTLTISSEQSEDFAVYYCQHSREVPLTFGQGTKVEIK (SEQ ID NO: 144) |

TABLE 6A-continued

Humanized light chain variable regions

| Antibody variant | Humanized sequences |
|---|---|
| Antibody 1A8 | Antibody 1A8 |

| 1A8V1-33 | DIQMTQSPSSESASVGDRVTITCKASQDINKYLSWYQQKPGKAPKELIYRANRLVDGVPSRFSGSGSGTDFTFTISSLQPEDIATYYCLQYDEFPLTFGQGTKVEIK (SEQ ID NO: 32) |
| 1A8V1-39 | DIQMTQSPSSESASVGDRVTITCKASQDINKYLSWYQQKPGKAPKELIYRANRLVDGVPSRFSGSGSGTDFTLTISSLQPEDFATYYCLQYDEFPLTFGQGTKVEIK (SEQ ID NO: 33) |
| 1A8V1-9 | DIQLTQSPSFLSASVGDRVTITCKASQDINKYLSWYQQKPGKAPKELIYRANRLVDGVPSRFSGSGSGTEFTLTISSLQPEDFATYYCLQYDEFPLTFGQGTKVEIK (SEQ ID NO: 145) |
| 1A8V1-5 | DIQMTQSPSTLSASVGDRVTITCKASQDINKYLSWYQQKPGKAPKELIYRANRLVDGVPSRFSGSGSGTEFTLTISSLQPDDFATYYCLQYDEFPLTFGQGTKVEIK (SEQ ID NO: 31) |
| 1A8V3-11 | EIVETQSPATESESPGERATESCKASQDINKYLSWYQQKPGQAPRELIYRANRLVDGIPARFSGSGSGTDFTLTISSLEPEDFAVYYCLQYDEFPLTFGQGTKVEIK (SEQ ID NO: 34) |
| 1A8V3-15 | EIVMTQSPATLSVSPGERATESCKASQDINKYLSWYQQKPGQAPRELIYRANRLVDGIPARFSGSGSGTEFTLTISSEQSEDFAVYYCLQYDEFPLTFGQGTKVEIK (SEQ ID NO: 146) |
| 1A8V3-20 | EIVETQSPGTESESPGERATESCKASQDINKYLSWYQQKPGQAPRELIYRANRLVDGIPDRFSGSGSGTDFTLTISRLEPEDFAVYYCLQYDEFPLTFGQGTKVEIK (SEQ ID NO: 147) |
| 1A8V2-28 | DIVMTQSPLSLPVTPGEPASISCKASQDINKYLSWYLQKPGQSPQLLIYRANRLVDGVPDRFSGSGSGTDFTLKISRVEAEDVGVYYCLQYDEFPLTFGQGTKVEIK (SEQ ID NO: 148) |
| 1A8V4-1 | DIVMTQSPDSLAVSLGERATINCKASQDINKYLSWYQQKPGQPPKELIYRANRLVDGVPDRFSGSGSGTDFTLTISSLQAEDVAVYYCLQYDEFPLTFGQGTKVEIK (SEQ ID NO: 149) |
| 1A8V2-30 | DVVMTQSPLSLPVTLGQPASISCKASQDINKYLSWFQQRPGQSPRRLIYRANRLVDGVPDRFSGSGSGTDFTLKISRVEAEDVGVYYCLQYDEFPLTFGQGTKVEIK (SEQ ID NO: 150) |
| Antibody 2E12 | Antibody 2E12 |
| 2E12V2-30 | DVVMTQSPLSLPVTLGQPASISCRASQSVSTSTYSYMHWFQQRPGQSPRRLIYYASNLESGVPDRFSGSGSGTDFTLKISRVEAEDVGVYYCQRSWEIPLTFGQGTKVEIK (SEQ ID NO: 41) |
| 2E12V2-28 | DIVMTQSPLSLPVTPGEPASISCRASQSVSTSTYSYMHWYLQKPGQSPQLLIYYASLESGVPDRFSGSGSGTDFTLKISRVEAEDVGVYYCQRSWEIPLTFGQGTKVEIK (SEQ ID NO: 40) |
| 2E12V4-1 | DIVMTQSPDSLAVSLGERATINCRASQSVSTSTYSYMHWYQQKPGQPPKELIYYASNLESGVPDRFSGSGSGTDFTLTISSLQAEDVAVYYCQRSWEIPLTFGQGTKVEIK (SEQ ID NO: 42) |
| 2E12V1-33 | DIQMTQSPSSESASVGDRVTITCRASQSVSTSTYSYMHWYQQKPGKAPKELIYYASNLESGVPSRFSGSGSGTDFTFTISSLQPEDIATYYCQRSWEIPLTFGQGTKVEIK (SEQ ID NO: 38) |
| 2E12V1-5 | DIQMTQSPSTESASVGDRVTITCRASQSVSTSTYSYMHWYQQKPGKAPKELIYYASNLESGVPSRFSGSGSGTEFTLTISSLQPDDFATYYCQRSWEIPLTFGQGTKVEIK (SEQ ID NO: 36) |
| 2E12V1-9 | DIQLTQSPSFLSASVGDRVTITCRASQSVSTSTYSYMHWYQQKPGKAPKELIYYASNLESGVPSRFSGSGSGTEFTLTISSLQPEDFATYYCQRSWEIPLTFGQGTKVEIK (SEQ ID NO: 37) |
| 2E12V1-39 | DIQMTQSPSSLSASVGDRVTITCRASQSVSTSTYSYMHWYQQKPGKAPKELIYYASNLESGVPSRFSGSGSGTDFTLTISSLQPEDFATYYCQRSWEIPLTFGQGTKVEIK (SEQ ID NO: 39) |
| 2E12V3-11 | EIVETQSPATESESPGERATESCRASQSVSTSTYSYMHWYQQKPGQAPRELIYYASNLESGIPARFSGSGSGTDFTLTISSLEPEDFAVYYCQRSWEIPLTFGQGTKVEIK (SEQ ID NO: 151) |

TABLE 6A-continued

Humanized light chain variable regions

| Antibody variant | Humanized sequences |
|---|---|
| 2E12V3-15 | EIVMTQSPATLSVSPGERATESCRASQSVSTSTYSYMHWYQQKPGQAPRELIYYAS NLESGIPARFSGSGSGTEFTLTISSLQSEDFAVYYCQRSWEIPLTFGQGTKVEIK (SEQ ID NO: 152) |
| 2E12V3-20 | EIVETQSPGTESESPGERATESCRASQSVSTSTYSYMHWYQQKPGQAPRELIYYASN LESGIPDRFSGSGSGTDFTLTISRLEPEDFAVYYCQRSWEIPLTFGQGTKVEIK (SEQ ID NO: 153) |
| Antibody 2B4 | Antibody 2B4 |
| 2B4V2-28 | DIVMTQSPLSLPVTPGEPASISCRPSKRISAYVFSYMHWYLQKPGQSPQLLIYLSCN LEXGVPDRFSGSGSGTDFTLKISRVEAEDVGVYYCQHSRELPLTFGQGTKVEIK (SEQ ID NO: 193) |
| 2B4V2-30 | DVVMTQSPLSLPVTLGQPASISCRPSKRISAYVFSYMHWFQQRPGQSPRRLIYLSC NLEXGVPDRFSGSGSGTDFTLKISRVEAEDVGVYYCQHSRELPLTFGQGTKVEIK (SEQ ID NO: 194) |
| 2B4V4-1 | DIVMTQSPDSLAVSLGERATINCRPSKRISAYVFSYMHWYQQKPGQPPKELIYLSC NLEXGVPDRFSGSGSGTDFTLTISSLQAEDVAVYYCQHSRELPLTFGQGTKVEIK (SEQ ID NO: 195) |
| 2B4V1-33 | DIQMTQSPSSLSASVGDRVTITCRPSKRISAYVFSYMHWYQQKPGKAPKLLIYLSC NLEXGVPSRFSGSGSGTDFTFTISSLQPEDIATYYCQHSRELPLTFGQGTKVEIK (SEQ ID NO: 196) |
| 2B4V1-5 | DIQMTQSPSTESASVGDRVTITCRPSKRISAYVFSYMHWYQQKPGKAPKLLIYLSC NLEXGVPSRFSGSGSGTEFTLTISSLQPDDFATYYCQHSRELPLTFGQGTKVEIK (SEQ ID NO: 197) |
| 2B4V3-11 | EIVETQSPATESESPGERATESCRPSKRISAYVFSYMHWYQQKPGQAPRELIYLSCN LEXGIPARFSGSGSGTDFTLTISSLEPEDFAVYYCQHSRELPLTFGQGTKVEIK (SEQ ID NO: 198) |
| 2B4V1-9 | DIQLTQSPSFLSASVGDRVTITCRPSKRISAYVFSYMHWYQQKPGKAPKLLIYLSCN LEXGVPSRFSGSGSGTEFTLTISSLQPEDFATYYCQHSRELPLTFGQGTKVEIK (SEQ ID NO: 199) |
| 2B4V1-39 | DIQMTQSPSSLSASVGDRVTITCRPSKRISAYVFSYMHWYQQKPGKAPKLLIYLSC NLEXGVPSRFSGSGSGTDFTLTISSLQPEDFATYYCQHSRELPLTFGQGTKVEIK (SEQ ID NO: 200) |
| 2B4V3-15 | EIVMTQSPATLSVSPGERATESCRPSKRISAYVFSYMHWYQQKPGQAPRELIYLSC NLEXGIPARFSGSGSGTEFTLTISSLQSEDFAVYYCQHSRELPLTFGQGTKVEIK (SEQ ID NO: 201) |
| 2B4V3-20 | EIVETQSPGTESESPGERATESCRPSKRISAYVFSYMHWYQQKPGQAPRELIYLSCN LEXGIPDRFSGSGSGTDFTLTISRLEPEDFAVYYCQHSRELPLTFGQGTKVEIK (SEQ ID NO: 202) |

TABLE 6B

Humanized heavy chain variable regions

| Antibody variant | Humanized sequences |
|---|---|
| Antibody 2F5 | Antibody 2F5 |
| 2F5V1-46 | QVQLVQSGAEVKKPGASVKVSCKASGYTFTDYNLHWVRQAPGQGLEWIGFIYPSNGITGY NQKFQGRVTMTRDTSTSTVYMELSSLRSEDTAVYYCARSTVDYFDYWGQGTLVTVSS (SEQ ID NO: 55) |
| 2F5V5-51 | EVQLVQSGAEVKKPGESLKISCKGSGYTFTDYNLHWVRQMPGKGLEWIGFIYPSN GITGYNPSFQGQVTISADKSISTAYLQWSSLKASDTAMYYCARSTVDYFDYWGQG TLVTVSS (SEQ ID NO: 58) |
| 2F5V3-23 | EVQLLESGGGLVQPGGSLRLSCAASGYTFTDYNLHWVRQAPGKGLEWIGFIYPSN GITGYNDSVKGRFTISRDNSKNTLYLQMNSLRAEDTAVYYCARSTVDYFDYWGQG TLVTVSS (SEQ ID NO: 57) |
| 2F5V1-69 | QVQLVQSGAEVKKPGSSVKVSCKASGYTFTDYNLHWVRQAPGQGLEWIGFIYPSN GITGYNQKFQGRVTITADESTSTAYMELSSLRSEDTAVYYCARSTVDYFDYWGQG TLVTVSS (SEQ ID NO: 56) |

TABLE 6B -continued

Humanized heavy chain variable regions

| Antibody variant | Humanized sequences |
|---|---|
| 2F5V3-48 | EVQLVESGGGLVQPGGSLRLSCAASGYTFTDYNLHWVRQAPGKGLEWIGFIYPSN GITGYNDSVKGRFTISRDNAKNSLYLQMNSLRAEDTAVYYCARSTVDYFDYWGQ GTLVTVSS (SEQ ID NO: 155) |
| 2F5V3-30 | QVQLVESGGGVVQPGRSLRLSCAASGYTFTDYNLHWVRQAPGKGLEWIGFIYPSN GITGYNDSVKGRFTISRDNSKNTLYLQMNSLRAEDTAVYYCARSTVDYFDYWGQG TLVTVSS (SEQ ID NO: 156) |
| 2F5V3-7 | EVQLVESGGGLVQPGGSLRLSCAASGYTFTDYNLHWVRQAPGKGLEWIGFIYPSN GITGYNDSVKGRFTISRDNAKNSLYLQMNSLRAEDTAVYYCARSTVDYFDYWGQ GTLVTVSS (SEQ ID NO: 155) |
| 2F5V4-59 | QVQLQESGPGLVKPSETLSLTCTVSGYTFTDYNLHWIRQPPGKGLEWIGFIYPSNGI TGYNPSLKSRVTISVDTSKNQFSLKLSSVTAADTAVYYCARSTVDYFDYWGQGTL VTVSS (SEQ ID NO: 157) |
| 2F5V3-15 | EVQLVESGGGLVQPGGSLRLSCAASGYTFTDYNLHWVRQAPGKGLEWIGFIYPSN GITGYNAPVKGRFTISRDDSKNTLYLQMNSLKTEDTAVYYCARSTVDYFDYWGQG TLVTVSS (SEQ ID NO: 158) |
| 2F5V4-30-4 | QVQLQESGPGLVKPSQTLSLTCTVSGYTFTDYNLHWIRQPPGKGLEWIGFIYPSNGI TGYNPSLKSRVTISVDTSKNQFSLKLSSVTAADTAVYYCARSTVDYFDYWGQGTL VTVSS (SEQ ID NO: 159) |
| Antibody 3A12 | Antibody 3A12 |
| 3A12V3-15 | EVQLVESGGGLVKPGGSLRLSCAASGFTFSNYCMNWVRQAPGKGLEWVAEIRLKS NNYVTNYVAPVKGRFTISRDDSKNTLYLQMNSLKTEDTAVYYCTRDGYYVPFAY WGQGTLVTVSS (SEQ ID NO: 66) |
| 3A12V3-48 | EVQLVESGGGLVQPGGSLRLSCAASGFTFSNYCMNWVRQAPGKGLEWVAEIRLKS NNYVTNYVDSVKGRFTISRDNAKNSLYLQMNSLRAEDTAVYYCTRDGYYVPFAY WGQGTLVTVSS (SEQ ID NO: 160) |
| 3A12V3-7 | EVQLVESGGGLVQPGGSLRLSCAASGFTFSNYCMNWVRQAPGKGLEWVAEIRLKS NNYVTNYVDSVKGRFTISRDNAKNSLYLQMNSLRAEDTAVYYCTRDGYYVPFAY WGQGTLVTVSS (SEQ ID NO: 160) |
| 3A12V3-23 | EVQLLESGGGLVQPGGSLRLSCAASGFTFSNYCMNWVRQAPGKGLEWVAEIRLKS NNYVTNYVDSVKGRFTISRDNSKNTLYLQMNSLRAEDTAVYYCTRDGYYVPFAY WGQGTLVTVSS (SEQ ID NO: 161) |
| 3A12V3-30 | QVQLVESGGGVVQPGRSLRLSCAASGFTFSNYCMNWVRQAPGKGLEWVAEIRLK SNNYVTNYVDSVKGRFTISRDNSKNTLYLQMNSLRAEDTAVYYCTRDGYYVPFAY WGQGTLVTVSS (SEQ ID NO: 162) |
| 3A12V1-69 | QVQLVQSGAEVKKPGSSVKVSCKASGFTFSNYCMNWVRQAPGQGLEWVAEIRLK SNNYVTNYVQKFQGRVTITADESTSTAYMELSSLRSEDTAVYYCTRDGYYVPFAY WGQGTLVTVSS (SEQ ID NO: 163) |
| 3A12V1-46 | QVQLVQSGAEVKKPGASVKVSCKASGFTFSNYCMNWVRQAPGQGLEWVAEIRLK SNNYVTNYVQKFQGRVTMTRDTSTSTVYMELSSLRSEDTAVYYCTRDGYYVPFA YWGQGTLVTVSS (SEQ ID NO: 164) |
| 3A12V5-51 | EVQLVQSGAEVKKPGESLKISCKGSGFTFSNYCMNWVRQMPGKGLEWVAEIRLKS NNYVTNYVPSFQGQVTISADKSISTAYLQWSSLKASDTAMYYCTRDGYYVPFAYW GQGTLVTVSS (SEQ ID NO: 165) |
| 3A12V4-59 | QVQLQESGPGLVKPSETLSLTCTVSGFTFSNYCMNWIRQPPGKGLEWVAEIRLKSN NYVTNYVPSLKSRVTISVDTSKNQFSLKLSSVTAADTAVYYCTRDGYYVPFAYWG QGTLVTVSS (SEQ ID NO: 166) |
| 3A12V4-39 | QLQLQESGPGLVKPSETLSLTCTVSGFTFSNYCMNWIRQPPGKGLEWVAEIRLKSN NYVTNYVPSLKSRVTISVDTSKNQFSLKLSSVTAADTAVYYCTRDGYYVPFAYWG QGTLVTVSS (SEQ ID NO: 167) |
| Antibody 6A3a | Antibody 6A3a |
| 6A3aV1-46 | QVQLVQSGAEVKKPGASVKVSCKASGYSFTGYYMHWVRQAPGQGLEWIGEINPS TGGTSYNQKFQGRVTMTRDTSTSTVYMELSSLRSEDTAVYYCTRGHYGSYLTFDY WGQGTLVTVSS (SEQ ID NO: 61) |
| 6A3aV1-69 | QVQLVQSGAEVKKPGSSVKVSCKASGYSFTGYYMHWVRQAPGQGLEWIGEINPS TGGTSYNQKFQGRVTITADESTSTAYMELSSLRSEDTAVYYCTRGHYGSYLTFDY WGQGTLVTVSS (SEQ ID NO: 62) |

TABLE 6B -continued

Humanized heavy chain variable regions

Antibody variant Humanized sequences

6A3aV3-23
EVQLLESGGGLVQPGGSLRLSCAASGYSFTGYYMHWVRQAPGKGLEW**IGEINPST
GGTSYNDSVKGRFTISRDNSKNTLYLQMNSLRAEDTAVYYCTRGHYGSYLTFDY**
WGQGTLVTVSS (SEQ ID NO: 63)

6A3aV5-51
EVQLVQSGAEVKKPGESLKISCKGSGYSFTGYYMHWVRQMPGKGLEW**IGEINPST
GGTSYNPSFQGQVTISADKSISTAYLQWSSLKASDTAMYYCTRGHYGSYLTFDYW**
GQGTLVTVSS (SEQ ID NO: 64)

Antibody 6A3b        Antibody 6A3b

6A3bV1-46
QVQLVQSGAEVKKPGASVKVSCKASGYTFTSYWMHWVRQAPGQGLEW**IGNIYP
GSISSNYDQKFQGRVTMTRDTSTSTVYMELSSLRSEDTAVYYCTRGHYGSYLTFD
Y**WGQGTLVTVSS (SEQ ID NO: 169)

6A3bV5-51
EVQLVQSGAEVKKPGESLKISCKGSGYTFTSYWMHWVRQMPGKGLEW**IGNIYPG
SISSNYDPSFQGQVTISADKSISTAYLQWSSLKASDTAMYYCTRGHYGSYLTFDYW**
GQGTLVTVSS (SEQ ID NO: 170)

6A3bV3-7
EVQLVESGGGLVQPGGSLRLSCAASGYTFTSYWMHWVRQAPGKGLEW**IGNIYPG
SISSNYDDSVKGRFTISRDNAKNSLYLQMNSLRAEDTAVYYCTRGHYGSYLTFDY**
WGQGTLVTVSS (SEQ ID NO: 171)

6A3bV1-69
QVQLVQSGAEVKKPGSSVKVSCKASGYTFTSYWMHWVRQAPGQGLEW**IGNIYPG
SISSNYDQKFQGRVTITADESTSTAYMELSSLRSEDTAVYYCTRGHYGSYLTFDYW**
GQGTLVTVSS (SEQ ID NO: 172)

6A3bV3-48
EVQLVESGGGLVQPGGSLRLSCAASGYTFTSYWMHWVRQAPGKGLEW**IGNIYPG
SISSNYDDSVKGRFTISRDNAKNSLYLQMNSLRAEDTAVYYCTRGHYGSYLTFDY**
WGQGTLVTVSS (SEQ ID NO: 171)

6A3bV3-23
EVQLLESGGGLVQPGGSLRLSCAASGYTFTSYWMHWVRQAPGKGLEW**IGNIYPGS
ISSNYDDSVKGRFTISRDNSKNTLYLQMNSLRAEDTAVYYCTRGHYGSYLTFDYW**
GQGTLVTVSS (SEQ ID NO: 173)

6A3bV3-30
QVQLVESGGGVVQPGRSLRLSCAASGYTFTSYWMHWVRQAPGKGLEW**IGNIYPG
SISSNYDDSVKGRFTISRDNSKNTLYLQMNSLRAEDTAVYYCTRGHYGSYLTFDY**
WGQGTLVTVSS (SEQ ID NO: 174)

6A3bV4-59
QVQLQESGPGLVKPSETLSLTCTVSGYTFTSYWMHWIRQPPGKGLEW**IGNIYPGSI
SSNYDPSLKSRVTISVDTSKNQFSLKLSSVTAADTAVYYCTRGHYGSYLTFDYWGQ**
GTLVTVSS (SEQ ID NO: 175)

6A3bV3-15
EVQLVESGGGLVKPGGSLRLSCAASGYTFTSYWMHWVRQAPGKGLEW**IGNIYPG
SISSNYDAPVKGRFTISRDDSKNTLYLQMNSLKTEDTAVYYCTRGHYGSYLTFDY**
WGQGTLVTVSS (SEQ ID NO: 176)

6A3bV4-30-4
QVQLQESGPGLVKPSQTLSLTCTVSGYTFTSYWMHWIRQPPGKGLEW**IGNIYPGSI
SSNYDPSLKSRVTISVDTSKNQFSLKLSSVTAADTAVYYCTRGHYGSYLTFDYWGQ**
GTLVTVSS (SEQ ID NO: 177)

Antibody 6C7        Antibody 6C7

6C7V3-15
EVQLVESGGGLVKPGGSLRLSCAASGFTFSNYCMNWVRQAPGKGLEW**VAEIRLKS
NNYVTNYVAPVKGRFTISRDDSKNTLYLQMNSLKTEDTAVYYCTRDGYYVPFAY**
WGQGTLVTVSS (SEQ ID NO: 66)

6C7V3-48
EVQLVESGGGLVQPGGSLRLSCAASGFTFSNYCMNWVRQAPGKGLEW**VAEIRLKS
NNYVTNYVDSVKGRFTISRDNAKNSLYLQMNSLRAEDTAVYYCTRDGYYVPFAY**
WGQGTLVTVSS (SEQ ID NO: 160)

6C7V3-7
EVQLVESGGGLVQPGGSLRLSCAASGFTFSNYCMNWVRQAPGKGLEW**VAEIRLKS
NNYVTNYVDSVKGRFTISRDNAKNSLYLQMNSLRAEDTAVYYCTRDGYYVPFAY**
WGQGTLVTVSS (SEQ ID NO: 160)

6C7V3-23
EVQLLESGGGLVQPGGSLRLSCAASGFTFSNYCMNWVRQAPGKGLEW**VAEIRLKS
NNYVTNYVDSVKGRFTISRDNSKNTLYLQMNSLRAEDTAVYYCTRDGYYVPFAY**
WGQGTLVTVSS (SEQ ID NO: 161)

6C7V3-30
QVQLVESGGGVVQPGRSLRLSCAASGFTFSNYCMNWVRQAPGKGLEW**VAEIRLK
SNNYVTNYVDSVKGRFTISRDNSKNTLYLQMNSLRAEDTAVYYCTRDGYYVPFAY**
WGQGTLVTVSS (SEQ ID NO: 162)

6C7V1-69
QVQLVQSGAEVKKPGSSVKVSCKASGFTFSNYCMNWVRQAPGQGLEW**VAEIRLK
SNNYVTNYVQKFQGRVTITADESTSTAYMELSSLRSEDTAVYYCTRDGYYVPFAY**
WGQGTLVTVSS (SEQ ID NO: 163)

TABLE 6B -continued

Humanized heavy chain variable regions

| Antibody variant | Humanized sequences |
|---|---|
| 6C7V1-46 | QVQLVQSGAEVKKPGASVKVSCKASGFTFSNYCMNWVRQAPGQGLEWVAEIRLK SNNYVTNYVQKFQGRVTMTRDTSTSTVYMELSSLRSEDTAVYYCTRDGYYVPFA YWGQGTLVTVSS (SEQ ID NO: 164) |
| 6C7V5-51 | EVQLVQSGAEVKKPGESLKISCKGSGFTFSNYCMNWVRQMPGKGLEWVAEIRLKS NNYVTNYVPSFQGQVTISADKSISTAYLQWSSLKASDTAMYYCTRDGYYVPFAYW GQGTLVTVSS (SEQ ID NO: 165) |
| 6C7V4-59 | QVQLQESGPGLVKPSETLSLTCTVSGFTFSNYCMNWIRQPPGKGLEWVAEIRLKSN NYVTNYVPSLKSRVTISVDTSKNQFSLKLSSVTAADTAVYYCTRDGYYVPFAYWG QGTLVTVSS (SEQ ID NO: 166) |
| 6C7V4-39 | QLQLQESGPGLVKPSETLSLTCTVSGFTFSNYCMNWIRQPPGKGLEWVAEIRLKSN NYVTNYVPSLKSRVTISVDTSKNQFSLKLSSVTAADTAVYYCTRDGYYVPFAYWG QGTLVTVSS (SEQ ID NO: 167) |
| Antibody 1A8 | Antibody 1A8 |
| 1A8V5-51 | EVQLVQSGAEVKKPGESLKISCKGSGYTFTSYDINWVRQMPGKGLEWIGWIFPGD GSTKYNPSFQGQVTISADKSISTAYLQWSSLKASDTAMYYCARGYHYAMDSWGQ GTLVTVSS (SEQ ID NO: 53) |
| 1A8V1-46 | QVQLVQSGAEVKKPGASVKVSCKASGYTFTSYDINWVRQAPGQGLEWIGWIFPG DGSTKYNQKFQGRVTMTRDTSTSTVYMELSSLRSEDTAVYYCARGYHYAMDSW GQGTLVTVSS (SEQ ID NO: 50) |
| 1A8V1-69 | QVQLVQSGAEVKKPGSSVKVSCKASGYTFTSYDINWVRQAPGQGLEWIGWIFPGD GSTKYNQKFQGRVTITADESTSTAYMELSSLRSEDTAVYYCARGYHYAMDSWGQ GTLVTVSS (SEQ ID NO: 51) |
| 1A8V3-23 | EVQLLESGGGLVQPGGSLRLSCAASGYTFTSYDINWVRQAPGKGLEWIGWIFPGD GSTKYNDSVKGRFTISRDNSKNTLYLQMNSLRAEDTAVYYCARGYHYAMDSWGQ GTLVTVSS (SEQ ID NO: 52) |
| 1A8V3-48 | EVQLVESGGGLVQPGGSLRLSCAASGYTFTSYDINWVRQAPGKGLEWIGWIFPGD GSTKYNDSVKGRFTISRDNAKNSLYLQMNSLRAEDTAVYYCARGYHYAMDSWGQ GTLVTVSS (SEQ ID NO: 178) |
| 1A8V3-7 | EVQLVESGGGLVQPGGSLRLSCAASGYTFTSYDINWVRQAPGKGLEWIGWIFPGD GSTKYNDSVKGRFTISRDNAKNSLYLQMNSLRAEDTAVYYCARGYHYAMDSWGQ GTLVTVSS (SEQ ID NO: 178) |
| 1A8V3-30 | QVQLVESGGGVVQPGRSLRLSCAASGYTFTSYDINWVRQAPGKGLEWIGWIFPGD GSTKYNDSVKGRFTISRDNSKNTLYLQMNSLRAEDTAVYYCARGYHYAMDSWGQ GTLVTVSS (SEQ ID NO: 179) |
| 1A8V4-59 | QVQLQESGPGLVKPSETLSLTCTVSGYTFTSYDINWIRQPPGKGLEWIGWIFPGDGS TKYNPSLKSRVTISVDTSKNQFSLKLSSVTAADTAVYYCARGYHYAMDSWGQGTL VTVSS (SEQ ID NO: 180) |
| 1A8V3-15 | EVQLVESGGGLVQPGGSLRLSCAASGYTFTSYDINWVRQAPGKGLEWIGWIFPGD GSTKYNAPVKGRFTISRDDSKNTLYLQMNSLKTEDTAVYYCARGYHYAMDSWGQ GTLVTVSS (SEQ ID NO: 181) |
| 1A8V4-39 | QLQLQESGPGLVKPSETLSLTCTVSGYTFTSYDINWIRQPPGKGLEWIGWIFPGDGS TKYNPSLKSRVTISVDTSKNQFSLKLSSVTAADTAVYYCARGYHYAMDSWGQGTL VTVSS (SEQ ID NO: 182) |
| Antibody 2E12 | Antibody 2E12 |
| 2E12V1-46 | QVQLVQSGAEVKKPGASVKVSCKASGYTFTDYNLHWVRQAPGQGLEWIGFIYPS NGITGYNQKFQGRVTMTRDTSTSTVYMELSSLRSEDTAVYYCARSTVDYFDYWG QGTLVTVSS (SEQ ID NO: 55) |
| 2E12V5-51 | EVQLVQSGAEVKKPGESLKISCKGSGYTFTDYNLHWVRQMPGKGLEWIGFIYPSN GITGYNPSFQGQVTISADKSISTAYLQWSSLKASDTAMYYCARSTVDYFDYWGQG TLVTVSS (SEQ ID NO: 58) |
| 2E12V1-69 | QVQLVQSGAEVKKPGSSVKVSCKASGYTFTDYNLHWVRQAPGQGLEWIGFIYPSN GITGYNQKFQGRVTITADESTSTAYMELSSLRSEDTAVYYCARSTVDYFDYWGQG TLVTVSS (SEQ ID NO: 56) |
| 2E12V3-23 | EVQLLESGGGLVQPGGSLRLSCAASGYTFTDYNLHWVRQAPGKGLEWIGFIYPSN GITGYNDSVKGRFTISRDNSKNTLYLQMNSLRAEDTAVYYCARSTVDYFDYWGQG TLVTVSS (SEQ ID NO: 57) |

TABLE 6B -continued

Humanized heavy chain variable regions

| Antibody variant | Humanized sequences |
|---|---|
| 2E12V3-48 | EVQLVESGGGLVQPGGSLRLSCAASGYTFTDYNLHWVRQAPGKGLEWIGFIYPSN GITGYNDSVKGRFTISRDNAKNSLYLQMNSLRAEDTAVYYCARSTVDYFDYWGQ GTLVTVSS (SEQ ID NO: 155) |
| 2E12V3-30 | QVQLVESGGGVVQPGRSLRLSCAASGYTFTDYNLHWVRQAPGKGLEWIGFIYPSN GITGYNDSVKGRFTISRDNSKNTLYLQMNSLRAEDTAVYYCARSTVDYFDYWGQG TLVTVSS (SEQ ID NO: 156) |
| 2E12V3-7 | EVQLVESGGGLVQPGGSLRLSCAASGYTFTDYNLHWVRQAPGKGLEWIGFIYPSN GITGYNDSVKGRFTISRDNAKNSLYLQMNSLRAEDTAVYYCARSTVDYFDYWGQ GTLVTVSS (SEQ ID NO: 155) |
| 2E12V4-59 | QVQLQESGPGLVKPSETLSLTCTVSGYTFTDYNLHWIRQPPGKGLEWIGFIYPSNGI TGYNPSLKSRVTISVDTSKNQFSLKLSSVTAADTAVYYCARSTVDYFDYWGQGTL VTVSS (SEQ ID NO: 157) |
| 2E12V3-15 | EVQLVESGGGLVKPGGSLRLSCAASGYTFTDYNLHWVRQAPGKGLEWIGFIYPSN GITGYNAPVKGRFTISRDDSKNTLYLQMNSLKTEDTAVYYCARSTVDYFDYWGQG TLVTVSS (SEQ ID NO: 158) |
| 2E12V4-39 | QLQLQESGPGLVKPSETLSLTCTVSGYTFTDYNLHWIRQPPGKGLEWIGFIYPSNGI TGYNPSLKSRVTISVDTSKNQFSLKLSSVTAADTAVYYCARSTVDYFDYWGQGTL VTVSS (SEQ ID NO: 183) |
| Antibody 2B4 | Antibody 2B4 |
| 2B4V1-46 | QVQLVQSGAEVKKPGASVKVSCKASGYTFTSYWMHWVRQAPGQGLEWIGNIYP GSGSTYYDQKFQGRVTMTRDTSTSTVYMELSSLRSEDTAVYYCTRGHYGNYLTF DYWGQGTLVTVSS (SEQ ID NO: 204) |
| 2B4V5-51 | EVQLVQSGAEVKKPGESLKISCKGSGYTFTSYWMHWVRQMPGKGLEWIGNIYPG SGSTYYDPSFQGQVTISADKSISTAYLQWSSLKASDTAMYYCTRGHYGNYLTFDYWGQGTLVTVSS (SEQ ID NO: 205) |
| 2B4V3-23 | EVQLLESGGGLVQPGGSLRLSCAASGYTFTSYWMHWVRQAPGKGLEWIGNIYPGS GSTYYDDSVKGRFTISRDNSKNTLYLQMNSLRAEDTAVYYCTRGHYGNYLTFDYWGQGTLVTVSS (SEQ ID NO: 206) |
| 2B4V3-7 | EVQLVESGGGLVQPGGSLRLSCAASGYTFTSYWMHWVRQAPGKGLEWIGNIYPG SGSTYYDDSVKGRFTISRDNAKNSLYLQMNSLRAEDTAVYYCTRGHYGNYLTFDYWGQGTLVTVSS (SEQ ID NO: 207) |
| 2B4V3-30 | QVQLVESGGGVVQPGRSLRLSCAASGYTFTSYWMHWVRQAPGKGLEWIGNIYPG SGSTYYDDSVKGRFTISRDNSKNTLYLQMNSLRAEDTAVYYCTRGHYGNYLTFDYWGQGTLVTVSS (SEQ ID NO: 208) |
| 2B4V3-48 | EVQLVESGGGLVQPGGSLRLSCAASGYTFTSYWMHWVRQAPGKGLEWIGNIYPG SGSTYYDDSVKGRFTISRDNAKNSLYLQMNSLRAEDTAVYYCTRGHYGNYLTFDYWGQGTLVTVSS (SEQ ID NO: 209) |
| 2B4V1-69 | QVQLVQSGAEVKKPGSSVKVSCKASGYTFTSYWMHWVRQAPGQGLEWIGNIYPG SGSTYYDQKFQGRVTITADESTSTAYMELSSLRSEDTAVYYCTRGHYGNYLTFDYWGQGTLVTVSS (SEQ ID NO: 210) |
| 2B4V4-59 | QVQLQESGPGLVKPSETLSLTCTVSGYTFTSYWMHWIRQPPGKGLEWIGNIYPGSG STYYDPSLKSRVTISVDTSKNQFSLKLSSVTAADTAVYYCTRGHYGNYLTFDYWG QGTLVTVSS (SEQ ID NO: 211) |
| 2B4V3-15 | EVQLVESGGGLVKPGGSLRLSCAASGYTFTSYWMHWVRQAPGKGLEWIGNIYPG SGSTYYDAPVKGRFTISRDDSKNTLYLQMNSLKTEDTAVYYCTRGHYGNYLTFDYWGQGTLVTVSS (SEQ ID NO: 212) |
| 2B4V4-30-4 | QVQLQESGPGLVKPSQTLSLTCTVSGYTFTSYWMHWIRQPPGKGLEWIGNIYPGS GSTYYDPSLKSRVTISVDTSKNQFSLKLSSVTAADTAVYYCTRGHYGNYLTFDYW GQGTLVTVSS (SEQ ID NO: 213) |

Example 2: Epitope Mapping of CD33 Antibodies

CD33 antibodies were tested for their ability to bind 15 or 25-mer peptides spanning the entire human CD33. The CD33 antibodies were also compared to a reference CD33 antibody by determining their CD33 binding region.

Methodology

Linear 15-mer peptides were synthesized based on the sequence of human CD33 (SEQ ID NO:1), with a 14 residue overlap. In addition, linear 25-mer peptides were synthesized based on sequence of human CD33 (SEQ ID NO:1) or mouse CD33 (SEQ ID NO:2) with a single residue shift. The binding of CD33 antibodies to each of the synthesized peptides was tested in an ELISA based method. In this assay, the peptide arrays were incubated with primary antibody solution (overnight at 4° C.). After washing, the peptide arrays were incubated with a 1/1000 dilution of an antibody peroxidase conjugate (SBA, cat. nr. 2010-05) for one hour at 25° C. After washing, the peroxidase substrate 2,2'-azino-di-3-ethylbenzthiazoline sulfonate (ABTS) and 2 µl/ml of 3% $H_2O_2$ were added. After one hour, the color development was measured. The color development was quantified with a charge coupled device (CCD) camera and an image processing system.

Epitope binning of the antibodies was performed on a Forte Bio Octet Red384 system (Pall Forte Bio Corporation, Menlo Park, Calif.) using a standard sandwich format binning assay (see Estep et al, (2013) *MAbs* 5(2):270-8). Control anti-target IgG was loaded onto AHQ sensors and unoccupied Fc-binding sites on the sensor were blocked with a non-relevant human IgG1 antibody. The sensors were then exposed to 100 nM target antigen followed by a second anti-target antibody. Data was processed using ForteBio's Data Analysis Software 7.0. Additional binding by the second antibody after antigen association indicates an unoccupied epitope (non-competitor), while no binding indicates epitope blocking (competitor).

Alternatively, to reconstruct epitopes of the target molecule, libraries of looped and combinatorial peptides were synthesized. An amino functionalized polypropylene support was obtained by grafting with a proprietary hydrophilic polymer formulation, followed by reaction with t-butyloxycarbonyl-hexamethylenediamine (BocHMDA) using dicyclohexylcarbodiimide (DCC) with N-hydroxybenzotriazole (HOBt) and subsequent cleavage of the Boc-groups using trifluoroacetic acid (TFA). Standard Fmoc-peptide synthesis was used to synthesize peptides on the amino-functionalized solid support by custom modified JANUS liquid handling stations (Perkin Elmer).

Synthesis of structural mimics was done using Pepscan's proprietary Chemically Linked Peptides on Scaffolds (CLIPS) technology. CLIPS technology allows to structure peptides into single loops and double-loops. CLIPS templates are coupled to cysteine residues. The side-chains of multiple cysteines in the peptides are coupled to one or two CLIPS templates. For example, a 0.5 mM solution of the mP2 CLIPS (2,6-bis(bromomethyl)pyridine) is dissolved in ammonium bicarbonate (20 mM, pH 7.8)/acetonitrile (1:3 (v/v)). This solution is added onto the peptide arrays. The CLIPS template will bind to side-chains of two cysteines as present in the solid-phase bound peptides of the peptide-arrays (455 wells plate with 3 µl wells). The peptide arrays are gently shaken in the solution for 30 to 60 minutes while completely covered in solution. Finally, the peptide arrays are washed extensively with excess of $H_2O$ and sonicated in disrupt-buffer containing 1% SDS/0.1% β-mercaptoethanol in PBS (pH 7.2) at 70° C. for 30 minutes, followed by sonication in $H_2O$ for another 45 minutes. The T3 CLIPS (2,4,6-tris(bromomethyl)pyridine) carrying peptides were made in a similar way but now with three cysteines.

Looped peptides: constrained peptides of length 17. Positions 2-16 are 15-mers derived from the target sequence. Native Cys residues are protected by acetamidomethyl group (ACM). Positions 1 and 17 are Cys that are linked by mP2 CLIPS moieties.

Combinatorial peptides (discontinuous mimics): constrained peptides of length 33. Positions 2-16 and 18-32 are 15-mer peptides derived from the target sequence with native Cys residues protected by ACM. Positions 1, 17 and 33 are Cys that are linked by T3 CLIPS moieties.

The binding of antibody to each of the synthesized peptides is tested in a PEPSCAN-based ELISA. The peptide arrays are incubated with test antibody solution composed of the experimentally optimized concentration of the test antibody and blocking solution (for example 4% horse serum, 5% ovalbumin (w/v) in PBS/1% Tween80). The peptide arrays are incubated with the test antibody solution overnight at 4° C. After extensive washing with washing buffer (1×PBS, 0.05% Tween80), the peptide arrays are incubated with a 1/1000 dilution of an appropriate antibody peroxidase conjugate for one hour at 25° C. After washing with the washing buffer, the peroxidase substrate 2,2'-azino-di-3-ethylbenzthiazoline sulfonate (ABTS) and 2 µl/ml of 3% $H_2O_2$ are added. After one hour, the color development is measured. The color development is quantified with a charge coupled device (CCD)—camera and an image processing system.

Alternatively a mass spectrometry method is used to identify conformational epitopes. In order to determine the key residues of conformational epitopes on the CD33 protein that anti-CD33 antibodies bind to, with high resolution, antibody/antigen complexes are incubated with deuterated cross-linkers and subjected to multi-enzymatic proteolytic cleavage. After enrichment of the cross-linked peptides, the samples are analyzed by high resolution mass spectrometry (nLC-Orbitrap MS) and the data generated is analyzed using XQuest software. Specifically, CD33 ECD/antibody complexes are generated by mixing equimolar solutions of CD33 antigen and antibody (4 µM in 5 µl each). One µl of the mixture obtained is mixed with 1 µl of a matrix composed of a re-crystallized sinapinic acid matrix (10 mg/ml) in acetonitrile/water (1:1, v/v), TFA 0.1% (K200 MALDI Kit). After mixing, 1 µl of each sample is spotted on a MALDI plate (SCOUT 384). After crystallization at room temperature, the plate is introduced in a MALDI mass spectrometer and analyzed immediately. The analysis is repeated in triplicate. Peaks representing monomeric antibody, the antigen, and antibody and antigen/antibody complexes are detected at the predicted molecular weights.

It is then determined whether the epitope in conformational binding competes with unstructured C1q peptides generated by proteolysis. Specifically, to determine if CD33 ECD/antibody complexes can compete with linear peptides, the CD33 ECD antigen is digested with immobilized pepsin. 25 µl of the antigen with a concentration of 10 µM are mixed with immobilized pepsin 5 µM and incubate at room temperature for 30 minutes. After the incubation time, the sample are centrifuged and the supernatant is pipetted. The completion of the proteolysis is controlled by High-Mass MALDI mass spectrometry in linear mode. The pepsin proteolysis is optimized in order to obtain a large amount of peptide in the 1000-3500 Da range. Next, 5 µl of the antigen peptides generated by proteolysis are mixed with 5 µl of antibodies (8 µM) and incubated at 37° C. for 6 hours. After incubation of the antibodies with the CD33 antigen peptides, 5 µl of the mixture is mixed with 5 µl of the intact CD33 antigen (4 µM) so the final mix contains 2 µM/2 µM/2.5 µM of CD33/antibody/CD33 antigen peptides. The MALDI ToF MS analysis is performed using CovalX's HM3 interaction module with a standard nitrogen laser and focusing on different mass ranges from 0 to 2000 kDa. For the analysis, the following parameters are applied for the mass spectrometer: Linear and Positive mode; Ion Source 1: 20 kV; Ion Source 2: 17 kV; Pulse Ion Extraction: 400 ns; for HM3: Gain Voltage: 3.14 kV; Gain Voltage: 3.14 kV; Acceleration Voltage: 20 kV. To calibrate the instrument, an external calibration with clusters of Insulin, BSA and IgG is being applied. For each sample, 3 spots are analyzed (300 laser shots per spots). Presented spectrum corresponds to the sum of 300 laser shots. The MS data are analyzed using the Complex Tracker analysis software version 2.0 (CovalX Inc). To identify the conformational epitopes for CD33 binding to antibodies, using chemical cross-linking, High-Mass MALDI mass spectrometry and nLCOrbitrap mass spectrometry the interaction interface between the antigen and antibodies the following procedure is followed. 5 µl of the sample antigen (concentration 4 µM) is mixed with 5 µl of the sample antibody (Concentration 4 µM) in order to obtain an antibody/antigen mix with final concentration 2 µM/2 µM. The mixture is incubated at 37° C. for 180 minutes. In a first step, 1 mg of DiSuccinimidylSuberate H12 (DSS-H12) cross-linker is mixed with 1 mg of DiSuccinimidylSuberate D12 (DSS-D12) cross-linker. The 2 mg prepared were mixed with 1 ml of DMF in order to obtain a 2 mg/ml solution of DSS H12/D12. 10 µl of the antibody/antigen mix prepared previously were mixed with 1 µl of the solution of cross-linker d0/d12 prepared (2 mg/ml). The solution is incubated 180 minutes at room temperature in order to achieve the cross-linking reaction.

In order to facilitate the proteolysis, it is necessary to reduce the disulfide bonds present in the protein. The cross-linked samples are mixed with 20 µl of ammonium bicarbonate (25 mM, pH 8.3). After mixing 2.5 µl of DTT (500 mM) is added to the solution. The mixture is then incubated 1 hour at 55° C. After incubation, 2.5 µl of iodioacetamide (1 M) is added before 1 hour of incubation at room temperature in a dark room. After incubation, the solution is diluted 1/5 by adding 120 µl of the buffer used for the proteolysis. 145 µl of the reduced/alkyled cross-linked sample is mixed with 2 µl of trypsin (Sigma, T6567). The proteolytic mixture is incubated overnight at 37° C. For a-chymotrypsin proteolysis, the buffer of proteolysis is Tris-HCL 100 mM, CaCl2 10 mM, pH7.8. The 145 µl of the reduced/alkyled cross-linked complex is mixed with 2 µl of α-chymotrypsin 200 µM and incubated overnight at 30° C. For this analysis, an nLC in combination with Orbitrap mass spectrometry is used. The cross-linker peptides are analyzed using Xquest version 2.0 and stavrox software. The peptides and cross-linked amino acids are then identified.

Results

Figure 6A:
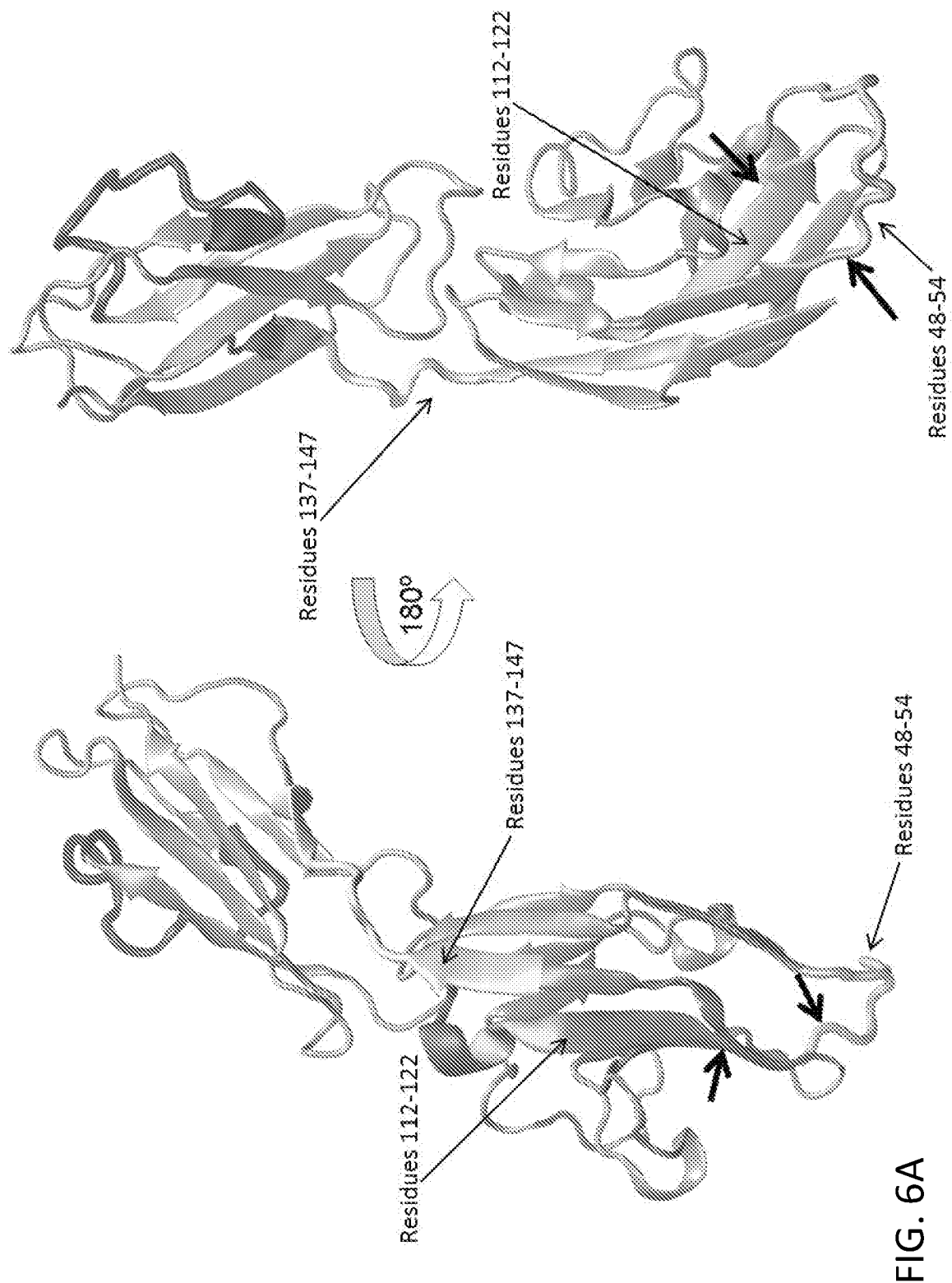
FIG. 6A and FIG. 6B depict antibody binding sites on human CD33 protein.
Figure 6B:
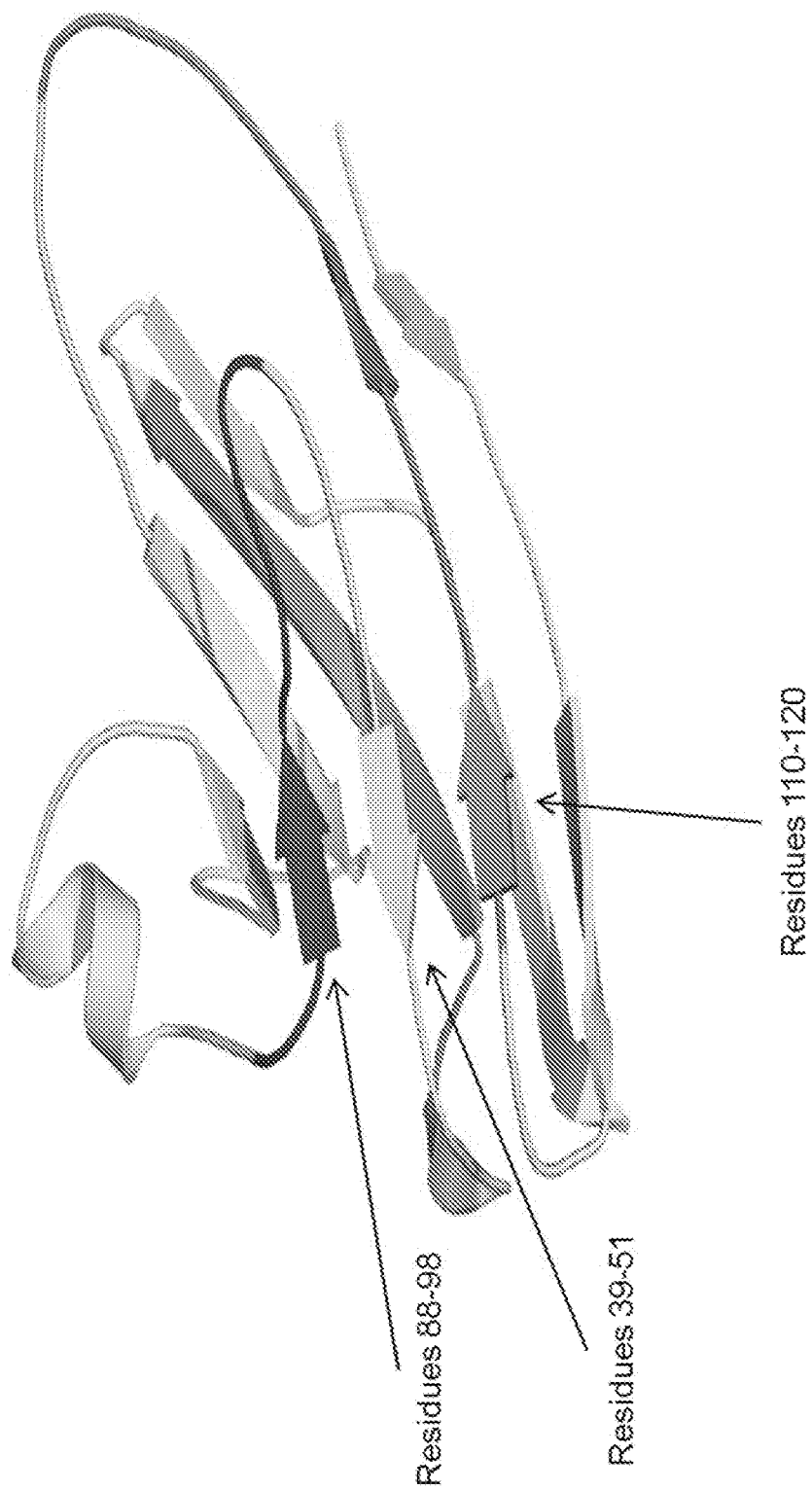
Figure 6D:
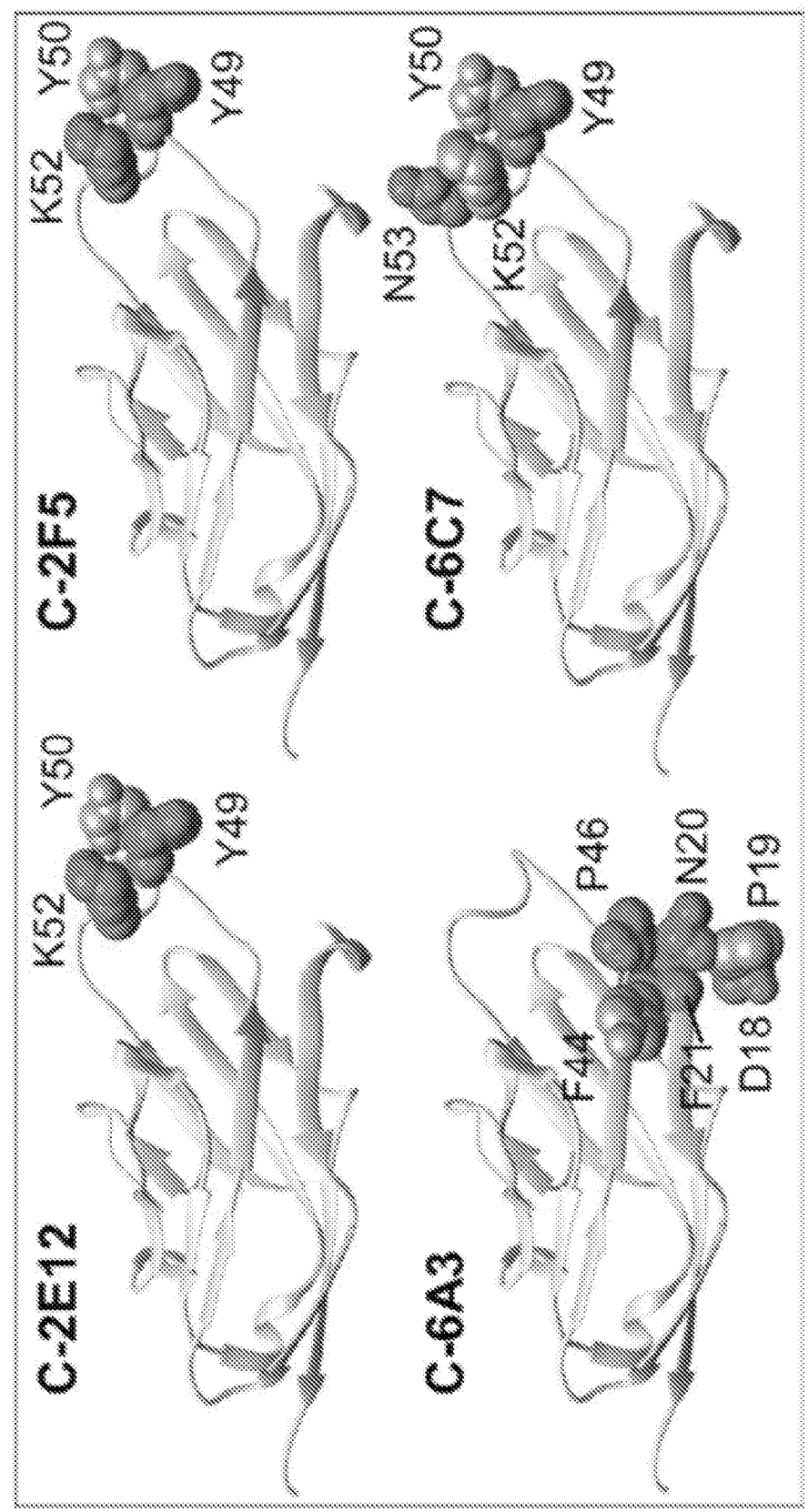
FIG. 6D depicts models of CD33 indicating amino acid residues involved in antibody binding.

The CD33 binding region was determined for 4 anti-CD33 antibodies. The binding regions are listed in Table 7A. FIGS. 6A and 6B show a schematic representation of human CD33, indicating the regions bound by the anti-CD33 antibodies.

TABLE 7A

CD33 antibody binding regions

| Antibody | CD33 binding region | Amino acid region of SEQ ID: 1 |
|---|---|---|
| 3A12 6C7 | $^{48}$PYYDKNS$^{54}$ | 48-54 |
| AF5 | $^{137}$HVTDLTHRPKI$^{147}$ | 137-147 |
| 1A8 | $^{39}$VPCTFFHPIPYYD$^{51}$, $^{88}$GRFRLLGDPSR$^{98}$, $^{110}$RRDNGSYFFRM$^{120}$, and $^{112}$DNGSYFFRMER$^{122}$ | 39-51, 88-98, 110-120, 112-122 |

As indicated in Table 7A, antibodies 3A12, 6C7, and 1A8 showed robust binding exclusively for peptides within the extracellular immunoglobulin-like variable-type (IgV) domain of CD33.

As indicated in Table 7A, the peptide recognized by antibodies 3A12 and 6C7 corresponds to amino acid residues 48-54 of SEQ ID NO:1 and has the amino acid sequence of: PYYDKNS. The peptide recognized by antibodyAF5 corresponds to amino acid residues 137-147 of SEQ ID NO:1 and has the amino acid sequence of: HVTDLTHRPKI. The peptides recognized by antibody of 1A8 corresponds to amino acid residues 39-51, 88-98, 110-120, and 112-122 of SEQ ID NO:1, and have the amino acid sequences of: VPCTFFHPIPYYD, GRFRLLGDPSR, RRDNGSYFFRM, and DNGSYFFRMER.

The peptides bound by each antibody are depicted in FIGS. 6A and 6B.

Functional Mapping

Shotgun mutagenesis epitope mapping of anti-CD33 antibodies 2E12, 2F5, 6C7, and 6A3 was performed using an alanine-scanning library for CD33 protein. A CD33 expression construct (Uniprot id P20138) encoding a C-terminal V5 epitope tag was subjected to high-throughput alanine scanning mutagenesis to generate a comprehensive mutation library (Davidson and Doranz, (2014) Immunology 143: 13-20). Each of residues 8 to 259, representing the CD33 extracellular domain, was mutated mostly to alanine, while alanine codons were mutated to serine. In total, 252 CD33 mutant expression constructs were generated, sequence confirmed, and arrayed into a 384-well plate, one mutant per well.

The CD33 mutation library clones, arrayed in a 384-well microplate, were transfected individually into HEK-293T cells and allowed to express for 22 hours. Cells were then incubated with the anti-CD33 antibodies diluted in 10% normal goat serum (NGS) (Sigma-Aldrich, St. Louis, Mo.). Prior to library screening, primary antibody screening concentrations were determined using an independent immunofluorescence titration curve against cells expressing wild-type CD33 (WT), this identified optimal signal-to-background ratios (>5:1) and ensured that signals were within the linear range of detection. Anti-CD33 antibodies were detected using 3.75 µg/ml AlexaFluor488-conjugated secondary antibody (Jackson ImmunoResearch Laboratories, Westgrove, Pa.) in 10% NGS. Cells were washed twice with PBS without calcium or magnesium and resuspended in Cellstripper (Cellgro, Manassas, Va.) with 0.1% BSA (Sigma-Aldrich, St. Louis, Mo.). Mean cellular fluorescence was detected using the Intellicyt high throughput flow cytometer (HTFC, Intellicyt, Albuquerque, N. Mex.). Background fluorescence was determined by fluorescence measurement of vector-transfected control cells. Antibody reactivities against each mutant clone were calculated relative to wild-type CD33 protein reactivity by subtracting the signal from mock-transfected controls and normalizing to the signal from wild-type CD33-transfected controls.

Mutated residues within critical clones were identified as critical to the anti-CD33 antibody epitope if they did not support reactivity of the test antibody but did support reactivity of a commercially available reference antibody WM53 Mab (Biolegend, Cat #: 303402) or additional anti-CD33 antibodies. This counter-screen strategy facilitated the exclusion of CD33 mutants that were locally misfolded or that had an expression defect.

FIG. 6C depicts the mean binding reactivities and ranges for all critical residues identified in the screens. The range is the difference between the duplicate experimental binding values. Primary critical residues are outlined in red and were identified as residues where mutations were negative for test antibody binding (<30% of binding to WT) but positive for the control antibody (>80% WT). Residues outlined in blue are additional secondary residues that did not meet the threshold guidelines, but whose decreased binding activity and proximity to critical residues indicate that they may be part of the antibody epitope (FIG. 6C). F TABLE 8A-continued CD33 antibodies reduce cell surface level of CD33 on human cells Percent CD33 Surface Expression

| Antibody | U937 ells | | Monocytes | | DCs | | Macrophages | |
|---|---|---|---|---|---|---|---|---|
| | % CD33 | % control | % CD33 | % CD33 | % CD33 | % control | % CD33 | % control |
| 6A3 | 33.1 | 99.7 | 26.0 | 100.2 | 16.38 | 107.77 | 59.30 | 94.84 |
| 6C7 | 47.2 | 100.5 | 24.1 | 105.8 | 15.76 | 117.15 | 58.89 | 101.52 |
| Isotype | 95.7 | 101.5 | 104.5 | 104.8 | 70.52 | 99.15 | 95.41 | 94.73 |

Table 8B depicts the results of CD33 cell surface levels from human microglial cells. In Table 8B, "Isotype" refers to an isotype mIgG1 control antibody, and "ND" refers to not determined.

TABLE 8B

CD33 antibodies reduce cell surface level of CD33 on human microglial cells

| | Percent CD33 Surface Expression Microglial cells | |
|---|---|---|
| Antibody | % CD33 | % control |
| 1A8 | 26.13 | 71.02 |
| 2B4 | ND | ND |
| 2E12 | 22.86 | 58.68 |
| 2F5 | 24.97 | 85.77 |
| 3A12 | ND | ND |
| 6A3 | 24.42 | 89.82 |
| 6C7 | 23.99 | 86.19 |
| Isotype | 92.12 | 86.34 |

As shown in Tables 8A and 8B and FIG. 16A-16H, antibodies 1A8, 2E12, 2F5, 3A12, 6A3, and 6C7, and to a lesser degree 2B4, were able to decrease cell surface levels of CD33 on multiple types of human cells.

Figure 16A:
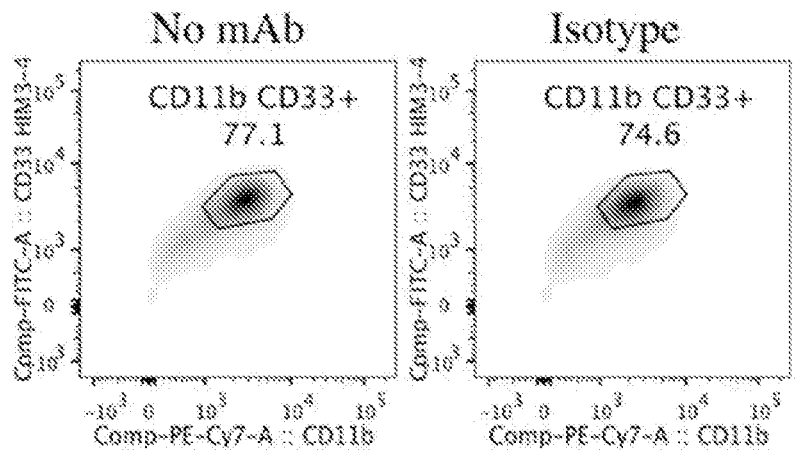
FIG. 16A-16J depict results showing a reduction in cell surface levels of CD33 on various primary immune cells.
Figure 16B:
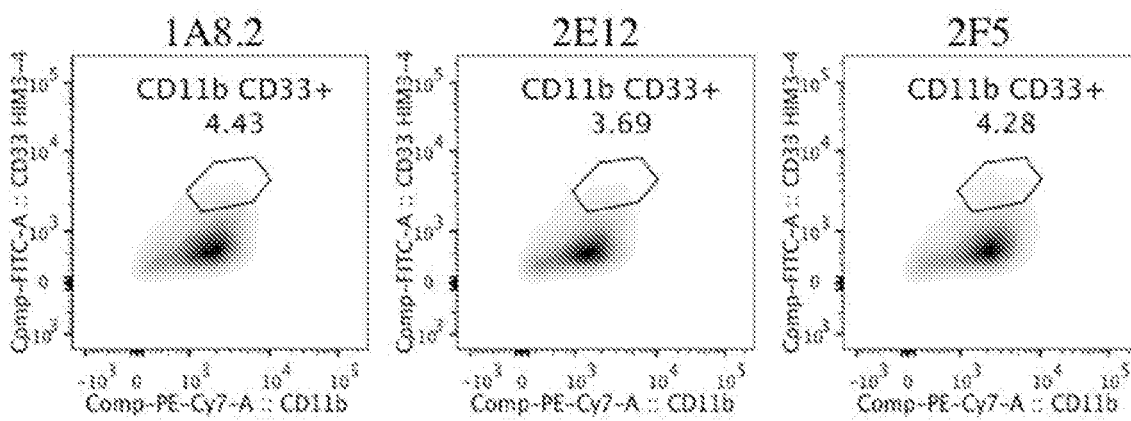
Figure 16C:
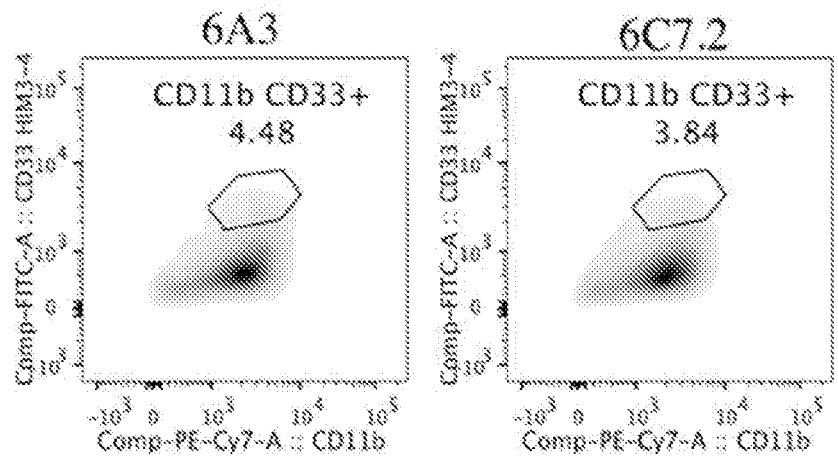
Figure 16D:
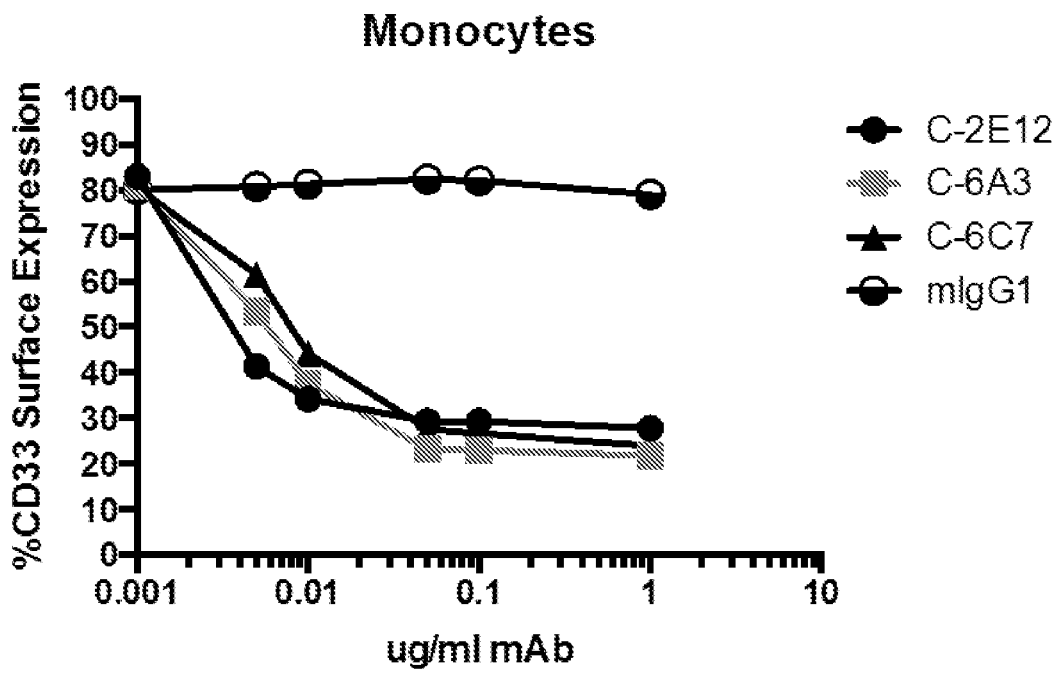
Figure 16E:
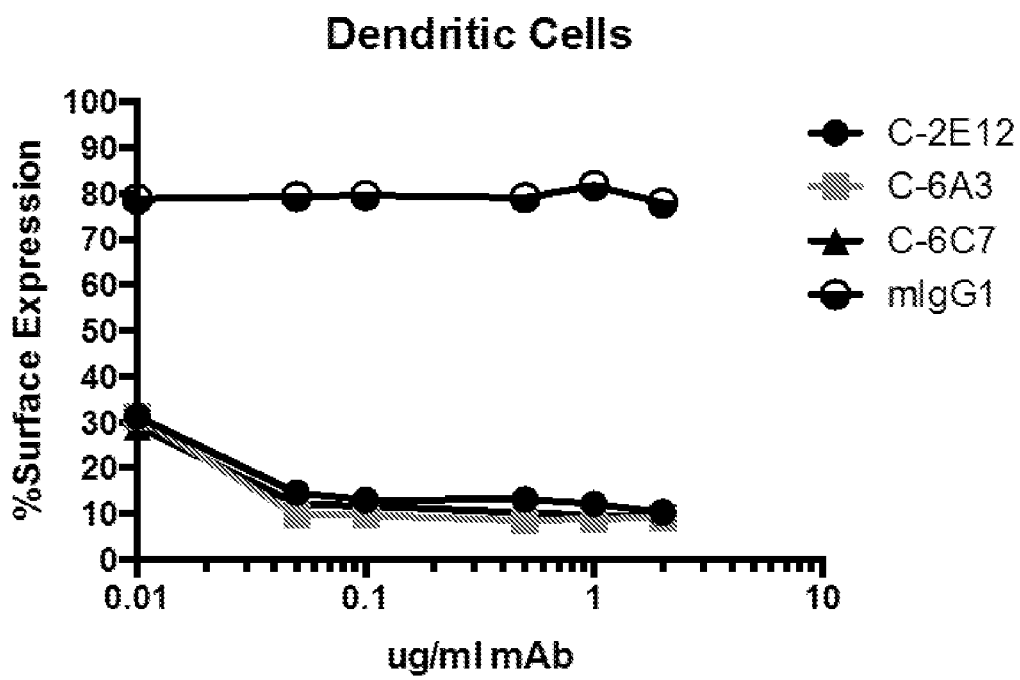
Figure 16F:
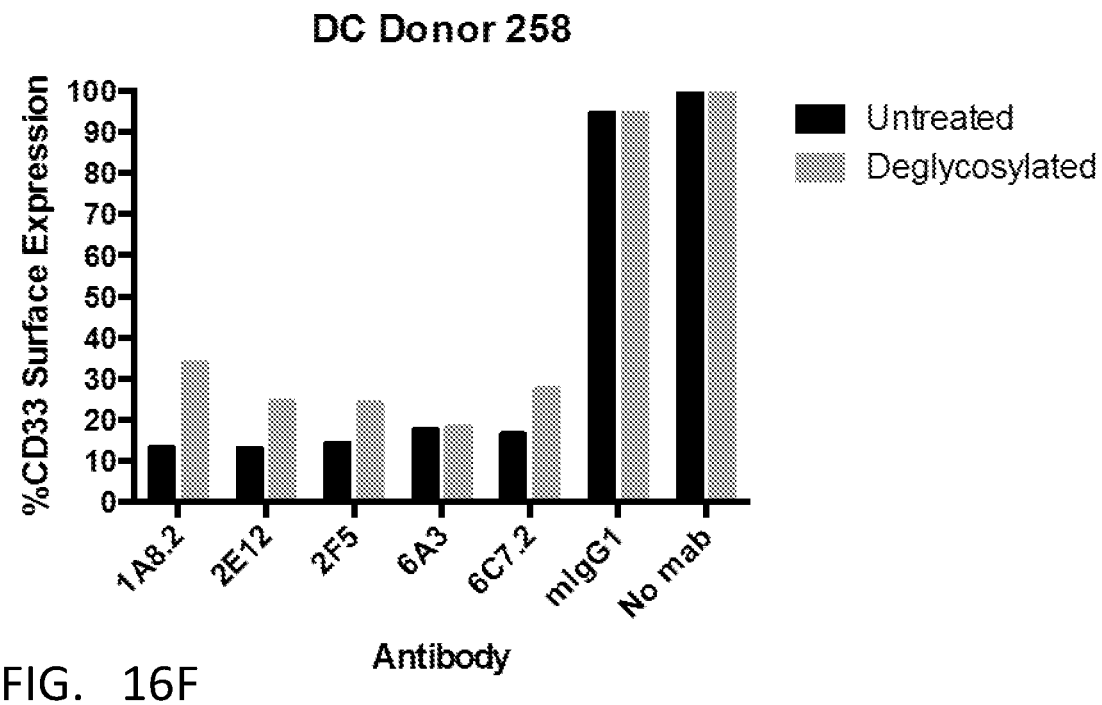
Figure 16G:
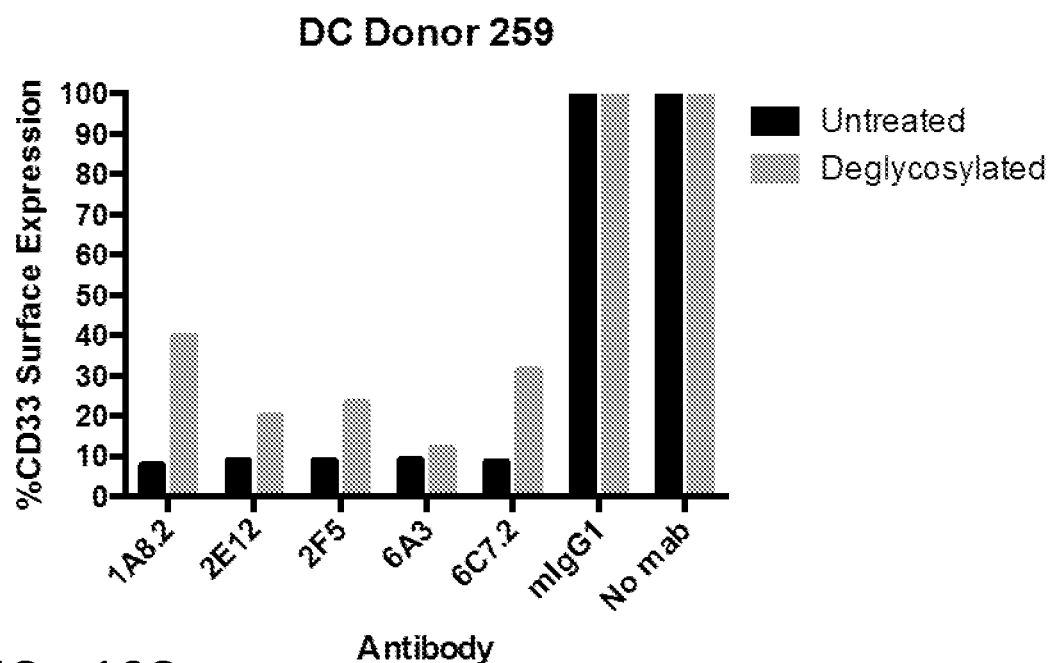
Figure 16H:
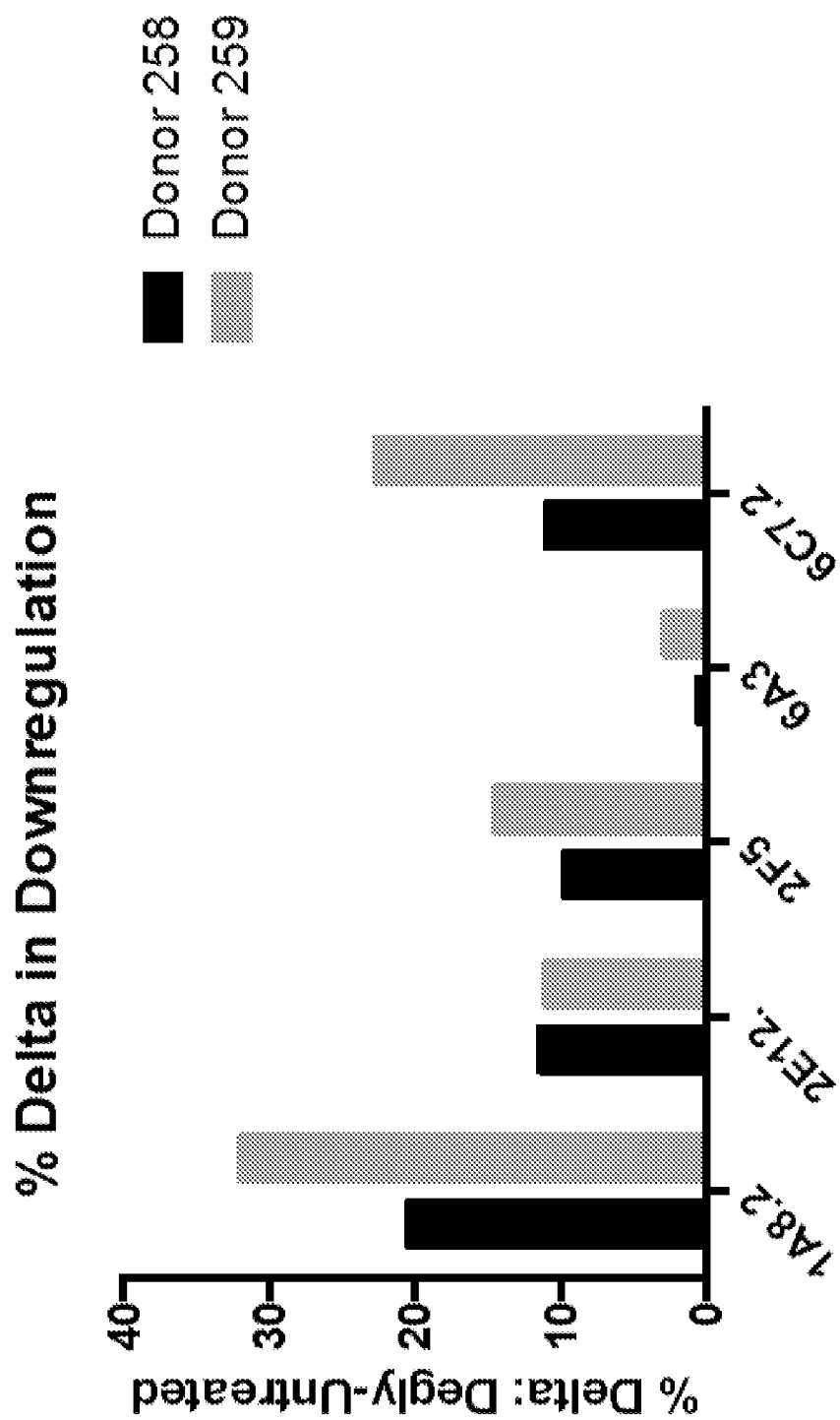
Figure 16I:
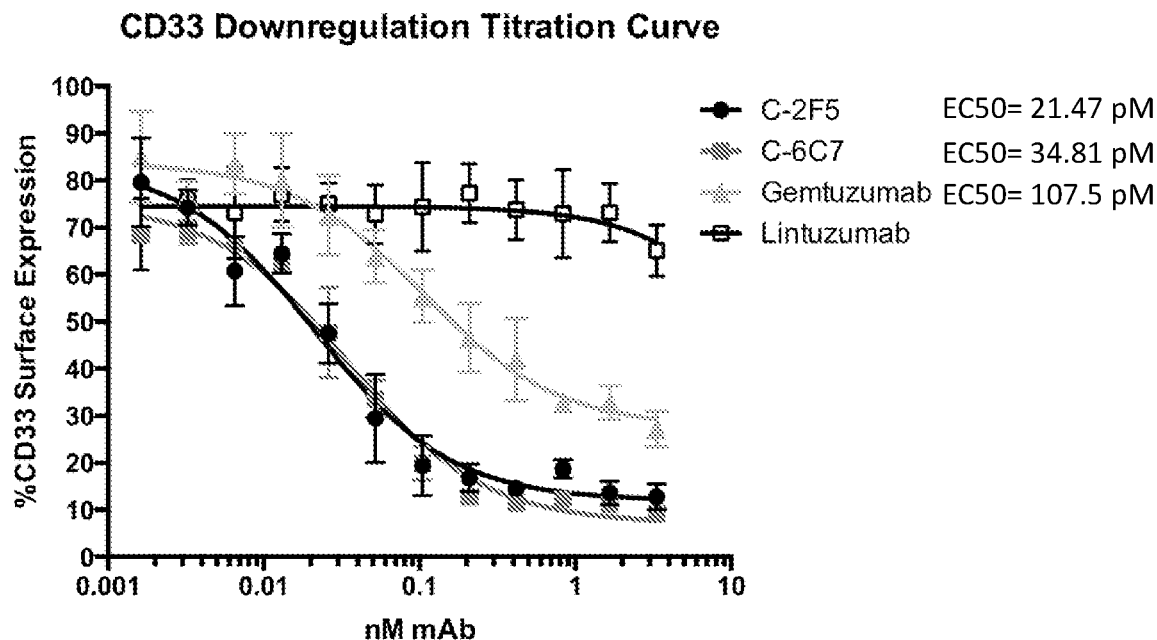
Figure 16J:
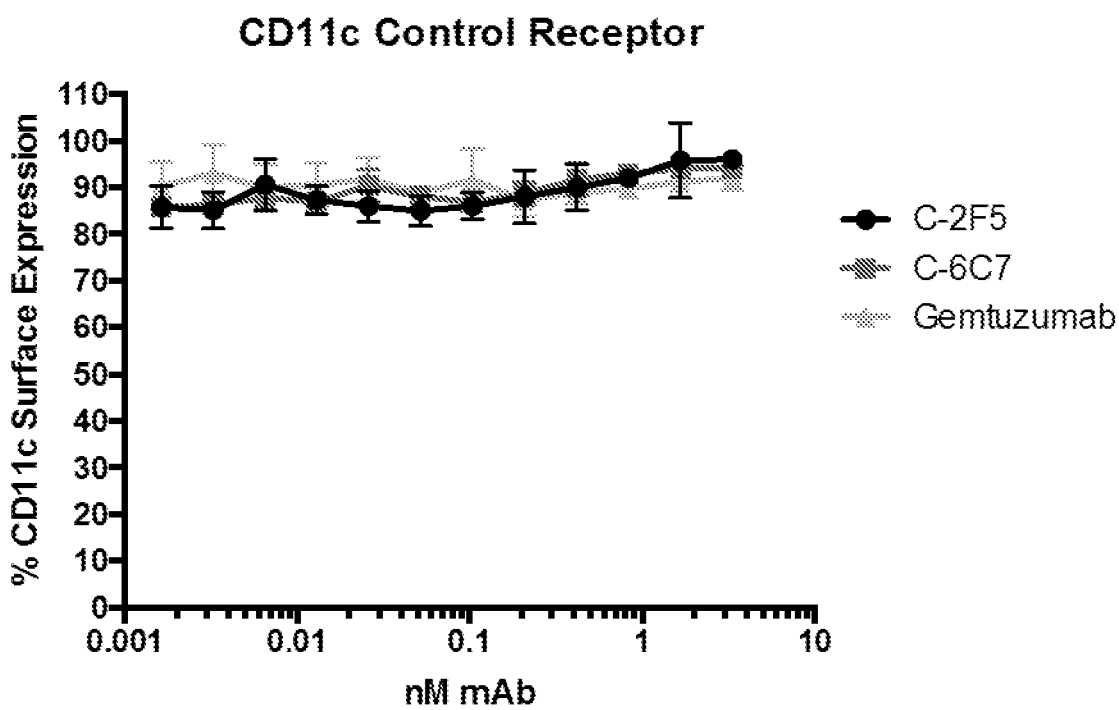

Additionally, in vitro surface CD33 downregulation studies were performed in which CD33 antibodies 2F5, 6C7, gemtuzumab, and lintuzumab were titrated 2-fold for a 12-point curve (FIG. 16I). A similar titration curve was performed for the control receptor CD11c (FIG. 16J). Half-maximal effective concentration ($EC_{50}$) calculations were then performed as described in Example 1. As shown in FIG. 16J, the cell surface expression of the control receptor CD11c was not modulated with any of the antibodies. The results shown that CD33 antibody 2F5 reduces cell surface expression of CD33 with an $EC_{50}$ of 21.47 pM, CD33 antibody 6C7 reduces cell surface expression of CD33 with an $EC_{50}$ of 34.81 pM, and commercial antibody gemtuzumab reduces cell surface expression of CD33 with an $EC_{50}$ of 107.5 pM (FIG. 16I). The results indicate that antibodies 2F5 and 6C7 are more potent and robust than commercial antibodies gemtuzumab or lintuzumab at reducing cell surface expression of CD33 at most concentrations tested (FIG. 16I).

In Vivo Expression of CD33

To test the ability of CD33 antibodies to reduce cell surface level of CD33 in vivo, humanized NSGS mice (hu-NSGS) were utilized. Hu-NSGS mice (also called NOD-scid IL2Rgnull-3/GM/SF) are transgenic NSG mice expressing human IL-3, human CSF2, and human KITL transgenes under the control of a CMV promoter. Hu-NSGS mice were also been engrafted with human CD34+ hematopoietic stem cells. Female Hu-NSGS mice were purchased from Jax and utilized 15 weeks after engraftment with human cells. Mice received an intraperitoneal injection of 40 mg/Kg anti-CD33 antibody 2F5 or isotype control mouse IgG1 antibody (clone MOPC-21) at day 0. At day −7, 1, 3, and 7 blood samples were drawn from mice into heparin and processed for FACS analysis. Briefly, blood samples were first incubated for 5 minutes in ice-cold ACK lysis buffer to lyse red blood cells and then washed extensively with cold PBS. This procedure was repeated twice. Cells were then incubated in FACS buffer (PBS+2% FBS, 2 mM EDTA) in the presence of anti-human-CD45-Pe-Cy7, anti-mouse-CD45-APC-Cy7, anti-human-CD3-PerCP-Cy5.5, anti-human-CD14-FITC, anti-human-CD11c-PB, anti-CD33-PE, anti-Siglec-9-APC, and a viability die (Life Technologies, Cat #L34957) for 30 min. on ice in the presence of Fc block solution, then washed twice with cold FACS buffer. 4% PFA-fixed samples were then acquired. Data were acquired on a BD FACS CANTO™ II cytometer (Becton Dickinson) and analyzed with FlowJo software. The level of expression of CD33 and Siglec 9 was determined in a hCD45+, hCD14+ cell population.

Figures 16K, 16L:
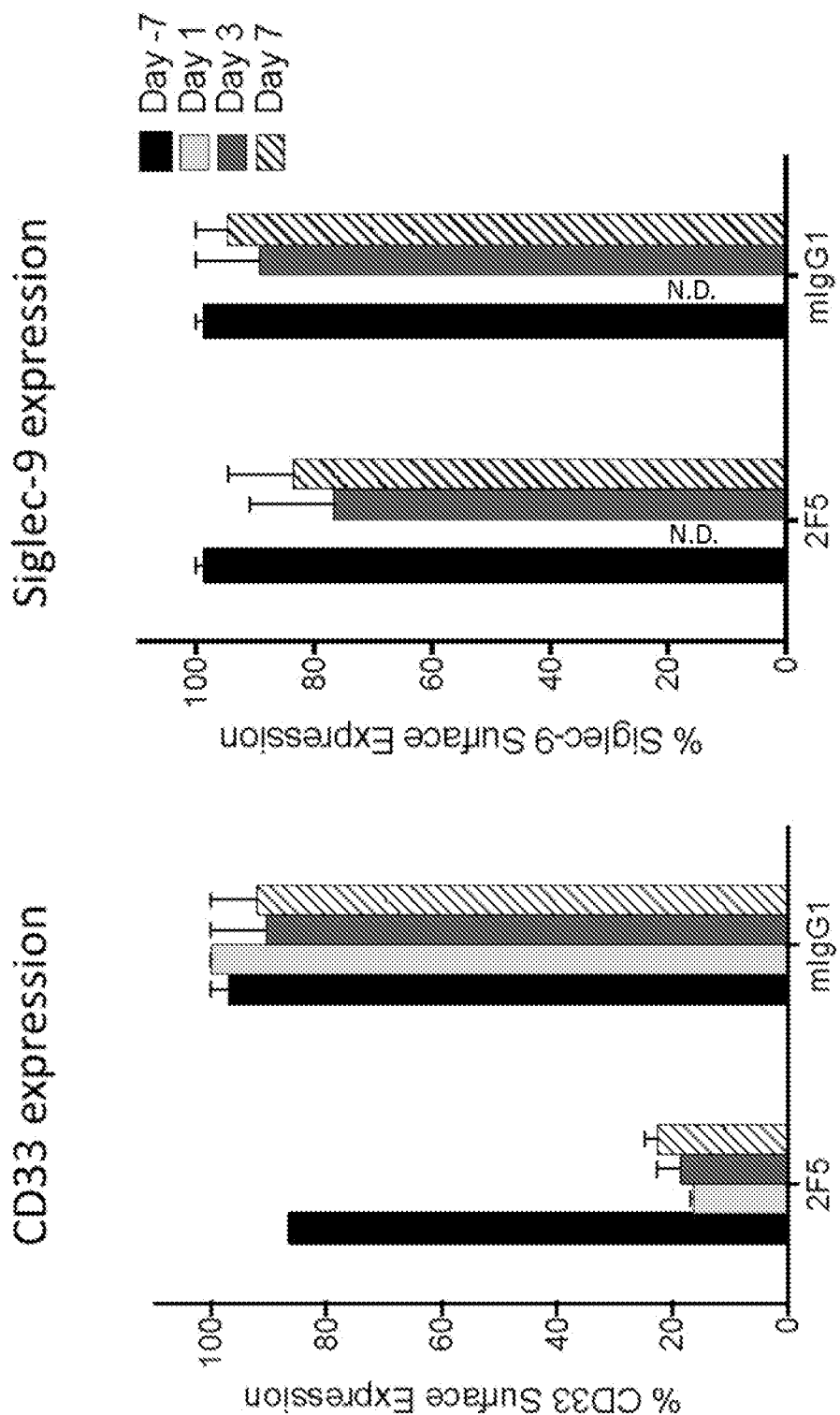
FIG. 16K shows in vivo reduction in cell surface levels of CD33 following antibody treatment in vivo.
FIG. 16L shows expression of unrelated receptor Siglec-9. Siglec-9 was used as a control. Cell surface levels of Siglec-9 were unchanged following antibody treatment in vivo.

As shown in FIGS. 16K and 16L, treatment with the anti-CD33 antibody 2F5 was able to decrease cell surface levels of CD33 in cells of peripheral blood of the treated hu-NSGS mice, when compared to control antibody treatment and pre-treatment levels. CD33 expression was decreased by ~80% as early as 1 day post antibody treatment and remained low until the last time point tested (7 days after treatment). As a comparison, cell surface expression of the unrelated surface receptor Siglec-9 remained unchanged compared to pre-treatment levels.

Figure 16M:
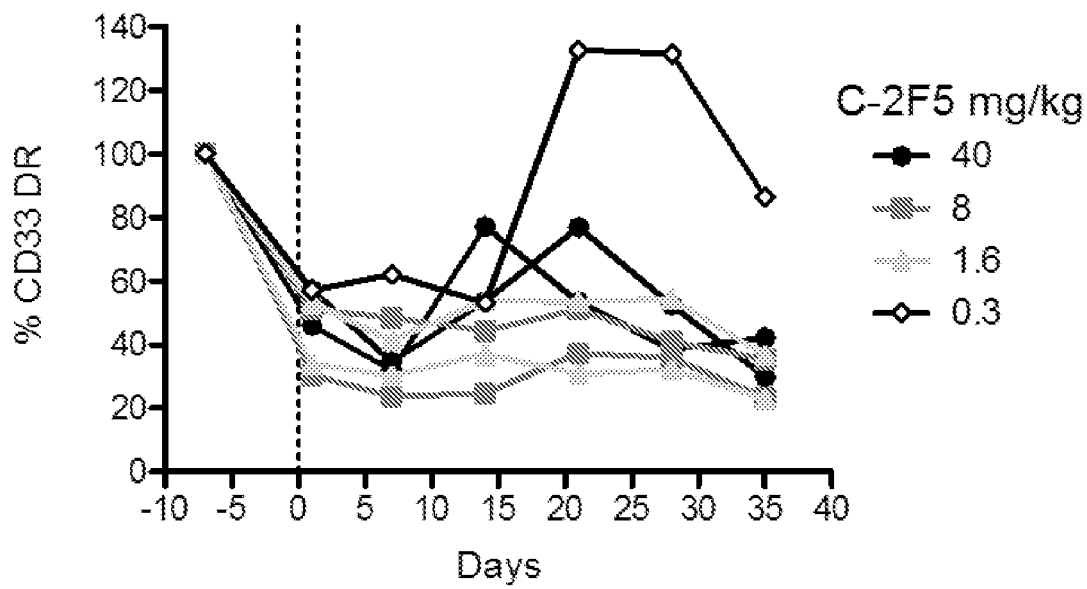
FIG. 16M shows in vivo reduction in cell surface levels of CD33 following in vivo treatment with 40 mg/kg, 8.0 mg/kg, 1.6 mg/kg, or 0.3 mg/kg CD33 antibody 2F5.
Figure 16N:
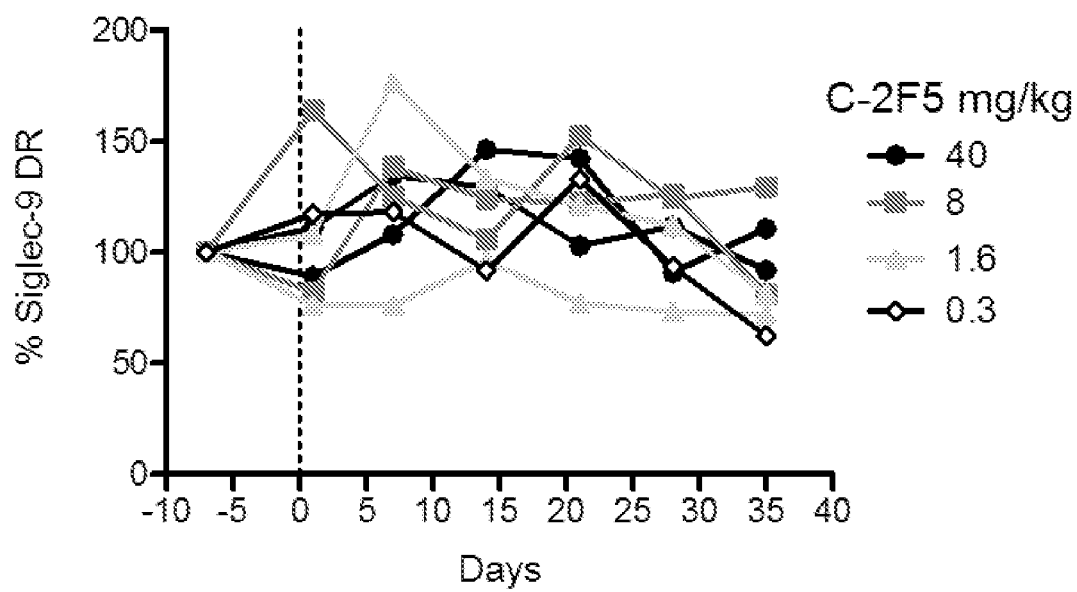
FIG. 16N shows in vivo cell surface levels of control receptor (Siglec-9) following in vivo treatment with 40 mg/kg, 8.0 mg/kg, 1.6 mg/kg, or 0.3 mg/kg CD33 antibody 2F5.

Additionally, in vivo surface CD33 downregulation studies were performed in which CD33 antibody 2F5 was titrated to determine the half-maximal effective concentration ($EC_{50}$) for reducing cell surface expression on peripheral monocytes. NOG humanized mice from Taconic were injected with a single intraperitoneal injection of either 40 mg/kg, 8.0 mg/kg, 1.6 mg/kg, or 0.3 mg/kg of the CD33 antibody 2F5. Cell surface levels of CD33 and control receptor Siglec-9 were measured by FACS at the following timepoints: 7 days prior to treatment (day −7), day 1 post treatment, and weekly thereafter until day 35. Cell surface levels of CD33 and Siglec-9 were assessed on peripheral human $CD45^+$ $CD14^+$ monocytes by FACS. MFI of day −7 was used to set a baseline of 100% cell surface expression to calculate % reduction. As shown in FIG. 16M, antibody 2F5 persistently reduced cell surface levels of CD33 over time in vivo in humanized mice on peripheral monocytes at all concentrations of antibody tested. A 50% reduction in cell surface levels of CD33, but not of control receptor, was observed at antibody concentrations of 40 mg/kg, 8.0 mg/kg, and 1.6 mg/kg (FIGS. 16M and 16N).

Example 4: CD33 Antibodies Compete with CD33 Ligand for Binding to Human CD33

The purpose of the following Example was to test whether anti-CD33 antibodies recognize the ligand-binding site on CD33 and compete with ligand binding on CD33 receptors.

To determine which antibodies compete with ligand binding to CD33, a red blood cell (RBC) solid adhesion assay was carried out in accordance with standard protocols (Kelm et al., *Current Biology*, 1994). Red blood cells are highly decorated with glycoproteins containing sialic acids; therefore, the ability of an antibody to block RBC binding to immobilized CD33 can be used to determine ligand interference. Briefly, 5 µg/ml CD33-Fc was coated overnight at RT in 96-well Immunolon plates, then washed with PBS, blocked for one hour with binding buffer (PBS containing %0.25 BSA 1 mM $CaCl_2$)). CD33 antibodies (0.5 µg/ml or 1.0 µg/ml) or Fabs (25 µg/ml) were bound for one hour at RT with gentle rocking. After removal of unbound antibody, red blood cells were added to each well at a concentration of $3.0 \times 10^6$ cells per ml and incubated at RT for one hour. Unbound RBCs were then carefully washed off 3× with PBS, and water was added to each well for hypotonic lysis of bound RBCs. The plate was transferred to −80° C. for 10 minutes, followed by 37° C. for 15 minutes. Bound RBCs were detected by peroxidase activity, followed by 2N sulfuric acid to stop the reaction. Signal was detected at 450 nM. Data was calculated as a percent of RBC binding to plate bound CD33-Fc in the absence of antibody.

The results of the ligand competition assay are depicted in Table 9. In Table 9, "Isotype" refers to an isotype mIgG1 control antibody.

TABLE 9

CD33 antibodies compete with ligand binding

| Antibody | Percent RBC Binding to CD33 1.0 µg/ml |
| --- | --- |
| 1A8 | 10.0 |
| 2B4 | 77.7 |
| 2E12 | 9.2 |
| 2F5 | 11.5 |
| 3A12 | 12.3 |
| 6A3 | 10.8 |
| 6C7 | 10.8 |
| Isotype | 83.8 |

As shown in Table 9, antibodies 1A8, 2E12, 2F5, 3A12, 6A3, and 6C7, and to a lesser extent 2B4, were able to block RBC binding to CD33, thus indicating competitive binding of the antibodies to the ligand-binding site on CD33, and their ability to inhibit the interaction between CD33 and one or more CD33 ligands (i.e., to block ligand binding to CD33).

Example 5: Summary of CD33 Antibody Functional Studies

Table 10 summarizes results of the cell surface expression and ligand binding studies described in Examples 3 and 4 above. As indicated in Table 10, there was one general class of CD33 antibodies. This class of antibodies decreases cell surface level of CD33 and inhibits the interaction between CD33 and one or more CD33 ligands.

Antibodies in the class of antibodies that decrease cell surface level of CD33 and inhibit the interaction between CD33 and one or more CD33 ligands include: 1A8, 2B4, 2E12, 2E12.1, 2F5, 2F5.1, 3A12a, 3A12b, 6A3a, 6A3b, 6C7a, 6C7b, and 6C7.2.

TABLE 10

CD33 antibody functional studies

| Antibody | Decreases cell surface CD33 | Inhibits CD33 ligand binding |
| --- | --- | --- |
| 1A8 | +++ | +++ |
| 2B4 | + | + |
| 2E12 | +++ | +++ |
| 2F5 | +++ | +++ |
| 3A12 | +++ | +++ |
| 6A3 | +++ | +++ |
| 6C7 | +++ | +++ |

Example 6: Ligand Binding to CD33 on Dendritic Cells Inhibits T Cell Proliferation and Phagocytosis Human dendritic cells (DCs) were differentiated from peripheral blood monocytes with GM-CSF and IL-4 and cultured for 5 days Immature (suspension) DCs were harvested and plated at a density of 200,000 cells per ml in a 12 well dish. DCs were activated with a cytokine cocktail of TNFa (50 µg/ml), IL-1β (50 µg/ml), IL-6 (150 ng/ml), and Prostaglandin E2 (1 µg/ml) for 24 hours. Dendritic cell maturation was determined by flow cytometry with commercially available antibodies for LIN, CD11c, HLA-DR, CD86, and CD83 (BD Biosciences) Immediately prior to co-culture with allogenic isolated T cells, activated DCs were sialidase treated, or left untreated, for 2 hours at 37° C. with 100 mU/ml neuraminidase from *Vibrio cholera* in serum free media. Enzymatic activity was quenched by addition of serum-containing media, cells pelleted and resuspended in complete media. Sialidased activated, untreated activated, or unactivated DCs were co-cultured at a ratio of 1:10 with allogenic CFSE labeled T cells. CD3/CD28 Dynal beads were added to T cells alone as a positive control. Five days later T cell proliferation was measured by CFSE dilution on a BD FACS Canto.

Figure 7:
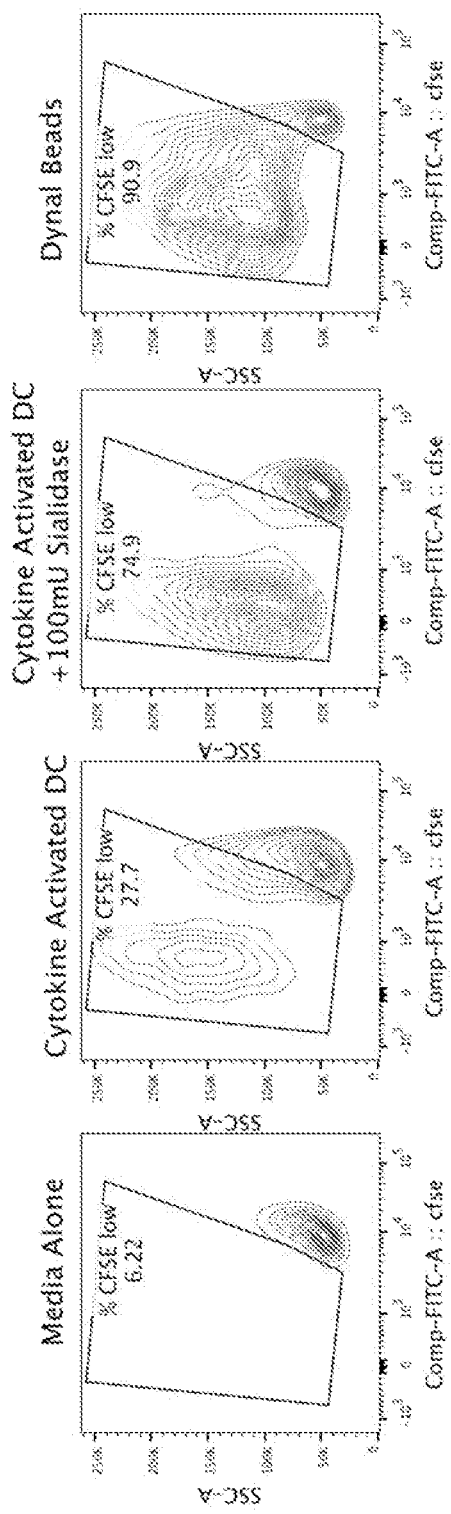
FIG. 7 depicts FACS analysis showing that sialic acid CD3 ligands on dendritic cells restrict T cell proliferation during mixed lymphocyte reaction with human primary cells.
Figure 8:
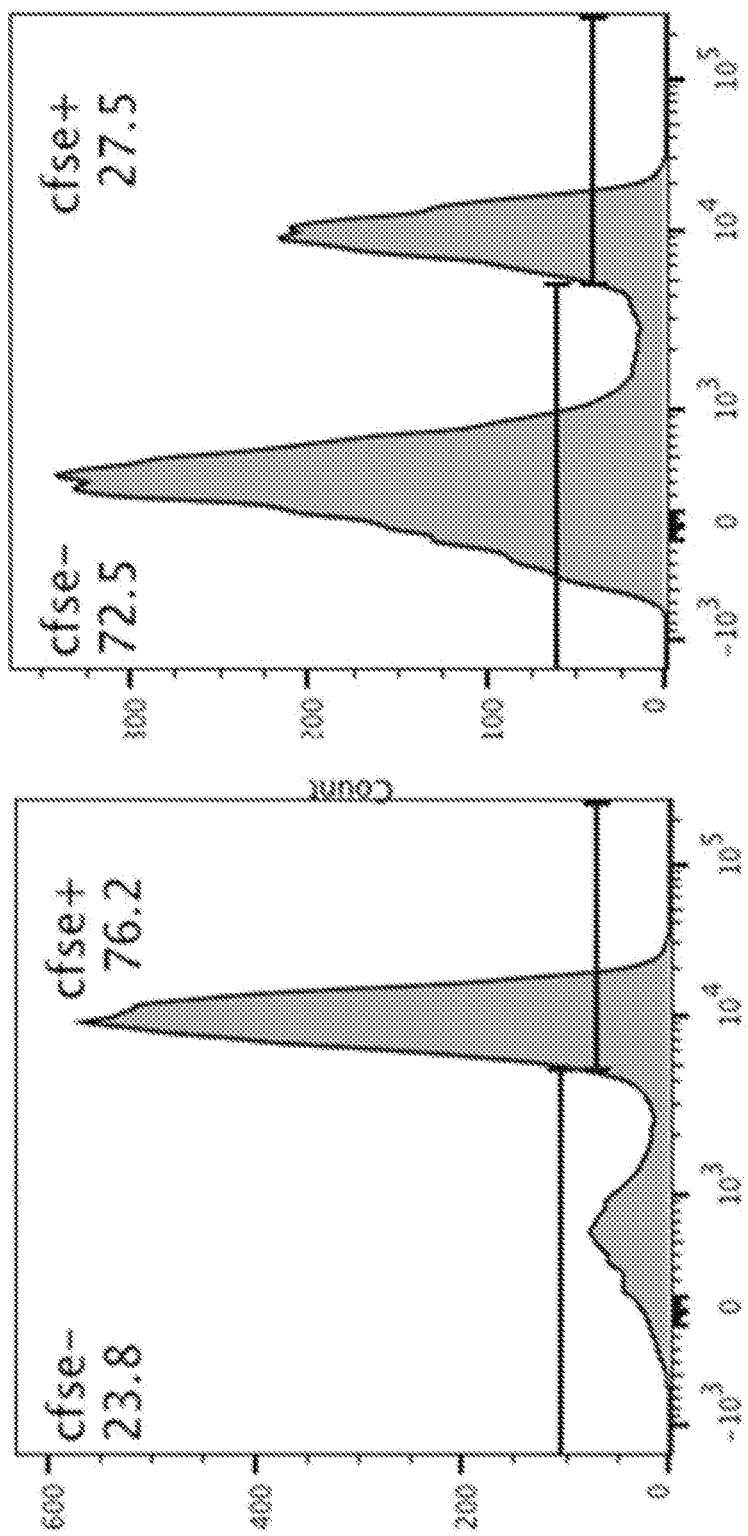
FIG. 8 depicts results showing that sialic acid CD33 ligands on dendritic cells restrict T cell proliferation during mixed lymphocyte reaction.

FIGS. 7 and 8 show that sialic acids on dendritic cells restrict T cell proliferation during mixed lymphocyte reaction (MLR). FIG. 8 shows that DCs that normally express inhibitory ligands induce low levels of T cell proliferation (left panel), while the removal of the inhibitory ligands on DCs increases T cell proliferation (right panel).

As shown in FIGS. 7 and 8, enzymatic removal of sialic acids from activated DCs increased T cell proliferation when compared to untreated activated DCs. These results indicate that sialic acids present on DCs act on T cells in a suppressive manner to restrict T cell proliferation when co-cultured with allogenic DCs. These results indicate that antibodies that block CD33 on T cells or dendritic cells enhance T cell and/or dendritic cell functionality. CD3/CD28 Dynal beads were used as a positive control. Furthermore, these results indicate that blocking sialic acid interactions with DCs or any other cellular or biological source may increase T cell function.

Example 7: Inflammatory Conditions Induce CD33 Expression in Myeloid Cells

Human dendritic cells (DCs) were differentiated from peripheral blood monocytes with GM-CSF and IL-4 and cultured for 5 days Immature human DCs were harvested on day 5 and co-cultured with sterile-filtered supernatant from B16, Lewis lung, MC38 tumor supernatant or 10 ng/ml LPS. 24 hours later CD33 expression was determined by flow cytometry with a directly conjugated CD33-PE antibody. Sialic acid ligand expression was assessed by incubation for 30 minutes on ice with 50 μg/ml soluble CD33 fused to human IgG1-Fc, IgG1-Fc alone was used a negative control in the presence of human Fc block. Binding of the soluble receptor to sialic acids on cells was detected after a wash step and incubation for 30 minutes on ice with anti-human secondary conjugated to PE. Flow cytometry analysis was performed on a BD FACS Canto.

To elicit primary macrophages, human monocytes from peripheral human blood samples are isolated and either used directly or differentiated into macrophages with 50 μg/ml M-CSF for 5 days. In order to determine the role of CD33 in inflammatory cytokine production, human macrophages are cultured with various inflammatory mediators, and cytokine levels are measured in the culture supernatants. To generate human macrophages, monocytes from peripheral human blood samples are isolated and either used directly or differentiated into macrophages with 50 μg/ml M-CSF or dendritic cells with 100 μg/ml GM-CSF and 100 μg/ml IL-4 for 5 days. Cells are cultured for 5 days, and adherent cells were detached with 1 mM EDTA in PBS. Cells are plated on 96-well plates at $10^5$ cells/well and allowed to adhere for 4 h at 37° C. Cells are then stimulated with TLR agonists LPS (*Salmonella abortus equi*) or zymosan (*Saccharomyces cerevisiae*) at concentrations ranging from 0.01-100 ng/ml (LPS) or 0.01-100 μg/ml (zymosan). Alternatively, macrophages are cultured in the presence of 10 ng/ml of the cytokine IL-4 or 50 ng/ml of IFN-g. Cell culture supernatant are collected 24 or 48 hours after stimulation and the levels of TNFa, IL-6, IL-10, and MCP-1 cytokines are measured by using Cytometric Bead Array Inflammation Kit (BD) according to manufacturer's protocol. Macrophages stimulated with the inflammatory mediators LPS or zymosan are expected to secrete more inflammatory cytokines TNFa, IL-6, IL-10, and MCP-1 when treated with CD33 antagonistic antibodies or with enzymes that remove the inhibitory glycol ligands.

Figure 9A:
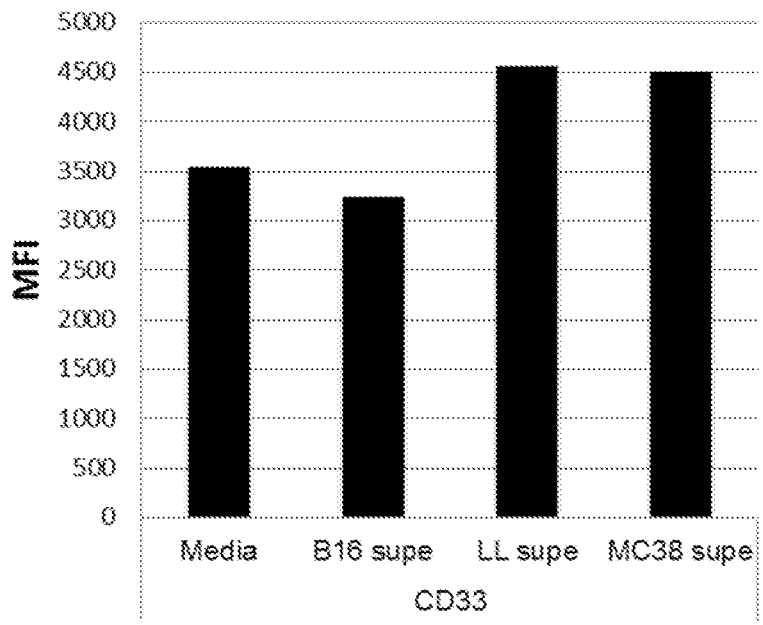
FIG. 9A-9F depict results showing increased CD33 and CD33 ligand expression on human myeloid cells induced by various stimuli.
Figure 9B:
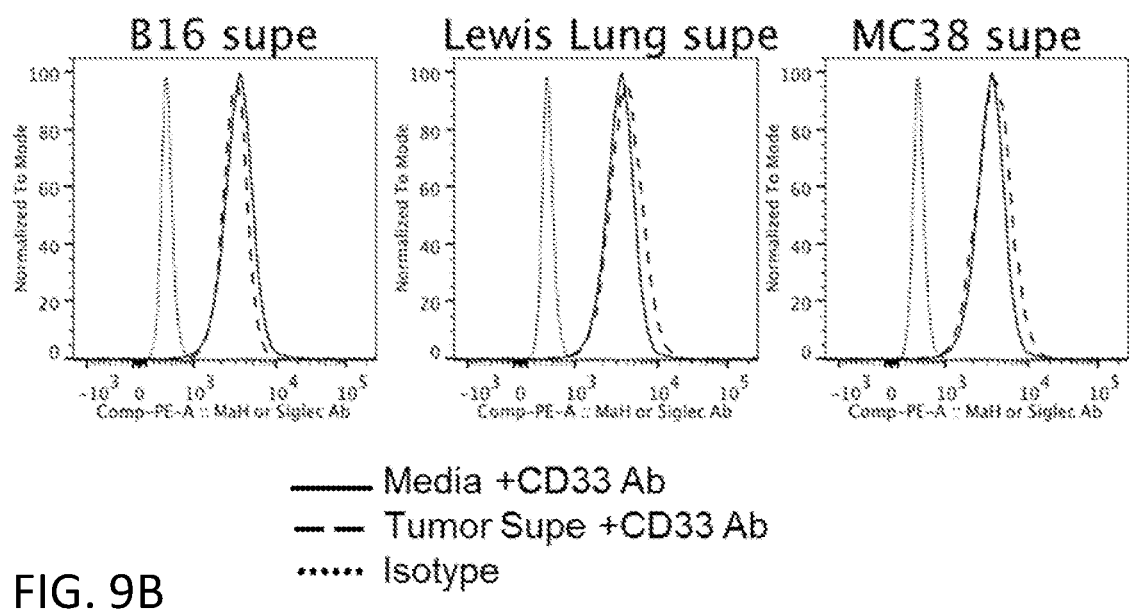
Figure 9C:
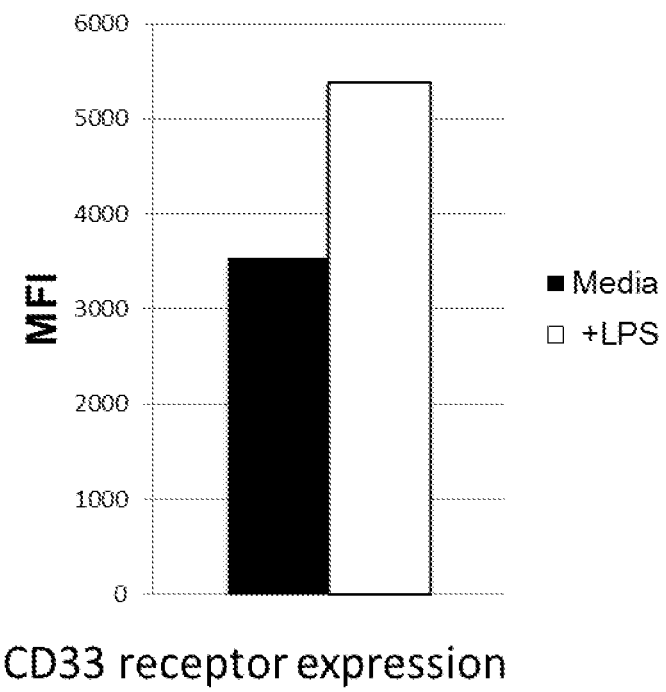
Figure 9D:
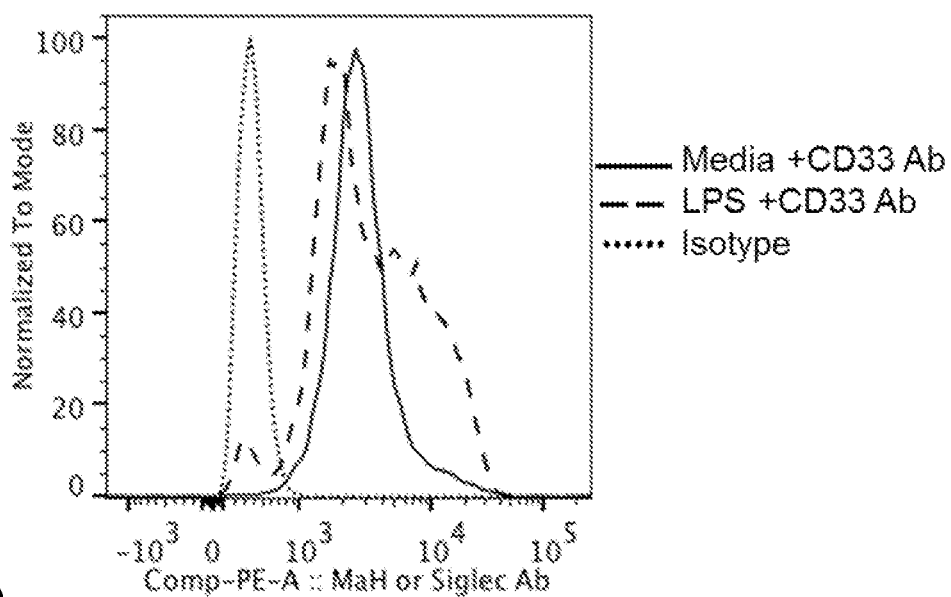
Figure 9E:
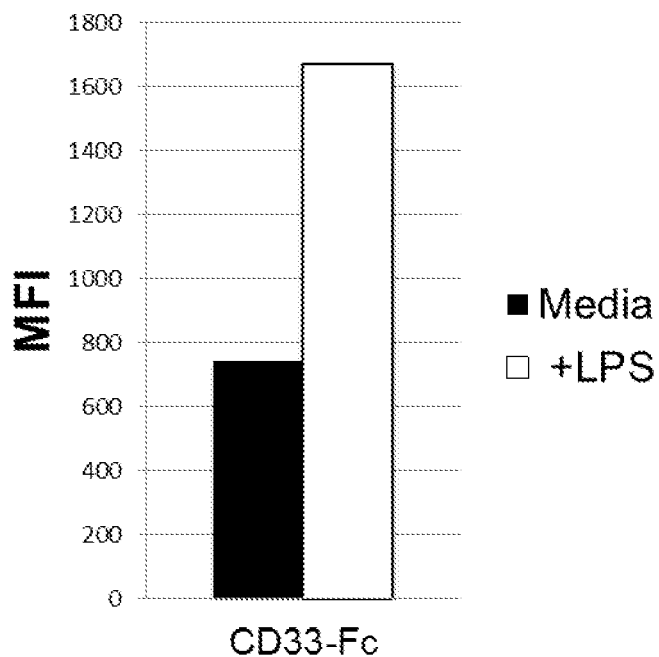
Figure 9F:
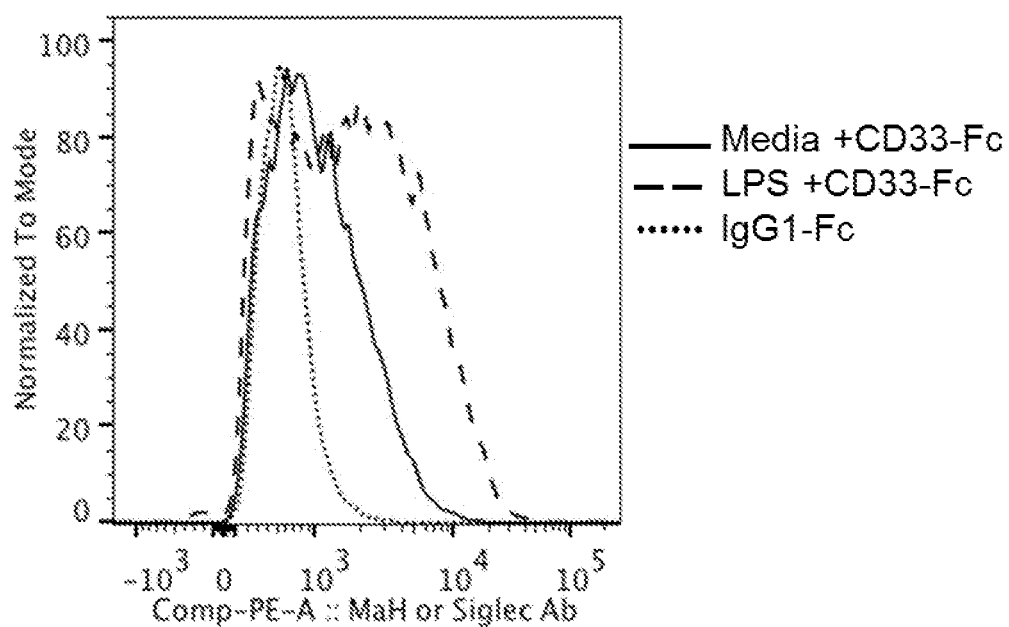

FIGS. 9A and 9B show that CD33 expression is increased on human dendritic cells after exposure to tumor supernatant. FIGS. 9C and 9D show that CD33 expression is increased on human dendritic cells during LPS-induced inflammation. FIGS. 9E and 9F show that LPS-induced inflammation increases expression of sialic acid (a CD33 ligand).

These results indicate that inflammatory conditions and tumor environment lead to upregulation of both CD33 and sialic acid ligands. The results also demonstrate that increased CD33 function can immunosuppress human primary dendritic cells. These results indicate that inhibiting CD33 with downregulating or blocking antibodies may relieve immunosuppressed myeloid-derived or tumor-associated myeloid cells and restore immune function. These results further indicate that antibodies that block CD33 on myeloid cells enhance myeloid cell functionality.

Example 8: Increased *E. coli* Phagocytosis by Dendritic Cells with Sialidase Treatment The purpose of the following Example was to test whether antagonistic anti-CD33 antibodies and/or CD33 bispecific antibodies induce phagocytosis of apoptotic neurons, nerve tissue debris, non-nerve tissue debris, bacteria, other foreign bodies, and disease-causing proteins, such as A beta peptide, alpha synuclain protein, Tau protein, TDP-43 protein, prion protein, huntingtin protein, RAN, translation products antigene, including the DiPeptide Repeats, (DPRs peptides) composed of glycine-alanine (GA), glycine-proline (GP), glycine-arginine (GR), proline-alanine (PA), or proline-arginine (PR) in cells from the myeloid lineage, such as monocytes, dendritic cells macrophages and microglia. The bispecific antibodies may be antibodies that recognize the CD33 antigen and a second antigen that includes, without limitation, CD3, A beta peptide, antigen or an alpha synuclain protein antigene or, Tau protein antigene or, TDP-43 protein antigene or, prion protein antigene or, huntingtin protein antigene, or RAN, translation Products antigene, including the DiPeptide Repeats, (DPRs peptides) composed of glycine-alanine (GA), glycine-proline (GP), glycine-arginine (GR), proline-alanine (PA), or proline-arginine (PR).

Monocytes from peripheral human blood samples were isolated using the RosetteSep™ monocyte isolation antibody cocktail (StemCell Technologies), and differentiated into dendritic cells with GM-CSF and IL-4 (PeproTech) and cultured for 5 days. Cells were plated on culture dishes in RPMI medium (Invitrogen) containing 10% fetal calf serum (Hyclone) and cultured at 37° C. in 5% $CO_2$. Non-adherent cells were collected and used for phagocytosis experiments.

To conduct bacterial phagocytosis assay, dendritic cells were harvested and plated in 96-well flat bottom plates without cytokine for 2 hours. pHrodo-labeled *E. coli* BioParticles were resuspended according to manufacturer's protocol and were treated with 0.2 U/ml or 0.4 U/ml sialidase from Vibro cholera, or PBS alone for 2.5 hours at 37° C. BioParticles were washed, resuspended in RPMI and added 20 μg/well. Dendritic cells and *E. coli* cells were mixed, pelleted, and incubated at 37° C. for 30 minutes. Cytochalasin D was added at 10 μM to control wells. Immediately prior to FACS analysis, cells were transferred to ice and washed 2× in FACS buffer at 4° C. pHrodo-labeled *E. coli* phagocytosis was detected in the PE channel by flow cytometry on a BD FACS Canto.

Figure 10:
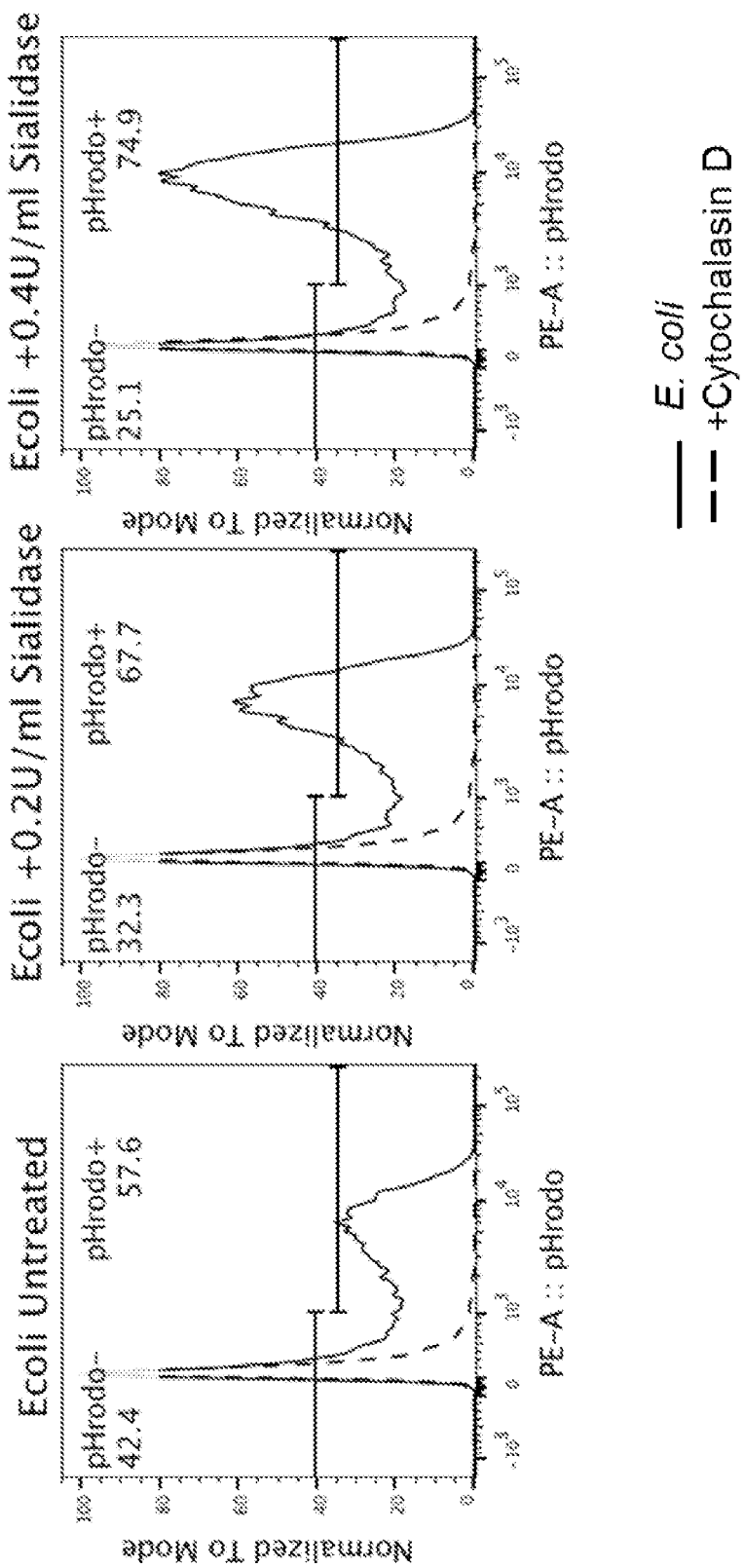
FIG. 10 depicts results showing that sialidase treatment to remove CD33 ligands from *E. coli* increases phagocytosis by human primary dendritic cells.

FIG. 10 shows that sialidase treatment increased dendritic cell-mediated phagocytosis of *E. coli*. These results indicate that antagonistic anti-CD33 antibodies and/or CD33 bispecific antibodies that, for example, decrease cell surface expression of CD33 and/or inhibit the binding of one or more CD33 ligands to CD33 can also be used to induce or otherwise increase phagocytosis.

Figure 11A:
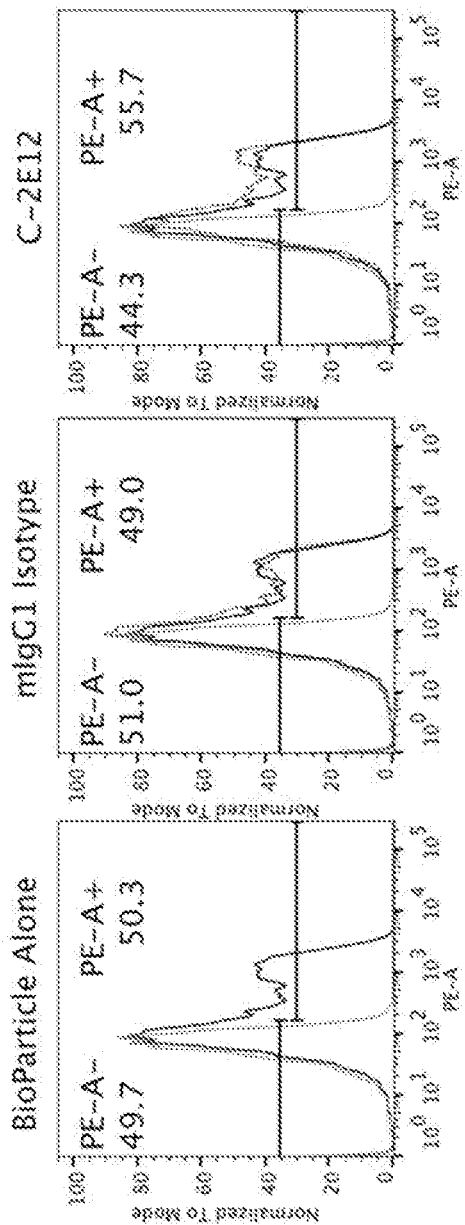
FIG. 11A and FIG. 11B depict results showing that anti-CD33 antibodies lead to increased phagocytosis of *E. coli* by primary human macrophages.
Figure 11B:
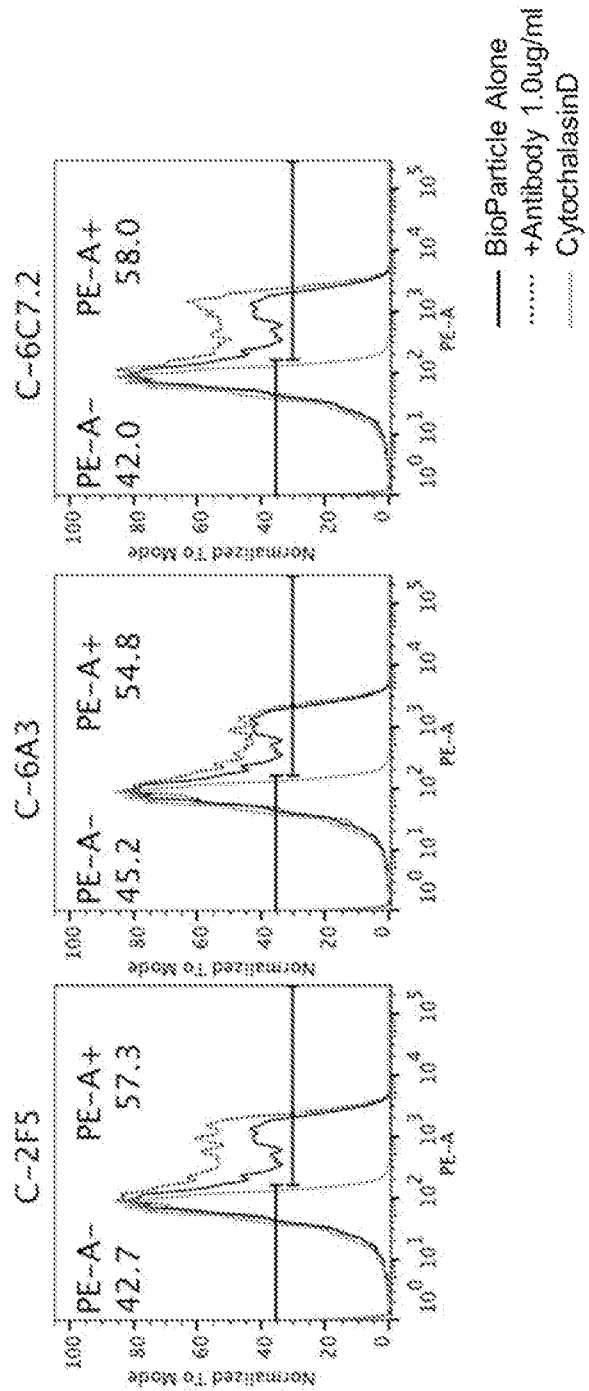

FIGS. 11A and 11B show that CD33 antibodies 2F5 and 6C7 increase macrophage phagocytosis of *E. coli*. These results indicate that CD33 antibodies that downregulate cell surface levels of CD33 can enable macrophages to become more phagocytic, and increase uptake of bacterial substrates in the presence of CD33 antibody, but not an isotype control. The results also indicate that macrophages increase their phagocytic functions due to reduced CD33 expression and therefore reduced CD33 functions.

Example 9: Increased Expression of CD33 Ligand in Brain Sections of Alzheimer's Disease Patients Sialic acid ligand expression was detected in the brains of normal and Alzheimer's disease (AD) patients by immunohistochemistry with biotinylated CD33-Fc (R&D) and IgG1-Fc as a negative control. The CD33-Fc and control IgG-Fc proteins were biotinylated with the EZ-Link Sulfo-NHS-Biotin (Thermo Scientific) according to manufacturer's instructions. The IHC procedure, with the exception of the overnight incubation, was performed on a shaker. Samples were incubated for 15 minutes in 10% MeOH, 3%

H$_2$O$_2$ in PBS, followed by 3 washes in PBS with 4% serum. Next, samples were incubated for 30 minutes in 0.2% triton-X, 4% serum, 0.019% L-lysine in PBS, followed by an hour in primary antibody then overnight at 4C in PBS with 4% serum. The next day samples were placed on a shaker for one hour followed by 3 washes, then samples were incubated for one hour in ABC buffer and washed 3 times. Samples were developed with a Vector DAB peroxidase kit, washed 3 times and dehydrated and imaged with a Nikon 90i microscope with color camera, magnification of 200×. The quantification was performed using Nikon Elements BR image analysis software.

Figure 12A:
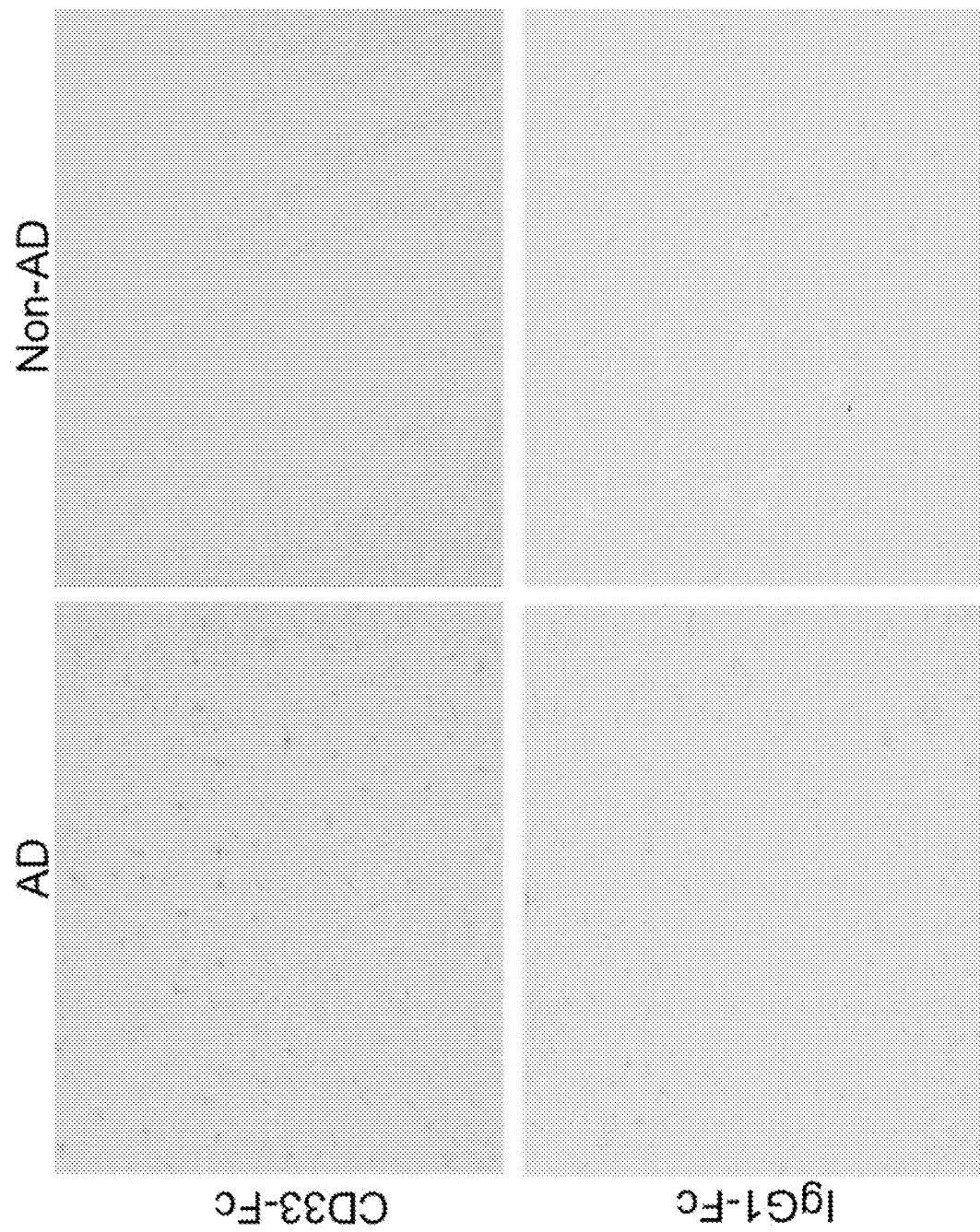
FIG. 12A and FIG. 12B depict CD33 ligand expression in brain sections from an Alzheimer's disease brain (AD) and a healthy brain (non-AD).
Figure 12B:
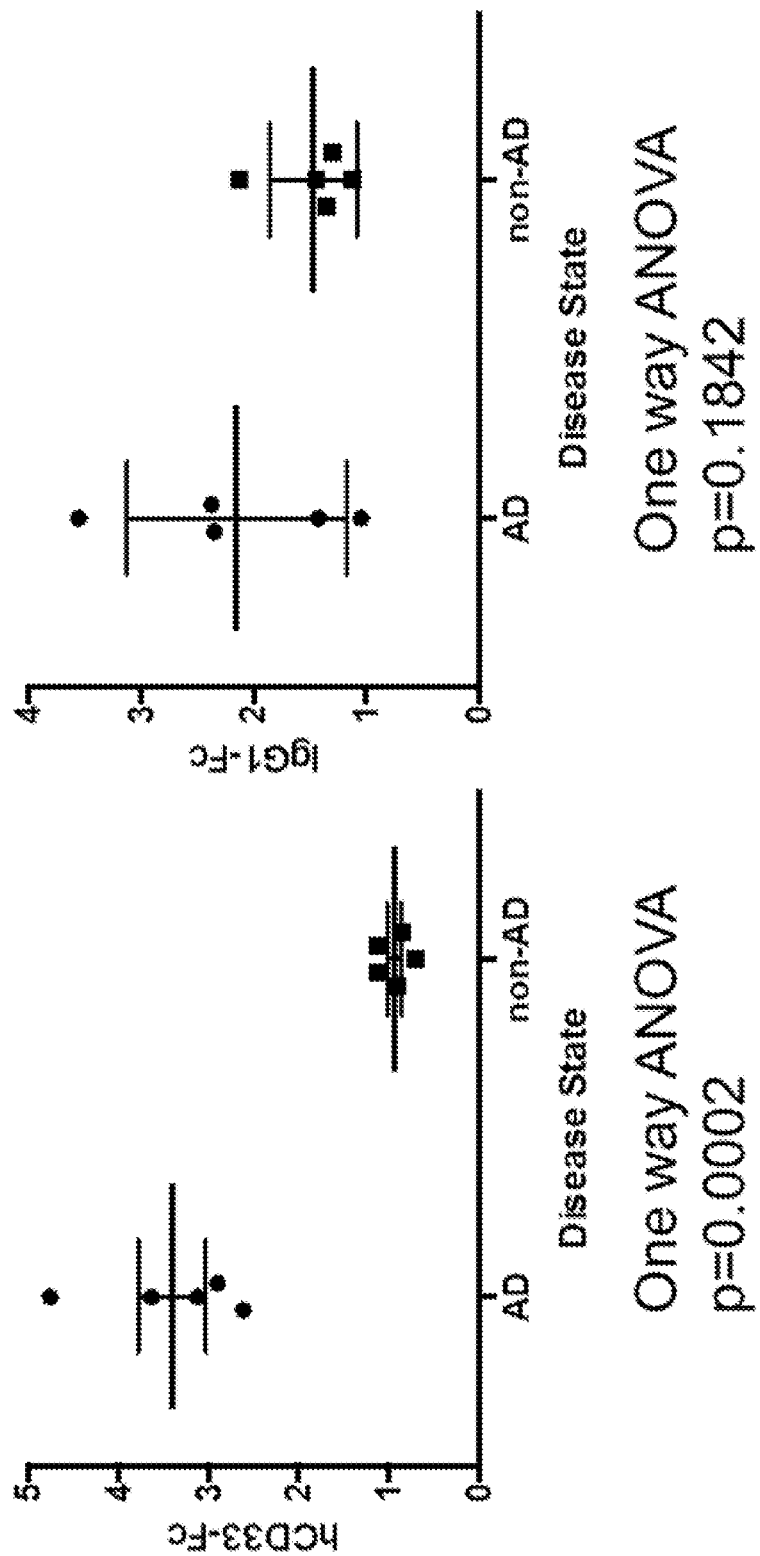
Figure 13A:
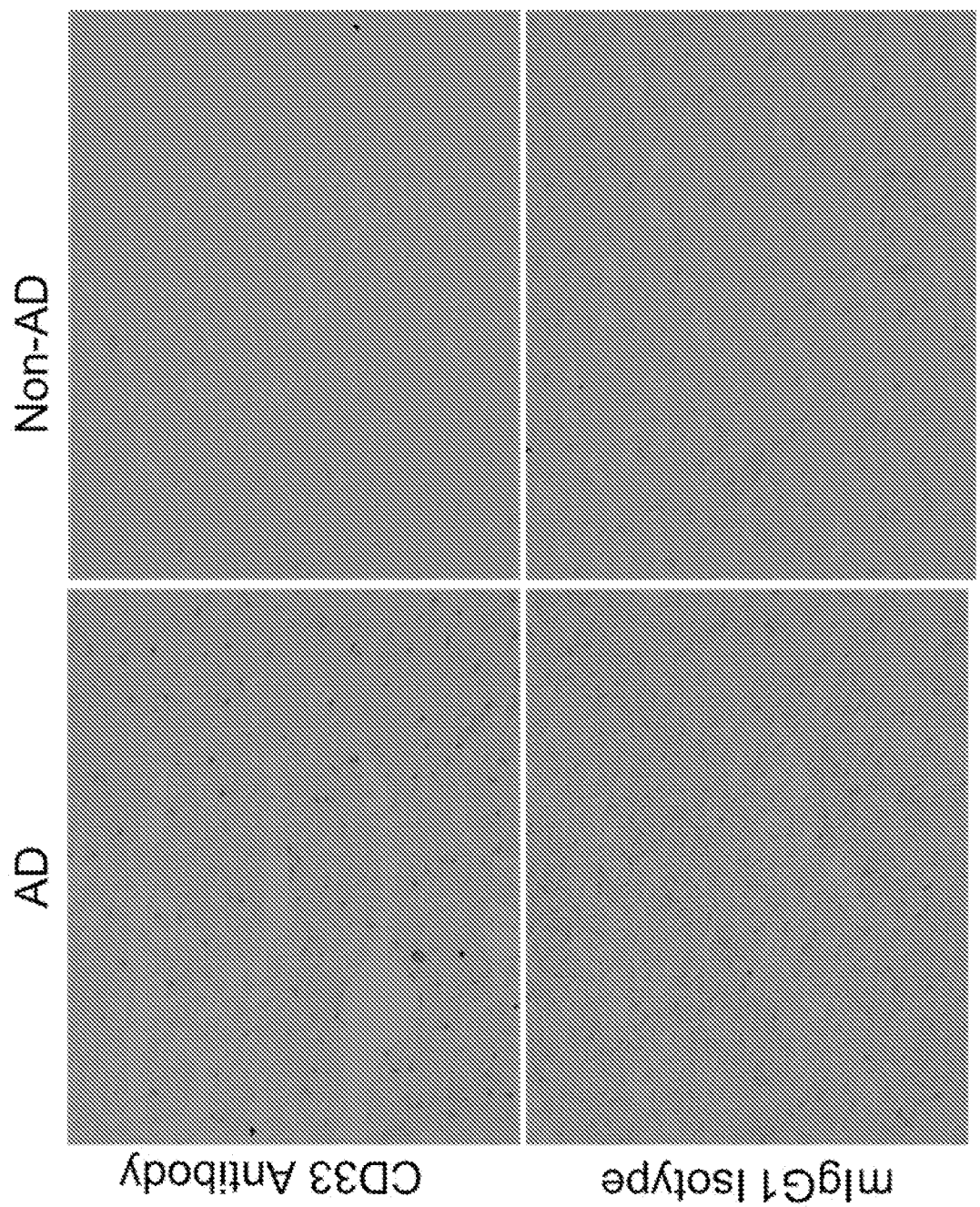
FIG. 13A and FIG. 13B depict CD33 receptor expression in brain sections from an Alzheimer's disease brain (AD) and a healthy brain (non-AD).
Figure 13B:
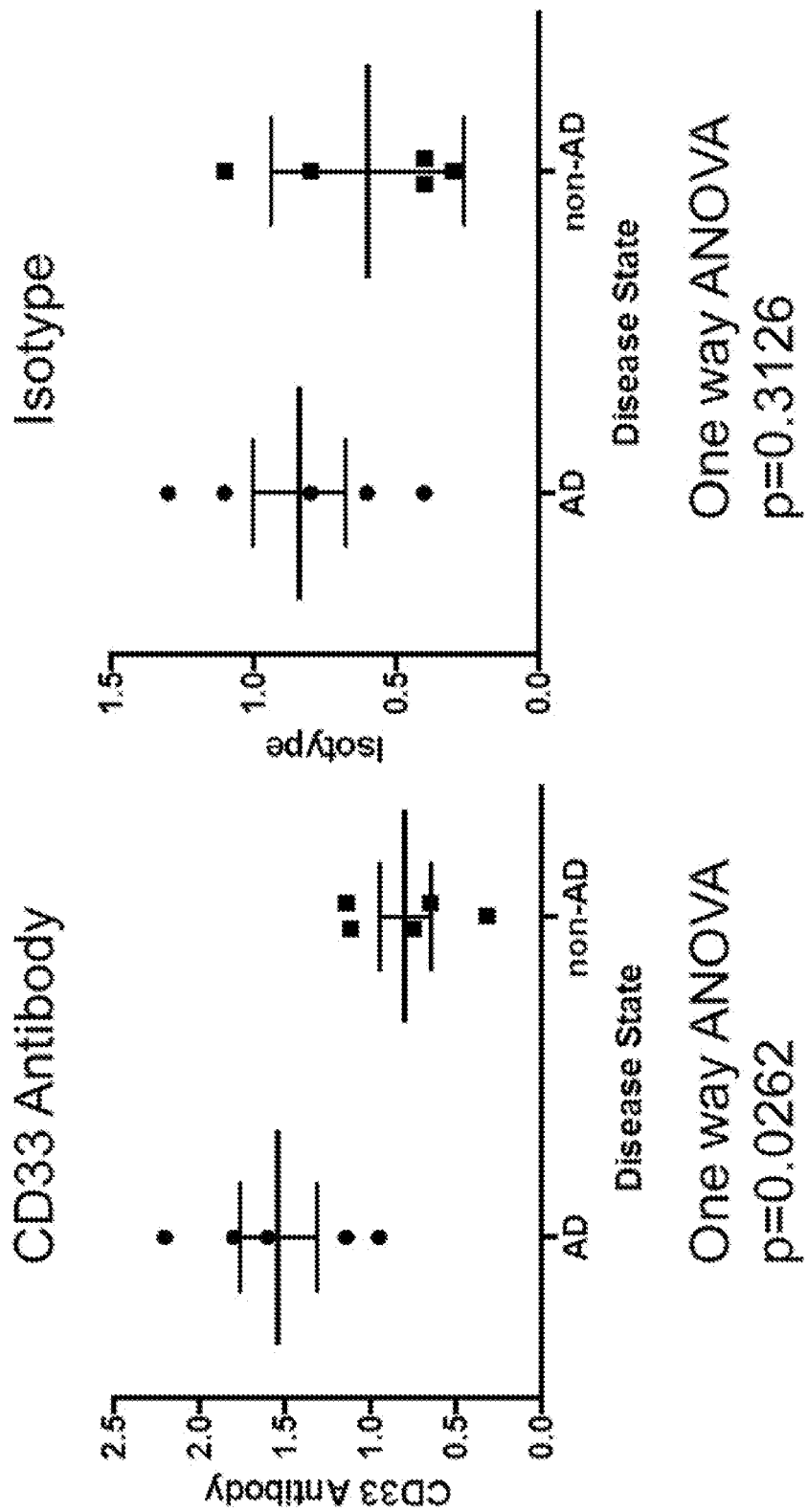

FIGS. 12A and 12B show that sialic acid CD33 ligands are upregulated in brain sections from an AD patient. Data from 5 AD and 5 non-AD human brains show a statistically significant increase in expression of CD33 sialic acid ligands by one way ANOVA, p=0.0002, compared to a control reagent, IgG1-Fc, p=0.1842 (FIG. 12B). FIGS. 13A and 13B show that CD33 expression is increased in brain sections from an AD patient, compared to a normal patient (non-AD). Data in FIG. 13B is from 5 AD and 5 non-AD human brains.

Genetic data identified SNPs associated with an increase in full length CD33 expression increases AD risk. The results depicted in FIGS. 12 and 13 indicate that in addition to CD33 upregulation in some AD brains, sialic acid ligands for CD33 are also increased in AD brains.

These results indicate that antibodies that remove CD33 from the cell surface or block increased ligand interactions may relieve inhibitory CD33-dependent signaling on microglia or other myeloid cells in the brain and restore normal functions to these cells, with beneficial effects for Alzheimer's disease.

Example 10: Increased Expression of CD33 and CD33 Ligand in Cancer Cells and Effect of CD33 Ablation In Vitro Studies Sialic acid ligand expression was assessed on B16, Lewis lung, and MC38 colon carcinoma cells by incubation for 30 minutes on ice with 50 µg/ml soluble CD33 receptor fused to human IgG1-Fc (R&D), IgG1-Fc alone was used a negative control in the presence of human Fc block. Binding of the soluble receptor to sialic acids on cells was detected after a wash step and incubation for 30 minutes on ice with anti-human secondary conjugated to PE. Flow cytometry analysis was performed on a BD FACS Canto.

Figure 14A:
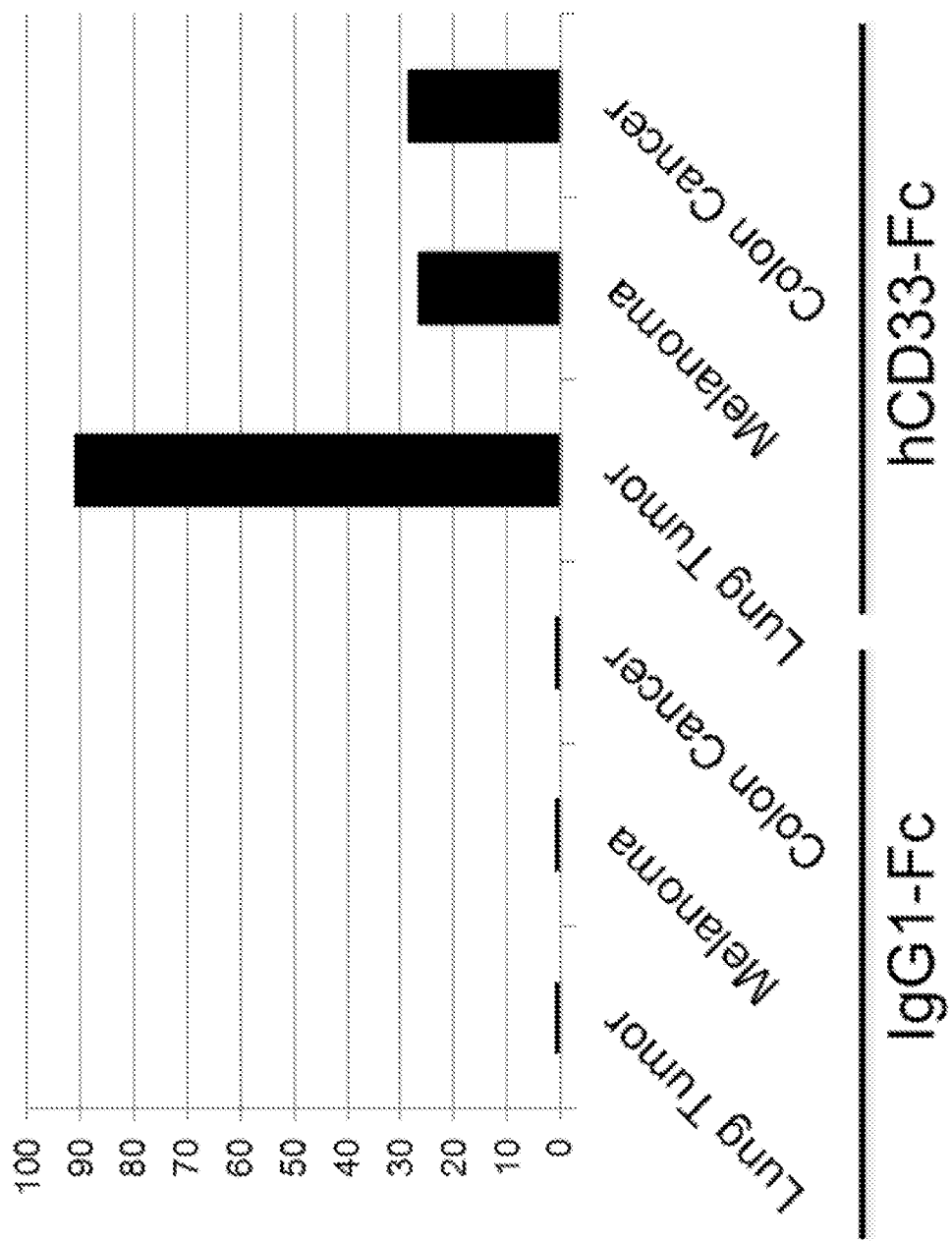
FIG. 14A-14D depict expression of CD33 and an inhibitory CD33 ligand in tumor cells in culture and in vivo.
Figure 14B:
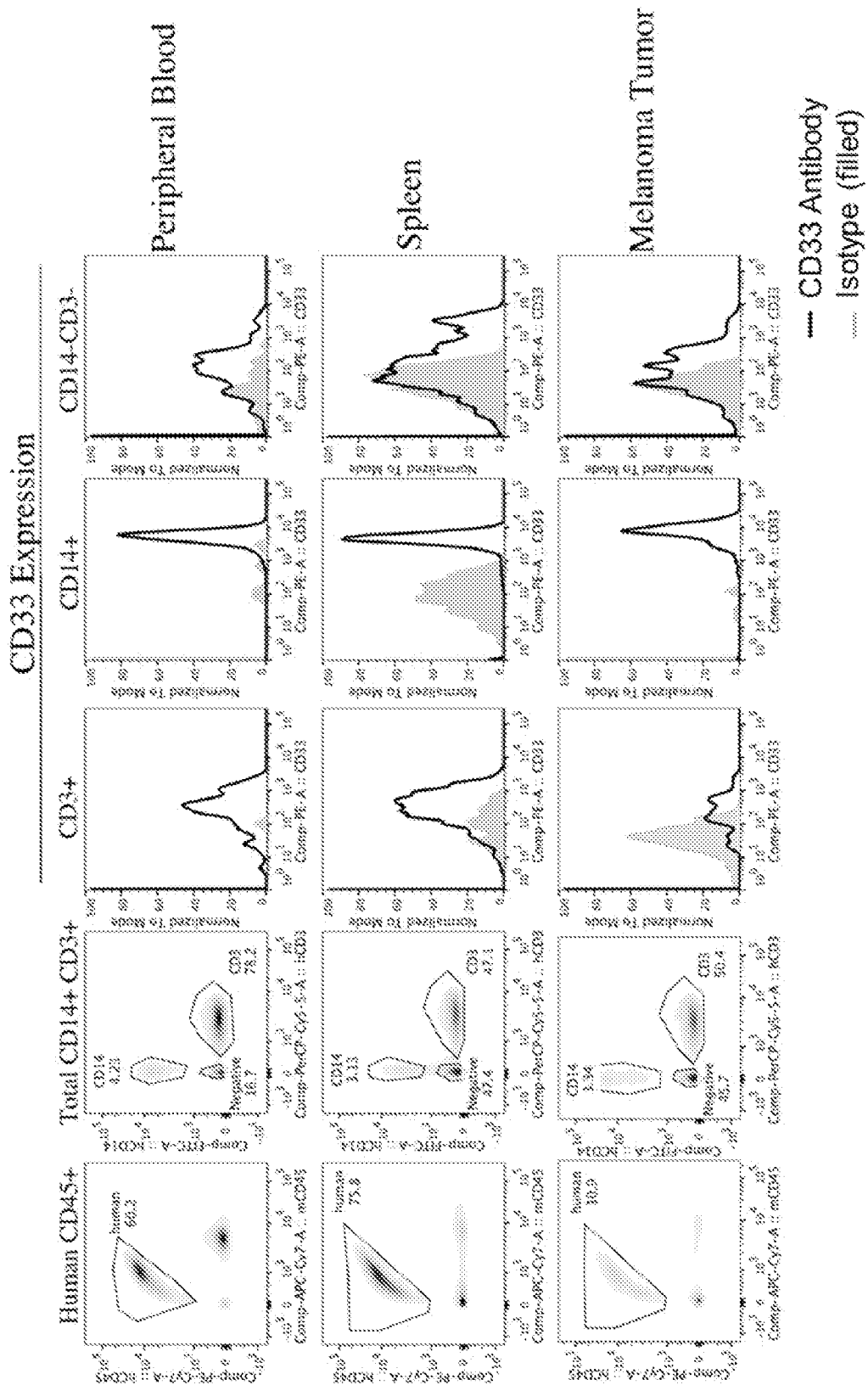
Figure 14C:
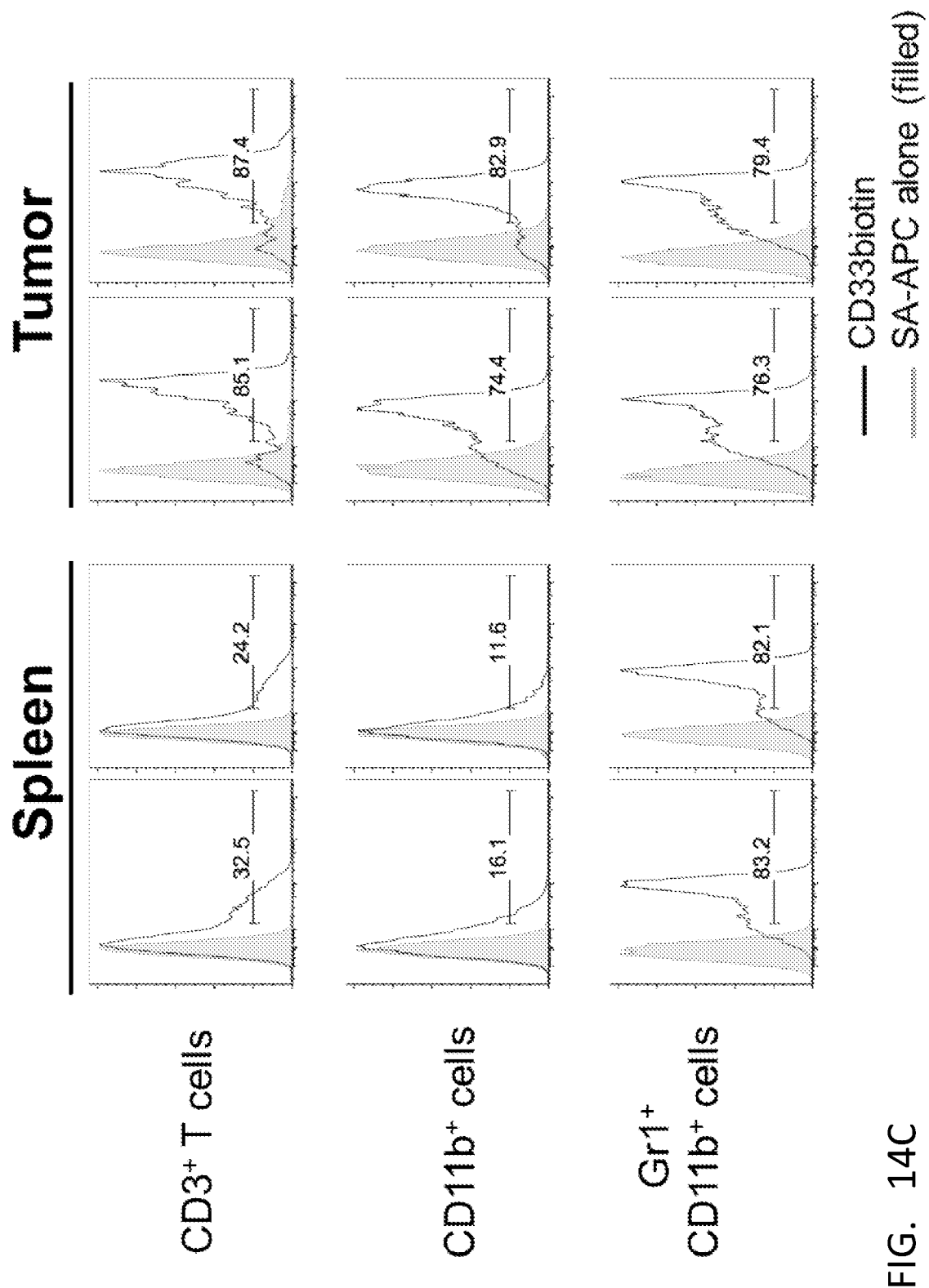
Figure 14D:
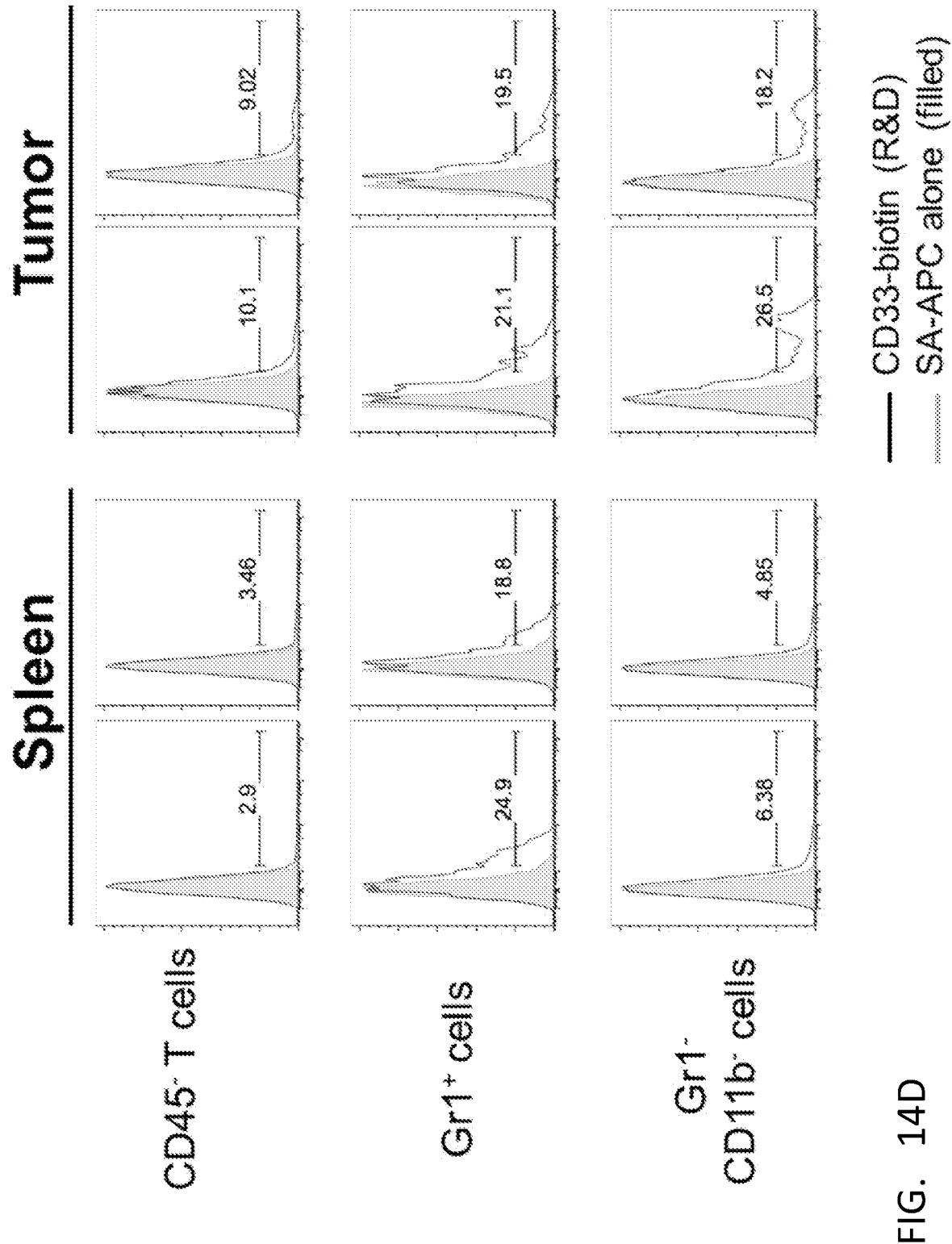

FIG. 14A shows that the expression of an inhibitory CD33 ligand is increased at least 20-fold over background in melanoma cells, lung tumor cells, and colon cancer cells. Without wishing to be bound by theory, identification of inhibitory sialic acid ligand expression on these tumor cells indicates a contributing mechanism by which cancer cells evade immune recognition and clearance. Sialic acid ligands on tumor cells can mediate immunosuppressive interactions via CD33 expressed on myeloid and lymphoid immune cells (FIG. 14B-14D). These results indicate that antibodies that remove CD33 from the cell surface or block increased ligand interactions may relieve inhibitory effects of tumors on the immune system and enhance cancer therapy.

In Vivo Studies

To study in vivo MC38 colon carcinoma growth in the absence or presence of CD33, 8-10 weeks old C57BL/6NJ wild type mice (WT; n=7) or CD33 knock-out mice (KO; n=10) were challenged subcutaneously with 1×10$^6$ MC38 colon carcinoma cells in 0.1 mL PBS in the flank. Tumor growth was monitored every 3-4 days with a caliper, until the tumor reached a size of 2000 mm$^3$.

To determine expression of CD33 in vivo, four week-old female Taconic NOG mice were myeloablated approximately 24 hours before engraftment with human fetal liver CD34$^+$ cells (100,000 cells/mouse) by intravenous injection. Reconstitution of immune cells was monitored by flow cytometry of peripheral blood. Twelve weeks after engraftment, the Champions TumorGraft™ melanoma model was implanted subcutaneously. Approximately 8-10 weeks later, when the tumor reached a size of 150-200 mm$^3$, blood, spleen, and tumor cells were harvested and processed for analysis by flow cytometry on a BD FACSCanto™. Flow cytometric analysis was performed to determine the expression of CD33 in different compartments of the human (hCD45$^+$) immune system. Specifically, expression was analyzed in CD3$^+$ T cells, CD14$^+$ monocyte/macrophages, and other CD3-CD14-human immune cells cells. Data were analyzed with FlowJo software version 10.0.6 by TreeStar.

FIG. 14B-14D show expression of CD33 in tumor cells in vivo. FIG. 14B shows CD33 expression in human immune cells from peripheral blood and spleen and cell infiltrates from patient-derived melanoma from an immunodeficient mouse model lacking mature mouse T cells, B cells, and NK cells that was transplanted with human CD45+ immune cells and with patient derived melanoma. FIG. 14C shows CD33 expression in CD3+ T cells, CD11b+ immune cells, and Gr1+ CD11b+ immune cells from spleen and cell infiltrates from breast cancer tumor EMT-6 from a mouse tumor model. FIG. 14D shows CD33 expression in CD45− T cells, Gr1+ cells, and Gr1− CD11b− immune cells from spleen and cell infiltrates from breast cancer tumor EMT-6 from a mouse tumor model.

Figure 15A:
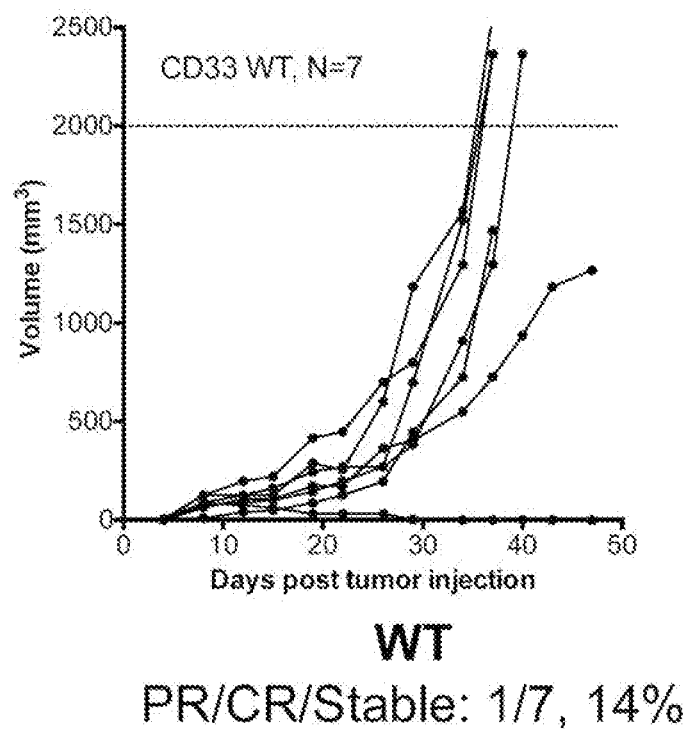
FIG. 15A-15E depict results showing inhibition of colon carcinoma tumor growth in mice in which CD33 was neutralized by genetic means.
Figure 15B:
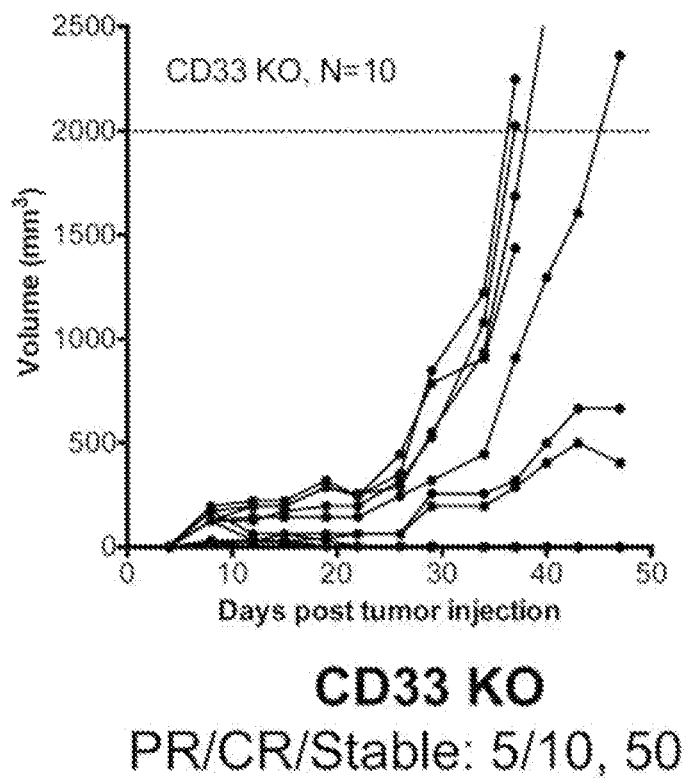
Figure 15C:
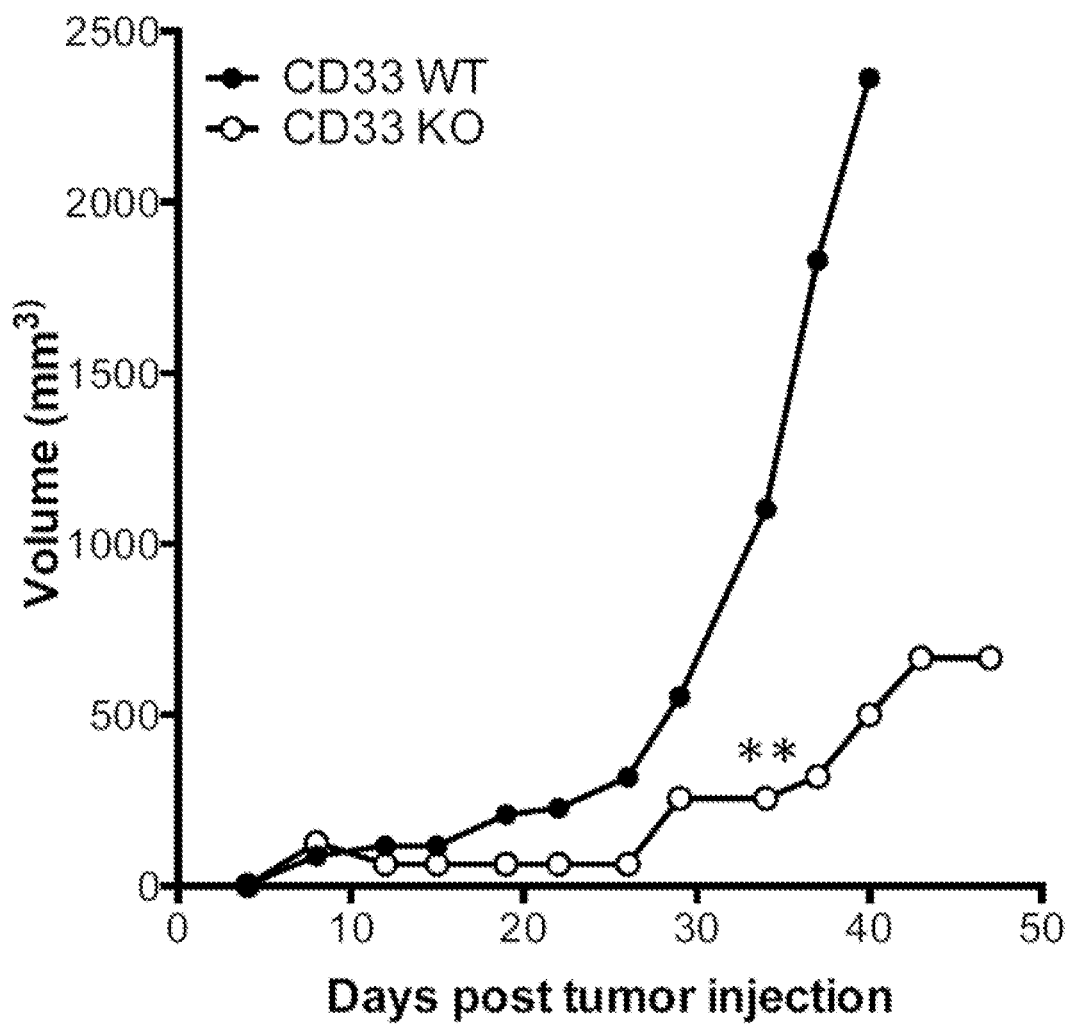
Figure 15D:
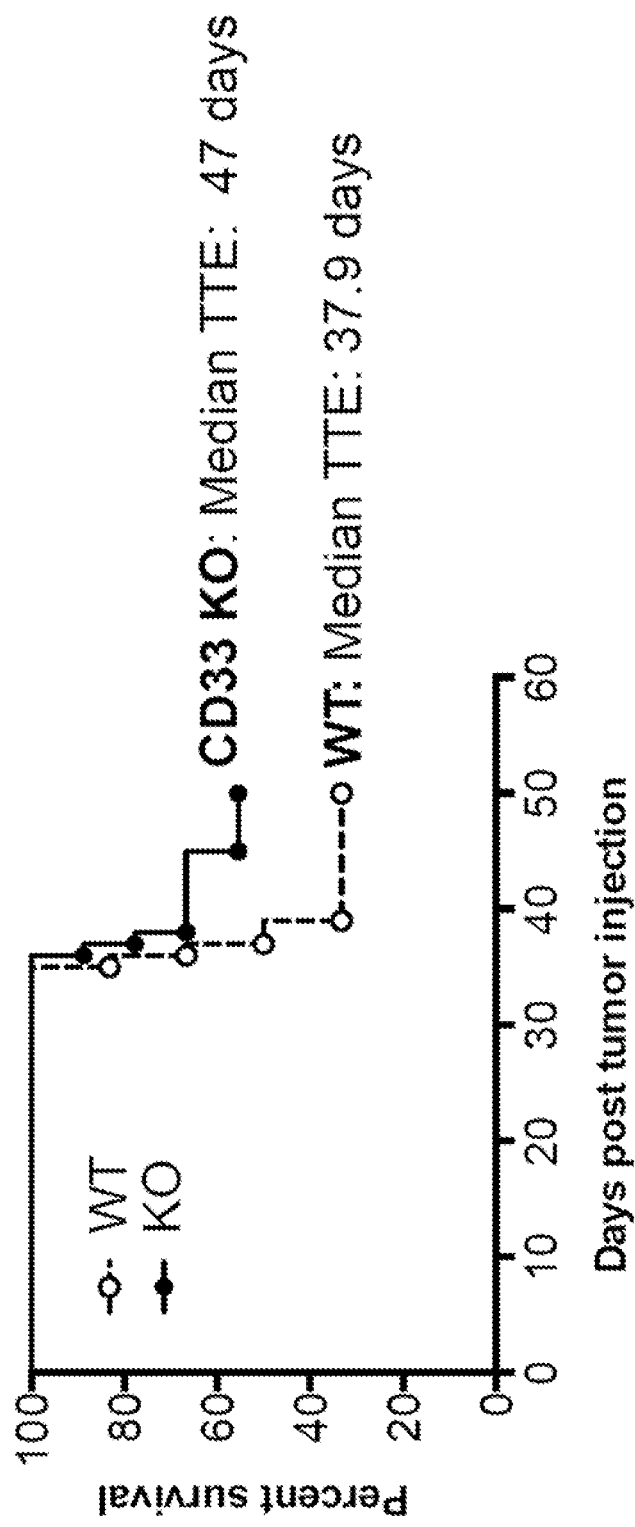

FIG. 15A-15C show that CD33 KO mice have reduced subcutaneous MC38 tumor volume compared to wild type mice. FIG. 15D shows Kaplan-Meier survival data demonstrating that CD33 KO mice survive MC38 tumor challenge better than wild type mice.

Figure 15E:
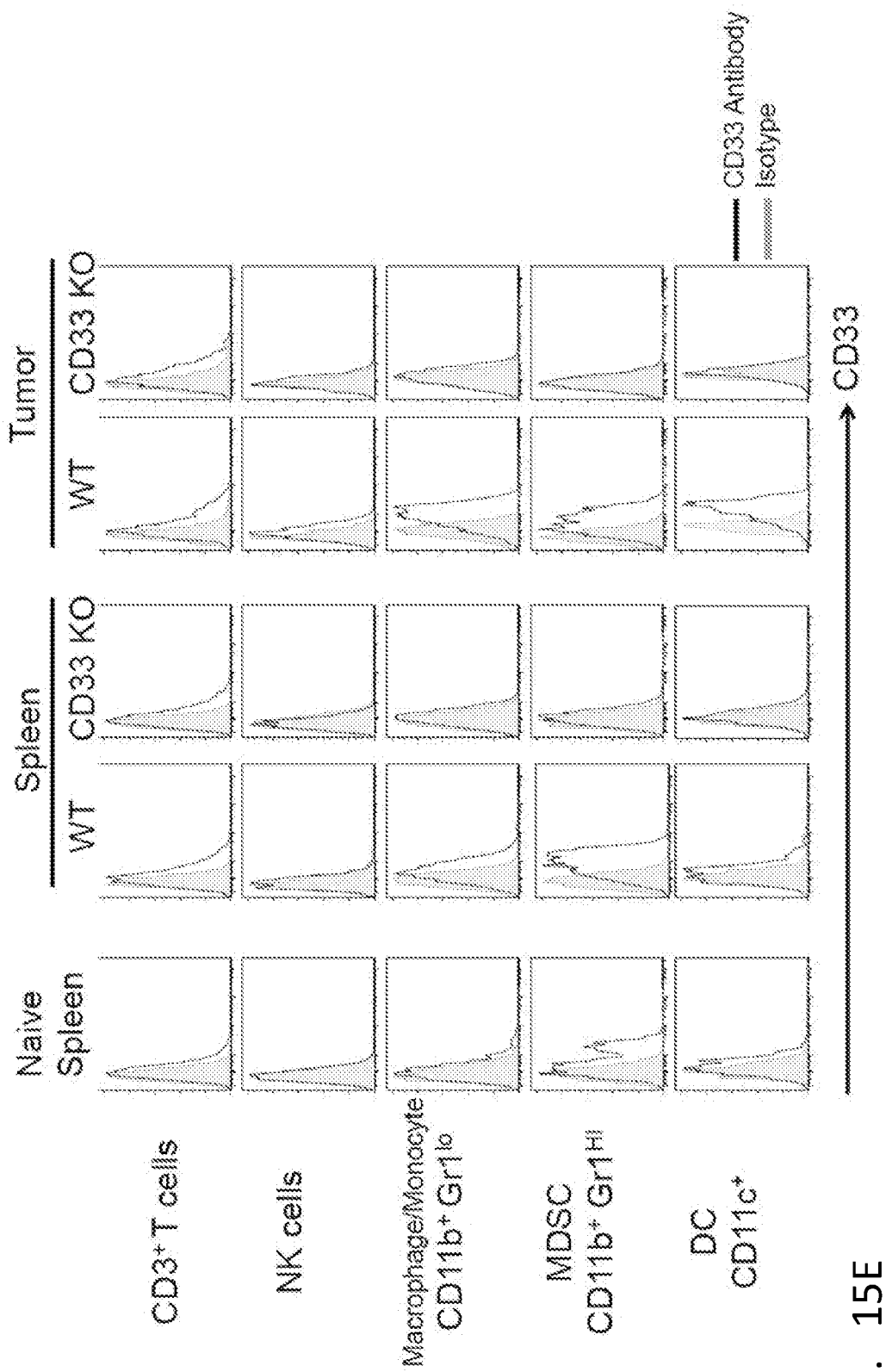

FIG. 15E demonstrates expression of CD33 on immune cells from wild type mice (WT), but not CD33 KO mice, isolated from spleens and tumors, CD33 is upregulated on splenic macrophage/monocytic CD45$^+$CD11b$^+$Gr1$^{lo}$ cells, CD45$^+$CD11b$^+$Gr1$^{hi}$ myeloid-derived suppressor cells, and CD11c$^+$ dendritic cells in tumor-challenged WT mice compared to naïve mice. CD33 expression is further increased on tumor-infiltrated CD45$^+$CD11b$^+$Gr1$^{lo}$ cells, remains the same level as splenic CD45$^+$CD11b$^+$Gr1$^{hi}$ cells, is highly upregulated on tumor-infiltrated CD11c$^+$ cells, and is slightly upregulated on NK cells, when compared to WT tumor-challenged or naïve WT mice.

These results demonstrate that inhibition of CD33 allows limited growth or restriction of subcutaneous tumors. The results also indicate that CD33 function suppresses beneficial immune responses that restrict tumor growth and allow the immune system to undergo tumor clearance. These results further indicate that CD33 blocking antibodies may reduce solid tumor growth in part by decreasing the number of tumor-infiltrated immunosuppressor cells, altering their function, and/or increasing the number of infiltrating cytotoxic T-cells, natural killer cells, or increasing other immunological tumor clearance mechanisms. CD33 antibodies may do so by either reducing CD33 expression or blocking inhibitory sialic acid ligand interactions. As demonstrate herein, CD33 KO mice survive better than WT mice upon tumor challenge, indicating that CD33 blocking antibodies may have beneficial effects in treating cancer. It is further demonstrated herein that tumor-infiltrating myeloid cells upregulate CD33, as compared to splenic CD33$^+$ cells, in tumor-challenged mice, and even more so compared to naïve mice.

In Vivo Effects of Anti-CD33 Antibody Treatment

To test the beneficial effect of CD33 blocking antibodies, wild-type (WT) female BALB/c mice are injected with syngeneic tumors, such as MC38 colon carcinoma, B16 melanoma, or EMT-6 murine breast carcinoma. 8-12 week-old mice are injected with $5 \times 10^6$ EMT-6 tumor cells in 0% Matrigel sc in flank in a volume of 0.1 mL/mouse. Mice are randomized into treatment groups based on day 1 body-weight. Body weight is measured every other week until termination of the experiment. Mice that received the tumor are injected with 20-100 mg/kg of CD33 or control antibody at days 1, 4, 8, 15, and 22 either alone or in combination with anti-CTLA4 9H10 antibody or anti-PD1 antibody. Tumor size is then measured with a Caliper Measurement every other week until termination. Adverse reactions or death are monitored. Any individual animal with > than 30% body weight loss or three consecutive measurements of tumor size>25% body weight loss is euthanized. The endpoint of the experiment is a tumor volume of 2000 mm³ or 45 days, whichever comes first. Responders can be followed longer. When the endpoint is reached, the animals are euthanized. Effect of antibodies on tumor volume and survival is monitored.

In Vivo Effects of Anti-CD33 and Anti-PD-1 Antibody Combination Treatment

A CTG-0202 patient-derived melanoma tumor was first passaged in pre-study mice prior to implantation to humanized mice. When tumors reached 1-1.5 cm³ in volume in stock mice, they were harvested for re-implantation into pre-study mice. Pre-study mice were implanted unilaterally on the left flank with tumor fragments. The CTG-0202 melanoma tumors were used at passage number 6.

Figure 15F:
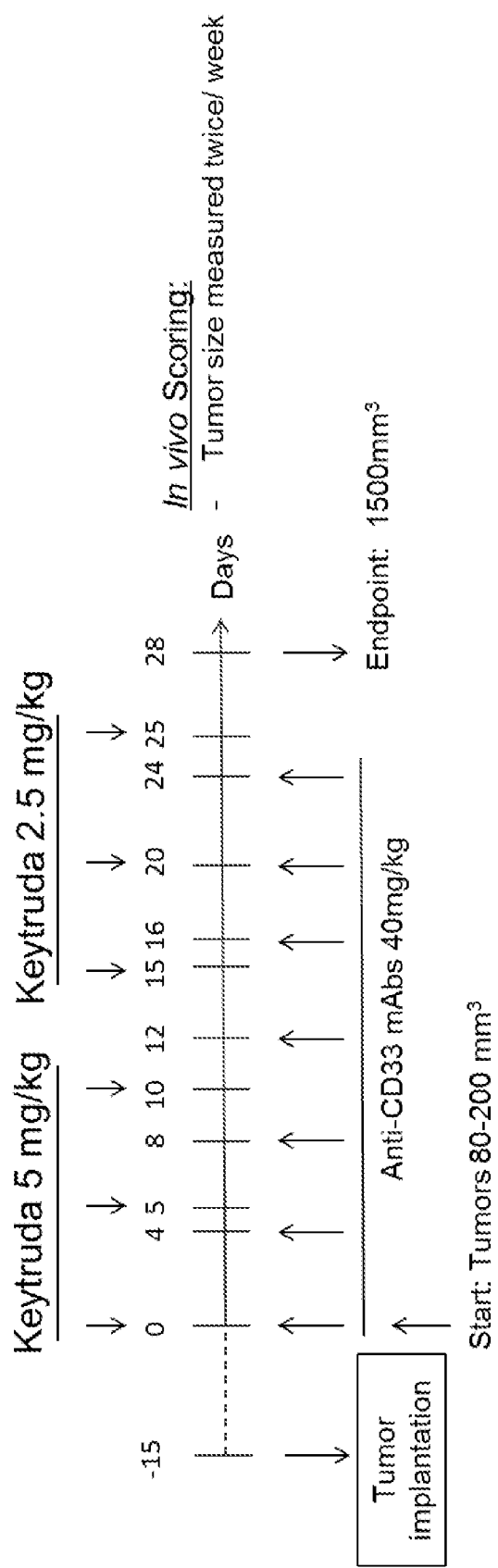
FIG. 15F depicts a PD-1/CD33 combination antibody treatment protocol for a mouse model of patient-derived cancer in immunologically humanized mice.

Immunocompromised female mice (Taconic NOG) were humanized with fetal liver-derived CD34$^+$ hematopoietic cells (Champion TumorGraft™ Melanoma Model CTG-0202). Mice were housed on irradiated papertwist-enriched ⅛" corncob bedding (Sheperd) in individual HEPA ventilated cages (Innocage® IVC, Innovive USA) on a 12-hour light-dark cycle at 68-74° F. (20-23° C.) and 30-70% humidity. Mice were fed water ad libitum (reverse osmosis, 2 ppm Cl$_2$) and an irradiated test rodent diet (Teklad 2919) consisting of 19% protein, 9% fat, and 4% fiber. Forty-eight humanized mice were implanted and pre-study tumor volumes were recorded for each experiment beginning seven to ten days after implantation. When tumors reached approximately 80-200 mm³ in volume, mice were matched by tumor volume into treatment or control groups to be used for dosing initiated on Day 0. Treatment groups were administered anti-PD-1 antibody Keytruda® (pembrolizumab) alone, or in combination with anti-CD33 antibody 2F5. The control group was administered a combination of the anti-PD-1 antibody and an isotype control antibody or a low affinity/non-ligand blocking anti-CD33 antibody. Dosing was then initiated on Day 0. Table 11 and FIG. 15F depict the dosing schedule, dosing amounts, and route of administration.

TABLE 11

Antibody dosing schedule

| Group | N | Treatment | Dose (mg/kg) | Dose Vol. (mL/kg) | ROA | Schedule | Total Number of doses |
|---|---|---|---|---|---|---|---|
| 1 | 8 | Pembrolizumab | 5/2.5 | 5/2.5 | IP | q5dx6 | 6 |
|   |   | CTR mAb | 40 | 3 | IP | q5dx6 | 6 |
| 2 | 8 | Pembrolizumab | 5/2.5 | 5/2.5 | IP | q5dx6 | 6 |
|   |   | 2F5 mAb | 40 | 3 | IP | q5dx6 | 6 |

In Table 11, "N" refers to the number of replicates in each treatment group; "CTR mAb" refers to isotype control antibody or a low affinity/non-ligand blocking anti-CD33 antibody; "2F5 mAb" refers to anti-CD33 antibody 2F5; "ROA" refers to route of administration; "IP" refers to intraperitoneal; "q5dx6" refers to a dosing schedule of administration every five days for a total of six times.

Beginning at Day 0, mice were observed daily and weighed twice weekly using a digital scale. Tumor dimensions were measured twice weekly by digital caliper and data including individual and mean estimated tumor volumes (Mean TV±SEM) recorded for each group. Tumor volume was calculated using the formula (1): TV=width$^2$×length×0.52. At study completion, percent tumor growth inhibition (% TGI) values were calculated and reported for each treatment group (T) versus control (C) using initial (i) and final (f) tumor measurements by the formula (2): % TGI=1−(T$_f$−T$_i$)/(C$_f$−C$_i$).

Individual mice reporting a tumor volume≤50% of the Day 0 measurement for two consecutive measurements were considered partial responders (PR). Individual mice lacking palpable tumors (<4×4 mm² for two consecutive measurements) were classified as complete responders (CR); a CR that persisted until study completion was considered a tumor-free survivor (TFS). Tumor doubling time (DT) was determined for the vehicle treated groups using the formula (3): DT=(D$_i$−D$_f$)*log$^2$/(log TV$_i$−log TV$_f$), where D=Day and TV=Tumor Volume. Statistical differences in tumor volume were determined using two-way ANOVA. The study was concluded when the mean tumor volume of the control group reached 1500 mm³ at day 28.

At study termination harvested tumors were shipped overnight in media on ice packs and processed the following day. Whole blood samples were collected by cardiac puncture and shipped in sodium heparin and processed the following day upon delivery. Tumor samples were treated with collagenase for 30 min at 37° C. Samples were dissociated through cell strainer and resuspended in 2% FBS in PBS. Red blood cells in whole blood samples were lysed using ACK lysing buffer and cells were then washed in 2% FBS in PBS twice. Cells were counted using a hemocytometer and one million cells were stained with fluorochrome-conjugated antibodies for 30 min. on ice, then washed with 2% FBS in PBS. Cells were fixed with 4% paraformaldehyde in PBS. All the stained cells were analyzed on a FACS Canto (BD Biosciences) and data analyzed with FlowJo software (TreeStar). To assess receptor downregulation, mouse (m) CD45, human (h) CD45, human (h) CD3, and human (h) CD14 antibodies were used to gate on the CD14$^+$ population. To identify tumor-infiltrating immune cells, hCD45, hCD3, hCD4, hCD8, and hCD14 antibodies were used to gate on populations according to standard procedure.

Figure 15G:
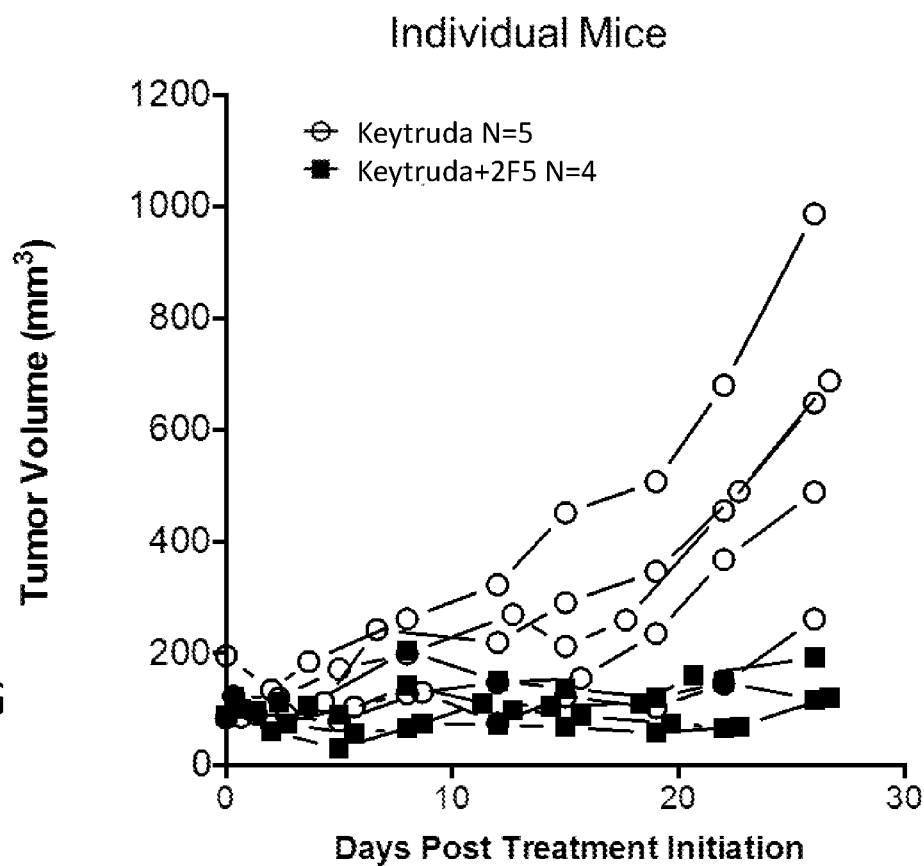
FIG. 15G depicts tumor volume after antibody treatment in individual mice that were engrafted with immune stem cells from human donors 165547112 and 17509112. Mice were treated either with Keytruda® (pembrolizumab) anti-PD-1 antibody alone or in combination with anti-CD33 antibody 2F5.
Figure 15H:
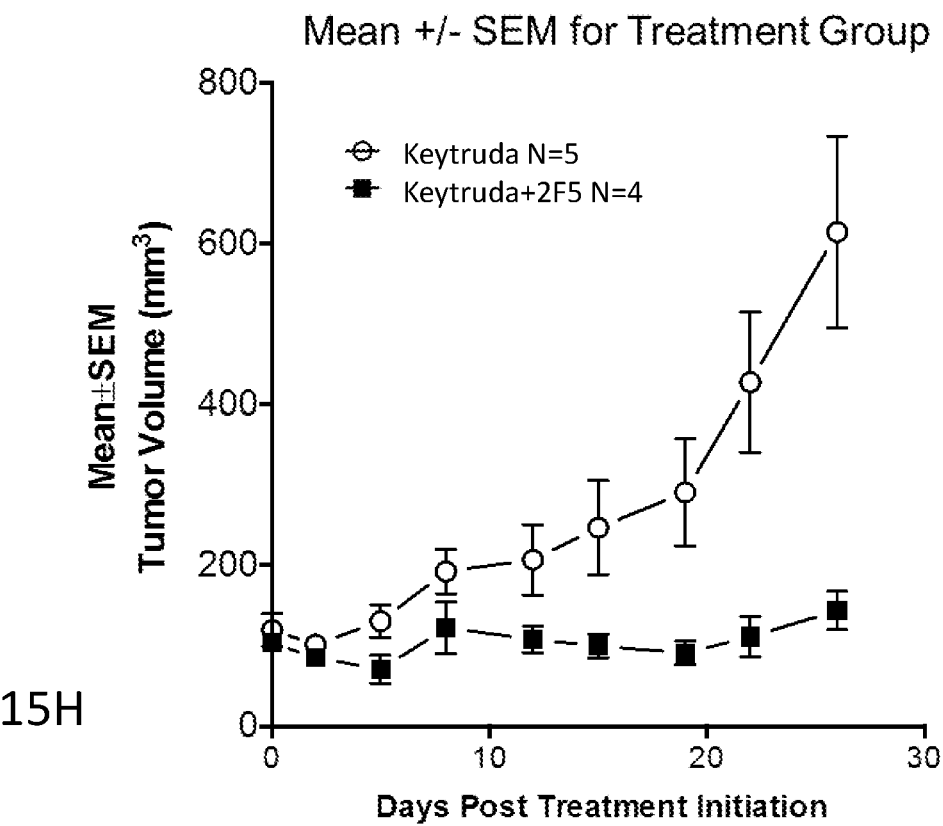
FIG. 15H depicts mean tumor volume after treatment for 25 days with Keytruda® (pembrolizumab) anti-PD-1 antibody alone or in combination with anti-CD33 antibody 2F5 in mice engrafted human immune stem cells from human donors 165547112 and 17509112.

FIG. 15G and FIG. 15H depict pre-clinical efficacy of anti-CD33 antibody 2F5 as a therapeutic for treating human cancer. Antibody 2F5 is a potent receptor downregulator and ligand blocking antibody. When administered in combination with the anti-PD-1 antibody pembrolizumab, antibody 2F5 significantly reduced tumor volume in melanoma tumors (FIGS. 15G and 15H). Notably, pembrolizumab in combination with an isotype control or a lower affinity/non-ligand blocking CD33 antibody (CTRmAb) did not inhibit tumor growth (FIGS. 15G and 15H).

Figure 15I:
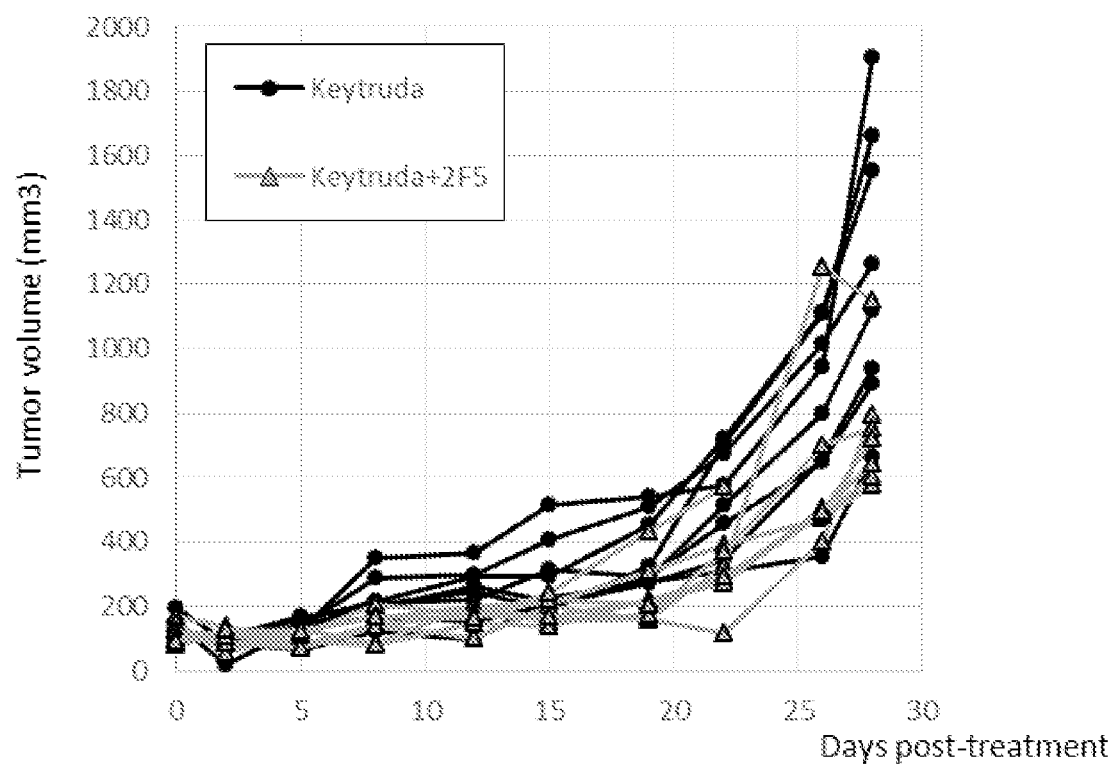
FIG. 15I depicts tumor volume after treatment with Keytruda® (pembrolizumab) anti-PD-1 antibody alone or with Keytruda® (pembrolizumab) anti-PD-1 antibody together with anti-CD33 antibody 2F5 in individual mice engrafted with immune stem cells from human donors 165547112, 17509112, and 984480112. *: $p<0.05$; : $p<0.01$; *: $p<0.001$ for 2F5 vs Isotype Ctl. Means per treatment groups are presented. Error bars represent SEM.
Figure 15J:
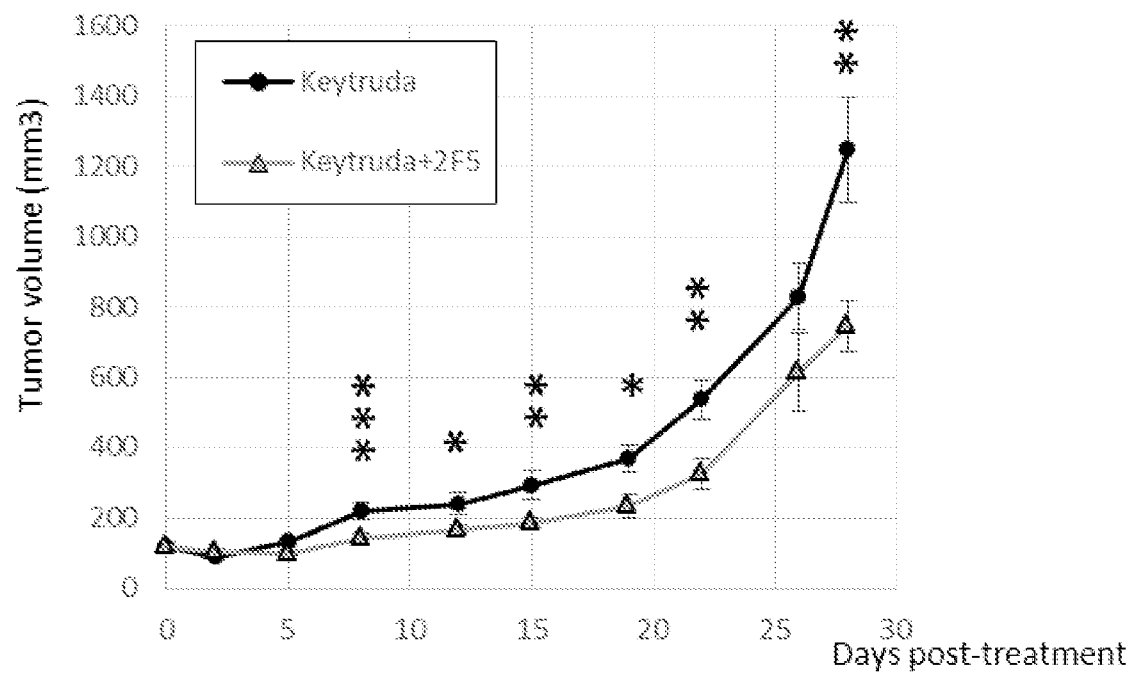
FIG. 15J depicts mean tumor volume after treatment with Keytruda® (pembrolizumab) anti-PD-1 antibody alone or in combination with anti-CD33 antibody 2F5 in mice. *: $p<0.05$; : $p<0.01$; *: $p<0.001$ for 2F5 vs Isotype Ctl. Means per treatment groups are presented. Error bars represent SEM.

As shown in FIGS. 15I and 15J, the combination treatment with CD33 antibody2F5 and the anti-PD-1 antibody inhibited tumor growth in vivo in the patient-derived melanoma tumor model in mice engrafted with human immune stem cells. Tumor volume at each time point was corrected for donor, tumor size at time 0 and mouse weight by multiple linear regression using R lm( ) function. At each time point, statistical significance was assessed by using R lm( ) function.

Figure 15L:
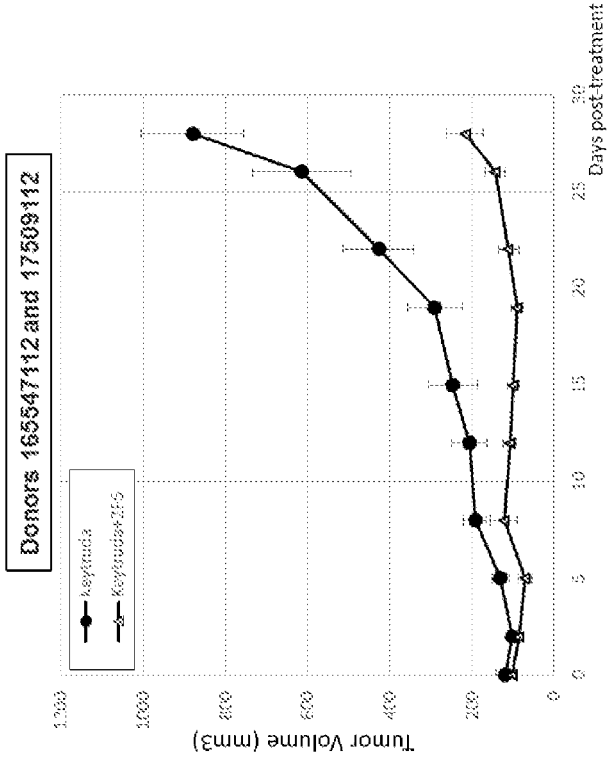
FIG. 15L depicts mean tumor volume after treatment for 28 days with Keytruda® (pembrolizumab) anti-PD-1 antibody alone or in combination with anti-CD33 antibody 2F5 in mice engrafted human immune stem cells from human donors 165547112 and 17509112.
Figure 15K:
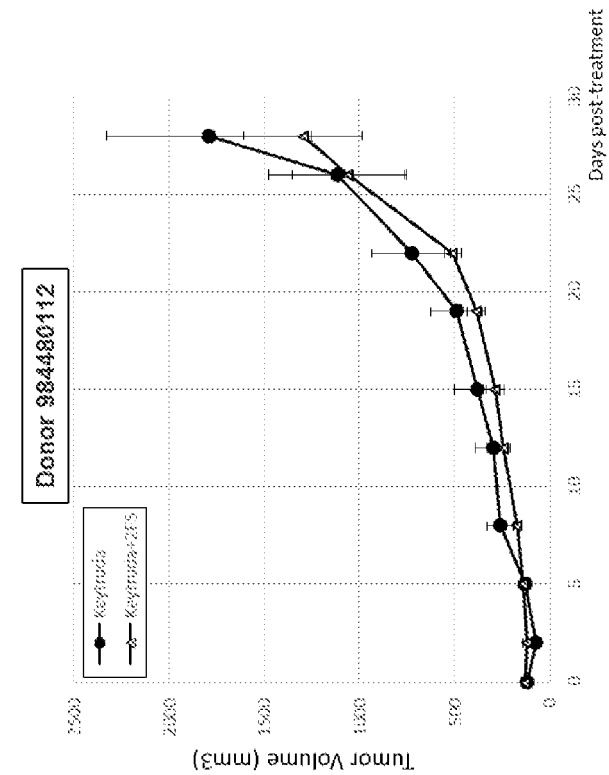
FIG. 15K depicts mean tumor volume after treatment with Keytruda® (pembrolizumab) anti-PD-1 antibody alone or in combination with anti-CD33 antibody 2F5 in mice engrafted human immune stem cells from human donor 984480112.

As shown in FIGS. 15K and 15L, the combination treatment with CD33 antibody2F5 and the anti-PD-1 antibody inhibited tumor growth in vivo in the patient-derived melanoma tumor model that was implanted in mice engrafted human immune stem cells from different human donors (984480112, 16554711, and 17509112). The anti-tumor effect is shown by donor.

Figure 15M:
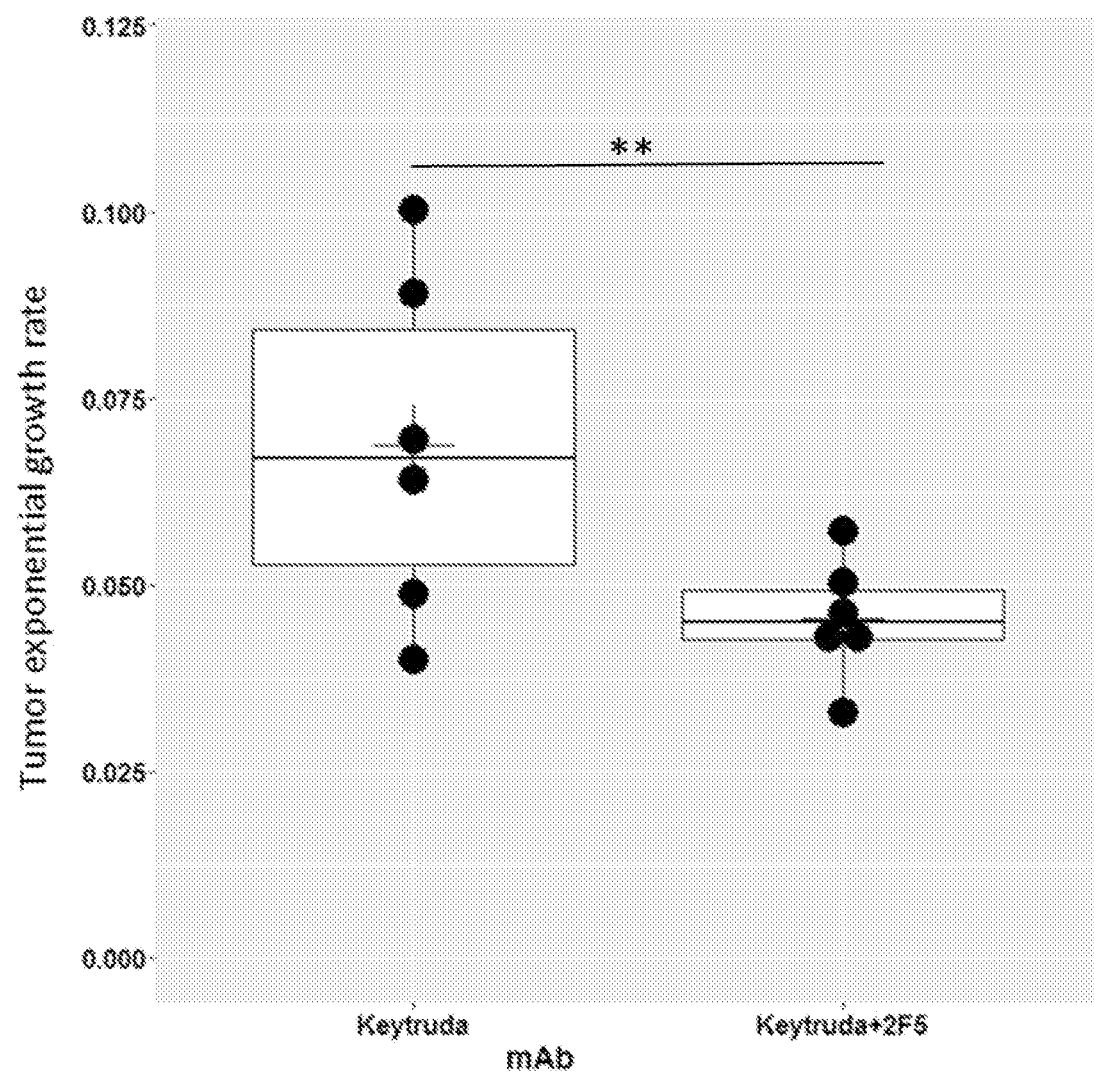
FIG. 15M depicts in vivo tumor growth rate in mice treated with Keytruda® (pembrolizumab) anti-PD-1 antibody alone or in combination with anti-CD33 antibody 2F5. : $p<0.01$; +: mean; boxplot midline: median; upper and lower boundaries of the boxes correspond to the first and third quartiles (25th and 75th percentiles).

As shown in FIG. 15M, the combination treatment with CD33 antibody2F5 and the anti-PD-1 antibody slowed tumor growth rate in vivo in the patient-derived melanoma tumor model in mice engrafted with human immune stem cells. Tumor exponential growth was assessed using R tumgr package, from day 0 to day 12, correcting for mouse weight. Statistical significance was assessed by multiple linear regression using R lm( ) function, correcting for donor, animal weight and tumor initial volume.

Figure 15N:
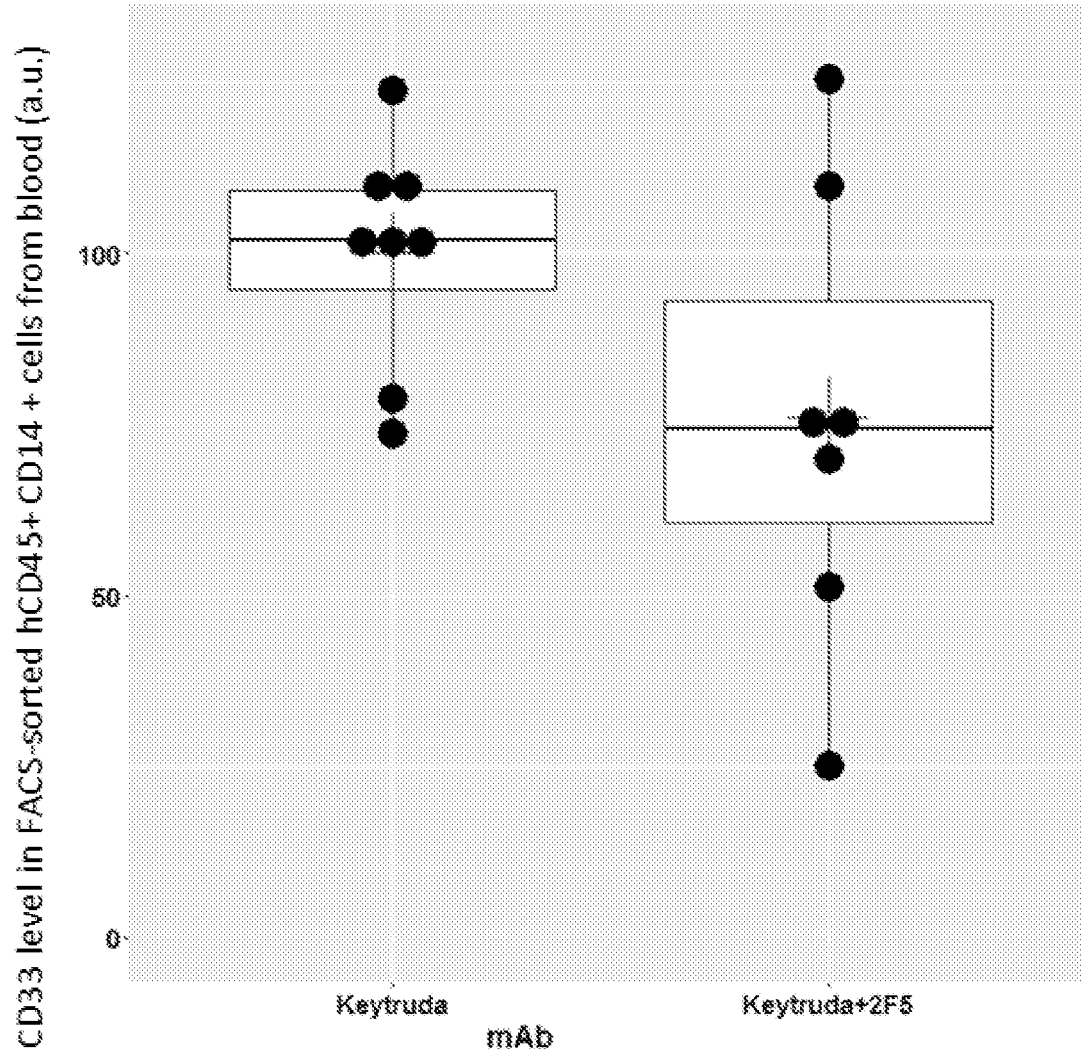
FIG. 15N depicts in vivo reduction in cell surface levels of CD33 in peripheral blood human (h) CD45$^+$CD14$^+$ myeloid cells from mice treated with Keytruda® (pembrolizumab) anti-PD-1 antibody alone or in combination with anti-CD33 antibody 2F5. +: mean; boxplot midline: median; upper and lower boundaries of the boxes correspond to the first and third quartiles (25th and 75th percentiles).

As shown in FIG. 15N, the combination treatment with CD33 antibody2F5 and the anti-PD-1 antibody reduced cell surface levels of CD33 in peripheral blood hCD45$^+$ CD14$^+$ myeloid cells from in a mouse tumor model that was engrafted with human immune stem cells and the patient-derived xenograft CTG-0202 melanoma tumors. Statistical significance was assessed by multiple linear regression using R lm( ) function.

Figure 15O:
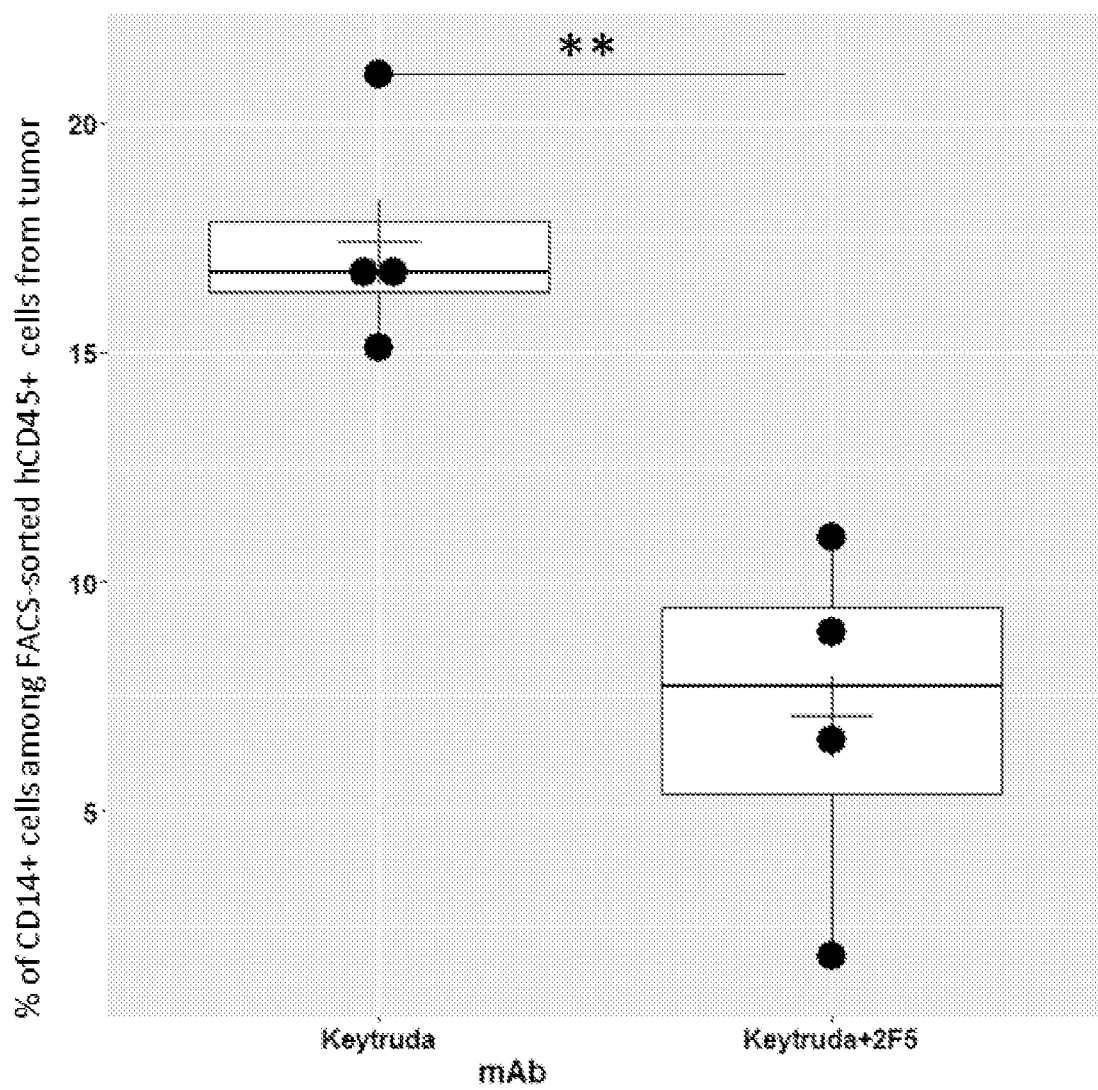
FIG. 15O depicts in vivo reduction in tumor infiltrating human (h) CD45$^+$CD14$^+$ myeloid cells from mice treated with Keytruda® (pembrolizumab) anti-PD-1 antibody alone or in combination with anti-CD33 antibody 2F5. : $p<0.01$; ***: $p<0.001$; +: mean; boxplot midline: median; upper and lower boundaries of the boxes correspond to the first and third quartiles (25th and 75th percentiles.

As shown in FIG. 15O, the combination treatment with CD33 antibody2F5 and the anti-PD-1 antibody reduced the number of tumor infiltrating hCD45$^+$ CD14$^+$ myeloid cells in a mouse tumor model that was engrafted with human immune stem cells and the patient-derived xenograft CTG-0202 melanoma tumors. Statistical significance was assessed by multiple linear regression using R lm( ) function.

Figure 15P:
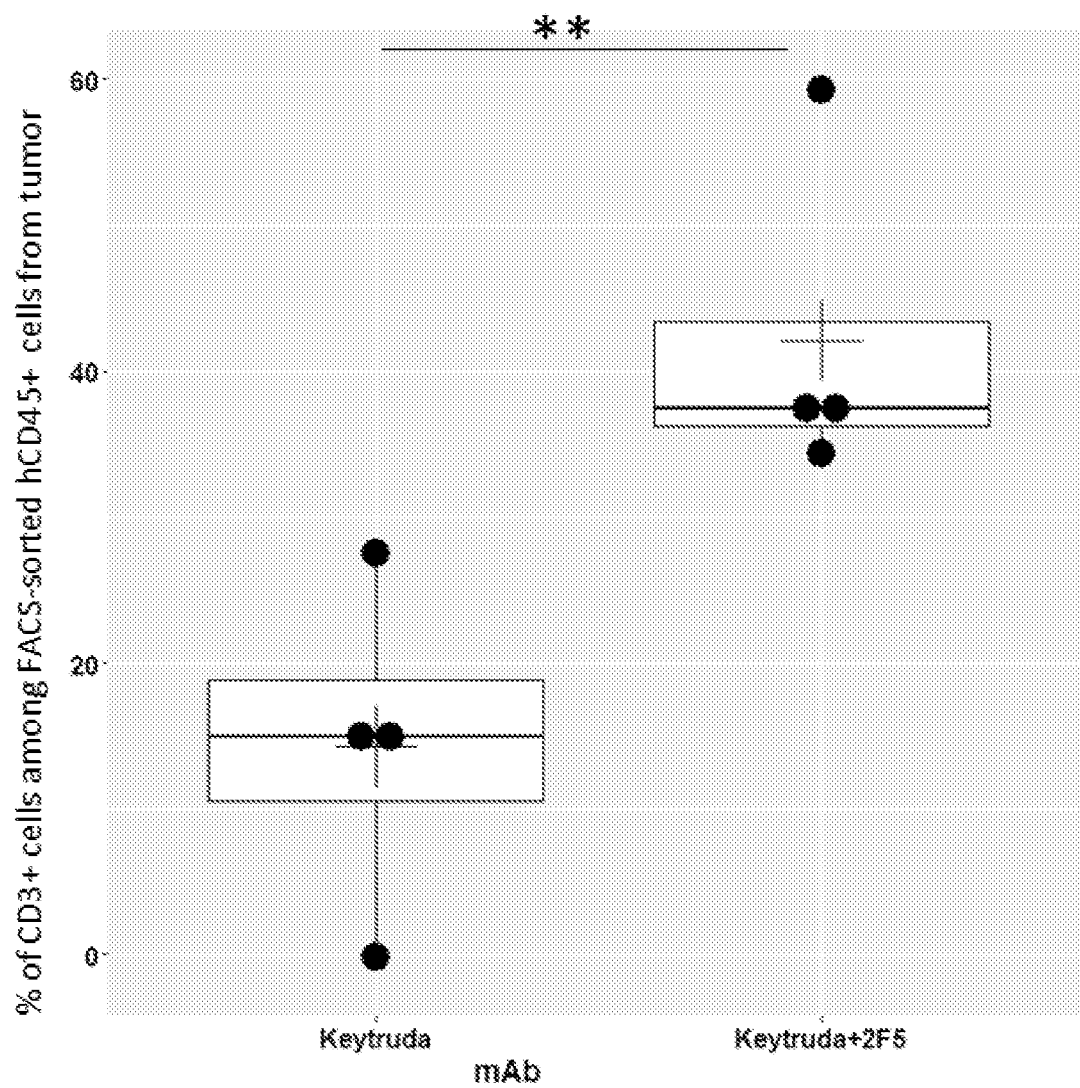
FIG. 15P depicts in vivo increase in tumor infiltrating human (h) CD45$^+$CD3$^+$ T cells from mice treated with Keytruda® (pembrolizumab) anti-PD-1 antibody alone or in combination with anti-CD33 antibody 2F5. (*): $p<0.10$, : $p<0.01$ for 2F5 vs Isotype Ctl, correcting for donor and day of animal sacrifice; +: mean; boxplot midline: median; upper and lower boundaries of the boxes correspond to the first and third quartiles (25th and 75th percentiles).

As shown in FIG. 15P, the combination treatment with CD33 antibody2F5 and the anti-PD-1 antibody increased the number of tumor infiltrating hCD45$^+$ CD3$^+$ T cells in a mouse tumor model that was engrafted with human immune stem cells and the patient-derived xenograft CTG-0202 melanoma tumors. Statistical significance was assessed by multiple linear regression using R lm( ) function.

Figure 15Q:
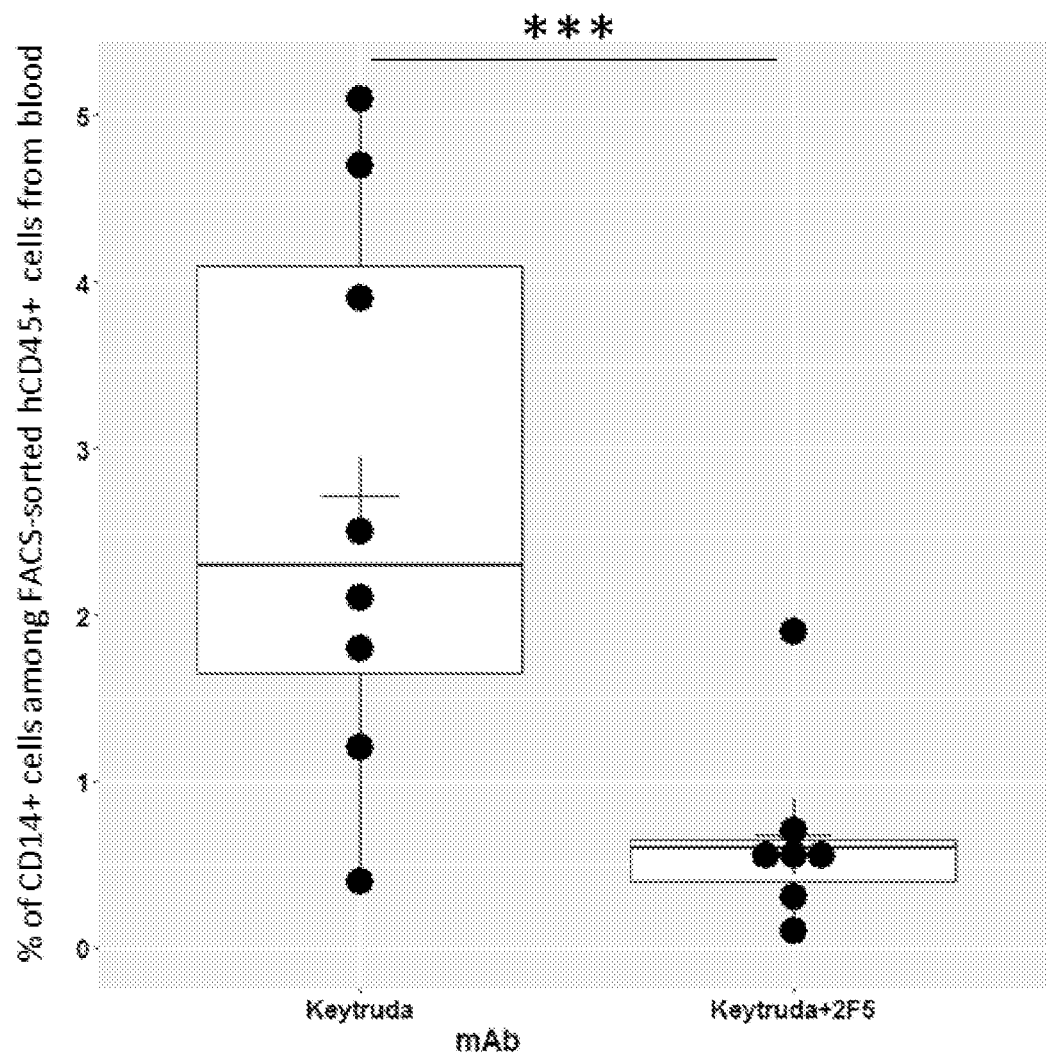
FIG. 15Q depicts in vivo reduction in peripheral blood human (h) CD45$^+$CD14$^+$ myeloid cells from mice treated with Keytruda® (pembrolizumab) anti-PD-1 antibody alone or in combination with anti-CD33 antibody 2F5. *: $p<0.001$; **: $p<0.01$; *: $p<0.05$ for 2F5 vs Isotype Ctl, correcting for donor and day of animal sacrifice; +: mean; boxplot midline: median; upper and lower boundaries of the boxes correspond to the first and third quartiles (25th and 75th percentiles).

As shown in FIG. 15Q, the combination treatment with CD33 antibody2F5 and the anti-PD-1 antibody reduced the number of peripheral blood hCD45$^+$ CD14$^+$ myeloid cells in a mouse tumor model that was engrafted with human immune stem cells and the patient-derived xenograft CTG-0202 melanoma tumors. Statistical significance was assessed by multiple linear regression using R lm( ) function.

In Vivo Effects of Anti-CD33 Antibody Treatment

A CTG-0202 patient-derived melanoma tumor was first passaged in pre-study mice prior to implantation to humanized mice. When tumors reached 1-1.5 cm$^3$ in volume in stock mice, they were harvested for re-implantation into pre-study mice. Pre-study mice were implanted unilaterally on the left flank with tumor fragments. The CTG-0202 melanoma tumors were used at passage number 7.

Immunocompromised female mice (Taconic NOG) were humanized with fetal liver derived CD34$^+$ hematopoietic cells. Mice were housed on irradiated papertwist-enriched ⅛" corncob bedding (Sheperd) in individual HEPA ventilated cages (Innocage® IVC, Innovive USA) on a 12-hour light-dark cycle at 68-74° F. (20-23° C.) and 30-70% humidity. Mice were fed water ad libitum (reverse osmosis, 2 ppm Cl$_2$) and an irradiated test rodent diet (Teklad 2919) consisting of 19% protein, 9% fat, and 4% fiber. Humanized mice were implanted and pre-study tumor volumes were recorded for each experiment beginning seven to ten days after implantation. When tumors reached approximately 80-200 mm$^3$ mice were matched by tumor volume into treatment or control groups to be used for dosing and dosing initiated on Day 0.

Figure 15R:
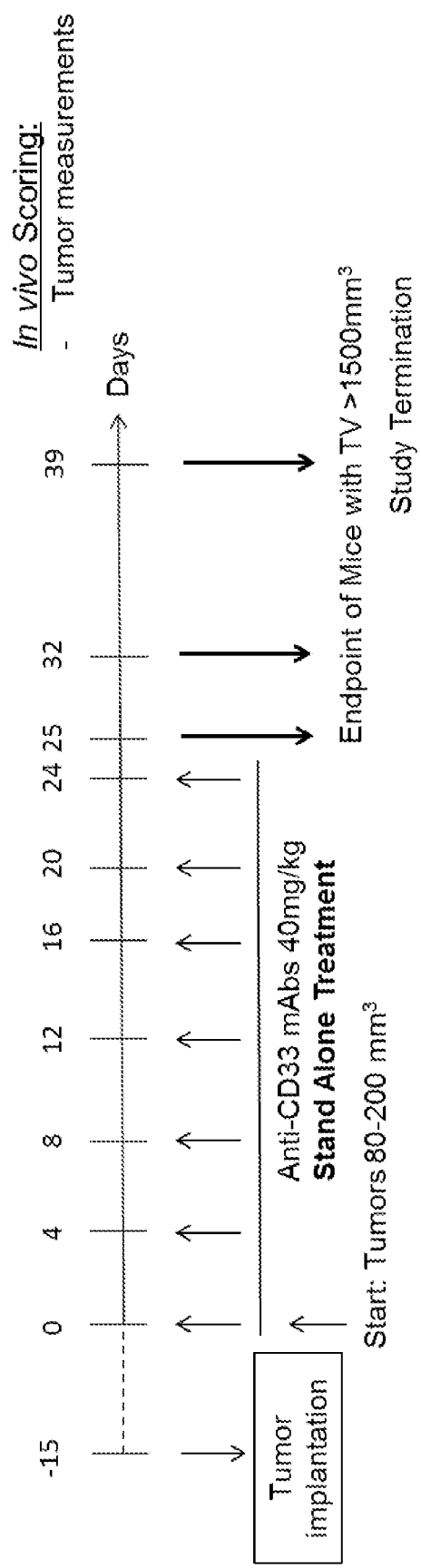
FIG. 15R depicts anti-CD33 antibody treatment protocol for a mouse model of patient-derived cancer in immunologically humanized mice.

Treatment groups were administered anti-CD33 antibody 2F5. The control group was administered an isotype control antibody. Dosing was then initiated on Day 0. Table 12 and FIG. 15R depict the dosing schedule, dosing amounts, and route of administration.

TABLE 12

Antibody dosing schedule

| Group | N | Treatment | Dose (mg/kg) | Dose Vol. (mL/kg) | ROA | Schedule | Total Number of doses |
|---|---|---|---|---|---|---|---|
| 1 | 10 | CTR mAb | 40 | 13.5 | IP | q4dx6 | 6 |
| 2 | 10 | 2F5 mAb | 40 | 13.5 | IP | q4dx6 | 6 |

In Table 12, "N" refers to the number of replicates in each treatment group; "CTR mAb" refers to isotype control antibody or a low affinity/non-ligand blocking anti-CD33 antibody; "2F5 mAb" refers to anti-CD33 antibody 2F5; "ROA" refers to route of administration; "IP" refers to intraperitoneal; "q4dx6" refers to a dosing schedule of administration every four days for a total of six times.

Beginning at Day 0, mice were observed daily and weighed twice weekly using a digital scale. Tumor dimensions were measured twice weekly by digital caliper and data including individual and mean estimated tumor volumes (Mean TV±SEM) recorded for each group. Tumor volume was calculated using the formula (1): TV=width$^2$×length×0.52. At study completion, percent tumor growth inhibition (% TGI) values were calculated and reported for each treatment group (T) versus control (C) using initial (i) and final (f) tumor measurements by the formula (2): % TGI=1−($T_f$−$T_i$)/($C_f$−$C_i$).

Individual mice reporting a tumor volume≤50% of the Day 0 measurement for two consecutive measurements were considered partial responders (PR). Individual mice lacking palpable tumors (<4×4 mm² for two consecutive measurements) were classified as complete responders (CR); a CR that persisted until study completion was considered a tumor-free survivor (TFS). Tumor doubling time (DT) was determined for the vehicle treated groups using the formula (3): DT=($D_i$−$D_f$)*$log^2$/(log $TV_i$−log $TV$)$_f$, where D=Day and TV=Tumor Volume. Statistical differences in tumor volume were determined using two-way ANOVA. Multiple harvest time points occurred during the study. Mice were taken down according to the endpoint requirement of tumor volume>1500 mm³ regardless of treatment group at day 25, 32, and 39 for final study termination.

At study termination harvested tumors were shipped overnight in media on ice packs and processed the following day. Whole blood samples were collected by cardiac puncture and shipped in sodium heparin and processed the following day upon delivery. Tumor samples were treated with collagenase for 30 min at 37° C. Samples were dissociated through cell strainer and resuspended in 2% FBS in PBS. Red blood cells in whole blood samples were lysed using ACK lysing buffer and cells were then washed in 2% FBS in PBS twice. Cells were counted using a hemocytometer and one million cells were stained with fluorochrome-conjugated antibodies for 30 min. on ice, then washed with 2% FBS in PBS. Cells were fixed with 4% paraformaldehyde in PBS. All the stained cells were analyzed on a FACS Canto (BD Biosciences) and data analyzed with FlowJo software (TreeStar). To assess receptor downregulation, mouse (m) CD45, human (h) CD45, human (h) CD3, and human (h) CD14 antibodies were used to gate on the CD14⁺ population. To identify tumor-infiltrating immune cells, hCD45, hCD3, hCD4, hCD8, and hCD14 antibodies were used to gate on populations according to standard procedure.

Figure 15S:
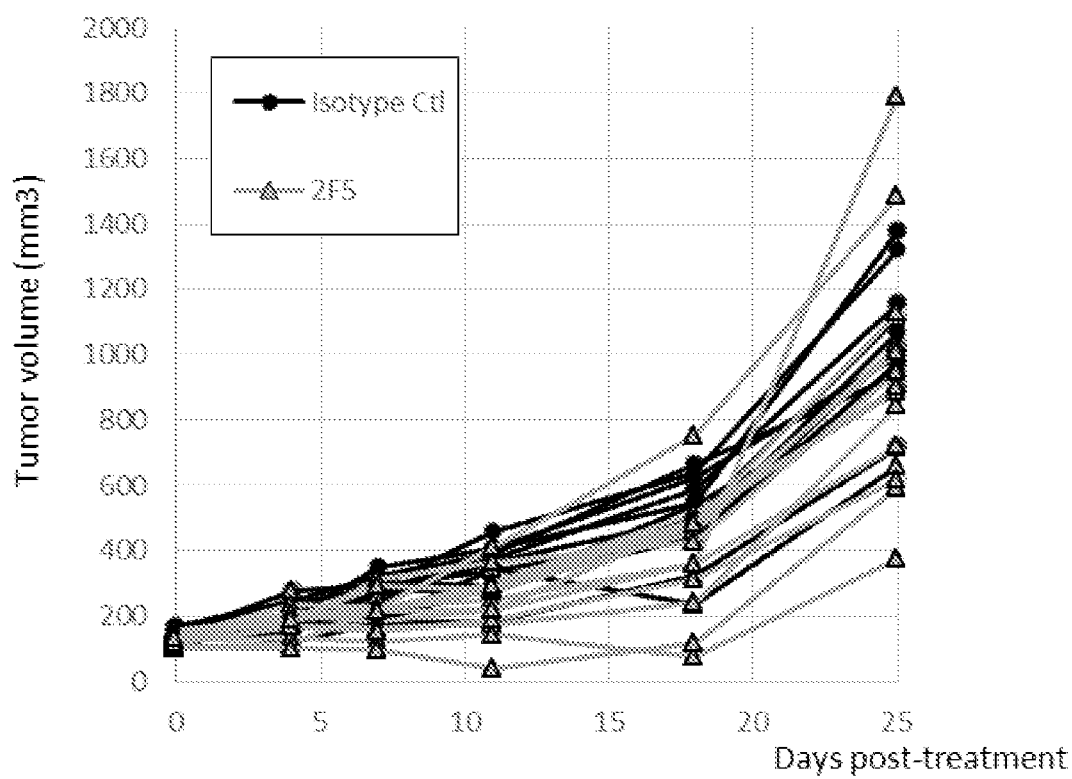
FIG. 15S depicts tumor volume after treatment with anti-CD33 antibody 2F5 or isotype control (Ctl) antibody in individual mice. *: $p<0.05$; : $p<0.01$; *: $p<0.001$ for 2F5 vs Isotype Ctl. Means per treatment groups are presented. Error bars represent SEM.
Figure 15T:
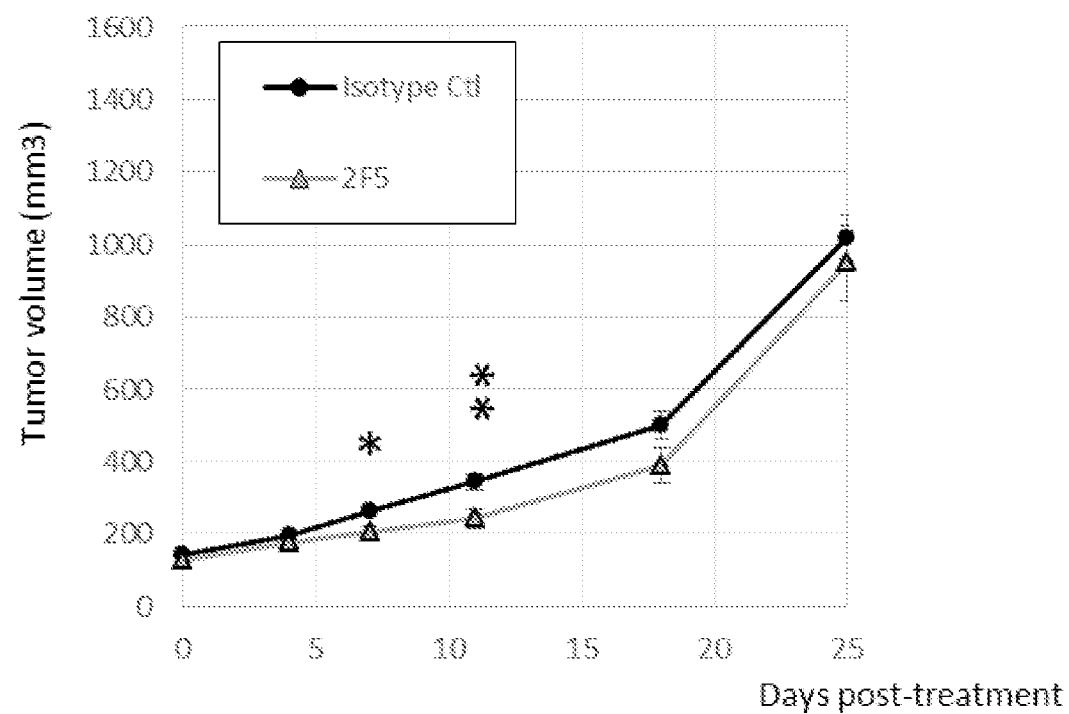
FIG. 15T depicts mean tumor volume after treatment with anti-CD33 antibody 2F5 or isotype control (Ctl) antibody in mice. *: $p<0.05$; : $p<0.01$; *: $p<0.001$ for 2F5 vs Isotype Ctl. Means per treatment groups are presented. Error bars represent SEM.

As shown in FIGS. 15S and 15T, treatment with CD33 antibody2F5 alone inhibited tumor growth in vivo in the patient-derived melanoma tumor model in mice engrafted with human immune stem cells. Tumor volume at each time point was corrected for donor, tumor size at time 0 and mouse weight by multiple linear regression using R lm( ) function. At each time point, statistical significance was assessed by using R lm( ) function.

Figure 15U:
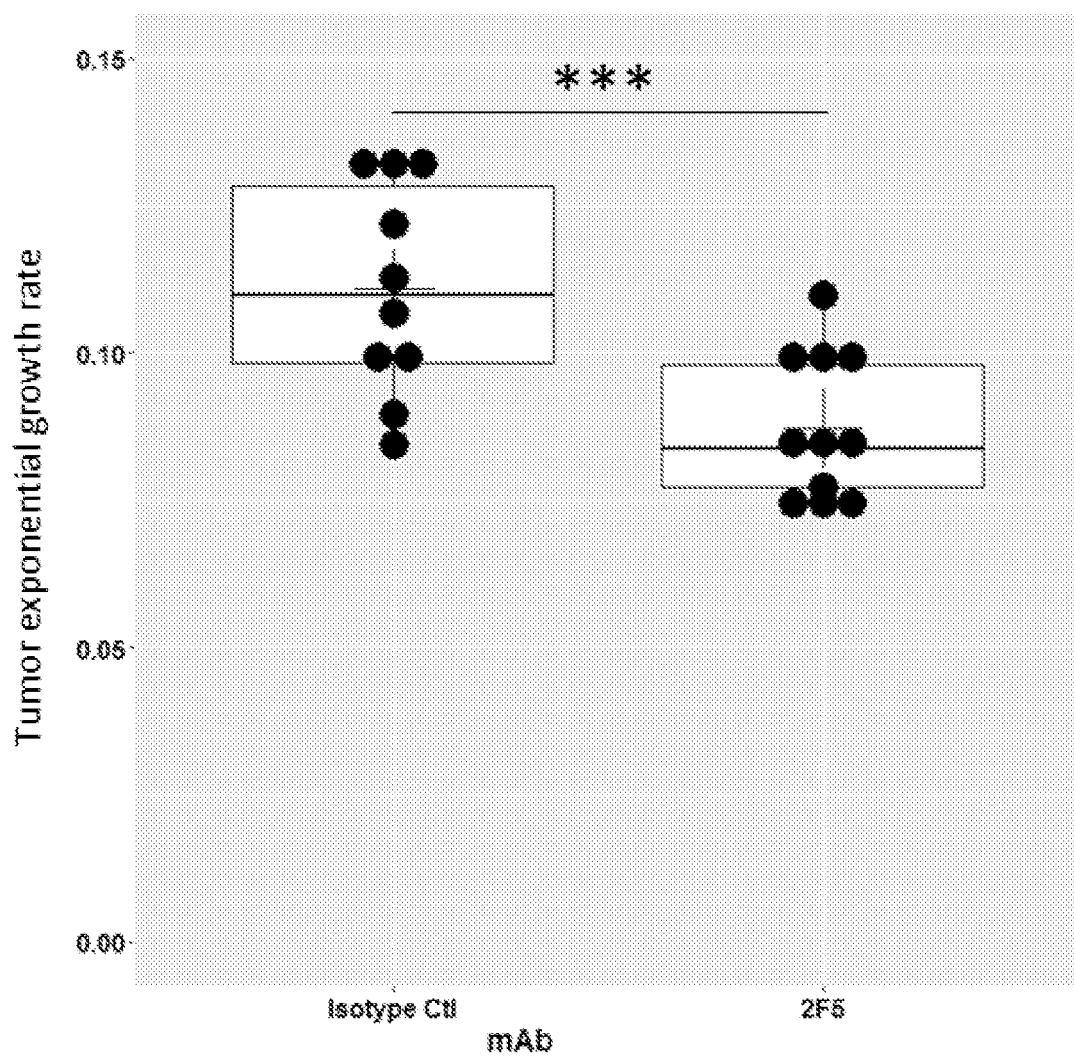
FIG. 15U depicts in vivo tumor growth rate in mice treated with anti-CD33 antibody 2F5 or isotype control (Ctl) antibody. : $p<0.01$; *: $p<0.001$ for 2F5 vs Isotype Ctl, +: mean; boxplot midline: median; upper and lower boundaries of the boxes correspond to the first and third quartiles (25th and 75th percentiles).

As shown in FIG. 15U, treatment with CD33 antibody2F5 alone slowed tumor growth rate in vivo in the patient-derived melanoma tumor model in mice engrafted with human immune stem cells. Tumor exponential growth was assessed using R tumgr package, from day 0 to day 11, correcting for mouse weight. Statistical significance was assessed by multiple linear regression using R lm( ) function, correcting for donor, animal weight and tumor initial volume.

Figures 15V, 15W, 15X:
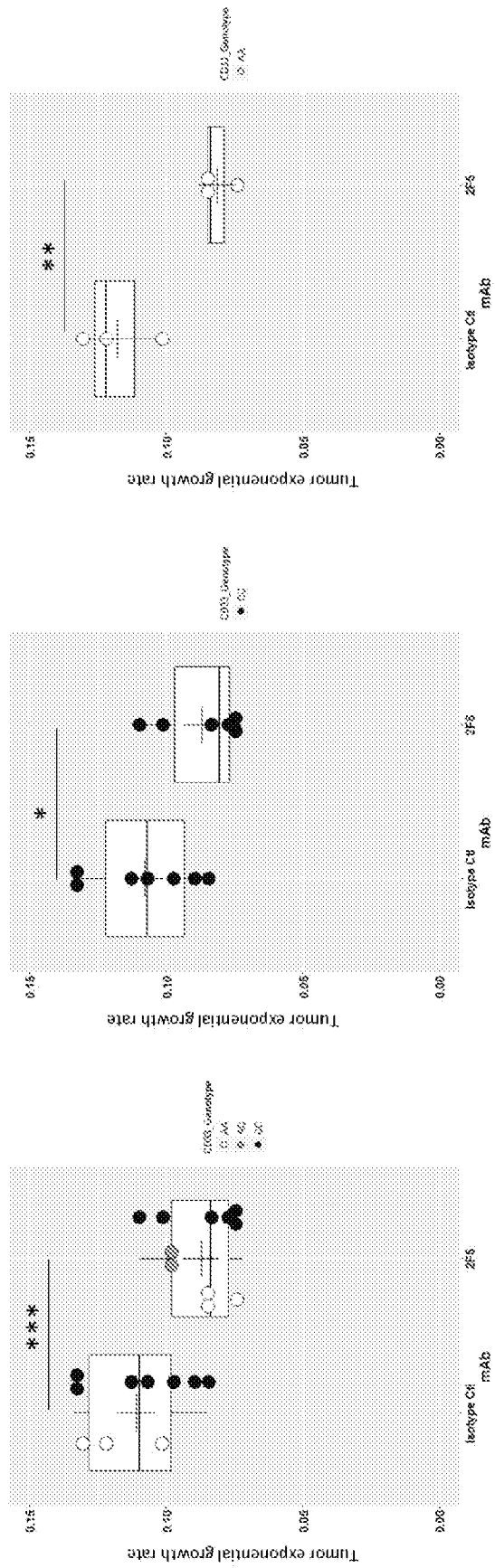
FIG. 15V depicts in vivo tumor growth rate in mice containing any of the Alzheimer's disease CD33 alleles rs3865444 A/A allele, A/C allele and C/C allele and that were treated with anti-CD33 antibody 2F5 or isotype control (Ctl) antibody. *: $p<0.05$; : $p<0.01$; *: $p<0.001$ for 2F5 vs Isotype Ctl, +: mean; boxplot midline: median; upper and lower boundaries of the boxes correspond to the first and third quartiles (25th and 75th percentiles).
FIG. 15W depicts in vivo tumor growth rate in mice containing the Alzheimer's disease rs3865444 C/C allele. *: $p<0.05$; : $p<0.01$; *: $p<0.001$ for 2F5 vs Isotype Ctl, +: mean; boxplot midline: median; upper and lower boundaries of the boxes correspond to the first and third quartiles (25th and 75th percentiles).
FIG. 15X depicts in vivo tumor growth rate in mice containing the Alzheimer's disease rs3865444 A/A allele. *: $p<0.05$; : $p<0.01$; *: $p<0.001$ for 2F5 vs Isotype Ctl, +: mean; boxplot midline: median; upper and lower boundaries of the boxes correspond to the first and third quartiles (25th and 75th percentiles).

As shown in FIGS. 15V, 15W, and 15X, treatment with CD33 antibody2F5 alone reduced tumor growth rate independent of the CD33 single nucleotide polymorphism (SNP) CD33 alleles rs3865444 A/A, A/C, or C/C present in a mouse tumor model that was engrafted with human immune stem cells and the patient-derived xenograft CTG-0202 melanoma tumor. The rs3865444 C/C allele is a risk allele for Alzheimer's disease, while the rs3865444 A/A allele is a protective allele for Alzheimer's disease.

Figure 15Y:
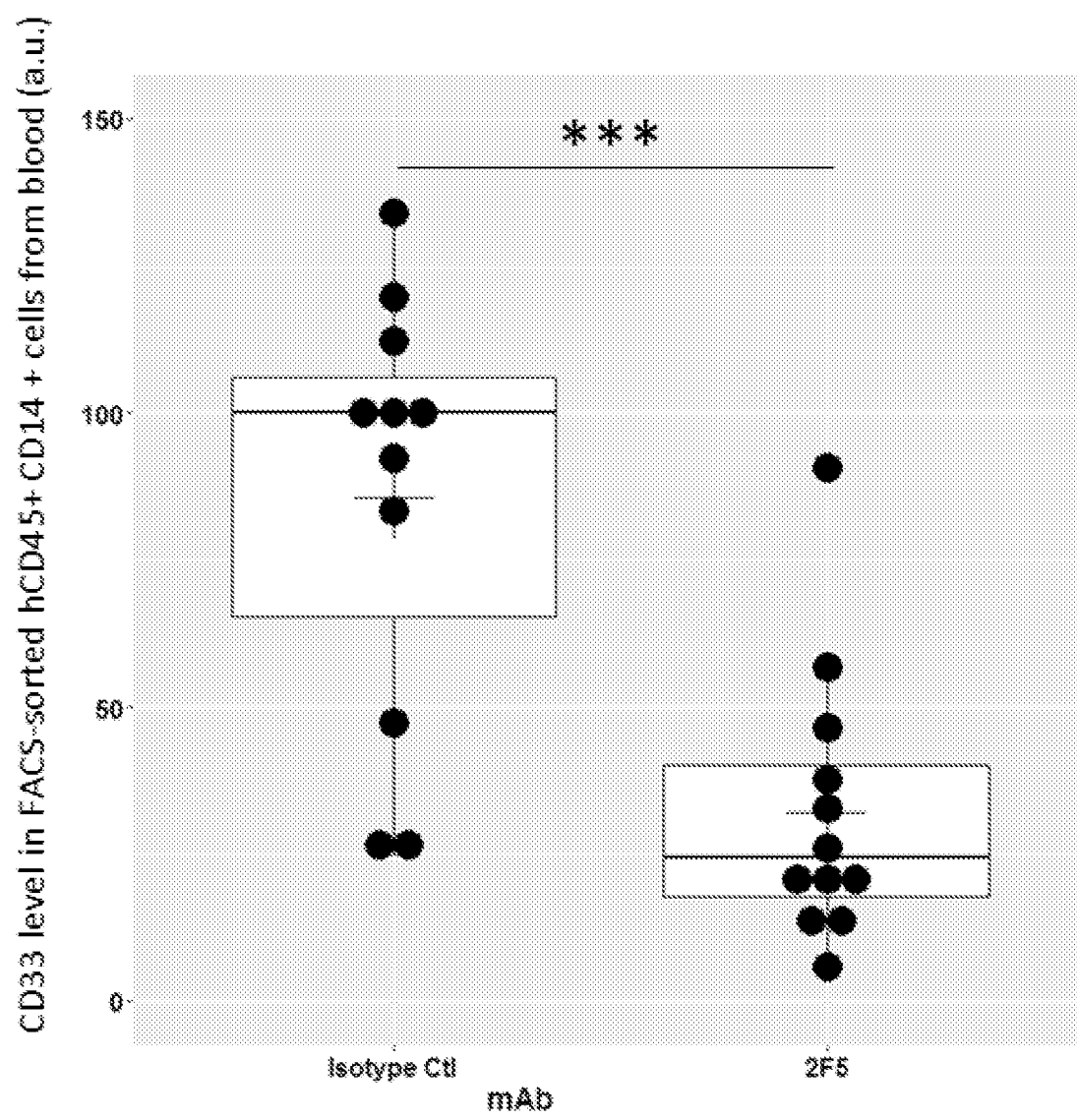
FIG. 15Y depicts in vivo reduction in cell surface levels of CD33 in peripheral blood human (h) CD45$^+$CD14$^+$ myeloid cells from mice treated with anti-CD33 antibody 2F5 or isotype control (Ctl) antibody. *: $p<0.001$ for 2F5 vs Isotype Ctl, correcting for donor and day of animal sacrifice, +: mean; boxplot midline: median; upper and lower boundaries of the boxes correspond to the first and third quartiles (25th and 75th percentiles).

As shown in FIG. 15Y, treatment with CD33 antibody2F5 alone reduced cell surface levels of CD33 in peripheral blood hCD45⁺ CD14⁺ myeloid cells from a mouse tumor model that was engrafted with human immune stem cells and the patient-derived xenograft CTG-0202 melanoma tumors. Statistical significance was assessed by multiple linear regression using R lm( ) function.

Figures 15A, 15B, 15Z:
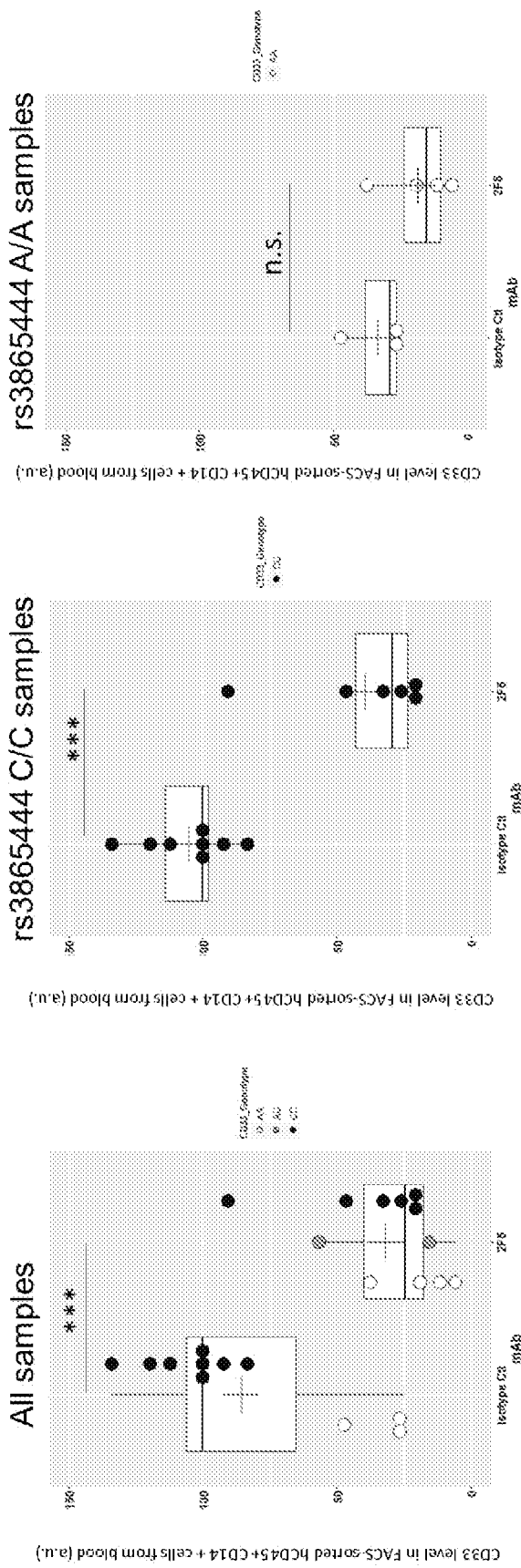
FIG. 15Z depicts in vivo reduction in cell surface levels of CD33 in peripheral blood human (h) CD45$^+$CD14$^+$ myeloid cells from mice containing any of the Alzheimer's disease CD33 alleles rs3865444 A/A allele, A/C allele and C/C allele and that were treated with anti-CD33 antibody 2F5 or isotype control (Ctl) antibody. *: $p<0.001$ for 2F5 vs Isotype Ctl, correcting for donor and day of animal sacrifice, +: mean; boxplot midline: median; upper and lower boundaries of the boxes correspond to the first and third quartiles (25th and 75th percentiles).
Figure 15C:
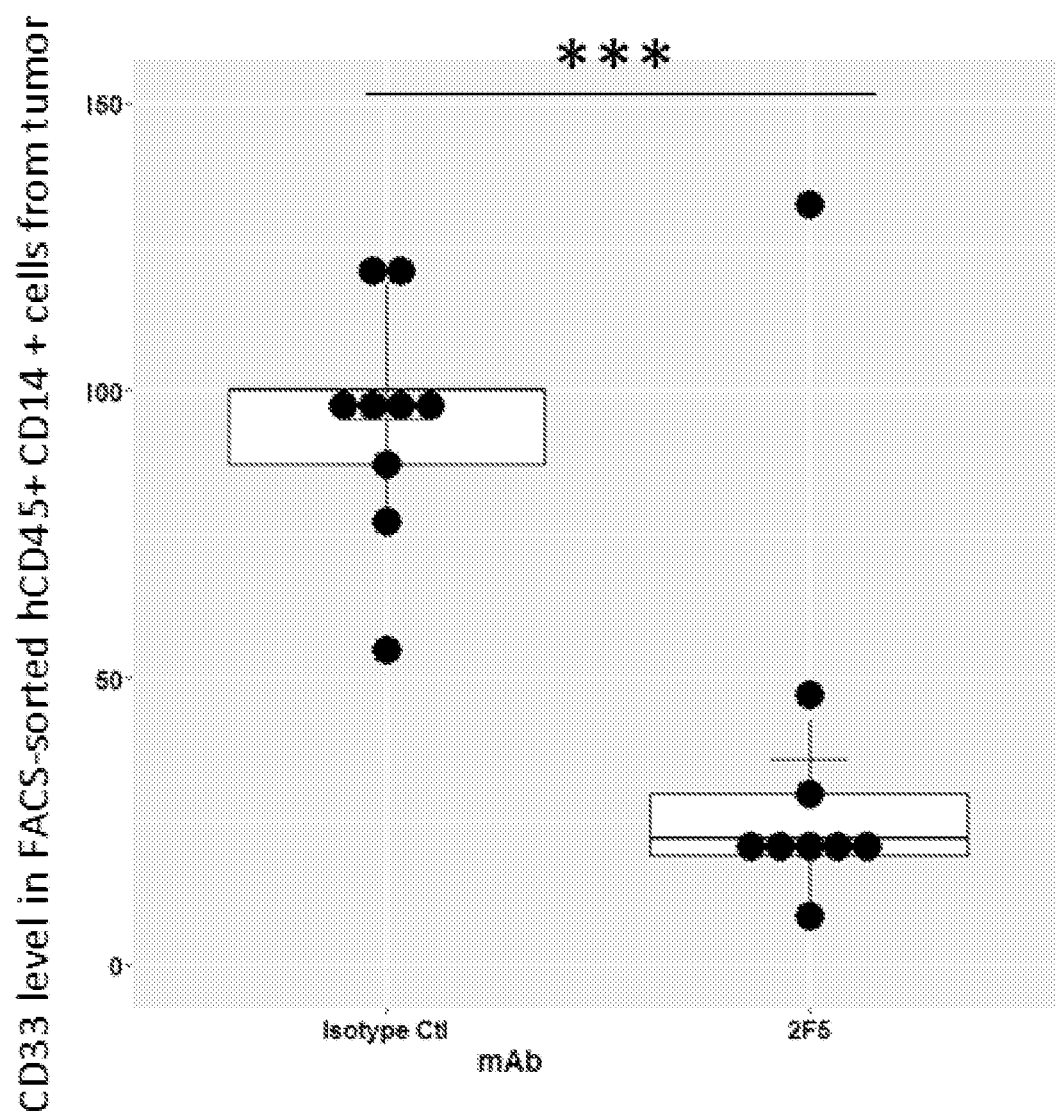
Figures 15D, 15E, 15F:
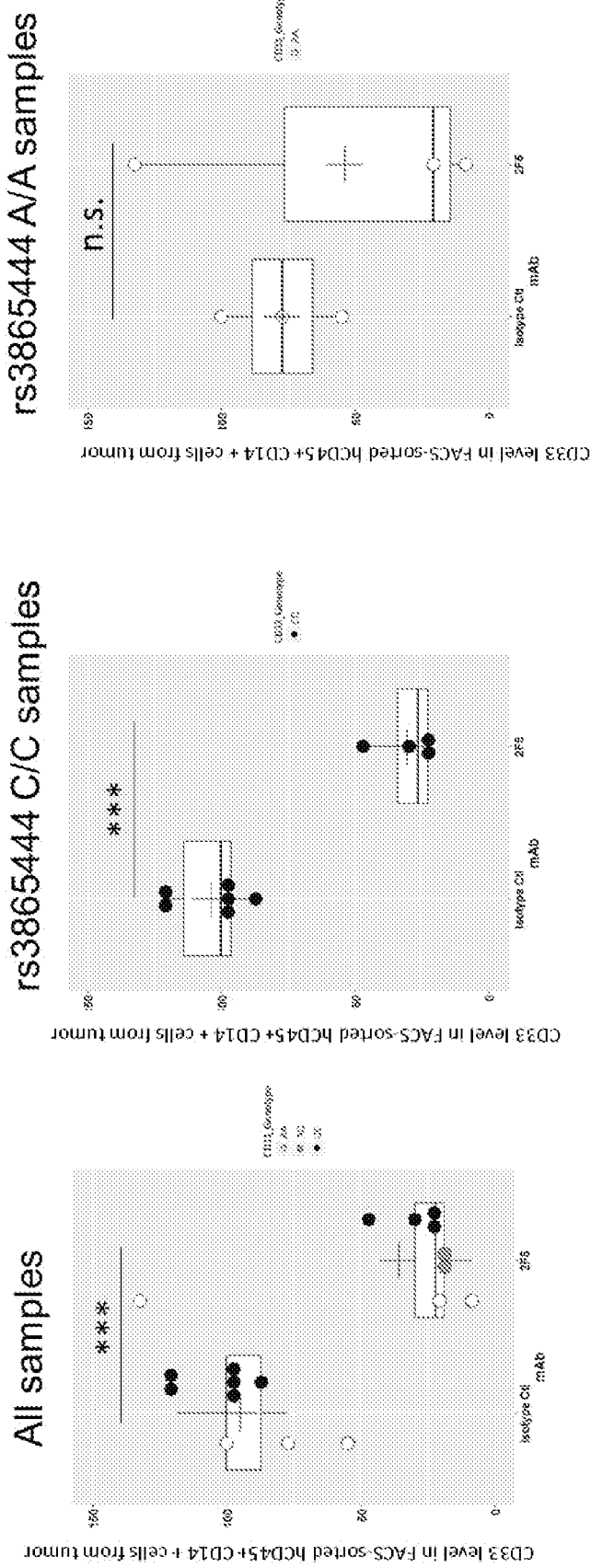
Figure 15G:
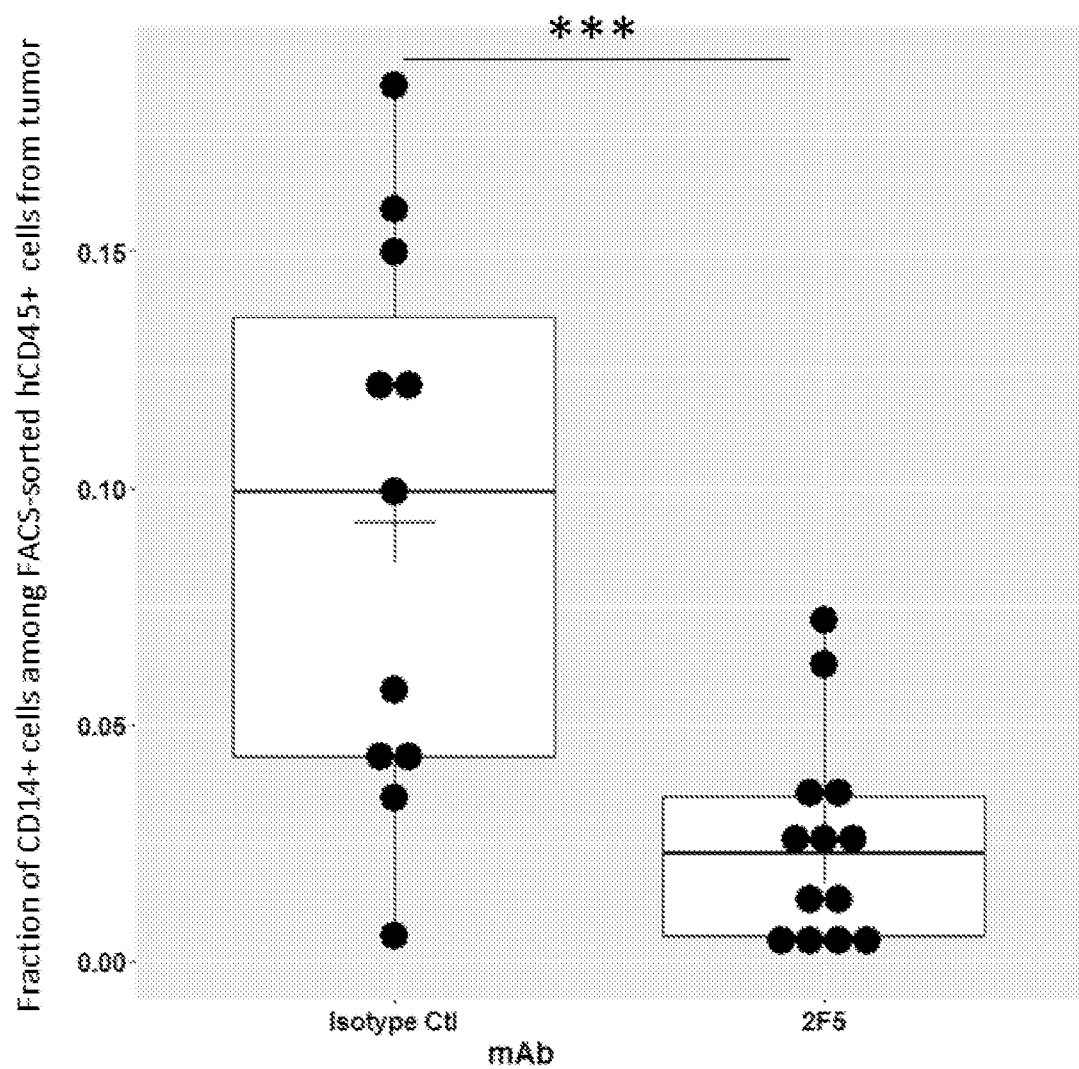
Figures 15H, 15I, 15J:
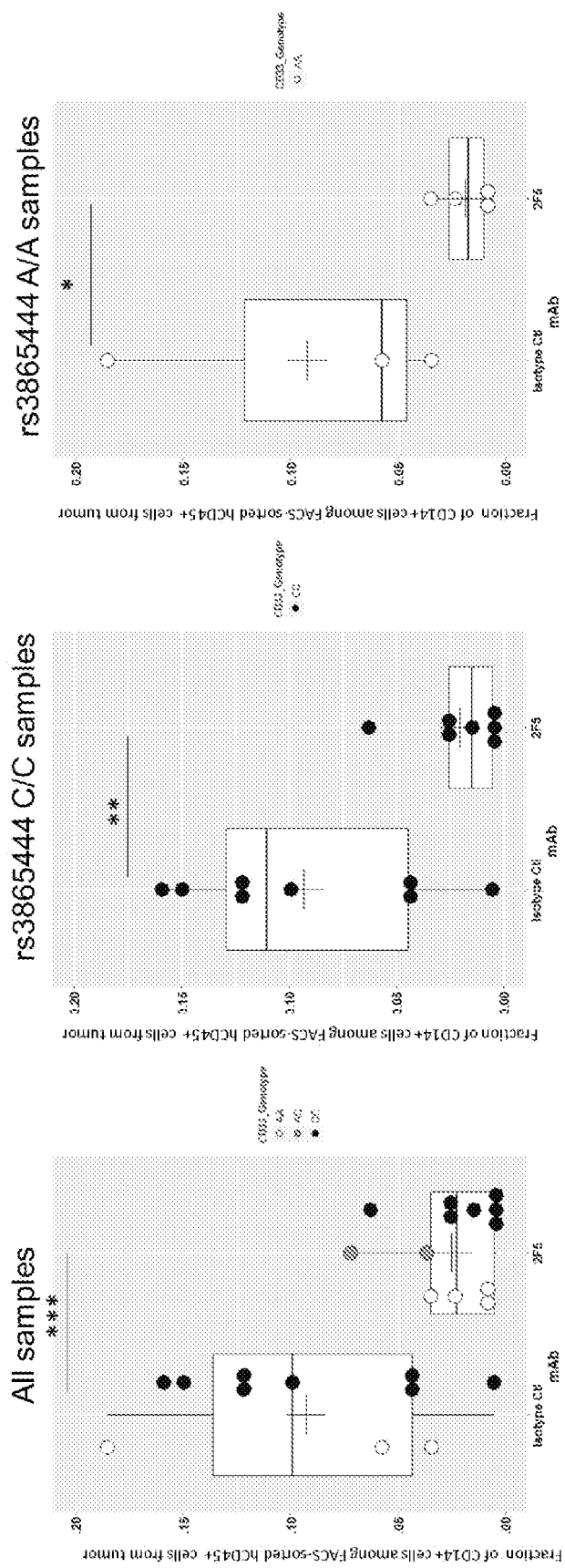
Figure 15K:
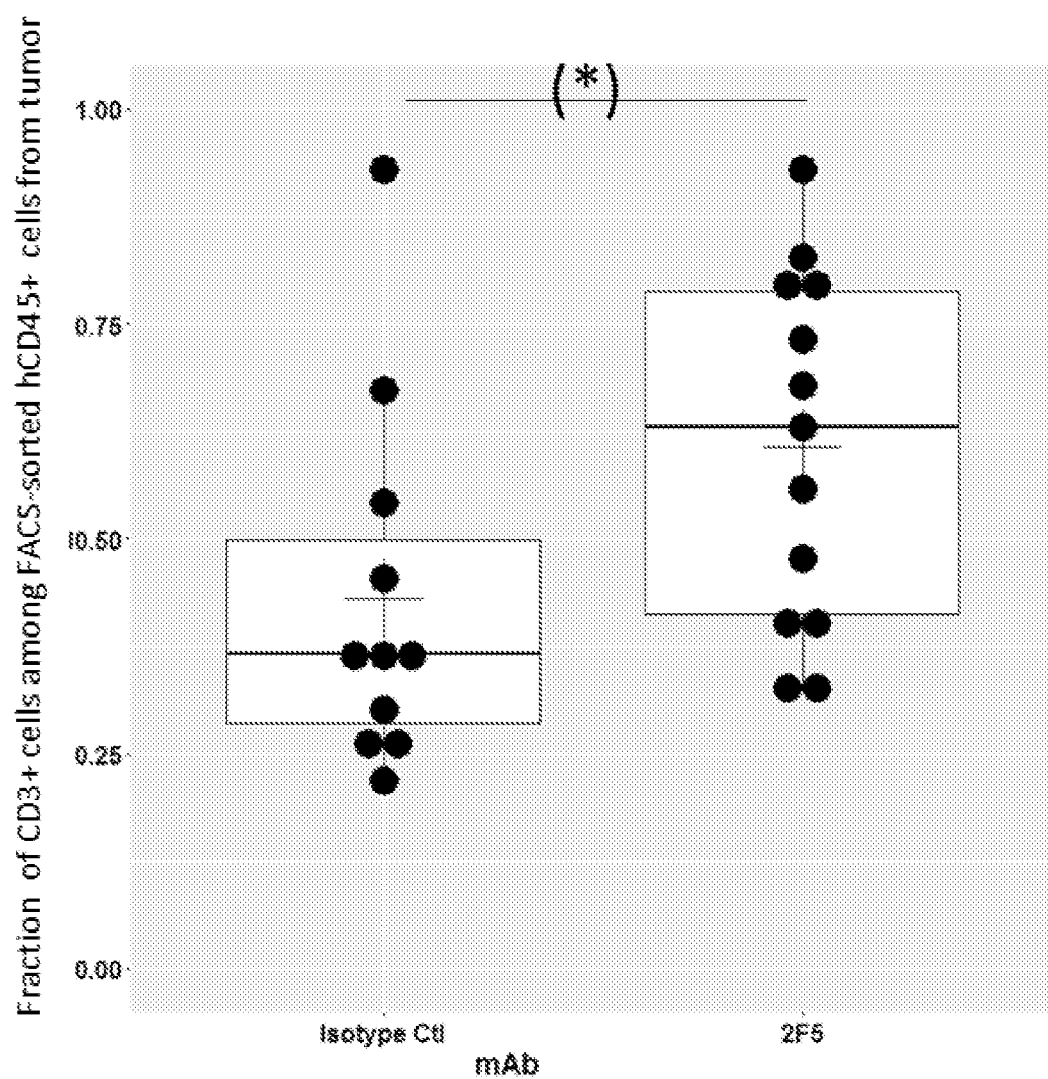
Figures 15L, 15M, 15N:
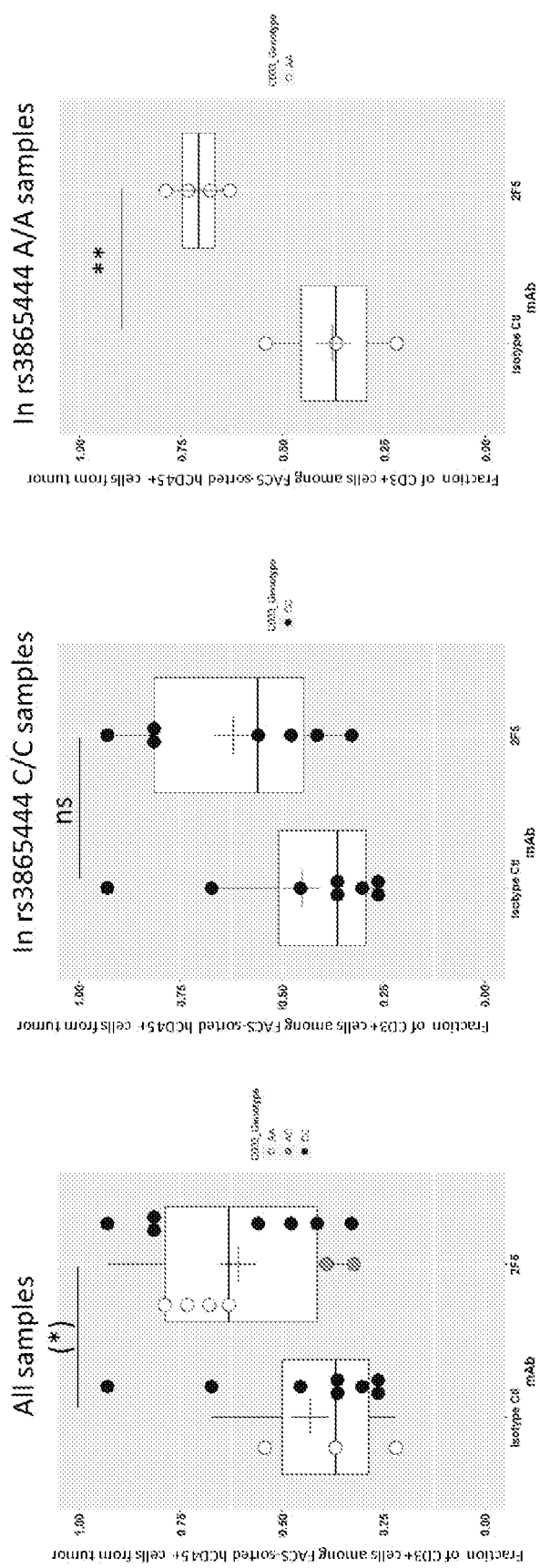
Figure 15O:
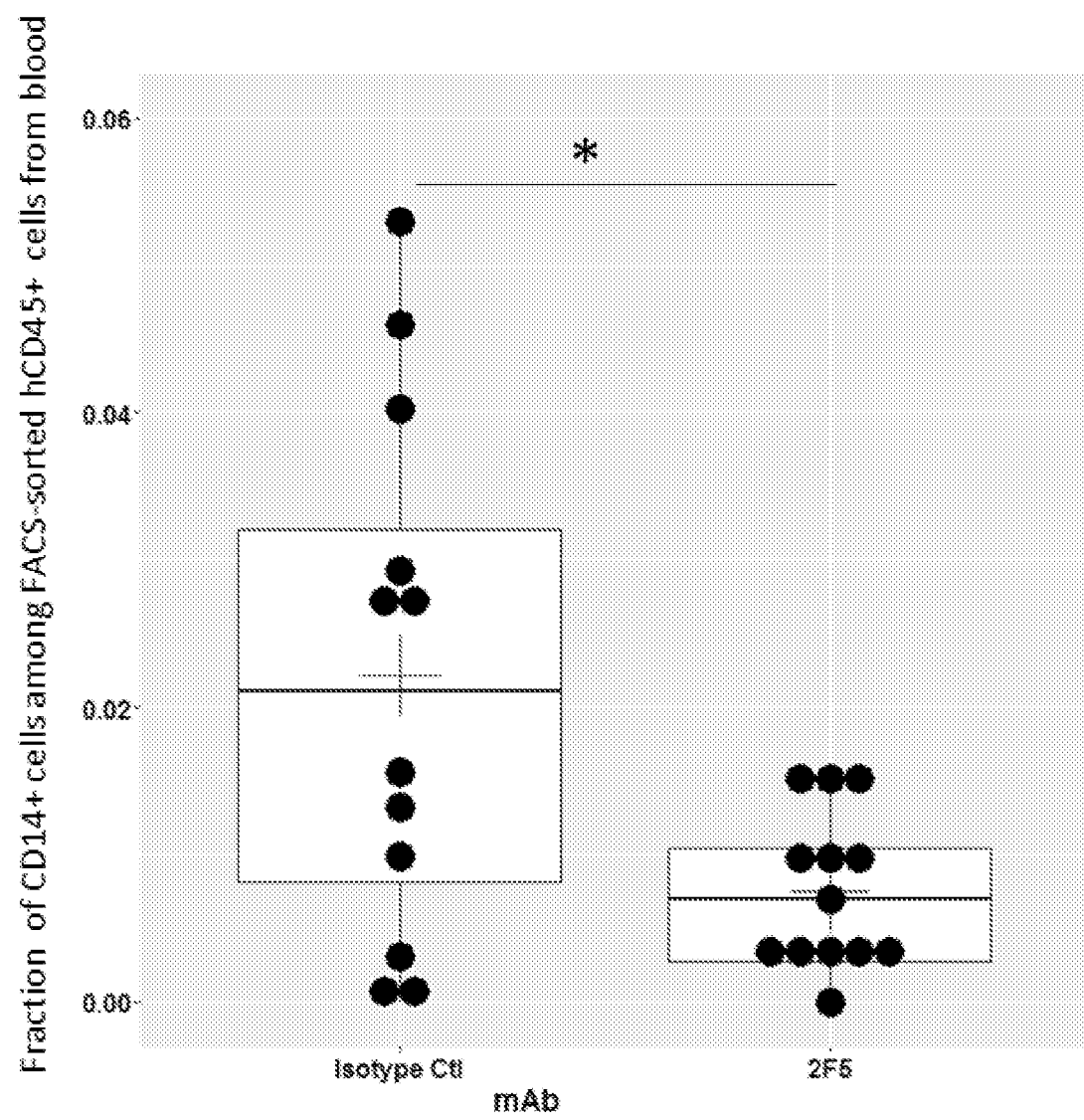
Figures 15P, 15Q, 15R:
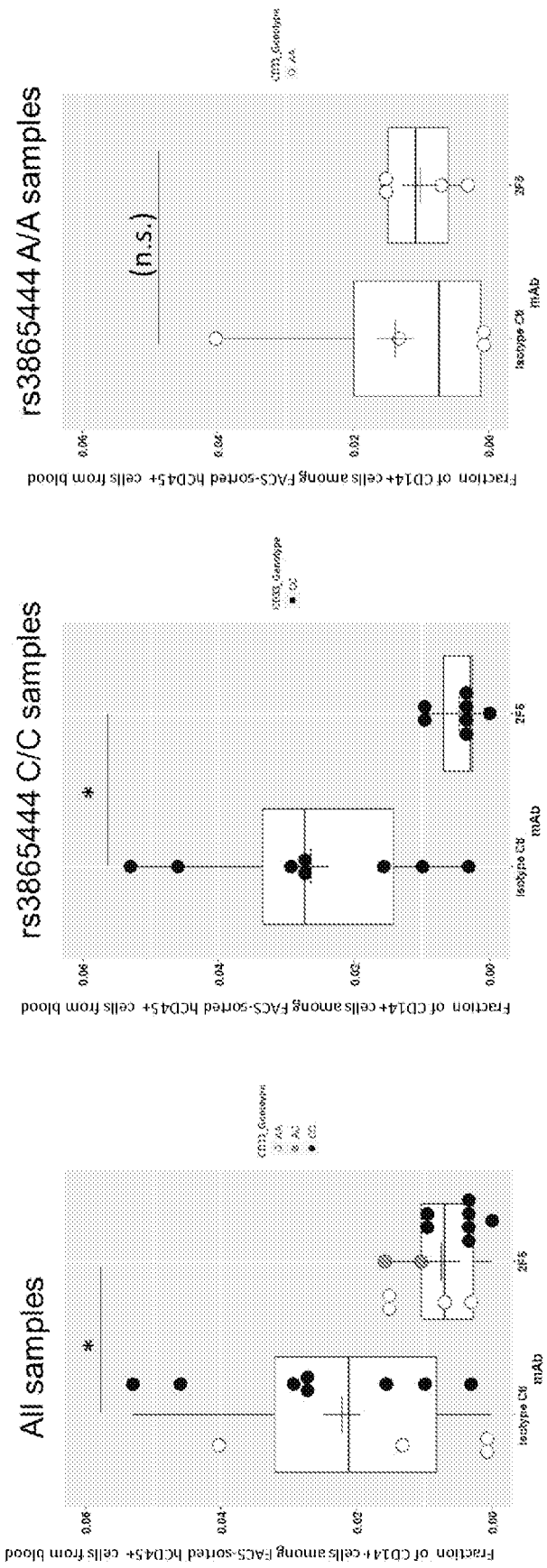

As shown in FIGS. 15Z, 15AA, and 15BB, treatment with CD33 antibody2F5 alone reduced cell surface levels of CD33 in peripheral blood hCD45⁺ CD14⁺ myeloid cells from a mouse tumor model that was engrafted with human immune stem cells and the patient-derived xenograft CTG-0202 melanoma tumors, where single nucleotide polymorphism (SNP) CD33 alleles rs3865444 A/A, A/C, or C/C were present in the mice. The reduction in cell surface levels of CD33 was statistically significant in mice that were carriers for the Alzheimer's disease risk allele rs3865444 C/C (FIGS. 15Z and 15AA), but not for mice that were carriers of the Alzheimer's disease protective allele rs3865444 A/A (FIG. 15BB).

As shown in FIG. 15CCC, treatment with CD33 antibody2F5 alone reduced cell surface levels of CD33 in tumor infiltrating hCD45⁺ CD14⁺ myeloid cells from a mouse tumor model that was engrafted with human immune stem cells and the patient-derived xenograft CTG-0202 melanoma tumors. Statistical significance was assessed by multiple linear regression using R lm( ) function.

As shown in FIGS. 15DD, 15EE, and 15FF, treatment with CD33 antibody2F5 alone reduced cell surface levels of CD33 in tumor infiltrating hCD45⁺ CD14⁺ myeloid cells from a mouse tumor model that was engrafted with human immune stem cells and the patient-derived xenograft CTG-0202 melanoma tumors, where single nucleotide polymorphism (SNP) CD33 alleles rs3865444 A/A, A/C, or C/C were present in the mice. The reduction in cell surface levels of CD33 was statistically significant in mice that were carriers for the Alzheimer's disease risk allele rs3865444 C/C (FIGS. 15DD and 15EE), but not for mice that were carriers of the Alzheimer's disease protective allele rs3865444 A/A (FIG. 15FF).

As shown in FIG. 15GG, treatment with CD33 antibody2F5 alone reduced the number of tumor infiltrating hCD45⁺ CD14⁺ myeloid cells in a mouse tumor model that was engrafted with human immune stem cells and the patient-derived xenograft CTG-0202 melanoma tumors. Statistical significance was assessed by multiple linear regression using R lm( ) function.

As shown in FIGS. 15HH, 15II, and 15JJ, treatment with CD33 antibody2F5 alone reduced the number of tumor infiltrating hCD45⁺ CD14⁺ myeloid cells in a mouse tumor model that was engrafted with human immune stem cells and the patient-derived xenograft CTG-0202 melanoma tumors, where single nucleotide polymorphism (SNP) CD33 alleles rs3865444 A/A, A/C, or C/C were present in the mice. The reduction in tumor infiltrating hCD45⁺ CD14⁺ myeloid cells was statistically significant in mice that were carriers for the Alzheimer's disease risk allele rs3865444 C/C and the Alzheimer's disease protective allele rs3865444 A/A (FIG. FIGS. 15HH, 15II, and 15JJ).

As shown in FIG. 15KK, treatment with CD33 antibody2F5 alone increased the number of tumor infiltrating hCD45⁺ CD3⁺ T cells in a mouse tumor model that was engrafted with human immune stem cells and the patient-derived xenograft CTG-0202 melanoma tumors. Statistical significance was assessed by multiple linear regression using R lm( ) function.

As shown in FIGS. 15LL, 15MM, and 15NN, treatment with CD33 antibody2F5 alone increased the number of tumor infiltrating hCD45⁺ CD3⁺ T cells independent of the CD33 single nucleotide polymorphism (SNP) CD33 alleles rs3865444 A/A, A/C, or C/C present in a mouse tumor model that was engrafted with human immune stem cells and the patient-derived xenograft CTG-0202 melanoma tumors. The rs3865444 C/C allele is a risk allele for Alzheimer's disease, while the rs3865444 A/A allele is a protective allele for Alzheimer's disease.

As shown in FIG. 15OO, treatment with CD33 antibody2F5 alone reduced the number of peripheral blood hCD45$^+$ CD14$^+$ myeloid cells in a mouse tumor model that was engrafted with human immune stem cells and the patient-derived xenograft CTG-0202 melanoma tumors. Statistical significance was assessed by multiple linear regression using R lm( ) function.

As shown in FIGS. 15PP, 15QQ, and 15RR, treatment with CD33 antibody2F5 alone reduced the number of peripheral blood hCD45$^+$ CD14$^+$ myeloid cells independent of the CD33 single nucleotide polymorphism (SNP) CD33 alleles rs3865444 A/A, A/C, or C/C present in a mouse tumor model that was engrafted with human immune stem cells and the patient-derived xenograft CTG-0202 melanoma tumors. The rs3865444 C/C allele is a risk allele for Alzheimer's disease, while the rs3865444 A/A allele is a protective allele for Alzheimer's disease.

Conclusions of In Vivo Effects of Antibody Treatments

The results depicted in FIG. 15F-15RR demonstrate the pre-clinical efficacy of anti-CD33 antibody 2F5 as a therapeutic for treating human cancer (e.g., melanoma). The 2F5 antibody is a potent receptor downregulator and ligand-blocking antibody. The 2F antibody, when administered as a monotherapy therapy (FIG. 15R-15RR) or in combination with an anti-PD-1 antibody (FIG. 15F-15Q), significantly reduces tumor volume and tumor growth rate in melanoma tumors. Notably, administration of an isotype control (or a lower affinity/non-ligand blocking CD33 antibody) alone or in combination with the anti-PD-1 antibody did not inhibit tumor growth.

Analysis of the tumor infiltrating immune cell populations treated with either the CD33 antibody monotherapy or in combination with the anti-PD-1 antibody demonstrated a significant increase in the number of tumor infiltrating CD3$^+$ T cells (FIGS. 15P and 15KK-15NN). Myeloid cell populations were reduced by CD33 antibody monotherapy or in combination with the anti-PD-1 antibody (FIGS. 15O, 15Q, 15GG-15JJ, and 15OO-15RR). A significant decrease in both tumor infiltrating CD14$^+$ myeloid cells and peripheral blood iCD14$^+$ myeloid cells was observed.

Notably, both the tumor and immune system responding to the tumor are human in this mouse study. The immune system of the mouse is humanized using a method whereby the mouse immune system is genetically ablated and replaced with human donor CD34$^+$ hematopoietic stem and progenitor cells that repopulate and develop myeloid and lymphoid immune cells. The tumor is a patient-derived melanoma. The results demonstrate that a human-specific anti-CD33 antibody (2F5) displays target specific engagement and reduces cell surface levels of human CD33. Downregulation of cell surface levels of CD33 was significant on peripheral and tumor CD14$^+$ myeloid cells. Therefore any effects on tumor volume, tumor growth rate, increased number of tumor infiltration of CD3$^+$ T cells, and reduced number of CD14$^+$ cells are a result of 2F5 antibody-mediated downregulation of CD33 on human myeloid immune cells.

Additionally, the results takes into account the CD33 genotype of human donors used to re-populate the immune systems of the tumor-implanted mice. Upon assessment of the CD33 SNP rs3865444, which has been demonstrated to be an Alzheimer's disease risk allele, donors with the protective rs3865444 A/A allele showed lower CD33 cell surface levels and reduced tumor growth rates as compared to donors who were carriers of the rs3865444 C risk allele. Furthermore, treatment with CD33 antibody 2F5 phenocopied the CD33 genotype, in that the 2F5 antibody reduced cell surface CD33 levels on CD14$^+$ myeloid cells and reduced tumor growth rates in both studies.

Example 11: Reduction of the Anti-Inflammatory Cytokine IL-10 in Myeloid Cells by Antagonistic and/or Bispecific CD33 Antibodies The purpose of this Example is to test whether bone marrow-derived myeloid cells show a decrease in the anti-inflammatory cytokine IL-10 and other anti-inflammatory mediators following treatment with antagonistic anti-CD33 and/or CD33 bispecific antibodies and stimulation with 100 ng/ml LPS (Sigma), by co-culturing with apoptotic cells, or by a similar stimulus.

Isolation of human myeloid precursor cells is performed as previously described. Medium is changed after 5 d and cells are cultured for an additional 10-11 d. Supernatant is collected after 24 h, and the level of IL-10 and other anti-inflammatory cytokines released from the cells is determined by IL-10 ELISA according to manufacturer's instructions (R&D Systems) (JEM (2005), 201; 647-657; and PLoS Medicine (2004), 4|Issue 4|e124).

Example 12: Induction of Phagocytosis in Cells from the Myeloid Lineage by Antagonistic and/or Bispecific CD33 Antibodies The purpose of this Example is to test whether antagonistic anti-CD33 antibodies and/or CD33 bispecific antibodies induce phagocytosis of apoptotic neurons, nerve tissue debris, non-nerve tissue debris, bacteria, other foreign bodies, and disease-causing proteins, such as A beta peptide, alpha synuclain protein, Tau protein, TDP-43 protein, prion protein, huntingtin protein, RAN, translation products anti-gene, including the DiPeptide Repeats, (DPRs peptides) composed of glycine-alanine (GA), glycine-proline (GP), glycine-arginine (GR), proline-alanine (PA), or proline-arginine (PR) in cells from the myeloid lineage, such as monocytes, Dendritic cells macrophages and microglia. The bispecific antibodies may be antibodies that recognize the CD33 antigen and a second antigen that includes, without limitation, A beta peptide, antigen or an alpha synuclain protein antigene or, Tau protein antigene or, TDP-43 protein antigene or, prion protein antigene or, huntingtin protein antigene, or RAN, translation Products antigene, including the DiPeptide Repeats, (DPRs peptides) composed of gly-cine-alanine (GA), glycine-proline (GP), glycine-arginine (GR), proline-alanine (PA), or proline-arginine (PR).

Monocytes from peripheral human blood samples are isolated using the RosetteSep monocyte isolation antibody cocktail (StemCell Technologies) and differentiated into macrophages with 50 μg/ml M-CSF (PeproTech) for 5 days. Cells are plated on culture dishes in RPMI medium (Invitrogen) containing 10% fetal calf serum (Hyclone) and cultured at 37° C. in 5% $CO_2$. Adherent cells are collected by gentle scraping and used for phagocytosis experiments.

Human microglial cells are prepared from peripheral blood monocytes by culture in serum-free RPMI with 1% Pen/Strep, 10 ng/ml GM-CSF, 10 ng/ml M-CSF, 10 ng/ml beta-NGF, 100 ng/ml CCL-2, 100 ng/ml IL-34 according to protocols described in Etemad et al., JI (2012), and Ohgidani et al., *Scientific Reports* (2014). Cells were harvested at day 7-10 when ramified morphology appeared.

To conduct phagocytosis assays microglia, macrophages or dendritic cells are cultured with apoptotic neurons, nerve tissue debris, non-nerve tissue debris, bacteria, other foreign bodies, and disease-causing proteins. Neurons are cultured for 5-10 d, and okadaic acid is then added at the final concentration of 30 nM for 3 h to induce apoptosis. Neuronal cell membranes are labeled with CellTracker CM-DiI membrane dye (Molecular Probes). After incubation, apoptotic neurons or other targets of phagocytosis are washed two times and added to the transduced microglial culture at an effector/target ratio of 1:20. At 1 and 24 h after addition of apoptotic neurons, the number of microglia having phagocytosed neuronal cell membranes is counted under a confocal fluorescence microscope (Leica). Apoptotic cells are counted in three different areas at a magnification of 60. The amount of phagocytosis is confirmed by flow cytometry. Moreover, 24, 48, or 72 h after the addition of apoptotic neurons, cells are collected and used for RT-PCR of cytokines.

To conduct microsphere bead or bacterial phagocytosis assay, microglia, macrophages or dendritic cells are treated with anti-CD33 agonistic antibodies. Cells are harvested and plated in 96-well flat bottom plates without cytokine for 2 hours. pHrodo-labeled *E. coli* BioParticles are resuspended according to manufacturer's protocol and are treated with 0.2 U/ml or 0.4 U/ml sialidase from Vibro cholera, or PBS alone for 2.5 hours at 37 C. BioParticles are washed, resuspended in RPMI and added 20 µg/well. Cells and *E. coli* were mixed, pelleted, and incubated at 37C for 30 minutes. Cytochalasin D is added at 10 uM to control wells Immediately prior to FACS analysis, cells are transferred to ice and washed 2× in FACS buffer at 4 C. The pHrodo-labeled *E. coli* phagocytosis is detected in the PE channel by flow cytometry on a BD FACS Canto.

After 24 h, 1.00 µm of red fluorescent microsphere beads (Fluoresbrite Polychromatic Red Mi-crospheres; Polysciences Inc.) are added for 1 h. Phagocytosis of microsphere beads by microglia is analyzed by fluorescence microscopy. Furthermore, microglia are collected from the culture plates and analyzed by flow cytometry. The percentage of microglia having phagocytosed beads is determined. Because phagocytosis varies from one experiment to the other, the relative change in phagocytosis is also determined. Data are shown as the relative change in phagocytosis between microglia cultured with agonistic antibodies and control antibody.

To conduct RT-PCR for analysis of inflammatory gene transcripts, microglia are transduced with a CD33 vector or a GFP1 control vector. Cells are then cultured on dishes and treated with anti-CD33 agonistic antibodies. After 24, 48, and 72 h, RNA is isolated from microglia using an RNeasy Mini Kit (QIAGEN). RNA is also collected from microglia that have been transduced with sh-CD33 RNA, sh-control RNA, wCD33, GFP2, mtDAP12-GFP, and GFP1 vector and co-cultured with apoptotic neurons for 48 h.

Reverse transcription of RNA is then performed. Quantitative RT-PCR by SYBR Green is performed on an ABI Prism 5700 Sequence Detection System (PerkinElmer). Amplification of GAPDH is used for sample normalization. The amplification protocol followed the GeneAmp 5700 Sequence Detection System Software (version 1.3). For detection of GAPDH, TNF-alpha, IL-1, NOS2, and TGF-beta transcripts, the following forward and reverse primers were used at final concentrations of 200 nM:

```
GAPDH forward primer:
                              (SEQ ID NO: 218)
5'-CTCCACTCACGGCAAATTCAA-3',
and GAPDH reverse primer:
                              (SEQ ID NO: 219)
5'-GATGACAAGCTTCCCATTCTCG-3';

TNF-α forward primer:
                              (SEQ ID NO: 220)
5'-CCGTCAGCCGATTTGCTATCT-3',
and TNF-α reverse primer:
                              (SEQ ID NO: 221)
5'-ACGGCAGAGAGGAGGTTGACTT-3';

IL-1α forward primer:
                              (SEQ ID NO: 222)
5'-ACAA- CAAAAAAGCCTCGTGCTG-3',
and IL-1α reverse primer:
                              (SEQ ID NO: 223)
5'-CCATTGAGGTGGAGAGCTTTCA-3';

NOS2 forward primer:
                              (SEQ ID NO 224)
5'-GGCAAACCCAAGGTCTACGTTC-3', NOS2 reverse primer:
                              (SEQ ID NO: 225)
5'-TACCTCATTGGCCAGCTGCTT-3';
and TGF-β1 forward primer:
                              (SEQ ID NO: 226)
5'-AGGACCTGGGTTGGAAGTGG-3',
and TGF-β1 reverse primer:
                              (SEQ ID NO: 227)
5'-AGTTGGCATGGTAGCCCTTG-3'.
```

To conduct amyloid phagocytosis assay, HiLyteFluor™ 647 (Anaspec)-Abeta-(1-40) is resuspended in Tris/EDTA (pH 8.2) at 20 mM and then incubated in the dark for 3 d at 37° C. to promote aggregation. Microglia, macrophages or dendritic cells are pretreated in low serum (0.5% FBS supplemented with insulin), LPS (50 ng/ml), IFNc (100 units/ml), and anti-CD33 antagonistic antibodies for 24 h prior to the addition of aggregated fluorescently labeled a beta peptide. Amyloid phagocytosis and surface expression of CD33 are determined by flow cytometric analysis 5 h post-addition of 100 nM aggregated HiLyteFluor™ 647-Ab-(1-40) (ASN NEURO (2010) 2(3): 157-170). Phagocytosis of other disease-causing proteins is conducted in a similar manner.

Example 13: Induction of SYK and/or ERK Activation by Antagonistic CD33 Antibodies and/or Bispecific Antibodies The purpose of this Example is to test whether agonistic anti-CD33 antibodies and/or CD33/bispecific antibodies induce Syk and ERK activation.

Microglia, macrophages or dendritic cells are exposed to agonistic anti-CD33 and/or CD33 bispecific antibodies for 1 h. After stimulation, cells are lysed in reducing sample buffer for Western blot analysis. Phosphorylation of ERK and total amount of Syk and/or ERK are determined by immunodetection with anti-phospho-Syk or ERK and anti-Syk or ERK antibodies, respectively (both from Cell Signaling Technology) by Western blot analysis (JEM (2005), 201, 647-657).

Example 14: CD33 Antibodies and/or Bispecific Antibodies Induce Syk Phosphorylation Spleen tyrosine kinase (Syk) is an intracellular signaling molecule that functions downstream of CD33 by phosphorylating several substrates, thereby facilitating the formation of a signaling complex leading to cellular activation and inflammatory processes. The ability of agonist CD33 antibodies to induce Syk activation is determined by culturing human macrophages and human primary dendritic cells and measuring the phosphorylation state of Syk protein in cell extracts.

Human primary dendritic cells are starved for 4 hours in 1% serum RPMI and then removed from tissue culture dishes with PBS-EDTA, washed with PBS, and counted. The cells are coated with full-length agonist CD33 antibodies, or control antibodies for 15 minutes on ice. After washing with cold PBS, cells are incubated at 37° C. for the indicated period of time in the presence of goat anti-human IgG. After stimulation, cells are lysed with lysis buffer (1% v/v NP-40%, 50 Mm Tris-HCl (pH 8.0), 150 mM NaCl, 1 mM EDTA, 1.5 mM $MgCl_2$, 10% glycerol, plus protease and phosphatase inhibitors) followed by centrifugation at 16,000 g for 10 min at 4° C. to remove insoluble materials. Lysates are then immunoprecipitated with anti-Syk Ab (4D10 for human DCs, Santa Cruz Biotechnology). Precipitated proteins are fractionated by SDS-PAGE, transferred to PVDF membranes and probed with anti-phosphotyrosine Ab (4G10, Millipore). To confirm that all substrates are adequately immunoprecipitated, immunoblots are reprobed with anti-Syk (Novus Biological, for human DCs). Visualization is performed with the enhanced chemiluminescence (ECL) system (GE healthcare), as described (e.g., Peng et al., (2010) Sci Signal., 3(122): ra38).

Example 15: Induction of CCR7 and Migration Toward CCL19 and CCL21 in Microglia, Macrophages, T Cells, and Dendritic Cells by Antagonistic CD33 Antibodies and/or Bispecific Antibodies The purpose of this Example is to test whether anti-CD33 and/or CD33/bispecific antibodies induce CCR7 and migration toward CCL19 and CCL21 in microglial cells, macrophages, and dendritic cells.

Microglial, macrophages or dendritic cells are either cultured with agonistic anti-CD33 and/or CD33/DAP12 bispecific antibodies, or with a control antibody. Cells are collected after 72 h, immuno-labeled with CCR7 specific anti-bodies, and analyzed by flow cytometry.

To determine any functional consequences of increased CCR7 expression, a chemotaxis assay is performed. Microglia, macrophages or dendritic cells are stimulated via CD33 with the antagonistic anti-CD33 and/or CD33/DAP12 bispecific antibodies and placed in a two-chamber system. The number of microglial cells migrating toward the chemokine ligands CCL19 and CCL21 is quantified (JEM (2005), 201, 647-657).

For the chemotaxis assay, microglial, macrophages or dendritic cells are exposed to the antagonistic anti-CD33 or CD33/bispecific antibodies and treated with 1 µg/ml LPS. Microglia, macrophages or dendritic cells are transferred into the upper chamber of a transwell system (3 µm pore filter; Millipore) containing 450 µl medium with 100 ng/ml CCL19 or CCL21 (both from PeproTech) in the lower chamber. After a 1 h incubation period, the number of microglial macrophages or dendritic cells that have migrated to the lower chamber is counted in three independent areas by microscopy (JEM (2005), 201, 647-657).

Example 16: Induction of F-Actin in Microglia, Macrophages, T Cells, and Dendritic Cells by Antagonistic CD33 Antibodies and/or Bispecific Antibodies The purpose of this Example is to test whether antagonistic anti-CD33, or CD33 bispecific antibodies induce F-actin in microglial cells, macrophages, and dendritic cells.

Microglia, macrophages or dendritic cells and other cells of interest that are transduced with CD33 or that express CD33 are added to culture plates and then exposed to antagonistic anti-CD33 and/or CD33 bispecific antibodies, or a control antibody. Cells are fixed, blocked, and then stained with Alexa Fluor 546-conjugated phalloidin (Molecular Probes) after 1 h and F-actin is labeled with a fluorescence dye. Images are collected by confocal laser scanning microscopy with a 40× objective lens (Leica). (JEM (2005), 201, 647-657).

Example 17: Induction of Osteoclast Production and Increased Rate of Osteoclastogenesis by Antagonistic CD33 Antibodies and/or Bispecific Antibodies The purpose of this Example is to test whether antagonistic anti-CD33 antibodies and/or CD33 bispecific antibodies induce osteoclast production and increase the rate of osteoclastogenesis.

Human monocyte derived monocyte/macrophage are maintained in RPMI-1640 medium (Mediatech), or another appropriate medium, supplemented with 10% FBS (Atlantic Biologics, Atlanta, Ga., USA) and penicillin-streptomycin-glutamine (Mediatech). Cells are seeded in 96-well plates with 3000 cells/well in alpha-MEM medium supplemented with 10% FBS, penicillin-streptomycin-glutamine, 50 ng/ml RANKL, and 20 ng/ml M-CSF. The medium is changed every 3 days, exposed to anti-CD33 antagonistic antibodies and the number of multinucleated (at least three nuclei) TRACP$^+$ osteoclasts are counted and scored by light microscopy. To determine complexity and size, osteoclasts are counted by number of nuclei (>10 or 3-10 nuclei). The surface area of osteoclasts is also measured by using Image J software (NIH). In addition, expression levels of osteoclasts genes are determined. Total RNA is extracted from osteoclastogenic cultures at different time points using TRIzol reagent (Invitrogen). After first-strand cDNA synthesis using a SuperScript III kit (Invitrogen), real-time quantitative PCR reactions are performed for Nfatc1, Acp5, Ctsk, Calcr, and Ccnd1. Relative quantification of target mRNA expression is calculated and normalized to the expression of cyclophilin and expressed as (mRNA of the target gene/mRNA of cyclophilin) $3 \times 10^6$. (J. OF BONE AND MINERAL RESEARCH (2006), 21, 237-245; *J Immunol* 2012; 188:2612-2621).

Alternatively, Macrophages are seeded onto the plates in triplicate wells and treated with RANKL, M-CSF, and with an anti-CD33 and/or CD33 bispecific antibody, or an isotype-matched control monoclonal antibody. The medium is changed every 3 days until large multinucleated cells are visible. After 3 to 5 days in culture, cells are fixed with 3.7% formaldehyde in PBS for 10 min. Plates are then washed twice in PBS, incubated for 30 s in a solution of 50% acetone and 50% ethanol, and washed with PBS. Cells are stained for tartrate-resistant acid phosphatase (TRAP) with a kit from Sigma (product 435). Multinucleated (more than two nuclei), TRAP-positive cells are then counted by light microscopy, as described (e.g., Peng et al., (2010) Sci Signal., 3(122): ra38).

Example 18: In Vivo Protection from EAE and Cuprizone in a Whole Animal

Adult 7-9 week-old female C57BL/6 mice (obtained from Charles River Laboratories) are injected in the tail base bilaterally with 200 µl of an innoculum containing 100 µg of myelin oligodendrocyte glycoprotein peptide 35-55 (amino acids MEVGWYRSPFSRVVHLYRNGK (SEQ ID NO: 215); Seqlab) and 1 mg of *Mycobacterium tuberculosis* H37 Ra (Difco) in incomplete Freund adjuvant (Difco). Pertussis toxin (200 ng; List Bio-logical Laboratories) is injected at day 0 and at day 2 after immunization. Clinical signs are scored as follows: 0, no clinical signs; 1, complete limp tail; 2, complete limp tail and abnormal gait; 3, one hind-limb paraparesis; 4, complete hindlimb paraparesis; and 5, fore- and hind-limb paralysis or moribund. Only mice having disease onset (clinical score of 1 or more) at day 14 are used for experiments. Agonistic anti-CD33 and/or CD33 bispecific antibodies are injected intraperitoneally or intravenously in EAE-diseased mice at the day of the first clinical symptoms or at any other desired time (PLoS Med (2007) 4(4): e124).

Young or aged wild-type (WT) mice are fed a standard diet (Harlan) containing 0.2% cuprizone (CPZ) powdered oxalic bis(cyclohexylidenehydrazide) (Sigma-Aldrich) for 4, 6 or 12 weeks. For Histological and immunohistochemical analyses brains are removed after mouse perfusion with 4% paraformaldehyde (PFA), fixed in 4% PFA for 24 h, followed by immersion in 30% sucrose for 24-48 h. To evaluate myelin integrity and damage, as well as cell proliferation and inflammation sections or mouse brain are stained with anti-MBP (1:100; Abcam, ab7349), -dMBP (1:2000; Millipore, ab5864), -β APP (1:100; Invitrogen, 51-2700), -SMI-31 (1:1000; Covance, smi-31R), -Iba1 (1:600; Wako, 019-19741), -BrdU (1:250; Abcam, ab1893), -GFAP (1:200; Invitrogen, 13-0300), -iNOS (1:100; BD Pharmingen, 610329), -LPL (1:400, from Dr. G. Olivecrona) and -MHC II (1:100; BD Pharmingen, 553549). For behavioral effects of the antibodies, mice are analyzed for locomotor activity using transparent polystyrene enclosures and computerized photobeam instrumentation. General activity variables (total ambulations, vertical rearings), along with indices of emotionality including time spent, distance traveled and entries, are analyzed. A battery of sensorimotor tests is performed to assess balance (ledge and platform), strength (inverted screen), coordination (pole and inclined screens) and initiation of movement (walking initiation). Motor coordination and balance are studied using a rotarod protocol (Cantoni et al., Acta Neuropathol (2015)129(3): 429-47).

Example 19: Characterization of the Therapeutic Use of Antagonistic CD33 Antibodies and/or CD33 Bispecific Antibodies in Established Animal Models of Traumatic Brain Injury The therapeutic utility of antagonistic anti-CD33 and/or CD33 bispecific antibodies is tested in established animal models of traumatic brain injury (Tanaka, Y et al. (2013) Neuroscience 231 49-60). Either regular mice or mice that express the human CD33 gene under a Bacterial artificial chromosome or under a myeloid promoter can be used. For example, a model of traumatic brain injury that induces the activation of microglia and astrocytes is used. Eight or nine week-old male C57BL/6J WT mice are used (purchased from Charles River Laboratories or Jackson Laboratories). Mice are anesthetized by intraperitoneal administration of xylazine hydrochloride (8 mg/kg) and chloral hydrate (300 mg/kg) dissolved in sterile saline, and subsequently placed in a stereotaxic apparatus (Narishige, Tokyo, Japan). An incision is made in the scalp and the cranium is exposed. The periosteum is cleaned from the skull, a hole is drilled over the right cerebral hemisphere with a dental drill, and the duramater is removed with a needle tip. A stainless steel cannula, with a 0.5 mm outer diameter, is used to make a longitudinal stab wound in the right hemisphere. The cannula is positioned at 1.3 mm lateral to the midline, and 1 mm posterior to bregma, and introduced into the brain until the tip reaches a depth of 2 mm. The cannula is then shifted 2 mm caudally (bregma 3 mm), and then shifts back 2 mm rostrally to its initial position. Finally, the cannula is removed from the brain, and the scalp wound is sutured. Mice are then treated with antagonistic anti-CD33 and/or CD33 bispecific antibodies according to standard procedures and then analyzed by histology and immunofluorescence staining and behavioral tests. Such experiment can be also conducted in in mice that express the human CD33 gene from a Bacterial artificial chromosome or from a cDNA driven by a myeloid promoter or in mice that were transduced with lenti or AAV virus containing hCD33 cDNA.

Example 20: Characterization of Therapeutic Use of Antagonistic CD33 Antibodies and/or CD33 Bispecific Antibodies in a Model of Neuro-Inflammation and Neuron Loss Following Toxin-Induced Injury The therapeutic utility of agonistic anti-CD33 and/or CD33 bispecific antibodies is tested in a model of neuro-inflammation and neuron loss following toxin-induced injury (Martens, L H et al., (2012) The Journal of Clinical Investigation, 122, 3955). Three-month-old regular mice, are treated with 4 intraperitoneal injections of MPTP (1-methyl-4-phenyl-1,2,3,6-tetrahydropyridine) per day for 2 days (4 µg/g body weight) (Sigma-Aldrich) or PBS. Mice are treated with agonistic anti-CD33 and/or CD33 bispecific antibodies according to standard protocols and then analyzed using Stereological counting to quantify dopamine neurons and microglia in the substantia nigra pars compacta (SNpc), as described. Such experiment can be also conducted in in mice that express the human CD33 gene from a Bacterial artificial chromosome or from a cDNA driven by a myeloid promoter or in mice that were transduced with lenti or AAV virus containing hCD33 cDNA.

Example 21: Characterization of the Therapeutic Use of Antagonistic CD33 Antibodies and/or CD33 Bispecific Antibodies in Animal Models of Aging, Seizures, Spinal Cord Injury, Retinal Dystrophy, Frontotemporal Dementia, and Alzheimer's Disease The therapeutic utility of antagonistic anti-CD33 and/or CD33 bispecific antibodies is tested in animal models for aging, seizures, spinal cord injury, retinal dystrophy, frontotemporal dementia, Huntington disease, Parkinson's disease amyotrophic lateral sclerosis and Alzheimer's disease, as previously described (e.g., Beattie, M S et al., (2002) Neuron 36, 375-386; Volosin, M et al., (2006) J. Neurosci. 26, 7756-7766; Nykjaer, A et al., (2005) Curr. Opin. Neurobiol. 15, 49-57; Jansen, P et al., (2007) Nat. Neurosci. 10, 1449-1457; Volosin, M et al., (2008) J. Neurosci. 28, 9870-9879; Fahnestock, M et al., (2001) Mol. Cell Neurosci. 18, 210-220; Nakamura, K et al., (2007) Cell Death. Differ. 14, 1552-1554; Yune, T et al., (2007) Brain Res. 1183, 32-42; Wei, Y et al., (2007) Neurosci. Lett. 429, 169-174; Provenzano, M J et al., (2008) Laryngoscope 118, 87-93; Nykjaer, A et al., (2004) Nature 427, 843-848; Harrington, A W et al., (2004) Proc. Natl. Acad. Sci. U.S.A. 101, 6226-6230; Teng, H K et al., (2005) J. Neurosci. 25, 5455-5463; Jansen, P et al., (2007) Nat. Neurosci. 10, 1449-1457; Volosin, M et al., (2008) J. Neurosci. 28, 9870-9879; Fan, Y J et al., (2008) Eur. J. Neurosci. 27, 2380-2390; Al-Shawi, R et al., (2008) Eur. J. Neurosci. 27, 2103-2114; and Yano, H et al., (2009) J. Neurosci. 29, 14790-14802). Such experiment can be also conducted in in mice that express the human CD33 gene from a Bacterial artificial chromosome or from a cDNA driven by a myeloid promoter or in mice that were transduced with lenti or AAV virus containing hCD33 cDNA.

Example 22: Characterization of the Therapeutic Use of Antagonistic CD33 Antibodies and/or CD33 Bispecific Antibodies in a Model of Infection The therapeutic utility of antagonistic anti-CD33 antibodies and/or CD33 bispecific antibodies is tested in a model of infection. For example, *Listeria monocytogenes* or other infection in normal mice can be used, as previously described (e.g., Yin, F et al., (2009) J. Exp. Med, 207, 117-128). Either regular mice or mice that express the human CD33 gene under a Bacterial artificial chromosome or under a myeloid promoter can be used.

Example 23: Characterization of the Therapeutic Use of Antagonistic CD33 Antibodies and/or CD33 Bispecific Antibodies in a Model of Inflammatory Diseases The therapeutic utility of antagonistic anti-CD33 and/or CD33 bispecific antibodies is tested in a model of inflammatory diseases. For example rheumatoid arthritis or in an established model of another inflammatory disease (Mizoguchi (2012) Prog Mol Biol Transl Sci., 105:263-320; and Asquith et al., (2009) Eur J Immunol. 39:2040-4). Such experiment can be also conducted in in mice that express the human CD33 gene from a Bacterial artificial chromosome or from a cDNA driven by a myeloid promoter or in mice that were transduced with lenti or AAV virus containing hCD33 cDNA.

Example 24: Screening for Anti-CD33 Antibodies and/or CD33 Bispecific Antibodies that Induce or Inhibit Phosphorylation of CD33 and Downstream Signaling Molecules Cells (J774, RAW 264.7, BMM cells, human primary monocytes, macrophages, dendritic cells, T cells Microglia or osteoclasts) are removed from tissue culture dishes with PBS-EDTA, washed with PBS, and counted. Cells are incubated with an anti-CD33 antibodies and/or CD33 bispecific antibody or with an isotype-matched control antibody at 1 µg/$10^6$ cells for 20 min on ice or under other conditions. Cells are lysed in ice-cold radioimmunoprecipitation assay (RIPA) buffer for 20 min followed by centrifugation at 16,000 g for 10 min at 4° C. to remove insoluble materials. The resulting supernatant is subjected to immunoprecipitation reactions with the indicated antibodies (DAP12, ERK, or AKT) and protein A- or protein G-agarose (Sigma). The beads are extensively washed with RIPA buffer and the proteins are separated by SDS-polyacrylamide gel electrophoresis (SDS-PAGE). The proteins are then transferred to nitrocellulose membranes by Western blotting, incubated with the appropriate antibodies (antibodies that specifically recognize phosphorylated tyrosine or phosphorylated form of DAP12, ERK, Syk, LCK, FYN, C-Cbl, VAV, or AKT) and visualized with the enhanced chemiluminescence (ECL) system (Pierce), as described (e.g., Peng et al., (2010) Sci Signal., 3(122): ra38).

Example 25: Screening for Anti-CD33 and/or CD33 Bispecific Antibodies that Induce or Inhibit Calcium Flux BMM cells are washed twice with HEPES-containing buffer [20 mM HEPES (pH 7.3), 120 mM NaCl, 1 mM CaCl, 1 mM MgCl, 5 mM KCl, glucose (1 mg/ml), bovine serum albumin (1 mg/ml)] followed by incubation in 0.05% Pluronic F-127 (Invitrogen) and 1 µM Indo-1 AM (Invitrogen) for 20 min at 37° C. Cells are washed twice with HEPES buffer and are then stimulated with an anti-CD33 antibodies and/or CD33 bispecific antibody (16 µg/ml) or with a control antibody (16 µg/ml) and monitored by spectrophotometer (PTL Photon Technology International). The Indo-1 fluorescence emission is converted to calcium ($Ca^{2+}$) according to manufacturer's instructions (e.g., Peng et al., (2010) Sci Signal., 3(122): ra38).

Example 26: CD33 Increases the Survival of Macrophages, T Cells, and Dendritic Cells To evaluate the role of CD33 in cell survival, human or mouse macrophages, microglia, T cells and dendritic cells are cultured in the presence of inflammatory mediators, and cell survival is measured.

Murine bone marrow precursor cells from CD33 WT, Het, and KO mice are obtained by flushing tibial and femoral marrow cells with cold PBS. After one wash with PBS, erythrocytes are lysed using ACK Lysing Buffer (Lonza), washed twice with PBS and suspended at $0.5 \times 10^6$ cells/ml in complete RPMI media (10% FCS, Pen/Strep, Gln, neAA) with the indicated amounts of 50 ng/ml M-CSF to produce macrophages, or 10 ng/ml GM-CSF to produce dendritic cells. For M2-type macrophages, 10 ng/ml IL-4 is added to the cultured cells. For M1-type macrophages, 50 ng/ml IFN is added. In some experiments LPS or zymosan is added to the cell culture at day 5 at a concentration range of 1 µg/ml-0.01 ng/ml. Recombinant cytokines are purchased from Peprotech.

To analyze viability of bone marrow-derived macrophages, cells are prepared as above and cultured in MCSF. Cells are either plated at $10^5$/200 ul in a 96-well plate (for viability analysis using a luciferase based-assay) or at $0.5 \times 10^6$/1 ml in a 6-well plate (for Tripan Blue exclusion cell count) in non-tissue culture treated plates. Media containing fresh M-CSF is added at day 3. At the indicated time points cells are gently detached from the plates with 3 mM EDTA and counted using a Burker chamber. For FACS analysis of live cells, macrophages are cultured either in 50 ng/ml MCSF for 6 days (+MCSF) or in 50 ng/ml MCSF for 4 days before MCSF is removed for an additional 36 hrs (−MCSF).

Cells are stained using CD11b antibody and DAPI. For luciferase viability assays, cell viability is measured at day 5 of culture in graded concentrations of growth factors GMCSF (dendritic cells), MCSF (M1 macrophages), or MCSF+IL-4 (M2 macrophages). Cells are directly incubated with ToxGlo reagent (Promega) and luciferase activity (luminescence) is determined. For FACS analysis of viable macrophages cultured in the presence of inflammatory mediators IFN, LPS, or zymosan, cells are collected at day 5 and stained using CD11b antibody and DAPI.

Example 27: CD33 Increases the Expression of Inflammatory Cell Surface Markers on Macrophages In order to determine the role of CD33 in inflammatory marker expression, macrophages are cultured with various inflammatory mediators, and the expression of surface markers CD86 and CD206 is measured in the presence or absence of CD33 antibodies.

Macrophages are plated and allowed to adhere for 4 h at 37° C., and TLR agonists LPS (*Salmonella abortus equi*) and zymosan (*Saccharomyces cerevisiae*) are added at concentrations ranging from 0.01-100 ng/ml (LPS) or 0.01-10 μg/ml (zymosan). Alternatively, macrophages are cultured in the presence of the cytokines IL-4 (10 ng/ml) or IFN (0.5-50 ng/ml). FACS analysis of CD86 and CD206 is performed on a BD FACS Canto 48 hours later. Data analysis is performed with FlowJo (TreeStar) software version 10.0.7.

Example 28: Analysis of Tumor Growth in CD33 Deficient Mice

Cohorts of 10 CD33 wild-type (WT), CD33 heterozygous (HET), and CD33 knockout (KO) mice (sex and age-matched littermates, 8 weeks old (+/−2 weeks)) are challenged subcutaneously with tumor cells (for example $1 \times 10^5$-$1 \times 10^6$ MC38 colon carcinoma, Lewis Lung carcinoma, or B16 melanoma cells) suspended in 100 ul PBS Animals are anesthetized with isoflurane prior to implant. Tumor growth is monitored with a caliper biweekly to measure tumor growth starting at day 4. The endpoint of the experiment is a tumor volume of 2000 mm$^3$ or 60 days. Tumor growth and % survival are the outcome measures. Reduced tumor take and growth rate and a reduced number of tumor infiltrating immunosuppressor macrophages indicate increased effector T cell influx into the tumor in CD33 KO mice.

To determine the number of infiltrating tumor associated immune suppressor macrophages and T cells, groups of 6-8 sex and age-matched littermates are used. 8-week old (+/−2 weeks) WT-HET-KO littermates are challenged subcutaneously with tumor cells (e.g. $1 \times 10^5$-$1 \times 10^6$ MC38, Lewis Lung, or B16 cells) suspended in 200 ul Matrigel (Matrigel Matrix Growth Factor Reduced; BD). Animals are anesthetized with isoflurane prior to implant. 7 and 10 days after tumor injection, the matrigel plug is resected, incubated for 1 hour at 37° C. with 1 mg/ml Collagenase D (Sigma), dissociated to obtain a single-cell suspension, and filtered through a cell strainer. To determine the amount of T cells recruited in the tumor and the ratio between effector T cells and regulatory T cells, $5 \times 10^6$ cells are stained with anti-CD45.2 PercpCy5.5, anti-CD3-FITC, anti-CD8-PE-Cy7, anti-CD4-APC, anti-FoxP3-PE (BD), and DAPI. To determine the amount of monocyte/macrophage lineage cells recruited into the tumor, $5 \times 10^6$ cells are stained with anti-CD45.2 PercpCy5.5, anti-CD11b-PECY7, anti-F4/80-FITC, anti-Ly6C/G-APC, anti-CD86-PE, and DAPI. Cells are acquired on a BD FACS Canto. Data analysis is performed with FlowJo (TreeStar) software version 10.0.7.

Example 29: Analysis of the Anti-Cancer Effect of CD33 Antibodies and/or Bispecific Antibodies Groups of 10 C57B16/NTac mice at 8 weeks (+/−2 weeks) of age, either regular mice or mice that express the human CD33 gene from a Bacterial artificial chromosome or from a myeloid promoter, are challenged subcutaneously with tumor cells (e.g. $1 \times 10^5$ to $1 \times 10^6$ MC38, Lewis Lung, or B16 cells) suspended in 100 ul PBS. Animals are anesthetized with isoflurane prior to implant. Starting at day 2, groups of mice are injected i.p. every 3 days for 4 doses with 200 ug of each of antagonistic anti-CD33 antibodies, such as those described in Examples 38 and 40. Tumor growth is monitored with a caliper biweekly to measure tumor growth starting at day 4. The endpoint of the experiment is a tumor volume of 2000 mm$^3$ or 60 days. Tumor growth and % survival are the outcome measures. Reduced tumor take and growth rate, reduced number of tumor infiltrating immune suppressor macrophages, and increased effector T cell influx into the tumor indicate the anti-cancer effects of blocking anti-CD33 antibodies.

Immunodeficient mice or immunodeficient transgenic mice that express human IL-3, human GM-CSF, human IL-6, human IL-2, and were seeded with human immune cells from human placenta, fetal liver, peripheral blood or another source can also be used for such studies (Ito M et al., (2008) Curr Top Microbiol Immunol.; 324:53-76; Ito R., et al., (2012) *Cellular & Molecular Immunology* 9, 208-214; Brehm et al., (2010) Curr Opin Endocrinol Diabetes Obes. 17(2): 120-125; Zhou et al., (2013) Cancer Letters. 344, 13-19). Such mice can be used in conjunction with either cell line tumors or patient-derived human tumor xenografts (Siolas et al., (2013) Cancer Res.; 73(17): 5315-5319).

Such experiment can be also conducted in in mice that express the human CD33 gene from a bacterial artificial chromosome or from a cDNA driven by a myeloid promoter or in mice that were transduced with lenti or AAV virus containing hCD33 cDNA.

Example 30: Analysis of Additive Anti-Tumor Effect of Combination Therapy that Combines CD33 Antibodies and/or Bispecific Antibodies with Antibodies Against Inhibitory Checkpoint Proteins or Inhibitory Cytokines/Chemokines and their Receptors Groups of 15 C57B16/NTac mice at 8 weeks (+/−2 weeks) of age are challenged subcutaneously with tumor cells as described in Example 35 Animals are anesthetized with isoflurane prior to implant. Starting at day 2, mice are injected i.p. every 3 days for 4 doses with 200 ug anti-CD33 antibodies alone or in combination with antibodies against checkpoint proteins (e.g. anti-PDL1 mAb clone 10F.9G2 and/or anti-CTLA4 mAb clone UC10-4F10-11) at day 3, 6, and 9. Treatment groups include anti-CD33; anti-CTLA4; anti-PDL1; anti-CD33+anti-CTLA4; anti-CD33+anti-PDL1; and isotype control. Tumor growth is monitored with a caliper biweekly to measure tumor growth starting at day 4. The endpoint of the experiment is a tumor volume of 2000 mm$^3$ or 60 days. Tumor growth and % survival are the outcome measures. A decrease in tumor growth and an increase in % survival with combination therapy indicate that anti-CD33 antibodies have additive or synergistic therapeutic effects with anti-checkpoint antibodies. Antagonistic antibodies against checkpoint molecules include antibodies against PDL1, PDL2, PD1, CTLA4, B7-H3, B7-H4, HVEM, BTLA, KIR, GAL9, TIM3, A2AR, LAG-3, and Phosphatidyl Serine. Antagonist antibodies against inhibitory cytokines include antibodies against CCL2, CSF-1, and IL-2 Immuno-deficient mice or immuno-deficient transgenic mice that express human IL-3, human GM CSF, human IL-6, human 112, and were seeded with human immune cells from human placenta, fatal liver, peripheral blood or another source can also be used for such studies (Ito M et al., (2008) Curr Top Microbiol Immunol.; 324:53-76; Ito R., et al., (2012) *Cellular & Molecular Immunology* 9, 208-214; Brehm et al., (2010) Curr Opin Endocrinol Diabetes Obes. 17(2): 120-125; Zhou et al., (2013) Cancer Letters. 344, 13-19). Such mice can be used in conjunction with either cell line tumors or Patient derived human tumors xenografts (Siolas et al., (2013) Cancer Res.; 73(17): 5315-5319).

Such experiment can be also conducted in in mice that express the human CD33 gene from a Bacterial artificial chromosome or from a cDNA driven by a myeloid promoter or in mice that were transduced with lenti or AAV virus containing hCD33 cDNA.

Example 31: Analysis of Additive Anti-Tumor Effect of Combination Therapy that Combines CD33 Antibodies and/or Bispecific Antibodies with Antibodies that Activate Stimulatory Checkpoint Proteins Groups of 15 C57B16/NTac mice at 8 weeks (+/−2 weeks) of age are challenged subcutaneously with tumor cells as described in Example 35 Animals are anesthetized with isoflurane prior to implant. Starting at day 2, mice are injected i.p. every 3 days for 4 doses with 200 ug anti-CD33 antibodies alone or in combination with agonistic antibodies that activate stimulatory checkpoint proteins (e.g. OX40 or ICOS mAb) at day 3, 6, and 9. Tumor growth is monitored with a caliper biweekly to measure tumor growth starting at day 4. The endpoint of the experiment is a tumor volume of 2000 mm³ or 60 days. Tumor growth and % survival are the outcome measures. A decrease in tumor growth and an increase in % survival with combination therapy indicate that anti-CD33 antibodies have additive or synergistic therapeutic effects with stimulatory checkpoint antibodies. Stimulatory checkpoint antibodies include agonistic/stimulatory antibodies against CD28, ICOS, CD137, CD27, CD40, and GITR.

Immuno-deficient mice or immuno-deficient transgenic mice that express human IL-3, human GM CSF, human IL-6, human 112, and were seeded with human immune cells from human placenta, fatal liver, peripheral blood or another source can also be used for such studies (Ito M et al., (2008) Curr Top Microbiol Immunol.; 324:53-76; Ito R., et al., (2012) *Cellular & Molecular Immunology* 9, 208-214; Brehm et al., (2010) Curr Opin Endocrinol Diabetes Obes. 17(2): 120-125; Zhou et al., (2013) Cancer Letters. 344, 13-19). Such mice can be used in conjunction with either cell line tumors or Patient derived human tumors xenografts (Siolas et al., (2013) Cancer Res.; 73(17): 5315-5319).

Such experiment can be also conducted in in mice that express the human CD33 gene from a bacterial artificial chromosome or from a cDNA driven by a myeloid promoter or in mice that were transduced with lentivirus or AAV virus containing human CD33 cDNA.

Example 32: Analysis of Additive Anti-Tumor Effect of Combination Therapy that Combines CD33 Antibodies and/or Bispecific Antibodies with Stimulatory Cytokines Groups of 15 C57B16/NTac mice at 8 weeks (+/−2 weeks) of age are challenged subcutaneously with tumor cells as described in Example 35 Animals are anesthetized with isoflurane prior to implant. Starting at day 2, mice are injected i.p. every 3 days for 4 doses with 200 ug anti-CD33 antibodies alone or in combination with stimulatory cytokines (e.g. IL-12, IFN-α). Tumor growth is monitored with a caliper biweekly to measure tumor growth starting at day 4. The endpoint of the experiment is a tumor volume of 2000 mm³ or 60 days. Tumor growth and % survival are the outcome measures. A decrease in tumor growth and an increase in % survival with combination therapy indicate that anti-CD33 antibodies have additive or synergistic therapeutic effects with immune-stimulatory cytokines. Stimulatory cytokines include IFN-α/b, IL-2, IL-12, IL-18, GM-CSF, and G-CSF.

Immuno-deficient mice or immuno-deficient transgenic mice that express human IL-3, human GM CSF, human IL-6, human 112, and were seeded with human immune cells from human placenta, fatal liver, peripheral blood or another source can also be used for such studies (Ito M et al., (2008) Curr Top Microbiol Immunol.; 324:53-76; Ito R., et al., (2012) *Cellular & Molecular Immunology* 9, 208-214; Brehm et al., (2010) Curr Opin Endocrinol Diabetes Obes. 17(2): 120-125; Zhou et al., (2013) Cancer Letters. 344, 13-19). Such mice can be used in conjunction with either cell line tumors or Patient derived human tumors xenografts (Siolas et al., (2013) Cancer Res.; 73(17): 5315-5319).

Such experiment can be also conducted in in mice that express the human CD33 gene from a Bacterial artificial chromosome or from a cDNA driven by a myeloid promoter or in mice that were transduced with lenti or AAV virus containing hCD33 cDNA.

Example 33: Analysis of Ability of CD33 Antibody and/or Bispecific Antibody Fabs to Stimulate Viability of Innate and Adaptive Immune Cells The agonistic functionality of plate bound, cross-linked anti-CD33 antibody Fab fragments is evaluated in innate immune cells (e.g., macrophages) or adaptive immune cells (e.g., T cells).

Macrophages were cultured in the presence of M-CSF and plate bound CD33 antibody Fabs, and cell viability was measured.

Macrophages and DC derived from human monocytes, as well as T cells and human microglia derived from human monocytes were plated on non-tissue-culture-treated 96-well plates, pre-coated with either 12.5 nM or 100 nM of cross-linked CD33 Fabs. Cells were cultured for 48 hours in the presence of 10 ng/ml M-CSF. Analysis of viability was performed using CellTiter-Glo® kit (Promega). Plates were read with a BioTek Synergy Microplate Reader using GEN5 2.04 software.

Example 34: Analysis of the Ability of CD33 Antibodies and/or Bispecific Antibodies to Modulate NFAT-Dependent Genes The ability of antagonistic anti-CD33 antibodies activate NFAT-dependent genes is evaluate using a luciferase reporter gene under the control of an NFAT (nuclear factor of activated T cells) promoter.

A cell line derived from mouse T lymphocytes BW5147.G.1.4 (ATCC® TIB48™) that express the ITAM motif containing co-receptor DAP12 and its ligand binding partner TREM2 is infected with human CD33, and with Cignal Lenti NFAT-Luciferase virus (Qiagen). Luciferase signaling is activated by plate bound anti-TREM2 antibodies. Full-length and Fab fragment anti-CD33 antibodies are either co-plated with the TREM2 antibodies or applied in solution. For plate binding, antibodies are applied at 10 µg/ml in DPBS on tissue-culture treated clear bottom white 96 well plates (100 µL/well), overnight at 4° C. Wells are rinsed three times with DPBS and subsequently plated at 100,000 cells/well in media with 1% serum. As a positive control for signaling, PMA (0.05 µg/ml) and ionomycin (0.25 uM) are added together. Cells are incubated for 6 hours and luciferase activity is measured by adding ONE-Glo™ reagent (Promega) to each well and incubating 3 min at RT on a plate shaker. Luciferase signal is measured using a BioTek plate reader.

Example 35: Analysis of Anti-Stroke Effect of CD33 Antibodies and/or Bispecific Antibodies Transient occlusion of the middle cerebral artery (MCAO)—a model that closely resembles human stroke is used to induce cerebral infarction in mice. Monofilament (70SPRe, Doccol Corp, USA) is introduced into the internal carotid artery through an incision of the right common carotid artery. The middle cerebral artery is occluded for 30 minutes with a range of reperfusion times (6 h, 12 h, 24 h, 2 d, 7 d and 28 d). The effect of surgery is controlled using sham animals at 12 h and at 7 d. Sham animals undergo the same surgical procedure without occlusion of the middle cerebral artery. MCAO animals treated with antagonistic anti-CD33 antibodies or control antibodies are tested for infarct volumetry, acute inflammatory response (12 h reperfusion), transcription of pro-inflammatory cytokines TNFa, IL-1a, and IL-1β, microglial activity (CD68, Iba1), transcription of chemokines CCL2 (MCP1), CCL3 (MIP1a and the chemokine receptor CX3CR1 and invasion of CD3-positive T cells (Sieber et al. (2013) PLoS ONE 8(1): e52982. doi:10.1371/journal.pone.0052982). Such experiment can be conducted in regular mice or alternatively in mice that express the human CD33 gene from a Bacterial artificial chromosome or from a cDNA driven by a myeloid promoter or in mice that were transduced with lenti or AAV virus containing hCD33 cDNA.

Example 36: Analysis of Anti-Alzheimer's Disease Effect of Anti-CD33 Antibodies and/or Bispecific Antibodies To evaluate the ability of antagonistic anti-CD33 antibodies to delay, prevent, or reverse the development of Alzheimer's disease (AD), 5×FAD mice are used. 5×FAD mice overexpress mutant human APP (695) with the Swedish (K670N, M671L), Florida (1716V), and London (V717I) familial Alzheimer's disease (FAD) mutations, along with human PS1 harboring two FAD mutations, M146L and L286V. Both transgenes are regulated by the mouse Thy1 promoter to drive over expression on the brain and recapitulate major features of AD. Mice treated with the agonistic anti-CD33 antibodies or with control antibodies are tested for A beta plaque load with immunohistochemistry and by ELISA of tissue extracts. They are further tested for the number of microglia in the brain, and for reduction in cognitive deficit using Morris Water maze, a spatial learning and memory task, Radial Arm Water Maze, a spatial learning and memory task, Y Maze (quantifies spontaneous alternation as a measure of spatial cognition), novelty preference in in an open field, operant learning to assess learning and memory, and fear conditioning (mousebiology.org website; Wang et al., (2015) Cell. pii: S0092-8674(15)00127-0). Such experiment can be also conducted in in mice that express the human CD33 gene from a Bacterial artificial chromosome or from a cDNA driven by a myeloid promoter or in mice that were transduced with lenti or AAV virus containing hCD33 cDNA.

Example 37: Analysis of the Protective Effect of CD33 Antibodies and/or Bispecific Antibodies in Respiratory Tract Infections To evaluate the ability of antagonist CD33 antibodies to delay, prevent, or treat bacterial respiratory tract infections, a preclinical mouse model involving challenge of C57B16 mice with *Streptococcus pneumoniae* is used. This model involves intranasal (i.n.) administration of 105 CFU *S. pneumoniae* serotype 3 (ATCC 6303) as described (see, e.g., Sharif O et al, 2014 *PLoS Pathog.* 2014 June; 10(6): e1004167; and Schabbauer G et al, 2010 *J Immunol* 185: 468-476). In this model ~90% WT C57B16 mice succumb to infection within 6 days post infection.

Ten to fifteen mice/group are challenged with *S. pneumoniae* and concomitantly are treated with antagonist anti-CD33 antibodies every other day starting from day 0. The first dose of anti-CD33 antibodies is administered 3 hours prior to challenge with *S. pneumonia*. Mice are monitored daily for 15 days to check for death events. % of mice surviving bacteria challenge is determined.

In separate experiments, count of bacterial load and cytokine expression in the blood and in the lungs is also determined. 24 or 48 hours after infection blood is collected in EDTA-containing tubes and plated on agar plates to enumerate bacterial CFU in the plasma. Plasma is stored at −20° C. for cytokine analysis by ELISA. Lungs are harvested, homogenized and plated on agar plates to enumerate bacterial CFU, or incubated for 30 min in lysis buffer and supernatants analyzed for cytokine measurements.

In separate experiments, lungs are collected 40 hours post bacterial infection, fixed in 10% formalin, and embedded in paraffin for H&E pathology analysis.

Such experiment can be also conducted in in mice that express the human CD33 gene from a Bacterial artificial chromosome or from a cDNA driven by a myeloid promoter or in mice that were transduced with lenti or AAV virus containing hCD33 cDNA.

Example 38: Analysis of the Protective Effect of CD33 Antibodies and/or Bispecific Antibodies in Sepsis To evaluate the ability of antagonist CD33 antibodies to delay, prevent, or treat sepsis, a preclinical mouse model involving systemic challenge of C57B16 mice with LPS is used. This model involves intraperitoneal (i.p.) administration of 37 mg/ml LPS as described (see, e.g., Gawish R et al, 2014 *FASEB J*). In this model>95% WT C57B16 mice succumb infection within 40 hours post LPS injection.

Cohorts of mice are challenged with LPS and concomitantly are treated with antagonist anti-CD33 antibodies every day starting from day 0. The first dose of anti-CD33 antibodies is administered 3 hours prior to challenge with LPS. Mice are monitored every ~4 hours during daytime, to check for death events. Percentage of mice surviving LPS challenge is determined.

In separate experiments, peritoneal lavage fluid (PLF) is collected. Supernatants are stored at −20° C. for cytokine analysis by ELISA; pelleted cells are counted to quantify inflammatory cells recruited in the peritoneal cavity. Similar studies can be conducted to test the efficacy of CD33 antibodies in other models of infection (see, e.g., Sun et al., (2013) Invest Ophthalmol Vis Sci. 17; 54(5):3451-62).

Such experiment can be also conducted in in mice that express the human CD33 gene from a Bacterial artificial chromosome or from a cDNA driven by a myeloid promoter or in mice that were transduced with lenti or AAV virus containing hCD33 cDNA.

Example 39: Analysis of the Protective Effect of CD33 Antibodies and/or Bispecific Antibodies in Acute and Chronic Colitis To evaluate the ability of antagonist anti-CD33 antibodies to delay, prevent, or treat colitis, preclinical mouse models of acute or chronic colitis are used. For DSS-induced colitis, mice receive 3% DSS in drinking water ad libitum for 8 days. For TNBS-induced colitis, mice are anesthetized and treated with an intra-rectal injection of 3 mg TNBS in 20% ethanol (vol/vol) or vehicle alone as a control. For the chronic colitis model, all mice are treated with 3 cycles of 2% DSS for 5 days, followed by a 10-day recovery period. For all models, weight loss, stool consistency, and presence of fecal occult blood are monitored daily and used to calculate the disease activity index, as described (see, e.g., Correale C, 2013, Gastroenterology, February 2013, pp. 346-356.e3).

Cohorts of mice are treated with antagonist anti-CD33 antibodies every day starting from day 0 and subjected to DSS or TNBS administration. Mice are monitored every day, to check for weight loss, stool consistency, and presence of fecal occult blood were monitored daily and used to calculate the disease activity index, as described (see, e.g., S. Vetrano, Gastroenterology, 135 (2008), pp. 173-184).

In separate experiments, endoscopic and histological images of mucosal damage are collected to evaluate inflammatory cell infiltration and mucosal damage. Similar studies can be conducted to test the benefit of CD33 antibodies in other models of autoimmunity including Crohn's disease, inflammatory bowel disease, and ulcerative colitis (see, e.g., Low et al., (2013) Drug Des Devel Ther.; 7: 1341-1357; and Sollid et al., (2008) PLoS Med 5(9): e198).

Such experiment can be also conducted in in mice that express the human CD33 gene from a Bacterial artificial chromosome or from a cDNA driven by a myeloid promoter or in mice that were transduced with lenti or AAV virus containing hCD33 cDNA.

Example 40: Analysis of the Protective Effect of CD33 Antibodies and/or Bispecific Antibodies in Wound Healing To evaluate the ability of agonist anti-CD33 antibodies to increase colonic wound repair following injury, a mouse model of biopsy injury in the colon is used. In this model, the endoscope with outer operating sheath is inserted to the mid-descending colon and the mucosa is surveyed to the ano-rectal junction. Then, a single full thickness area of the entire mucosa and submucosa is removed with flexible biopsy forceps with a diameter of 3 French, avoiding penetration of the muscularis propria. Each mouse is biopsy injured at 3-5 sites along the dorsal side of the colon (see, e.g., Seno H, 2008, Proc Natl Acad Sci USA. 2009 Jan. 6; 106(1): 256-261).

Cohorts of mice are treated with agonist anti-CD33 antibodies 2 or 3 days after biopsy injury. Mice are monitored every day for 15 days, to check for weight loss and wound healing by measuring the surface area of lesions.

Such experiment can be also conducted in in mice that express the human CD33 gene from a Bacterial artificial chromosome or from a cDNA driven by a myeloid promoter or in mice that were transduced with lenti or AAV virus containing hCD33 cDNA.

Example 41: Analysis of the Protective Effect of CD33 Antibodies and/or Bispecific Antibodies in Retinal Degeneration AMD is a degenerative disease of the outer retina. It is thought that inflammation, particularly inflammatory cytokines and macrophages, contribute to AMD disease progression.

The presence of macrophages in the proximity of AMD lesions is documented, in the drusen, Bruch's membrane, choroid and retina. Macrophages release tissue factor (TF) and vascular endothelial growth factor (VEGF), which triggers the expansion of new blood vessels formation in patients showing choroidal neovasulcarization.

The type of macrophage present in the macular choroid changes with age, displaying elevated levels of M2 macrophages in older eyes compared to younger eyes. However, advanced AMD maculae had higher M1 to M2 rations compared to normal autopsied eyes of similar age. (see, e.g., Cao X et al, (2011), Pathol Int 61(9): pp 528-35). This suggests a link between classical M1 macrophage activation in the eye in the late onset of AMD progression.

Retinal microglia cells are tissue-resident macrophages that are also normally present in the inner retina. In the event of damage, microglia can be activated and act as mediator of inflammation. Activated microglia has been detected in the AMD tissue samples and has been proposed as one potential contributor of inflammatory processed that lead to AMD pathogenesis (Gupta et al., (2003) Exp Eye Res., 76(4):463-71). The ability of CD33 antibodies to prevent, delay, or reverse AMD is tested in one or more of AMD models (see, e.g., Pennesi et al., (2012) Mol Aspects Med.; 33(4): 487-509).

Overall inflammatory macrophages (either M1 and/or activated microglia) are documented to correlate with AMD disease progression and therefore represent a therapeutic target for antagonist CD33 antibodies. Similar therapeutic benefit can be achieved in glaucoma and genetic forms or retinal degeneration such as retinitis pigmentosa.

The ability of CD33 antibodies to prevent, delay, or reverse retinal ganglion cell degeneration in glaucoma is tested in a glaucoma model (see, e.g., El-Danaf et al., (2015) J Neurosci. 11; 35(6):2329-43). Likewise, the therapeutic benefit of REM2 in genetically induced retinal degeneration and retinitis pigmentosa is tested as described in Chang et al., (2002) Vision Res.; 42(4):517-25, and in "Retinal Degeneration Rat Model Resource Availability of P23H and S334ter Mutant Rhodopsin Transgenic Rats and RCS Inbred and RCS Congenic Strains of Rats," MM LaVail, Jun. 30, 2011.

Such experiment can be also conducted in in mice that express the human CD33 gene from a Bacterial artificial chromosome or from a cDNA driven by a myeloid promoter or in mice that were transduced with lenti or AAV virus containing hCD33 cDNA.

Example 42: Analysis of the Protective Effect of CD33 Antibodies and/or Bispecific Antibodies in Adipogenesis and Diet-Induced Obesity To test the effect of CD33 antibodies in adipogenesis and obesity, a mouse model of high-fat diet (HFD) is used (see, e.g., Park et al., (2015) Diabetes. 64(1):117-27).

Such experiment can be also conducted in in mice that express the human CD33 gene from a Bacterial artificial chromosome or from a cDNA driven by a myeloid promoter or in mice that were transduced with lenti or AAV virus containing hCD33 cDNA.

Example 43: Analysis of the Protective Effect of Antagonist CD33 Antibodies and/or Bispecific Antibodies in Osteoporosis Bone is a dynamic organ constantly remodeled to support calcium homeostasis and structural needs. The osteoclast is the cell responsible for removing both the organic and inorganic components of bone. The osteoclast is derived from hematopoietic progenitors in the macrophage lineage and differentiates in response to the tumor necrosis factor family cytokine receptor activators of NFκB ligand. Osteoclasts, the only bone-resorbing cells, are central to the pathogenesis of osteoporosis and osteopetrosis (Novack et al., (2008) Annual Rev Pathol., 3:457-84).

Osteoporosis is a progressive bone disease that is characterized by a decrease in bone mass and density which can lead to an increased risk of fracture. It is mostly manifested in the first years following menopause, when bone turnover is accelerated, with increased activity of both osteoclasts and osteoblasts. Owing to an imbalance in the processes of resorption and synthesis, however, the net effect is bone loss, which is largely trabecular. Thus, the most prevalent sites of fracture in osteoporosis are the wrist, femoral neck, and vertebral bodies, in which the trabecular structure is key to overall bone strength.

Reduced osteoclast function results in osteopetrosis, with increased bone mass and elimination of bone marrow space, as observed in animal models lacking DAP12 ITAM signaling adapter and resulting in a significant defect in differentiation of osteoclast-like cells (Koga, et al., (2004) Nature 428: 758-763).

Thus, administering an antagonist anti-CD33 antibody of the present disclosure can prevent, reduce the risk of, and/or treat osteoporosis. In some embodiments, administering an agonist anti-CD33 antibody may induce one or more CD33 activities in an individual having osteopetrosis (e.g., DAP12 phosphorylation, Syk activation, and accelerated differentiation into osteoclasts) (Peng et al (2010). Sci Signal. 2010 18; 3 122; and Humphrey et al., (2006) J Bone Miner Res., 21(2):237-45).

Such experiment can be also conducted in in mice that express the human CD33 gene from a Bacterial artificial chromosome or from a cDNA driven by a myeloid promoter or in mice that were transduced with lenti or AAV virus containing hCD33 cDNA.

Example 44: Analysis of the Ability of CD33 Antibodies and/or Bispecific Antibodies to Modulate Binding of CD33 to SHP1, SHP2 and Other Signaling Molecules Human primary monocytes, macrophages, dendritic cells, T cells, microglia or osteoclasts are removed from tissue culture dishes with PBS-EDTA, washed with PBS, and counted. Cells are incubated with an anti-CD33 and/or CD33 bispecific antibody or with an isotype-matched control antibody at 1 µg/$10^6$ cells for 20 min on ice or under other conditions. Cells are lysed in ice-cold radioimmunoprecipitation assay (RIPA) buffer for 20 min followed by centrifugation at 16,000 g for 10 min at 4° C. to remove insoluble materials. The resulting supernatant is subjected to immunoprecipitation reactions with the indicated antibodies (SHP1, SHP2, c-Cbl, Vav, Syk, LcK, Fyn, GRb2, PLC-gamma Toll like receptor, DAMP receptors, pattern recognition receptor) and protein A- or protein G-agarose (Sigma). The beads are extensively washed with RIPA buffer and the proteins are separated by SDS-polyacrylamide gel electrophoresis (SDS-PAGE). The proteins are then transferred to nitrocellulose membranes by Western blotting, incubated with the appropriate CD33 antibodies and visualized with the enhanced chemiluminescence (ECL) system (Pierce), as described (e.g., Peng et al., (2010) Sci Signal., 3(122): ra38). Alternatively, the cells are incubated with an anti-CD33 and/or CD33 bispecific antibody or with an isotype-matched control antibody at 1 µg/$10^6$ cells for 20 min on ice or under other conditions. Cells are lysed in ice-cold radioimmunoprecipitation assay (RIPA) buffer for 20 min followed by centrifugation at 16,000 g for 10 min at 4° C. to remove insoluble materials. The resulting supernatant is subjected to immunoprecipitation reactions with a second CD33 antibody. The proteins are then transferred to nitrocellulose membranes by Western blotting and incubated with the indicated antibodies (SHP1, SHP2, c-Cbl, Vav, Syk, LcK, Fyn, GRb2, PLC-gamma Toll like receptor, DAMP receptors, pattern recognition receptor).

Example 45: Comparison of Ability of CD33 Antibodies to Bind CD33 and Decrease Cell Surface Levels of CD33 In Vitro Comparisons of CD33 Antibody Binding The ability of different anti-CD33 antibodies to bind CD33 expressed on human primary monocytes was determined. The binding ability of anti-CD33 antibodies 2F5, 2E12, 6A3, and 6C7 was compared with the binding ability of commercial anti-CD33 antibodies gemtuzumab and lintuzumab. A mouse IgG1 (mIgG1) isotype control and a human isotype control were used as controls. Cells were harvested, plated at $10^6$/ml in a 96-well plate, and incubated in 100 µl PBS containing 2% FBS, 2 mM EDTA and 1 µg/ml, 0.1 µg/ml, or 0.01 µg/ml of anti-CD33 antibody and Fc blocking reagent for 1 hour on ice. Cells were washed twice and incubated in 100 µl PBS containing 2% FBS, 2 mM EDTA and 5 µg/ml PE-conjugated secondary antibody for 30 minutes on ice. Cells were washed twice in cold PBS and analyze by flow cytometry on a BD FACS Canto. Data analysis and calculation of mean fluorescence intensity (MFI) values was performed with FlowJo (TreeStar) software version 10.0.7.

Figure 17A:
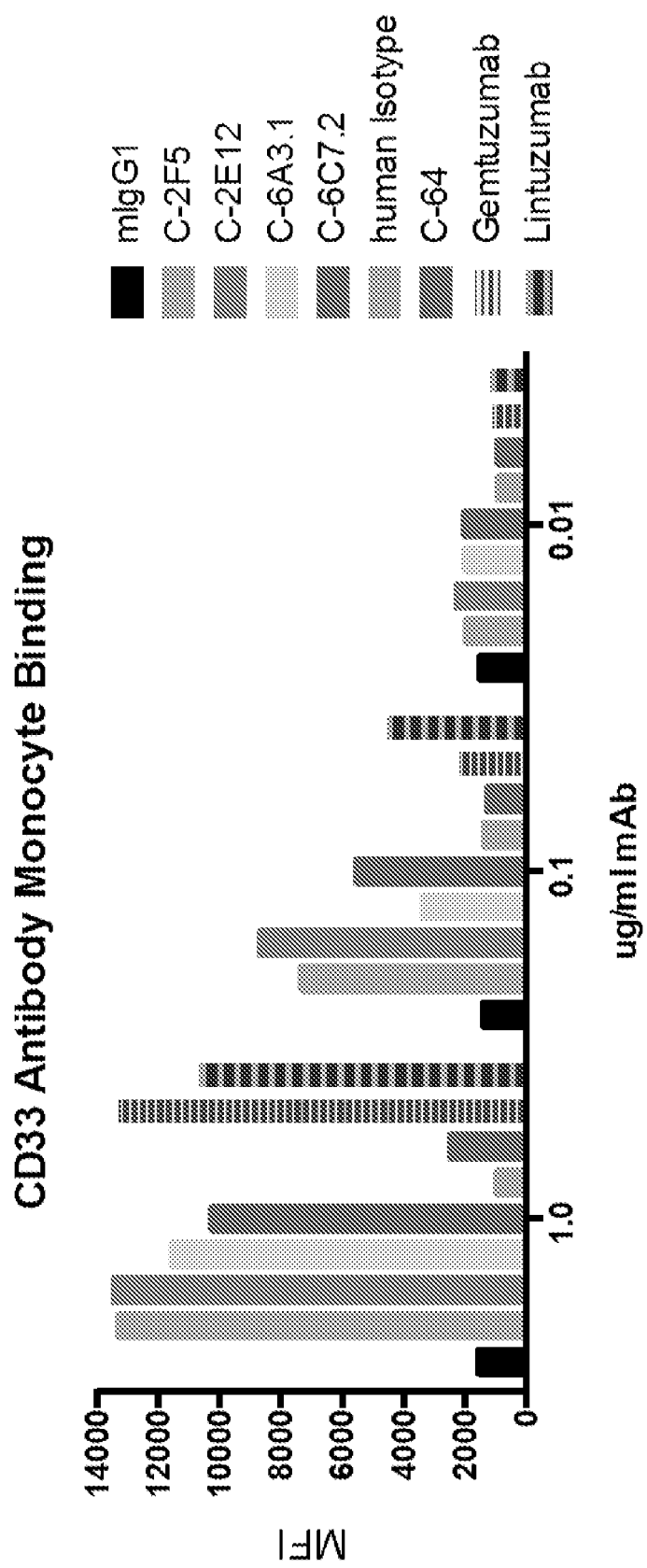
FIG. 17A depicts CD33 antibody binding to human primary monocytes at different antibody concentrations. In the figure the following antibodies are ordered from left to right for each indicated concentration: mouse isotype control antibody (mIgG1), anti-CD33 antibody 2F5 (C-2F5), anti-CD33 antibody 2E12 (C-2E12), anti-CD33 antibody 6A3 (C-6A3.1), anti-CD33 antibody 6C7 (C-6C7.2), human isotype control antibody (human isotype), anti-CD33 antibody C-64, anti-CD33 antibody gemtuzumab, and anti-CD33 antibody lintuzumab.

As shown in FIG. 17A, anti-CD33 antibodies 2F5, 2E12, 6A3, and 6C7 bind to human primary monocytes with higher MFI at a concentration of 0.1 µg/ml antibody than do the commercial antibodies gemtuzumab and lintuzumab. The results demonstrate that the anti-CD33 antibodies of the present disclosure exhibit improved target engagement in human primary myeloid cells, as compared to commercial antibodies.

Comparisons of In Vitro Expression of CD33

The ability of anti-CD33 antibodies 2F5, 2E12, 6A3, and 6C7 to reduce the cell surface level of CD33 on human primary monocytes was compared with the ability of commercial anti-CD33 antibodies gemtuzumab and lintuzumab to reduce the cell surface level of CD33 on human primary monocytes. A mouse IgG1 (mIgG1) isotype control and a human isotype control were used as controls.

Monocytes from peripheral human blood samples were isolated using the RosetteSep™ monocyte isolation antibody cocktail (StemCell Technologies). Cell samples were plated in 24-well plates at 200,000 cells per ml or in 6-well dishes at 500,000 cells in 2 ml of RPMI supplemented with 10% Hyclone FBS, 2 mM glutamine, pen/strep, and non-essential amino acids. CD33 antibodies or control isotypes were added at 1.0 µg/ml, 0.1 µg/ml, 0.01 µg/ml, 0.001 µg/ml, 0.0001 µg/ml, and 0.00001 µg/ml, and incubated for 24 hours at 37° C. with 5% $CO_2$.

To assess receptor dynamics, antibodies were allowed to bind cells for one hour, washed out and surface levels of CD33 were determined 24 and 48 hours later.

Cell surface receptor expression was detected by FACS analysis. Cells were incubated with anti-CD33-FITC clone HIM3-4 (FIG. 17B), as well as control surface marker CD14 (FIG. 17C) for 30 minutes on ice in the dark. Cells were washed 2× in FACS buffer (PBS+2% FBS, 2 mM EDTA) and flow cytometry was performed on a BD FACS Canto. Data was analyzed using TreeStar FlowJo software. Data was calculated as a percent of receptor expression in the absence of antibody using MFI values for the respective fluorophores.

Figure 17B:
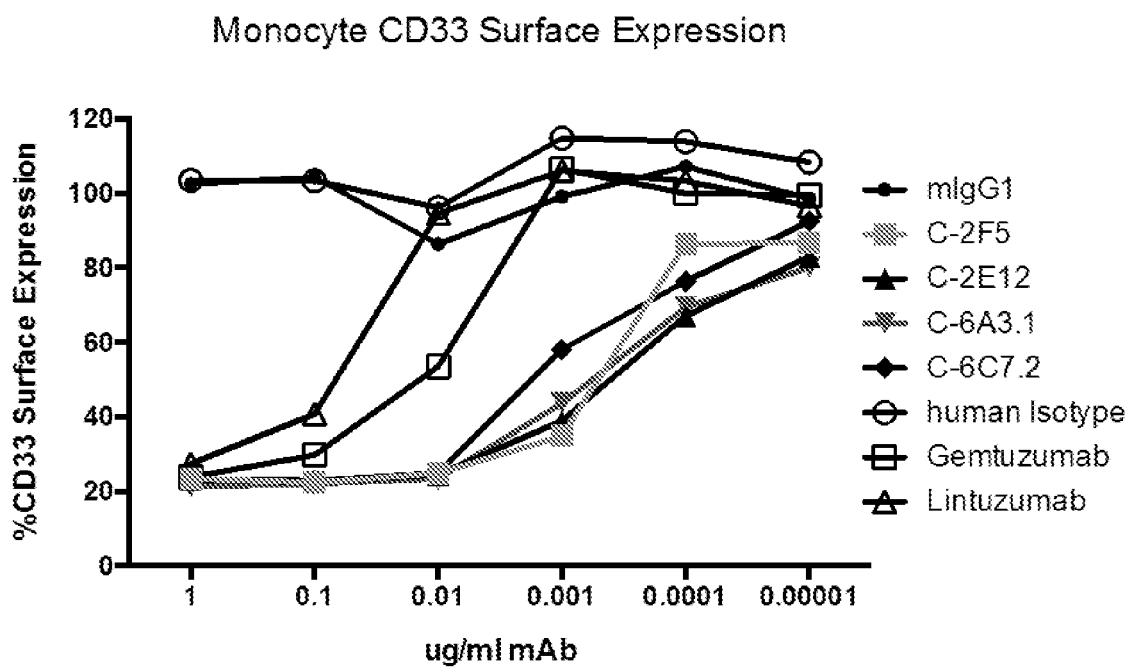
FIG. 17B depicts cell surface levels of CD33 in human primary monocytes after treatment with CD33 antibody at different antibody concentrations.
Figure 17C:
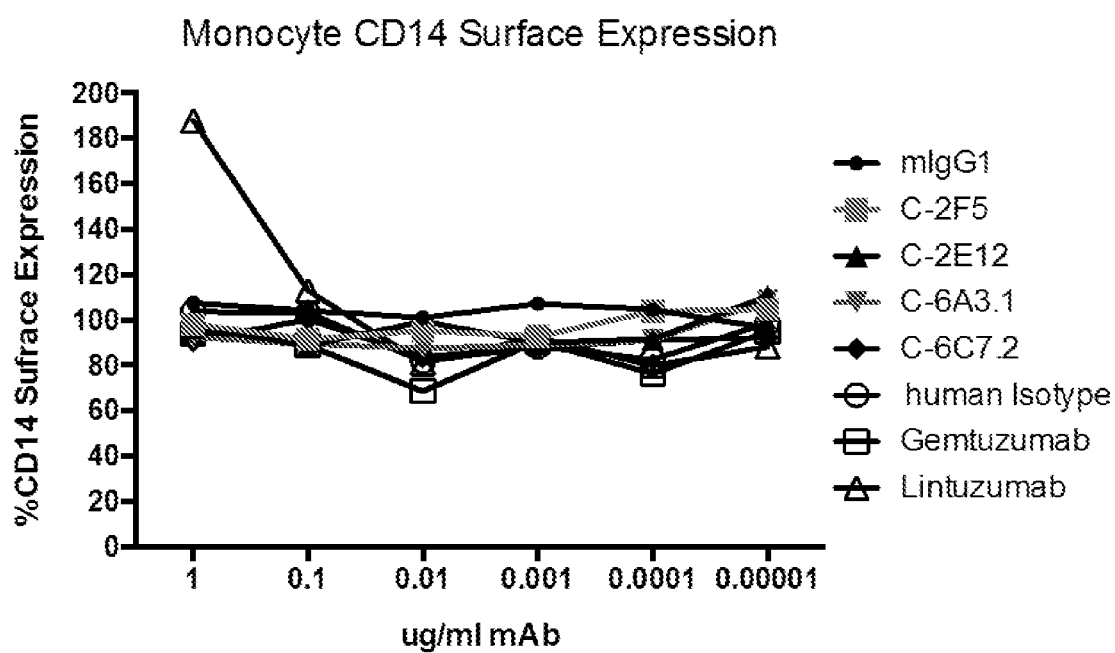
FIG. 17C depicts cell surface levels of CD14 in human primary monocytes after treatment with CD33 antibody at different antibody concentrations.

FIG. 17B depicts the results of CD33 cell surface levels from human cells in which the anti-CD33 antibodies were titrated 10-fold for a 6-point curve. The results demonstrate reduced surface levels of CD33, but not with control receptor CD14, at antibody concentrations of less than 1.0 µg/ml (FIGS. 17B and 17C). Antibodies 2F5, 2E12, 6A3, and 6C7 at a concentration of 0.01 µg/ml reduced cell surface levels of CD33 to about 20%, whereas the ability of commercial antibody lintuzumab to reduce cell surface levels of CD33 were completely abolished at a concentration of 0.01 µg/ml (FIG. 17B). Moreover, the ability of commercial antibody gemtuzumab to reduce cell surface levels of CD33 was also significantly decreased downregulation function at a concentration of 0.01 µg/ml, and completely lost at a concentration of 0.001 µg/ml (FIG. 17B). In contrast antibodies 2F5, 2E12, 6A3, and 6C7 at a concentration of 0.001 µg/ml were able to reduce surface levels of CD33 to about 50-30% (FIG. 17B). As shown in FIG. 17C, cell surface levels of the CD14 control receptor were not modulated by any of the anti-CD33 antibodies.

The results demonstrate that anti-CD33 antibodies 2F5, 2E12, 6A3, and 6C7 robustly reduce cell surface levels of CD33 with an improved capability as compared to commercial antibodies. In particular, antibodies 2F5, 2E12, 6A3, and 6C7 were approximately 10-fold better than commercial antibody gemtuzumab in reducing cell surface levels of CD33, and approximately 100-fold better than commercial antibody lintuzumab in reducing cell surface levels of CD33 (FIG. 17B).

Figures 18A, 18B:
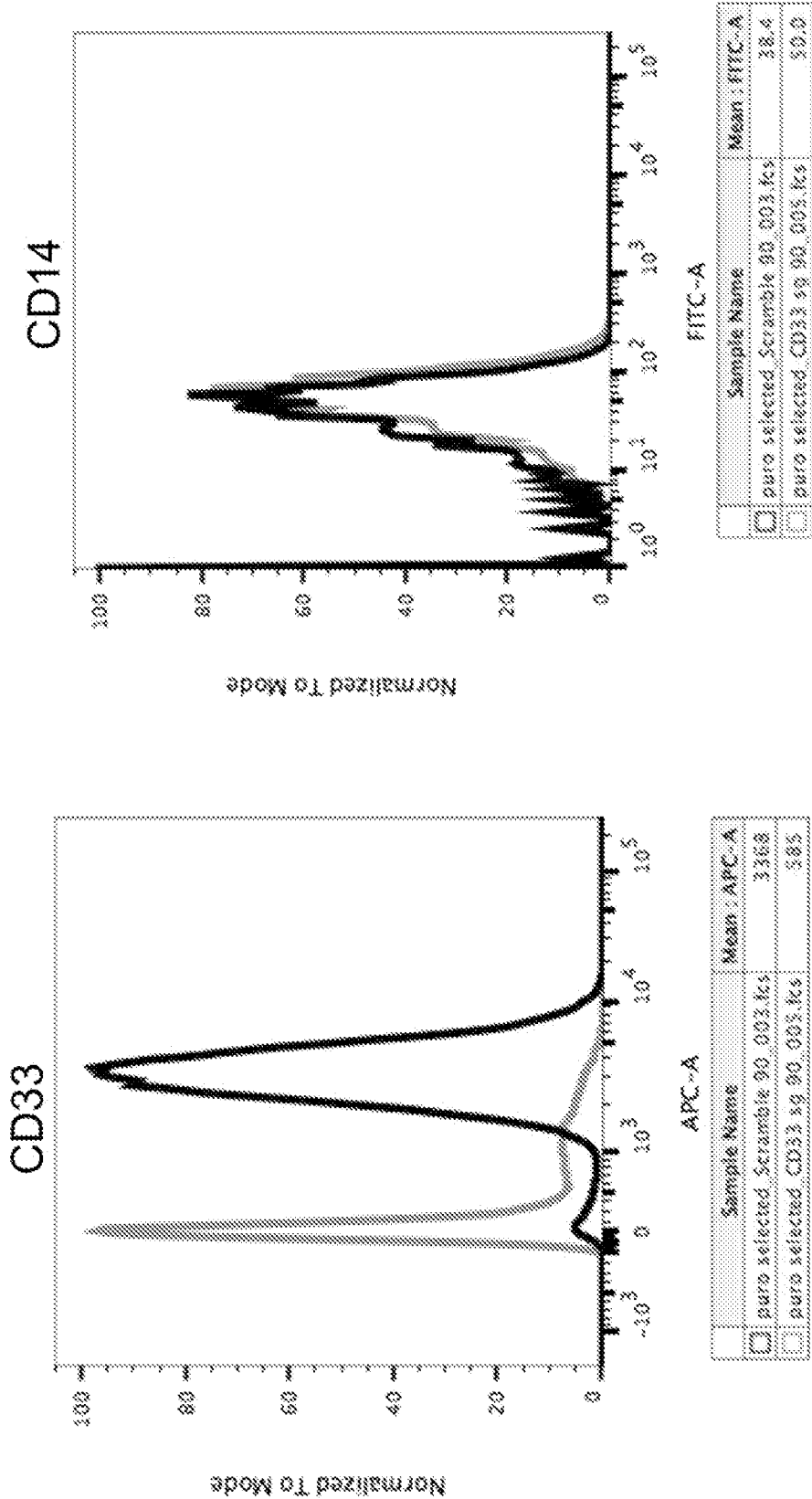
FIG. 18A depicts expression levels of CD33 in wild-type and CD33 knock-out THP-1 cells.
FIG. 18B depicts expression levels of CD14 in wild-type and CD33 knock-out THP-1 cells.

Example 46: Effects of Loss CD33 Expression on Cytokine Production and Cellular Activation The monocytic cell line THP-1 was lentivirally transduced with a scramble small guide RNA (target sequence: GCACTCACATCGCTACATCA (SEQ ID NO: 216)) or a CD33 small guide RNA (target sequence: CTAGAGTGCCAGGGATG (SEQ ID NO: 217)) expressed from CRISPR/Cas9 All-in-One Lentivector (pLenti-U6-sgRNA-SFFV-Cas9-2A-Puro, ABM) overnight at 37° C., 5% $CO_2$ in a 24-well dish, at 50,000 cells per well. Media was added the following day. Three days post lentivirus addition, transduced cells were selected with 0.5 µg/ml puromycin for two weeks, with fresh media and antibiotic added every 2-3 days. CD33 receptor expression and control CD14 expression was detected by FACS (FIGS. 18A and 18B).

Figure 18C:
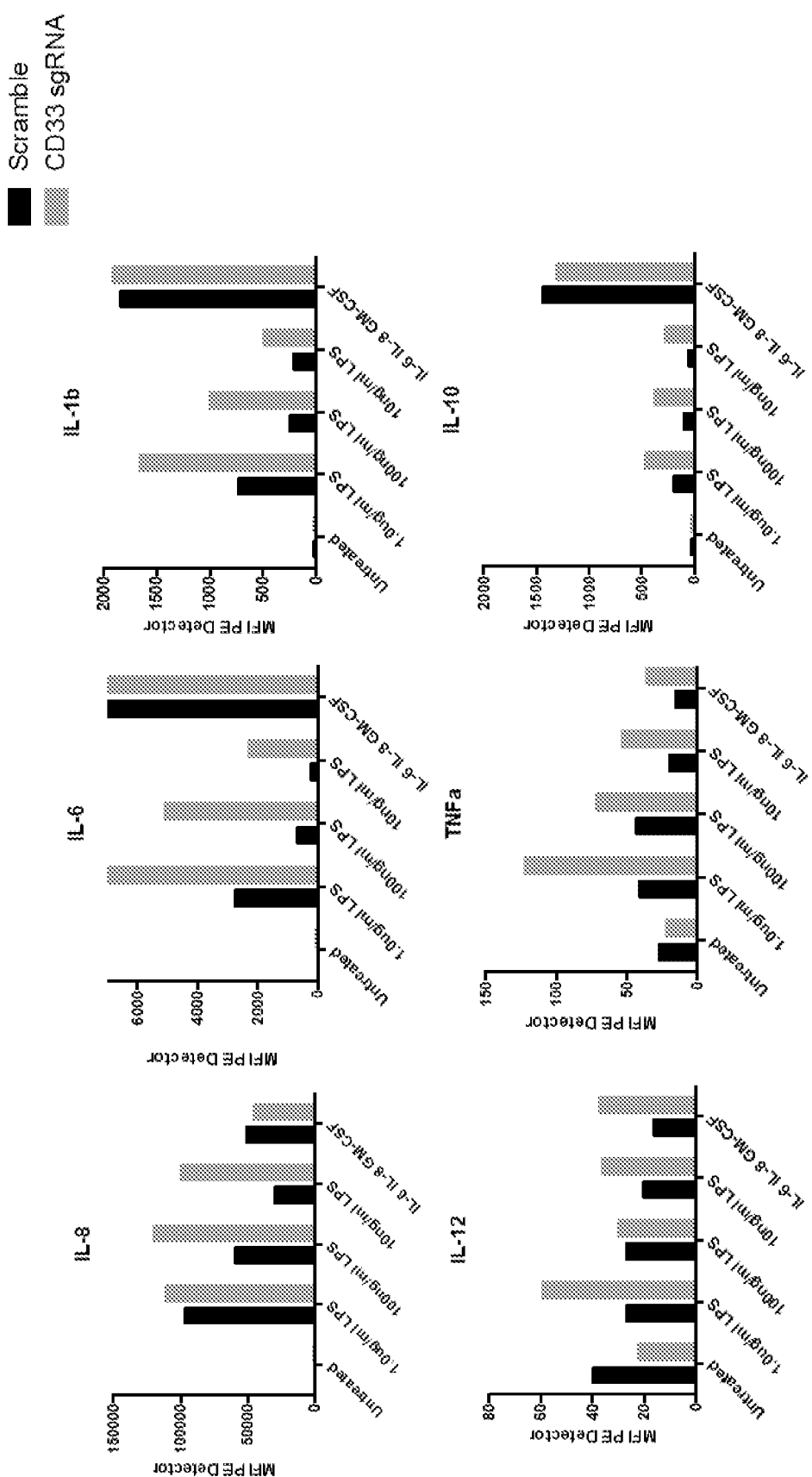
FIG. 18C depicts levels of cytokines in wild-type and CD33 knock-out THP-1 cells treated with different concentrations of LPS or with IL-6, IL-8, and GM-CSF.
Figure 18D:
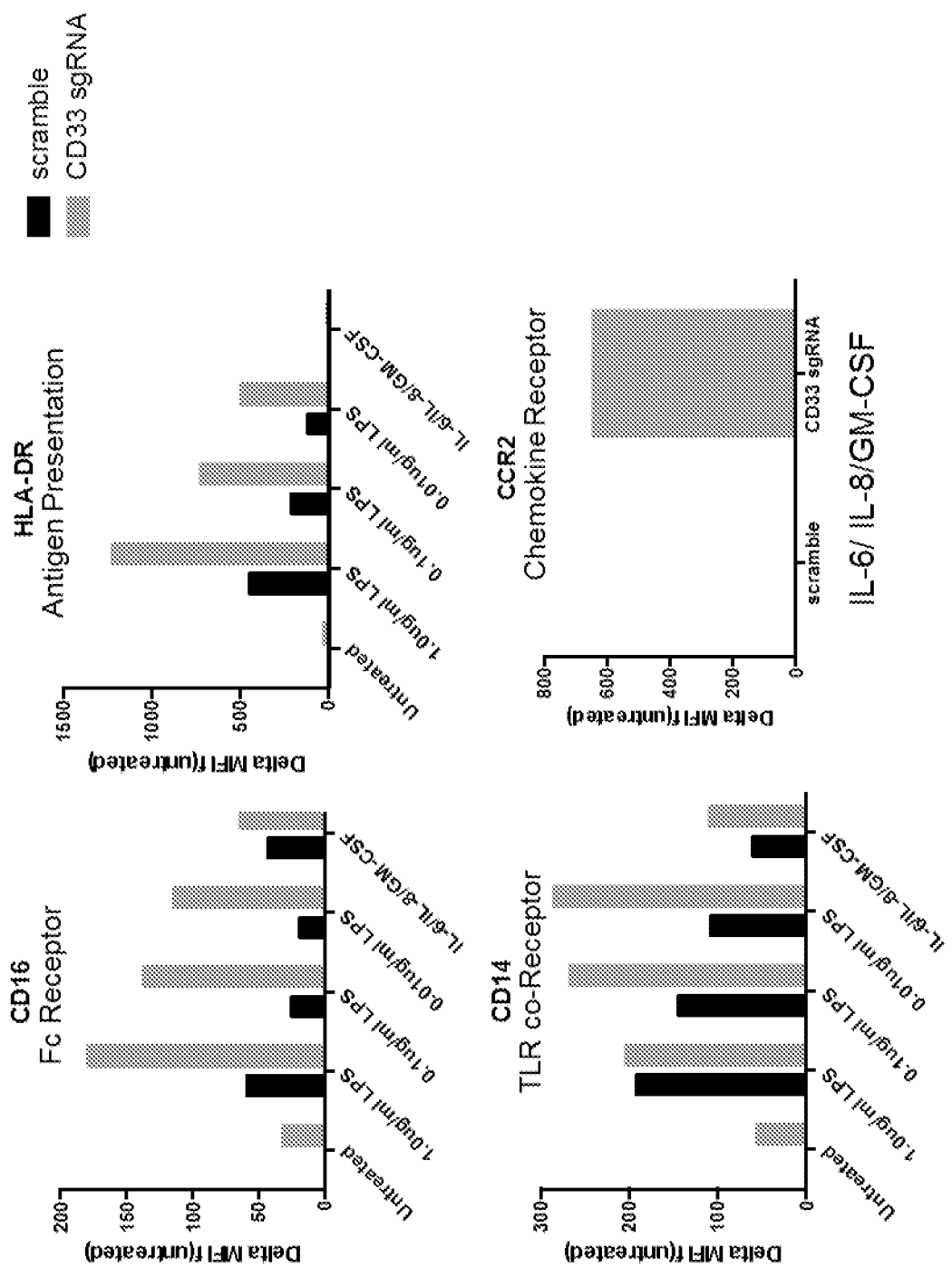
FIG. 18D depicts levels of activation markers in wild-type and CD33 knock-out THP-1 cells treated with different concentrations of LPS or with IL-6, IL-8, and GM-CSF.

To assess cytokine production and cellular activation status, scramble sgRNA-expressing or CD33 sgRNA-expressing THP-1 cells were plated at 100,000 cells per well in a 24-well dish and treated with no LPS, 1.0 µg/ml LPS, 100 ng/ml LPS, or 10 ng/ml LPS. In cytokine stimulated wells, 10 ng/ml GM-CSF, 10 ng/ml IL-6, and 10 ng/ml IL-8 were added. Three days post stimulation, cell supernatants were analyzed for cytokine production with a human inflammatory cytometric bead array kit (BD Biosciences) (FIG. 18C). Data are presented as mean fluorescence intensity (MFI) of PE detector. Three days post stimulation, cells were FACS analyzed for CD14 (Pacific Blue, BD Biosciences), CD16 (v500, BD Biosciences), HLA-DR (APC-Cy7, BD Biosciences), and CCR2 (PE, Biolegend) expression on a FACS Canto (BD Biosciences) and data processed with FlowJo 10.1r5 (TreeStar) (FIG. 18D). Data are presented as the change in MFI compared to untreated.

To assess the effects of loss of CD33 expression on cytokine production and cellular activation, a CRISPR CD33 KO THP-1 cell line was generated and compared to control scramble sgRNA transduced cells. At basal state, CD33 CRISPR KO cells did not display large differential cytokine or activation marker expression (FIGS. 18C and 18D). However, upon stimulus with titrating amounts of LPS, CD33 KO cells produced increased levels of IL-6, IL-8, IL-1β, IL-12, TNF-α, and IL-10 and upregulated CD14, CD16, HLA-DR, and CCR2 (FIGS. 18C and 18D). These results indicate that cells lacking CD33 are more immuno-reactive.

Example 47: Effects of CD33 Antibodies on Immune Checkpoints

Human peripheral blood mononuclear cells (PBMCs) were separated from whole blood by ficoll centrifugation. After ACK lysis of red blood cells, human PBMCs were cultured in RPMI media supplemented 10% FBS (Hyclone), L-glutamine, Pen/Strep, non-essential amino acids, sodium pyruvate, and a suppressive cytokine cocktail containing: 10 ng/ml recombinant IL-6 (Sigma-Aldrich), IL-8 (R&D Systems), and GM-CSF (R&D Systems). In some experiments, human PBMCs were cultured with tumor conditioned media supplemented with 10 ng/ml GM-CSF. Tumor conditioned media is RPMI media with supplements noted above except IL-6 and IL-8 that has been harvested from tumor cell line cultures (cervical cancer cells or glioblastoma cells) and sterile filtered with 0.2 µM membrane. Cytokines, antibodies (CD33 antibody 2F5 or isotype control), or rhGM-CSF spiked tumor supernatant were added to human PBMCs every 2-3 days for a week.

For FACS analysis, suspension and adherent cells were harvested and tested for expression of indicated receptors by standard FACS procedure.

For T cell proliferation assays, myeloid-derived suppressor cells (MDSC) were isolated by magnetic-based negative selection using a cocktail of antibodies to CD2, CD3, CD8, CD19, and CD56 (STEMCELL Technologies) after 7 days of culturing. Isolated MDSC were plated at 50,000 cells per well in a flat-bottom 96-well non-TC plate and treated with CD33 antibody 2F5, mouse isotype control antibody (mIgG1), or anti-PD-L1 antibody prior to addition of T cells.

Non-autologous donor CD3 T cells or CD8 T cells were isolated from whole blood using RosetteSep selection technology (STEMCELL Technologies), labeled with CFSE (Life Technologies), and activated with 10 U/ml IL-2 and 1:1 ratio CD3/CD28 T-Activator Dynabeads (Life Technologies). MDSC and T cells were co-cultured at a ratio of 1:2 or 50,000:100,000 cells per well. CFSE was detected on a FACS Canto (BD Biosciences) 3 days post co-culture. Data were analyzed with FlowJo version 10.1 (TreeStar) software.

Figure 19A:
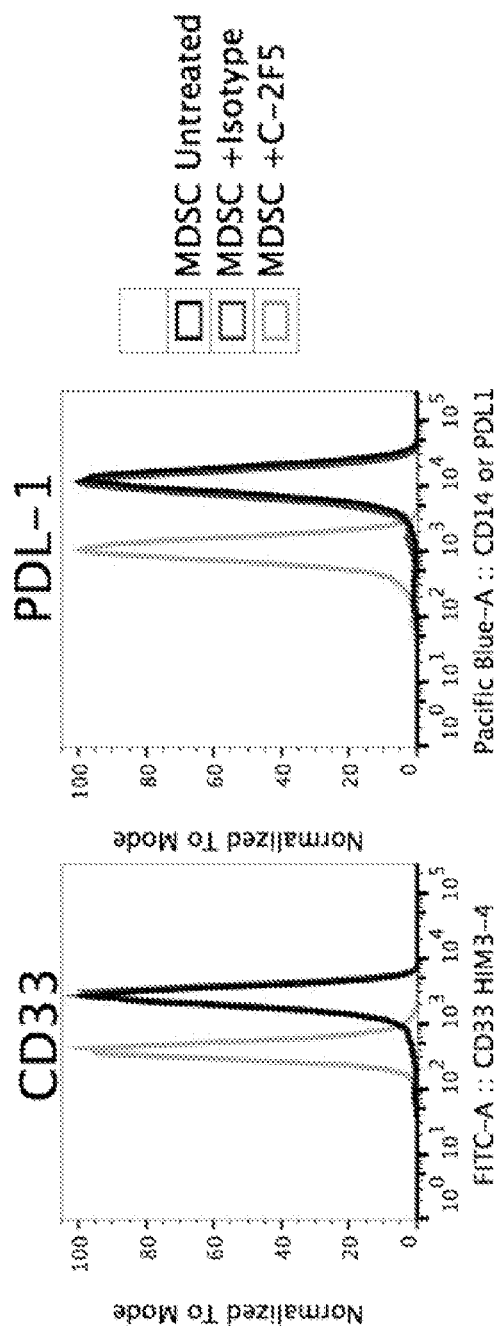
FIG. 19A depicts expression levels of CD33 and PD-L1 in myeloid-derived suppressor cells (MDSC) treated with anti-CD33 antibody 2F5. In the figure "MDSC Untreated" refers to cells not treated with an antibody, "MDSC+Isotype" refers to cells treated with isotype control antibody; and "MDSC+C-2F5" refers to cells treated with anti-CD33 antibody 2F5.
Figure 19B:
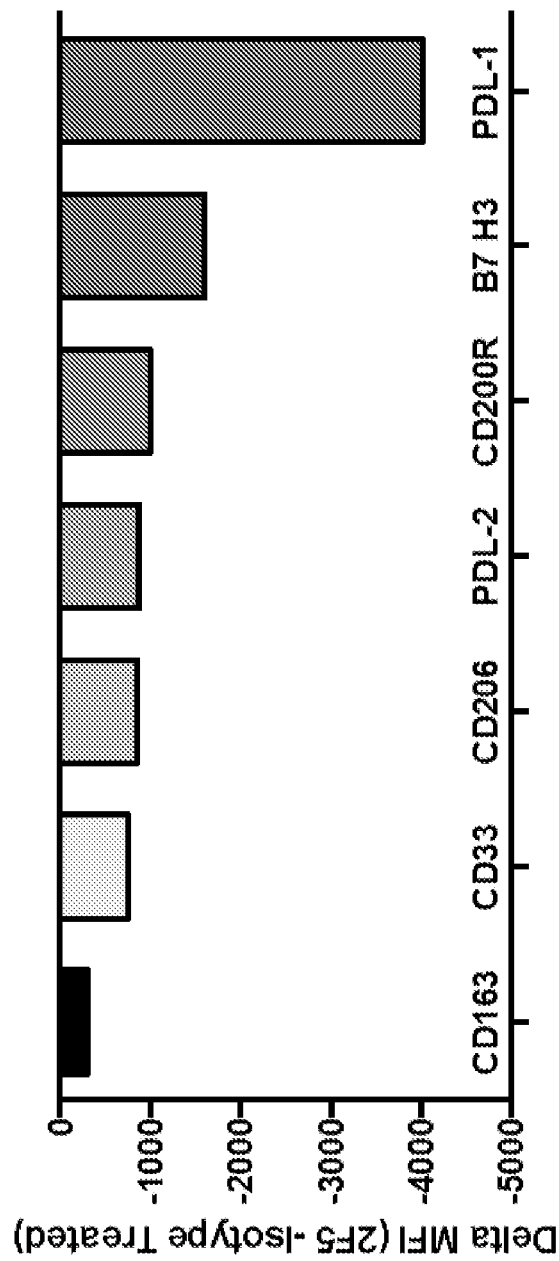
FIG. 19B depicts quantification of change in expression of CD163, CD33, CD206, PD-L2, CD200R, B7 H3, and PD-L1 between myeloid-derived suppressor cells (MDSC) treated with isotype control antibody and cells treated with anti-CD33 antibody 2F5.

As shown in FIG. 19A, anti-CD33 antibody 2F5 decreased expression of the immune inhibitory ligand PD-L1 on MDSC, leading to decreased inhibition of T cell function against tumors. MDSC cultured with anti-CD33 antibody 2F5 also display phenotypic changes, suggesting diminished immunosuppressive capacity. Compared to the media only control (MDSC Untreated) or the isotype control antibody-treated cells (MDSC+Isotype), MDSC cultured with the 2F5 antibody (MDSC+C-2F5) express lower levels of PD-1 ligands (PD-L1 and PD-L2), reduced levels of B7-H3 (a potent T cell check point inhibitor), reduced levels of CD200R (an inhibitory signaling receptor), and reduced levels of the M2-type markers CD163 and CD206 (FIG. 19B). The results indicate that antibody-mediated target engagement and subsequent downregulation of cell surface levels of CD33 leads to phenotype alterations in such a manner that reduces suppressive ligands and receptors.

Figure 19C:
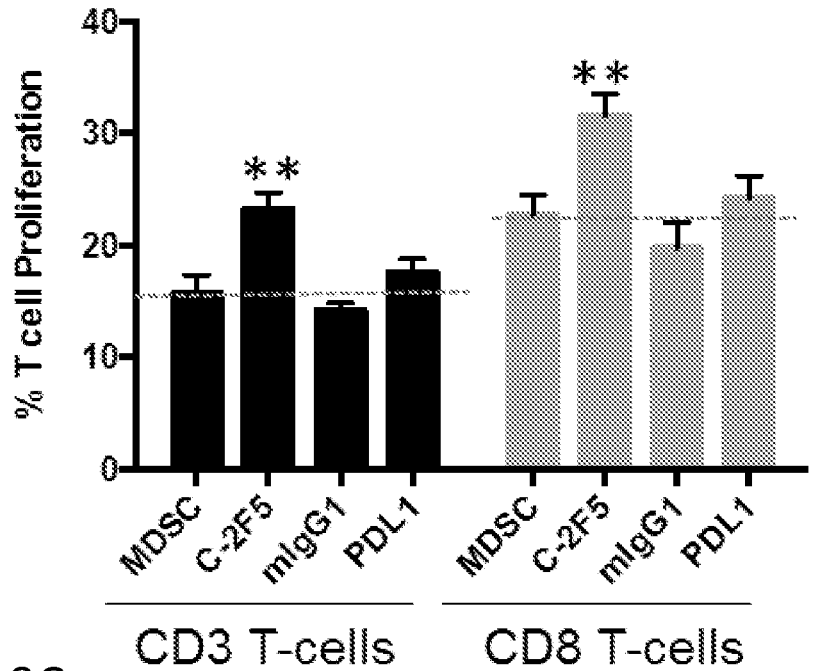
FIG. 19C depicts percentage of CD3+ T cell proliferation and CD8+ T cell proliferation induced by myeloid-derived suppressor cells (MDSC) that were left untreated or that were treated with anti-CD33 antibody 2F5, a mouse isotype control antibody (mIgG1), or an anti-PD-L1 antibody (PDL1). The MDCS were co-cultured with the T cells in cervical cancer cell conditioned media. \*\*: $p<0.01$.
Figure 19D:
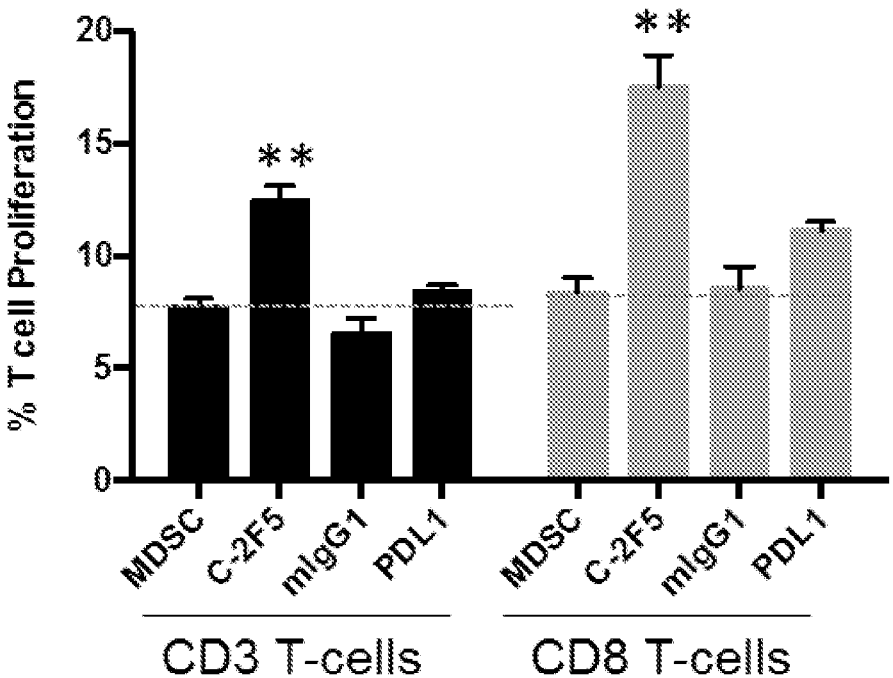
FIG. 19D depicts percentage of CD3+ T cell proliferation and CD8+ T cell proliferation induced by myeloid-derived suppressor cells (MDSC) that were left untreated or that were treated with anti-CD33 antibody 2F5, a mouse isotype control antibody (mIgG1), or an anti-PD-L1 antibody (PDL1). \*\*: $p<0.01$. The MDCS were co-cultured with the T cells in glioblastoma cell conditioned media.

As shown in FIGS. 19C and 19D, anti-CD33 antibody 2F5 increased T cell proliferation in the presence of MDSC, allowing for the generation of more tumor-fighting T cells. MDSC co-cultured with activated T cells suppress T-cell proliferation. In these studies, MDSC treated with antibody 2F5 induced less suppression of T cell proliferation of either total CD3 T cells or cytotoxic CD8 T cells (FIGS. 19C and 19D). An isotype control antibody (mIgG1) did not change MDSC-dependent suppression of T cell proliferation (FIGS. 19C and 19D). Moreover, the 2F5 antibody was more effective in alleviating MDSC-mediated T cell suppression as compared to an anti-PD-L1 antibody (FIGS. 19C and 19D). The results indicate that anti-CD33 antibodies that are able to phenotypically alter MDSC by reducing expression of suppressive ligands and receptors are also capable of effecting downstream functions, such as T cell proliferation.

Example 48: Effects of CD33 Antibodies on Myeloid-Derived Suppressor Cells (MDSC)

Human peripheral blood cells were ficolled, red blood cells were lysed with ACK lysis buffer, and cells were washed 3 times before plating in RPMI with 10% FBS, Pen/Strep, 1 mM glutamine, non-essential amino acids, and sodium pyruvate. Human peripheral blood mononuclear cells (PBMCs) were cultured for one week at 37° C. in 5% $CO_2$, with the following cytokines: 10 ng/ml rhGM-CSF (R&D), 10 ng/ml rhIL-8 (R&D), and 10 ng/ml rhIL-6 (Sigma). The mIgG1 (BioXcell) isotype, or the CD33 antibody 2F5 or 6C7 was then added to flasks. Every 2-3 days, media, cytokines, and antibodies (where applicable) were replenished. After 7 days of culture, cells were harvested by scraping and triterating, and resuspended in PBS with 2% FBS and 1 mM EDTA for FACS analysis. For assessment of live and dead cell populations, Live/Dead Fixable Aqua dead cell stain (Thermo Fisher) was diluted 1:500 in PBS with 2% FBS and 1 mM EDTA and incubated for 30 minutes on ice. Cell were washed 3 times in buffer and analyzed on a BD FACS Canto (BD Biosciences) for forward and side scatter and AmCyan fluorescence. Data were analyzed with FlowJo (Tree Star Software).

Figure 20:
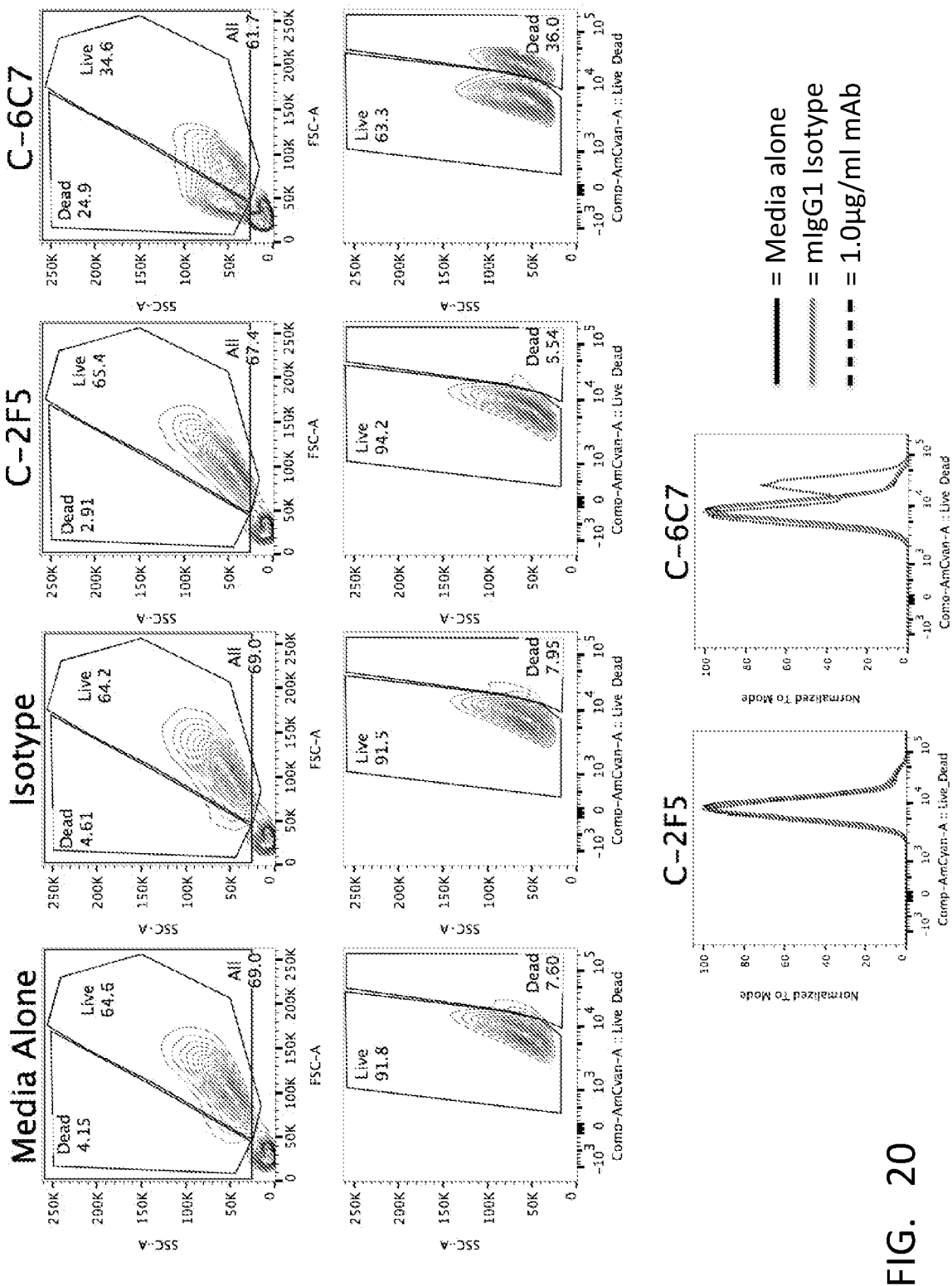
FIG. 20 depicts results showing anti-CD33 antibodies selectively kill non tumorigenic myeloid-derived suppressor cells. Top row: Live/Dead Gates by cell morphology: increase in dead cell gate with C-6C7. Middle row: Gating on Live/Dead cells using dye: Dye HIGH positive cells are DEAD, dye low cells are alive. 30% increase in dead cells in 6C7 treated cells. Histograms: showing Live/Dead cell dye in histogram format, No peak in 2F5, Peak of dead cells in other mAbs.

As shown in FIG. 20, CD33 antibody 6C7, is capable of inducing cell death in differentiating myeloid-derived suppressor cells (MDSC).

What is claimed is:

1. An isolated humanized anti-CD33 antibody that binds to a human CD33 protein, wherein the anti-CD33 antibody comprises a light chain variable domain and a heavy chain variable domain, wherein:

the light chain variable domain comprises an HVR-L1 comprising the amino acid sequence of SEQ ID NO: 10, or an amino acid sequence with at least about 90% homology to the amino acid sequence of SEQ ID NO: 10; an HVR-L2 comprising the amino acid sequence of SEQ ID NO: 13, or an amino acid sequence with at least about 90% homology to the amino acid sequence of SEQ ID NO: 13; and an HVR-L3 comprising the amino acid sequence of SEQ ID NO: 72, or an amino acid sequence with at least about 90% homology to the amino acid sequence of SEQ ID NO: 72; and the heavy chain variable domain comprises an HVR-H1 comprising the amino acid sequence of SEQ ID NO: 231, or an amino acid sequence with at least about 90% homology to the amino acid sequence of SEQ ID NO: 231; an HVR-H2 comprising the amino acid sequence of SEQ ID NO: 23; and an HVR-H3 comprising the amino acid sequence of SEQ ID NO: 27, or an amino acid sequence with at least about 90% homology to the amino acid sequence of SEQ ID NO: 27.

2. The humanized anti-CD33 antibody of claim 1, wherein the anti-CD33 antibody competes for binding to CD33 with an antibody comprising a light chain variable domain and a heavy chain variable domain, wherein the light chain variable domain comprises an FR 1 of SEQ ID NO: 234, an HVR L1 of SEQ ID NO: 10, an FR 2 of SEQ ID NO: 83, an HVR L2 of SEQ ID NO: 13, an FR 3 of SEQ ID NO: 91, an HVR L3 of SEQ ID NO: 72, and an FR 4 of SEQ ID NO: 94, and wherein the heavy chain variable domain comprises an amino acid sequence of SEQ ID NO: 244.

3. The humanized anti-CD33 antibody of claim 1, wherein the antibody is of the IgG class, the IgM class, or the IgA class.

4. The humanized anti-CD33 antibody of claim 3, wherein the anti-CD33 antibody has an IgG1, IgG2, IgG3, or IgG4 isotype.

5. The humanized anti-CD33 antibody of claim 4, wherein the antibody binds an inhibitory Fc receptor.

6. The humanized anti-CD33 antibody of claim 5, wherein the inhibitory Fc receptor is inhibitory Fc-gamma receptor IIB (FcγIIB).

7. The humanized anti-CD33 antibody of claim 6, wherein:

(a) the anti-CD33 antibody has a human IgG1 isotype and comprises one or more amino acid substitutions in the Fc region at a residue position selected from the group consisting of: N297A, D265A, D270A, L234A, L235A, G237A, P238D, L328E, E233D, G237D, H268D, P271G, A330R, C226S, C229S, E233P, L234V, L234F, L235E, P331S, S267E, L328F, A330L, M252Y, S254T, T256E, N297Q, P238S, P238A, A327Q, A327G, P329A, K322A, T394D, and any combination thereof, wherein the numbering of the residues is according to EU numbering, or comprises an amino acid deletion in the Fc region at a position corresponding to glycine 236;

(b) the anti-CD33 antibody has a human IgG1 isotype and comprises an IgG2 isotype heavy chain constant domain 1 (CH1) and hinge region and wherein the antibody Fc region comprises a S267E amino acid substitution, or a L328F amino acid substitution, or both, and/or a N297A or N297Q amino acid substitution, wherein the numbering of the residues is according to EU numbering;

(c) the anti-CD33 antibody has a human IgG2 isotype and comprises one or more amino acid substitutions in the Fc region at a residue position selected from the group consisting of: P238S, V234A, G237A, H268A, H268Q, V309L, A330S, P331S, C214S, C232S, C233S, S267E, L328F, M252Y, S254T, T256E, H268E, N297A, N297Q, A330L, and any combination thereof, wherein the numbering of the residues is according to EU numbering;

(d) the anti-CD33 antibody has a human IgG4 isotype and comprises one or more amino acid substitutions in the Fc region at a residue position selected from the group consisting of: L235A, G237A, S228P, L236E, S267E, E318A, L328F, M252Y, S254T, T256E, E233P, F234V, L234A/F234A, S228P, S241P, L248E, T394D, N297A, N297Q, L235E, and any combination thereof, wherein the numbering of the residues is according to EU numbering; or (e) the anti-CD33 antibody has a hybrid IgG2/4 isotype, and comprises an amino acid sequence comprising amino acids 118 to 260 of human IgG2 and amino acids 261 to 447 of human IgG4, wherein the numbering of the residues is according to EU or Kabat numbering.

8. The humanized anti-CD33 antibody of claim 1, wherein the CD33 protein is expressed on one or more cells selected from the group consisting of human dendritic cells, human macrophages, human monocytes, human neutrophils, human granulocytes, and human microglia.

9. The humanized anti-CD33 antibody of claim 1, wherein the anti-CD33 antibody is an antibody fragment, and wherein the antibody fragment is an Fab, Fab', Fab'-SH, F(ab')2, Fv, or scFv fragment.

10. The humanized anti-CD33 antibody of claim 1, wherein the anti-CD33 antibody is a bispecific antibody, a monoclonal antibody, a multivalent antibody, or a conjugated antibody.

11. The humanized anti-CD33 antibody of claim 1, wherein the antibody inhibits interaction between human CD33 and one or more CD33 ligands.

12. The humanized anti-CD33 antibody of claim 1, wherein the antibody decreases cell surface levels of CD33.

13. A method of treating a disease, disorder, or injury selected from the group consisting of Alzheimer's disease, acute lymphoblastic leukemia (ALL), acute myeloid leukemia (AML), chronic lymphocytic leukemia (CLL), chronic myeloid leukemia (CML), and multiple myeloma, wherein the method comprises administering to an individual in need thereof a therapeutically effective amount of the anti-CD33 antibody of claim 1.

14. An isolated humanized anti-CD33 antibody that binds to a human CD33 protein, wherein the anti-CD33 antibody comprises a light chain variable domain and a heavy chain variable domain, wherein:
   the light chain variable domain comprises an HVR-L1 comprising the amino acid sequence of SEQ ID NO: 10, or an amino acid sequence with at least about 90% homology to the amino acid sequence of SEQ ID NO: 10; an HVR-L2 comprising the amino acid sequence of SEQ ID NO: 13, or an amino acid sequence with at least about 90% homology to the amino acid sequence of SEQ ID NO: 13; and an HVR-L3 comprising the amino acid sequence of SEQ ID NO: 72, or an amino acid sequence with at least about 90% homology to the amino acid sequence of SEQ ID NO: 72; and
   the heavy chain variable domain comprises an HVR-H1 comprising the amino acid sequence of SEQ ID NO: 231, or an amino acid sequence with at least about 90% homology to the amino acid sequence of SEQ ID NO: 231; an HVR-H2 comprising the amino acid sequence of SEQ ID NO: 23, or an amino acid sequence with at least about 90% homology to the amino acid sequence of SEQ ID NO: 23; and an HVR-H3 comprising the amino acid sequence of SEQ ID NO: 27.

15. The humanized anti-CD33 antibody of claim 14, wherein the anti-CD33 antibody competes for binding to CD33 with an antibody comprising a light chain variable domain and a heavy chain variable domain, wherein the light chain variable domain comprises an FR 1 of SEQ ID NO: 234, an HVR L1 of SEQ ID NO: 10, an FR 2 of SEQ ID NO: 83, an HVR L2 of SEQ ID NO: 13, an FR 3 of SEQ ID NO: 91, an HVR L3 of SEQ ID NO: 72, and an FR 4 of SEQ ID NO: 94, and wherein the heavy chain variable domain comprises an amino acid sequence of SEQ ID NO: 244.

16. The humanized anti-CD33 antibody of claim 14, wherein the antibody is of the IgG class, the IgM class, or the IgA class.

17. The humanized anti-CD33 antibody of claim 16, wherein the anti-CD33 antibody has an IgG1, IgG2, IgG3, or IgG4 isotype.

18. The humanized anti-CD33 antibody of claim 17, wherein the antibody binds an inhibitory Fc receptor.

19. The humanized anti-CD33 antibody of claim 18, wherein the inhibitory Fc receptor is inhibitory Fc-gamma receptor IIB (FcγIIB).

20. The humanized anti-CD33 antibody of claim 19, wherein:
   (a) the anti-CD33 antibody has a human IgG1 isotype and comprises one or more amino acid substitutions in the Fc region at a residue position selected from the group consisting of: N297A, D265A, D270A, L234A, L235A, G237A, P238D, L328E, E233D, G237D, H268D, P271G, A330R, C226S, C229S, E233P, L234V, L234F, L235E, P331S, S267E, L328F, A330L, M252Y, S254T, T256E, N297Q, P238S, P238A, A327Q, A327G, P329A, K322A, T394D, and any combination thereof, wherein the numbering of the residues is according to EU numbering, or comprises an amino acid deletion in the Fc region at a position corresponding to glycine 236;
   (b) the anti-CD33 antibody has a human IgG1 isotype and comprises an IgG2 isotype heavy chain constant domain 1 (CH1) and hinge region and wherein the antibody Fc region comprises a S267E amino acid substitution, or a L328F amino acid substitution, or both, and/or a N297A or N297Q amino acid substitution, wherein the numbering of the residues is according to EU numbering;
   (c) the anti-CD33 antibody has a human IgG2 isotype and comprises one or more amino acid substitutions in the Fc region at a residue position selected from the group consisting of: P238S, V234A, G237A, H268A, H268Q, V309L, A330S, P331S, C214S, C232S, C233S, S267E, L328F, M252Y, S254T, T256E, H268E, N297A, N297Q, A330L, and any combination thereof, wherein the numbering of the residues is according to EU numbering;
   (d) the anti-CD33 antibody has a human IgG4 isotype and comprises one or more amino acid substitutions in the Fc region at a residue position selected from the group consisting of: L235A, G237A, S228P, L236E, S267E, E318A, L328F, M252Y, S254T, T256E, E233P, F234V, L234A/F234A, S228P, S241P, L248E, T394D, N297A, N297Q, L235E, and any combination thereof, wherein the numbering of the residues is according to EU numbering; or
   (e) the anti-CD33 antibody has a hybrid IgG2/4 isotype, and comprises an amino acid sequence comprising amino acids 118 to 260 of human IgG2 and amino acids 261 to 447 of human IgG4, wherein the numbering of the residues is according to EU or Kabat numbering.

21. The humanized anti-CD33 antibody of claim 14, wherein the CD33 protein is expressed on one or more cells selected from the group consisting of human dendritic cells, human macrophages, human monocytes, human neutrophils, human granulocytes, and human microglia.

22. The humanized anti-CD33 antibody of claim 14, wherein the anti-CD33 antibody is an antibody fragment, and wherein the antibody fragment is an Fab, Fab', Fab'-SH, F(ab')2, Fv, or scFv fragment.

23. The humanized anti-CD33 antibody of claim 14, wherein the anti-CD33 antibody is a bispecific antibody, a monoclonal antibody, a multivalent antibody, or a conjugated antibody.

24. The humanized anti-CD33 antibody of claim 14, wherein the antibody inhibits interaction between human CD33 and one or more CD33 ligands.

25. The humanized anti-CD33 antibody of claim 14, wherein the antibody decreases cell surface levels of CD33.

26. A method of treating a disease, disorder, or injury selected from the group consisting of Alzheimer's disease, acute lymphoblastic leukemia (ALL), acute myeloid leukemia (AML), chronic lymphocytic leukemia (CLL), chronic myeloid leukemia (CML), and multiple myeloma, wherein the method comprises administering to an individual in need thereof a therapeutically effective amount of the anti-CD33 antibody of claim 14.

* * * * *